US006566372B1

(12) United States Patent
Zhi et al.

(10) Patent No.: US 6,566,372 B1
(45) Date of Patent: May 20, 2003

(54) BICYCLIC ANDROGEN AND PROGESTERONE RECEPTOR MODULATOR COMPOUNDS AND METHODS

(75) Inventors: Lin Zhi, San Diego, CA (US); Christopher Tegley, San Diego, CA (US); Barbara Pio, San Diego, CA (US); Cornelis Arjan Van Oeveren, San Diego, CA (US); Mehrnouch Motamedi, San Diego, CA (US); Esther Martinborough, San Diego, CA (US); Sarah West, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 09/649,466

(22) Filed: Aug. 24, 2000

Related U.S. Application Data

(60) Provisional application No. 60/150,987, filed on Aug. 27, 1999.

(51) Int. Cl.$^7$ .................. A61K 31/47; C07D 215/227
(52) U.S. Cl. ................. 514/312; 514/212; 514/254; 514/311; 514/313; 514/314; 540/599; 544/363; 546/144; 546/157; 546/159; 546/152; 546/167; 546/171; 546/173; 546/180; 546/181
(58) Field of Search ................. 546/144, 157, 546/159, 152, 167, 171, 173, 180, 181; 540/599; 544/363; 514/312, 313, 212, 254, 314, 311

(56) References Cited

U.S. PATENT DOCUMENTS

| | | | |
|---|---|---|---|
| 3,775,332 A | 11/1973 | Heins et al. .................. 252/98 |
| 3,798,031 A | 3/1974 | Janssens et al. .............. 96/1.8 |
| 3,830,647 A | 8/1974 | Janssens et al. .............. 96/1.5 |
| 3,832,171 A | 8/1974 | Janssens et al. .............. 96/1.5 |
| 3,928,686 A | 12/1975 | Poot et al. ................... 428/457 |
| 3,936,461 A | 2/1976 | Schwender et al. ......... 424/258 |
| 3,979,394 A | 9/1976 | Janssens et al. ............. 252/501 |
| 3,993,656 A | 11/1976 | Rooney et al. .............. 424/250 |
| 4,138,490 A | 2/1979 | Brittain et al. .............. 424/258 |
| 4,193,931 A | 3/1980 | Loeliger ..................... 424/308 |
| 4,326,055 A | 4/1982 | Loeliger ..................... 568/426 |
| 4,415,572 A | 11/1983 | Tominaga et al. ........... 544/360 |
| 4,427,654 A | 1/1984 | Austin ......................... 424/95 |
| 4,505,852 A | 3/1985 | Rasnick et al. ......... 260/112.5 R |
| 4,534,979 A | 8/1985 | Loev et al. .................. 514/529 |
| 4,539,134 A | 9/1985 | Martin et al. ................ 252/156 |
| 4,578,498 A | 3/1986 | Frickel et al. .................. 560/8 |
| 4,710,507 A | 12/1987 | Campbell et al. ........... 514/312 |
| 4,728,653 A | 3/1988 | Campbell et al. ........... 514/312 |
| 4,801,733 A | 1/1989 | Wuest et al. ................. 560/56 |
| 4,831,052 A | 5/1989 | Shudo ......................... 514/455 |
| 4,833,240 A | 5/1989 | Maignan et al. ........... 536/55.2 |
| 4,874,747 A | 10/1989 | Shroot et al. ................. 514/23 |
| 4,879,284 A | 11/1989 | Lang et al. ................... 514/62 |
| 4,898,864 A | 2/1990 | Maignan et al. ......... 514/237.5 |
| 4,925,979 A | 5/1990 | Shudo ........................ 562/462 |
| 4,933,336 A | 6/1990 | Martin et al. .............. 514/222.5 |
| 4,943,502 A | 7/1990 | Terrell et al. ................. 430/58 |
| 4,981,784 A | 1/1991 | Evans et al. ................... 435/6 |
| 5,004,730 A | 4/1991 | Philippe et al. .............. 514/29 |
| 5,071,773 A | 12/1991 | Evans et al. ................ 436/507 |
| 5,081,242 A | 1/1992 | Combs ......................... 544/52 |
| 5,091,528 A | 2/1992 | Gluchowski et al. ....... 544/105 |
| 5,124,473 A | 6/1992 | Shroot et al. ................ 560/56 |
| 5,147,844 A | 9/1992 | Weber et al. ............... 503/227 |
| 5,198,567 A | 3/1993 | Lang et al. ................... 560/56 |
| 5,320,833 A | 6/1994 | Deckers et al. .............. 424/59 |
| 5,391,569 A | 2/1995 | Brion et al. ................ 514/456 |
| 5,391,766 A | 2/1995 | Klaus et al. ................ 549/311 |
| 5,688,808 A | 11/1997 | Jones et al. ................ 514/285 |
| 5,688,810 A | 11/1997 | Jones et al. ................ 514/311 |
| 5,693,646 A | 12/1997 | Jones et al. ................ 514/285 |
| 5,693,647 A | 12/1997 | Jones et al. ................ 514/285 |
| 5,696,127 A | 12/1997 | Jones et al. ................ 514/285 |
| 5,696,130 A | 12/1997 | Jones et al. ................ 514/291 |
| 5,705,167 A | 1/1998 | Bernardon et al. ......... 424/401 |
| 5,721,103 A | 2/1998 | Boehm et al. .............. 435/7.1 |
| 5,776,699 A | 7/1998 | Klein et al. ................ 435/7.2 |
| 5,910,508 A | 6/1999 | Thoreau et al. ............ 514/432 |
| 5,968,908 A | 10/1999 | Epstein et al. ............... 514/42 |
| 5,977,125 A | 11/1999 | Hibi et al. .................. 514/277 |
| 5,997,108 A | 12/1999 | Claussen et al. ........... 514/429 |
| 6,030,964 A | 2/2000 | Hibi et al. .................... 514/18 |
| 6,133,309 A | 10/2000 | Bollag et al. .............. 514/432 |
| 6,147,224 A | 11/2000 | Vuligonda et al. ......... 548/518 |

FOREIGN PATENT DOCUMENTS

DE        21 11 938        10/1971
DE        2334738        * 1/1975

(List continued on next page.)

OTHER PUBLICATIONS

Patel et al, Indian J. of Chem., vol. 29B, p. 836–842 (1990).*
Alabaster et al, J. Med. Chem., vol. 32, p. 575–583 (1989).*
Chem. Abstracts 113:243983, print–out of online search provided.*
Allegretto, et al., "Retinoid X Receptor Acts as a Hormone Receptor in Vivo to Induce a Key Metabolic Enzyme for 1,25–Dihydroxyvitamin $D_3$," *J.of Biol. Chem* 270:23906 (1995).

(List continued on next page.)

*Primary Examiner*—Bernard Dentz
(74) *Attorney, Agent, or Firm*—Paul, Hastings, Janofsky & Walker LLP

(57) ABSTRACT

The present invention is directed to compounds, pharmaceutical compositions, and methods for modulating processes mediated by AR and PR. More particularly, the invention relates to nonsteroidal compounds and compositions that are high affinity, high specificity agonists, partial agonists (i.e., partial activators and/or tissue-specific activators) and antagonists for AR and PR. Also provided are methods of making such compounds and pharmaceutical compositions, as well as critical intermediates used in their synthesis.

24 Claims, No Drawings

FOREIGN PATENT DOCUMENTS

| | | |
|---|---|---|
| DE | 26 11 824 | 9/1976 |
| DE | 3810706 | 10/1989 |
| EP | 0272910 | 11/1988 |
| EP | 0356230 | 2/1990 |
| EP | 0 542 609 | 5/1993 |
| EP | 0 718 285 | 6/1996 |
| GB | 2 058 788 | 4/1981 |
| SU | 555119 | 6/1977 |
| WO | 89/07441 | 8/1989 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |
| WO | 94/20093 | 9/1994 |
| WO | 95/24394 | 9/1995 |
| WO | 96/05165 | 2/1996 |
| WO | 96/19458 | 3/1996 |
| WO | 96/20913 | 7/1996 |
| WO | 97/00876 | 1/1997 |
| WO | 97/12853 | 4/1997 |
| WO | 97/49709 | 12/1997 |
| WO | 99/43708 | 9/1999 |
| WO | 99/58486 | 11/1999 |
| WO | 00/53562 | 9/2000 |
| WO | 00/66680 | 11/2000 |

OTHER PUBLICATIONS

Allegretto, et al., "Transactivation Properties of Retinoic Acid and Retinoid X Receptors in Mammalian Cells and Yeast," J. Biol. Chem., 268(35):26625–26633 (1993).

Apfel, et al., "A retinoic acid receptor α antagonist selectively counteracts retinoic acid effects," Proc. Natl. Acad. Sci. 89:7129 (1992).

Atarashi, et al., "Asymmetric Reduction of 7,8–Difluoro–3–methyl–2H–1,4–benzoxazine. Synthesis of a Key Intermediate of (S)–(–)–Ofloxacin (DR–3355)," J. Heterocyclic Chem. 28:329–31 (1991).

Atkins, R.L. et al., "Substituted Coumarins and Azacoumarins. Synthesis and Fluorescent Properties," J. Org. Chem., 43(10):1975–1980 (1978).

Aurell, et al., "Trienediolates of Hexadienoic Acids in Synthesis. Synthesis of Retinoid and nor Retinoic Acids." Tetrahedron 49:6089 (1993).

Barluenga, et al., "A New Method for the Syntheis of Pyridines," Synthesis 191 (1975).

Beard, et al., "Synthesis and Structure–Activity Relationships of Stilbene Retinoid Analogs Substituted with Heteroaromatic Carboxylic Acids," J. Med. Chem. 38:2820 (1995).

Bestmann, et al., "Cumulated Ylides as Building Blocks for the Synthesis of Heterocycles," Angew. Chem. Int. Ed. Engl. 15(2):115–116 (1976).

Bissonnette, et al., "9–cis Retinoic Acid Inhibition of Activation–Induced Apoptosis Is Mediated via Regulation of Fas Ligand and Requires Retinoic Acid Receptor and Retinoid X Receptor Activation," Mol. Cell. Biol. 15: 5576–5585 (1995).

Biswas, et al., "Montmorillonite clay as condensing agent in Pechmann reaction for the synthesis of courmarin derivatives," Indian J. Chem. 31B:628 (1992).

Blatt, The Fries Reaction Chapter 11 Org. React. 1:342 (1942).

Boehm, et al. "Synthesis and Structure–Activity Relationships of Novel Retinoid X Receptor Selective Retinoids," J. Med. Chem. 37:2930 (1994).

Boehm, et al., "Design and Synthesis of Potent Retinoid X Receptor Selective Ligands That Induce Apoptosis in Leukemia Cells," J. Med. Chem. 38:3146 (1995).

Boehm, et al., "Synthesis of High Specific activity [3H]–9–Cis Retinoic Acid and its Application for Identifying Retinoids with Unusual Binding Properties," J. Med. Chem., 37:408 (1994).

Canan–Koch, et al., "Identification of the First Retinoid X Receptor Homodimer Antagonist," J. Med. Chem. 39(17):3229 (1996).

Catellani, et al., "A New Palladium–catalyzed Synthesis of 3,4–Disubstituted Coumarins from 3–Alkenoates of ortho–Iodophenol, Phenylacetylene and Carbon Monoxide," Tetrahedron Lett. 35(23):5923 (1994).

Chapelo, et al., "Heteroaromatoc Analogues of the $\alpha_2$–Adrenoreceptor Partial Agonist Clonidine," J. Med. Chem., 32:1627–1630 (1989).

Chemistry and Biology of Synthetic Retinoids, Dawson and Okamuna, Eds., CRC Press, Florida: Chapters 3, 8, 14, and 16 (1990).

Clark and Miller, "Hydrogen Bonding in Organic Synthesis V: Potassium Fluoride in Carboxylic Acids as an Alternative To Crown Ether With Acid Salts in The Preparation of Phenacyl Esters," Tetrahedron Lett. 7:599 (1977).

Dawson and Hobbs, "Ch. 2—The Synthetic Chemistry of Retinoids," in The Retinoids: Biology, Chemistry and Medicine, 2nd edition, edited by Sporn et al., Raven Press, New York, pp. 5–178 (1994).

Dawson, et al., "Effects of Structural Modification in the C7–C11 Region of the Retinoid Skeleton on Biological Activity in a Series of Aromatic Retinoids," J. Med. Chem. 32:1504 (1989).

Edwards, et al., "New Nonsteroidal Androgen Receptor Modulators Based on 4–(Trifluormethyl)–2(1H)–Pyrrolidino[3,2–g]Quinolinone," Bioorg. Med. Chem. Lett. 8:745–750 (1998).

Edwards, J.P., et al., "Preparation, Resolution, and Biological Evaluation of 5–Aryl–1,2–dihydro–5H–chromeno[3,4–f]quinolines: Potent, Orally Active, Nonsteroidal Progesterone Receptor Agonists," J. Med. Chem., 41(15):2779–85 (1998).

Eyrolles, et al., "Retinoid Antagonists: Molecular Design Based on the Ligand Superfamily in Concept," Med. Chem. Res., 2:361–367 (1992).

Forman, et al., "Unique Response Pathways Are Established by Allosteric Interactions among Nuclear Hormone Receptors," Cell 81:541–550 (1995).

Fries and Fink, "Uber Homologe des Cumaranons und ihre Abkommlinge," Ber. 41:4271 (1980).

Freis and Pfaffendorf, "Uber ein Kondensationsprodukt des Cumaranons und seine Umwandlung in Oxindirubin," Ber. 43:212 (1910).

Giguere, et al., "Identification of a receptor for the morphogen retinoic acid," Nature 330:624–629 (1987).

Goralski, et al., "Boranes in Synthesis. 3. Conversion of the Morpholine and Pyrrolidine Enamines of Symmetrical Dialklketones to the Corresponding threo–β–Amino Alcohols via Hydroboration/Oxidation," Tetrahedron Lett. 35(20):3251–54 (1994).

Gromova, G.N. et al., Khim Prom St., 43(2):97–8 (1967).

Hershberger, et al., "Myotrophic Activity of 19–Nortestosterone and Other Steroids Determined by Modified Levator Ani Muscle Method" *Proc. Soc. Exptl. Biol. Med.* 83:175–178 (1953).

Heyman et al., "9–Cis Retenoic Acid is a High Affinity Ligand for the Retinoid X Receptor," *Cell* 68:397–406 (1992).

Hollenberg and Evans, "Multiple and Cooperative Trans–Activation Domains of the Human Glucocorticoid Receptor," *Cell* 55:899–906 (1988).

Ishikawa et al., "A Functional Retinoic Acid Receptor Encoded by the Gene of Human Chromosome 12," *Molecular Endocrinology* 4(6):837–844 (1990).

Ivanov, et al., Chem Abstracts No. 95:97624, "Synthesis and properties of derivatives of 2,2,4–trimethyl substituted quinolines and some of their analogs," *Izv. Akad. Nauk. SSSR Ser. Khim.*, 3:628–633 (1981).

Jones, "The Structure, Reactions, Synthesis and Uses of Heterocyclic Compounds," *Comprehensive Heterocyclic Chemistry* vol. 2, Chap. 2.08, 421–426 (1984).

Jow, et al, "The Human Peroxisome Proliferator–activated Receptor (PRAR) Subtype NUC1 Prepresses the Activation of hPRARα and Thyroid Hormone Receptors," *J. Biol. Chem*, 270(8):3836–3840 (1995).

Kagechika, et al. "Retinobenzoic Acids. 2. Structure–Activity Relationship of Chalcone–4–carboxylic Acids and Glavone–4'–carboxylic Acids," *J. Med. Chem.*, 32(4):834 (1989).

Kagechika, et al., "Retinobenzoic Acids. 3. Structure–Activity Relationships of Retinoidal Azobenzene–4–carboxylic Acids and Stilbene–4–carboxylic Acids," *J. Med. Chem.* 32(5):1098 (1989).

Kagechika, et al., "Retinobenzoic Acids. 4. Conformation of Aromatic Amides with Retinoidal Activity. Importance of trans–Amide Structure for the Activity," *J. Med. Chem.* 32(10):2292 (1989).

Kaneko, et al., "Retinoid Antagonist," *Med. Chem. Res.*, 1:220–225 (1991).

Keidel, et al., "Different Agonist– and Antagonist–Induced Conformational Changes in Retinoic Acid Receptors Analyzed by Protease Mapping," *Mol. Cell. Biol.* 14(1):287 (1994).

Kliewer et al., "Convergence of 9–cis retinoic acid and peroxisome proliferator signalling pathways through heterodimer formation of their receptors," *Nature* 358:771–774 (1992).

Kong, et al., "Effects of isosteric pyridone replacements in androgen antagonists based on 1,2–dihydro–and 1,2,3,4–tetrahydro–2,2–dimethyl–6–trifluoromethyl–8–pyridono 5,6–g quinolines" *Bioorg. Med. Chem. Lett.* 10(5), 411–414 (2000).

Kurokawa, et al., "Regulation of retinoid signalling by receptor polarity and allosteric control of ligand binding," *Nature*, 371:528–531 (1994).

Labrie, et al., "Science behind total androgen blockade: from gene to combination therapy," *Clin. Invest. Med.* 16(6):475–492 (1993).

Lee, et al., "A synthetic retinoid antagonist inhibits the human immunodeficiency virus type 1 promoter," *Proc. Natl. Acad. Sci.* 91:5632 (1994).

Levin, et al., "9–Cis retinoic acid stereoisomer binds and activates the nuclear receptor RXRα," *Nature*, 355:359–361 (1992).

Ley et al., "Tetrapropylammonium Perruthenate, $Pr_4N^+ RuO^-_4$, TPAP: A Catalytic Oxidant for Organic Synthesis," *Synthesis* 639 (1994).

Li, et al.,"Montmorillonite Clay Catalysts. Part 7. An Environmentally Friendly Procedure for the Synthesis of Coumarins via Pechmann Condensation of Phenols with Ethyl Acetoacetate," *J. Chem. Res.* 38–39 (1998).

Liu and Asato, "Photochemistry and Synthesis of Stereoisomers of Vitamin A," *Tetrahedron* 40(11):1931–1969 (1984).

Loeliger, et al., "Arotinoids, a new class of highly active retinoids," *Eur. J. Med. Chem* 15:9 (1980).

Luke, et al., "The Male Sex Accessory Tissues; Structure, Androgen Action, and Physiology," *The Physiology of Reproduction*, 1435–1487 (1994).

Mangelsdorf et al., "A Direct Repeat in the Cellular Retinol–Binding Protein Type II Gene Confers Differential Regulation by RXR and RAR," *Cell* 66:555–561 (1991).

Mangelsdorf et al., "Ch. 8—The Retinoid Receptors," in *The Retinoids: Biology, Chemistry and Medicine, 2nd edition,* Sporn ed., Raven Press Ltd., New York, pp. 319–349 (1994).

Mangelsdorf et al., "Nuclear receptor that identifies a novel retinoic acid response pathway," *Nature* 345:224–229 (1990).

Maryanoff and Reitz,, "The Wittig Olefination Reaction and Modifications Involving Phosphoryl–Stabilized Carbanions. Stereochemistry, Mechanism, and Sepected Synthetic Aspects," *Chem. Rev.* 89(4):863–927 (1989).

Matsumoto, et al., "Novel Potassium Channel Activators: Synthesis and Structure–Activity Relationship Studies of 3,4–Dihydro–2H–1,4–benzoxazine Derivatives," *Chem. Pharm. Bull.*, 44(1):103–114 (1996).

McDonnell, et al., "Analysis of Estrogen Receptor Function in Vitro Reveals Three Distinct Classes of Antiestrogens," *Mol. Endo.* 9(6):659–669 (1995).

Mitscher, et al., "Chiral DNA Gyrase Inhibitors. 2. Asymmetric Synthesis and Biological Activity of the Enantiomers of
9–Fluoro–3–methyl–10–(4–methyl–1–piperazinyl)–7–oxo –2,3–dihydro–7H–pyrido[1,2,3–de]–1, 4–benzoxaxine–6–carboxylic Acid (Ofloxacin)," *J. Med. Chem.* 30(12):2283 (1987).

Mukherjee et al., "Human and Rat Peroxisome Prolifertor Activated Receptors (PPARs) Demonstrate Similar Tissue Distribution but Different Responsiveness to PPAR Activators," *J. Steroid Biochem. Molec. Biol.* 51(3–4):157–166 (1994).

Mukherjee, et al., "Identification, characterization, and Tissue Distribution of Human Peroxisome Prolifertor–activated Receptor (PPAR) Isoforms PPARγ2 versus PPARγ1 and Activation with Retinoid X Receptor Agonists and Antagonists," *Journ. Biol. Chem.* 272(12): 8071–8076 (1997).

Munk, et al., "Synthesis and Evaluation of 2–[(5–Methylbenz–1–ox–4–azin–6–yl) imino]imidazoline, a Potent, Peripherally Acting $α_2$Adrenoreceptor Agonist," *J. Med. Chem.*, 39(18):3533–3538 (1996).

Okuda, et al., "Testosterone Dependent Regulation of the Enzymes Involved in DNA Synthesis in the Rat Ventral Prostate," *J. Urol.* 145:188–191 (1991).

Patent Abstracts of Japan, vol. 4, No. 019, Feb. 16, 1980; JP 54 154797.

Patent Abstracts of Japan, vol. 9, No. 188, Aug. 3, 1985; JP 60 056985.

Patent Abstracts of Japan, vol.. 1999, No. 14, Dec. 22, 1999; JP 11 242304.

Petkovich et al., "A human retinoic acid receptor which belongs to the family of nuclear receptors," *Nature* 330:444–450 (1987).

Pine, et al., "Carbonyl Methylenation Using a Titanium–Aluminum (Tebbe) Complex," *J. Org. Chem.* 50(8):1212–1216 (1985).

Quast, et al., "Synthesis and reactions of some pyrido 3, 2–g!quinolines (1,8–diazaanthracenes)," *Liebigs Ann. Chem.*, 133–46 (1984).

Rodbard, D. "Mathematics and statistics of ligand assays: an illustrated guide" In: J. Langon and J.J. Clapp, eds., Ligand Assay, Masson Publishing U.S.A, Inc., New York, pp. 45–99, (1981).

Roy, et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* 15(12):6481–6487 (1995).

Sala, et al., "Depsidone Synthesis. Part 14. The Total Synthesis of Psoromic Acid: Isopropyl Ethers as Useful Phenolic Protective Groups," *J. Chem. Soc. Perkin. Trans.* I:2593 (1979).

Sato and Otera, "CsF in Organic Synthesis. A Practical Method for Inversion of Secondary Mesylates," *Syn. Lett.* 336(1995).

Sato, et al., "CsF in Organic Synthesis. Tuning of N– or O–Alkylation of 2–Pyridone," *Synlett* 845–846 (1995).

Sethna and Phadke, *The Pechmann Reaction Organic Reactions* 7:1–58 (1953).

Sherman, et al., "Central Hypothyroidism Associated with Retinoid X Receptor–Selective Ligands," *N. Engl. J. Med.* 340(14):1075–1079 (1999).

Shridhar, et al., "A General and Convention Synthesis of 2H–1,4–Benzoxazin–3(4H)–ones," *Org. Prep. Proc. Int.* 14(3):195 (1982).

Simental, et al., "Transcriptional activation and nuclear targeting signals of the human androgen receptor," *J. Biol. Chem.* 266(1):510–518 (1991).

Strickland et al., "Structure–Activity Relationships of a New Series of Retinoidal Benzoic Acid Derivatives as Measured by Induction of Differentiation of Murine F9 Teratocarcinoma Cells and Human HL–60 Promyelocytic Leukemia Cells," *Cancer Research* 43:5268–5272 (1983).

Trost and Toste, "A New Palladium–Catalyzed Addition: A Mild Method for the Synthesis of Coumarins," *J. Am. Chem. Soc.* 118(26):6305 (1996).

Tzukerman et al., "Human estrogen receptor transactivational capacity is determined by both cellular and promoter context and mediated by two functionally distinct intramolecular regions," *Molecular Endocrinology* 8:21–30 (1994).

Umesono, et al. "Retinoic acid and thyroid hormone induce gene expression through a common responsive element," *Nature* 336:262 (1988).

Voss, "2,4–Bis(4–methoxyphenyl)–1,3,2,4–dithiadiphosphetane 2,4–Disulfide," *Encyclopedia of Reagents for Organic Synthesis*, 1:530–533 (1995).

Wagaw, et al., "Palladuim–Catalyzed Coupling of Optically Active Amines with Aryl Bromides," *J. Am. Chem. Soc.* 119:8451–8458 (1997).

Walsh, et al., "Inhibition of extratesticular stimuli to prostatic growth in the castrated rat by antiandrogens," *Endocrinology* 86:624 (1970).

Xie, et al., *Chinese Chemical Letters* 6:857 (1995).

Yoshimura, et al. "A Novel Type of Retinoic Acid Receptor Antagonist: Synthesis and Structure–Activity Relationships of Heterocyclic Ring Containing Benzoic Acid Derivatives," *J. Med. Chem.* 38(16):3163 (1995).

Evans, R.M., et al., "The Steroid and Thyroid Hormone Receptor Superfamily," *Science*, 240:889–895, (1998).

E.R. Bissel, et al., "Synthesis and Chemistry of 7–Amino–4–(trifluoromethyl) Coumarin and its Amino Acid and Peptide Derivatives", *J. Org. Chem.*, 45:2283–87, (1980).

Berger, T., et al., "Interaction of Glucocorticoid Analogues with the Human Glucocorticoid Receptor," *J. Steroid Biochem. Mol. Biol.*, 41:733–38 (1992).

Zhi, L., et al., "5–Aryl–1,2–dihydrochromeno[3,4–f]quinolines: A Novel Class of Nonsteroidal Human Progesterone Receptor Agonists," *J. Med. Chem.*, 41(3):291–302 (1998).

Edwards, J.P., et al., "5–Ayrl–1,2–dihydro–5H–chromeno[3, 4–f]quinolones as Potent, Orally Active, Nonsteriodal Progesterone Receptor Agonists: The Effect of D–Ring Substituents," *J. Med. Chem.*, 41(3):303–10 (1998).

Hamann, L.G., et al., "Synthesis and Biological Activity of a Novel Series of Nonsteriodal, Peripherally Selective Androgen Receptor Antagonists Derived from 1,2–Dihydropyridono[5,6–g]quinolines," *J. Med. Chem.*, 41(4):623–39 (1998).

Edwards, J.P., et al., "Preparation, Resolution, and Biological Evaluation of 5–Aryl–1,2–dihydro–5H–chromeno[3, 4–g]quinolines: Potent, Orally Active, Nonsteriodal Progesterone Receptor Agonists," *J. Med. Chem.*, 41(15):2779–85 (1998).

Tegley, C.M., et al., "5–Benzylidene 1,2–Dihydrochromeno [3,4–f]quinolines, A Novel Class of Nonsteriodal Human Progesterone Receptor Agonists," *J. Med. Chem.*, 41(22):4354–9 (1998).

Hamann, L.G., et al., "Discovery of a Potent, Oraly Active, Nonsteriodal Androgen Receptor Agonist: 4–Ethyl–1,2,3, 4–tetrahydro–6–(trifluoromethyl)–8–pyridono[5,6–g ]–quinoline," *J. Med. Chem.*, 42(2):210–12 (1999).

\* cited by examiner

BICYCLIC ANDROGEN AND PROGESTERONE RECEPTOR MODULATOR COMPOUNDS AND METHODS

This application claims priority to U.S. Provisional Application No. 60/150,987, filed Aug. 27, 1999, the entire disclosure of which is incorporated by reference herein.

FIELD OF THE INVENTION

This invention relates to nonsteroidal compounds that are modulators (i.e., agonists, partial agonists and antagonists) of androgen and progesterone receptors, and to methods for the making and use of such compounds.

BACKGROUND OF THE INVENTION

Intracellular receptors (IRs) form a class of structurally-related genetic regulators scientists have named "ligand dependent transcription factors" (R. M. Evans, *Science*, 240:889, 1988). Steroid receptors are a recognized subset of the IRs, including androgen receptor (AR), progesterone receptor (PR), estrogen receptor (ER), glucocorticoid receptor (GR), and mineralocoticoid receptor (MR). Regulation of a gene by such factors requires both the IR itself and a corresponding ligand, which has the ability to selectively bind to the IR in a way that affects gene transcription.

The natural hormones for steroid receptors have been known for a long time, such as testosterone for AR and progesterone for PR. A synthetic compound that binds to an IR and mimics the effect of the native hormone is referred to as an "agonist", while a compound that inhibits the effect of the native hormone is called an "antagonist". The term "modulators" refers to a group of compounds that have a spectrum of activities from agonist, partial agonist to antagonist.

Androgen and progesterone receptor modulators are known to play an important role in health of both men and women. For example, AR antagonists, such as cyproterone acetate, flutamide and casodex, are useful in the treatment of prostatic hyperplasia and cancer of the prostate. AR agonists, such as fluoxymesterone, are used in the treatment of hypogonadism. PR agonists, such as medroxyprogesterone acetate, are used in birth control formulations in combination with the female hormone estrogen or a synthetic estrogen analogue. Further, antagonists of PR are potentially useful for contraception and in the treatment of chronic disorders, such as certain hormone dependent cancers of the breast, ovary and uterus. Due to increased life expectancies, development of tissue selective, safer, orally active AR and PR modulators are desirable to improve quality of life.

A group of hydroquinoline derivatives was recently described as AR and PR modulators (e.g., U.S. Pat. Nos. 5,688,808, 5,688,810, 5,693,646, 5,693,647, 5,696,127, 5,696,130). This group of AR and PR modulators was developed by using cell-based high-throughput assays, termed cotransfection assays. Amino- or hydroxy-trifluoromethylquinolones or coumarins have been described as fluorescent markers in biological systems. See, e.g., U.S. Pat. No. 4,505,852 and E. R. Bissel et al., "Synthesis and Chemistry of 7-Amino-4-(trifluoromethyl) coumarin and Its Amino Acid and Peptide Derivatives", *J. Org. Chem.*, 45:2283, 1980). Analogues of quinolone, oxindole, benzooxazinone derivatives have been described as cardiotonic agents. See, e.g., U.S. Pat. Nos. 3,993,656; 4,415,572; 4,427,654; 4,710,507; 4,728,653; 4,933,336; 5,081,242.

SUMMARY OF THE INVENTION

The present invention is directed to compounds, pharmaceutical compositions, and methods for modulating processes mediated by AR and PR. More particularly, the invention relates to nonsteroidal compounds and compositions that are high affinity, high specificity agonists, partial agonists (i.e., partial activators and/or tissue-specific activators) and antagonists for AR and PR. Also provided are methods of making such compounds and pharmaceutical compositions, as well as critical intermediates used in their synthesis.

For a better understanding of the invention, its advantages, and objects obtained by its use, reference should be had to the accompanying descriptive matter, in which preferred embodiments of the invention are described.

DETAILED DESCRIPTION OF PREFERRED EMBODIMENTS

In accordance with the present invention and as used herein, the following structure definitions are provided for nomenclature purposes. Furthermore, in an effort to maintain consistency in the naming of compounds of similar structure but differing substituents, the compounds described herein are named according to the following general guidelines.

The term "alkyl" refers to an optionally substituted straight-chain or branched-chain hydrocarbon radical having from 1 to about 10 carbon atoms, preferably from 1 to about 6 carbon atoms, and most preferably from 1 to about 4 carbon atoms. Examples of alkyl radical include methyl, ethyl, n-propyl, isopropyl, n-butyl, isobutyl, sec-butyl, tert-butyl, pentyl, hexyl, octyl and the like.

The term "alkenyl" refers to a straight-chain or branched-chain hydrocarbon radical having one or more carbon-carbon double-bonds and having from 2 to about 10 carbon atoms, preferably from 2 to about 6 carbon atoms, and most preferably from 2 to about 4 carbon atoms. Preferred alkeny groups include allyl. Examples of alkenyl radicals include ethenyl, propenyl, 1,4-butadienyl and the like.

The term "allyl" refers to the radical $H_2C=CH-CH_2$.

The term "alkynyl" refers to a straight-chain or branched-chain hydrocarbon radical having one or more carbon-carbon triple-bonds and having from 2 to about 10 carbon atoms. Examples of alkynyl radicals include ethynyl, propynyl, butynyl and the like.

The term "aryl" refers to optionally substituted aromatic ring systems. The term aryl includes monocyclic aromatic rings, polycyclic aromatic ring systems, and polyaromatic ring systems. The polyaromatic and polycyclic ring systems may contain from two to four, more preferably two to three, and most preferably two, rings. Preferred aryl groups include 5-or 6-membered aromatic ring systems.

The term "heteroaryl" refers to optionally substituted aromatic ring systems having one or more heteroatoms such as, for example, oxygen, nitrogen and sulfur. The term heteroaryl may include five- or six-membered heterocyclic rings, polycyclic heteroaromatic ring systems, and polyheteroaromatic ring systems where the ring system has from two to four, more preferably two to three, and most preferably two, rings. The terms heterocyclic, polycyclic heteroaromatic, and polyheteroaromatic include ring systems containing optionally substituted heteroaromatic rings having more than one heteroatom as described above (e.g., a six membered ring with two nitrogens), including polyheterocyclic ring systems from two to four, more preferably two to three, and most preferably two, rings. The term heteroaryl includes ring systems such as, for example, pyridine, quinoline, furan, thiophene, pyrrole, imidazole and pyrazole.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy" refers to an aryl ether radical wherein the term aryl is defined as above. Examples of aryloxy radicals include phenoxy, benzyloxy and the like.

The term "cycloalkyl" refers to a saturated or partially saturated monocyclic, bicyclic or tricyclic alkyl radical wherein each cyclic moiety has about 3 to about 8 carbon atoms. Examples of cycloalkyl radicals include cyclopropyl, cyclobutyl, cyclopentyl, cyclohexyl and the like.

The term "cycloalkylalkyl" refers to an alkyl radical as defined above which is substituted by a cycloalkyl radical having from about 3 to about 8 carbon atoms.

The term "aralkyl" refers to an alkyl radical as defined above in which one hydrogen atom is replaced by an aryl radical as defined above, such as, for example, benzyl, 2-phenylethyl and the like.

The terms alkyl, alkenyl, and alkynyl include optionally substituted straight-chain, branched-chain, cyclic, saturated and/or unsaturated structures, and combinations thereof.

The terms haloalkyl, haloalkenyl and haloalkynyl include alkyl, alkenyl and alkynyl structures, as described above, that are substituted with one or more fluorines, chlorines, bromines or iodines, or with combinations thereof.

The terms heteroalkyl, heteroalkenyl and heteroalkynyl include optionally substituted alkyl, alkenyl and alkynyl structures, as described above, in which one or more skeletal atoms are oxygen, nitrogen, sulfur, or combinations thereof.

The substituents of an "optionally substituted" structure include, for example, one or more, preferably 1 to 4, more preferably 1 to 2 of the following preferred substituents: alkyl, alkenyl, alkynyl, aryl, heteroaryl, alkoxy, aryloxy, cycloalkyl, cycloalkylalkyl, arylalkyl, amino, alkylamino, dialkylamino, F, Cl, Br, I, CN, $NO_2$, $NH_2$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$ and $C(O)NH_2$.

Examples of compounds of the present invention are represented by those having the formula:

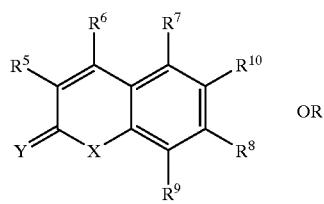
(I)

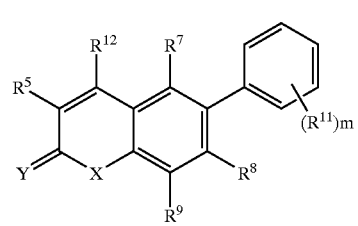
(II)

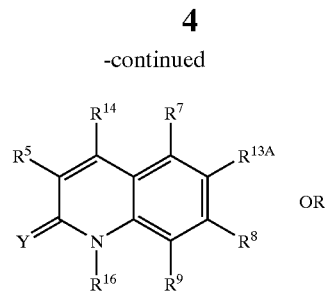
(IIIA)

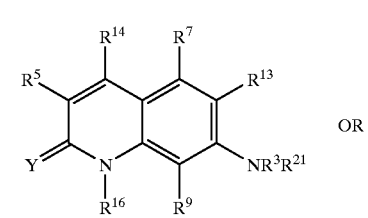
(III)

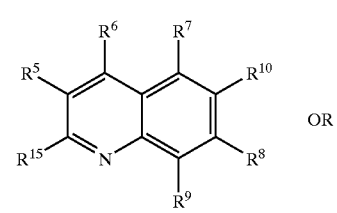
(IV)

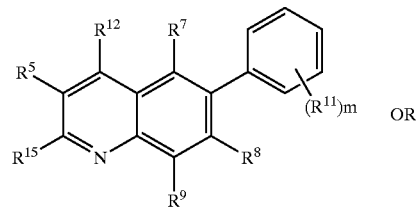
(V)

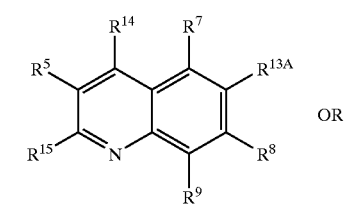
(VIA)

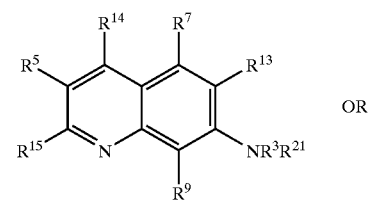
(VI)

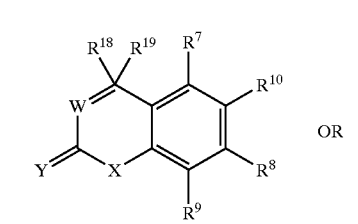
(VII)

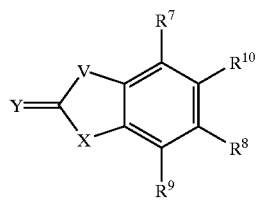

(VIII)

OR

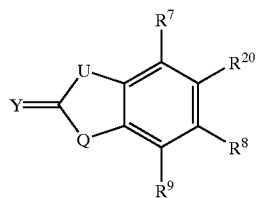

(IX)

wherein:

$R^1$ and $R^2$ each independently represent $COR^3$, $CSR^3$, $SO_2R^3$, NO, $NR^3R^4$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, $C_2$–$C_8$ heteroalkenyl, $C_2$–$C_8$ heteroalkynyl, $(CH_2)_nR^3$, aryl, or heteroaryl and wherein the alkyl, alkenyl, alkynyl, haloalkyl, haloalkenyl, haloalkynyl, heteroalkyl, heteroalkenyl, heteroalkynyl, aryl, and heteroaryl may be optionally substituted with F, Cl, Br, I, $OR^3$, $NR^3R^4$, $SR^3$, $SOR^3$, $SO_2R^3$, $C_1$–$C_4$ alkyl, $C_1$–$C_4$ haloalkyl or $C_1$–$C_4$ heteroalkyl, or alternatively, $R^1$ and $R^2$ may be taken together to form a three- to nine-membered alkyl, alkenyl, heteroalkyl, or heteroalkenyl ring and wherein the alkyl, alkenyl, heteroalkyl, or heteroalkenyl ring may be optionally substituted with F, Cl, Br, I, $NR^3R^4$, $C_1$–$C_4$ alkyl, $C_1$–$C_4$ haloalkyl or $C_1$–$C_4$ heteroalkyl, or $R^1$ and $R^2$ may be taken together to form one of:

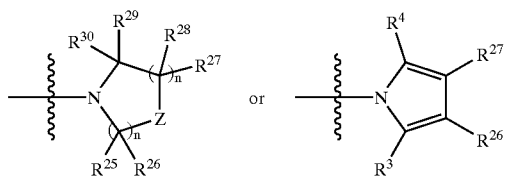

Preferably, $R^1$ and $R^2$ may be taken together to form:

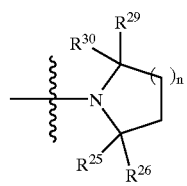

Most preferably, $R^1$ and $R^2$ may be taken together to form:

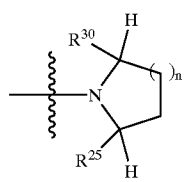

Most preferably, $R^1$ and $R^2$ may be taken together to form:

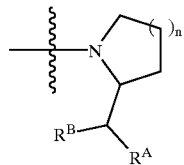

$R^A$ represents hydrogen, $OR^C$, $O_2CR^C$, $(CH_2)_nOR^C$, $NHR^C$, $NHCOR^C$, F, Cl, Br, I, CN, SCN, $SCH_3$;

$R^B$ represents hydrogen, F, Cl, Br, I, $CHF_2$, $CF_3$, $C_1$–$C_6$ alkyl, aryl, heteroaryl, wherein the alkyl, aryl and heteroaryl may be optionally substituted with F, Cl, Br, I, CN, $NO_2$, OH, $OCH_3$, $CF_3$, $C_1$–$C_6$ alkyl;

$R^C$ represents hydrogen, $C_1$–$C_8$ alkyl, $C_2$–$C_8$ alkenyl, $C_2$–$C_8$ alkynyl, $C_1$–$C_8$ haloalkyl, $C_1$–$C_8$ heteroalkyl, $(CH_2)_nR^D$;

$R^D$ represents aryl or heteroary, optionally substituted with F, Cl, Br, I, CN, $NO_2$, OH, $OCH_3$, $CF_3$, $C_1$–$C_6$ alkyl;

$R^3$ and $R^4$ each independently represent hydrogen, $C_1$–$C_8$ alkyl, $C_2$–$C_8$ alkenyl, $C_2$–$C_8$ alkynyl, $C_1$–$C_8$ haloalkyl, $C_1$–$C_8$ heteroalkyl, heteroaryl, or aryl and wherein the alkyl, alkenyl, alkynyl, haloalkyl, heteroalkyl, heteroaryl, and aryl may be optionally substituted with halogen, $C_1$–$C_4$ alkyl, $C_1$–$C_4$ haloalkyl or $C_1$–$C_4$ heteroalkyl;

$R^5$ represents hydrogen, F, Cl, Br, I, $OR^3$, $SR^3$, $SOR^3$, $SO_2R^3$, $NR^3R^4$, $C_1$–$C_4$ alkyl, $C_1$–$C_4$ haloalkyl or $C_1$–$C_4$ heteroalkyl;

$R^6$ represents F, Cl, Br, I, $CH_3$, $CF_3$, $CHF_2$, $CFH_2$, CN, $CF_2Cl$, $CF_2OR^3$, $OR^3$, $SR^3$, $SOR^3$, $SO_2R^3$, $NR^3R^4$, $C_1$–$C_4$ alkyl, $C_2$–$C_4$ alkenyl, $C_2$–$C_4$ alkynyl, $C_1$–$C_4$ haloalkyl, $C_2$–$C_4$ haloalkenyl, $C_2$–$C_4$ haloalkynyl, $C_1$–$C_4$ heteroalkyl, $C_2$–$C_4$ heteroalkenyl, or $C_2$–$C_4$ heteroalkynyl and wherein the alkyl, alkenyl, alkynyl, haloalkyl, haloalkenyl, haloalkynyl, heteroalkyl, heteroalkenyl, heteroalkynyl, aryl, and heteroaryl may be optionally substituted with halogen, $C_1$–$C_4$ alkyl, $C_1$–$C_4$ haloalkyl or $C_1$–$C_4$ heteroalkyl;

$R^7$ and $R^8$ each independently represent hydrogen, F, Cl, Br, I, CN, $OR^3$, $NR^3R^4$, $NR^3CR^3R^4CONR^3R^4$, $C_n(R^3)_{2n}$ $OR^3$, $SR^3$, $SOR^3$, $SO_2R^3$, $NR^3COR^4$, $C_1$–$C_8$ alkyl, $C_1$–$C_8$ haloalkyl, or $C_1$–$C_8$ heteroalkyl;

$R^9$ represents hydrogen, F, Br, Cl, I, $OR^3$, $NR^3R^4$, $SR^3$, $SOR^3$, $SO_2R^3$, $C_1$–$C_4$ alkyl, $C_1$–$C_4$ haloalkyl or $C_1$–$C_4$ heteroalkyl;

$R^{10}$ represents one of:

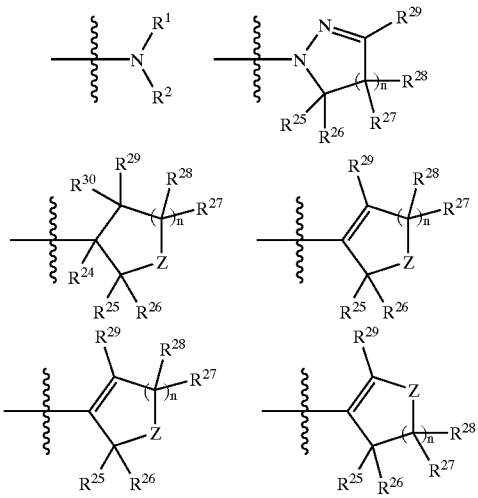

$R^{11}$ represents hydrogen, F, Br, Cl, I, $C_1$–$C_6$ alkyl, $C_1$–$C_6$ haloalkyl, $C_1$–$C_6$ heteroalkyl, $NO_2$, CN, $CF_3$, $OR^3$, $NR^3R^4$, $SR^3$, $SOR^3$, or $SO_2R^3$;

$R^{12}$ is F, Br, Cl, I, CN, $OR^3$, $SR^3$, $SOR^3$, $SO_2R^3$, $NR^3R^4$, $C_1$–$C_4$ alkyl, $C_1$–$C_4$ haloalkyl or $C_1$–$C_4$ heteroalkyl;

$R^{13}$ represents hydrogen, F, Cl, Br, I, CN, $OR^1$, $NHR^1$, $COR^3$, $CO_2R^3$, $SR^1$, $SOR^3$, $SO_2R^3$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, $C_2$–$C_8$ heteroalkenyl, $C_2$–$C_8$ heteroalkynyl, $(CH_2)_nR^3$, or heteroaryl and wherein the alkyl, alkenyl, alkynyl, haloalkyl, haloalkenyl, haloalkynyl, heteroalkyl, heteroalkenyl, heteroalkynyl, $(CH_2)_nR^3$, and heteroaryl may be optionally substituted with F, Cl, Br, I, CN, $NO_2$, $NR^1R^3$, SR, $SOR^3$, $SO_2R^3$, $C_1$–$C_4$ alkyl, $C_1$–$C_4$ haloalkyl or $C_1$–$C_4$ heteroalkyl;

$R^{14}$ represents F, Br, Cl, I, $CF_3$, $CHF_2$, $CH_2F$, $CF_2Cl$, or $CF_2OR^3$;

$R^{15}$ represents hydrogen, F, Br, Cl, I, CN, $C_1$–$C_4$ alkyl, $C_1$–$C_4$ haloalkyl, $C_1$–$C_4$ heteroalkyl, $OR^{16}$, $NR^{16}R^4$, $SR^{16}$, $CH_2R^{16}$, $COR^3$, $CO_2R^3$, $CONR^3R^4$, $SOR^3$, or $SO_2R^3$;

$R^{16}$ represents hydrogen, $C_1$–$C_8$ alkyl, $C_1$–$C_8$ haloalkyl, $C_1$–$C_8$ heteroalkyl, aryl, heteroaryl, $COR^{17}$, $CO_2R^{17}$, or $CONR^{17}R^{17}$;

$R^{17}$ represents hydrogen, $C_1$–$C_4$ alkyl, $C_1$–$C_4$ haloalkyl or $C_1$–$C_4$ heteroalkyl;

$R^{18}$ and $R^{19}$ each independently represent hydrogen, $C_1$–$C_6$ alkyl, $C_1$–$C_6$ haloalkyl or $C_1$–$C_6$ heteroalkyl, or alternatively, $R^{18}$ and $R^{19}$ may be taken together to form a three- to seven-membered ring;

$R^{20}$ represents an aryl or heteroaryl wherein the aryl or heteroaryl may be optionally substituted with F, Cl, Br, CN, $OR^1$, $SR^1$, $SOR^3$, $SO_2R^3$, $NO_2$, $NR^1R^3$, $C_1$–$C_4$ alkyl, $C_1$–$C_4$ haloalkyl or $C_1$–$C_4$ heteroalkyl;

$R^{21}$ represents $CR^3R^4CONR^3R^4$, $C_n(R^3)_{2n}OR^3$, $SOR^3$, $SO_2R^3$, $C_2$–$C_8$ alkyl, $C_2$–$C_8$ haloalkyl, and $C_2$–$C_8$ heteroalkyl;

$R^{22}$ and $R^{23}$ each independently represent hydrogen, $C_1$–$C_6$ alkyl, $C_1$–$C_6$ haloalkyl or $C_1$–$C_6$ heteroalkyl, or alternatively $R^{22}$ and $R^{23}$ may be taken together to form a three- to seven-membered ring;

$R^{24}$ represents hydrogen, $C_1$–$C_4$ alkyl, $C_1$–$C_4$ haloalkyl, $C_1$–$C_4$ heteroalkyl, or $OR^3$;

$R^{25}$ through $R^{30}$ each independently represent hydrogen, F, Cl, Br, I, $OR^3$, $NR^3R^4$, $SR^3$, $SOR^3$, $SO_2R^3$, $C_1$–$C_6$ alkyl, $C_1$–$C_6$ haloalkyl, $C_1$–$C_6$ heteroalkyl, $C_2$–$C_6$ alkynyl or $C_2$–$C_6$ alkenyl, and wherein the alkyl, haloalkyl, heteroalkyl, alkynyl, and alkenyl may be optionally substituted with F, Cl, Br, I, $OR^3$, $NR^3R^4$, $C_1$–$C_4$ alkyl, $C_1$–$C_4$ haloalkyl, $C_1$–$C_4$ heteroalkyl, aryl or heteroaryl and wherein the aryl and heteroaryl may be optionally substituted with F, Cl, Br, I, CN, $NO_2$, OH, $OCH_3$, $CF_3$ or $C_1$–$C_6$ alkyl;

Any two of $R^{25}$ through $R^{30}$ when taken together can form a three to seven-membered alkyl or alkenyl or heteroalkyl ring; or any four of $R^{25}$ through $R^{30}$ when taken together can form a fused aromatic ring;

Q represents O or S;

U represents V, $OCR^{22}R^{23}$, $SCR^{22}R^{23}$, $NR^3CR^{22}R^{23}$, $CR^3R^4CR^{22}R^{23}$;

V represents O, S, $NR^3$, $CR^{22}R^{23}$, $CR^3R^4O$, or $CR^3R^4S$, but, V is not S when $R^1$ and $R^2$ are both methyl;

W represents O, S, $NR^3$, $CR^{25}R^{26}$;

X represents O, S or $NR^{16}$;

Y represents O, S, $NR^3$, $NOR^3$ or $CR^3R^4$;

Z represents O, S, $NR^3$, C=O, or $CR^3R^4$, or optionally Z may represent two hydrogens;

n is 1, 2, 3 or 4; and m is 1 to 5.

Preferred $R^1$ and $R^2$ groups include $COR^3$, $CSR^3$, $SO_2R^3$, $C_1$–$C_8$ alkyl, $C_2$–$C_8$ alkenyl, $C_1$–$C_8$ haloalkyl, $C_2$–$C_8$ haloalkenyl, $C_2$–$C_8$ heteroalkyl, $C_2$–$C_8$ heteroalkenyl, $(CH_2)_nR^{3A}$, aryl, and heteroaryl, wherein the aryl, or heteroaryl may be optionally substituted with F, Cl, Br, $OR^3$, $NR^3R^4$, CN, $NO_2$, $SR^3$, COMe, $COCF_3$, $C_1$–$C_4$ alkyl, $C_1$–$C_4$ haloalkyl. Also preferred, $R^1$ and $R^2$ groups may be taken together to form one of:

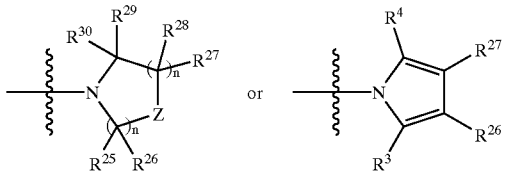

More preferred $R^1$ and $R^2$ groups include COR, $C_1$–$C_8$ alkyl, $C_2$–$C_8$ alkenyl, $C_1$–$C_8$ haloalkyl, $C_2$–$C_8$ haloalkenyl, $C_1$–$C_8$ heteroalkyl, $CH_2R^{3A}$, aryl and heteroaryl. The aryl or heteroaryl may be optionally substituted with F, Cl, Br, OH, OMe, SH, SMe, CN, $NO_2$, $CF_3$, Me, COMe, or $R^1$ and $R^2$ groups may be taken together to form:

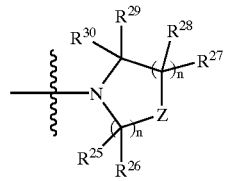

Most preferably, $R^1$ and $R^2$ groups include $C_1$–$C_8$ alkyl, $C_2$–$C_8$ alkenyl, $C_1$–$C_8$ haloalkyl, $C_1$–$C_8$ heteroalkyl, and $CH_2R^{3A}$, or, $R^1$ and $R^2$ groups may be taken together to form:

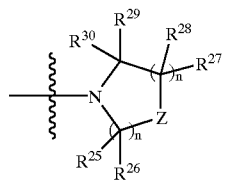

Preferred $R^3$ and $R^4$ groups include hydrogen, $C_1$–$C_8$ alkyl, $C_2$–$C_8$ alkenyl, $C_1$–$C_8$ haloalkyl, and $C_1$–$C_8$ heteroalkyl. More preferred $R^3$ and $R^4$ groups include hydrogen, $C_1$–$C_6$ alkyl and $C_1$–$C_8$ haloalkyl. Most preferably, $R^3$ and $R^4$ each independently is selected from group of hydrogen, $C_1$–$C_6$ alkyl, and $C_1$–$C_6$ haloalkyl.

Preferred $R^{3A}$ groups include aryl and heteroaryl, wherein the aryl and heteroaryl may be optionally substituted with halogen, CN, OMe, SMe, $C_1$–$C_4$ alkyl, or $C_1$–$C_4$ haloalkyl. More preferred $R^{3A}$ groups include heteroaryl and aryl, wherein the heteroaryl and aryl may be optionally substituted with F, Cl, Br, CN, OMe, $C_1$–$C_4$ alkyl, or $C_1$–$C_4$ haloalkyl. Most preferably, $R^{3A}$ groups include heteroaryl and aryl, wherein the heteroaryl and aryl may be optionally substituted with F, Cl, Br, CN, $CF_3$, OMe, or $C_1$–$C_4$ alkyl.

Preferred $R^5$ groups include hydrogen, F, Cl, Br, OH, OMe, $C_1$–$C_4$ alkyl, and $C_1$–$C_4$ haloalkyl. More preferred $R^5$ groups include hydrogen, F, Cl, OH, OMe, $C_1$–$C_4$ alkyl, and $CF_3$. Most preferred $R^5$ groups include hydrogen, F, Cl, OH, and OMe.

Preferred $R^6$ groups include F, Cl, Br, $CH_3$, $CF_3$, $CHF_2$, $CFH_2$, CN, $CF_2Cl$, $CF_2OR^3$, $OR^3$, $SR^3$, $NR^3R^4$, $C_1$–$C_4$ alkyl, $C_2$–$C_4$ alkenyl, $C_1$–$C_4$ haloalkyl, $C_2$–$C_4$ haloalkenyl, $C_1$–$C_4$ heteroalkyl, and $C_2$–$C_4$ heteroalkenyl. More preferred $R^6$ groups include F, Cl, Br, $CF_3$, $CHF_2$, $CFH_2$, CN, $CF_2Cl$, $CF_2OMe$, and $C_1$–$C_4$ alkyl. Most preferred $R^6$ groups include F, Cl, $C_1$–$C_4$ alkyl, $CF_3$, $CHF_2$, $CFH_2$, $CF_2Cl$, $CF_2OMe$, and OMe.

Preferred $R^7$ groups include hydrogen, F, Cl, Br, $OR^3$, $NR^3R^4$, $SR^3$, $C_1$–$C_8$ alkyl, $C_1$–$C_8$ haloalkyl, or $C_1$–$C_8$ heteroalkyl. More preferred $R^7$ groups include hydrogen, F, Cl, Me, OMe, and $CF_3$. Most preferred $R^7$ groups include hydrogen, F, Cl, Me, and OMe.

Preferred $R^8$ groups include hydrogen, F, Cl, Br, $OR^3$, $NR^3R^4$, $SR^3$, $C_1$–$C_8$ alkyl, $C_1$–$C_8$ haloalkyl, and $C_1$–$C_8$ heteroalkyl. More preferred $R^8$ groups include hydrogen, F, Cl, Br, $OR^3$, $NR^3R^4$, $C_1$–$C_6$ alkyl, $C_1$–$C_6$ haloalkyl, and $C_1$–$C_6$ heteroalkyl. Most preferred $R^8$ groups include hydrogen, F, Cl, Br, $OR^3$, $NR^3R^4$, $C_1$–$C_6$ alkyl, $C_1$–$C_6$ haloalkyl.

Preferred $R^9$ groups include hydrogen, F, Br, Cl, $OR^3$, $NR^3R^4$, $SR^3$, $C_1$–$C_4$ alkyl, and $C_1$–$C_4$ haloalkyl. More preferred $R^9$ groups include hydrogen, F, Br, OH, Me, OMe, and $CF_3$. Most preferred $R^9$ groups include hydrogen, F, Cl, OH, Me, OMe, and $CF_3$.

Preferred $R^{10}$ groups include:

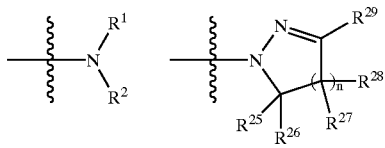

More preferred $R^{10}$ groups include:

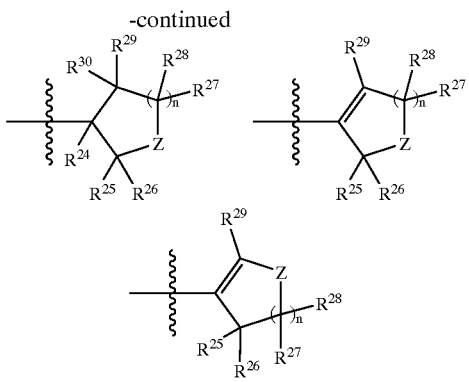

Preferred $R^{11}$ groups include F, Br, Cl, I, $C_1$–$C_6$ alkyl, $CC_1$–$C_6$ haloalkyl, $NO_2$, CN, $CF_3$, OH, OMe, $NR^3R^4$, and $SR^3$. More preferred $R^{11}$ groups include F, Br, Cl, $C_1$–$C_6$ alkyl, $NO_2$, CN, $CF_3$, OH, OMe.

Preferred $R^{12}$ groups include F, Br, Cl, and $C_1$–$C_4$ haloalkyl. More preferred $R^{12}$ groups include F, Br, Cl, $CF_3$, $CF_2H$ and $CFH_2$.

Preferred $R^{13}$ groups include hydrogen, F, Cl, Br, I, CN, $OR^3$, $NR^3R^4$, $SR^3$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, and $(CH_2)_nR^{3A}$. More preferred $R^{13}$ groups include hydrogen, F, Cl, Br, $OR^3$, $SR^3$, $C_1$–$C_8$ alkyl, $C_2$–$C_8$ alkenyl, $C_1$–$C_8$ haloalkyl. Most preferred $R^{13}$ groups include hydrogen, F, Cl, Br, $C_1$–$C_4$ alkyl, $C_2$–$C_4$ alkenyl, or $C_1$–$C_8$ haloalkyl.

Preferred $R^{13}A$ groups include $NHR^1$ or heteroaryl, wherein the heteroaryl may be optionally substituted with F, Cl, Br, CN, $NMe_2$, $NO_2$, $CF_3$, Me or OMe. More preferred $R^{13}A$ is $NHR^1$.

Preferred $R^{14}$ groups include F, Br, Cl, $CF_3$, $CHF_2$, $CH_2F$, $CF_2Cl$, and $CF_2OMe$. More preferred $R^{14}$ groups include F, Cl, $CF_3$, $CHF_2$, $CH_2F$, and $CF_2Cl$. Most preferred $R^{14}$ groups include Cl, $CF_3$, $CHF_2$, $CH_2F$, and $CF_2Cl$.

Preferred $R^{15}$ groups include F, Br, Cl, CN, $C_1$–$C_4$ alkyl, $C_1$–$C_4$ haloalkyl, $C_1$–$C_4$ heteroalkyl, $OR^{16}$, $NR^{16}R^4$, and $SR^{16}$. More preferred $R^{15}$ groups include F, Cl, CN, $OR^{16}$, and $SR^{16}$. Most preferred $R^{15}$ groups include Cl, $OR^{16}$, $NR^{16}R^4$ and $SR^{16}$.

Preferred $R^{16}$ groups include hydrogen, $C_1$–$C_8$ alkyl, $C_1$–$C_8$ haloalkyl, $C_1$–$C_8$ heteroalkyl, $COR^{17}$, $CO_2R^{17}$, and $CONR^{17}R^{17}$. More preferred $R^{16}$ groups include hydrogen, $C_1$–$C_6$ alkyl, $C_1$–$C_6$ haloalkyl, $COR^{17}$, $CO_2R^{17}$, and $CONR^{17}R^{17}$. Most preferred $R^{16}$ groups include hydrogen, $C_1$–$C_6$ alkyl, $COR^{17}$, $CO_2R^{17}$, and $CONR^{17}R^{17}$.

Preferred $R^{17}$ groups include $C_1$–$C_4$ alkyl, $C_1$–$C_4$ haloalkyl and $C_1$–$C_4$ heteroalkyl.

Preferred $R^{18}$ and $R^{19}$ groups include $C_1$–$C_6$ alkyl, $C_1$–$C_6$ haloalkyl, $C_1$–$C_6$ heteroalkyl and $R^{18}$ and $R^{19}$ may be taken together to form a four- to seven-membered ring. More preferred $R^{18}$ and $R^{19}$ groups include $C_1$–$C_6$ alkyl, and $C_1$–$C_6$ haloalkyl and $R^{18}$ and $R^{19}$ may be taken together to form a five- to six-membered ring. Most preferred $R^{18}$ and $R^{19}$ groups include $C_1$–$C_4$ alkyl, $C_1$–$C_4$ haloalkyl and $R^{18}$ and $R^{19}$ may be taken together to form a five- to six-membered ring.

Preferred $R^{20}$ groups include aryl and heteroaryl. The aryl or heteroaryl may be optionally substituted with F, Cl, Br, CN, $NO_2$, $CF_3$ and $C_1$–$C_4$ alkyl.

Preferred $R^{21}$ groups include $C_2$–$C_8$ alkyl, $C_2$–$C_8$ haloalkyl, and $C_2$–$C_8$ heteroalkyl. More preferred $R^{21}$ groups include $C_2$–$C_8$ alkyl, and $C_2$–$C_8$ haloalkyl.

Preferred $R^{22}$ and $R^{23}$ groups include hydrogen, $C_1$–$C_6$ alkyl, $C_1$–$C_6$ haloalkyl, and $C_1$–$C_6$ heteroalkyl and $R^{22}$ and $R^{23}$ groups may be taken together to form a three- to seven-membered ring. More preferred $R^{22}$ and $R^{23}$ groups include hydrogen, $C_1$–$C_6$ alkyl, $C_1$–$C_6$ haloalkyl and $R^{22}$ and $R^{23}$ groups taken together to form a four- to six-membered ring.

Preferred $R^{24}$ groups include hydrogen and $OR^3$. More preferred $R^{24}$ groups include hydrogen and OH.

Preferred $R^{25}$, $R^{26}$, $R^{27}$, $R^{28}$, $R^{29}$ and $R^{30}$ groups include hydrogen, F, Cl, Br, $OR^3$, $NR^3R^4$, $C_1$–$C_6$ alkyl, $C_1$–$C_6$ haloalkyl, $C_1$–$C_6$ heteroalkyl, and $C_2$–$C_6$ alkenyl, wherein the alkyl, haloalkyl, heteroalkyl, alkynyl, or alkenyl may be optionally substituted with F, Cl, Br, $OR^3$, $NR^3R^4$, aryl or heteroaryl and the aryl and heteroaryl may be optionally substituted with F, Cl, Br, CN, $NO_2$, OH, $OCH_3$, $CF_3$ or $C_1$–$C_6$ alkyl. Also preferred is any two of $R^{25}$, $R^{26}$, $R^{27}$, $R^{28}$, $R^{29}$ and $R^{30}$ groups taken together to form a three- to seven-membered alkyl or alkenyl or heteroalkyl ring. Also preferred is any four of $R^{25}$, $R^{26}$, $R^{27}$, $R^{28}$, $R^{29}$ and $R^{30}$ groups taken together to form a fused aromatic ring. More preferred $R^{25}$ through $R^{30}$ groups include hydrogen, F, Cl, OH, OMe, $C_1$–$C_6$ alkyl, $C_1$–$C_6$ haloalkyl, $C_1$–$C_6$ heteroalkyl and $C_2$–$C_6$ alkenyl. Also more preferred is any two of $R^{25}$, $R^{26}$, $R^{27}$, $R^{28}$, $R^{29}$ and $R^{30}$ groups taken together to form a four to six-membered alkyl or alkenyl ring. Also more preferred is any four of $R^{25}$, $R^{26}$, $R^{27}$, $R^{28}$, $R^{29}$ and $R^{30}$ groups taken together to form a fused aromatic ring. Most preferred $R^{25}$ through $R^{30}$ groups include hydrogen, F, Cl, OH, OMe, $C_1$–$C_4$ alkyl, and $C_1$–$C_4$ haloalkyl.

Preferably Q is O.

Preferred U groups include V, $OCR^{22}R^{23}$, $NR^3CR^{22}R^{23}$, $CR^3R^4CR^{22}R^{23}$.

Preferred V groups include $CR^{22}R^{23}$, $CR^3R^4O$, and $CR^3R^4S$.

Preferred W groups include O, $NR^3$, and $CR^3R^4$. More preferred W groups include O, and $CR^3R^4$. Most preferably, W is O.

Preferred X groups include S and $NR^{16}$. More preferred X groups include O and $NR^{16}$. Most preferably, X is $NR^{16}$.

Preferred Y groups include O, S, $NR^3$, and $NOR^3$. More preferred Y groups include O, S, and $NOR^3$. Most preferably, Y is O or S.

Preferred Z groups include O, S, $NR^3$, $CR^{25}R^{26}$ and two hydrogens. More preferred Z groups include O, $CR^{25}R^{26}$ and two hydrogens. Most preferably, Z groups include O, $CR^3R^4$ and two hydrogens.

Preferably, n is 1 or 2.

Preferably, m is 1 to 4. More preferably, m is 1 to 3.

In a preferred embodiment of the invention, $R^1$ and $R^2$ are each independently selected from the group of $COR^3$, $CSR^3$, $SO_2R^3$, NO, $NR^3R^4$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, $C_2$–$C_8$ heteroalkenyl, $C_2$–$C_8$ heteroalkynyl, $(CH_2)_nR^{3A}$, aryl, and heteroaryl, wherein the alkyl, alkenyl, alkynyl, haloalkyl, haloalkenyl, haloalkynyl, heteroalkyl, heteroalkenyl, heteroalkynyl, aryl, and heteroaryl are optionally substituted with F, Cl, Br, I, $OR^3$, $NR^3R^4$, CN, $NO_2$, $SR^3$, $SOR^3$, $SO_2R^3$, $C_1$–$C_4$ alkyl, $C_1$–$C_4$ haloalkyl or $C_1$–$C_4$ heteroalkyl. $R^3$ and $R^4$ are each independently hydrogen or optionally substituted $C_1$–$C_6$ alkyl. $R^{3A}$ is optionally substituted alkyl or heteroaryl. $R^5$ is selected from the group of hydrogen, halogen and optionally substituted $C_1$–$C_6$ alkyl. $R^7$ and $R^8$ are each independently hydrogen or halogen; and $R^9$ is hydrogen or halogen. $R^{11}$ is selected from the group of halogen, CN, $NO_2$ and optionally substituted $C_1$–$C_6$ haloalkyl. $R^{12}$ is halogen or optionally substituted haloalkyl. $R^{13}$ is selected from the group of hydrogen, $C_1$–$C_6$ alkyl and $C_1$–$C_6$ heteroalkyl, wherein said $C_1$–$C_6$ alkyl and $C_1$–$C_6$ heteroalkyl are optionally substituted. $R^{15}$ is halogen or $OR^{16}$. $R^{18}$ and $R^{19}$ are each independently optionally substituted $C_1$–$C_6$ alkyl; or $R^{18}$ and $R^{19}$ taken together form a five- to six-membered ring. $R^{22}$ and $R^{23}$ are each independently hydrogen or optionally substituted $C_1$–$C_6$ alkyl; or $R^{22}$ and $R^{23}$ together form a three- to seven-membered ring. $R^{25}$ through $R^{30}$ are each independently hydrogen, $C_1$–$C_6$ alkyl, or $C_1$–$C_6$ haloalkyl, wherein said $C_1$–$C_6$ alkyl and $C_1$–$C_6$ haloalkyl are optionally substituted; Y is selected from the group of O, S, and $NR^3$; and m is 1 to 3.

In another preferred embodiment of the invention $R^1$ and $R^2$ taken together form a three- to nine-membered alkyl, alkenyl, heteroalkyl, or heteroalkenyl ring, wherein the alkyl, alkenyl, heteroalkyl, or heteroalkenyl ring are optionally substituted with F, Cl, Br, I, $OR^3$, $NR^3R^4$, $C_1$–$C_4$ alkyl, $C_1$–$C_4$ haloalkyl or $C_1$–$C_4$ heteroalkyl. $R^3$ and $R^4$ are each independently hydrogen or optionally substituted $C_1$–$C_6$ alkyl. $R^{3A}$ is optionally substituted alkyl or heteroaryl. $R^5$ is selected from the group of hydrogen, halogen and optionally substituted $C_1$–$C_6$ alkyl. $R^7$ and $R^8$ are each independently hydrogen or halogen. $R^9$ is hydrogen or halogen. $R^{11}$ is selected form the group of halogen, CN, $NO_2$ and optionally substituted $C_1$–$C_6$ haloalkyl. $R^{12}$ is halogen or optionally substituted haloalkyl. $R^{13}$ is selected from the group of hydrogen, $C_1$–$C_6$ alkyl and $C_1$–$C_6$ heteroalkyl, wherein said $C_1$–$C_6$ alkyl and $C_1$–$C_6$ heteroalkyl are optionally substituted. $R^{15}$ is halogen or $OR^{16}$. $R^{18}$ and $R^{19}$ are each independently optionally substituted $C_1$–$C_6$ alkyl; or $R^{18}$ and $R^{19}$ taken together form a five- to six-membered ring. $R^{22}$ and $R^{23}$ are each independently hydrogen or optionally substituted $C_1$–$C_6$ alkyl; or $R^{22}$ and $R^{23}$ together form a three- to seven-membered ring. $R^{25}$ through $R^{30}$ are each independently hydrogen, $C_1$–$C_6$ alkyl, or $C_1$–$C_6$ haloalkyl, wherein said $C_1$–$C_6$ alkyl and $C_1$–$C_6$ haloalkyl are optionally substituted. Y is selected from the group of O, S, and $NR^3$; and m is 1 to 3.

In still another preferred embodiment of the invention, $R^1$ and $R^2$ taken together form one of:

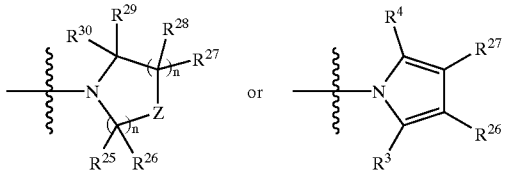

$R^3$ and $R^4$ are each independently hydrogen or optionally substituted $C_1$–$C_6$ alkyl. $R^{3A}$ is optionally substituted alkyl or heteroaryl. $R^5$ is selected from the group of hydrogen, halogen and optionally substituted $C_1$–$C_6$ alkyl. $R^7$ and $R^8$ are each independently hydrogen or halogen. $R^9$ is hydrogen or halogen. $R^{11}$ is selected form the group of halogen, CN, $NO_2$ and optionally substituted $C_1$–$C_6$ haloalkyl. $R^{12}$ is halogen or optionally substituted haloalkyl. $R^{13}$ is selected from the group of hydrogen $C_1$–$C_6$ alkyl and $C_1$–$C_6$ heteroalkyl, wherein said $C_1$–$C_6$ alkyl and $C_1$–$C_6$ heteroalkyl are optionally substituted. $R^{15}$ is halogen or $OR^{16}$, $R^{18}$ and $R^{19}$ are each independently optionally substituted $C_1$–$C_6$ alkyl; or $R^{18}$ and $R^{19}$ taken together form a five- to six-membered ring. $R^{22}$ and $R^{23}$ are each independently hydrogen or optionally substituted $C_1$–$C_6$ alkyl; or $R^{22}$ and $R^{23}$ together form a three- to seven-membered ring. $R^{25}$ through $R^{30}$ are each independently hydrogen, $C_1$–$C_6$ alkyl, or $C_1$–$C_6$ haloalkyl, wherein said $C_1$–$C_6$ alkyl and $C_1$–$C_6$ haloalkyl are optionally substituted; Y is selected from the group of O, S, and $NR^3$; and m is 1 to 3.

The present invention further provides methods of modulating processes mediated by AR or PR or combinations thereof comprising administering to a patient an effective amount of a pharmaceutical composition of the present invention comprising one or more compounds represented by those having the following formulas as well as pharmaceutical compositions of the above compounds:

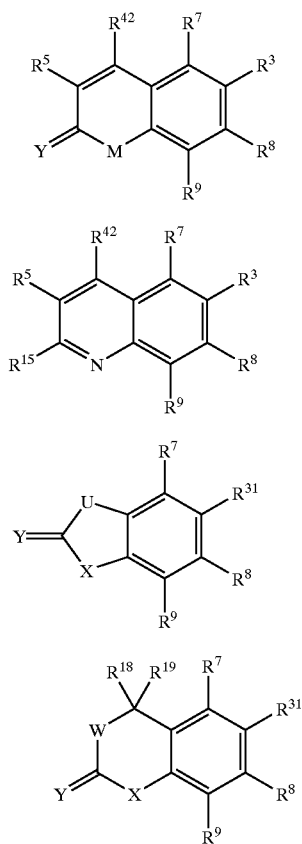

wherein:
$R^1$ and $R^2$ each independently represent $COR^3$, $CSR^3$, $SO_2R^3$, NO, $NR^3R^4$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, $C_2$–$C_8$ heteroalkenyl, $C_2$–$C_8$ heteroalkynyl, $(CH_2)_nR^3$, aryl, or heteroaryl and wherein the alkyl, alkenyl, alkynyl, haloalkyl, haloalkenyl, heteroalkynyl, aryl, and heteroaryl may be optionally substituted with F, Cl, Br, I, $OR^3$, $NR^3R^4$, $SR^3$, $SOR^3$, $SO_2R^3$ $C_1$–$C_4$ alkyl, $C_1$–$C_4$ haloalkyl or $C_1$–$C_4$ heteroalkyl, or alternatively, $R^1$ and $R^2$ may be taken together to form a three- to nine-membered alkyl, alkenyl, heteroalkyl, or heteroalkenyl ring and wherein the alkyl, alkenyl, heteroalkyl, and heteroalkenyl ring may be optionally substituted with F, Cl, Br, I, $OR^3$, $NR^3R^4$, $C_1$–$C_4$ alkyl, $C_1$–$C_4$ haloalkyl or $C_1$–$C_4$ heteroalkyl, or $R^1$ and $R^2$ may be taken together to form one of:

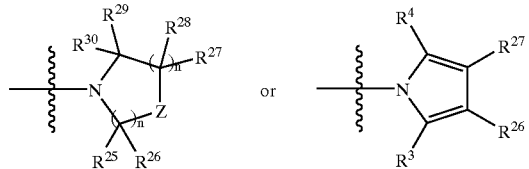

$R^3$ and $R^4$ each independently represent hydrogen, $C_1$–$C_8$ alkyl, $C_2$–$C_8$ alkenyl, $C_1$–$C_8$ alkynyl, $C_1$–$C_8$ haloalkyl, $C_1$–$C_8$ heteroalkyl, heteroaryl, or aryl and wherein the alkyl, alkenyl, alkynyl, haloalkyl, heteroalkyl, heteroaryl, and aryl may be optionally substituted with halogen, $C_1$–$C_4$ alkyl, $C_1$–$C_4$ haloalkyl or $C_1$–$C_4$ heteroalkyl;

$R^5$ represents hydrogen, F, Cl, Br, I, $OR^3$, $SR^3$, $SOR^3$, $SO_2R^3$, $NR^3R^4$, $C_1$–$C_4$ alkyl, $C_1$–$C_4$ haloalkyl or $C_1$–$C_4$ heteroalkyl;

$R^7$ and $R^8$ each independently represent hydrogen, F, Cl, Br, I, CN, $OR^3$, $NR^3R^4$, $NR^3CR^3R^4CONR^3R^4$, $C_n(R^3)_{2n}OR^3$, $SR^3$, $SOR^3$, $SO_2R^3$, $NR^3COR^4$, $C_1$–$C_8$ alkyl, $C_1$–$C_8$ haloalkyl, or $C_1$–$C_8$ heteroalkyl;

$R^9$ represents hydrogen, F, Br, Cl, I, $OR^3$, $NR^3R^4$, $SR^3$, a $C_1$–$C_4$ alkyl, $C_1$–$C_4$ haloalkyl or $C_1$–$C_4$ heteroalkyl;

$R^{11}$ represents hydrogen, F, Br, Cl, I, $C_1$–$C_6$ alkyl, $C_1$–$C_6$ haloalkyl, $C_1$–$C_6$ heteroalkyl, $NO_2$, CN, $CF_3$, $OR^3$, $NR^3R^4$, $SR^3$, $SOR^3$ or $SO_2R^3$;

$R^{15}$ represents hydrogen, F, Br, Cl, I, CN, $C_1$–$C_4$ alkyl, $C_1$–$C_4$ haloalkyl, $C_1$–$C_4$ heteroalkyl, $OR^{16}$, $NR^{16}R^4$, $SR^{16}$, $CH_2R^{16}$, $COR^3$, $CO_2R^3$, $CONR^3R^4$, $SOR^3$, or $SO_2R^3$;

$R^{16}$ represents hydrogen, $C_1$–$C_8$ alkyl, $C_1$–$C_8$ haloalkyl, $C_1$–$C_8$ heteroalkyl, aryl, heteroaryl, $COR^{17}$, $CO_2R^{17}$, or $CONR^{17}R^{17}$;

$R^{17}$ represents hydrogen, $C_1$–$C_4$ alkyl, $C_1$–$C_4$ haloalkyl or $C_1$–$C_4$ heteroalkyl;

$R^{18}$ and $R^{19}$ each independently represent hydrogen, $C_1$–$C_6$ alkyl, $C_1$–$C_6$ haloalkyl or $C_1$–$C_6$ heteroalkyl, or alternatively, $R^{18}$ and $R^{19}$ may be taken together to form a three- to seven-membered ring;

$R^{22}$ and $R^{23}$ each independently represent hydrogen, $C_1$–$C_6$ alkyl, $C_1$–$C_6$ haloalkyl or $C_1$–$C_6$ heteroalkyl, or alternatively, $R^{22}$ and $R^{23}$ may be taken together to form a three- to seven-membered ring;

$R^{24}$ represents hydrogen, $C_1$–$C_4$ alkyl, $C_1$–$C_4$ haloalkyl, $C_1$–$C_4$ heteroalkyl, or $OR^3$;

$R^{25}$ through $R^{30}$ each independently represent hydrogen, F, Cl, Br, I, $OR^3$, $NR^3R^4$, $SR^3$, $SOR^3$, $SO_2R^3$, $C_1$–$C_6$ alkyl, $C_1$–$C_6$ haloalkyl, $C_1$–$C_6$ heteroalkyl, $C_2$–$C_6$ alkynyl or $C_2$–$C_6$ alkenyl, and wherein the alkyl, haloalkyl, heteroalkyl, alkynyl, and alkenyl may be optionally substituted with F, Cl, Br, I, $OR^3$, $NR^3R^4$, $C_1$–$C_4$ alkyl, $C_1$–$C_4$ haloalkyl, $C_1$–$C_4$ heteroalkyl, aryl or heteroaryl and wherein the aryl and heteroaryl may be optionally substituted with F, Cl, Br, I, CN, $NO_2$, OH, $OCH_3$, $CF_3$ or $C_1$–$C_6$ alkyl;

Any two Rs of $R^{25}$ through $R^{30}$ when taken together can form a three to seven-membered alkyl or alkenyl or heteroalkyl ring; or any four Rs of $R^{25}$ through $R^{30}$ when taken together can form a fused aromatic ring;

$R^{31}$ represents hydrogen, F, Cl, Br, I, CN, $OR^1$, $NHR^1$, $COR^3$, $CO_2R^3$, $SR^1$, $SOR^3$, $SO_2R^3$, $C_1$–$C_8$ alkyl, $C_2$–$C_8$ alkenyl, $C_1$–$C_8$ haloalkyl, $C_2$–$C_8$ haloalkenyl, $C_1$–$C_8$ heteroalkyl, $C_2$–$C_8$ heteroalkenyl, $C_2$–$C_8$ alkynyl, $C_2$–$C_8$ haloalkynyl, $C_2$–$C_8$ heteroalkynyl, $(CH_2)_nR^3$ or heteroaryl and wherein the alkyl, alkenyl, haloalkyl, haloalkenyl, heteroalkyl, heteroalkenyl, allyl, alkynyl, haloallyl, haloalkynyl, heteroalkynyl, $(CH_2)_nR^3$, and heteroaryl may be optionally substituted with F, Cl, Br, I, CN, $OR^1$, $NO_2$, $NR^1R^3$, $SR^1$, $SOR^3$, $SO_2R^3$, $C_1$–$C_4$ alkyl, $C_1$–$C_4$ haloalkyl, or $C_1$–$C_4$ heteroalkyl or optionally, $R^{31}$ represents one of:

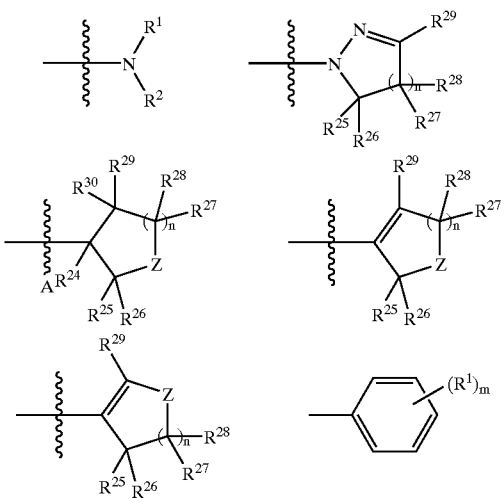

$R^{42}$ represents hydrogen, F, Cl, Br, I, $CH_3$, $CF_3$, $CHF_2$, $CFH_2$, CN, $CF_2Cl$, $CF_2OR^3$, $OR^3$, $SR^3$, $SOR^3$, $SO_2R^3$, $NR^3R^4$, $C_1$–$C_4$ alkyl, $C_2$–$C_4$ alkenyl, $C_2$–$C_4$ alkynyl, $C_1$–$C_4$ haloalkyl, $C_2$–$C_4$ haloalkenyl, $C_2$–$C_4$ haloalkynyl, $C_1$–$C_4$ heteroalkyl, $C_2$–$C_4$ heteroalkenyl, or $C_2$–$C_4$ heteroalkynyl, and wherein the alkyl, alkenyl, alkynyl, haloalkyl, haloalkenyl, haloalkynyl, heteroalkyl, heteroalkenyl, heteroalkynyl, aryl, and heteroaryl may be optionally substituted with halogen, $C_1$–$C_4$ alkyl, $C_1$–$C_4$ haloalkyl or $C_1$–$C_4$ heteroalkyl;

M represents O, S, $NR^{16}$;

U represents O, S, $NR^3$, $CR^{22}R^{23}$, $CR^3R^4O$, or $CR^3R^4S$;

W represents O, S, $NR^3$, $CR^{22}R^{23}$;

X represents O, S or $NR^{16}$, but when $R^{31}$ is an aryl or heteroaryl, X is not $NR^{16}$;

Y represents O, S, $NR^{16}$, $NOR^{16}$ or $CR^{116}R^{17}$;

Z represents O, S, $NR^3$, C=O, or $CR^3R^4$, or optionally Z may represent two hydrogens;

n is 1, 2 or 3; and m is 1 to 5.

In a preferred aspect, the present invention provides a pharmaceutical composition comprising an effective amount of an AR or PR modulating compound of formulas I through XIII shown above wherein $R^1$ through $R^{42}$, M, Q, U, V, W, X, Y and Z all have the same definitions as given above.

In a further preferred aspect, the present invention comprises a method of modulating processes mediated by ARs or PRs or combinations comprising administering to a patient an effective amount of a compound of the formulae I through XIII shown above wherein $R^1$ through $R^{42}$, M, Q, U, V, W, X, Y and Z all have the same definitions as given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl) aminomethane. Additional pharmaceutically acceptable salts are known to those skilled in the art.

AR agonist, partial agonist and antagonist compounds (including compounds with tissue-selective AR modulator activity) of the present invention are useful in the treatment of hypogonadism (agonist), male hormone replacement therapy (agonist), wasting diseases (agonist), cancer cachexia (agonist), male contraception, hirsutism (antagonist), stimulation of hematopoiesis (agonist), acne (antagonist), male-pattern baldness (antagonist), prostatic hyperplasia (antagonist), various hormone-dependent cancers, including, without limitation, prostate (antagonist), and breast cancer and as anabolic agents (agonist). It is understood by those of skill in the art that a partial agonist may be used where agonist activity is desired, or where antagonist activity is desired, depending upon the AR modulator profile of the particular partial agonist.

PR agonist, partial agonist and antagonist compounds of the present invention are useful in female hormone replacement therapy and as modulators of fertility (e.g., as contraceptives, contragestational agents or abortifacients), either alone or in junction with ER modulators. The PR modulators are also useful in the treatment of dysfunctional uterine bleeding, dysmenorrhea, endometriosis, leiomyomas (uterine fibroids), hot flashes, mood disorders, meningiomas as well as in various hormone-dependent cancers, including, without limitation, cancers of ovary, breast, endometrium and prostate.

It is understood by those skilled in the art that although the compounds of the present invention are typically employed as selective agonists, partial agonists or antagonists, there may be instances where a compound with a mixed steroid receptor profile is preferred.

Furthermore, it is understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists and antagonists) according to the present invention include:

6-Amino-4-trifluoromethyl-2(1H)-quinolinone (Compound 200);

6-Propylamino-4-trifluoromethyl-2(1H)-quinolinone (Compound 204);
6-Isopropylamino-4-trifluoromethyl-2(1H)-quinolinone (Compound 205);
6-Isobutylamino-4-trifluoromethyl-2(1H)-quinolinone (Compound 206);
6-(2,2-Dimethylpropyl)amino-4-trifluoromethyl-2(1H)-quinolinone (Compound 207);
6-Cyclopentylamino-4-trifluoromethyl-2(1H)-quinolinone (Compound 208);
6-(2,2,2-Trifluoroethyl)amino-4-trifluoromethyl-2(1H)-quinolinone (Compound 209);
6-(2,2,3,3,3-Pentafluoropropyl)amino-4-trifluoromethyl-2(1H)-quinolinone (Compound 210);
6-(2,2-Difluoroethyl)amino-4-trifluoromethyl-2(1H)-quinolinone (Compound 211);
6-(2-Chloro-2,2-difluoroethyl)amino-4-trifluoromethyl-2(1H)-quinolinone (Compound 212);
6-Acetylamino-4-trifluoromethyl-2(1H)-quinolinone (Compound 213);
6-Trifluoroacetylamino-4-trifluoromethyl-2(1H)-quinolinone (Compound 214);
6-Benzoylamino-4-trifluoromethyl-2(1H)-quinolinone (Compound 215);
6-Dimethylacetylamino-4-trifluoromethyl-2(1H)-quinolinone (Compound 216);
6-Dimethylamino-4-trifluoromethyl-2(1H)-quinolinone (Compound 217);
6-Diethylamino-4-trifluoromethyl-2(1H)-quinolinone (Compound 218);
6-Dipropylamino-4-trifluoromethyl-2(1H)-quinolinone (Compound 219);
6-Dibutylamino-4-trifluoromethyl-2(1H)-quinolinone (Compound 220);
6-Diisobutylamino-4-trifluoromethyl-2(1H)-quinolinone (Compound 221);
6-(bis-Cyclopropylmethyl)amino-4-trifluoromethyl-2(1H)-quinolinone (Compound 222);
6-(bis-2,2,2-Trifluoroethyl)amino-4-trifluoromethyl-2(1H)-quinolinone (Compound 223);
6-(bis-2,2,3,3,3-Pentafluoropropyl)amino-4-trifluoromethyl-2(1H)-quinolinone (Compound 224);
6-(bis-2-Chloro-2,2-difluoroethyl)amino-4-trifluoromethyl-2(1H)-quinolinone (Compound 225);
6-(bis-2-Bromoethyl)amino-4-trifluoromethyl-2(1H)-quinolinone (Compound 226);
6-(N-2,2,2-Trichloroethyl)amino-4-trifluoromethyl-2(1H)-quinolinone (Compound 227);
6-(bis-N-2,2,2-Trichloroethyl)amino-4-trifluoromethyl-2(1H)-quinolinone (Compound 228);
6-(N-2,2,2-Chlorodifluoroethyl-N-2,2,2-Trichloroethyl)amino-4-trifluoromethyl-2(1H)-quinolinone (Compound 229);
6-(bis-N-2,2-Difluoroethyl)amino-4-trifluoromethyl-2(1H)-quinolinone (Compound 230);
6-(N-2,2-Dichloroethyl-N-2,2,2-trichloroethyl)amino-4-trifluoromethyl-2(1H)-quinolinone (Compound 231);
6-(bis-N-2,2-Dichloroethyl)amino-4-trifluoromethyl-2(1H)-quinolinone (Compound 232);
6-(N-2,2-Dichloroethyl-N-2,2-difluoroethyl)amino-4-trifluoromethyl-2(1H)-quinolinone (Compound 233);
6-(N-2,2-Dichloroethyl-N-2,2,2-chlorodifluoroethyl)amino-4-trifluoromethyl-2(1H)-quinolinone (Compound 234);
6-(N-Isopropyl-N-methyl)amino-4-trifluoromethyl-2(1H)-quinolinone (Compound 235);
6-(N-Methyl-N-cyclopentyl)amino-4-trifluoromethyl-2(1H)-quinolinone (Compound 236);
6-(N-Methyl-N-isobutyl)amino-4-trifluoromethyl-2(1H)-quinolinone (Compound 237);
6-(N-Ethyl-N-propyl)amino-4-trifluoromethyl-2(1H)-quinolinone (Compound 238);
6-(N-Ethyl-N-isopropyl)amino-4-trifluoromethyl-2(1H)-quinolinone (Compound 239);
6-(N-Ethyl-N-1-methylpropyl)amino-4-trifluoromethyl-2(1H)-quinolinone (Compound 240);
6-(N-Ethyl-N-isobutyl)amino-4-trifluoromethyl-2(1H)-quinolinone (Compound 241);
6-(N-Ethyl-N-2,2-dimethylpropyl)amino-4-trifluoromethyl-2(1H)-quinolinone (Compound 242);
6-(N-Ethyl-N-cyclopentyl)amino-4-trifluoromethyl-2(1H)-quinolinone (Compound 243);
6-(N-Ethyl-N-1-acetylethyl)amino-4-trifluoromethyl-2(1H)-quinolinone (Compound 244);
(±)-6-(N-Ethyl-N-1-methyl-2-hydroxypropyl)amino-4-trifluoromethyl-2(1H)-quinolinone (Compound 245);
6-(N-Ethyl-N-2,2,2-trifluoroethyl)amino-4-trifluoromethyl-2(H11)-quinolinone (Compound 246);
6-(N-Ethyl-N-3-furylmethyl)amino-4-trifluoromethyl-2(1H)-quinolinone (Compound 247);
(±)-6-(N-Ethyl-N-2,2-dimethoxyisopropyl)amino-4-trifluoromethyl-2(1H)-quinolinone (Compound 248);
6-(N-Isopropyl-N-propyl)amino-4-trifluoromethyl-2(1H)-quinolinone (Compound 249);
6-(N-2-Hydroxyethyl-N-propyl)amino-4-trifluoromethyl-2(1H)-quinolinone (Compound 250);
(±)-6-(N-Propyl-N-1-methylbutyl)amino-4-trifluoromethyl-2(1H)-quinolinone (Compound 251);
(±)-6-(N-Propyl-N-1,2-dimethylpropyl)amino-4-trifluoromethyl-2(1H)-quinolinone (Compound 252);
6-(N-Propyl-N-isobutyl)amino-4-trifluoromethyl-2(1H)-quinolinone (Compound 253);
6-(N-Propyl-N-cyclopropylmethyl)amino-4-trifluoromethyl-2(1H)-quinolinone (Compound 254);
(±)-6-(N-Propyl-N-1-methylpropyl)amino-4-trifluoromethyl-2(1H)-quinolinone (Compound 255);
6-(N-2-Hydroxyethyl-N-isopropyl)amino-4-trifluoromethyl-2(1H)-quinolinone (Compound 256);
6-(N-Isopropyl-N-cyclopropylmethyl)amino-4-trifluoromethyl-2(1H)-quinolinone (Compound 257);
6-(N-Methyl-N-2,2,2-trifluoroethyl)amino-4-trifluoromethyl-2(1H)-quinolinone (Compound 258);
6-(N-2,2,2-trifluoroethyl-N-isobutyl)amino-4-trifluoromethyl-2(1H)-quinolinone (Compound 259);
6-(N-2,2,2-trifluoroethyl-N-isopropyl)amino-4-trifluoromethyl-2(1H)-quinolinone (Compound 260);
6-(N-2,2,2-Trifluoroethyl-N-cyclopropylmethyl)amino-4-trifluoromethyl-2(1H)-quinolinone (Compound 261);
(±)-6-(N-2,2,2-Trifluoroethyl-N-1-methylpropyl)amino-4-trifluoromethyl-2(1H)-quinolinone (Compound 262);
(±)-6-(N-2,2,2-Trifluoroethyl-N-2-chloroisopropyl)amino-4-trifluoromethyl-2(1H)-quinolinone (Compound 263);
(+)-6-(N-2,2,2-Trifluoroethyl-N-2-chloroisopropyl)amino-4-trifluoromethyl-2(1H)-quinolinone (Compound 264);

(−)-6-(N-2,2,2-Trifluoroethyl-N-2-chloroisopropyl) amino-4-trifluoromethyl-2(1H)-quinolinone (Compound 265);

6-(N-2,2,2-Trifluoroethyl-N-3-furfuryl)amino-4-trifluoromethyl-2(1H)-quinolinone (Compound 266);

6-(N-2,2,2-Trifluoroethyl-N-3-thiophenemethyl)amino-4-trifluoromethyl-2(1H)-quinolinone (Compound 267);

6-(N-2,2,2-Trifluoroethyl-N-3,3-dimethylbutyl)amino-4-trifluoromethyl-2(1H)-quinolinone (Compound 268);

6-(N-2,2,2-Trifluoroethyl-N-2-thiophenemethyl)amino-4-trifluoromethyl-2(1H)-quinolinone (Compound 269);

6-(N-2,2,2-Trifluoroethyl-N-2-furfuryl)amino-4-trifluoromethyl-2(1H)-quinolinone (Compound 270);

6-(N-Butyl-N-2,2,2-trifluoroethyl)amino-4-trifluoromethyl-2(1H)-quinolinone (Compound 271);

6-(bis-N,N-Benzyl)amino-4-trifluoromethyl-2(1H)-quinolinone (Compound 272);

6-(N-2,2,2-Trifluoroethyl-N-cyclobutyl)amino-4-trifluoromethyl-2(1H)-quinolinone 12 (Compound 273);

6-(N-2,2,2-Trifluoroethyl-N-2,2-dichloroethyl)amino-4-trifluoromethyl-2(1H)-quinolinone (Compound 274);

6-(N-2,2,2-Trifluoroethyl-N-2-chloroethyl)amino-4-trifluoromethyl-2(1H)-quinolinone (Compound 275);

6-(N-Benzyl-N-2,2,2-trifluoroethyl)amino-4-trifluoromethyl-2(1H)-quinolinone (Compound 276);

6-(N-4-Fluorobenzyl-N-2,2,2-trifluoroethyl)amino-4-trifluoromethyl-2(1H)-quinolinone (Compound 277);

6-(N-Propyl-N-2,2,2-trifluoroethyl)amino-4-trifluoromethyl-2(1H)-quinolinone (Compound 278);

6-(N-2,2,3,3,3-Pentafluoropropyl-N-2,2,2-trifluoroethyl) amino-4-trifluoromethyl-2(1H)-quinolinone (Compound 279);

6-Diallylamino-4-trifluoromethyl-2(1H)-quinolinone (Compound 280);

6-(N-Isobutyl-N-allyl)amino-4-trifluoromethyl-2(1H)-quinolinone (Compound 281);

6-(N-Isopropyl-N-allyl)amino-4-trifluoromethyl-2(1H)-quinolinone (Compound 282);

6-(N-Allyl-N-2,2,2-trifluoroethyl)amino-4-trifluoromethyl-2(1H)-quinolinone (Compound 283);

6-Allylamino-4-trifluoromethyl-2(1H)-quinolinone (Compound 284);

6-(N-Allyl-N-cyclopropylmethyl)amino-4-trifluoromethyl-2(1H)-quinolinone (Compound 285);

6-(N-Allyl-N-2,2,2-trifluoroacetyl)amino-4-trifluoromethyl-2(1H)-quinolinone (Compound 286);

6-(N-2,2,2-Trifluoroethyl-N-2,2,2-trifluoroacetyl)amino-4-trifluoromethyl-2(1H)-quinolinone (Compound 287);

6-(N-Allyl-N-propyl)amino-4-trifluoromethyl-2(1H)-quinolinone (Compound 288);

(±)-6-(N-2-Hydroxyisopropyl-N-2,2,2-trifluoroethyl) amino-4-trifluoromethyl-2(1H)-quinolinone (Compound 289);

(±)-6-(N-Isobutyl-N-2,2,2-trifluoroisopropyl)amino-4-trifluoromethyl-2(1H)-quinolinone (Compound 290);

6-(N-2,2-Difluoroethyl-N-2,2,2-trifluoroethyl)amino-4-trifluoromethyl-2(1H)-quinolinone (Compound 291);

6-(N-2,2-Dimethylpropyl-N-2,2,2-trifluoroethyl)amino-4-trifluoromethyl-2(1H)-quinolinone (Compound 292);

6-(N-2,2-Difluoro-2-chloroethyl-N-2,2,2-trifluoroethyl) amino-4-trifluoromethyl-2(1H)-quinolinone (Compound 293);

6-(N-2,2-Difluoro-2-chloroethyl-N-2,2-difluoroethyl) amino-4-trifluoromethyl-2(1H)-quinolinone (Compound 294);

6-(N-2,2,2-Trifluoroethyl-N-methylsufonyl)amino-4-trifluoromethyl-2(1H)-quinolinone (Compound 295);

1-Methyl-6-(N-propyl-N-isobutyl)amino-4-trifluoromethyl-2(1H)-quinolinone (Compound 296);

1-Methyl-6-(bis-2,2,2-trifluoroethyl)amino-4-trifluoromethyl-2(1H)-quinolinone (Compound 297);

1-Ethyl-6-(bis-2,2,2-trifluoroethyl)amino-4-trifluoromethyl-2(1H)-quinolinone (Compound 298);

6-(N-2,2,2-Trifluoroethyl)amino-4-trifluoromethyl-2 (1H)-thioquinolinone (Compound 299);

6-(bis-N,N-2,2,2-Trifluoroethyl)amino-4-trifluoromethyl-2(1H)-thioquinolinone (Compound 300);

(±)-6-(N-2,2,2-Trifluoroethyl-N-2,2,2-trifluoroisopropyl) amino-4-trifluoromethyl-2(1H)-quinolinone (Compound 301);

(+)-6-(N-2,2,2-Trifluoroethyl-N-2,2,2-trifluoroisopropyl) amino-4-trifluoromethyl-2(1H)-quinolinone (Compound 302);

(−)-6-(N-2,2,2-Trifluoroethyl-N-2,2,2-trifluoroisopropyl) amino-4-trifluoromethyl-2(1H)-quinolinone (Compound 303);

6-Methoxythiocarbonylmercapto-4-trifluoromethyl-2 (1H)-quinolinone (Compound 304);

6-Mercapto-4-trifluoromethyl-2(1H)-quinolinone (Compound 305);

6-(1,1-Dimethyl-2-propynyl)amino-4-trifluoromethyl-2 (1H)-quinolinone (Compound 306);

6-tert-Butylamino-4-trifluoromethyl-2(1H)-quinolinone (Compound 307);

6-Bromo-4-trifluoromethyl-2(1H)-quinolinone (Compound 308);

6-Bromo-4-trifluoromethyl-2-isopropyloxyquinoline (Compound 309);

6-tert-Butylamino-2-isopropyloxy-4-trifluoromethylquinolines (Compound 310);

6-(1-Piperdinyl)-4-trifluoromethyl-2(1H)-quinolinone (Compound 311);

6-(1-Pyrrolidinyl)-4-trifluoromethyl-2(1H)-quinolinone (Compound 312);

6-(1-Morpholino)-4-trifluoromethyl-2(1H)-quinolinone (Compound 313);

(±)-6-(2-Methyl-1-piperidino)-4-trifluoromethyl-2(1H)-quinolinone (Compound 314);

(+)-6-(2-Methyl-1-piperidino)-4-trifluoromethyl-2(1H)-quinolinone (Compound 315);

(−)-6-(2-Methyl-1-piperidino)-4-trifluoromethyl-2(1H)-quinolinone (Compound 316);

6-(N-phenylamino)-4-trifluoromethyl-2(1H)-quinolinone (Compound 317);

6-(N-phenyl-N-ethylamino)-4-trifluoromethyl-2(1H)-quinolinone (Compound 319);

6-(N-phenyl-N-ethylamino)-4-trifluoromethyl-2-isopropyloxyquinoline (Compound 320);

6-(N-phenyl-N-2,2,2-trifluoroethylamino)-4-trifluoromethyl-2(1H)-quinolinone (Compound 321);

(±)-6-(3-Methyl-1-piperidino)-4-trifluoromethyl-2(1H)-quinolinone (Compound 322);
6-(4-Methyl-1-piperidino)-4-trifluoromethyl-2(1H)-quinolinone (Compound 323);
6-(cis-3,5-Dimethyl-1-piperidino)-4-trifluoromethyl-2(1H)-quinolinone (Compound 324);
6-(2,6-cis-Dimethyl-1-piperidino)-4-trifluoromethyl-2(1H)-quinolinone (Compound 325);
6-(2,6-trans-Dimethyl-1-piperidino)-4-trifluoromethyl-2(1H)-quinolinone (Compound 326);
(±)-6-(2-Methyl-1-pyrrolidino)-4-trifluoromethyl-2(1H)-quinolinone (Compound 327);
6-(2,5-cis-Dimethyl-1-pyrrolidino)-4-trifluoromethyl-2(1H)-quinolinone (Compound 328);
(±)-6-(2,5-trans-Dimethyl-1-pyrrolidino)-4-trifluoromethyl-2(1H)-quinolinone (Compound 329);
6-(1-Azepano)-4-trifluoromethyl-2(1H)-quinolinone (Compound 330);
(±)-6-(2-Hydroxymethyl-1-piperidino)-4-trifluoromethyl-2(1H)-quinolinone (Compound 331);
6-(2,5-cis-Dimethyl-1-pyrrolino)-4-trifluoromethyl-2(11)-quinolinone (Compound 332);
(±)-6-(2-Propyl-1-piperidino)-4-trifluoromethyl-2(1H)-quinolinone (Compound 333);
(±)-6-(2-Methoxymethyl-1-piperidino)-4-trifluoromethyl-2(1H)-quinolinone (Compound 334);
(±)-6-(2-Ethyl-1-piperidino)-4-trifluoromethyl-2(1H)-quinolinone (Compound 335);
6-(1-Cycloheptylamino)-4-trifluoromethyl-2(1H)-quinolinone (Compound 336);
(±)-6-(2-Ethoxycarbonyl-1-piperidino)-4-trifluoromethyl-2(1H)-quinolinone (Compound 337);
(±)-6-(2-Isopropyl-1-pyrrolidino)-4-trifluoromethyl-2(1H)-quinolinone (Compound 338);
(±)-6-(2-Hydroxycarbonyl-1-piperidino)-4-trifluoromethyl-2(1H)-quinolinone (Compound 339);
6-(3,5-cis-Dimethyl-1-piperazino)-4-trifluoromethyl-2(1H)-quinolinone (Compound 340);
(±)-6-(2-Benzyl-1-pyrrolidino)-4-trifluoromethyl-2(1H)-quinolinone (Compound 341);
(±)-6-(5-Methyl-2-oxo-1-pyrrolidino)-4-trifluoromethyl-2(1H)-quinolinone (Compound 342);
(±)-6-(2-(2-Hydroxyethyl)-1-piperidino)-4-trifluoromethyl-2(1H)-quinolinone (Compound 343);
(±)-6-(3-Hydroxy-1-pyrrolidino)-4-trifluoromethyl-2(1H)-quinolinone-(Compound 344);
(±)-6-(3-Acetyloxy-1-pyrrolidino)-4-trifluoromethyl-2(1H)-quinolinone (Compound 345);
(±)-6-(3-Hydroxy-1-pyrrolidino)-4-trifluoromethyl-2(1H)-quinolinone (Compound 346);
6-(1-Indolino)-4-trifluoromethyl-2(1H)-quinolinone (Compound 347);
6-(1-Tetrahydroquinolino)-4-trifluoromethyl-2(1H)-quinolinone (Compound 348);
6-(2-Tetrahydroisoquinolino)-4-trifluoromethyl-2(1H)-quinolinone (Compound 349);
(±)-6-(1,3,3-Trimethyl-6-azabicyclo[3.2.1]octanyl-6-)-4-trifluoromethyl-2(1H)-quinolinone (Compound 350);
(±)-6-(2-Trifluoromethyl-5-cis-methyl-1-oxazolidino)-4-trifluoromethyl-2(1H)-quinolinone (Compound 351);
(±)-6-(2-Trifluoromethyl-5-trans-methyl-1-oxazolidino)-4-trifluoromethyl-2(1H)-quinolinone (Compound 352);
6-N-(1-Hydroxyisopropyl)amino-4-trifluoromethyl-2(1H)-quinolinone (Compound 353);
(±)-6-(2-Trifluoromethyl-5-cis-ethyl-1-oxazolidino)-4-trifluoromethyl-2(1H)-quinolinone 270 (Compound 354);
(±)-6-(2-Trifluoromethyl-5-trans-ethyl-1-oxazolidino)-4-trifluoromethyl-2(1H)-quinolinone (Compound 355);
(±)-6-(5-Methyl-1-oxazolidino)-4-trifluoromethyl-2(1H)-quinolinone (Compound 356);
6-(2,5-Dimethyl-1-pyrrolyl)-4-trifluoromethyl-2(1H)-quinolinone (Compound 357);
6-(N-2,2,2-Trifluoroethyl-N-3,3,3-trifluoropropyl)amino-4-trifluoromethyl-2(1H)-quinolinone (Compound 358);
6-(N-3,3,3-Trifluoropropyl)amino-4-trifluoromethyl-2-isopropyloxyquinoline (Compound 360);
6-bis-N,N-Thiomethoxymethylamino-4-trifluoromethyl-2(1H)-quinolinone (Compound 361);
6-bis-N,N-Thiomethoxymethylamino-4-trifluoromethyl-2-thiomethoxymethyloxyquinoline (Compound 362);
(±)-6-(2,5-trans-Diethyl-1-pyrrolidino)-4-trifluoromethyl-2(1H)-quinolinone (Compound 363);
6-(2,5-cis-Diethyl-1-pyrrolidino)-4-trifluoromethyl-2(1H)-quinolinone (Compound 364);
(±)-6-(2,5-trans-Dipropyl-1-pyrrolidino)-4-trifluoromethyl-2(1H)-quinolinone (Compound 365);
6-(2,5-cis-Dipropyl-1-pyrrolidino)-4-trifluoromethyl-2(1H)-quinolinone (Compound 366);
6-(2,5-Dipropyl-1-pyrrolo)-4-trifluoromethyl-2(1H)-quinolinone (Compound 367);
6-(2,5-cis-Dibutyl-1-pyrrolidino)-4-trifluoromethyl-2(1H)-quinolinone (Compound 368);
(±)-6-(2,5-trans-Dibutyl-1-pyrrolidino)-4-trifluoromethyl-2(1H)-quinolinone (Compound 369);
6-(2,6-cis-Diethyl-1-piperidino)-4-trifluoromethyl-2(1H)-quinolinone (Compound 370);
(±)-6-(2,6-trans-Diethyl-1-piperidino)-4-trifluoromethyl-2(1H)-quinolinone (Compound 371);
6-(2,6-cis-Dimethyl-1-piperidino)-4-trifluoromethyl-2(1H)-quinolinone (Compound 372);
(±)-6-(2,6-trans-Dimethyl-1-piperidino)-4-trifluoromethyl-2(1H)-quinolinone (Compound 373);
6-(N-Propyl-N-2,2,2-trifluoroethyl)amino-4-methyl-2(1H)-quinolinone (Compound 374);
6-Amino-4-methyl-2(1H)-quinolinone (Compound 375);
6-(bis-2,2,2 Trifluoroethyl)amino-4-methyl-2(1H)-quinolinone (Compound 377);
6-(2,5-Dimethyl-1-pyrrolyl)-4-methyl-2(1H)-quinolinone (Compound 378);
(±)-6-(2,5-trans-dimethyl-1-pyrrolidino)-4-methyl-2(1H)-quinolinone (Compound 379);
6-(2,5-cis-dimethyl-1-pyrrolidino)-4-methyl-2(1H)-quinolinone (Compound 380);
6-(N-Isobutyl-N-2,2,2-trifluoroethyl)amino-4-methyl-2(1H)-quinolinone (Compound 381);
6-(N-2,2,2-Chlorodifluoroethyl)amino-4-methyl-2(1H)-quinolinone (Compound 382);
6-(bis-N,N-2,2,2-Chlorodifluoroethyl)amino-4-methyl-2(1H)-quinolinone (Compound 383);
6-(N-2,2,2-Chlorodifluoroethyl-N-2,2,2-trifluoroethyl)amino-4-methyl-2(1H)-quinolinone (Compound 384);
6-N-Ethylamino-4-methyl-2(1H)-quinolinone (Compound 385);

6-(N-Ethyl-N-2,2 2-trifluoroethyl)amino-4-methyl-2 (1H)-quinolinone (Compound 386);

6-N,N-Diethylamino-4-methyl-2(1H)-quinolinone (Compound 387);

6-(bis-2,2,2-trifluoroethyl)amino-4-ethyl-2(1H)-quinolinone (Compound 388);

6-Amino-4-ethyl-2(1H)-quinolinone (Compound 389);

6-(bis-2,2,2-trifluoroethyl)amino-4-isopropyl-2(1H)-quinolinone (Compound 391);

6-Amino-4-isopropyl-2(1H)-quinolinone (Compound 392);

7-Fluoro-6-(bis-trifluoroethyl)amino-4-trifluoromethyl-2(1H)-quinolinone (Compound 393);

7-Fluoro-4-trifluoromethyl-2(1H)-quinolinone (Compound 394);

5-Fluoro-4-trifluoromethyl-2(1H)-quinolinone (Compound 395);

6-Amino-7-fluoro-4-trifluoromethyl-2(1H)-quinolinone (Compound 396);

8-Fluoro-6-(bis-2,2,2-trifluoroethyl)amino-4-trifluoromethyl-2(1H)-quinolinone (Compound 397);

8-Fluoro-4-trifluoromethyl-2(1H)-quinolinone (Compound 316); 6-Amino-8-fluoro-4-trifluoromethyl-2(1H)-quinolinone (Compound 399);

8-Fluoro-6-(N-2,2,2-trifluoroethyl)amino-4-trifluoromethyl-2(1H)-quinolinone (Compound 400);

8-Fluoro-6-(N-2,2,2-trifluoroethyl-N-isopropyl)amino-4-trifluoromethyl-2(1H)-quinolinone (Compound 401);

6-Amino-3-fluoro-4-trifluoromethyl-2(1H)-quinolinone (Compound 402);

3-Fluoro-6-(2,2,2-trifluoroethyl)amino-4-trifluoromethyl-2(1H)-quinolinone (Compound 403);

3-Fluoro-6-(bis-2,2,2-trifluorofluoroethyl)amino-4-trifluoromethyl-2(1H)-quinolinone (Compound 404);

6-(bis-Isobutylamino)-4-methyl-2(1H)-quinolinone (Compound 405);

3-Fluoro-6-(N-methyl-N-2,2,2-trifluorofluoroethyl)amino-4-trifluoromethyl-2(1H)-quinolinone (Compound 406);

7-Bromo-6-isopropylamino-4-trifluoromethyl-2(1H)-quinolinone (Compound 407);

6-Amino-7-bromo-4-trifluoromethyl-2(1H)-quinolinone (Compound 408);

6-(bis-N,N-2,2,2-Trifluoroethyl)amino-4-hydroxy-2(1H)-quinolinone (Compound 409);

6-amino-4-hydroxy-2(1H)-quinolinone (Compound 410);

6-(bis-N,N-2,2,2-Trifluoroethyl)amino-4-methoxy-2(1H)-quinolinone (Compound 411);

6-amino-4-methoxy-2(1H)-quinolinone (Compound 412);

6-(bis-N,N-2,2,2-Trifluoroethyl)amino-4-difluoromethyl-2(1H)-quinolinone (Compound 413);

6-amino-4-difluoromethyl-2(1H)-quinolinone (Compound 414);

6-(bis-N,N-2,2,2-Trifluoroethyl)amino-2(1H)-quinolinone (Compound 415);

6-amino-2(1H)-quinolinone (Compound 416);

4-Chloro-6-(bis-N,N-2,2,2-trifluoroethyl)amino-2(1H)-quinolinone (Compound 417);

6-amino-4-chloro-2(1H)-quinolinone (Compound 418);

7-Methoxy-4-trifluoromethyl-2(1H)-quinolinone (Compound 419);

5,7-Dimethoxy-4-trifluoromethyl-2(1H)-quinolinone (Compound 420);

(R)-6-(2-Hydroxymethyl-1-pyrrolidino)-4-trifluoromethyl-2(1H)-quinolinone (Compound 421);

(R)-6-(2-Methoxycarbonyl-1-pyrrolidino)-4-trifluoromethyl-2-isopropyloxyquinoline (Compound 422);

(R)-6-(2-Methoxymethyl-1-pyrrolidino)-4-trifluoromethyl-2(1H)-quinolinone (Compound 423);

(±)-6-(2-Chloromethyl-1-piperidino)-4-trifluoromethyl-2(1H)-quinolinone (Compound 424);

(±)-6-(2-Cyanothiomethyl-1-piperidino)-4-trifluoromethyl-2(1H)-quinolinone (Compound 425);

(±)-6-(2-Thiomethoxymethyl-1-piperidino)-4-trifluoromethyl-2(1H)-quinolinone (Compound 426);

(±)-6-(2-Cyanomethyl-1-piperidino)-4-trifluoromethyl-2(1H)-quinolinone (Compound 427);

(±)-6-(2-Bromomethyl-1-piperidino)-4-trifluoromethyl-2(1H)-quinolinone (Compound 428);

(±)-6-(2-Iodomethyl-1-piperidino)-4-trifluoromethyl-2(1H)-quinolinone (Compound 429);

(+)R-6-(2-Iodomethyl-1-pyrrolidino)-4-trifluoromethyl-2(1H)-quinolinone (Compound 430);

(±)-6-(2-Fluoromethyl-1-piperidino)-4-trifluoromethyl-2(1H)-quinolinone (Compound 431);

(+)S-6-(2-Chloromethyl-1-piperidino)-4-trifluoromethyl-2(1H)-quinolinone (Compound 432);

(−)R-6-(2-Chloromethyl-1-piperidino)-4-trifluoromethyl-2(1H)-quinolinone (Compound 433);

(+)R-6-(2-Chloromethyl-1-pyrrolidino)-4-trifluoromethyl-2(1H)-quinolinone (Compound 434);

(−)S-6-(2-Chloromethyl-1-pyrrolidino)-4-trifluoromethyl-2(1H)-quinolinone (Compound 435);

R-6-(2-Difluoromethyl-1-pyrrolidino)-4-trifluoromethyl-2(1H)-quinolinone (Compound 436);

(±)-6-(2l-(1l-Hydroxy-2,2,2-trifluoroethyl)-1-piperidino)-4-trifluoromethyl-2(1H)-quinolinone (Compound 437);

(±)-6-(2l-(1u-Hydroxy-2,2,2-trifluoroethyl)-1-piperidino)-4-trifluoromethyl-2(1H)-quinolinone (Compound 438);

(±)-6-(2-Formyl-1-piperidino)-4-trifluoromethyl-2(1H)-quinolinone (Compound 439);

(±)-6-(2-Difluoromethyl-1-piperidino)-4-trifluoromethyl-2(1H)-quinolinone (Compound 440);

(±)-6-(2-Aminomethyl-1-piperidino)-4-trifluoromethyl-2(1H)-quinolinone (Compound 441);

(R)-6-(2-Vinyl-1-pyrrolidino)-4-trifluoromethyl-2(1H)-quinolinone (Compound 442);

(R)-6-(2-Formyl-1-pyrrolidino)-4-trifluoromethyl-2(1H)-quinolinone (Compound 443);

(±)-6-(2-Vinyl-1-piperidino)-4-trifluoromethyl-2(1H)-quinolinone (Compound 444);

(±)-6-(2-Benzyloxyethyl-1-piperidino)-4-trifluoromethyl-2(1H)-quinolinone (Compound 445);

(±)-6-(2-(2,2-Difluoroethyl)-1-piperidino)-4-trifluoromethyl-2(1H)-quinolinone (Compound 446);

(±)-6-(2-Trifluoroacetamidomethyl-1-piperidino)-4-trifluoromethyl-2(1H)-quinolinone (Compound 447);

(±)-6-(2-(2-Ethoxyethyl)-1-piperidino)-4-trifluoromethyl-2(1H)-quinolinone (Compound 448);

(±)-6-(2-(4-Trifluoromethyl)benzyloxyethyl-1-piperidino)-4-trifluoromethyl-2(1H)-quinolinone (Compound 449);

(+)-6-(2R-(1R-Hydroxy-2,2,2-trifluoroethyl)-1-pyrrolidino)-4-trifluoromethyl-2(1H)-quinolinone (Compound 450);

(−)6-(2R-(1S-Hydroxy-2,2,2-trifluoroethyl)-1-pyrrolidino)-4-trifluoromethyl-2(1H)-quinolinone (Compound 451);

6-(2S-(1R-Hydroxy-2,2,2-trifluoroethyl)-1-pyrrolidino)-4-trifluoromethyl-2(1H)-quinolinone (Compound 452);

6-(2S-(1S-Hydroxy-2,2,2-trifluoroethyl)-1-pyrrolidino)-4-trifluoromethyl-2(1H)-quinolinone (Compound 453);

(±)-6-(2l-(1l-Hydroxyethyl)-1-piperidino)-4-trifluoromethyl-2(1H)-quinolinone (Compound 454);

(±)-6-(2l-(1u-Hydroxyethyl)-1-piperidino)-4-trifluoromethyl-2(1H)-quinolinone (Compound 455);

(−)-6-(2S-(1S-Hydroxy-2,2,2-trifluoroethyl)-1-piperidino)-4-trifluoromethyl-2(1H)-quinolinone (Compound 456);

(+)-6-(2R-(1R-Hydroxy-2,2,2-trifluoroethyl)-1-piperidino)-4-trifluoromethyl-2(1H)-quinolinone (Compound 457);

(+)-6-(2R-(1S-Hydroxy-2,2,2-trifluoroethyl)-1-piperidino)-4-trifluoromethyl-2(1H)-quinolinone (Compound 458);

(−)-6-(2S-(1R-Hydroxy-2,2,2-trifluoroethyl)-1-piperidino)-4-trifluoromethyl-2(1H)-quinolinone (Compound 459);

(±)-6-(2l-(1l-Acetyloxyethyl)-1-piperidino)-4-trifluoromethyl-2(1H)-quinolinone (Compound 460);

(±)-6-(2l-(1u-Acetyloxyethyl)-1-piperidino)-4-trifluoromethyl-2(1H)-quinolinone (Compound 461);

(±)-6-(2l-(1u-Methoxy-2,2,2-trifluoroethyl)-1-piperidino)-4-trifluoromethyl-2(1H)-quinolinone (Compound 462);

(±)-6-(2l-(1l-Methoxy-2,2,2-trifluoroethyl)-1-piperidino)-4-trifluoromethyl-2(1H)-quinolinone (Compound 463);

7-Methoxy-6-(N-methyl-N-2,2,2-trifluoroethyl)amino-4-trifluoromethyl-2(1H)-quinolinone (Compound 464);

4-Amino-2-methoxy-N-2,2,2-trifluoroethylaniline (Compound 466);

7-Methoxy-6-(N-2,2,2-trifluoroethyl)amino-4-trifluoromethyl-2(1H)-quinolinone (Compound 467);

7-Methoxy-6-(N-ethyl-N-2,2,2-trifluoroethyl)amino-4-trifluoromethyl-2(1H)-quinolinone (Compound 468);

7-Hydroxy-6-(2,2,2-trifluoroethyl)amino-4-trifluoromethyl-2(1H)-quinolinone (Compound 469);

6-(N-Cyclopropylmethyl-N-2,2,2-trifluoroethyl)amino-7-methoxy-4-trifluoromethyl-2(1H)-quinolinone (Compound 470);

6-(N-Cyclopropylmethyl-N-2,2,2-trifluoroethyl)amino-7-hydroxy-4-trifluoromethyl-2(1H)-quinolinone (Compound 471);

6-(N-Isobutyl-N-2,2,2-trifluoroethyl)amino-7-methoxy-4-trifluoromethyl-2(1H)-quinolinone (Compound 472);

6-(N-Isobutyl-N-2,2,2-trifluoroethyl)amino-7-hydroxy-4-trifluoromethyl-2(1H)-quinolinone (Compound 473);

6-(bis-2,2,2-Trifluoroethyl)amino-4-trifluoromethylcoumarin (Compound 474);

6-Amino-4-trifluoromethylcoumarin (Compound 475);

(±)-3,4-Dihydro-6-(bis-2,2,2-trifluoroethyl)amino-4-trifluoromethylcoumarin (Compound 476);

6-(2,2,2-trifluoroethyl)amino-4-trifluoromethylcoumarin (Compound 477);

6-(N-Isopropyl-N-2,2,2-trifluoroethyl)amino-4-trifluoromethylcoumarin (Compound 478);

6-N-Isobutylamino-4-trifluoromethylcoumarin (Compound 479);

6-N,N-Diethylamino-4-trifluoromethylcoumarin (Compound 480);

6-N,N-Dipropylamino-4-trifluoromethylcoumarin (Compound 481);

6-N-Propylamino-4-trifluoromethylcoumarin (Compound 482);

6-(N-Isobutyl-N-propylamino)-4-trifluoromethylcoumarin (Compound 483);

6-(N-2,2,2-Trifluoroethyl-N-propylamino)-4-trifluoromethylcoumarin (Compound 484);

1,4-Dihydro-4,4-dimethyl-6-methylamino-1,3-benzo[d]oxazin-2-one (Compound 485);

6-Amino-1,4-dihydro-4,4-dimethyl-1,3-benzo[d]oxazin-2-one (Compound 487);

1,4-Dihydro-4,4-dimethyl-6-dimethylamino-1,3-benzo[d]oxazin-2-one (Compound 488);

1,4-Dihydro-4,4-dimethyl-6-dipropylamino-1,3-benzo[d]oxazin-2-one (Compound 489);

1,4-Dihydro-4,4-dimethyl-6-(bis-N,N-2,2,2-trifluoroethyl)amino-1,3-benzo[d]oxazin-2-one (Compound 490);

1,4-Dihydro-4,4-dimethyl-6-(N-2,2,2-trifluoroethyl)amino-1,3-benzo[d]oxazin-2-one (Compound 491);

(±)-1,4-Dihydro-4-methyl-6-diallylamino-1,3-benzo[d]oxazin-2-one (Compound 492);

(±)-6-Amino-1,4-dihydro-4-methyl-1,3-benzo[d]oxazin-2-one (Compound 494);

6-Amino-3,4-dihydro-4,4-dimethyl-2(1H)-quinolinone (Compound 495);

6-Diallylamino-3,4-dihydro-4,4-dimethyl-2(1H)-quinolinone (Compound 497);

3,4-Dihydro-4,4-dimethyl-6-dipropylamino-2(1H)-quinolinone (Compound 498);

3,4-Dihydro-4,4-dimethyl-6-propylamino-2(1H)-quinolinone (Compound 499);

3,4-Dihydro-4,4-dimethyl-6-(N-2,2,2-trifluoroethyl)amino-2(1H)-quinolinone (Compound 500);

3,4-Dihydro-4,4-dimethyl-6-(bis-N,N-2,2,2-trifluoroethyl)amino-2(1H)-quinolinone (Compound 501);

3,4-Dihydro-6-(N-2,2,2-trifluoroethyl)amino-2(1H)-quinolinone (Compound 502);

6-Amino-3,4-dihydro-2(1H)-quinolinone (Compound 503);

3,4-Dihydro-6-(bis-N,N-2,2,2-trifluoroethyl)amino-2(1H)-quinolinone (Compound 505);

5-(bis-N,N-2,2,2-Trifluoroethyl)amino-3,3-spirocyclohexyl-2-indolone (Compound 506);

5-Amino-3-spirocyclohexyloxindole (Compound 507);

7-(bis-N,N-2,2,2-Trifluoroethyl)amino-1,4-benzoxazin-3(4H)-one (Compound 508);

7-amino-1,4-benzoxazin-3(4H)-one (Compound 509);

6-(bis-N,N-2,2,2-Trifluoroethyl)amino-2,4-dichloroquinoline (Compound 510);

6-amino-1,4-dichloro-2(1H)-quinolinone (Compound 511);

7-Amino-4-trifluoromethyl-2(1H)-quinolinone (Compound 512);

7-Propylamino-4-trifluoromethyl-2(1H)-quinolinone (Compound 513);

7-Isopropylamino-4-trifluoromethyl-2(1H)-quinolinone (Compound 514);

7-(2,2-Dimethylpropyl)amino-4-trifluoromethyl-2(1H)-quinolinone (Compound 515);

7-(2-Methylpropyl)amino-4-trifluoromethyl-2(1H)-quinolinone (Compound 516);

7-Methylamino-4-trifluoromethyl-2(1H)-quinolinone (Compound 517);

7-Dimethylamino-4-trifluoromethyl-2(1H)-quinolinone (Compound 518);

7-Benzylamino-4-trifluoromethyl-2(1H)-quinolinone (Compound 519);

7-(2,2,3,3,3-Pentafluoropropyl)amino-4-trifluoromethyl-2(1H)-quinolinone (Compound 520);

7-Butylamino-4-trifluoromethyl-2(1H)-quinolinone (Compound 521);

7-Ethylamino-4-trifluoromethyl-2(1H)-quinolinone (Compound 522);

7-(-2,2,2-Trifluoroethyl)amino-4-trifluoromethyl-2(1H)-quinolinone (Compound 523);

7-Cyclohexylamino-4-trifluoromethyl-2(1H)-quinolinone (Compound 524);

7-Cyclopentylamino-4-trifluoromethyl-2(1H)-quinolinone (Compound 525);

7-Cyclobutylamino-4-trifluoromethyl-2(1H)-quinolinone (Compound 526);

7-(2-Hydroxy-2-methylpropionyl)amino-4-trifluoromethyl-2(1H)-quinolinone (Compound 527);

7-(Trifluoroacetamido)-4-trifluoromethyl-2(1H)-quinolinone (Compound 528); 1-Methyl-7-methylamino-4-trifluoromethyl-2(1H)-quinolinone (Compound 529);

1-Methyl-7-dimethylamino-4-trifluoromethyl-2(1H)-quinolinone (Compound 530);

1-Methyl-7-(N-methyl-N-isopropylamino)-4-trifluoromethyl-2(1H)-quinolinone (Compound 531);

1-Methyl-7-(2,2,2-trifluoromethyl)amino-4-trifluoromethyl-2(1H)-quinolinone (Compound 532);

3-Fluoro-7-(2,2,2-trifluoromethyl)amino-4-trifluoromethyl-2(1H)-quinolinone (Compound 533);

3-Fluoro-7-amino-4-trifluoromethyl-2(1H)-quinolinone (Compound 534);

3-Fluoro-7-isopropylamino-4-trifluoromethyl-2(1H)-quinolinone (Compound 535);

3-Fluoro-7-cyclopentylamino-4-trifluoromethyl-2(1H)-quinolinone (Compound 536);

3-Fluoro-7-cyclohexylamino-4-trifluoromethyl-2(1H)-quinolinone (Compound 537);

3-Fluoro-7-cyclobutylamino-4-trifluoromethyl-2(1H)-quinolinone (Compound 538);

3-Fluoro-7-propylamino-4-trifluoromethyl-2(1H)-quinolinone (Compound 539);

3-Fluoro-1-methyl-7-(N-methyl-N-isopropyl)amino-4-trifluoromethyl-2(1H)-quinolinone (Compound 540);

3-Fluoro-1-methyl-7-propylamino-4-trifluoromethyl-2(1H)-quinolinone (Compound 541);

6-Fluoro-7-amino-4-trifluoromethyl-2(1H)-quinolinone (Compound 542);

6-Fluoro-7-propylamino-4-trifluoromethyl-2(1H)-quinolinone (Compound 543);

6-Fluoro-7-isobutylamino-4-trifluoromethyl-2(1H)-quinolinone (Compound 544);

6-Fluoro-1-methyl-7-propylamino-4-trifluoromethyl-2(1H)-quinolinone (Compound 545);

6-Fluoro-1-methyl-7-(N-methyl-N-propylamino)-4-trifluoromethyl-2(1H)-quinolinone (Compound 546);

7-Amino-6-methyl-4-trifluoromethyl-2(1H)-quinolinone (Compound 547);

7-Isobutylamino-6-methyl-4-trifluoromethyl-2(1H)-quinolinone (Compound 548);

7-Propylamino-6-methyl-4-trifluoromethyl-2(1H)-quinolinone (Compound 549);

7-(1,1-Dimethyl-3-oxobutyl)amino-4-trifluoromethyl-2(1H)-quinolinone (Compound 550);

7-(1,1,3-Trimethyl-3-hydroxybutyl)amino-4-trifluoromethyl-2(1H)-quinolinone (Compound 551);

7-(1,1,3-Trimethyl-3-butenylamino)-4-trifluoromethyl-2(1H)-quinolinone (Compound 552);

7-(1-Phenylaminocarbonylisopropyl)amino-4-trifluoromethyl-2(1H)-quinolinone (Compound 553);

7-(2-Hydroxy-1,1-dimethylethyl)amino-4-trifluoromethyl-2(1H)-quinolinone (Compound 556);

7-(N-1-Formylisopropyl)amino-4-trifluoromethyl-2(1H)-quinolinone (Compound 558);

7-(1,1-Dimethylallyl)amino-4-trifluoromethyl-2(1H)-quinolinone (Compound 559);

7-(1,1-Dimethylpropyl)amino-4-trifluoromethyl-2(1H)-quinolinone (Compound 560);

7-(1-Methyl-1-acetylenylpropyl)amino]-4-(trifluoromethyl)-2(1H)-quinolinone (Compound 561);

7-(1-Ethyl-1-methylpropyl)amino-4-(trifluoromethyl)-2(1H)-quinolinone (Compound 562);

8-Methyl-7-(3-methyl-2-butenyl)amino-4-trifluoromethyl-2(1H)-quinolinone (Compound 563);

8-Methyl-7-(3-methylbutyl)amino-4-(trifluoromethyl)-2(1H)-quinolinone (Compound 566);

8-Methyl-7-propylamino-4-(trifluoromethyl)-2(1H)-quinolinone (Compound 567);

8-Methyl-7-isobutylamino-4-(trifluoromethyl)-2(1H)-quinolinone (Compound 569);

7-Amino-6-(2,2,2-trifluoroethoxy)-4-trifluoromethyl-2(1H)-quinolinone (Compound 571);

7-Isobutylmino-6-(2,2,2-trifluoroethoxy)-4-trifluoromethyl-2(1H)-quinolinone (Compound 574);

7-(2-Picolylamino)-6-(2,2,2-trifluoroethoxy)-4-trifluoromethyl-2(1H)-quinolinone (Compound 575);

7-Amino-6-methyl-4-trifluoromethyl-2(1H)-quinolinone (Compound 576);

7-Amino-6-ethyl-4-trifluoromethyl-2(1H)-quinolinone (Compound 577);

7-Amino-6-propyl-4-trifluoromethyl-2(1H)-quinolinone (Compound 580);

7-Amino-6-sec-butyl4-trifluoromethyl-2(1H)-quinolinone (Compound 581);

7-Amino-6-cyclohexyl-4-trifluoromethyl-2(1H)-quinolinone (Compound 582);

6-Ethyl-7-(2,2,2-trifluoroethyl)amino-4-trifluoromethyl-2(1H)-quinolinone (Compound 585);

6-Ethyl-7-methylamino-4-trifluoromethyl-2(1H)-quinolinone (Compound 586);
6-Ethyl-7-dimethylamino-4-trifluoromethyl-2(1H)-quinolinone (Compound 587);
6-Isobutyl-7-methylamino-4-trifluoromethyl-2(1H)-quinolinone (Compound 588);
7-(1-Morpholino)-4-trifluoromethyl-2(1H)-quinolinone (Compound 589);
5-Amino-7-chloro-4-trifluoromethyl-2(1H)-quinolinone (Compound 592);
5-Propylamino-7-chloro-4-trifluoromethyl-2(1H)-quinolinone (Compound 594);
7-Chloro-5-hydroxy-4-trifluoromethyl-2(1H)-quinolinone (Compound 595);
5-Amino-6-bromo-3,4-dihydro-4-hydroxy-4-trifluoromethyl-2(1H)-quinolinone (Compound 596);
6-Bromo-5-chloro-4-trifluoromethyl-2(1H)-quinolinone (Compound 598);
6-(bis-N,N-2,2,2-trifluoroethyl)amino-5-methoxy-4-trifluoromethyl-2(1H)-quinolinone (Compound 600);
6-amino-5-methoxy-4-trifluoromethyl-2(1H)-quinolinone (Compound 601);
6-(N-2,2,2-Trifluoroethyl)amino-5-propyloxy-4-trifluoromethyl-2(1H)-quinolinone (Compound 602);
6-amino-5-propyloxy-4-trifluoromethyl-2(1H)-quinolinone (Compound 603);
6-(bis-N,N-2,2,2-Trifluoroethyl)amino-5-propyloxy-4-trifluoromethyl-2(1H)-quinolinone (Compound 604);
6-(N-2,2,2-Trifluoroethyl)amino-5-ethoxy-4-trifluoromethyl-2(1H)-quinolinone (Compound 605);
6-amino-5-ethoxy-4-trifluoromethyl-2(1H)-quinolinone (Compound 606);
6-(bis-N,N-2,2,2-Trifluoroethyl)amino-5-ethoxy-4-trifluoromethyl-2(1H)-quinolinone (Compound 607);
6-(N-2,2,2-Trifluoroethyl)amino-5-(3,3,3-trifluoropropyloxy)-4-trifluoromethyl-2(1H)-quinolinone (Compound 608);
6-amino-5-(3,3,3-trifluoropropyloxy)-4-trifluoromethyl-2(1H)-quinolinone (Compound 609);
6-(N-2,2,2-Trifluoroethyl)amino-5-chloro-4-trifluoromethyl-2(1H)-quinolinone (Compound 610);
6-amino-5-chloro-4-trifluoromethyl-2(1H)-quinolinone (Compound 611);
6-(bis-N,N-2,2,2-Trifluoroethyl)amino-5-chloro-4-trifluoromethyl-2(1H)-quinolinone (Compound 612);
6-Fluoro-4-trifluoromethyl-2(1H)-quinolinone (Compound 613);
6-Chloro-4-trifluoromethyl-2(1H)-quinolinone (Compound 614);
6-Isopropyl-4-trifluoromethyl-2(1H)-quinolinone (Compound 615);
6-Cyclohexyl-4-trifluoromethyl-2(1H)-quinolinone (Compound 616);
6-(1-trans-Propenyl)-4-trifluoromethyl-2(1H)-quinolinone (Compound 617);
6-Cyclohexyl-3-fluoro-4-trifluoromethyl-2(1H)-quinolinone (Compound 618);
7-Fluoro-6-methyl-4-trifluoromethyl-2(1H)-quinolinone (Compound 619);
5,7-Difluoro-4-trifluoromethyl-2(1H)-quinolinone (Compound 620);
6-Methoxy-4-trifluoromethyl-2(1H)-quinolinone (Compound 621);
6-Hydroxy-4-trifluoromethyl-2(1H)-quinolinone (Compound 622);
6-Benzyloxy-4-trifluoromethyl-2(1H)-quinolinone (Compound 623);
6-(3-Pentyloxy)-4-trifluoromethyl-2(1H)-quinolinone (Compound 624);
6-(1-Hydroxy-3,3,5,5-tetramethyl)cyclohexyl-4-trifluoromethyl-2(1H)-quinolinone (Compound 625);
6-(3,3,5,5-Tetramethyl)cyclohexenyl-4-trifluoromethyl-2(1H)-quinolinone (Compound 626);
6-(5,5-Dimethycyclopentenyl)-4-trifluoromethyl-2(1H)-quinolinone (Compound 627);
6-(2,2-Dimethycyclopentyl)-4-trifluoromethyl-2(1H)-quinolinone (Compound 628);
6-(1-Hydroxycyclohexyl)-4-trifluoromethyl-2(1H)-quinolinone (Compound 629);
6-Cyclohexenyl-4-trifluoromethyl-2(1H)-quinolinone (Compound 630);
6-Cyclohexyl-4-trifluoromethyl-2(1H)-thioquinolinone (Compound 631);
6-Cyclopentenyl-4-trifluoromethyl-2(1H)-quinolinone (Compound 632);
6-Cycloheptenyl-4-trifluoromethyl-2(1H)-quinolinone (Compound 633);
6-Bromo-3-fluoro-4-trifluoromethyl-2(1H)-quinolinone (Compound 634);
6-Cyclohexenyl-3-fluoro-4-trifluoromethyl-2(1H)-quinolinone (Compound 635);
6-Cyclohexyl-7-methoxy-4-trifluoromethyl-2(1H)-quinolinone (Compound 636);
6-Bromo-7-methoxy-4-trifluoromethyl-2(1H)-quinolinone (Compound 637);
6-Cyclopentyl-3-fluoro-4-trifluoromethyl-2(1H)-quinolinone (Compound 638);
(Z)-6-(1-Propyl-1-)butenyl-4-trifluoromethyl-2(1H)-quinolinone (Compound 639);
(E)-6-(1-Propyl-1-)butenyl-4-trifluoromethyl-2(1H)-quinolinone (Compound 640);
6-(1-Propyl)butyl-4-trifluoromethyl-2(1H)-quinolinone (Compound 641);
(E)-6-(1-Methyl-1-)butenyl-4-trifluoromethyl-2(1H)-quinolinone (Compound 642);
(Z)-6-(1-Methyl-1-)butenyl-4-trifluoromethyl-2(1H)-quinolinone (Compound 643);
(±)-6-(1-Methyl)butyl-4-trifluoromethyl-2(1H)-quinolinone (Compound 644);
(E)-6-(1-Ethyl-1-)propenyl-4-trifluoromethyl-2(1H)-quinolinone (Compound 645);
(Z)-6-(1-Ethyl-1-)propenyl-4-trifluoromethyl-2(1H)-quinolinone (Compound 646);
6-(1-Ethyl)propyl-4-trifluoromethyl-2(1H)-quinolinone (Compound 647);
6-(1-Isopropyl-2-methyl-1-)propenyl-4-trifluoromethyl-2(1H)-quinolinone (Compound 648);
6-(1-Isopropyl-2-methyl)propyl-4-trifluoromethyl-2(1H)-quinolinone (Compound 649);
(Z)-6-(1-Isobutyl-3-methyl-1-)butenyl-4-trifluoromethyl-2(1H)-quinolinone (Compound 650);
(E)-6-(1-Isobutyl-3-methyl-1-)butenyl-4-trifluoromethyl-2(1H)-quinolinone (Compound 651);
6-(1-Isobutyl-3-methyl)butyl-4-trifluoromethyl-2(1H)-quinolinone (Compound 652);

6-(1-Propyl)butyl-4-trifluoromethyl-2(1H)-thioquinolinone (Compound 653);

6-(3-Oxo-1-)cyclopentenyl-4-trifluoromethyl-2(1H)-quinolinone (Compound 654);

6-(3-Oxo-1-)cyclohexenyl-4-trifluoromethyl-2(1H)-quinolinone (Compound 655);

6-(3-Oxo-1-)cyclopentenyl-3-methyl-4-difluoromethyl-2(1H)-quinolinone (Compound 656);

6-(3-Oxo-1-)cyclohexenyl-3-methyl-4-difluoromethyl-2(1H)-quinolinone (Compound 657);

(±)-6-(3-Hydroxy-1-)cyclohexenyl-4-trifluoromethyl-2(1H)-quinolinone (Compound 658);

6-(1-Hydroxy-1,1-diphenyl)methyl-4-trifluoromethyl-2(1H)-quinolinone (Compound 659);

6-Diphenylmethyl-4-trifluoromethyl-2(1H)-quinolinone (Compound 660);

6-(3-hydroxy-3-methyl-1-)butynyl-4-trifluoromethyl-2(1H)-quinolinone (Compound 661);

6-(1-Hydroxy)cyclopentyl-1,4-dihydro-4,4-dimethyl-1,3-benzo[d]oxazin-2-one (Compound 662);

6-Bromo-1,4-dihydro-4,4-dimethyl-1,3-benzo[d]oxazin-2-one (Compound 663);

6-(1-Cyclopentenyl)-1,4-dihydro-4,4-dimethyl-1,3-benzo[d]oxazin-2-one (Compound 664);

6-Cyclopentyl-1,4-dihydro-4,4-dimethyl-1,3-benzo[d]oxazin-2-one (Compound 665);

6-(1-Hydroxy)cyclohexyl-1,4-dihydro-4,4-dimethyl-1,3-benzo[d]oxazin-2-one (Compound 666);

6-(1-Cyclohexenyl)-1,4-dihydro-4,4-dimethyl-1,3-benzo[d]oxazin-2-one (Compound 667);

6-Cyclohexyl-1,4-dihydro-4,4-dimethyl-1,3-benzo[d]oxazin-2-one (Compound 668);

6-(1-Hydroxy)cycloheptyl-1,4-dihydro-4,4-dimethyl-1,3-benzo[d]oxazin-2-one (Compound 669);

6-(1-Cycloheptenyl)-1,4-dihydro-4,4-dimethyl-1,3-benzo[d]oxazin-2-one (Compound 670);

6-(1-Cycloheptyl)-1,4-dihydro-4,4-dimethyl-1,3-benzo[d]oxazin-2-one (Compound 671);

6-(2,6,6-Trimethyl-1-)cyclohexenyl-1,4-dihydro-4,4-dimethyl-1,3-benzo[d]oxazin-2-one (Compound 672);

(±)-6-(3,3,5-Trimethyl-1-)cyclohexenyl-1,4-dihydro-4,4-dimethyl-1,3-benzo[d]oxazin-2-one (Compound 673);

(±)-6-(3,5,5-Trimethyl-1-)cyclohexenyl-1,4-dihydro-4,4-dimethyl-1,3-benzo[d]oxazin-2-one (Compound 674);

(±)-6-(5-Methyl-1-)cyclohexenyl-1,4-dihydro-4,4-dimethyl-1,3-benzo[d]oxazin-2-one (Compound 675);

(±)-6-(3-Methyl-1-)cyclohexenyl-1,4-dihydro-4,4-dimethyl-1,3-benzo[d]oxazin-2-one (Compound 676);

(±)-6-(2,6-Dimethyl-1-)cyclohexenyl-1,4-dihydro-4,4-dimethyl-1,3-benzo[d]oxazin-2-one (Compound 677);

(±)-6-(2-Bicyclo[2.2.1]heptenyl)-1,4-dihydro-4,4-dimethyl-1,3-benzo[d]oxazin-2-one (Compound 678);

(±)-6-(4,5-trans-Dimethyl-1-)cyclohexenyl-1,4-dihydro-4,4-dimethyl-1,3-benzo[d]oxazin-2-one (Compound 679);

(±)-6-(3,4-trans-Dimethyl-1-)cyclohexenyl-1,4-dihydro-4,4-dimethyl-1,3-benzo[d]oxazin-2-one (Compound 680);

6-(6,6-Dimethyl-1-)cyclohexenyl-1,4-dihydro-4,4-dimethyl-1,3-benzo[d]oxazin-2-one (Compound 681);

6-(5,5-Dimethyl-1-)cyclopentenyl-1,4-dihydro-4,4-dimethyl-1,3-benzo[d]oxazin-2-one (Compound 682);

(±)-6-(3,3,5-cis-Trimethyl)cyclohexyl-1,4-dihydro-4,4-dimethyl-1,3-benzo[d]oxazin-2-one (Compound 683);

(±)-6-(3,3,5-trans-Trimethyl)cyclohexyl-1,4-dihydro-4,4-dimethyl-1,3-benzo[d]oxazin-2-one (Compound 684);

(±)-6-(3-cis-Methyl)cyclohexyl-1,4-dihydro-4,4-dimethyl-1,3-benzo[d]oxazin-2-one (Compound 685);

(±)-6-(3-trans-Methyl)cyclohexyl-1,4-dihydro-4,4-dimethyl-1,3-benzo[d]oxazin-2-one (Compound 686);

(±)-6-(2,6-cis,cis-Dimethyl)cyclohexyl-1,4-dihydro-4,4-dimethyl-1,3-benzo[d]oxazin-2-one (Compound 687);

(E)-6-1,4-Dimethyl-1-)pentenyl-1,4-dihydro-4,4-dimethyl-1,3-benzo[d]oxazin-2-one (Compound 688);

6-(1-Cyclohexenyl)-1,4-dihydro-4,4-dimethyl-1,3-benzo[d]oxazin-2-thione (Compound 689);

6-(3-Oxo-1-)cyclopentenyl-1,4-dihydro-4,4-dimethyl-1,3-benzo[d]oxazin-2-one (Compound 690);

6-(3-Oxo-1-)cyclohexenyl-1,4-dihydro-4,4-dimethyl-1,3-benzo[d]oxazin-2-one (Compound 691);

(±)-6-(3-Hydroxy-1-)cyclohexenyl-1,4-dihydro-4,4-dimethyl-1,3-benzo[d]oxazin-2-one (Compound 692);

(±)-6-(3-cis-Hydroxy)cyclohexyl-1,4-dihydro-4,4-dimethyl-1,3-benzo[d]oxazin-2-one (Compound 693);

(±)-6-(3-Butyl-3-hydroxy-1-)cyclohexenyl-1,4-dihydro-4,4-dimethyl-1,3-benzo[d]oxazin-2-one (Compound 694);

6-(3-Oxo-1-)cyclohexenyl-1,4-dihydro-4,4-dimethyl-1,3-benzo[d]oxazin-2-thione (Compound 695);

6-Bromo-1,4-dihydro-4,4-dimethyl-1,3-benzo[d]oxazin-2-thione (Compound 696);

(±)-6-(3-Hydroxy-1-)cyclohexenyl-1,4-dihydro-4,4-dimethyl-1,3-benzo[d]oxazin-2-thione (Compound 697);

(±)-6-(1-Cyclohexenyl)-1,4-dihydro-4-methyl-1,3-benzo[d]oxazin-2-one (Compound 698);

(±)-6-Bromo-1,4-dihydro-4-methyl-1,3-benzo[d]oxazin-2-one (Compound 700);

6-(1-Cyclohexenyl)-1,4-dihydro-4,4,5-trimethyl-1,3-benzo[d]oxazin-2-one (Compound 701);

6-Bromo-1,4-dihydro-4,4,5-trimethyl-1,3-benzo[d]oxazin-2-one (Compound 704);

6-(1-Cyclohexenyl)-3,4-dihydro-4,4-dimethyl-2(1H)-quinolinone (Compound 705);

6-Bromo-3,4-dihydro-4,4-dimethyl-2(1H)-quinolinone (Compound 706);

6-Cyclohexyl-3,4-dihydro-4,4-dimethyl-2(1H)-quinolinone (Compound 707);

(±)-8-Bromo-6-(1-cyclohexenyl)-1,4-dihydro-4-trifluoromethyl-1,3-benzo[d]oxazin-2-one (Compound 708);

(±)-6,8-Dibromo-1,4-dihydro-4-trifluoromethyl-1,3-benzo[d]oxazin-2-one (Compound 711);

5-(3-Oxo-1-)cyclohexenyl-3,3-dimethyl-2-indolone (Compound 712);

5-Bromo-3,3-dimethyl-2-indolone (Compound 542); (±)-5-(3-Hydroxy-1-)cyclohexenyl-3,3-dimethyl-2-indolone (Compound 714);

(±)-5-(3-Oxocyclohexyl)-3,3-dimethyl-2-indolone (Compound 715);

(±)-5-(3-Oxocyclohexyl)-3,3-dimethyl-2-indolone (Compound 544); 5-Cyclohexyl-3,3-spirocyclohexyl-2-indolone (Compound 716);

5-Bromo-3,3-spirocyclohexyl-2-indolone (Compound 717);

5-Cyclopentyl-3,3-spirocyclohexyl-2-indolone (Compound 718);
6-(1-Hydroxycyclohexyl)-2(3H)-benzothiozolone (Compound 719);
6-Cyclohexenyl-2(3H)-benzothiozolone (Compound 720);
3,4-Dihydro-6-isopropyl-3-methyl-2(1H)-quinazolinone (Compound 721);
6-Bromo-3,4-dihydro-3-methyl-2(1H)-quinazolinone (Compound 722);
1-Benzyl-6-bromo-3,4-dihydro-3-methyl-2(1H)-quinazolinone (Compound 723);
1-Benzyl-6-cyclohexyl-3,4-dihydro-3-methyl-2(1H)-quinazolinone (Compound 724);
6-(2,3-Difluoro)phenyl-4-trifluoromethyl-2(1H)-quinolinone (Compound 725);
4-Trifluoromethyl-6-(3-nitro)phenyl-2(1H)-quinolinone (Compound 727);
4-Trifluoromethyl-6-(3,5-dichloro)phenyl-2(1H)-quinolinone (Compound 728);
4-Trifluoromethyl-6-(3-fluoro-5-N-hydroxyliminomethyl)phenyl-2(1H)-quinolinone (Compound 729);
4-Trifluoromethyl-6-(3-fluoro-5-formylmethylphenyl)-2(1H)-quinolinone (Compound 730);
4-Trifluoromethyl-6-(3-fluoro-5-cyano)phenyl-2(1H)-quinolinone (Compound 731);
4-Trifluoromethyl-6-(3-fluoro-5-chloro)phenyl-2(1H)-quinolinone (Compound 732);
4-Trifluoromethyl-6-(4-hydroxymethyl)phenyl-2(1H)-quinolinone (Compound 734);
4-Trifluoromethyl-6-(3-acetylphenyl)-2(1H)-quinolinone (Compound 735);
4-Trifluoromethyl-6-(4-ethylphenyl)-2(1H)-quinolinone (Compound 736);
4-Trifluoromethyl-6-(3-ethoxylphenyl)-2(1H)-quinolinone (Compound 737);
4-Trifluoromethyl-6-(3-methylphenyl)-2(1H)-quinolinone (Compound 738);
4-Trifluoromethyl-6-(3-trifluoromethylphenyl)-2(1H)-quinolinone (Compound 739);
4-Trifluoromethyl-6-(3-chlorophenyl)-2(1H)-quinolinone (Compound 740);
4-Trifluoromethyl-6-(3-fluorophenyl)-2(1H)-quinolinone (Compound 741); 4-Trifluoromethyl-6-(2-methylphenyl)-2(1H)-quinolinone (Compound 742);
4-Trifluoromethyl-6-(4-formyl)phenyl-2(1H)-quinolinone (Compound 743);
4-Trifluoromethyl-6-(4-tert-butylphenyl)-2(1H)-quinolinone (Compound 744);
4-Trifluoromethyl-6-(2-methoxyphenyl)-2(1H)-quinolinone (Compound 745);
4-Trifluoromethyl-6-(2-fluorophenyl)-2(1H)-quinolinone (Compound 746);
4-Trifluoromethyl-6-(4-acetylphenyl)-2(1H)-quinolinone (Compound 747);
4-Trifluoromethyl-6-(4-methylphenyl)-2(1H)-quinolinone (Compound 748);
4-Trifluoromethyl-6-(4-fluorophenyl)-2(1H)-quinolinone (Compound 749);
4-Trifluoromethyl-6-(4-methoxyphenyl)-2(1H)-quinolinone (Compound 750);
4-Trifluoromethyl-6-(3,5-bis-trifluoromethyl)phenyl-2(1H)-quinolinone (Compound 751);
4-Trifluoromethyl-6-(4-trifluoromethoxyphenyl)-2(1H)-quinolinone (Compound 752);
4-Trifluoromethyl-6-(2,4-dichlorophenyl)-2(1H)-quinolinone (Compound 753);
3-Fluoro-4-trifluoromethyl-6-(2-fluorophenyl)-2(1H)-quinolinone (Compound 754);
3-Fluoro-4-trifluoromethyl-6-(2,4-dichlorophenyl)-2(1H)-quinolinone (Compound 755);
4-Trifluoromethyl-6-(4-hydroxyphenyl)-2(1H)-quinolinone (Compound 756);
6-Bromo-4-methyl-2(1H)-quinolinone (Compound 757);
4-Methyl-6-(3-methoxyphenyl)-2(1H)-quinolinone (Compound 758);
4-Methyl-6-(3B-chlorophenyl)-2(1H)-quinolinone (Compound 759);
4-Methyl-6-(3-chloro-2-methylphenyl)-2(1H)-quinolinone (Compound 760);
4-Methyl-6-(2,3-dichlorophenyl)-2(1H)-quinolinone (Compound 761);
4-Methyl-6-(2,4-dichlorophenyl)-2(1H)-quinolinone (Compound 762);
4-Methyl-6-(2-methylphenyl)-2(1H)-quinolinone (Compound 763);
4-Trifluoromethyl-6-phenyl-2(1H)-quinolinone (Compound 764);
4-Trifluoromethyl-6-propio-2(1H)-quinolinone (Compound 765);
4-Trifluoromethyl-6-(1-ethylaminopropyl)-2(1H)-quinolinone (Compound 767);
4-Trifluoromethyl-6-(1-N-ethyl-N-methylaminopropyl)-2(1H)-quinolinone (Compound 768);
4-Trifluoromethyl-6-(1-hydroxy-1-methyl-2-oxopropyl)-2(1H)-quinolinone (Compound 769);
4-Trifluoromethyl-6-(4,4,4-trifluoro-1(E)-butenyl)-2(1H)-quinolinone (Compound 771);
4-Trifluoromethyl-6-(4,4,4-trifluorobutyro)-2-isopropyloxyquinoline (Compound 772);
4-Trifluoromethyl-6-(1-hydroxy-4,4,4-trifluorobutyl)-2-isopropyloxyquinoline (Compound 773);
4-Trifluoromethyl-6-(1-(3,3,3-trifluoropropyl)-1(E)-propenyl)-2(1H)-quinolinone (Compound 774);
4-Trifluoromethyl-6-(1-ethyl-1-hydroxy-4,4,4-trifluorobutyl)-2-isopropyloxyquinoline (Compound 775);
4-Trifluoromethyl-6-(1-ethyl-4,4,4-trifluoro-1(E)-butenyl)-2(1H)-quinolinone (Compound 776);
4-Trifluoromethyl-6-(1-ethyl-4,4,4-trifluoro-1(Z)-butenyl)-2(1H)-quinolinone (Compound 777);
2-Chloro-4-trifluoromethyl-6-(bis-N,N-2,2,2-trifluoroethyl)aminoquinoline (Compound 778);
2-Methoxy-4-trifluoromethyl-6-(bis-2,2,2-trifluoroethyl)aminoquinoline (Compound 779);
2-Isopropyloxy-4-trifluoromethyl-6-(bis-2,2,2-trifluoroethyl)aminoquinoline (Compound 780);
2-Ethoxy-4-trifluoromethyl-6-(bis-2,2,2-trifluoroethyl)aminoquinoline (Compound 781);
2-Acetyloxy-4-trifluoromethyl-6-(bis-2,2,2-trifluoroethyl)aminoquinoline (Compound 782);
2-(2-Dimethylamino)ethoxy-4-trifluoromethyl-6-(bis-2,2,2-trifluoroethyl)aminoquinoline (Compound 783);

2-Isobutyryloxy-4-trifluoromethyl-6-(bis-2,2,2-trifluoroethyl)aminoquinoline (Compound 784);
2-(2,2-Dimethyl)propyryloxy-4-trifluoromethyl-6-(bis-2,2,2-trifluoroethyl)aminoquinoline (Compound 785);
2-N,N-Dimethylcarbamyloxy-4-trifluoromethyl-6-(bis-2,2,2-trifluoroethyl)aminoquinoline (Compound 786);
2-Cyano-4-trifluoromethyl-6-(bis-2,2,2-trifluoroethyl)aminoquinoline (Compound 787);
4-Trifluoromethyl-6-(bis-2,2,2-trifluoroethyl)amino-2(1H)-quinolinone oxime (Compound 788);

Representative PR modulator compounds (i.e., agonists and antagonists) according to the present invention include:
6-(N-Ethyl-N-2,2-dimethylpropyl)amino-4-trifluoromethyl-2(1H)-quinolinone (Compound 242);
(±)-6-(N-Propyl-N-1-methylbutyl)amino-4-trifluoromethyl-2(1H)-quinolinone (Compound 251);
6-Cyclohexyl-4-trifluoromethyl-2(1H)-thioquinolinone (Compound 631);
6-(1-Cyclohexenyl)-1,4-dihydro-4,4-dimethyl-1,3-benzo[d]oxazin-2-one (Compound 667);
-6-(1-Cycloheptyl)-1,4-dihydro-4,4-dimethyl-1,3-benzo[d]oxazin-2-one (Compound 671);
6-(1-Cyclohexenyl)-1,4-dihydro-4,4-dimethyl-1,3-benzo[d]oxazin-2-thione (Compound 689);
6-(3-Oxo-1-)cyclohexenyl-1,4-dihydro-4,4-dimethyl-1,3-benzo[d]oxazin-2-thione (Compound 695);
(±)-6-(3-Hydroxy-1-)cyclohexenyl-1,4-dihydro-4,4-dimethyl-1,3-benzo[d]oxazin-2-thione (Compound 697);
6-(2,3-Difluoro)phenyl-4-trifluoromethyl-2(1H)-quinolinone (Compound 725);
4-Trifluoromethyl-6-(3-nitro)phenyl-2(1H)-quinolinone (Compound 727);
4-Trifluoromethyl-6-(3-fluoro-5-cyano)phenyl-2(1H)-quinolinone (Compound 731);
4-Trifluoromethyl-6-(3-acetylphenyl)-2(1H)-quinolinone (Compound 735).

The sequences of steps for several general schemes to synthesize the compounds of the present invention are shown below. In each of the Schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulas I through XXXIII also comprise potential substituents for the analogous positions on the structures within the Schemes.

Preparation of Quinolinone Compounds from Anilines

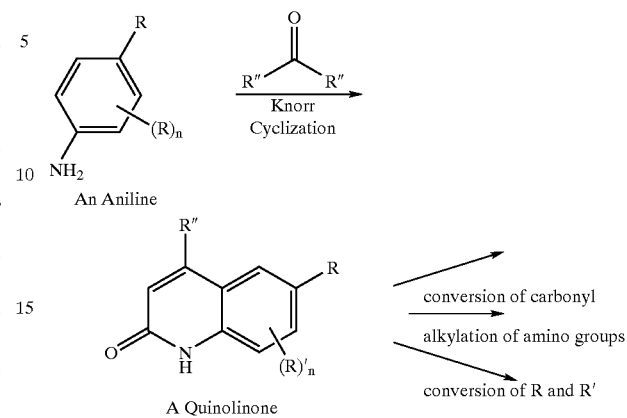

The above reaction-sequence shows the general formulation of quinolinone compounds which are modulators of androgen and progesterone receptors. In the above reaction sequence, an aniline compound is converted to a quinolinone compound by a Knorr cyclization with an alpha-keto ester compound. The quinolinone may then be converted to various derivatives including but not limited to thioquinolinones, quinolines, alkylated quinolinones, and functionalized quinolinones. In the above scheme, R represents various aromatic substituents contained on the aniline compound known to those skilled in the art. The R group on the quinolinone compounds may be interconverted to various substituents including but not limited to nitro, amino, alkylamino, halogen, alkyl, aryl, dialkylamino, pyrrole, and oxazolidene groups by various chemical reactions known to those skilled in the art. The R' group represents various aromatic subsitutents known to those skilled in the art and may originate from any of the 3, 5, and 6 positions on the ring, and n may be from 0 to 3. The R' groups on the quinolinone compounds may also be interconverted to various substitutents by chemistry known to those skilled in the art to form derivative quinolinone compounds. Schemes I through VI below show various preferred embodiments of the current invention.

Scheme I

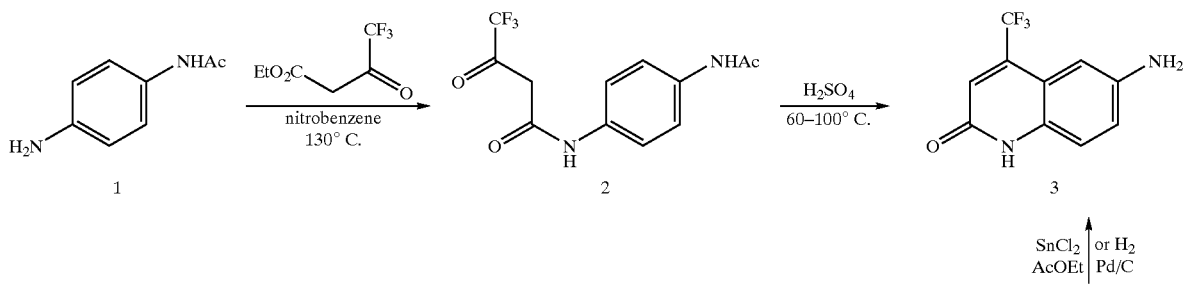

-continued

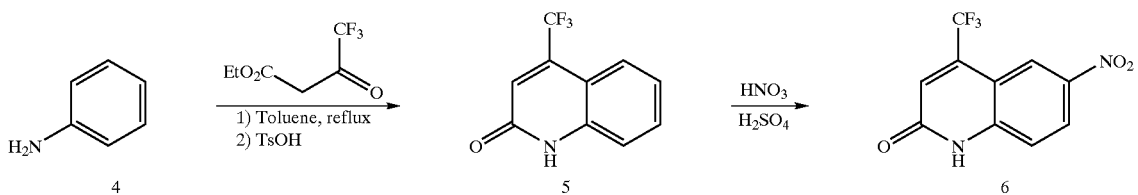

Scheme I describes a method to prepare quinolinone compounds such as Structure 5, nitro-quinolinone compounds such as Structure 6, and amino-2-quinolinone compounds such as Structure 3 through modified Knorr reactions. Thermal condensation of a 4-aminoacetanilide (Structure 1) with a 3-ketoester, for example, ethyl 4,4,4-trifluoroacetoacetate in nitrobenzene affords a bis-amide such as Structure 2. When a bis-amide compound of Structure 2 is treated with concentrated sulfuric acid at 60–100° C., aminoquinolinone compounds of Structure 3 are produced. An alternate process of preparing 6-aminoquinolinone compounds such as Structure 3 starts with a similar Knorr reaction. The synthesis begins with reaction of an aniline such as Structure 4 and a 3-ketoester in refluxing toluene followed by treatment of a Lewis acid such as p-toluenesulfonic acid to produce a 2-quinolinone such as Structure 5. Classic nitration of the 2-quinolinone (e.g., Structure 5) selectively provides a 6-nitroquinolinone compound (e.g., Structure 6). Reduction of the nitroquinolinone such as Structure 6 under standard reduction conditions (e.g., metal catalyzed hydrogenation or tin chloride reduction) affords aminoquinolinone compounds such as Structure 3.

Scheme II

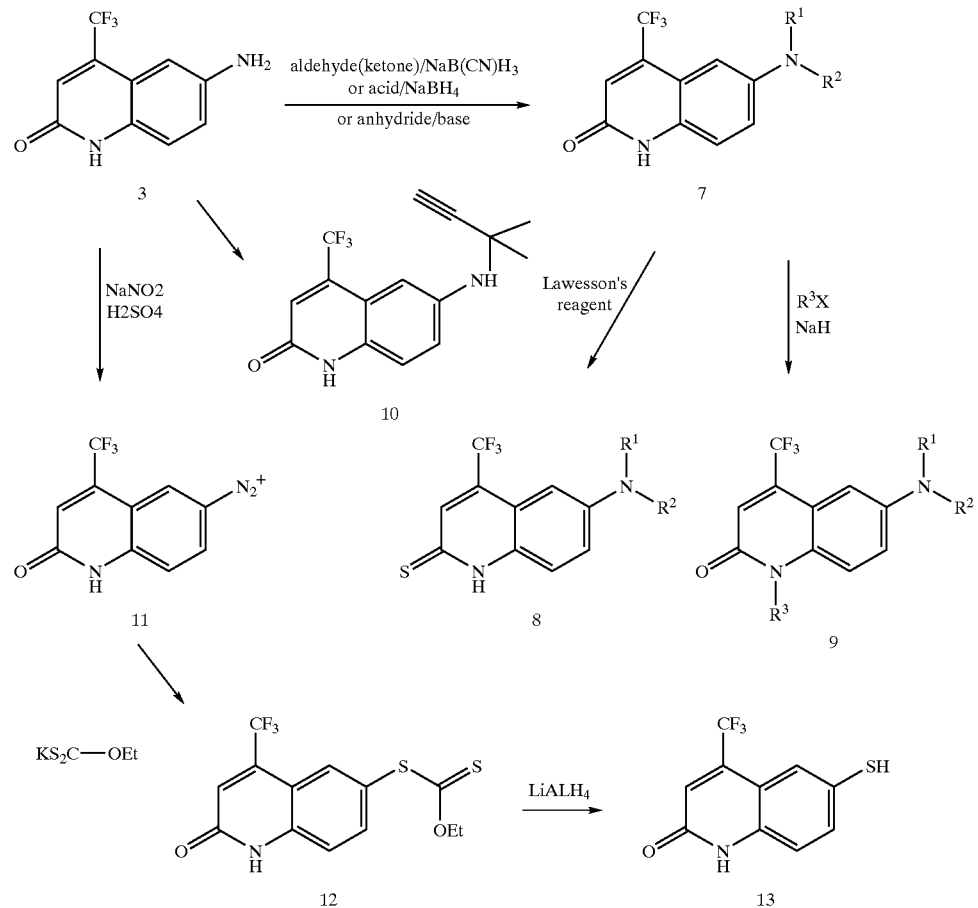

Scheme II describes the N-substitution of the 6-amino-2-quinolinone such as Structure 3 and the conversion of Structure 3 to mercapto analogues. A two-step sequential reductive alkylation of the aminoquinolinone (e.g., Structure 3) with an aldehyde or ketone or acid in the presence of a reducing agent, such as sodium cyanoborohydride or sodium borohydride affords compounds of Structure 7. Treatment of an amino-2-quinolinone compound (e.g., Structure 3) with an acylating agent, such as acetyl chloride or anhydride, in the presence of a base such as pyridine or triethylamine provides amides or sulfonamides compounds as shown in Structure 7. Treatment of quinolinones of Structure 7 with Lawesson's reagent provides a corresponding thioquinolinone compound of Structure 8. Treatment of compounds of Structure 7 with an alkylating agent such as alkyl iodide in the presence of sodium hydride in a polar solvent, such as tetrahydrofuran gives compounds of Structure 9. Direct alkylation of Structure 3 provides compounds of Structure 10. The mercapto analogues of Structures 12 and 13 are prepared through diazo intermediate of Structure 11.

Scheme III describes an alternate method for the syntheses of 6-amino compounds of Structures 7, 20, 21 and 22. The process begins with a step-wise Knorr reaction, in which 4-Bromoaniline (Structure 14) and a 3-ketoester such as the trifluoroacetoacetate are heated in reflux in toluene provides an amide such as Structure 15 and heating in concentrated sulfuric acid affords 4-bromoquinolinone such as Structure 16. Treatment of quinolinones such as Structure 16 with 2-iodopropane, catalyzed by cesium fluoride in DMF afford alkoxyquinoline compounds such as Structure 17. Palladium-catalyzed coupling reaction between bromoquinolines such as Structure 17 and alkylamines gives compounds of Structures 18 and 19. Hydrolysis of the quinoline compounds (Structures 18 and 19) in acidic con-

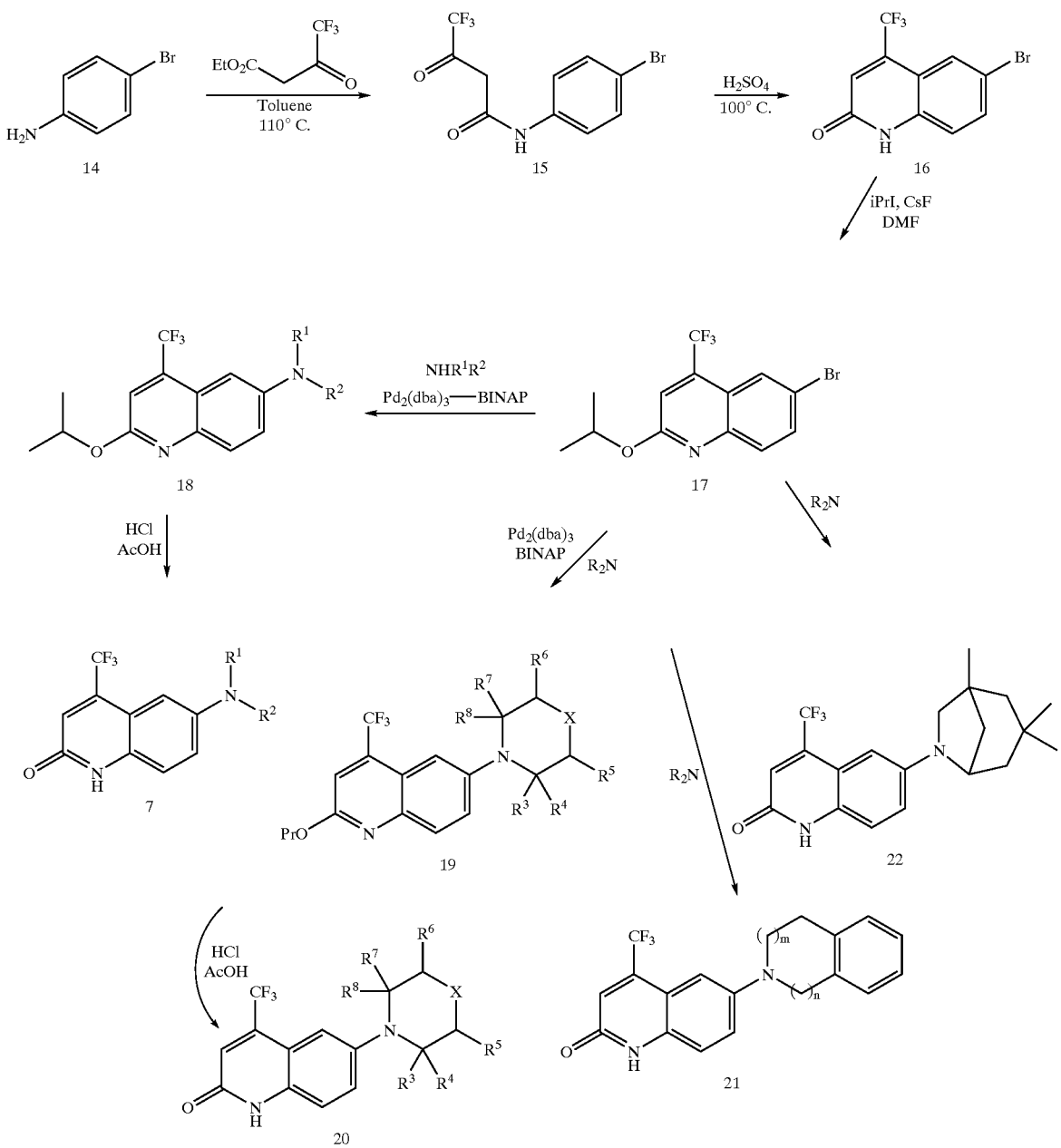

Scheme III dition provide compounds of Structures 7 and 20. Compounds of Structures 21 and 22 are prepared in a similar fashion.

Scheme IV

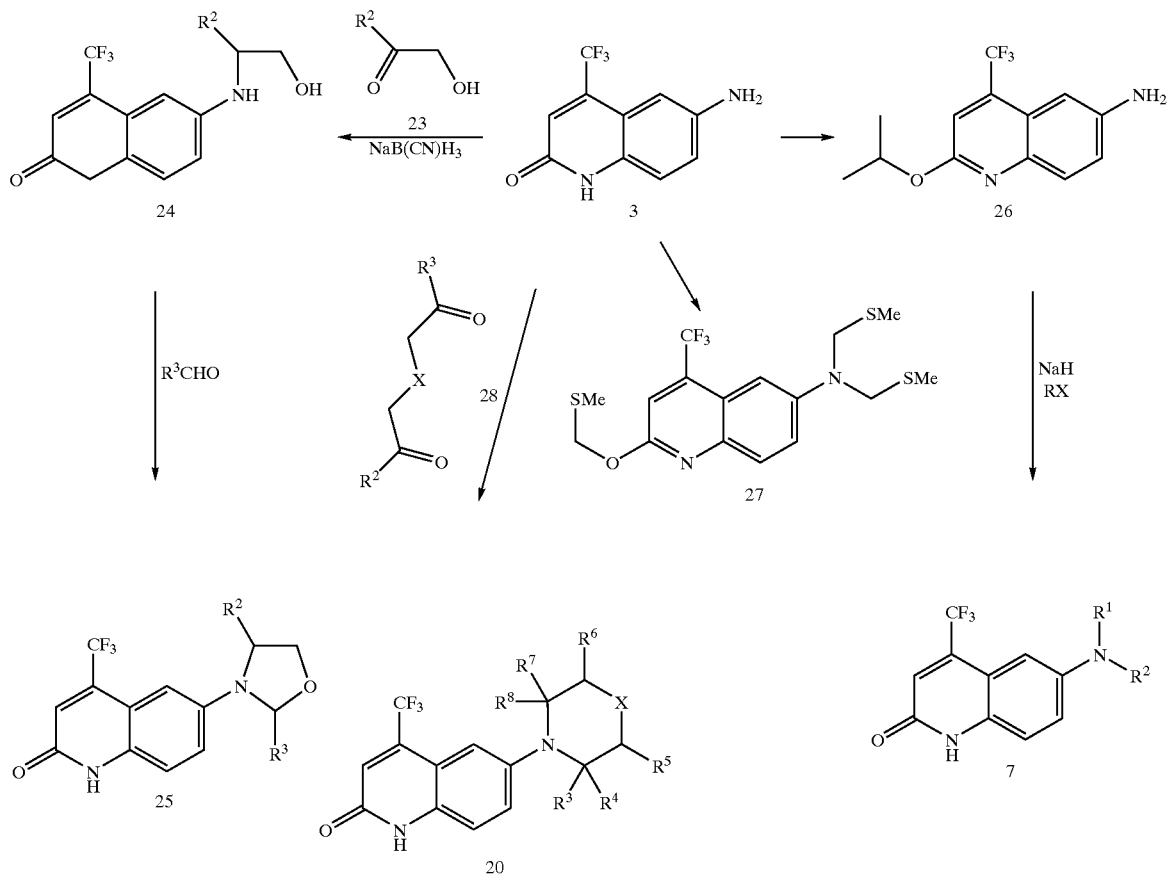

Scheme IV shows additional alkylation strategies of 6-aminoquinolinone of Structure 3 to provide 6-oxazolidine-quinolinone compounds (e.g., Structure 25), 6-cycloalkylamino-quinolinone compounds (e.g., Structure 20) and compounds of Structures 7 and 27.

The process of Scheme IV begins with reductive alkylation of an aminoquinolinone (e.g., Structure 3), with α-hydroxyketones of Structure 23 in the presence of a reducing agent such as sodium cyanoborohydride to provide compounds of Structure 24. Formation of an oxazolidine compound such as Structure 25 is carried out by treatment of an aminol compound such as Structure 24 with an aldehyde or its corresponding hydrate in the presence of an acid. Quinolinone compounds of Structure 20 are prepared by condensation of an aminoquinolinone (e.g., Structure 3) and a diketone such as Structure 23 in the presence of a reducing agent. Compounds such as Structure 7 are prepared by alkylation of quinoline intermediate of Structure 26 derived from Structure 3 with an alkyl halide. Direct alkylation of Structure 3 with halides affords mixture compounds of Structures 7 and 27.

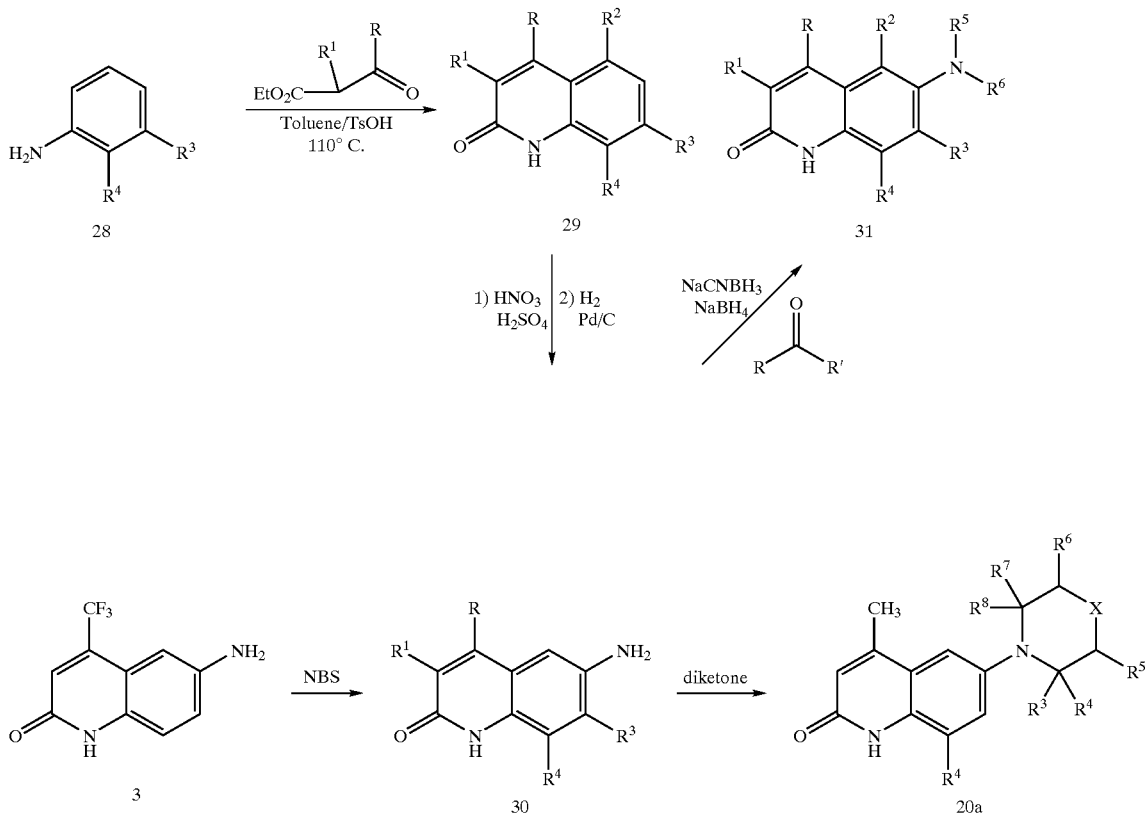

Scheme V shows the preparation of substituted quinolinones of Structures 20a and 31 from anilines of Structure 28 or 6-aminoquinolinones such as Structure 3. The process begins with a Knorr cyclization of a meta- or ortho-substituted aniline (e.g., Structure 28) with a 3-ketoester to afford compounds of Structure 29. Nitration of compounds such as Structure 29 followed by reduction of the nitro group affords predominantly 6-amino compounds of Structure 30. Alternately compounds of Structure 30 are also obtained by modification of 6-aminoquinolinones such as Structure 3. For example, bromination of compounds of Structure-3 with NBS provides a 7-bromo-2-quinolinone compound (e.g., Structure 30, where $R^3$=bromo). Quinolinone compounds as shown in Structures 20a and 31 are synthesized in a similar fashion as that described in Schemes II and IV from the substituted 6-amino-2-quinolinones of Structure 30.

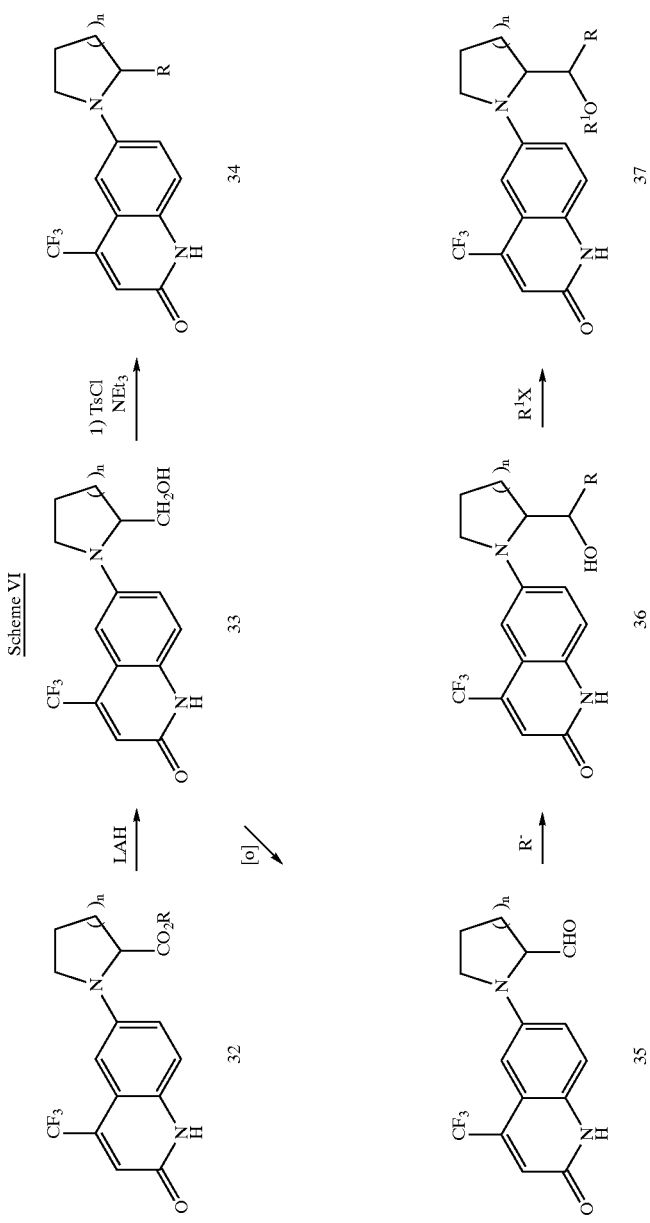

Scheme VI describes the side-chain modification of the 6-cycloamino-2-quinolinones of Structure 32. The process of Scheme VI starts with the reduction of an ester derivative of Structure 32 to give hydroxycompounds of Structure 33. Conversion of compounds of Structure 33 to tosylated analogues followed by nucleophilic substitution affords compounds of Structure 34. Oxidation of compounds of Structure 33 provides the formyl derivatives of Structure 35. Addition of a nucleophile to compounds of Structure 35 gives secondary alcohol analogues of Structure 36. Further manipulation affords compounds of Structure 37.

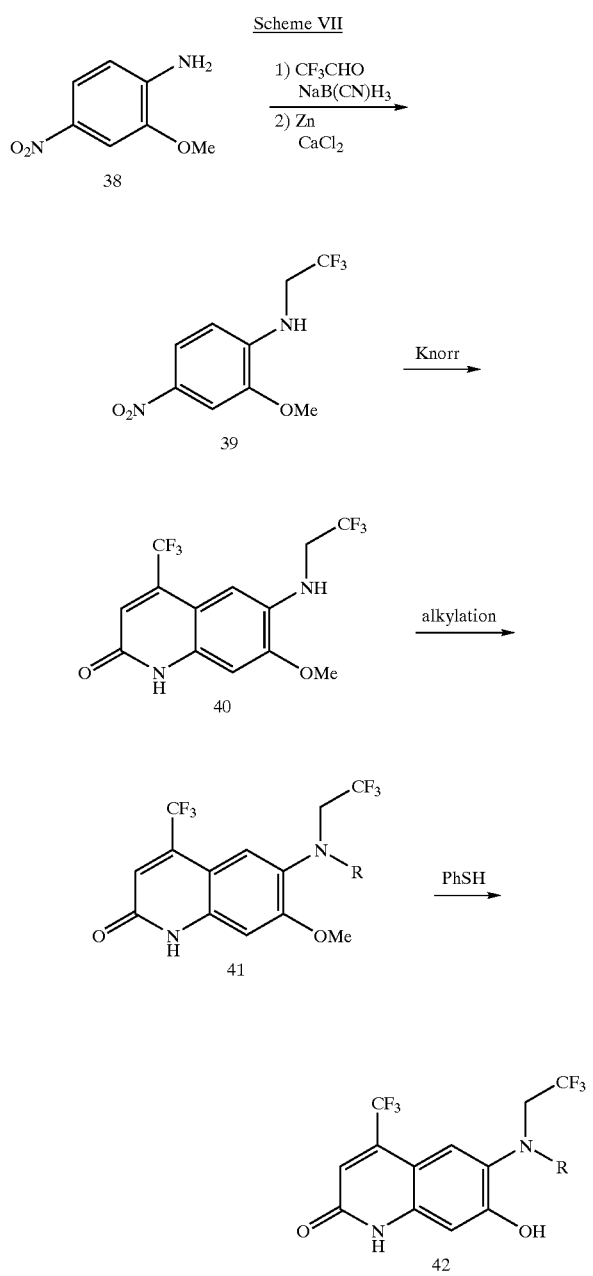

Scheme VII describes Knorr reactions of substituted anilines to produce functionalized quinolinone compounds. The process of Scheme VII starts with alkylation of an aniline compound such as Structure 38 with trifluoroacetaldehyde in the presence of sodium cyanoborohydride followed by zinc reduction to provide an alkylated bis-amine compound such as Structure 39. A typical Knorr procedure converts the alkylated amine compound 39 and ethyl 4,4,4-trifluoroacetoacetate to a quinolinone compound such as 40. Reductive alkylation of compounds of 40 provides a bis-alkylaminoquinolinone such as Structure 41. Treatment of compounds of Structure 41 with thiophenol affords 7-hydroxyquinolinone compounds such as 42.

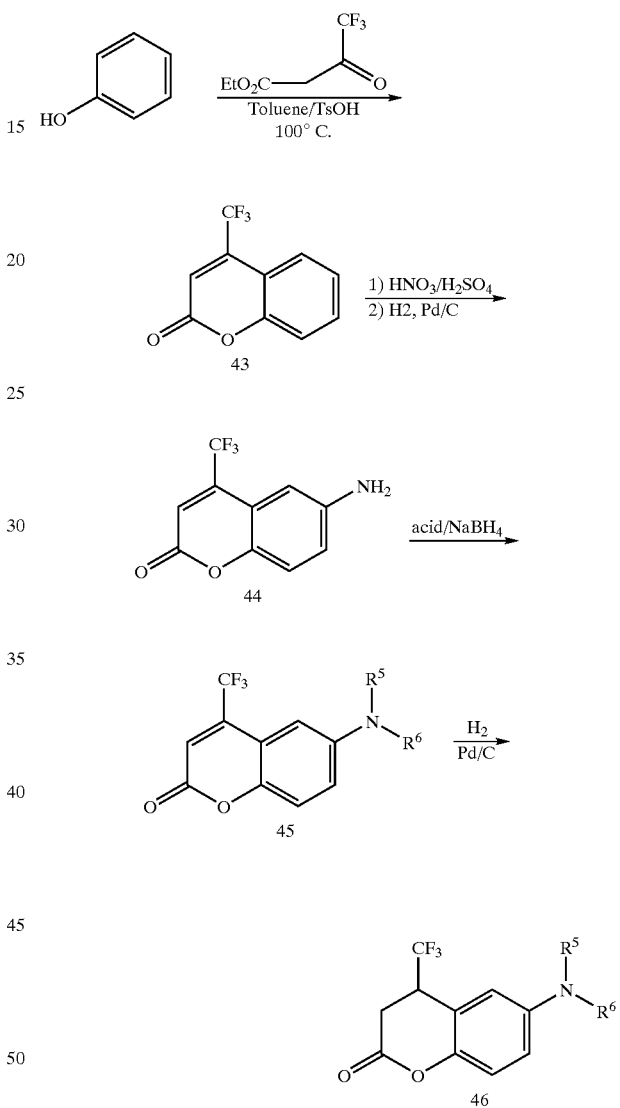

Scheme VIII describes the synthesis of 6-alkylaminocoumarins, as demonstrated by Structure 45, from phenol through a similar route as that described in Schemes I and II. A mixture of a phenol compound and a 3-ketoester such as ethyl 4,4,4-trifluoroacetoacetate are heated in refluxing toluene in the presence of TsOH to afford a coumarin compound e.g., Structure 43. Nitration of coumarin compounds (e.g., Structure 43) followed by hydrogenation give aminocoumarin compounds such as Structure 44. Sequential reductive alkylation provides dialkylamino-coumarin compounds as shown in Structure 45. Hydrogenation of a dialkylaminocoumarin compound (e.g., Structure 45) affords compounds Structure 46.

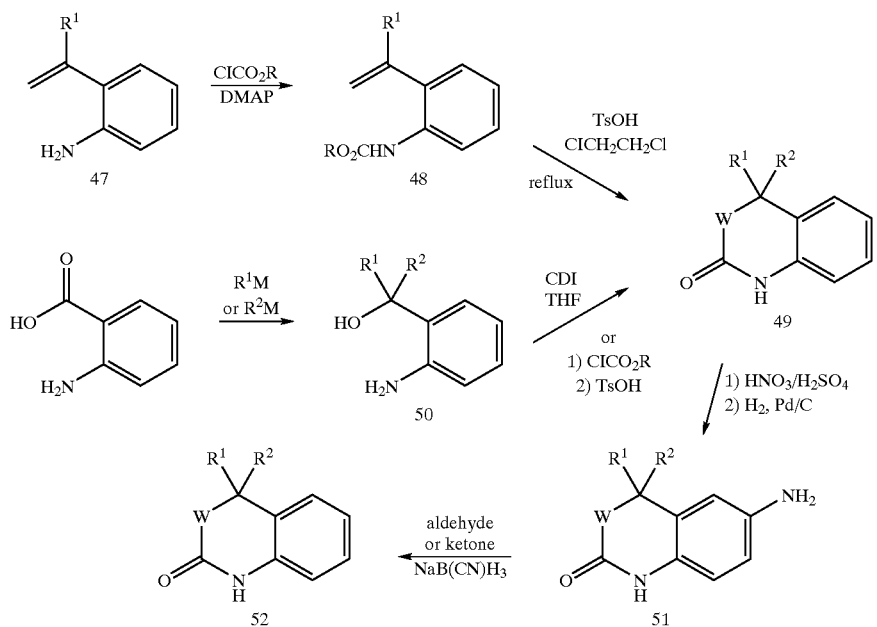

In another preferred embodiment, the syntheses of benzo-oxazinone compounds (e.g., Structure 49) and derivatives thereof (e.g., Structures 51 and 52) are shown in Scheme IX.

The process of Scheme IX begins with the treatment of an alkenylaniline compound such as Structure 47 with chloroformate in the presence of DMAP in THF to produce carbamates such as Structure 48. Benzoxazinone compounds such as Structure 49 (W=O) are produced by p-tolylsulfonic acid catalyzed intra-molecular cyclization of a carbamate (e.g., Structure 48).

An alternate synthesis of benzo-oxazinone compounds of Structure 49 is also shown in Scheme IX. In this synthetic route, carbon nucleophiles are added to 2-aminobenzoic acid to give the amino-alcohol compound 50, which is converted to an aminobenzo-oxazinone compound such as Structure 49 by either 1,1'-carbonyldiimidazole in THF or the carbonate-cyclization route as described above. A classic nitration reaction of the aromatic benzoxazinone compound by nitric acid in concentrate sulfuric acid followed by palladium catalyzed hydrogenation produces amino compounds such as Structure 51. A two-step sequential reductive alkylation as described previously produces dialkylamine-benzoxazinone compounds as shown in Structure 52.

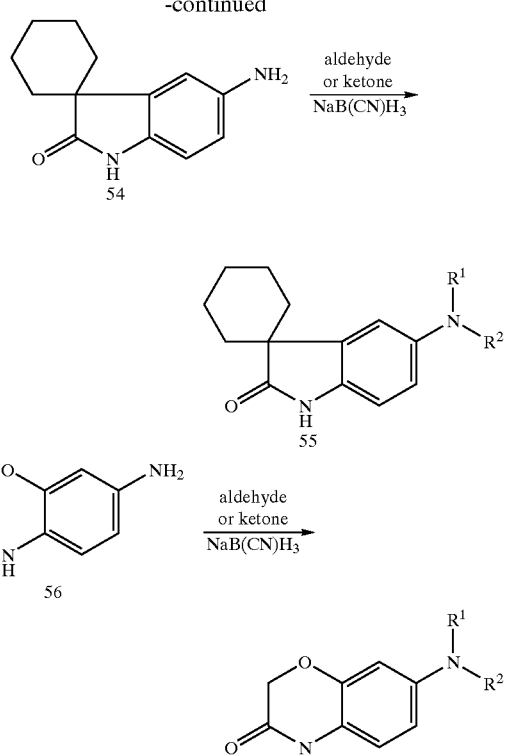

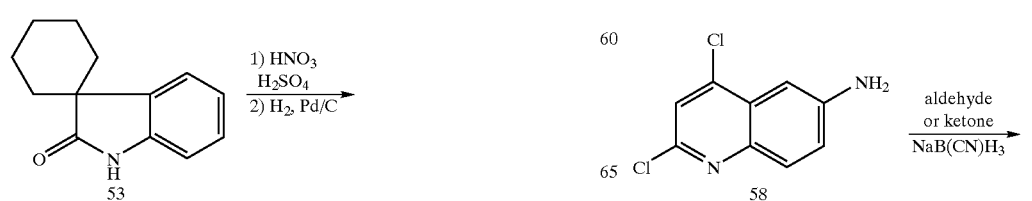

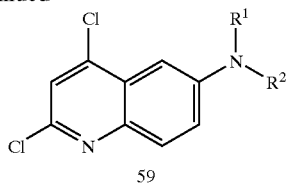

In another preferred embodiment, bioisosteres of 6-amino-2-quinolinones such as 5-amino-oxinole, 6-amino-benzoxazinone and quinoline compounds, which are useful AR and PR modulators, are prepared from a corresponding bicyclic compound. The bicyclic compounds such as Structures 53, 56 and 58 are prepared by synthetic methods known to those skilled in the art.

Scheme X describes a synthetic process for preparing 5-bisalkylamino-oxindole compounds such as Structure 55 and 6-bisalkylated compounds of Structures 57 and 59. The method for preparing these compounds is described in Scheme IX and is analogous to the preparation of compounds such as Structure 52 from the corresponding quinolinone compound. The process involves sequential nitration, reduction and/or alkylation of the amine to produce compounds of Structures 55, 57 and 59.

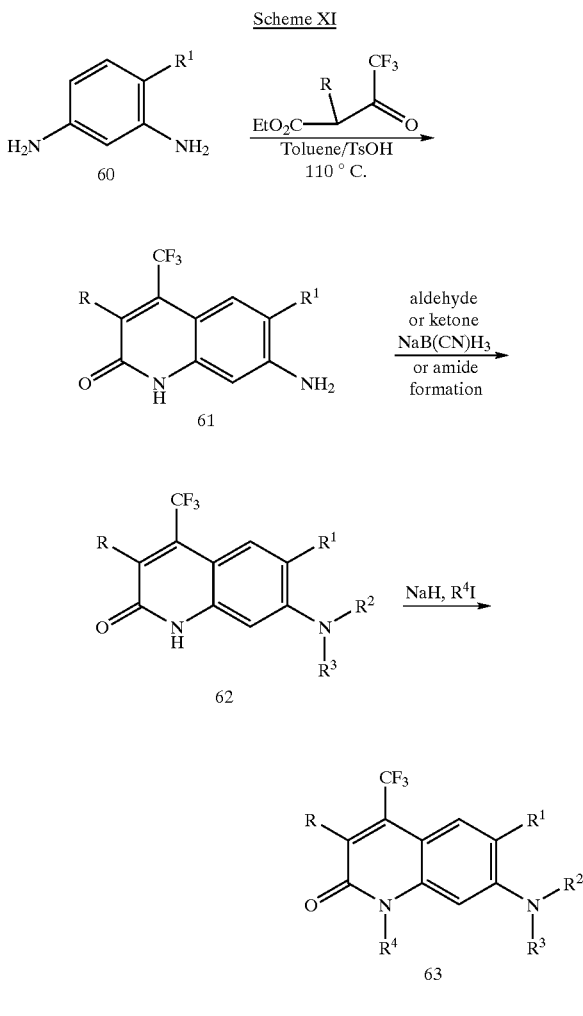

Scheme XI describes a preferred synthetic method to prepare 7-alkylamino-2-quinolinones such as Structure 63 via the Knorr reaction as previously described. The process of Scheme XI begins with a modified Knorr cyclization of 1,3-phenylenediamines of Structure 60 to give a 7-amino-quinolinone compound such as Structure 61. A sequential reductive alkylation of Structure 61 in a similar process as that described in Scheme II affords compounds such as Structure 62. Alkylation of quinolinone such as 62 with alkyl iodide in the presence of sodium hydride generates 1-alkyl quinolinone compounds such as Structure 63.

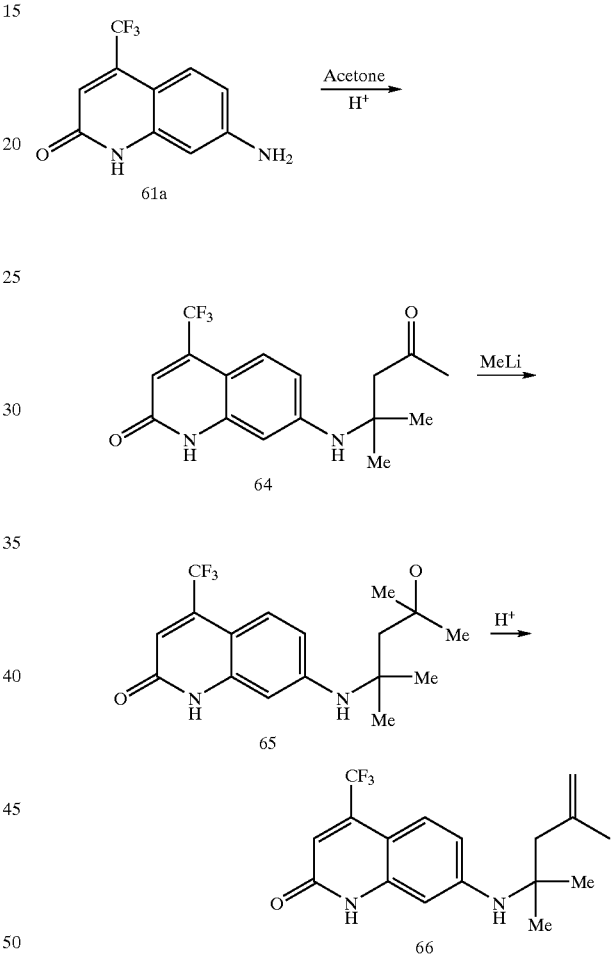

In another preferred aspect of the invention, alkylamino-quinolinone compounds (e.g., Structure 66) are prepared from a corresponding amino-quinolinone compound. Schemes XII, XIII and XIV describe the methods of introducing a quaternary carbon next to the amino position.

The process of Scheme XII begins with the treatment of a 7-aminoquinolinone such as Structure 61a with acetic acid in acetone to afford an alkyl amino-quinolinone compound such as Structure 64. Methyllithium addition to a compound such as Structure 64 in THF provides the corresponding alcohol adduct e.g., Structure 65. An acid catalyzed dehydration of an amino alcohol compound such as 65 gives an alkene amino-quinolinone compound such as 66.

Scheme XIII

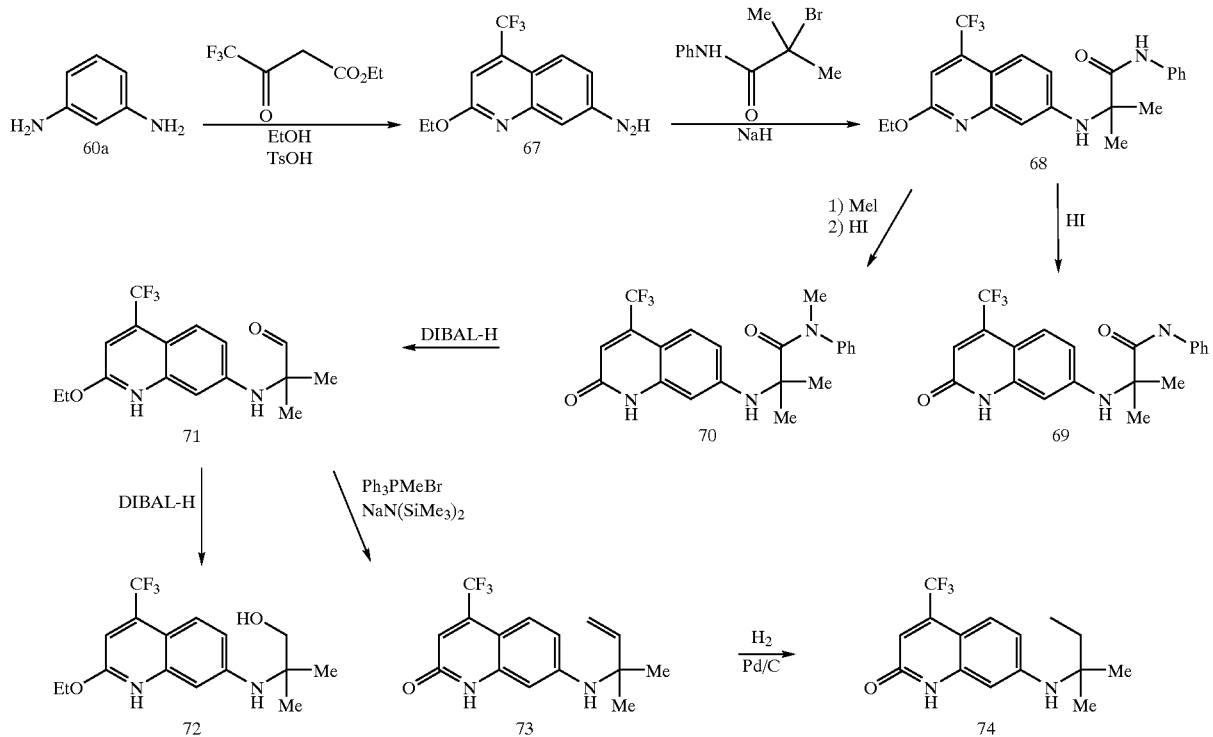

In another preferred reaction sequence, alkyl-quinolinones are produced by a Knorr cyclization of a diamine compound as previously described. Subsequent alkylation and oxidation produces alkyl-quinolinone compounds. The alkylamine-quinolinones may then be further converted to various derivative compounds by reactions known to those skilled in the art as exemplified in the examples below.

Scheme XIII describes an alternate procedure to synthesize 2-quinolinones with a quaternary carbon adjacent to the 7-nitrogen. The process of Scheme XIII begins with a typical Knorr cyclization of a 1,3-phenylenediamine with a α-ketoester, ethyl 4,4,4-trifluoroacetoacetate, to afford an aminoquinoline compound such as 67 as a minor product. Alkylation of an aminoquinoline compound such as 67 with an amide such as N-phenyl-α-bromoisobutyramide in the presence of sodium hydride affords an alkylated quinoline product such as 68 in good yield. Hydrolysis of an alkylated quinoline compound (e.g., Structure 68) with HI provides a 2-quinolinone such as 69. Methylation of an alkylated quinoline compound such as 68 with iodomethane in the presence of sodium hydride followed by HI mediated hydrolysis produces a quinolinone such as Structure 70. Reduction of an amide compound such as 70 with DIBAL-H affords an aldehyde compound such as 71 and an alcohol product such as 72. Wittig reaction of aldehydes such as 71 affords olefins such as Structure 73. Hydrogenation of an allylamino-quinolinone compound such as Structure 73 produces a corresponding alkylamino-quinolinone compound as shown in Structure 74.

Scheme XIV

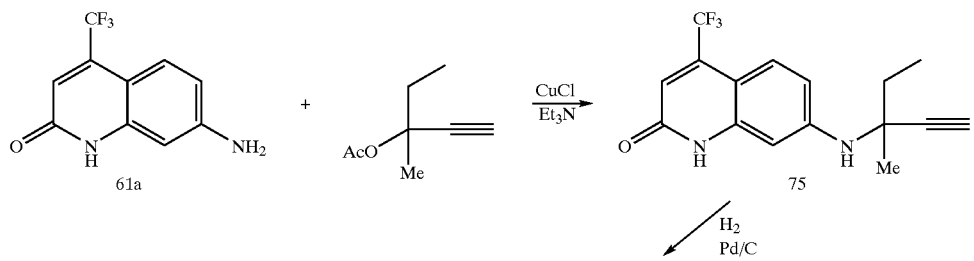

-continued

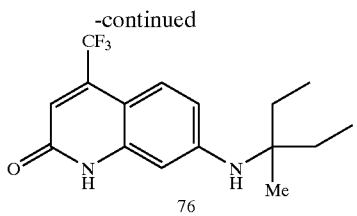

In another preferred aspect of the invention, alkylamino-quinolinone compounds are produced by copper chloride catalyzed substitution of an amino-quinolinone compound. Scheme XIV describes an alternate N-alkylation method for the preparation of alkylamino-quinolinone compounds. Treatment of an amino quinolinone compound such as 61a and propargyl acetate with copper chloride and a base such as triethylamine in THF affords alkylamine-quinolinone products such as 75. Hydrogenation of an amino-acetylene compound such as 75 provides an alkylamino quinolinone compound as shown in Structure 76 in excellent yield.

Scheme XV

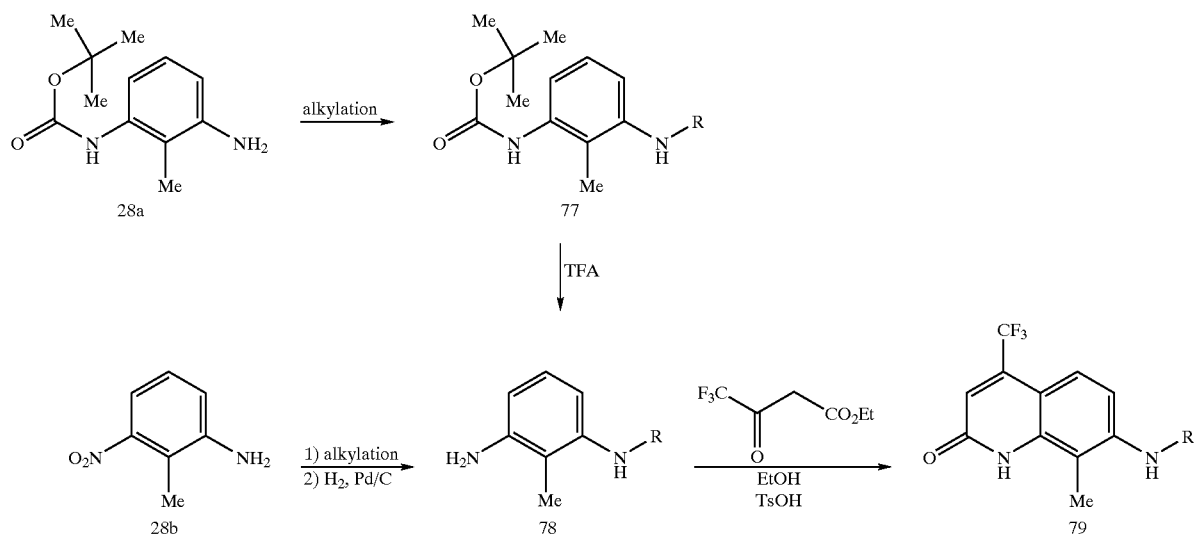

Alkyl-diamino compounds (e.g. Structure 78) are produced by two alternate synthetic methods in another preferred synthetic route as shown in Scheme XV. Alkylations of amino compounds as shown below are reactions known to those skilled in the art. The reaction as shown below is as an example of the preparation of these types of compounds.

The process of Scheme XV begins with alkylation of a mono-protected 1,3-phenylenediamine followed by trifluoroacetic acid (TFA) mediated de-protection to produce diamino compounds such as Structure 78. Alternately, alkylation of a 3-nitroaniline followed by a reduction of the nitro group generates the same intermediates of Structure 78. Knorr cyclization as previously described in the presence of a α-keto-ester such as ethyl 4,4,4-trifluoroacetoacetate affords compounds such as Structure 79 in good yield.

Scheme XVI

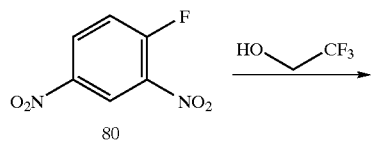

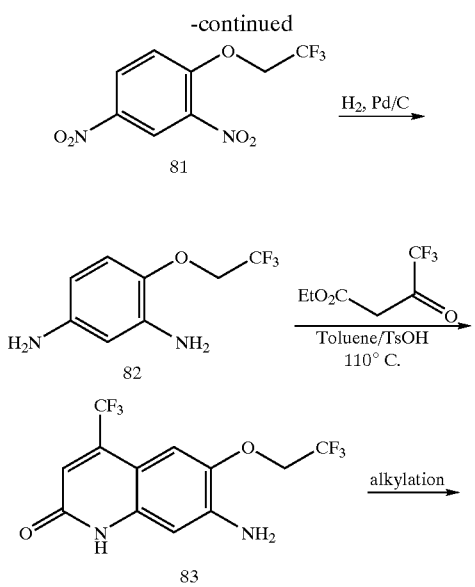

pounds are then further reacted to produce quinolinone compounds via the Knorr reaction as previously described. Scheme XVI describes a synthetic process for producing alkoxy-alkylamino-quinolinone compounds such as Structure 84.

The process starts with substitution of a bis-nitrofluorobenzene with 2,2,2-trifluoroethyanol in the presence of a base, such as sodium hydride to provide an alkoxy-nitrobenzene compound such as Structure 81. Conversion of bis-nitro groups to bis-amino groups is accomplished by hydrogenation or metal reduction to give aniline compounds such as Structure 82. A standard Knorr reaction with ethyl 4,4,4-trifluoroacetoacetate and p-tolylsufonic acid affords alkoxy-quinolinones such as Structure 83 in high yield. An alkoxy-amino-quinolinone compound such as 83 may subsequently be alkylated as previously described. For example, reductive alkylation of a compound such as Structure 83 with an aldehyde and sodium cyanoborohydride gives alkoxy-alkylamino-quinolinone compounds as shown in Structure 84.

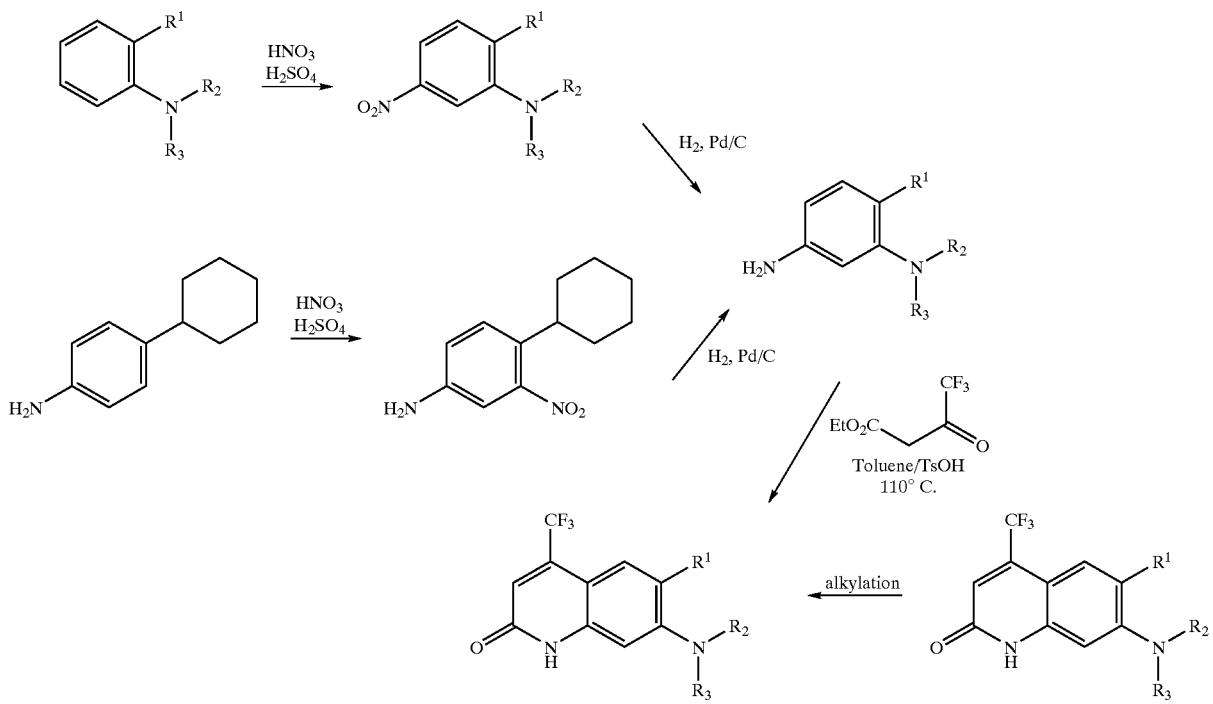

Substituted diamino compounds are produced in another preferred embodiment of the invention. The diamino com- In another preferred reaction, substituted diamine compounds (e.g., Structure 87) are produced by electrophilic aromatic substitution of activated aromatic amino-benzene rings. The substituted diamine compounds are then further reacted to produce quinolinone compounds (e.g., Structure 88) and subsequent quinolinone derivatives thereof (e.g., Structure 89) as previously described. Quinolinone compounds as shown in Scheme XVII are useful PR and AR modulators as described herein.

Scheme XVII describes processes to synthesize substituted alkylaminoquinolinone compounds such as 89. Treatment of ortho-substituted aniline such as Structure 85 or a 4-substituted aniline such as 90 with nitric acid in concentrated sulfuric acid generates meta-nitrated products such as 86 or 91 in high yield. Hydrogenation of the nitro group on compounds such as 86 or 91 provides the Knorr precursors as shown as Structure 87. Treatment of 1,3-phenylenediamines such as 87 with ethyl 4,4,4-trifluoroacetoacetate in refluxing toluene in the presence of a catalytic amount of acid, such as p-tolylsufonic acid, affords quinolinone compounds as shown in Structure 88. Additional alkylation at the 7-amino group provides more functionalized compounds such as Structure 89 as previously described.

Scheme XVIII above describes methods of preparing functionalized quinolinones. The process of Scheme XVIII begins with modified Knorr reactions of diamine 92 with ethyl 4,4,4-trifluoroacetoacetate. In the p-tolylsufonic acid catalyzed refluxing toluene condition quinolinone compounds such as 94 are major products. In an alternate synthesis, the reaction is carried out in refluxing ethanol, which produces compounds such as Structure 93 as major products. Compounds such as 93 may then be converted to

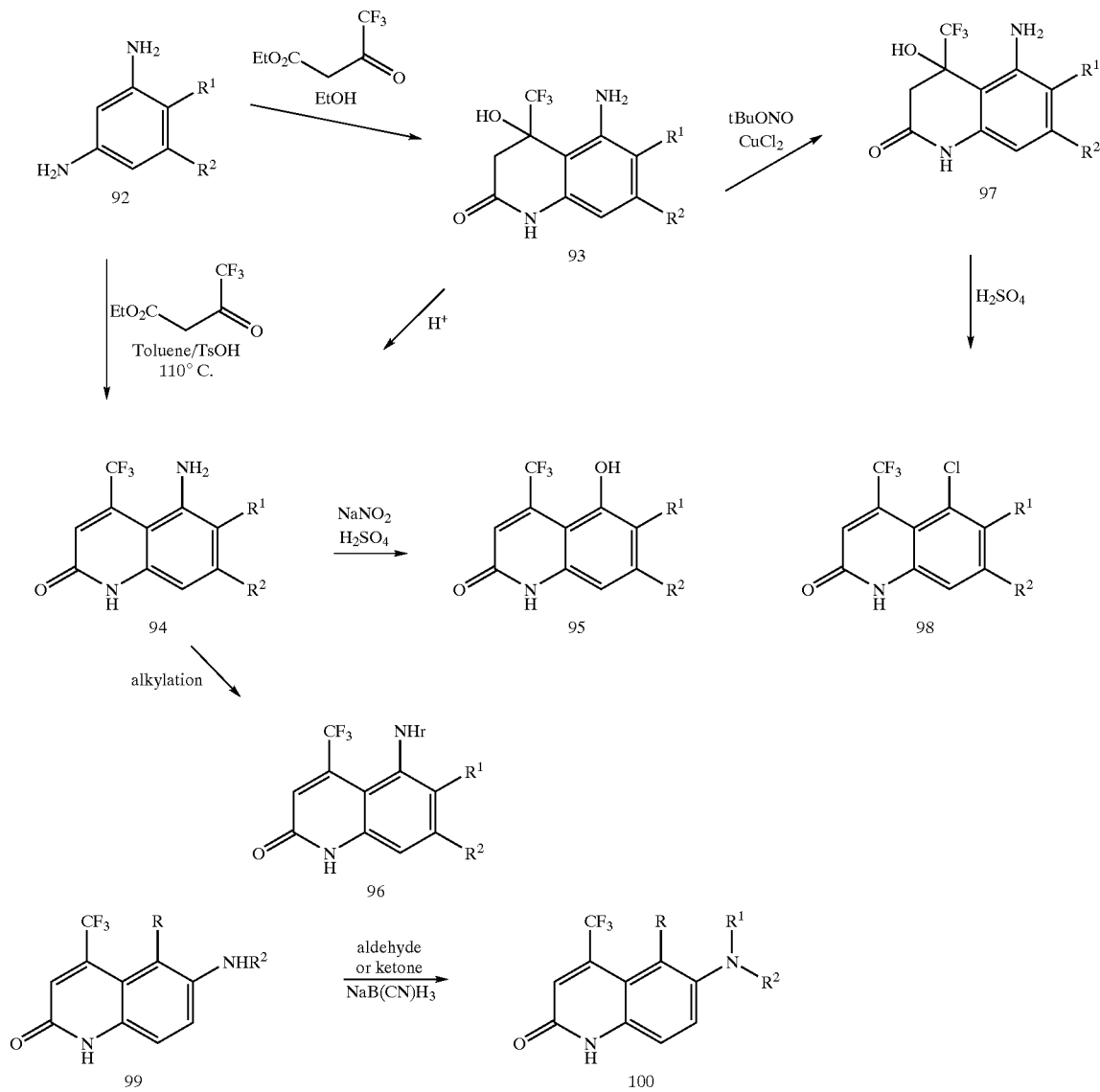

Scheme XVIII

In a preferred aspect of the invention, functionalized quinolinones or functionalized dihydro-quinolinones are prepared from the corresponding substituted diamino-benzene compound (e.g. Structure 92). The amino portion of the quinolinone and dihydro-quinolinone compounds (e.g. Structures 94 and 93), may then be converted to other functional groups by chemical reactions known to those skilled in the art. Examples of such conversions are demonstrated in Scheme XVIII, for example in the preparation of compounds such as 95, 96, 97 and 100.

quinolinones such as 94 by acid catalyzed dehydration. The 5-amino group of compounds 93 or 94 is converted to 5-hydroxy derivatives of Structure 95 by diazotization-hydrolysis conditions using sodium nitrite and sulfuric acid. A similar condition by sodium nitrite and chloride converts the 5-amino to 5-chloro derivatives of Structure 98. Reductive alkylation of compounds of Structures 94 and 99 affords compounds of Structures 96 and 100.

Scheme XIX

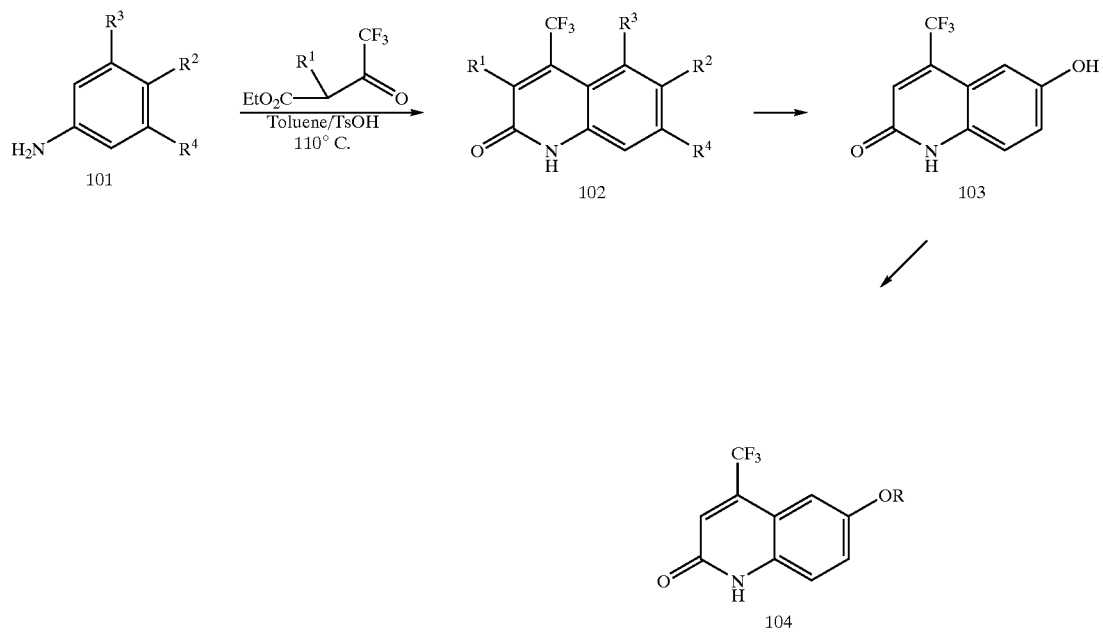

Another synthetic route into functionalized quinolinone compounds (e.g. Structures 102 and 104) is shown in Scheme XIX. Scheme XIX describes the synthesis of substituted quinolinone compounds such as Structures 102 and 104 under similar Knorr reaction conditions as that described in Scheme 1. The Knorr reaction may also be used on substituted aniline compounds (e.g. Structure 101) to produce functionalized quinolinone compounds such as Structure 102. The functionalized quinolinone compounds as shown above may then be converted to other functional groups to produce additional quinolinone derivatives such as compounds of Structure 104 as described herein.

-continued

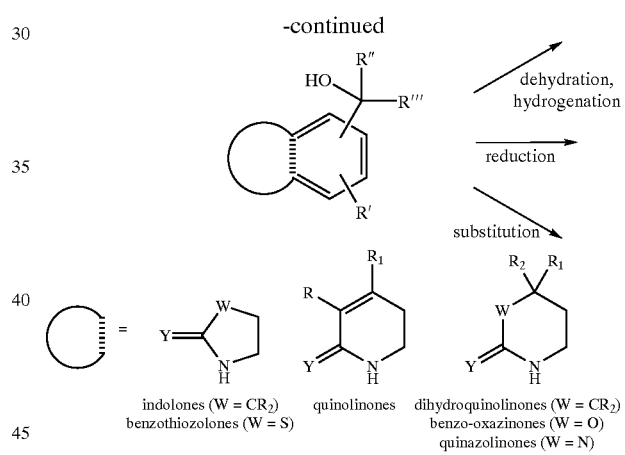

indolones (W = CR$_2$)  quinolinones  dihydroquinolinones (W = CR$_2$)
benzothiozolones (W = S)               benzo-oxazinones (W = O)
                                       quinazolinones (W = N)

Alkylated Aryl Compounds from Arylhalogens and Ketones

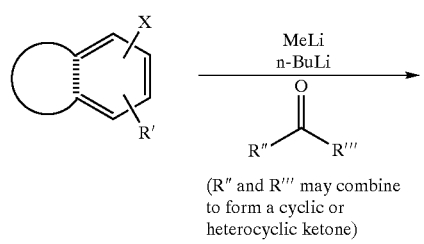

(R″ and R‴ may combine to form a cyclic or heterocyclic ketone)

In another aspect of the invention, halogenated quinolinones, benzo-oxazinones, indolones, benzothiozolones, and quinazolinones (i.e., arylhalogen compounds) produce alkylated derivatives by a C—C coupling of the arylhalogen carbon and a ketone with a lithium reagent. The above reaction sequence depicts the conversion of arylhalogen compounds to arylalkyl compounds by reaction of the aryl halide compound with a ketone. Schemes XX through XXIX depict further examples of this type of functional group conversion and are provided to further illustrate the reaction with various ketones and aryl compounds.

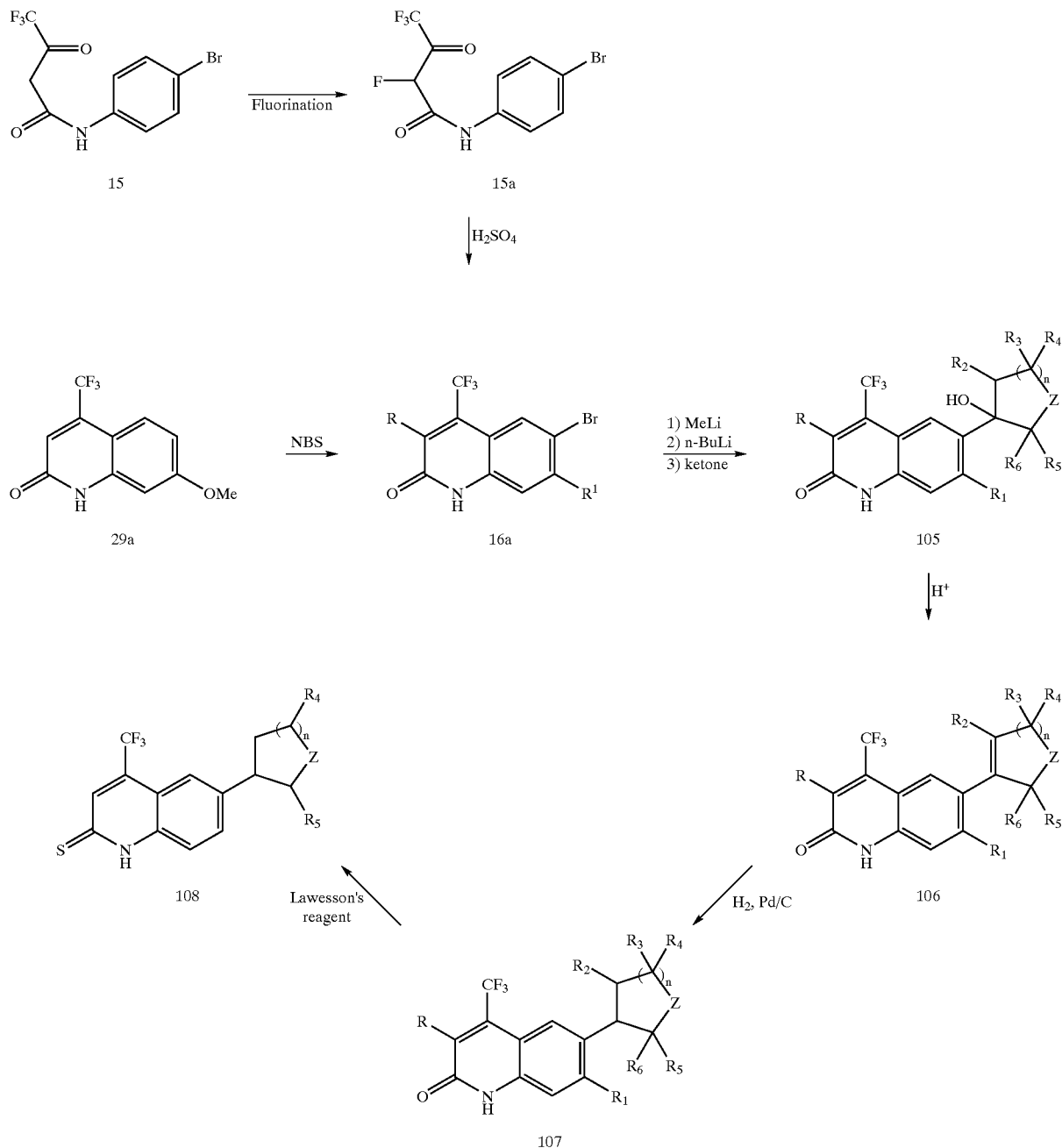

In another aspect of the invention, functionalized quinolinone compounds (e.g., Structure 105 and 109) are produced by a C—C coupling of a halo-quinolinone such as Structure 16a and a ketone as shown in Schemes XX and XXI. The halo-quinolinone may be produced by either of two synthetic routes as shown below in Scheme XX. Scheme XX describes the synthesis of a number of functionalized quinolinone compounds.

3-Fluorinated-quinolinone compounds such as Structure 16a may be formed by treatment of a 3-ketoamide 15 with a fluorination reagent, such as fluorobenzenesulfonimide, to provide a fluorinated derivative product such as Structure 15a, which is converted to the 3-fluoro quinolinone compound 16a (R=fluorine) by the Knorr cyclization with concentrated sulfuric acid.

A 7-methoxy analogue of Structure 16a is prepared by NBS bromination of quinolinone 29a. Addition of a dianion generated from a bromo-quinolinone such as 16a by two equivalents of base, such as alkyllithium, to a ketone affords the tertiary alcohols as shown in Structure 105. Dehydration of an alcohol such as 105 with a catalytic amount of acid, such as sulfuric acid, gives olefins of Structure 106. Subsequent hydrogenation of olefins such as 106 provides an alkyl-quinolinone such as Structure 107. A thioquinolinone derivative may be synthesized by treatment of compounds 107 with Lawesson's reagent in toluene as previously described.

Scheme XXI

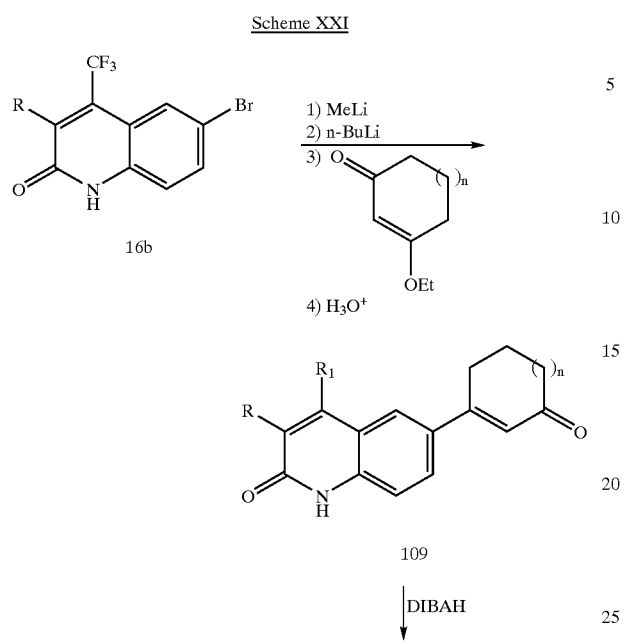

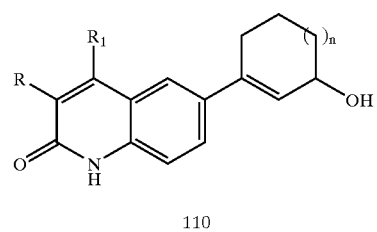

Scheme XXI describes a process of preparing alkenyl-quinolinone compounds. Addition of the dianion generated from a bromoquinolinone such as 16b by methyllithium and n-butyllithium to a protected cyclic 1,3-diketone affords oxo-alkenyl-quinolinone compounds such as Structure 109 upon acid mediated hydrolysis of the adducts. Reduction of the oxo group on a compound such as 109 with DIBAH provides the alcohol derivative as shown in Structure 110.

Scheme XXII

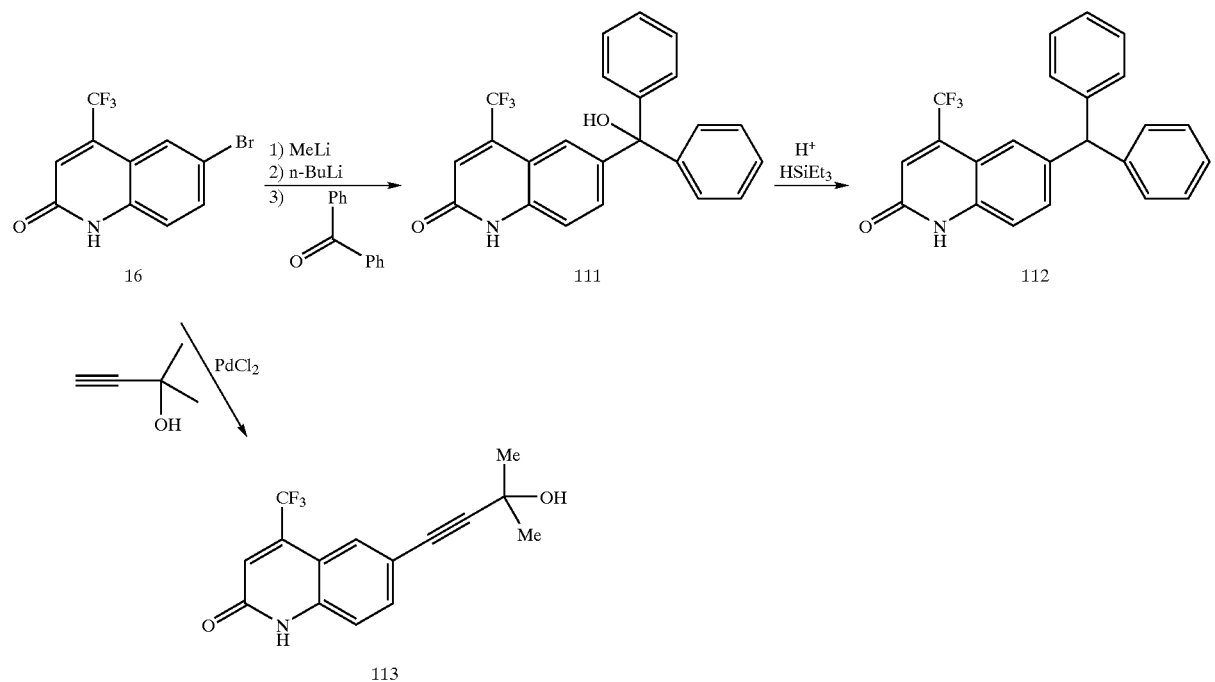

A further example of the conversion of arylhalogen compounds (e.g. Structure 16) to arylalkyl compounds is shown in Scheme XXII. Scheme XXII describes the preparation of additional 6-alkyl 2-quinolinone compounds from the quinolinone dianion in a preferred aspect of the invention. Addition of a dianion generated from a bromo quinolinone, methyllithium and n-butyllithium to benzophenone gives an alkyl quinolinone such as compound 111. Reduction of compound 111 with triethylsilane in the presence of an acid catalyst, such as TFA, affords an alkyl-quinolinone compound such as 112.

In a further embodiment of the invention, aryl halogen compounds are converted to aryl alkynes by a palladium catalyzed coupling reaction between the aryl halogen (e.g., Structure 16) and a terminal alkyne as shown above in Scheme XXII. For example, a palladium(II) catalyzed reaction of a bromoquinolinone such as 16 and a terminal alkyne such as dimethyl propargyl alcohol provides an alkynyl-quinolinone compound such as 113.

Scheme XXIII

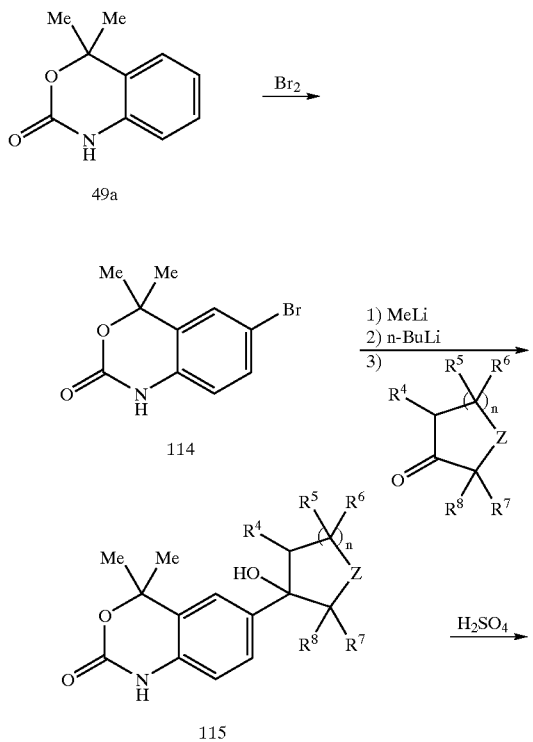

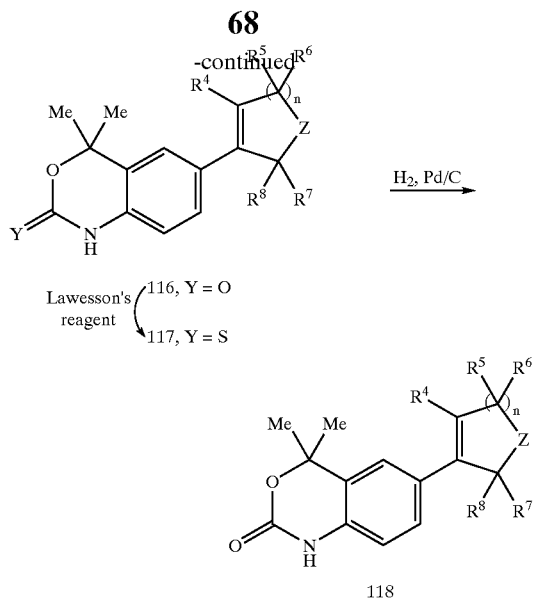

A method of converting arylhalides to arylalkyl compounds is also employed with benzo-oxazinone compounds as shown in the above example. Scheme XXIII describes methods of synthesizing alkyl 1,3-benzo[d]oxazin-2-one compounds.

The process of Scheme XXIII begins with a bromination of a compound such as 49a with bromine to give a bromobenzo-oxazinone compound such as 114. Addition of the dianion generated from the lithiation of a compound such as 49a to a ketone provides the hydroxy-alkyl adducts of Structure 115. Dehydration of alcohol derivative 115 with a catalytic amount of sulfuric acid affords compounds such as Structure 116, which may be hydrogenated to give compounds such as Structure 118. Benzothiooxazinone compounds as shown in Structure 117 are prepared from the corresponding carbonyl compound (e.g., such as Structure 116) by treatment with Lawesson's reagent as previously described.

Scheme XXIV

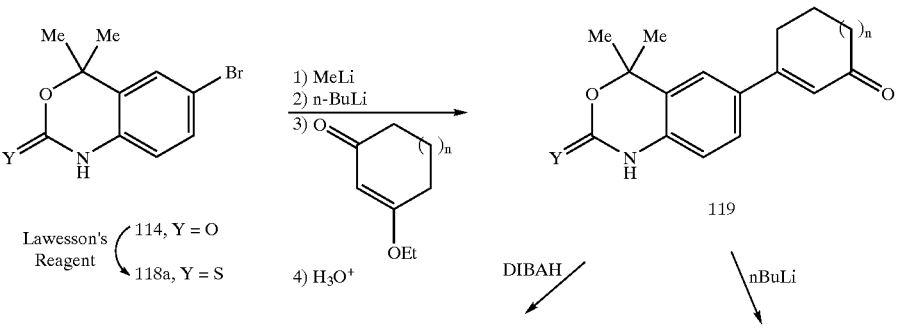

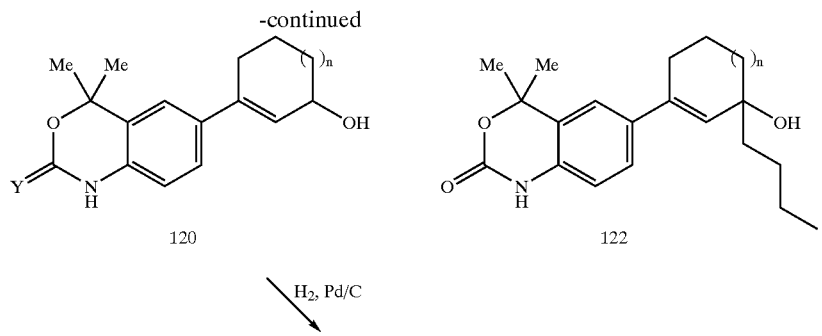

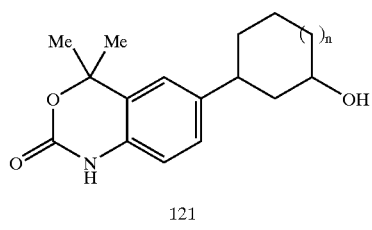

Scheme XXIV describes additional methods to prepare alkyl benzo-oxazinones. The process of Scheme XXIV begins with addition of the dianion generated from lithiation of compound 114 by alkyllithium to a protected 1,3-cyclodiketone. Hydrolysis of adducts with an acid affords alkene compounds Structure 119. Addition of n-butyllithium to an enone such as 119 provides a tertiary alcohol such as 122. Reduction of the enone 119 with DIBAL-H gives a secondary alcohol such as 120. Hydrogenation affords compound such as 121. Alkyl thio-benzo-oxazinone compounds are prepared by a similar process but using a thiobenzo-oxazinone 10 such as 118a in place of the oxo compound.

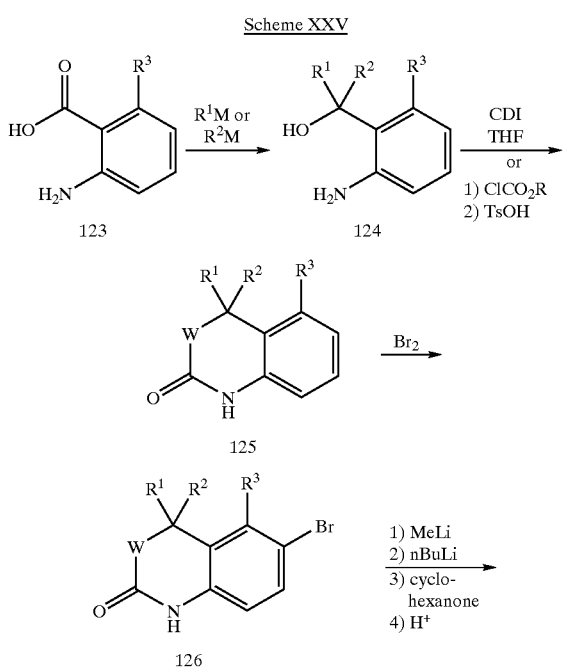

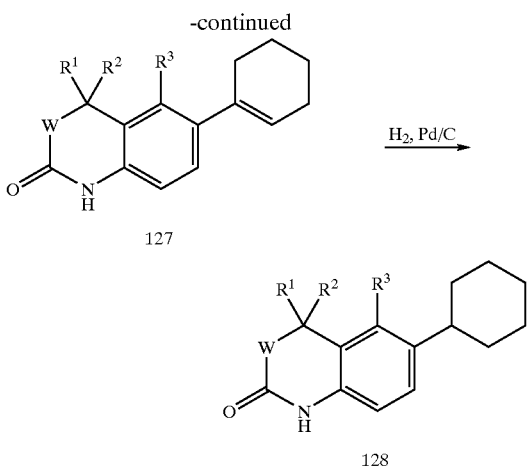

In another preferred aspect of the invention, substituted benzo-oxazinone compounds (e.g., Structure 125) are prepared for an amino-benzoic acid and an organometallic reagent to form a hydroxy-aniline compound (e.g., Structure 124) with either a halide or carbonyl diimidazole to form a benzo-oxazinone. The process of Scheme XXV begins with addition of either alkyl lithium or a Grignard reagent to a 2-aminobenzoic acid such as Structure 123 to generate amino alcohol compound such as Structure 124. A previously described cyclization procedure from either 1,1'-carbonyldiimidazole treatment or acid catalyzed carbamate intermediate affords compounds such as Structure 125. Treatment of benzo-oxazinone compounds (e.g., Structure 125) with bromine provides brominated benzo-oxazinone compounds such as Structure 126. Addition of an anion generated from compounds such as 126 and an alkyl lithium reagent to a ketone such as cyclohexanone affords compounds such as Structure 127. The alkenyl-benzo-oxazinone compound (e.g., 127) may be hydrogenated to give alkyl compounds such as Structure 128.

Scheme XXVI

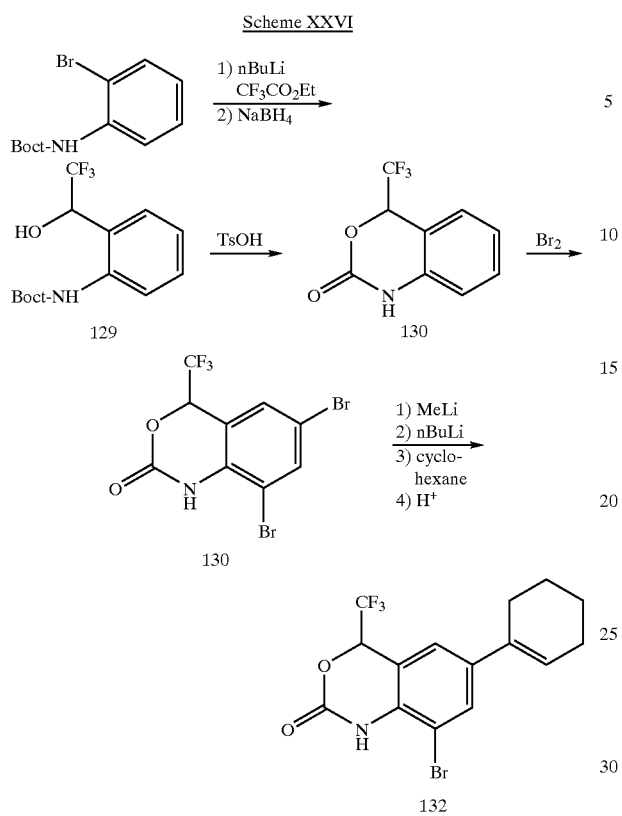

Scheme XXVI describes a process to introduce a trifluoromethyl group at the 4-position of benzo-oxazinone compounds. The process starts with addition of an N-protected 2-aminoaryl lithium generated by metal halogen exchange of 2-aminobromobenzene and n-butyllithium to ethyl trifluoroacetate followed by a reduction with sodium borohydride to provide compounds such as 129. Acid catalyzed cyclization of compounds such as 129 afford benzo-oxazinone compounds such as 130. The benzo-oxazinone compound may subsequently be treated with bromine to generate a bis-brominated product such as 131. As previously described, the bromine may be substituted with an alkyl group. For example, the 6-cyclohexenyl derivative 132 is prepared in a similar fashion as that described in Scheme XXV.

Scheme XXVII

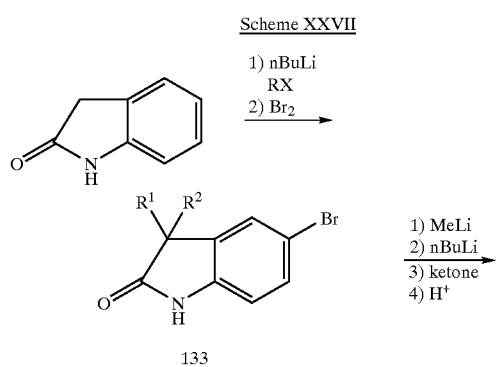

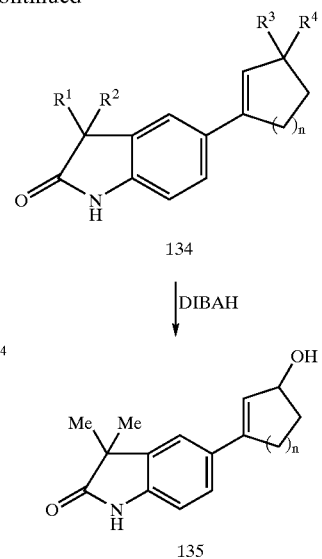

Scheme XXVII describes methods to prepare alkyl oxindole derivatives by bromination of the oxindole followed by substitution of the bromine group with an alkyl group as previously described. The process starts with alkylation of 2-indolone with alkyl halides in the presence of n-butyllithium followed by selective bromination to afford brominated oxindole compounds (e.g., Structure 133). The alkyl-indolone compounds are prepared from a bromo compound such as 133 by a procedure similar to that as described in Scheme XXV.

Scheme XXVIII

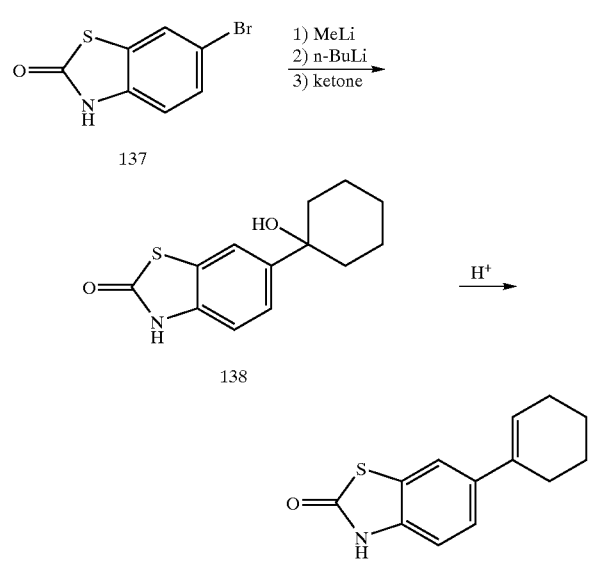

Scheme XXVIII describes a synthetic route of producing alkyl-benzothiozolones. The process is similar to that as described in Scheme XXV but using a halogenated benzothiozolone compound.

Scheme XXIX

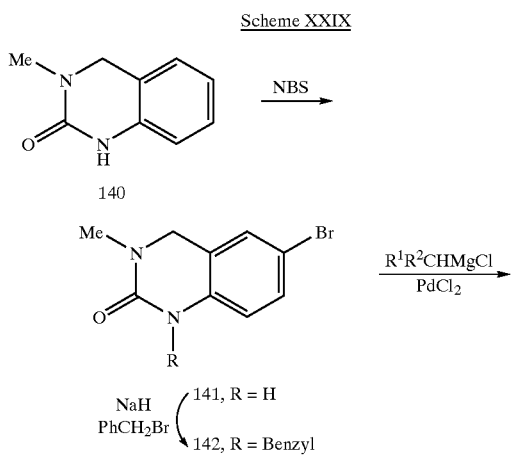

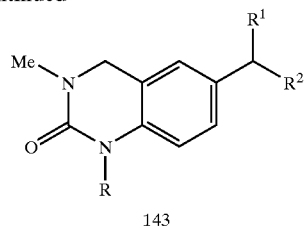

Scheme XXIX describes a process to prepare 2-quinazolinones. The process of Scheme XXIX begins with bromination of compound 140 to afford compound 141, which is derivatized by treatment with benzyl bromide in the presence of sodium hydride to give compound 142. A palladium catalyzed aromatic substitution of compounds of Structure 141 or 142 by Grignard reagents provides compounds of Structure 143.

Scheme XXX

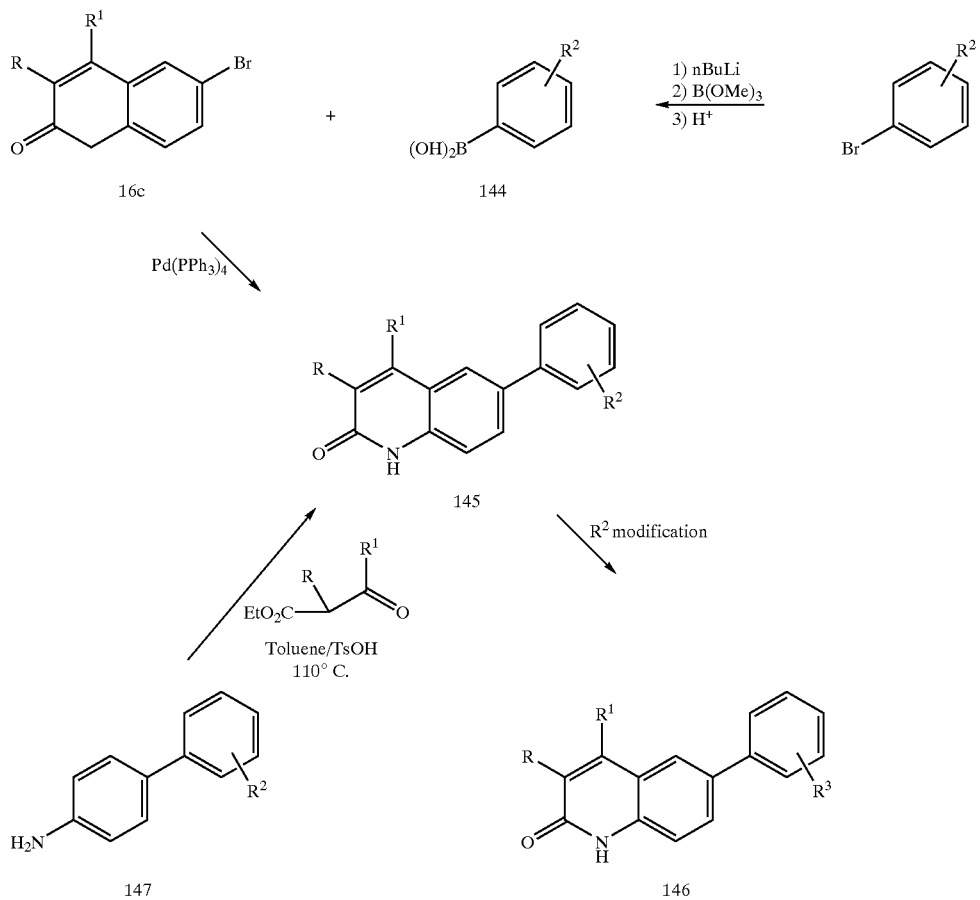

Scheme XXX describes an alternate method of preparing aryl-quinolinones by a modified Suzuki coupling reaction. The process starts with palladium catalyzed biaryl coupling of a bromo compound such as Structure 16c, a brominated quinolinone, with an aryl boronic acid (e.g., Structure 144).

Aryl compounds such as Structure 145 are produced in this manner. The boronic acids of Structure 144 come from commercial sources or may be generated from aryl bromides by a standard three-step procedure which includes metal halogen exchange, addition to methyl borate and acidic work-up. Aryl substituted compounds of the present invention (e.g., Structure 145) may be further functionalized by modification of the substituents on the aryl group by standard synthetic methods known to those skilled in the art. Alternately, aryl substituted compounds of the present invention such as Structure 145 may be prepared from the aryl aniline (e.g., 6-arylaniline, Structure 147) as shown above by a Knorr reaction procedure as previously described.

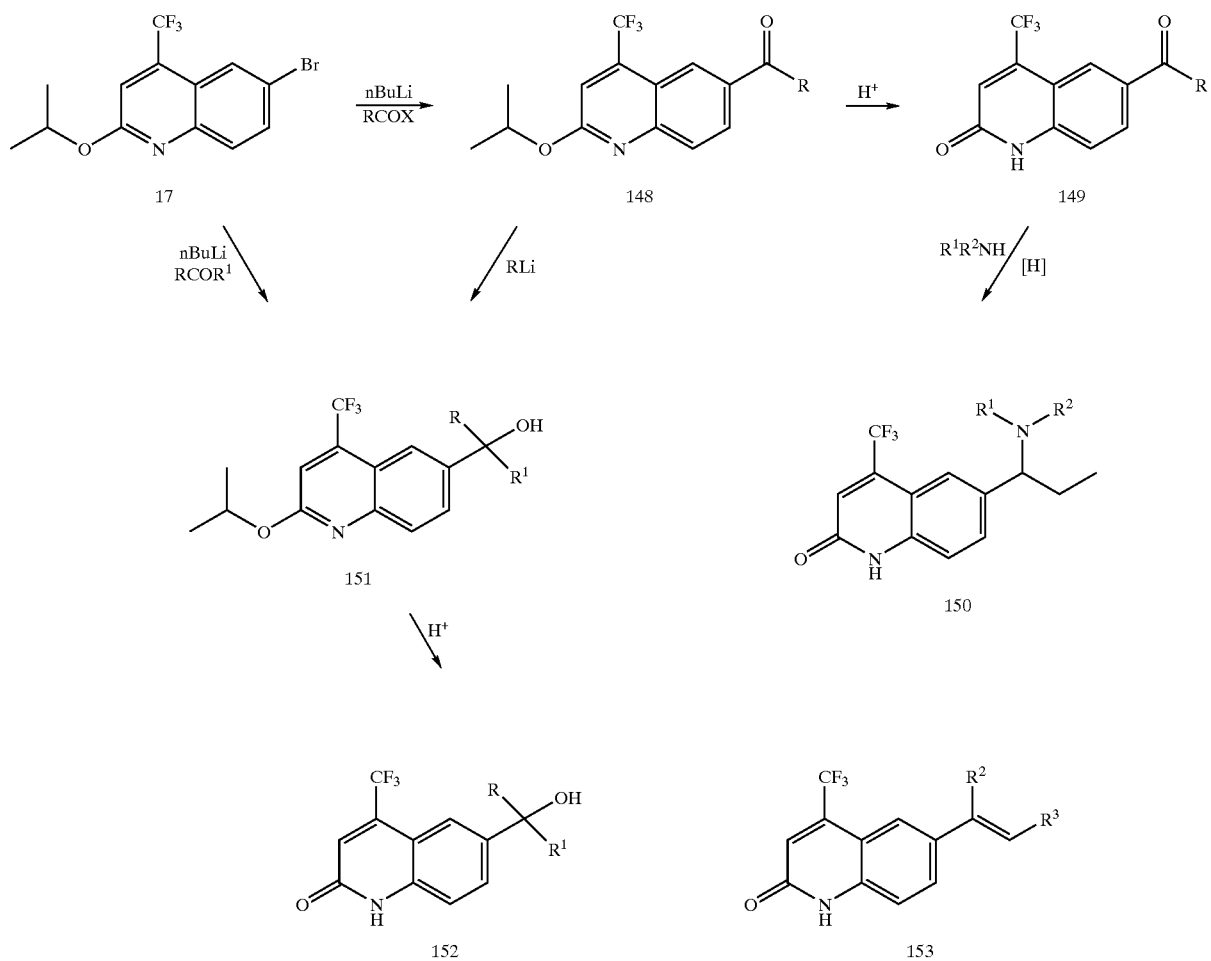

Scheme XXXI

Scheme XXXI describes additional methods to prepare 6-substituted 2-quinolinones such as Structures 149, 150, 152 and 153. Lithiation of Structure 17 followed by addition to a Weinreb's amide afford compounds of Structure 148. Hydrolysis of quinolines such as Structure 148 provides compounds of Structure 149. Compounds of Structure 150 are obtained by reductive amination of compounds such as Structure 149. Addition of a nucleophile to quinoline ketones of Structure 148 generates alcohols of Structure 151, which are treated with acid to afford compounds of Structures 152 and 153.

Scheme XXXII

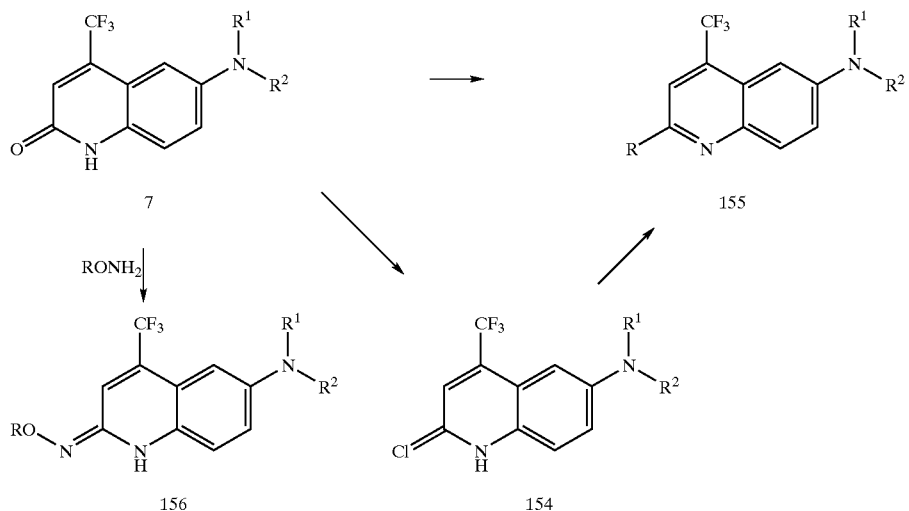

Scheme XXXII describes the conversion of 2-quinolinones of Structure 7 to 2-substituted quinoline such as Structures 154, 155 and 156 by the chemical transformations known to those skilled in the art.

Scheme XXXIII

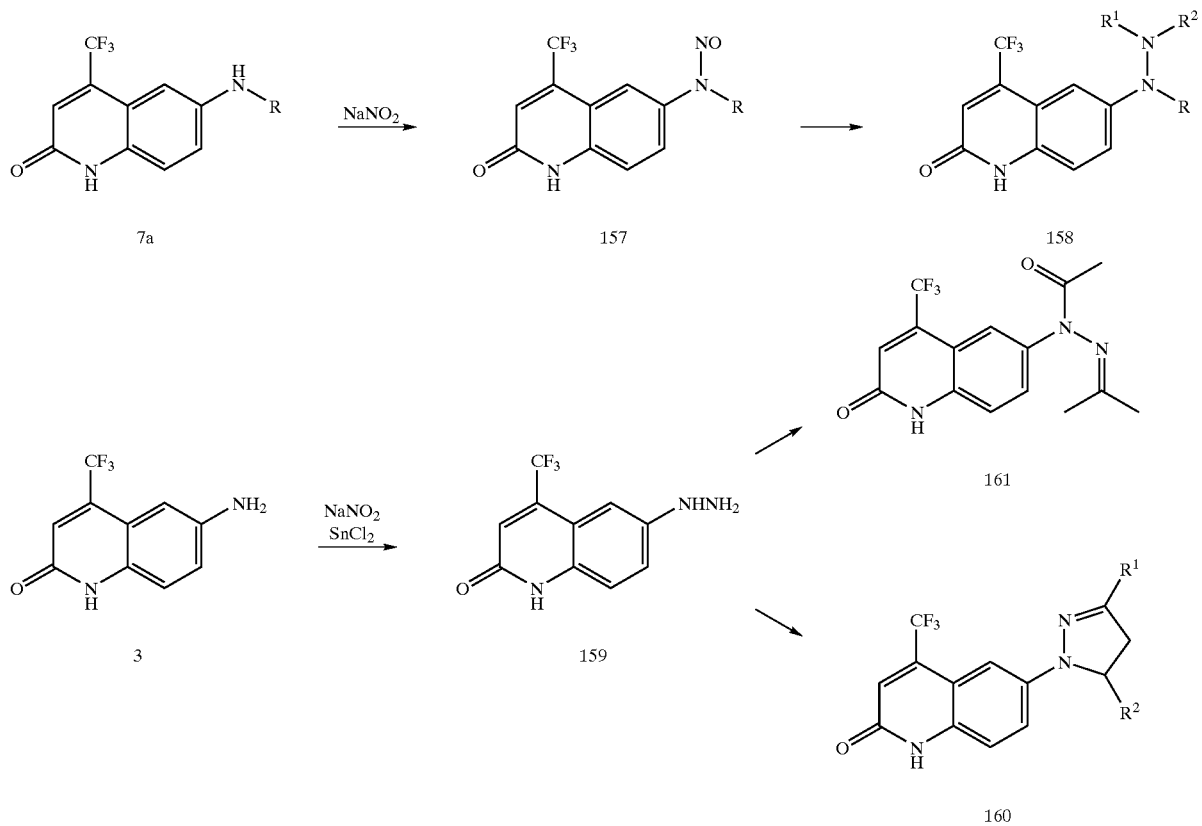

Scheme XXXIII describes methods to prepare compounds with a diazo containing side chain. Treatment of 6-aminoquinolinones such as Structure 7a with $NaNO_2$ affords compounds of Structure 157. Reduction of nitroso compounds such as Structure 157 followed by alkylation provide analogues of Structure 158. Alkylation or acylation of hydrazine such as Structure 159 generates compounds of Structures 160 and 161.

The compounds of the present invention also include racemates, stereoisomers and mixtures of said compounds, including isotopically labeled and radio-labeled compounds. Such isomers can be isolated by standard resolution techniques, including fractional crystallization and chiral column chromatography.

As noted above, any of the steroid modulator compounds of the present invention can be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 100 mg/kg, and most preferably from about 20 μg/kg to about 20 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of AR or PR in a cell background or extract. They are particularly useful due to their ability to selectively activate androgen receptors or progesterone receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques which are known to those of skill in the art. These techniques include column separation, filtration, centrifugation, tagging and physical separation, and antibody complexing, among others.

The compounds and pharmaceutical compositions of the present invention can advantageously be used in the treatment of the diseases and conditions described herein. In this regard, the compounds and compositions of the present invention will prove particularly useful as modulators of male sex steroid-dependent diseases and conditions such as the treatment of acne, male-pattern baldness, male hormone replacement therapy, wasting diseases, hirsutism, stimulation of hematopoiesis, hypogonadism, prostatic hyperplasia, osteoporosis (agonist), male contraception (agonist), impotence (agonist), cancer cachexia (agonist) various hormone-dependent cancers, including, without limitation, prostate and breast cancer and as anabolic agents.

The compounds and pharmaceutical compositions of the present invention possess a number of advantages over previously identified steroidal and non-steroidal compounds.

Furthermore, the compounds and pharmaceutical compositions of the present invention possess a number of advantages over previously identified steroid modulator compounds. For example, the compounds are extremely potent activators of AR, preferably displaying 50% maximal activation of AR at a concentration of less than 100 nM, more preferably at a concentration of less than 50 nM, more preferably yet at a concentration of less than 20 nM, and most preferably at a concentration of 10 mM or less. Also, the selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration. In addition, the compounds of the present invention, as small organic molecules, are easier to synthesize, provide greater stability and can be more easily administered in oral dosage forms than other known steroidal compounds.

The invention will be further illustrated by reference to the following non-limiting Examples.

EXAMPLE 1

6-Amino-4-trifluoromethyl-2(1H)-quinolinone
(Compound 200, Structure 3 of Scheme I)
N-(4-Acetylaminophenyl)-4,4,4-trifluoroacetoacetylamide Hydrate (Compound 201, Structure 2 of Scheme I):

In a 100 mL round bottom flask fitted with a reflux condenser, a mixture of 4-aminoacetanilide (Structure 1 of Scheme I) (7.5 g, 50 mmol), ethyl 4,4,4-trifluoroacetoacetate (17 g, 95 mmol, 1.9 equiv), nitrobenzene (30 mL), and water (2 mL, 0.11 mol) was heated in an oil bath at 130° C. for 1 h, then water (1 mL) was added and the mixture was heated at 130° C. for 2 h. After cooling to room temperature $Et_2O$ (30 mL) was added to the solid mass and the solids were filtered and washed with $Et_2O$ (3×30 mL), and dried under vacuum at 120° C. to give 12 g (85%) of Compound 201 as a ray crystalline solid.

6-Amino-4-trifluoromethyl-2(1H)-quinolinone (Compound 200, Structure 3 of Scheme I):

To a 50 mL r.b. flask charged with Compound 201 (3.6 g, 12 mmol) was added conc. $H_2SO_4$ (20 mL) and the dark brown mixture was heated in an oil bath at 95° C. for 16 h. After cooling to room temperature the dark purple solution was poured onto crushed ice (50 g) and brought to pH~2 with conc. NaOH. EtOAc (50 mL) was added and the layers separated. The water layer was extracted with EtOAc (9×30 mL). The combined organic layers were washed with water and brine and dried over MgSO$_4$. Removal of solvent afforded 1.2 g of a bright yellow solid, which was purified by flash chromatography (silica gel, hexane:EtOAc 2:1 to 1:2 gradient) to give Compound 200 as a bright yellow solid (0.52 g, 18%): $^1$H NMR (500 MHz, acetone-d$_6$) 10.9 (bs, 1H), 7.31 (d, J=9.3, 1H), 7.10 (dd, J=9.3, 2.4, 1H), 7.04 (t, J=2.4, 1H), 6.85 (s, 1H), 4.91 (bs, 2H).

6-Amino-4-trifluoromethyl-2(1H)-quinolinone (Compound 200, Structure 3 of Scheme I) was also prepared by the following General Procedures I–III from aniline: 4-Trifluoromethyl-2(1H)-quinolinone (Compound 202, Structure 5 of Scheme I):

General Procedure I (Synthesis of 2(1H)-Quinolinone from Aniline):

A solution of aniline in benzene or toluene (2–10 mL/mmol) and an acetoacetate derivative (1.2 equiv) was heated at reflux for 12–48 hrs. The resulting mixture was cooled to room temperature and concentrated under reduced pressure. The crude reaction mixture was diluted in concentrated sulfuric acid (8 mL/mmol) and heated to 80–100° C. for 6–16 hrs. The resulting mixture was poured over ice and neutralized with 6 M NaOH solution to pH 7.0, extracted with CH$_2$Cl$_2$ (3×30 mL/mmol), washed with pH 7 phosphate buffer (50 mL/mmol) and brine (50 mL/mmol). The organic solution was dried (MgSO$_4$) and concentrated under reduced pressure. Purification was performed either by flash chromatography (silica gel, 20:1, CH$_2$Cl$_2$/MeOH) or by crystallization to afford the desired quinolinone as a fluorescent-yellow solid.

Alternatively, a mixture of aniline and a 3-ketoester such as ethyl 4,4,4-trifluoroacetoacetate (1.2 equiv) in toluene (0.1–0.5 M) was heated at reflux for 24 h until the starting material was completely consumed by TLC. A catalytic amount of p-tolylsulfonic acid (1–10%) was added and the mixture was refluxed for additional 24 h. Similar work-up as described above afforded Compound 202 as a yellow solid: $^1$H NMR (400 MHz, acetone-d$_6$) 11.25 (bs, 1H),7.70 (d, J=8.0, 1H), 7.65 (t, J=8.0, 1H), 7.44 (d, J=8.0, 1H), 7.32 (t, J=8.0, 1H), 6.99 (s, 1H).

6-Nitro-4-trifluoromethyl-2(1H)-quinolinone (Compound 203, Structure 6 of Scheme I):

General Procedure II (Nitration Reaction):

To solution of a 2(1H)-quinolinone, such as Compound 202, in conc. H$_2$SO$_4$ (0.2–1.0 M) at room temperature was added HNO$_3$ (1.0 equiv). The reaction mixture was stirred for 10 min and was poured into ice water. The mixture was neutralized to PH~7 and extracted with EtOAc. Recystallization provided Compound 203 as a yellow solid: $^1$H NMR (500 MHz, acetone-d$_6$) 12.82 (bs, 1H), 8.47 (dd, J=9.5, 2.5, 1H), 8.44 (m, 1H), 7.59 (d, J=9.5, 1H), 7.21 (s, 1H).

6-Amino-4-trifluoromethyl-2(1H)-quinolinone (Compound 200, Structure 3 of Scheme I)

General Procedure III (Hydrogenation Reaction):

Compound 203 in EtOAc (0.2–1.0 M) was hydrogenated with a hydrogen balloon in the presence of 5% or 10% Pd/C (1–5 mol %). Filtration from the catalyst on Celite afforded Compound 200 as yellow solid.

EXAMPLE 2

6-Propylamino-4-trifluoromethyl-2(1H)-quinolinone (Compound 204, Structure 7 of Scheme II, Where R$^1$=H, R$^2$=Propyl)

This compound was prepared from Compound 200 and propionaldehyde by the following General Procedure IV (Reductive alkylation of amine by aldehyde):

To a solution of Compound 200 (Structure 3 of Scheme II) (35 mg, 0.15 mmol) in methanol (20 mL) was added a propionaldehyde (2–5 equiv) followed by NaCNBH$_3$ (2–5 equiv). The mixture was stirred at room temperature for 4 h and water (20 mL) was added. The water layer was extracted with EtOAc (2×20 mL) and the combined organic layers were washed with brine and dried over MgSO$_4$. Concentration and purification by flash chromatography (silica gel, hex/EtOAc 3:1) afforded Compound 204 as a yellow solid (70–95%): $^1$H NMR (500 MHz, CDCl$_3$) 11.2 (bs, 1H), 7.22 (d, J=8.8, 1H), 7.05 (s, 1H), 6.96 (dd, J=8.8, 2.4, 1H), 6.88 (s, 1H), 3.77 (t, J=4.4, 1H), 3.12 (dt, J=7.5, 4.4, 2H), 1.72–1.63 (m, 2H), 1.04 (t, J=7.3, 3H).

EXAMPLE 3

6-Isopropylamino-4-trifluoromethyl-2(1H)-quinolinone (Compound 205, Structure 7 of Scheme II, Where R$^1$=H, R$^2$=Isopropyl)

This compound was prepared from Compound 200 and acetone by the following General Procedure V (Reductive alkylation of amine by ketone):

To a solution of Compound 200 (Structure 3 of Scheme II) (35 mg, 0.15 mmol) in 10 mL MeOH was added acetone (0.5 mL, excess) followed by NaCNBH$_3$ (30 mg, 0.50 mmol) and AcOH (0.5 mL). The mixture was stirred at room temperature for 1 h and 10 mL water was added. The water layer was extracted with EtOAc (2×15 mL) and the combined organic layers were washed with brine and dried over MgSO$_4$. Concentration and purification by flash chromatography (silica gel, hex/EtOAc 2:1) afforded 33 mg (81%) of Compound 205 as a bright yellow solid: $^1$H NMR (500 MHz, acetone-d$_6$) 10.9 (bs, 1H), 7.33 (d, J=8.8, 1H), 7.08 (dd, J=8.8, 2.4, 1H), 6.87 (t, J=2.4, 1H), 6.86 (s, 1H), 5.00 (d, J=6.8, 1H), 3.70–3.63 (m, 1H), 1.23 (d, J=6.9, 6H).

EXAMPLE 4

6-Isobutylamino-4-trifluoromethyl-2(1H)-quinolinone (Compound 206, Structure 7 of Scheme II, Where R$^1$=H, R$^2$=Isobutyl)

This compound was prepared in a similar fashion as that described in Example 2, General Procedure IV but using isobutyraldehyde in place of propionaldehyde. Compound 206 was isolated as a yellow solid: $^1$H NMR (500 MHz, CDCl$_3$) 11.1 (bs, 1H), 7.20 (d, J=8.8, 1H), 7.04 (s, 1H), 6.95 (dd, J=8.8, 2.4, 1H), 6.87 (s, 1H), 3.83 (bs, 1H), 2.97 (t, J=6.3, 1H), 1.95–1.89 (m, 1H), 1.02 (d, J=6.8, 6H).

EXAMPLE 5

6-(2,2-Dimethylpropyl)amino-4-trifluoromethyl-2 (1)-quinolinone (Compound 207, Structure 7 of Scheme II, Where R$^1$=H, R$^2$=2,2-Dimethylpropyl)

This compound was prepared in a similar fashion as that described in Example 2, General Procedure IV but using trimethylacetaldehyde in place of propionaldehyde. Compound 207 was isolated as a yellow solid: $^1$H NMR (500 MHz, CDCl$_3$) 10.4 (bs, 1H), 7.14 (d, J=8.8, 1H), 7.03 (s, 1H), 6.97 (dd, J=8.8, 2.4, 1H), 6.90 (s, 1H), 3.79 (t, J=5.9, 1H), 2.94 (d, J=5.9, 2H), 1.03 (s, 9H).

EXAMPLE 6

6-Cyclopentylamino-4-trifluoromethyl-2(1H)-quinolinone (Compound 208, Structure 7 of Scheme II, Where R$^1$=H, R$^2$=Cyclopentyl)

This compound was prepared in a similar fashion as that described in Example 3, General Procedure V but using cyclopentanone in place of acetone. Compound 208 was isolated as a yellow solid: $^1$H NMR (500 MHz, acetone-d$_6$) 10.9 (bs, 1H), 7.32 (d, J=8.8, 1H), 7.08 (dd, J=8.8, 2.4, 1H), 6.87 (t, J=2.4, 1H), 6.85 (s, 1H), 5.21 (d, J=6.4, 1H), 3.84–3.81 (m, 1H), 2.04–2.00 (m, 2H) 1.76–1.71 (m, 2H), 1.67–1.59 (m, 2H), 1.58–1.52 (m, 2H).

EXAMPLE 7

6-(2,2,2-Trifluoroethyl)amino-4-trifluoromethyl-2 (1H)-quinolinone (Compound 209, Structure 7 of Scheme II, Where R$^1$=H, R$^2$=2,2,2-Trifluoroethyl)

This compound was prepared in a similar fashion as that described in Example 2, General Procedure IV but using trifluoroacetaldehyde in place of propionaldehyde. Compound 209 was isolated as a yellow solid: $^1$H NMR (400 MHz, CDCl$_3$) 11.05 (s, 1H), 7.36 (d, J=8.7, 1H), 7.09 (s, 1H), 7.04 (d, J=8.7, 1H), 7.02 (s, 1H), 4.10 (t, J=6.9, 1H), 3.86–3.78 (m, 2H).

EXAMPLE 8

6-(2,2,3,3,3-Pentafluoropropyl)amino-4-trifluoromethyl-2(1H)-quinolinone (Compound 210, Structure 7 of Scheme II, Where R$^1$=H, R$^2$=2,2,3,3,3-Pentafluoropropyl)

This compound was prepared in a similar fashion as that described in Example 2, General Procedure IV but using pentafluoropropyraldehyde in place of propionaldehyde. Compound 210 was isolated as a yellow solid: $^1$H NMR (500 MHz, CDCl$_3$) 12.2 (bs, 1H), 7.35 (d, J=8.8, 1H), 7.09 (s, 1H), 7.05 (dd, J=8.8, 2.4, 1H), 7.03 (s, 1H), 4.05 (t, J=6.8, 1H), 3.91–3.84 (m, 2H).

EXAMPLE 9

6-(2,2-Difluoroethyl)amino-4-trifluoromethyl-2 (1H)-quinolinone (Compound 211, Structure 7 of Scheme II, Where R$^1$=H, R$^2$=2,2-Difluoroethyl)

This compound was prepared from Compound 200 and difluoroacetic acid by the following General Procedure VI (Reductive alkylation of amine by acid):

To a solution of an aniline such as Compound 200 (Structure 3 of Scheme II) in an acid such as difluoroacetic acid as solvent was added sodium borohydride (excess) slowly, the resulting mixture was stirred at room temperature for several hours until the reaction went completion by TLC (addition of additional sodium borohydride or at elevate temperature would result in the formation of bis-alkylated product). The reaction was quenched by 10% NaOH and extracted with EtOAc (2×). Removal of solvent and chromatography of the crude residue afforded the N-alkylated product.

Compound 211 was isolated as a yellow solid: $^1$H NMR (400 MHz, CDCl$_3$) 7.37 (d, J=8.8, 1H), 7.09 (s, 1H), 7.03 (dd, J=2.5, 8.9, 1H), 6.97 (s, 1H), 5.97 (tt, J=3:9, 55.8, 1H), 4.03 (t, J=6.8, 1H), 3.65–3.55 (m, 2H).

EXAMPLE 10

6-(2-Chloro-2,2-difluoroethyl)amino-4-trifluoromethyl-2(1H)-quinolinone (Compound 212, Structure 7 of Scheme II, Where R$^1$=H, R$^2$=2-Chloro-2,2-difluoroethyl)

This compound was prepared in a similar fashion as that described in Example 9, General Procedure VI but using chlorodifluoroacetic acid in place of difluoroacetic acid. Compound 212 was isolated as a yellow solid: $^1$H NMR (400 MHz, CDCl$_3$) 7.38 (d, J=8.7, 1H), 7.09 (s, 1H), 7.08–7.05 (m, 2H), 4.26 (t, J=6.8, 1H), 3.99–3.92 (m, 2H).

EXAMPLE 11

6-Acetylamino-4-trifluoromethyl-2(1H)-quinolinone (Compound 213, Structure 7 of Scheme II, Where R$^1$=H, R$^2$=Acetyl)

This compound was prepared from Compound 200 and acetic anhydride by the following General Procedure VII (Acylation of amine):

To a solution of an amine such as Compound 200 (Structure 3 of Scheme II) in methylene chloride (0.1–0.5 M) was added an acid chloride or anhydride (1.5 equiv) and triethylamine (1.5 equiv) and the resulting mixture was stirred at room temperature for 1 h till the reaction went completion. The mixture was quenched with water and extracted with EtOAc. Removal of solvent and chromatography afforded the amide in good yield. Compound 213 was isolated as a yellow solid: $^1$H NMR (500 MHz, acetone-d$_6$) 11.0 (bs, 1H), 9.4 (bs, 1H), 8.23 (s, 1H), 7.91 (dd, J=8.8, 2.4, 1H), 7.46 (d, J=8.8, 1H), 6.93 (s, 1H), 2.11 (s, 3H).

EXAMPLE 12

6-Trifluoroacetylamino-4-trifluoromethyl-2(1H)-quinolinone (Compound 214, Structure 7 of Scheme II, Where R$^1$=H, R$^2$=Trifluoroacetyl)

This compound was prepared in a similar fashion as that described in Example 11, General Procedure VII but using trifluoroacetic anhydride in place of acetic anhydride. Compound 214 was isolated as a yellow solid: $^1$H NMR (500 MHz, acetone-d$_6$) 11.2 (bs, 1H), 10.5 (bs, 1H), 8.25 (t, J=2.0, 1H), 8.04 (dd, J=8.8, 2.4, 1H), 7.58 (d, J=8.8, 1H), 7.00 (s, 1H).

EXAMPLE 13

6-Benzoylamino-4-trifluoromethyl-2(1H)-quinolinone (Compound 215, Structure 7-of Scheme II, Where R$^1$=H, R$^2$=Benzoyl)

This compound was prepared in a similar fashion as that described in Example 11, General Procedure VII but using benzoyl chloride in place of acetic anhydride. Compound 215 was isolated as a yellow solid: $^1$H NMR (500 MHz, DMSO-d$_6$) 12.3 (bs, 1H), 10.5 (bs, 1H), 8.38 (s, 1H), 8.06 (dd, J=8.8, 0.9, 1H), 7.98 (d, J=6.8, 2H), 7.62–7.59 (m, 1H), 7.56–7.53 (m, 2H), 7.43 (d, J=8.8, 1H), 7.00 (s, 1H).

EXAMPLE 14

6-Dimethylacetylamino-4-trifluoromethyl-2(1H)-quinolinone (Compound 216, Structure 7 of Scheme II, Where R$^1$=H, R$^2$=Dimethylacetyl)

This compound was prepared in a similar fashion as that described in Example 11, General Procedure VII but using isobutyric anhydride in place of acetic anhydride. Compound 216 was isolated as a yellow solid: $^1$H NMR (500 MHz, acetone-d$_6$) 11.1 (bs, 1H), 9.3 (bs, 1H), 8.30 (t, J=1.9, 1H), 7.95 (dd, J=8.8, 2.4, 1H), 7.47 (d, J=8.8, 1H), 6.94 (s, 1H), 2.68–2.62 (m, 1) 1.19 (d, J=6.8, 6H).

EXAMPLE 15

6-Dimethylamino-4-trifluoromethyl-2(1H)-quinolinone (Compound 217, Structure 7 of Scheme II, Where R$^1$=R$^2$=Methyl)

This compound was prepared from Compound 200 and formaldehyde by the following General Procedure VIII (Dialkylation of amine):

To a solution of Compound 200 (Structure 3 of Scheme II) (35 mg, 0.15 mmol) in methanol (20 mL) was added an aldehyde (2–5 equiv) followed by NaCNBH$_3$ (2–5 equiv). The mixture was stirred at room temperature for 4 h and water (20 mL) was added. The water layer was extracted with EtOAc (2×20 mL) and the combined organic layers were washed with brine and dried over MgSO$_4$. Concentration and purification by flash chromatography (silica gel, hex/EtOAc 3:1) afforded the mono-alkylated product as a yellow solid (70–95%). Repeating the same procedure in the presence of the second aldehyde or ketone afforded the dialkylated product (50–90%). In case that both alkyl groups were same, the double alkylation was carried out in one step, in which a catalytic amount of acetic acid was needed to accelerate the reaction. The acetic acid was also needed when a ketone was used as an alkylating agent.

Compound 217 was isolated as a bright yellow solid: $^1$H NMR (500 MHz, acetone-d$_6$) 10.9 (bs, 1H), 7.42 (d, J=9.3, 1H), 7.28 (dd, J9.3, 2.9, 1H), 6.94 (s, 1H), 6.89 (s, 1H), 2.99 (s, 6H).

EXAMPLE 16

6-Diethylamino-4-trifluoromethyl-2(1H)-quinolinone (Compound 218, Structure 7 of Scheme II, Where R$^1$=R$^2$=Ethyl)

This compound was prepared in a similar fashion as that described in Example 15, General Procedure VIII but using acetaldehyde in place of paraformaldehyde. Compound 218 was isolated as a yellow solid: $^1$H NMR (500 MHz, CDCl$_3$) 10.3 (bs, 1H), 7.18 (d, J=9.3, 1H), 7.07 (dd, J=9.3, 2.4, 1H), 7.03(s, 1H), 6.95 (s, 1H), 3.39 (q, J=6.8, 4H), 1.18 (t, J=6.8, 6H).

EXAMPLE 17

6-Dipropylamino-4-trifluoromethyl-2(1H)-quinolinone (Compound 219, Structure 7 of Scheme II, Where R$^1$=R$^2$=Propyl)

This compound was prepared in a similar fashion as that described in Example 15, General Procedure VIII but using propionaldehyde in place of paraformaldehyde. Compound 219 was isolated as a yellow solid: $^1$H NMR (500 MHz, CDCl$_3$) 11.0 (bs, 1H); 7.22 (d, J=9.3, 1H), 7.03 (dd, J=9.3, 2.4, 1H), 7.03 (s, 1H), 6.90 (s, 1H), 3.28 (t, J=7.3, 4H), 1.66–1.58 (m, 4H), 0.95 (t, J=7.3, 6H).

EXAMPLE 18

6-Dibutylamino-4-trifluoromethyl-2(1H)-quinolinone (Compound 220, Structure 7 of Scheme II, Where R$^1$=R$^2$=Butyl)

This compound was prepared in a similar fashion as that described in Example 15, General Procedure VIII but using butyraldehyde in place of paraformaldehyde. Compound 220 was isolated as a yellow solid: $^1$H NMR (500 MHz, CDCl$_3$) 12.2 (bs, 1H), 7.32 (d, J=8.8, 1H), 7.06 (dd, J=8.8, 2.4, 1H), 7.04 (s, 1H), 6.90 (s, 1H), 3.31 (t, J=6.8, 4H), 1.60–1.50 (m, 4H), 1.41–1.33 (m, 4H), 0.97 (t, J=7.3, 6H).

EXAMPLE 19

6-Diisobutylamino-4-trifluoromethyl-2(1H)-quinolinone (Compound 221, Structure 7 of Scheme II, Where R$^1$=R$^2$=Isobutyl)

This compound was prepared in a similar fashion as that described in Example 15, General Procedure VIII but using isobutyraldehyde in place of paraformaldehyde. Compound 221 was isolated as a yellow solid: $^1$H NMR (500 MHz, CDCl$_3$) 11.7 (bs, 1H), 7.27 (d, J=9.3, 1H), 7.06 (dd, J=9.3, 2.9, 1H), 7.04 (s, 1H), 6.90 (s, 1H), 3.18 (d, J=6.8, 3H), 2.09–2.02 (m, 2H), 0.92 (d, J=6.3, 12H).

EXAMPLE 20

6-(bis-Cyclopropylmethyl)amino-4-trifluoromethyl-2(1H)-quinolinone (Compound 222, Structure 7 of Scheme II, Where R$^1$=R$^2$=Cyclopropylmethyl)

This compound was prepared in a similar fashion as that described in Example 15, General Procedure VIII but using cyclopropanecarboxaldehyde in place of paraformaldehyde. Compound 222 was isolated as a yellow solid: $^1$H NMR (500 MHz, CDCl$_3$) 11.5 (bs, 1H), 7.29 (d, J=9.3, 1H), 7.22 (dd, J=9.3, 2.4, 1H), 7.12 (s, 1H), 7.05 (s, 1H), 2.31 (d, J=5.8, 4H), 1.07–1.01 (m, 2H), 0.57–0.53 (m, 4H), 0.26–0.23 (m, 4H).

EXAMPLE 21

6-(bis-2,2,2-Trifluoroethyl)amino-4-trifluoromethyl-2(1H)-quinolinone (Compound 223, Structure 7 of Scheme II, Where R$^1$=R$^2$=2,2,2-Trifluoroethyl)

This compound was prepared in a similar fashion as that described in Example 15, General Procedure VIII but using trifluoroaldehyde sequentially in place of paraformaldehyde alone. Compound 223 was isolated as a yellow solid: $^1$H NMR (400 MHz, CDCl$_3$) 10.99 (s, 1H), 7.44 (d, J=8.9, 1H), 7.32 (s, 1H), 7.29 (d, J=8.9, 1H), 7.11 (s, 1H), 4.07 (q, J=8.4, 4H).

EXAMPLE 22

6-(bis-2,2,3,3,3-Pentafluoropropyl)amino-4-trifluoromethyl-2(1H)-quinolinone (Compound 224, Structure 7 of Scheme II, Where R$^1$=R$^2$= Pentafluoroethylmethyl)

This compound was prepared in a similar fashion as that described in Example 15, General Procedure VIII but using 2,2,3,3,3-pentafluoropropyraldehyde in place of paraformaldehyde. Compound 224 was isolated as a yellow solid: $^1$H NMR (500 MHz, CDCl$_3$) 11.1 (bs, 1H), 7.35 (s, 1H), 7.34 (d, J=8.8, 1H), 7.28 (dd, J=8.8, 2.4, 1H), 7.10 (s, 1H), 4.14 (t, J=16.9, 4H).

EXAMPLE 23

6-(bis-2-Chloro-2,2-difluoroethyl)amino-4-trifluoromethyl-2(1H)-quinolinone (Compound 225, Structure 7 of Scheme II, Where R$^1$=R$^2$= Chlorodifluoroethyl)

This compound was prepared in a similar fashion as that described in Example 9, General Procedure VI but using chlorodifluoroacetic acid in place of difluoroacetic acid. Compound 225 was isolated as a yellow solid: $^1$H NMR (400 MHz, acetone-d$_6$) 11.12 (bs, 1H), 7.66 (dd, J=2.6, 9.1, 1H),7.50(d, J=9.1, 1H), 7.46 (s, 1H), 6.95 (s, 1H), 4.55 (t, J=12.1, 4H).

EXAMPLE 24

6-(bis-2-Bromoethyl)amino-4-trifluoromethyl-2(1H)-quinolinone (Compound 226, Structure 7 of Scheme II, Where R$^1$=R$^2$=2-Bromoethyl)

This compound was prepared in a similar fashion as that described in Example 9, General Procedure VI but using bromoacetic acid in place of difluoroacetic acid. Compound 226 was isolated as a yellow solid: $^1$H NMR (CDCl$_3$) 11.06(bs, 1H), 7.41 (d, J=9.0, 1H), 7.12 (d, J=9.0, 1H), 7.09 (s, 1H), 6.98 (s, 1H), 3.85 (t, J=7.2, 4H), 3.50 (t, J=7.2, 4H).

EXAMPLE 25

6-(N-2,2,2-Trichloroethyl)amino-4-trifluoromethyl-2(1H)-quinolinone (Compound 227, Structure 7 of Scheme II, Where R$^1$=H, R$^2$=2,2,2-Trichloroethyl)

This compound was prepared in a similar fashion as that described in Example 9, General Procedure VI from Compound 200 (Structure 3 of Scheme II) and trichloroacetic acid. Compound 227 was isolated as a yellow solid: $^1$H NMR (CDCl$_3$) 10.53 (bs, 1H), 7.40 (d, J=9.6, 1H), 7.15 (d, J=9.6, 1H), 7.13 (s, 1H), 7.09 (s, 1H), 4.62 (t, J=7.2, 1H), 4.19 (d, J=7.2, 2H).

EXAMPLE 26

6-(bis-N-2,2,2-Trichloroethyl)amino-4-trifluoromethyl-2(1H)-quinolinone (Compound 228, Structure 7 of Scheme II, Where R$^1$=R$^2$=2,2,2-Trichloroethyl)

This compound was prepared in a similar fashion as that described in Example 9, General Procedure VI from Compound 200 (Structure 3 of Scheme II) and trichloroacetic acid. Compound 228 was isolated as a yellow solid: $^1$H NMR (CDCl$_3$) 10.82 (bs, 1H), 7.65 (s, 1H); 7.57 (d, J=8.8, 1H), 7.45 (d, J=8.8, 1H), 7.10 (s, 1H), 4.70 (s, 4H).

EXAMPLE 27

6-(N-2,2,2-Chlorodifluoroethyl-N-2,2,2-Trichloroethyl)amino-4-trifluoromethyl-2(1H)-quinolinone (Compound 229, Structure 7 of Scheme II, Where R$^1$=2,2,2-Chlorodifluoroethyl, R$^2$=2,2,2-Trichloroethyl)

This compound was prepared in a similar fashion as that described in Example 9, General Procedure VI from Compound 200 (Structure 3 of Scheme II) and trichloroacetic acid and chlorodifluoroacetic acid. Compound 229 was isolated as a yellow solid: $^1$H NMR (CDCl$_3$) 10.86(bs, 1H), 7.34 (d, J=9.0, 1H), 7.21 (dd, J=9.1, 2.6, 1H), 7.16 (s, 1H), 7.09 (s, 1H), 5.97 (tt, J=55, 3.8, 1H), 3.83 (td, J=13.9, 3.9, 4H).

EXAMPLE 28

6-(bis-N-2,2-Difluoroethyl)amino-4-trifluoromethyl-2(1H)-quinolinone (Compound 230, Structure 7 of Scheme II, Where R$^1$=R$^2$=2,2-Difluoroethyl)

This compound was prepared in a similar fashion as that described in Example 9, General Procedure VI from Compound 200 (Structure 3 of Scheme II) and difluoroacetic acid. Compound 230 was isolated as a yellow solid: $^1$H NMR (CDCl$_3$) 11.47 (bs, 1H), 7.34 (d, J=9.0, 1H), 7.21 (dd, J=9.1, 2.6, 1H), 7.16 (s, 1H), 7.09 (s, 1H), 5.97 (tt, J=55, 3.8, 1H), 3.83 (td, J=13.9, 3.9, 4H).

EXAMPLE 29

6-(N-2,2-Dichloroethyl-N-2,2,2-trichloroethyl)amino-4-trifluoromethyl-2(1H)-quinolinone (Compound 231, Structure 7 of Scheme II, Where R$^1$=2,2,2-Trichloroethyl, R$^2$=2,2-Dichloroethyl)

This compound was prepared in a similar fashion as that described in Example 9, General Procedure VI from Compound 200 (Structure 3 of Scheme II) and dichloroacetic acid and trichloroacetic acid. Compound 231 was isolated as a yellow solid: $^1$H NMR (CDCl$_3$) 11.01 (bs, 1H), 7.44 (s, 2H), 7.42 (s, 1H), 7.41(s, 1H), 7.12 (s, 1H), 5.74 (t, J=6.3, 1H), 4.58 (s, 2H) 4.33 (d, J=6.3, 2H).

EXAMPLE 30

6-(bis-N-2,2-Dichloroethyl)amino-4-trifluoromethyl-2(1H)-quinolinone (Compound 232, Structure 7 of Scheme II, Where R$^1$=R$^2$=2,2-Dichloroethyl)

This compound was prepared in a similar fashion as that described in Example 9, General Procedure VI from Compound 200 (Structure 3 of Scheme II) and dichloroacetic acid. Compound 232 was isolated as a yellow solid: $^1$H NMR (400 MHz, acetone-d$_6$) 11.2 (bs, 1H), 7.51 (s, 2H), 7.19 (s, 1H), 6.94 (s, 1H), 6.25 (t, J=6.3, 2H), 4.29 (d, J=6.3, 4H).

EXAMPLE 31

6-(N-2,2-Dichloroethyl-N-2,2-difluoroethyl)amino-4-trifluoromethyl-2(1H)-quinolinone (Compound 233, Structure 7 of Scheme II, Where R$^1$=2,2-Dichloroethyl, R$^2$=2,2-Difluoroethyl)

This compound was prepared in a similar fashion as that described in Example 9, General Procedure VI from Compound 200 (Structure 3 of Scheme II) and dichloroacetic acid and difluoroacetic acid. Compound 233 was isolated as a yellow solid: $^1$H NMR (CDCl$_3$): 10.60 (bs, 1H), 7.47 (d, J=9.1, 1H), 7.2 (dd, J=9.1, 2.6, 1H), 7.11 (s, 2H), 5.95 (tt, J=55, 3.8, 1H), 5.87 (t, J=6.2, 1H), 4.1 (d, J=6.2, 2H), 3.94, (td, J=13.9, 3.9, 2H).

EXAMPLE 32

6-(N-2,2-Dichloroethyl-N-2,2,2-chlorodifluoroethyl)amino-4-trifluoromethyl-2(1H)-quinolinone (Compound 234, Structure 7 of Scheme II, Where R$^1$=2,2-Dichloroethyl, R$^2$=2,2,2-Chlorodifluoroethyl)

This compound was prepared in a similar fashion as that described in Example 9, General Procedure VI from Compound 200 (Structure 3 of Scheme II) and dichloroacetic acid and chlorodifluoroacetic acid. Compound 234 was isolated as a yellow solid: $^1$H NMR (CDCl$_3$) 11.21 (bs, 1H), 7.43 (d, J=9.0, 1H), 7.24 (d, J=9.0, 1H), 7.21(s, 1H), 7.11 (s, 1H), 5.84 (t, J=6.2, 1H), 4.3 (t, J=11.5, 2H), 4.15 (d, J=6.2, 2H).

EXAMPLE 33

6-(N-Isopropyl-N-methyl)amino-4-trifluoromethyl-2(1)-quinolinone (Compound 235, Structure 7 of Scheme II, Where R$^1$=Methyl, R$^2$=Isopropyl)

This compound was prepared in a similar fashion as that described in Example 15, General Procedure VIII but using paraformaldehyde and acetone sequentially in place of paraformaldehyde alone. Compound 235 was isolated as a yellow solid: $^1$H NMR (500 MHz, acetone-d$_6$) 10.9 (bs, 1H), 7.41 (d, J=9.3, 1H), 7.36 (dd, J=9.3, 2.9, 1H), 7.00 (bs, 1H) 6.88 (s, 1H), 4.16–4.11 (m, 1H), 2.78 (s, 3H), 1.19 (d, J=6.8, 6H).

EXAMPLE 34

6-(N-Methyl-N-cyclopentyl)amino-4-trifluoromethyl-2(1H)-quinolinone (Compound 236, Structure 7 of Scheme II, Where R$^1$=Cyclopentyl, R$^2$=Methyl)

This compound was prepared in a similar fashion as that described in Example 15, General Procedure VIII but using paraformaldehyde and cyclopentanone sequentially in place of paraformaldehyde alone. Compound 236 was isolated as a yellow solid: $^1$H NMR (500 MHz, CDCl$_3$) 11.4 (bs, 1H), 7.28 (d, J=8.8, 1H), 7.25 (dd, J=8.8, 2.4, 1H), 7.10 (s, 1H), 7.06, 1H), 4.14–4.06 (m, 1H), 2.84 (s, 3H), 1.94–1.87 (m, 2H), 1.78–1.73 (m, 2H), 1.67–1.59 (m, 4H).

EXAMPLE 35

6-(N-Methyl-N-isobutyl)amino-4-trifluoromethyl-2 (1H)-quinolinone (Compound 237, Structure 7 of Scheme II, Where R$^1$=Methyl, R$^2$=Isobutyl)

This compound was prepared in a similar fashion as that described in Example 15, General Procedure VIII but using paraformaldehyde and isobutyraldehyde sequentially in place of paraformaldehyde alone. Compound 237 was isolated as a yellow solid: $^1$H NMR (500 MHz, CDCl$_3$) 11.0 (bs, 1H), 7.25 (d, J=9.3, 1H), 7.08 (dd, J=9.3, 2.9, 1H), 7.04 (s, 1H), 6.93 (s, 1H), 3.14 (d, J=7.3, 2H), 3.01 (s, 3H), 2.08–2.03 (m, 1H), 0.94 (d, J=6.8, 6H).

EXAMPLE 36

6-(N-Ethyl-N-propyl)amino-4-trifluoromethyl-2 (1H)-quinolinone (Compound 238, Structure 7 of Scheme II, Where R$^1$=Propyl, R$^2$=Ethyl)

This compound was prepared in a similar fashion as that described in Example 15, General Procedure VIII but using propyraldehyde and acetaldehyde sequentially in place of paraformaldehyde alone. Compound 238 was isolated as a yellow solid: $^1$H NMR (500 MHz, CDCl$_3$) 10.7 (bs, 1H), 7.21 (d, J=9.3, 1H), 7.06, (dd, J=9.3, 2.4, 1H), 7.03 (s, 1H), 6.93 (s, 1H), 3.41 (q, J=7.3, 2H), 3.25 (t, J=7.3, 2H), 1.66–1.61 (m, 2H), 1.18 (t, J=7.3, 3H), 0.97 (t, J 7.3, 3H).

EXAMPLE 37

6-(N-Ethyl-N-isopropyl)amino-4-trifluoromethyl-2 (1H)-quinolinone (Compound 239, Structure 7 of Scheme II, Where R$^1$=Isopropyl, R$^2$=Ethyl)

This compound was prepared in a similar fashion as that described in Example 15, General Procedure VIII but using acetaldehyde and acetone sequentially in place of paraformaldehyde alone. Compound 239 was isolated as a yellow solid: $^1$H NMR (500 MHz, CDCl$_3$) 11.6 (bs, 1H), 7.29 (d, J=8.8, 1H), 7.17, (dd, J=8.8, 2.9, 1H), 7.05 (s, 1H), 7.03 (s, 1H), 4.04–3.99 (m, 1H), 3.28 (q, J=6.8, 2H), 1.22 (d, J=6.8, 6H), 1.18 (t, J=6.8, 3H).

EXAMPLE 38

6-N-Ethyl-N-1-metylpropyl)amino-4-trifluoromethyl-2(1H)-quinolinone (Compound 240, Structure 7 of Scheme II, Where R$^1$=Ethyl, R$^2$=1-Methylpropyl)

This compound was prepared in a similar fashion as that described in Example 15, General Procedure VIII but using acetaldehyde and 2-butanone sequentially in place of paraformaldehyde alone. Compound 240 was isolated as a yellow solid: $^1$H NMR (500 MHz, CDCl$_3$) 11.5(bs, 1H), 7.27(d, J=9.3, 1H), 7.16 (dd, J=9.3, 2.4, 1H), 7.04 (s, 1H), 7.02 (s, 1H), 3.76–3.69 (m, 1H), 3.33–3.24 (m, 2H), 1.71–1.62 (m, 1H), 1.54–1.49 (m, 1H), 1.19 (d, J=6.8, 3H), 1.17 (t, J=6.8, 3H), 0.93 (t, J=7.3, 3H).

EXAMPLE 39

6-(N-Ethyl-N-isobutyl)amino-4-trifluoromethyl-2 (1H)-quinolinone (Compound 241, Structure 7 of Scheme II, Where R$^1$=Ethyl, R$^2$=Isobutyl)

This compound was prepared in a similar fashion as that described in Example 15, General Procedure VIII but using acetaldehyde and isobutyraldehyde sequentially in place of paraformaldehyde alone. Compound 241 was isolated as a yellow solid: $^1$H NMR (500 MHz, CDCl$_3$) 11.6 (bs, 1H), 7.28 (d, J=9.3, 1H), 7.07 (dd, J=9.3, 2.4, 1H), 7.04 (s, 1H), 6.92 (s, 1H), 3.43 (q, J=6.8, 2H), 3.08 (d, J=7.3, 2H), 2.03–2.01 (m, 1H), 1.15 (t, J=6.8, 3H), 0.95 (d, J=6.8, 6H).

EXAMPLE 40

6-(N-Ethyl-N-2,2-dimethylpropyl)amino-4-trifluoromethyl-2(1H)-quinolinone (Compound 242, Structure 7 of Scheme II, Where R$^1$=Ethyl, R$^2$=2,2-Dimethylpropyl)

This compound was prepared in a similar fashion as that described in Example 15, General Procedure VIII but using acetaldehyde and trimethylacetaldehyde sequentially in place of paraformaldehyde alone. Compound 242 was isolated as a yellow solid: $^1$H NMR (500 MHz, CDCl$_3$) 11.2 (bs, 1H), 7.23 (d, J 8.8, 1H), 7.07 (dd, J=8.8, 2.9, 1H), 7.05 (s, 1H), 7.03 (s, 1H), 3.47 (q, J=6.8, 2H), 3.12 (s, 2H), 1.11 (t, J 6.8, 3H), 0.99 (s, 9H).

EXAMPLE 41

6-(N-Ethyl-N-cyclopentyl)amino-4-trifluoromethyl-2(1H)-quinolinone (Compound 243, Structure 7 of Scheme II, Where R$^1$=Cyclopentyl, R$^2$=Ethyl)

This compound was prepared in a similar fashion as that described in Example 15, General Procedure VIII but using acetaldehyde and cyclopentanone sequentially in place of paraformaldehyde alone. Compound 243 was isolated as a yellow solid: $^1$H NMR (500 MHz, CDCl$_3$) 11.6 (bs, 1H), 7.29 (d, J=9.3, 1H), 7.22, (dd, J=9.3, 2.4, 1H), 7.12 (s, 1H), 7.06 (s, 1H), 3.98–3.93 (m, 1H), 3.32 (q, J=7.3, 2H), 1.98–1.95 (m, 2H), 1.77–1.73 (m, 2H), 1.66–1.62 (m, 2H), 1.59–1.53 (m, 2H), 1.14 (t, J=7.3, 3H).

EXAMPLE 42

6-(N-Ethyl-N-1-acetylethyl)amino-4-trifluoromethyl-2(1H)-quinolinone (Compound 244, Structure 7 of Scheme II, Where R$^1$=Ethyl, R$^2$=1-Acetylethyl)

This compound was prepared in a similar fashion as that described in Example 15, General Procedure VIII but using acetaldehyde and 2,3-butanedione sequentially in place of paraformaldehyde alone. Compound 244 was isolated as a yellow solid: $^1$H NMR (500 MHz, CDCl$_3$) 11.6 (bs, 1H), 7.31 (d, J=8.8, 1H), 7.10 (dd, J=8.8, 2.4, 1H), 7.07 (s, 1H), 7.01 (s, 1H), 4.21 (q, J=6.8, 1H), 3.42–3.30 (m, 2H), 2.18 (s, 3H), 1.39 (d, J=6.8, 3H), 1.22 (t, J=7.3, 3H).

EXAMPLE 43

(±)-6-(N-Ethyl-N-1-methyl-2-hydroxypropyl)amino-4-trifluoromethyl-2(1H)-quinolinone (Compound 245, Structure 7 of Scheme II, Where R$^1$=Ethyl, R$^2$=1-Methyl-2-hydroxypropyl)

This compound was prepared by sodium borohydride reduction of Compound 244 (Structure 7 of Scheme II, where R$^1$=ethyl, R$^2$=1-acetylethyl) in methanol. Compound 245 was isolated as a yellow solid: $^1$H NMR (500 MHz, acetone-d$_6$) 10.9 (bs, 1H), 7.40–7.39 (m, 2H), 7.12, (s, 1H), 6.88 (s, 1H), 3.93–3.82 (m, 1H), 3.65 (d, J=2.9, 1H), 3.61–3.56 (m, 1H), 3.42–3.37 (m, 2H), 1.21–1.13 (m, 9H).

EXAMPLE 44

6-(N-Ethyl-N-2,2,2-trifluoroethyl)amino-4-trifluoromethyl-2(1H)-quinolinone (Compound 246, Structure 7 of Scheme II, Where R$^1$=Ethyl, R$^2$=2,2,2-Trifluoroethyl)

This compound was prepared in a similar fashion as that described in Example 15, General Procedure VIII but using acetaldehyde and trifluoroacetaldehyde sequentially in place of paraformaldehyde alone. Compound 246 was isolated as a yellow solid: $^1$H NMR (400 MHz, acetone-d$_6$) 11.02 (s, 1H), 7.46 (d, J=9.1, 1H), 7.38 (dd, J=9.1, 2.7, 1H), 7.10 (s, 1H), 6.92 (s, 1H), 4.18 (q, J=9.3, 2H), 3.61 (q, J=7.0, 2H), 1.22 (t, J=7.0, 3H).

EXAMPLE 45

6-(-Ethyl-N-3-furylmethyl)amino-4-trifluoromethyl-2(1H)-quinolinone (Compound 247, Structure 7 of Scheme II, Where R$^1$=Ethyl, R$^2$=3-Furylmethyl)

This compound was prepared in a similar fashion as that described in Example 15, General Procedure VIII but using acetaldehyde and 3-furaldehyde sequentially in place of paraformaldehyde alone. Compound 247 was isolated as a yellow solid: $^1$H NMR (500 MHz, CDCl$_3$) 11.3 (bs, 1H), 7.37 (t, J=1.0, 1H), 7.30 (s, 1H), 7.25 (d, J=9.3, 1H), 7.13 (dd, J=9.3, 2.4, 1H), 7.04 (s, 2H), 6.30 (s, 1H), 4.36 (s, 2H), 3.46 (q, J=7.3, 2H), 1.20 (t, J=7.3, 3H).

EXAMPLE 46

(±)-6-(N-Ethyl-N-2,2-dimethoxyisopropyl)amino-4-trifluoromethyl-2(1H)-quinolinone (Compound 248, Structure 7 of Scheme II, Where R$^1$=Ethyl, R$^2$=2,2-Dimethoxyisopropyl)

This compound was prepared in a similar fashion as that described in Example 15, General Procedure VIII but using acetaldehyde and α,α-dimethoxyacetone sequentially in place of paraformaldehyde alone. Compound 248 was isolated as a yellow solid: $^1$H NMR (500 MHz, CDCl$_3$) 11.4 (bs, 1H), 7.27 (d, J=9.3, 1H), 7.20, (dd, J=9.3, 2.4, 1H), 7.08 (s, 1H), 7.05 (s, 1H), 4.23 (d, J=5.4, 1H), 3.93 (dq, J=6.8, 5.4, 1H), 3.43 (s, 3H), 3.42–3.33 (m, 2H), 3.35 (s, 3H), 1.26 (d J=6.8, 3H), 1.17 (t, J=7.3, 3H).

EXAMPLE 47

6-(N-Isopropyl-N-propyl)amino-4-trifluoromethyl-2(1H)-quinolinone (Compound 249, Structure 7 of Scheme II, Where R$^1$=Propyl, R$^2$=Isopropyl)

This compound was prepared in a similar fashion as that described in Example 15, General Procedure VIII but using propyraldehyde and acetone sequentially in place of paraformaldehyde alone. Compound 249 was isolated as a yellow solid: $^1$H NMR (500 MHz, CDCl$_3$) 12.1 (bs, 1H), 7.33 (d, J=9.3, 1H), 7.15 (dd, J=9.3, 2.4, 1H), 7.05 (s, 1H), 7.00 (s, 1H), 4.04–3.99 (m, 1H), 3.11 (t, J=6.8, 1H), 1.60–1.54 (m, 2H), 1.20 (d, J=6.3, 6H), 0.95 (t, J=7.3, 3H)

EXAMPLE 48

6-(N-2-Hydroxyethyl-N-propyl)amino-4-trifluoromethyl-2(1H)-quinolinone (Compound 250, Structure 7 of Scheme II, Where R$^1$=2-Hydroxyethyl, R$^2$=Propyl)

This compound was prepared in a similar fashion as that described in Example 15, General Procedure VIII but using propyraldehyde and glyoxal sequentially in place of paraformaldehyde alone. Compound 250 was isolated as a yellow solid: $^1$H NMR (500 MHz, acetone-d$_6$) 10.8 (bs, 1H), 7.38 (d, J=9.3, 1H), 7.25 (dd, J=9.3, 2.9, 1H), 6.93 (s, 1H), 6.86 (s, 1H), 3.85 (t, J=5.8, 1H), 3.75 (dt, J=7.8, 5.8, 2H), 3.53 (t, J=6.3, 2H), 3.39 (t, J=7.8, 2H), 1.67–1.61 (m, 2H), 0.95 (t, J=7.3, 3H).

EXAMPLE 49

(±)-6-(N-Propyl-N-1-methylbutyl)amino-4-trifluoromethyl-2(1H)-quinolinone (Compound 251, Structure 7 of Scheme II, Where R$^1$=Propyl, R$^2$=1-Methylbutyl)

This compound was prepared in a similar fashion as that described in Example 15, General Procedure VIII but using propyraldehyde and 3-methyl-2-butanone sequentially in place of paraformaldehyde alone. Compound 251 was isolated as a yellow solid: $^1$H NMR (500 MHz, CDCl$_3$), 11.7 (bs, 1H), 7.29 (d, J=8.8, 1H), 7.15 (dd, J=8.8, 2.5, 1H), 7.04 (s, 1H), 6.99 (s, 1H), 3.84–3.80 (m, 1H), 3.12–3.09 (m, 2H), 1.65–1.31 (m, 6H), 1.17 (d, J=6.3, 3H), 0.94 (t J=7.3, 3H), 0.91 (t, J=7.3, 3H).

EXAMPLE 50

(±)-6-(N-Propyl-N-1,2-dimethylpropyl)amino-4-trifluoromethyl-2(1H)-quinolinone (Compound 252, Structure 7 of Scheme II, Where R$^1$=Propyl, R$^2$=1,2-Dimethylpropyl)

This compound was prepared in a similar fashion as that described in Example 15, General Procedure VIII but using propyraldehyde and 3-methyl-2-butanone sequentially in place of paraformaldehyde alone. Compound 252 was isolated as a yellow solid: $^1$H NMR (500 MHz, CDCl$_3$) 10.8 (bs, 1H), 7.21 (d, J=9.3, 1H), 7.16, (dd, J=9.3, 2.4, 1H), 7.03 (s, 1H), 6.98 (s, 1H), 3.42–3.39 (m, 1H), 3.12 (t, J=6.8, 2H), 1.92–1.86 (m, 1H), 1.61–1.55 (m, 2H), 1.19 (d, J=6.3, 3H), 0.99 (d, J=6.3, 3H), 0.97 (t, J=7.3, 3H), 0.91 (d, J=6.3, 3H).

EXAMPLE 51

6-(N-Propyl-N-isobutyl)amino-4-trifluoromethyl-2(1H)-quinolinone (Compound 253, Structure 7 of Scheme II, Where R$^1$=Propyl, R$^2$=Isopropyl)

This compound was prepared in a similar fashion as that described in Example 15, General Procedure VIII but using propyraldehyde and isobutyraldehyde sequentially in place of paraformaldehyde alone. Compound 253 was isolated as a yellow solid: $^1$H NMR (500 MHz, CDCl$_3$) 11.5 (bs, 1H), 7.26 (d, J=8.8, 1H 7.05, (dd, J=8.8, 2.4, 1H), 7.03 (s, 1H), 6.90 (s, 1H), 3.31 (t, J=7.3, 2H), 3.11 (d, J=7.3, 2H), 2.05–2.00 (m, 1H), 1.64–1.58 (m, 2H), 0.94 (d, J=6.8, 6H), 0.93 (t, J=7.3, 3H).

EXAMPLE 52

6-(N-Propyl-N-cyclopropylmethyl)amino-4-trifluoromethyl-2(1H)-quinolinone (Compound 254, Structure 7 of Scheme II, Where R$^1$=Propyl, R$^2$=Cyclopropylmethyl)

This compound was prepared in a similar fashion as that described in Example 15, General Procedure VIII but using propyraldehyde and cyclopropanecarboxaldehyde sequentially in place of paraformaldehyde alone. Compound 254 was isolated as a yellow solid: $^1$H NMR (500 MHz, CDCl$_3$) 9.9 (bs, 1H), 7.15 (d, J=8.8, 1H), 7.12 (dd, J=8.8, 2.4, 1H), 7.02 (s, 1H), 7.00 (s, 1H), 3.35 (t, J=6.8, 2H), 3.24 (d, J=6.3, 2H), 1.66–1.61 (m, 2H), 1.04–1.01 (m, 1H), 0.95 (t, J=7.3, 3H), 0.57–0.55 (m, 2H), 0.26–0.24 (m,2H).

EXAMPLE 53

(±)-6-(N-Propyl-N-1-methylpropyl)amino-4-trifluoromethyl-2(1H)-quinolinone (Compound 255, Structure 7 of Scheme II, Where R$^1$=Propyl, R$^2$=sec-Butyl)

This compound was prepared in a similar,fashion as that described in Example 15, General Procedure VIII but using propyraldehyde and 2-butanone sequentially in place of paraformaldehyde alone. Compound 255 was isolated as a yellow solid: $^1$H NMR (500 MHz, CDCl$_3$) 11.2 (bs, 1H), 7.25 (dd, J=9.3, 2.4, 1H), 7.15 (dd, J=9.3, 2.4, 1H), 7.03 (s, 1H), 7.00 (s, 1H), 3.70 (q, J=6.8, 1H), 3.12–3.09 (m, 2H), 1.58–1.47 (m, 2H), 1.18 (d, J=6.3, 3H), 0.93–0.91 (m, 6H).

EXAMPLE 54

6-(N-2-Hydroxyethyl-N-isopropyl)amino-4-trifluoromethyl-2(1H-quinolinone (Compound 256, Structure 7 of Scheme II, Where R$^1$=2-Hydroxyethyl, R$^2$=Isopropyl)

This compound was prepared in a similar fashion as that described in Example 15, General Procedure VIII but using acetone and glyoxal sequentially in place of paraformaldehyde alone. Compound 256 was isolated as a yellow solid: $^1$H NMR (500 MHz, acetone-d$_6$) 10.9 (bs, 1H), 7.41 (d, J=8.8, 1H), 7.37 (dd, J=8.8, 2.9, 1H), 7.10 (s, 1H), 6.88 (s, 1H), 4.09–4.03 (m, 1H), 3.83 (t, J=5.6, 1H), 3.68 (dt, J=6.8, 5.6, 2H), 3.38 (t, J=6.8, 2H), 1.23 (d, J=6.8, 6H).

EXAMPLE 55

6-(N-Isopropyl-N-cyclopropylmethyl)amino-4-trifluoromethyl-2(1H)-quinolinone (Compound 257, Structure 7 of Scheme II, Where R$^1$=Isopropyl, R$^2$=Cyclopropylmethyl)

This compound was prepared in a similar fashion as that described in Example 15, General Procedure VIII but using acetone and cyclopropanecarboxaldehyde sequentially in place of paraformaldehyde alone. Compound 257 was isolated as a yellow solid: $^1$H NMR (500 MHz, CDCl$_3$) 11.0 (bs, 1H), 7.19 (s, 2H), 7.04 (s, 2H), 4.03–3.98 (m, 1H), 3.08 (d, J=5.4, 2H), 1.21 (d, J=6.4, 6H), 0.98–0.93 (m, 1H), 0.58–0.55(m, 2H), 0.26–0.23 (m, 2H).

EXAMPLE 56

6-(N-Methyl-N-2,2,2-trifluoroethyl)amino-4-trifluoromethyl-2(1H)-quinolinone (Compound 258, Structure 7 of Scheme II, Where R$^1$=Methyl, R$^2$=2,2,2-Trifluoroethyl)

This compound was prepared in a similar fashion as that described in Example 15, General Procedure VIII but using paraformaldehyde and trifluoroacetaldehyde sequentially. Compound 258 was isolated as a yellow solid: $^1$H NMR (500 MHz, CDCl$_3$) 11.3 (bs, 1H), 7.31 (d, J=9.3, 1H), 7.18 (dd, J=9.3, 2.9, 1H), 7.11 (s, 1H), 7.08 (s, 1H), 3.91 (q, J$_{H-F}$=8.8, 2H), 3.13 (s, 3H).

EXAMPLE 57

6-(N-2,2,2-Trifluoroethyl-N-isobutyl)amino-4-trifluoromethyl-2(1H)-quinolinone (Compound 259, Structure 7 of Scheme II, Where R$^1$=2,2,2-Trifluoroethyl, R$^2$=Isobutyl)

This compound was prepared in a similar fashion as that described in Example 15, General Procedure VIII but using trifluoroacetaldehyde and isobutyraldehyde sequentially in place of paraformaldehyde alone. Compound 259 was isolated as a yellow solid: $^1$H NMR (500 MHz, CDCl$_3$) 11.31 (s, 1H), 7.29 (d, J=9.3, 1H), 7.23 (d, J=9.3, 1H), 7.19 (s, 1H), 7.06 (s, 1H), 3.94 (q, J=8.9, 2H), 3.25 (d, J=7.3, 2H), 2.09–2.03 (m, 1H), 0.94 (d, J=6.3, 6H).

EXAMPLE 58

6-(N-2,2,2-Trifluoroethyl-N-isopropyl)amino-4-trifluoromethyl-2(1H)-quinolinone (Compound 260, Structure 7 of Scheme II, Where R$^1$=2,2,2-Trifluoroethyl, R$^2$=Isopropyl)

This compound was prepared in a similar fashion as that described in Example 15, General Procedure VIII but using trifluoroacetaldehyde and isopropylaldehyde sequentially in place of paraformaldehyde alone. Compound 260 was isolated as a yellow solid: $^1$H NMR (400 MHz, CDCl$_3$) 11.10 (s, 1H), 7.45 (d, J=9.1, 1H), 7.33 (dd, J=9.1, 2.6, 1H), 7.30 (s, 1H), 7.11 (s, 1H), 4.07–3.95 (m, 1H), 3.83 (q, J=8.8, 2H), 1.24 (d, J=6.6, 6H).

EXAMPLE 59

6-N-2,2,2-Trifluoroethyl-N-Cyclopropylmethyl) amino-4-trifluoromethyl-2(1H)-quinolinone (Compound 261, Structure 7 of Scheme II, Where R$^1$=2,2,2-Trifluoroethyl, R$^2$=Cyclopropylmethyl)

This compound was prepared in a similar fashion as that described in Example 15, General Procedure VIII but using trifluoroacetaldehyde and cyclopropanecarboxaldehyde sequentially in place of paraformaldehyde alone. Compound 261 was isolated as a yellow solid: $^1$H NMR (400 MHz, CDCl$_3$) 10.83 (s, 1H), 7.42 (d, J=9.0, 1H), 7.27 (dd, J=9.0, 2.7, 1H), 7.22 (d, J=2.7, 1H), 7.09 (s, 1H), 4.03 (q, J=8.8, 2H), 3.34 (d, J=6.3, 2H), 1.09–1.00 (m, 1H), 0.64–0.59 (m, 2H), 0.31–0.27 (m, 2H).

EXAMPLE 60

(±)-6-(N-2,2,2-Trifluoroethyl-N-1-methylpropyl) amino-4-trifluoromethyl-2(1H)-quinolinone (Compound 262, Structure 7 of Scheme II, Where R$^1$=2,2,2-Trifluoroethyl, R$^2$=sec-Butyl)

This compound was prepared in a similar fashion as that described in Example 15, General Procedure VIII but using trifluoroacetaldehyde and 2-butanone sequentially in place of paraformaldehyde alone. Compound 262 was isolated as a yellow solid: $^1$H NMR (400 MHz, CDCl$_3$) 10.87 (s, 1H), 7.30–7.23 (m, 3H), 7.05 (s, 1H), 3.81 (q, J=8.6, 2H), 3.63–3.58 (m, 1H), 1.21 (d, J=6.7, 3H), 1.02–0.86 (m, 5H).

EXAMPLE 61

(±)-6-(N-2,2,2-Trifluoroethyl-N-2-chloroisopropyl) amino-4-trifluoromethyl-2(1H)-quinolinone (Compound 263, Structure 7of Scheme II Where R$^1$=2,2,2-Trifluoroethyl, R$^2$=2-chloroisopropyl)

This compound was prepared in a similar fashion as that described in Example 15, General Procedure VIII but using trifluoroacetaldehyde and chloroacetone sequentially. Compound 263 was isolated as a yellow solid: $^1$H NMR (400 MHz, acetone-d$_6$) 10.99 (s, 1H), 7.43 (s, 2H), 7.13 (s, 1H), 6.90 (s, 1H), 4.35 (q, J=7.8, 2H), 4.22–4.17 (m, 1H), 3.61 (dd, J=15.3, 3.6, 1H), 3.42 (dd, J=15.3, 8.3, 1H), 1.20 (d, J=6.2, 3H).

EXAMPLE 62

(+)-6-(N-2,2,2-Trifluoroethyl-N-2-chloroisopropyl) amino-4-trifluoromethyl-2(1H)-quinolinone (Compound 264, Structure 7 of Scheme II, Where R$^1$=2,2,2-Trifluoroethyl, R$^2$=2-chloroisopropyl) and (−)-6-(N-2,2,2-Trifluoroethyl-N-2-chloroisopropyl) amino-4-trifluoromethyl-2(1H)-quinolinone (Compound 265, Structure 7 of Scheme II, Where R$^1$=2,2,2-Trifluoroethyl, R$^2$=2-Chloroisopropyl)

Compounds 264 and 265 were prepared by chiral HPLC separation of Compound 263.

EXAMPLE 63

6-(N-2,2,2-Trifluoroethyl-N-3-furfuryl)amino-4-trifluoromethyl-2(1H)-quinolinone (Compound 266, Structure 7 of Scheme II, Where R$^1$=2,2,2-Trifluoroethyl, R$^2$=3-Furanylmethyl)

This compound was prepared in a similar fashion as that described in Example 15, General Procedure VIII but using trifluoroacetaldehyde and 3-furaldehyde sequentially. Compound 266 was isolated as a yellow solid: $^1$H NMR (400 MHz, acetone-d$_6$) 10.98 (s, 1H), 7.77 (s, 1H), 7.43 (s, 3H), 7.19 (s, 1H), 6.89 (s, 1H), 6.42 (s, 1H), 4.62 (s, 2H), 6.27 (q, J=9.1, 2H).

EXAMPLE 64

6-(N-2,2,2-Trifluoroethyl-N-3-thiophenemethyl) amino-4-trifluoromethyl-2(1H)-quinolinone (Compound 267, Structure 7 of Scheme II, Where R$^1$=2,2,2-Trifluoroethyl, R$^2$=3-Thiophenemethyl)

This compound was prepared in a similar fashion as that described in Example 15, General Procedure VIII but using trifluoroacetaldehyde and 3-thiophenecarboxaldehyde sequentially. Compound 267 was isolated as a yellow solid: $^1$H NMR (400 MHz, acetone-d$_6$) 10.99 (s, 1H), 7.31–7.29 (m, 3H), 7.13 (s, 1H), 7.02 (s, 1H), 6.92 (d, J=4.6, 1H), 6.76 (s, 1H), 4.66 (s, 2H), 4.21 (q, J=9.2, 2H).

EXAMPLE 65

6-(N-2,2,2-Trifluoroethyl-N-3,3-dimethylbutyl) amino-4-trifluoromethyl-2(1H)-quinolinone (Compound 268, Structure 7 of Scheme II, Where R$^1$=2,2,2-Trifluoroethyl, R$^2$=3,3-Dimethylbutyl)

This compound was prepared in a similar fashion as that described in Example 15, General Procedure VIII but using trifluoroacetaldehyde and 3,3-dimethylbutyraldehyde sequentially. Compound 268 was isolated as a yellow solid: $^1$H NMR (400 MHz, acetone-d$_6$) 10.99 (s, 1H), 7.33 (d, J=9.2, 1H), 7.21 (dd, J=9.1, 2.6, 1H), 6.97 (s, 1H), 6.79 (s, 1H), 4.06 (q, J=9.2, 2H), 3.45 (m, 2H), 1.45 (m, 2H), 0.88 (s, 9H).

EXAMPLE 66

6-(N-2,2,2-Trifluoroethyl-N-2-thiophenemethyl) amino-4-trifluoromethyl-2(1H)-quinolinone (Compound 269, Structure 7 of Scheme II, Where R$^1$=2,2,2-Trifluoroethyl, R$^2$=2-Thiophenemethyl)

This compound was prepared in a similar fashion as that described in Example 15, General Procedure VIII but using trifluoroacetaldehyde and 2-thiophenecarboxaldehyde sequentially. Compound 269 was isolated as a yellow solid: $^1$H NMR (400 MHz, acetone-d$_6$) 10.92 (s, 1H), 7.45–7.42 (m, 3H), 7.33 (d, J=5.4, 1H), 7.24 (s, 1H), 7.08 (s, 1H), 6.96 (t, J=4.4, 1H), 6.88 (s, 1H), 4.96 (s, 2H), 4.31 (q, J=9.0, 2H).

EXAMPLE 67

6-(N-2,2,2-Trifluoroethyl-N-2-furfuryl)amino-4-trifluoromethyl-2(1H)-quinolinone (Compound 270, Structure 7 of Scheme II, Where R$^1$=2,2,2-Trifluoroethyl, R$^2$=2-Furanylmethyl)

This compound was prepared in a similar fashion as that described in Example 15, General Procedure VIII but using trifluoroacetaldehyde and 2-furaldehyde sequentially. Compound 270 was isolated as a yellow solid. $^1$H NMR (400 MHz, acetone-d$_6$) 10.92 (s, 1H), 7.50 (s, 1H), 7.47–7.42 (m, 2H), 7.25 (s, 1H), 6.89 (s, 1H), 6.37–6.34 (m, 2H), 4.72 (s, 2H), 4.29 (q, J=9.2, 2H).

EXAMPLE 68

6-(N-Butyl-N-2,2,2-trifluoroethyl)amino-4-trifluoromethyl-2(1H)-quinolinone (Compound 271, Structure 7 of Scheme II, Where R$^1$=2,2,2-Trifluoroethyl, R$^2$=Butyl)

This compound was prepared in a similar fashion as that described in Example 15, General Procedure VIII but using trifluoroacetaldehyde and butyraldehyde sequentially. Compound 271 was isolated as a yellow solid. $^1$H NMR (400 MHz, acetone-d$_6$) 11.04 (s, 1H), 7.45 (d, J=9.1, 1H), 7;37 (dd, J=9.1, 2.5, 1H), 7.10 (s, 1H), 6.91 (s, 1H), 4.19 (q, J=9.3, 2H), 3.52 (t, J=7.7, 2H), 1.9–1.61 (m, 2H), 1.46–1.37 (m, 2H), 0.96 (t, J=7.4, 3H).

EXAMPLE 69

6-(bis-N,N-Benzyl)amino-4-trifluoromethyl-2(1H)-quinolinone (Compound 272, Structure 7 of Scheme II, Where R$^1$=R$^2$=Benzyl;

This compound was prepared in a similar fashion as that described in Example 15, General Procedure VIII but using benzaldehyde. Compound 272 was isolated as a yellow solid. $^1$H NMR (400 MHz, acetone-d$_6$) 11.60 (s, 1H), 7.41–7.25 (m, 12H), 6.98 (s, 1H), 6.83 (s, 1H), 4.79 (s, 4H).

EXAMPLE 70

6-(N-2,2,2-Trifluoroethyl-N-cyclobutyl)amino-4-trifluoromethyl-2(1H)-quinolinone (Compound 273, Structure 7 of Scheme II, Where R$^1$=2,2,2-Trifluoroethyl, R$^2$=Cyclobutyl)

This compound was prepared in a similar fashion as that described in Example 15, General Procedure VIII but using trifluoroacetaldehyde and cyclobutanone sequentially in place of paraformaldehyde alone. Compound 293 was isolated as a yellow solid: $^1$H NMR (400 MHz, CDCl$_3$) 10.85 (s, 1H), 7.30–7.25 (m, 2H), 7.16 (s, 1H), 7.06 (m, 1H), 4.18–4.08 (m, 1H), 3.86 (q, J=8.9, 2H), 2.40–2.34 (m, 2H), 1.97–1.92 (m, 2H), 1.79–1.77 (m, 2H).

EXAMPLE 71

6-(N-2,2,2-Trifluoroethyl-N-2,2-dichloroethyl) amino-4-trifluoromethyl-2(1H)-quinolinone (Compound 274, Structure 7 of Scheme II, Where R$^1$=2,2,2-Trifluoroethyl, R$^2$=2,2-Dichloroethyl)

This compound was prepared in a similar fashion as that described in Example 9, General Procedure VI but using trifluoroacetic acid and dichloroacetic acid sequentially in place of difluoroacetic acid. Compound 274 was isolated as a yellow solid: $^1$H NMR (400 MHz, acetone-d$_6$) 11.26 (s, 1H), 7.58 (dd, J=9.2, 2.7, 1H), 7.50 (d, J=9.1, 1H), 7.32 (s, 1H), 6.97 (s, 1H), 6.26 (t, J=6.4, 1H), 4.45 (q, J=9.0, 2H), 4.23 (d, J=6.4, 2H).

EXAMPLE 72

6-(N-2,2,2-Trifluoroethyl-N-2-chloroethyl)amino-4-trifluoromethyl-2(1H)-quinolinone (Compound 275, Structure 7 of Scheme II, Where R$^1$=2,2,2-Trifluoroethyl, R$^2$=2-Chloroethyl)

This compound was prepared in a similar fashion as that described in Example 9, General Procedure VI but using trifluoroacetic acid and chloroacetic acid sequentially in place of difluoroacetic acid. Compound 275 was isolated as a yellow solid: $^1$H NMR (400 MHz, acetone-d$_6$) 11.10 (s, 1H), 7.48 (d, J=2.5, 2H), 7.17 (s, 1H), 6.93 (s, 1H), 4.34 (q, J=9.2, 2H), 3.92 (dd, J=13.9, 7.1, 2H), 3.80 (dd, J=13.9, 7.1, 2H).

EXAMPLE 73

6-(N-Benzyl-N-2,2,2-trifluoroethyl)amino-4-trifluoromethyl-2(1H)-quinolinone (Compound 276, Structure 7 of Scheme II, Where R$^1$=2,2,2-Trifluoroethyl, R$^2$=Benzyl)

This compound was prepared in a similar fashion as that described in Example 15, General Procedure VIII using trifluoroacetaldehyde and benzaldehyde sequentially in place of paraformaldehyde alone. Compound 276 was isolated as a yellow solid: $^1$H NMR (400 MHz, acetone-d$_6$) 11.62 (s, 1H), 7.39 (d, J=2.3, 2H), 7.38–7.31 (m, 4H), 7.27–7.22 (m, 1H), 7.09 (s, 1H), 6.86 (s, 1H), 4.81 (s, 2H), 4.41 (q, J=9.2, 2H).

EXAMPLE 74

6-(N-4-Fluorobenzyl-N-2,2,2-trifluoroethyl)amino-4-trifluoromethyl-2(1H)-quinolinone (Compound 277, Structure 7 of Scheme II, Where R$^1$=2,2,2-Trifluoroethyl, R$^2$=Benzyl)

This compound was prepared in a similar fashion as that described in Example 15, General Procedure VIII but using trifluoroacetaldehyde and 4-fluorobenzaldehyde sequentially in place of paraformaldehyde alone. Compound 277 was isolated as a yellow solid: $^1$H NMR (400 MHz, acetone-d$_6$) 11.05 (s, 1H), 7.40 (s, 1H), 7.39–7.34 (m, 3H), 7.10–7.06 (m, 3H), 6.86 (s, 1H), 4.80 (s, 2H), 4.41 (q, J=9.2, 2H).

EXAMPLE 75

6-(N-Propyl-N-2,2,2-trifluoroethyl)amino4-trifluoromethyl-2(1H)-quinolinone (Compound 278, Structure 7 of Scheme II, Where R$^1$=Propyl, R$^2$=2,2,2-Trifluoroethyl)

This compound was prepared in a similar fashion as that described in Example 15, General Procedure VIII but using trifluoroacetaldehyde and propyraldehyde sequentially in place of paraformaldehyde alone. Compound 278 was isolated as a yellow solid: $^1$H NMR (400 MHz, acetone-d$_6$) 11.03 (s, 1H), 7.45 (d, J=9.1, 1H), 7.38 (dd, J=9.1, 2.3, 1H), 7.09 (s, 1H), 6.91 (s, 1H), 4.24–4.17 (m, 2H), 3.48 (t, J=7.6, 2H).

EXAMPLE 76

6-(N-2,2,3,3,3-Pentafluoropropyl-N-2,2,2-trifluoroethyl)amino-4-trifluoromethyl-2(1H)-quinolinone (Compound 279, Structure 7 of Scheme II, Where R$^1$=2,2,3,3,3-Pentafluoropropyl, R$^2$=2,2,2-Trifluoroethyl)

This compound was prepared in a similar fashion as that described in Example 15, General Procedure VIII but using trifluoroacetaldehyde and pentafluoropropyraldehyde sequentially in place of paraformaldehyde alone. Compound 279 was isolated as a yellow solid: $^1$H NMR (500 MHz, CDCl$_3$) 11.8 (bs, 1H), 7.39 (d, J=8.8, 1H), 7.33 (s, 1H), 7.29 (dd, J=8.8, 2.9, 1H), 7.10 (s, 1H), 4.13 (t, J$_{H-F}$=15.1, 2H), 4.08 (q, J$_{H-F}$=8.3, 2H).

EXAMPLE 77

6-Diallylamino-4-trifluoromethyl-2(1H)-quinolinone (Compound 280, Structure 7 of Scheme II, Where R$^1$=R$^3$=Allyl)

This compound was prepared from Compound 200 and allyl bromide by the following General Procedure IX (Allylation of amine):

To a solution of Compound 200 (Structure 3 of Scheme II) in methanol (0.05–0.2 M) was added K$_2$CO$_3$ powder (5–10 equiv) and an allyl bromide (3–10 equiv). The reaction mixture was stirred at room temperature for 3 hrs and extracted with EtOAc. The organic layer was washed with H$_2$O, dried (Na$_2$SO$_4$), and concentrated in vacuo. Purification by chromatography afforded a white solid in excellent yield (80–95%).

Compound 280 was isolated as a yellow solid: $^1$H NMR (400 MHz, CDCl$_3$) 11.01 (s, 1H), 7.27 (d, J=2.6, 1H), 7.20 (d, J=9.1, 1H), 7.07 (dd, J=9.1, 2.6, 1H), 7.02 (s, 1H), 5.90–5.81 (m, 2H), 3.20 (dd, J=15.6, 3.9, 4H), 397 (d, J=3.9, 4H).

EXAMPLE 78

6-(N-Isobutyl-N-allyl)amino-4-trifluoromethyl-2(1H-quinolinone (Compound 281, Structure 7 of Scheme II, Where R$^1$=Isobutyl, R$^2$=Allyl)

This compound was prepared in a similar fashion as that described in Example 15, General Procedure VIII to install isobutyl from isobutyraldehyde and sequentially in a similar fashion as that described in Example 77, General Procedure IX to install allyl group from allyl bromide. Compound 281 was isolated as a yellow solid: $^1$H NMR (500MHz, CDCl$_3$) 11.2 (bs, 1H), 7.23 (d, J=9.3, 1H), 7.06 (dd, J=9.3, 2.4, 1H), 7.03 (s, 1H), 6.97 (s, 1H), 5.85–5.77 (m, 1H), 5.19–5.12 (m, 2H), 4.00–3.99 (m, 2H), 3.15 (d, J=7.3, 2H), 2.09–2.03 (m, 1H), 0.97 (d, J=6.8, 6H).

EXAMPLE 79

6-(N-Isopropyl-N-allyl)amino-4-trifluoromethyl-2(1H)-quinolinone (Compound 282, Structure 7 of Scheme II, Where R$^1$=Isopropyl, R$^2$=Allyl)

This compound was prepared in a similar fashion as that described in Example 15, General Procedure VIII to install isopropyl from isopropyraldehyde and sequentially in a similar fashion as that described in Example 77, General Procedure IX to install allyl group from allyl bromide. Compound 282 was isolated as a yellow solid: $^1$H NMR (500 MHz, CDCl$_3$) 10.8 (bs, 1H), 7.21 (d, J=9.3, 1H), 7.13 (dd, J=9.3, 2.4, 1H), 7.06 (s, 1H), 7.02 (s, 1H), 5.89–5.82 (m, 1H), 5.26 (dd, J=17.1, 1.5, 1H), 5.18 (dd, J=10.3, 1.5, 1H), 4.12–4.07 (m, 1H), 3.84–3.83 (m, 2H), 1.22 (d, J=6.4, 6H).

EXAMPLE 80

6-(N-Allyl-N-2,2,2-trifluoroethyl)amino-4-trifluoromethyl-2(1H)-quinolinone (Compound 283, Structure 7 of Scheme II, Where R$^1$=Allyl, R$^2$=2,2,2-Trifluoroethyl)

6-Allylamino-4-trifluoromethyl-2(1H)-quinolinone (Compound 284, Structure 7 of Scheme II, where R$^1$=allyl, R$^2$=H):

To a solution of Compound 200 (Structure 3 of Scheme II) (340 mg, 1.49 mmol) in MeOH (20 mL) was added K$_2$CO$_3$ (1.0 g) followed by allylbromide (0.30 mL, 3.5 mmol). After stirring at room temperature for 6 h, water was added and the mixture was extracted with EtOAc (3×50 mL). The combined organic layers were washed with brine, and dried over MgSO$_4$, concentrated in vacuo and purified by column chromatography (Silica gel, hex:EtOAc, 3:1 to 1:1 gradient) to give 184 mg of Compound 284.

6-(N-Allyl-N-2,2,2-trifluoroethyl)amino-4-trifluoromethyl-2(1H)-quinolinone (Compound 283, Structure 7 of Scheme II, where R$^1$=allyl, R$^2$=2,2,2-trifluoroethyl):

To a solution of Compound 284 (261 mg, 0.97 mmol) in TFA (8 mL) was added trifluoroacetaldehyde hydrate (0.5 mL, 5 mmol) and the mixture was stirred at room temperature for 6 h. NaCNBH$_3$ (60 mg, 1 mmol) was added and the mixture was stirred for 16 h. Then additional NaCNBH$_3$ (60 mg, 1 mmol) was added and the mixture was stirred for 2 h. The reaction was quenched with water (20 mL) and was extracted with EtOAc (2×40 mL). The combined organic layer was dried over MgSO$_4$, concentrated in vacuo and purified by column chromatography (Silica gel, hex:EtOAc 5:2) to give Compound 283 (201 mg, 0.57 mmol) as a yellow solid: $^1$H NMR (500 MHz, CDCl$_3$) 2.0 (bs, 1H), 7.35 (d, J=9.8, 1H), 7.19–7.16 (m, 2H), 7.08 (s, 1H), 5.87–5.80 (m, 1H), 5.27 (dd, J=10.7, 1.5, 1H), 5.19 (dd, J=17.6, 1.5, 1H), 4.10 (d, J=4.9, 2H), 3.92 (q, J$_{H-F}$=8.8, 2H).

EXAMPLE 81

6-(N-Allyl-N-cyclopropylmethyl)amino-4-trifluoromethyl-2(1H)-quinolinone (Compound 285, Structure 7 of Scheme II, Where R$^1$=Allyl, R$^2$=Cyclopropylmethyl)

This compound was prepared in a similar fashion as that described in Example 15, General Procedure VIII to install cyclopropylmethyl group from cyclopropanecarboxaldehyde and sequentially in a similar fashion as that described in Example 77, General Procedure IX to install allyl group from allyl bromide. Compound 285 was isolated as a yellow solid: $^1$H NMR (400 MHz, CDCl$_3$) 10.7 (bs, 1H), 7.38 (d, J=9.1, 1H), 7.15 (dd, J=9.1, 2.5, 1H), 7.06 (s, 1H), 7.05 (s, 1H), 5.90–5.80 (m, 1H), 5.20 (d, J=5.4, 1H), 5.17 (s, 1H), 4.04 (d, J=4.7, 2H), 3.27 (d, J=6.2, 2H), 1.08–1.03 (m, 1H), 0.59–0.55 (m, 2H), 0.27–0.23 (m, 2H).

EXAMPLE 82

6-(N-Allyl-N-2,2,2-trifluoroacetyl)amino-4-trifluoromethyl-2(1H)-quinolinone (Compound 286, Structure 7 of Scheme II, Where R$^1$=Allyl, R$^2$=2,2,2-Trifluoroacetyl)

This compound was prepared in a similar fashion as that described in Example 11, General Procedure VII but using Compound 284 (Structure 7 of Scheme II, where R$^1$=H, R$^2$=allyl) and trifluoroacetic anhydride in place of Compound 200 and acetic anhydride. Compound 286 was isolated as a white solid: $^1$H NMR (500 MHz, CDCl$_3$) 12.9 (bs, 1H), 7.69 (s, 1H), 7.57 (d, J=8.8, 1H), 7.48 (dd, J=8.8, 2.4, 1H), 7.17 (s, 1H), 5.90–5.87 (m, 1H), 5.26 (d, J=9.8, 1H), 5.14 (d, J=17.1, 1H), 4.36 (s, 2H).

EXAMPLE 83

6-(N-2,2,2-Trifluoroethyl-N-2,2,2-trifluoroacetyl)amino-4-trifluoromethyl-2(1H)-quinolinone (Compound 287, Structure 7 of Scheme II, Where R$^1$=2,2,2-Trifluoroethyl, R$^2$=Trifluoroacetyl)

This compound was prepared in a similar fashion as that described in Example 11, General Procedure VII but using Compound 209 (Structure 7 of Scheme II, where R$^1$=H, R$^2$=2,2,2-Trifluoroethyl) and trifluoroacetic anhydride in place of Compound 200 and acetic anhydride. Compound 287 was isolated as a yellow solid: $^1$H NMR (400 MHz, CDCl$_3$) 11.57 (s, 1H), 7.78 (s, 1H) 7.53–7.32 (m, 2H), 7.17 (s, 1H), 4.45–4.39 (m, 2H).

EXAMPLE 84

6-(N-Allyl-N-propyl)amino-4-trifluoromethyl-2(1H)-quinolinone (Compound 288, Structure 7 of Scheme II, Where R$^1$=Allyl, R$^2$=Propyl)

This compound was prepared in a similar fashion as that described in Example 15, General Procedure VIII to install propyl group from propionaldehyde and sequentially in a similar fashion as that described in Example 77, General Procedure IX to install allyl group from allyl bromide. Compound 288 was isolated as a yellow solid: $^1$H NMR (500 MHz, CDCl$_3$) 10.9 (bs, 1H), 7.21 (d, J=9.3, 1H), 7.05 (dd, J=9.3, 2.9, 1H), 7.03 (s, 1H), 6.96 (s, 1H), 5.87–5.80 (m, 1H), 5.19–5.16 (m, 2H), 3.96 (d, J=4.9, 2H), 3.31 (t, J=7.3, 2H), 1.67–1.61 (m, 2H), 0.96 (t, J=7.3, 3H).

EXAMPLE 85

(±)-6-(N-2-Hydroxyisopropyl-N-2,2,2-trifluoroethyl)amino-4-trifluoromethyl-2(1H)-quinolinone (Compound 289, Structure 7 of Scheme II, Where R$^1$=2-Hydroxysopropyl, R$^2$=2,2,2-Trifluoroethyl)

This compound was prepared in a similar fashion as that described in Example 15, General Procedure VIII but using trifluoroacetaldehyde and acetol sequentially in place of paraformaldehyde alone. Compound 289 was isolated as a yellow solid: $^1$H NMR (500 MHz, CDCl$_3$) 11.6 (bs, 1H), 7.44 (s, 1H), 7.41 (dd, J=8.8, 2.4, 1H), 7.35 (d, J=8.8, 1H), 7.09 (s, 1H), 3.96–3.88 (m, 1H), 3.85–3.78 (m, 2H), 3.67–3.61 (m, 2H), 2.06 (d, J=1.4, 1H), 1.14 (d, J=6.8, 3H).

EXAMPLE 86

(±)-6-(N-Isobutyl-N-2,2,2-trifluoroisopropyl)amino-4-trifluoromethyl-2(1H)-quinolinone (Compound 290, Structure 7 of Scheme II, Where R$^1$=Isobutyl, R$^2$=2,2,2-Trifluoroisopropyl)

This compound was prepared in a similar fashion as that described in Example 15, General Procedure VIII but using trifluoroacetone and 2-butanone sequentially in place of paraformaldehyde alone. Compound 290 was isolated as a yellow solid: $^1$H NMR (500 MHz, CDCl$_3$) 12.3 (bs, 1H), 7.38 (d, J=8.8, 1H), 7.30 (dd, J=8.8, 2.4, 1H), 7.28 (s, 1H), 7.09 (s, 1H), 4.12–4.06 (m, 1H), 3.05 (d, J=7.3, 2H), 1.83–1.78 (m, 1) 1.41 (d, J=6.8, 3H), 0.89–0.87 (m, 6H).

EXAMPLE 87

6-(N-2,2-Difluoroethyl-N-2,2,2-trifluoroethyl)amino-4-trifluoromethyl-2(1H)-quinolinone (Compound 291, Structure 7 of Scheme II, Where R$^1$=2,2-Difluoroethyl, R$^2$=2,2,2-Trifluoroethyl)

This compound was prepared in a similar fashion as that described in Example 9, General Procedure VI but using Compound 211 (Structure 7 of Scheme II, where R$^1$=H, R$^2$=2,2-difluoroethyl) and trifluoroacetic acid in place of Compound 200 and difluoroacetic acid. Compound 291 was isolated as a yellow solid: $^1$H NMR (400 MHz, acetone-d$_6$) 11.55 (s, 1H), 7.54 (dd, J=9.1, 2.4, 1H), 7.49 (d, J=9.1, 1H), 7.29 (s, 1H), 6.96 (s, 1H), 6.21 (tt, J=55.5, 3.9, 1H), 4.37 (m, 2H), 4.02 (td, J 14.2, 3.9, 2H).

EXAMPLE 88

6-(N-2,2-Dimethylpropyl-N-2,2,2-trifluoroethyl)amino-4-trifluoromethyl-2(1H)-quinolinone (Compound 292, Structure 7 of Scheme II, Where R$^1$=2,2-Dimethylpropyl, R$^2$=2,2,2-Trifluoroethyl)

This compound was prepared in a similar fashion as that described in Example 9, General Procedure VI but using Compound 211 (Structure 7 of Scheme II, where R$^1$=H, R$^2$=2,2-difluoroethyl) and trimethylacetic acid in place of Compound 200 and difluoroacetic acid. Compound 292 was isolated as a yellow solid: $^1$H NMR (400 MHz, acetone-d$_6$) 12.2 (bs, 1H), 7.36 (d, J=9.8, 1H), 7.33–7.31 (m, 2H), 7.09 (s, 1H) 4.03 (q, J$_{H-F}$=8.8, 2H), 3.36 (s, 2H), 0.94 (s, 9H).

EXAMPLE 89

6-(N-2,2-Difluoro-2-chloroethyl-N-2,2,2-trifluoroethyl)amino-4-trifluoromethyl-2(1H)-quinolinone (Compound 293, Structure 7 of Scheme II, Where R$^1$=2,2-Difluoro-2-chloroethyl, R$^2$=2,2,2-Trifluoroethyl)

This compound was prepared in a similar fashion as that described in Example 9, General Procedure VI but using Compound 209 (Structure 7 of Scheme II, where R$^1$=H, R$^2$=2,2,2-Trifluoroethyl) and chlorodifluoroacetic acid in place of Compound 200 and difluoroacetic acid. Compound 293 was isolated as a yellow solid: $^1$H NMR (400 MHz, acetone-d$_6$) 11.18 (s, 1H), 7.64 (dd, J=9.1, 2.4, 1H), 7.52 (d, J=9.1, 1H), 7.43 (s, 1H), 6.99 (s, 1H), 4.52 (t, J=12.1, 2H), 4.43 (m, 2H).

EXAMPLE 90

6-(N-2,2-Difluoro-2-chloroethyl-N-2,2-difluoroethyl)amino-4-trifluoromethyl-2(1H)-quinolinone (Compound 294 Structure 7 of Scheme II, Where R$^1$=2,2-Difluoroethyl, R$^2$=2,2-Difluoro-2-chloroethyl)

This compound was prepared in a similar fashion as that described in Example 9, General Procedure VI but using Compound 211 (Structure 7 of Scheme II, where R$^1$=H, R$^2$=2,2-difluoroethyl) and chlorodifluoroacetic acid in place of Compound 200 and difluoroacetic acid. Compound 294 was isolated as a yellow solid: $^1$H NMR (400 MHz, CDCl$_3$) 7.44 (d, J=9.2, 1H), 7.27 (m, 2H), 7.11 (s, 1H), 5.97 (tt, J=3.9, 55.8 Hz), 4.20 (t, J=11.7, 2H), 3.90 (td, J$_d$=3.8, J$_t$=13.6, 2H).

EXAMPLE 91

6-(N-2,2,2-Trifluoroethyl-N-methylsufonyl)amino-4-trifluoromethyl-2(1H)-quinolinone (Compound 295, Structure 7 of Scheme II, Where R$^1$=2,2,2-Trifluoroethyl, R$^2$=Methylsulfonyl)

To pyridine (0.3 mL) was added Compound 209 (Structure 7 of Scheme II, where R$^1$=H, R$^2$=2,2,2-Trifluoroethyl) (10.0 mg, 0.03 mmol) followed by methanesulfonyl chloride (6.8 mg, 0.06 mmol) and the reaction mixture heated at 60° C. for 18 h. The cooled reaction mixture was diluted with EtOAc and with water. The organic layers were dried over MgSO$_4$, concentrated in vacuo, and chromatographed (MeOH:CH$_2$Cl$_2$, 1:19) to produce 2.2 mg (19%) Compound 295 as a brown solid: R$_f$0.80 (MeOH:CH$_2$Cl$_2$, 1:19); $^1$H NMR (400 MHz, CDCl$_3$) 7.90 (d, J=9.1, 1H), 7.46 (s, 1H), 7.26–7.28 (m, 1H), 7.13 (s, 1H), 3.93 (quin, J=7.3, 2H), 3.60 (s, 3H).

EXAMPLE 92

1-Methyl-6-(N-propyl-N-isobutyl)amino-4-trifluoromethyl-2(1H)-quinolinone (Compound 296, Structure 9 of Scheme II, Where R$^1$=Propyl, R$^2$=Isobutyl, R$^3$=Methyl)

This compound was prepared from Compound 243 and iodomethane by the following General Procedure X (Methylation of amide):

To a solution of a 2-quinolinone, such as Compound 253 (Structure 7 of Scheme II, where R$^1$=propyl, R$^2$=isobutyl) in THF (0.05–0.2 M) was added sodium hydride (60% in mineral oil, 1.2–2.0 equivalents) and iodomethane (2–5 equivalents), the resulting mixture was stirred at room temperature for 1 h until the alkylation went completion by TLC. The mixture was quenched with water, extracted with EtOAc, and concentrated. Chromatography of the crude mixture afforded the N-alkylated product in excellent yield (80–95%).

Compound 296 was isolated as a yellow solid: $^1$H NMR (500 MHz, CDCl$_3$) 7.30 (d, J=9.3, 1H), 7.07 (dd, J=9.3, 2.9, 1H), 7.07 (s, 1H), 6.97 (s, 1H), 3.71 (s, 3H), 3.33 (t, J=7.3, 2H), 3.13 (d, J=7.3, 2H), 2.07–2.01 (m, 1H), 1.64–1.59 (m, 2H), 0.96–0.93 (m, 9H).

EXAMPLE 93

1-Methyl-6-(bis-2,2,2-trifluoroethyl)amino-4-trifluoromethyl-2(1H)-quinolinone (Compound 297, Structure 9 of Scheme II, Where R$^1$=R$^2$=2,2,2-Trifluoroethyl, R$^3$=Methyl)

This compound was prepared in a similar fashion as that described in Example 92, General Procedure X but using Compound 223 (Structure 7 of Scheme II, where R$^1$=R$^2$=2,2,2-Trifluoroethyl) in place of Compound 253. Compound 297 was isolated as a yellow solid: $^1$H NMR (400 MHz, CDCl$_3$) 7.39 (d, J=9.4, 1H), 7.36 (s, 1H), 7.30 (d, J=9.4, 1H), 7.12 (s, 1H), 4.11–4.05 (m, 2H), 3.73 (s, 3H).

EXAMPLE 94

1-Ethyl-6-(bis-2,2,2-trifluoroethyl)amino-4-trifluoromethyl-2(1H)-quinolinone (Compound 298, Structure 9 of Scheme II, Where R$^1$=R$^2$=2,2,2-Trifluoroethyl, R$^3$=Ethyl)

This compound was prepared in a similar fashion as that described in Example 92, General Procedure X from Compound 223 (Structure 7 of Scheme II, where R$^1$=R$^2$=2,2,2-Trifluoroethyl) and iodoethane. Compound 298 was isolated as a yellow solid: $^1$H NMR (400 MHz, CDCl$_3$) 7.41 (d, J=9.3, 1H), 7.36 (s, 1H), 7.30 (dd, J=9.3, 2.9, 1H), 7.12 (s, 1H), 4.36 (q, J=7.3, 2H), 4.08 (q, J$_{H-F}$=8.8, 4H), 1.37 (t, J=7.3, 3H).

EXAMPLE 95

6-(N-2,2,2-Trifluoroethyl)amino-4-trifluoromethyl-2(1H)-thioquinolinone (Compound 299, Structure 8 of Scheme II, Where R$^1$=H, R$^2$=2,2,2-Trifluoroethyl)

This compound was prepared from Compound 209 by the following General Procedure XI (Thioamide formation):

An amide such as Compound 209 (Structure 7 of Scheme II, where R$^1$=H, R$^2$=2,2,2-Trifluoroethyl) in toluene (0.2–1.0 M) was treated with Lawsson's reagent (1.2 equiv). The reaction mixture was then stirred at room temperature overnight, diluted with EtOAc, washed with sat. NaHCO$_3$, water, brine, dried (MgSO$_4$), filtered and concentrated under reduced pressure to yield crude product. Purification by column chromatography (15–50% EtOAc/hexane) afforded the thioamide in good yield as a yellow solid.

Compound 299 was isolated as a yellow solid: $^1$H NMR (400 MHz, CDCl$_3$) 10.39 (s, 1H), 7.66 (d, J=9.1, 1H), 7.50 (s, 1H), 7.36 (dd, J=9.1, 2.4, 1H), 7.10 (s, 1H), 6.20 (s, 1H), 4.09 (m, 2H).

EXAMPLE 96

6-(bis-N,N-2,2,2-Trifluoroethyl)amino-4-trifluoromethyl-2(1H)-thioquinolinone (Compound 300, Structure 8 of Scheme II, Where $R^1=R^2=2,2,2$-Trifluoroethyl)

This compound was prepared from Compound 223 (Structure 7 of Scheme II, where $R^1=R^2=2,2,2$-Trifluoroethyl) by General Procedure XI described in Example 95. Compound 300 was isolated as yellow solid. $^1$H NMR (CDCl$_3$, 500 MHz) 12.0 (bs, 1H), 7.74 (s, 1H), 7.48 (d, J=9.3, 1H), 7.27–7.33 (m, 2H), 4.12 (q, J=7.8, 4H).

EXAMPLE 97

(±)-6-(N-2,2,2-Trifluoroethyl-N-2,2,2-trifluoroisopropyl)amino-4-trifluoromethyl-2(1H)-quinolinone (Compound 301, Structure 7 of Scheme II, Where $R^1=2,2,2$-Trifluoroethyl, $R^2=2,2,2$-Trifluoroisopropyl)

This compound was prepared in a similar fashion as that described in Example 15, General Procedure VIII but using trifluoroacetaldehyde and trifluoroacetone sequentially in place of paraformaldehyde alone. Compound 301 was isolated as a yellow solid: $^1$H NMR (400 MHz, acetone-d$_6$) 11.10 (s, 1H), 7.68 (d, J=2.4, 1H), 7.66 (d, J=2.4, 1H),7.55 (dd, J=1.7, 21.1, 1H), 6.96 (s, 1H), 4.36 (s, 1H), 4.23 (dq, J=2,2, 8.8, 2H), 1.47 (d, J=7.0, 3H).

EXAMPLE 98

(+)-6-(N-2,2,2-Trifluoroethyl-N-2,2,2-trifluoroisopropyl)amino-4-trifluoromethyl-2(1H)-quinolinone (Compound 302, Structure 7 of Scheme II, Where $R^1=2,2,2$-Trifluoroethyl, $R^2=2,2,2$-Trifluoroisopropyl) and (−)-6-(N-2,2,2-Trifluoroethyl-N-2,2,2-trifluoroisopropyl)amino-4-trifluoromethyl-2(1H)-quinolinone (Compound 303, Structure 7 of Scheme II, Where $R^1=2,2,2$-Trifluoroethyl, $R^2=2,2,2$-Trifluoroisopropyl)

Compounds 302 and 303 were prepared by chiral HPLC separation of Compound 301.

EXAMPLE 99

6-Mercapto-4-trifluoromethyl-2(1H)-quinolinone (Compound 305, Structure 13 of Scheme II)

6-Methoxythiocarbonylmercapto-4-trifluoromethyl-2 (1H)-quinolinone (Compound 304, Structure 12 of Scheme II)

To a mixture of Compound 200 (Structure 3 of Scheme II) in H$_2$SO$_4$ was added aqueous NaNO$_2$ at 0° C. and the resulting mixture was stirred for 1 h to give 6-diazo-4-trifluoromethyl-2(1H)-quinolinone (Structure 11 of Scheme II). To a solution of potassium O-ethylxanthate in water at 50° C. was added the above crude mixture and the reaction was stirred for 2h and cooled down to rt. The mixture was extracted with EtOAc, washed with brine and concentrated. Chromatography afforded Compound 304 as a white solid. $^1$H NMR (400 MHz, CDCl$_3$) 11.29 (s, 1H), 7.99 (s, 1H), 7.72 (dd, J=8.6, 1.7, 1H), 7.50 (d, J=8.6, 1H), 7.14 (s, 1H), 7.03 (s, 1H), 4.63 (q, J=7.2, 2H), 1.35 (t, J=7.2, 3H).

6-Mercapto-4-trifluoromethyl-2(1H)-quinolinone (Compound 305, Structure 13 of Scheme II):

To a solution of Compound 304 in THF was added LiAlH$_4$ in THF at 0° C. and the reaction mixture was warmed to rt till the starting material was consumed by TLC. The reaction was quenched with water, neutralized with HCl (3N aqueous), extracted and washed with brine. Removal of solvent and chromatography afforded Compound 305 as white solids. $^1$H NMR (400 MHz, CDCl$_3$) 11.02 (s, 1H), 7.73 (s, 1H), 7.54 (d, J=8.7, 1H), 7.48 (d, J=8.7, 1H), 7.08 (s, 1H), 3.62 (s, 1H).

EXAMPLE 100

6-(1,1-Dimethyl-2-propynyl)amino-4-trifluoromethyl-2(1H)-quinolinone (Compound 306, Structure 10 of Scheme II)

In a r.b. flask, a solution of compound 200 (Structure 3 of Scheme II) in THF was treated with Cu(I)Cl (10 mol %) and 2-acetoxy-2-methyl-3-butyne (1.5 equiv). The reaction mixture was heated to reflux for 18 h. After cooling to rt, the reaction mixture was filtered through a pad of celite and the celite cake was rinsed with EtOAc. The filtrate was washed with saturated aqueous NH$_4$Cl solution, H$_2$O, and brine. Dried (MgSO$_4$), filtered, and concentrated in vacuo. The residue was purified by flash column chromatography (SiO$_2$, 5% EtOAc in hexane as eluent) to afford compound 306 as a yellow solid. $^1$H NMR (500 MHz, CDCl$_3$) 12.9 (bs, 1H), 7.49 (s, 1H), 7.38 (d, J=8.8, 1H), 7.20 (dd, J=8.8, 2.4, 1H), 7.08 (s, 1H), 3.81 (bs, 1H), 2.42 (s, 1H), 1.63 (s, 6H).

EXAMPLE 101

6-tert-Butylamino-4-trifluoromethyl-2(1H)-quinolinone (Compound 307, Structure 7 of Scheme III, Where $R^1=H$, $R^2=$tert-Butyl)

6-Bromo-4-trifluoromethyl-2(1H)-quinolinone (Compound 308, Structure 16 of Scheme III):

This compound was prepared in a similar fashion as that described in Example 1, General Procedure I but using 4-bromoaniline in place of aniline. Compound 308 was isolated in 40–60% yield as a white solid: $^1$H NMR (400 MHz, acetone-d$_6$) 10.60 (s, 1H), 7.74 (dd, J=8.8, 1.9, 1H), 7.48 (d, J=8.8, 1H), 6.99 (s, 1H).

6-Bromo-4-trifluoromethyl-2-isopropyloxyquinoline (Compound 309, Structure 17 of Scheme III):

This compound was prepared by the following General Procedure XII:

To a solution of Compound 308 (0.40 g, 1.4 mmol) in DMF (7 mL) was added CsF (0.88 g, 5.8 mmol) and 2-iodopropane (0.66 g, 2.7 mmol) and the reaction mixture was stirred at room temperature overnight till the starting material was consumed. The resulting brown suspension was diluted with EtOAc (50 mL), washed with water (3×50 mL) and brine and concentrated. Chromatography afforded the 2-isopropyloxyquinoline in 50–90% yield.

Compound 309 was isolated as white crystalline needles (0.24 g, 51%): $^1$H NMR (400 MHz, CDCl$_3$) 8.10 (d, J=0.9, 1H), 7.74 (s, 2H), 7.19 (s, 1H), 5.57–5.51 (m, 1H), 1.41 (d, J=6.2, 6H).

6-tert-Butylamino-2-isopropyloxy-4-trifluoromethylquinolines (Compound 310, Structure 18 of Scheme III, where $R^1=H$, $R^2=$tert-butyl):

This compound was prepared by the following General Procedure XIII (Palladium mediated coupling of aryl bromide and alkylamine):

To a schlenk tube containing absolution of a bicyclic aryl bromide, such as Compound 309 in toluene (0.05–0.2 M) was added Cs$_2$CO$_3$ (2–3 equiv), Pd$_2$(dba)$_3$ (1–3 mol %), and (R)-BINAP (2.0 mg, 0.003 mmol, 1.5–4.5 mol %) followed by a primary or secondary amine (3–5 equiv). The resulting yellow reaction mixture was heated to 100° C. for 4–48 h, cooled to room temperature, diluted with Et$_2$O, filtered, and concentrated in vacuo. Chromatography (CH$_2$Cl$_2$:hexane or EtOAc:hexane mixtures) of the crude mixture afforded compounds of Structures 18 or 19.

Compound 310 was isolated as green oils.

6-tert-Butylamino-4-trifluoromethyl-2(1H)-quinolinone (Compound 307, Structure 7 of Scheme III, where R$^1$H, R$^2$=tert-butyl):

This compound was prepared by the following General Procedure XIV (Hydrolysis of 2-alkyloxyquinoline):

To a 50 mL r.b. flask containing a solution of 2-(isopropylether)-6-alkylamino-4-trifluoromethyl quinoline such as Compound 310 (0.1 mmol) in AcOH (0.5 mL) was added conc. HCl (0.2 mL) and the reaction mixture stirred at rt for 30 min and 100° C. for 30 min. The cooled reaction mixture was diluted with CH$_2$Cl$_2$ (25 mL) and neutralized by the dropwise addition of sat. NaHCO$_3$ (approx. 25 mL). The organic layers were washed with sat. NaHCO$_3$ (50 mL) and H$_2$O (50 mL) and the aqueous layers were back extracted with EtOAc (25 mL). The combined organic layers were dried over MgSO$_4$, concentrated in vacuo, and purified by flash chromatography (MeOH:CH$_2$Cl$_2$, 1:4 or 1:9) to afford compounds of Structures 7 or 14 in Scheme III (25–95%).

Compound 307 was isolated as a yellow solid: $^1$H NMR (500 MHz, CDCl$_3$) 12.2–12.4 (bs, 1H), 7.30 (d, J=8.8, 1H), 7.15 (bs, 1H), 7.03–7.06 (m, 2H), 1.37 (s, 9H).

EXAMPLE 102

6-(1-Piperidinyl)-4-trifluoromethyl-2(1H)-quinolinone (Compound 311, Structure 20 of Scheme III, Where R$^{3-8}$=H, X=Methylene)

This compound was prepared in a similar fashion as described in Example 101, General Procedures XIII and XIV from Compound 309 and piperidine as a yellow solid: R$_f$0.51 (MeOH:CH$_2$Cl$_2$, 1:9); $^1$H NMR (500 MHz, d$_6$-acetone) 10.92 (bs, 1H), 7.42–7.45 (m, 2H), 7.15 (d, J=2.0, 1H), 6.89 (s, 1H), 3.17(t, J=5.4, 4H), 1.73 (quin, J=5.9, 4H), 1.56–1.62 (m, 2H).

EXAMPLE 103

6-(1-Pyrrolidinyl)-4-trifluoromethyl-2(1H)-quinolinone (Compound 312, Structure 20 of Scheme III Where R$^{3-8}$=H, X=a Bond)

This compound was prepared in a similar fashion as that described in Example 101, General Procedures XIII and XIV but using pyrrolidine in place of piperidine. Compound 312 was isolated as a yellow solid: R$_f$0.55 (MeOH:CH$_2$Cl$_2$, 1:9); $^1$H NMR (500 MHz, d$_6$-acetone) 7.41 (d, J=9.3, 2H), 7.07 (dd, J=2.9, 9.3, 1H), 6.87 (s, 1H), 3.31–3.34 (m, 4H), 2.02–2.04 (m, 4H).

EXAMPLE 104

6-(1-Morpholino)-4-trifluoromethyl-2(1H)-quinolinone (Compound 313, Structure 20 of Scheme III, Where R$^{3-8}$=H, X=Oxygen)

This compound was prepared in a similar fashion as that described in Example 101, General Procedures XIII and XIV but using morpholine in place of piperidine. Compound 313 was isolated as a yellow solid: R$_f$0.35 (MeOH:CH$_2$Cl$_2$ 1:4); $^1$H NMR (500 MHz, d$_6$-acetone) 7.46–7.47 (m, 2H), 7.15–7.16 (m, 1H), 6.91 (s, 1H), 3.82–3.84 (m, 4H), 3.16–3.18 (m, 4H).

EXAMPLE 105

(±)-6-(2-Methyl-1-piperidino)-4-trifluoromethyl-2 (1H)-quinolinone (Compound 314, Structure 20 of Scheme III, Where R$^{4-8}$=H, R$^3$=Methyl, X= Methylene)

This compound was prepared in a similar fashion as that described in Example 101, General Procedures XIII and XIV but using 2-methylpiperidine in place of piperidine. Compound 314 was isolated as a yellow solid: R$_f$0.75 (MeOH:CH$_2$Cl$_2$, 1:4); $^1$H NMR (500 MHz, CDCl$_3$) 12.57 (bs, 1H), 7.34–7.41(m, 2H), 7.23–7.26 (m, 1H), 7.08 (s, 1H), 3.85–3.86 (m, 1H), 3.15–3.17 (m, 1H), 3.03 (t, J=8.8, 1H), 1.61–1.91(m, 6H), 0.99 (d, J=6.8, 3H).

EXAMPLE 106

(+)-6-(2-Methyl-1-piperidino)-4-trifluoromethyl-2 (1H)-quinolinone (Compound 315, Structure 20 of Scheme III, Where R$^{4-8}$=H, R$^3$=Methyl, X= Methylene) and (−)-6-(2-Methyl-1-piperidino)-4-trifluoromethyl-2(1H)-quinolinone (Compound 316, Structure 20 of Scheme III, Where R$^{4-8}$=H, R$^3$= Methyl, X=Methylene)

Compounds 315 and 316 were prepared by chiral HPLC separation of Compound 314. Compound 315: [α]$_D$=+23 and Compound 316: [α]$_D$=−30.

EXAMPLE 107

6-(N-Phenylamino)-4-trifluoromethyl-2(1H)-quinolinone (Compound 317, Structure 7 of Scheme III, Where R$^1$=Phenyl, R$^2$=H)

6-(N-phenylamino)-4-trifluoromethyl-2-isopropyloxyquinoline (Compound 318, Structure 18 of Scheme III, where R$^1$=phenyl, R$^2$=H):

This compound was prepared in a similar fashion as that described in Example 101, General Procedure XIII from aniline.

6-(N-phenylamino)-4-trifluoromethyl-2(1H)-quinolinone (Compound 317, Structure 7 of Scheme III, where R$^1$=phenyl, R$^2$=H):

This compound was prepared in a similar fashion as that described in Example 101, General Procedure XIV from Compound 318. Compound 317 was isolated as a yellow solid. $^1$H NMR (400 MHz, CDCl$_3$) 10.83 (s, 1H), 7.47–7.38 (m, 3H), 7.32–7.26 (m, 2H), 7.09–7.04 (m, 3H), 6.98 (t, J=7.3, 1H), 5.86 (s, 1H).

EXAMPLE 108

6-(N-Phenyl-N-ethylamino)-4-trifluoromethyl-2 (1H)-quinolinone (Compound 319, Structure 7 of Scheme III, Where R$^1$=Phenyl, R$^2$=Ethyl)

6-(N-phenyl-N-ethylamino)-4-trifluoromethyl-2-isopropyloxyquinoline (Compound 320, Structure 18 of Scheme III, where R$^1$=phenyl, R$^2$=ethyl):

A mixture of Compound 318 (Structure 18 of Scheme III, where R$^1$=phenyl, R$^2$=H), iodoethane and NaH in THF was stirred at rt overnight till the starting material was consumed.

The reaction was quenched with water, extracted with EtOAc and concentrated. Chromatography afforded Compound 320 as yellow oil.

6-(N-phenyl-N-ethylamino)-4-trifluoromethyl-2(1H)-quinolinone (Compound 319, Structure 7 of Scheme III, where $R^1$=phenyl, $R^2$=ethyl):

This compound was prepared in a similar fashion as that described in Example 101, General Procedure XIV from Compound 320. Compound 319 was isolated as a yellow solid. $^1$H NMR (400 MHz, CDCl$_3$) 11.27 (s, 1H), 7.37–7.27 (m, 6H), 7.01–6.99 (m, 3H), 3.82 (q, J=7.0, 2H), 1.25 (t, J=7.0, 3H).

EXAMPLE 109

6-Phenyl-N-2,2,2-trifluoroethylamino)-4-trifluoromethyl-2(1H)-quinolinone (Compound 321, Structure 7 of Scheme III, Where $R^1$=Phenyl, $R^2$= 2,2,2-Trifluoroethyl)

This compound was prepared in a similar fashion as that described in Example 2, General Procedure IV from Compound 317 and 2,2,2-trifluoroacetaldehyde. Compound 321 was isolated as a yellow solid. $^1$H NMR (400 MHz, acetone-d$_6$) 11.60 (s, 1H), 7.54 (d, J=8.7, 1H), 7.49–7.44 (m, 2H), 7.34–7.30 (m, 2H), 7.05–7.00 (m, 3H), 6.95 (s, 1H), 4.61(q, J=9.1, 2H).

EXAMPLE 110

(±)-6-(3-Methyl-1-piperidino)-4-trifluoromethyl-2(1H)-quinolinone (Compound 322, Structure 20 of Scheme III, Where $R^{3-4}$=$R^{6-8}$=H, R=Methyl, X= Methylene)

This compound was prepared in a similar fashion as that described in Example 101, General Procedures XIII and XIV but using 3-methylpiperidine in place of piperidine. Compound 322 was isolated as a yellow solid: R$_f$0.81 (EtOAc); $^1$H NMR (500 MHz, CDCl$_3$) 10.6–10.8 (bs, 1H), 7.33 (dd, J=2.9, 9.3, 1H), 7.15–7.24 (m, 2H), 7.05 (s, 1H), 3.51–3.58 (m, 2H), 2.69 (dt, J=2.9, 11.7, 1H), 2.38 (t, J=10.7, 1H), 1.71–1.85 (m, 3H), 1.68–1.71(m, 1), 1.05–1.11 (m, 1), 0.99 (d, J=6.3, 3H).

EXAMPLE 111

6-(4-Methyl-1-piperidino)-4-trifluoromethyl-2(1H)-quinolinone (Compound 323, Structure 20 of Scheme III, Where $R^{3-8}$=H, X=CHCH$_3$)

This compound was prepared in a similar fashion as that described in Example 101, General Procedures XIII and XIV but using 4-methylpiperidine in place of piperidine. Compound 323 was isolated as a yellow solid: R$_f$0.51 (MeOH:CH$_2$Cl$_2$, 1:4); $^1$H NMR (500MHz d$_6$-acetone) 7.42–7.45 (m, 2H), 7.15 (s, 1H), 6.89 (s, 1H), 3.66 (d, J=12.2, 2H), 2.65–2.74 (m, 2H), 1.79 (d, J=11.7, 2H), 1.50–1.60 (m, 1H), 1.32–1.38 (m, 2H), 0.99 (d, J=6.3, 3H).

EXAMPLE 112

6-(cis-3,5-Dimethyl-1-piperidino)-4-trifluoromethyl-2(1H)-quinolinone (Compound 324, Structure 20 of Scheme III, Where $R^{3-4}$=$R^{7-8}$H, $R^{5-6}$=Methyl, X= Methylene)

This compound was prepared in a similar fashion as that described in Example 101, General Procedures XIII and XIV but using cis-3,5-dimethylpiperidine in place of piperidine. Compound 324 was isolated as a yellow solid: R$_f$0.71 (MeOH:CH$_2$Cl$_2$, 1:4); $^1$H NMR (500 MHz, CDCl$_3$) 10.2–10.4 (bs, 1H), 7.32 (dd, J=2.4, 9.3, 1H), 7.14–7.22 (m, 2H), 7.05 (s, 1H), 3.55 (d, J=11.2, 2H), 2,26 (t, J=11.2, 2H), 1.83–1.85 (m, 3H), 0.97 (d, J=6.8, 3H), 0.71–0.74 (m, 1H).

EXAMPLE 113

6-(2,6-cis-Dimethyl-1-piperidino)-4-trifluoromethyl-2(1H)-quinolinone (Compound 325, Structure 20 of Scheme III, Where $R^{4-7}$=H, $R^3$=$R^8$=Methyl, X= Methylene) and (±)-6-(2,6-trans-Dimethyl-1-piperidino)-4-trifluoromethyl-2(1H)-quinolinone (Compound 326, Structure 20 of Scheme III, Where $R^{4-7}$=H, $R^3$=$R^8$=Methyl, X=Methylene)

These compounds were prepared in a similar fashion as that described in Example 101, General Procedures XIII and XIV but using 2,6-dimethylpiperidine in place of piperidine. Compounds 325 and 326 were isolated as a 1:1mixture as a yellow solid: Compound 325: $^1$H NMR (500 MHz, CDCl$_3$) 11.80–12.00 (bs, 1H), 7.34 (s, 2H), 7.21 (s, 1H), 7.08 (s, 1H), 3.56–3.64 (m, 2H), 2.75 (dt, J=2.4, 12,2, 1H), 2.38 (t, J=10.7, 1H), 1.68–1.85 (m, 2H), 1.35–1.43 (m, 1H), 1.21–1.28 (m, 1H), 0.99 (d, J=6.4, 6H); Compound 326: $^1$H NMR (500 MHz, CDCl$_3$) 11.80–12.00 (bs, 1H), 7.34 (s, 2H), 7.21 (s, 1H), 7.08 (s, 1H), 3.49–3.54 (m, 2H), 2.69 (dt, J=2.9, 11.7, 1H), 1.68–1.85 (m, 3H), 1.21–1.28 (m, 1H), 1.06–1.11 (m, 1H), 1.01(d, J=6.3, 6H);

EXAMPLE 114

(±)-6-(2-Methyl-1-pyrrolidino)-4-trifluoromethyl-2(1H)-quinolinone (Compound 327, Structure 20 of Scheme III, Where $R^{4-8}$=H, $R^3$=Methyl, X=a Bond)

This compound was prepared in a similar fashion as that described in Example 101, General Procedures XIII and XIV but using 2-methylpyrrolidine in place of piperidine. Compound 327 was isolated as a yellow solid: R$_f$0.68 (MeOH:CH$_2$Cl$_2$, 1:4); $^1$H NMR (500 MHz, CDCl$_3$) 11.6–11.8 (bs, 1H, 7.31(d, J=9.3, 1H), 7.06 (bs, 1H), 6.99 (dd, J=2.4, 9.3, 1H), 6.83 (m, 1H), 3.91–3.94 (m, 1H), 3.48 (dt, J=2.9, 9.8, 1H), 3.22 (q, J=7.3, 1H), 2.10–2.16 (m, 2H), 2.02–2.10 (m, 1H), 1.76–1.77 (m, 1H), 1.21 (d, J=6.3, 3H).

EXAMPLE 115

6-(2,5-cis-Dimethyl-1-pyrrolidino)-4-trifluoromethyl-2(1H)-quinolinone (Compound 328, Structure 20 of Scheme III, Where $R^{4-7}$=H, $R^3$=$R^8$=Methyl, X=a Bond)

This compound was prepared in a similar fashion as that described in Example 101, General Procedures XIII and XIV but using 2,5-dimethylpyrrolidine in place of piperidine. Compound 328 was isolated as a yellow solid: R$_f$0.60 (MeOH:CH$_2$Cl$_2$, 1:4); $^1$H NMR (500 MHz, CDCl$_3$) 11.4–11.8 (bs, 1H), 7.28–7.30 (m, 1H), 7.05 (bs, 1H), 7.02 (dd, J=2.4, 9.3, 1H), 6.86–6.90 (m, 1H), 3.79–3.82 (m, 2H), 2.08–2.14 (m, 2H), 1.75–1.80 (m, 2H), 1.31(d, J=6.8, 6H).

EXAMPLE 116

(±)-6-(2,5-trans-Dimethyl-1-pyrrolidino)-4-trifluoromethyl-2(1H)-quinolinone (Compound 329, Structure 20 of Scheme III, Where $R^{4-7}$=H, $R^3$=$R^8$=Methyl, X=a Bond)

Compound 329 was isolated as a miner isomer of Compound 328 as described in Example 115 as a yellow solid:

$R_f$ 0.60 (MeOH:CH$_2$Cl$_2$, 1:4); $^1$H NMR (400 MHz, CDCl$_3$) 11.2–11.4 (bs, 1H), 7.32 (d, J=8.9, 1H), 6.90–7.01 (m, 2H), 6.78–6.82 (m, 1H), 3.88–4.06 (m, 2H), 2,26–2,28 (m, 2H), 1.67–1.69 (m, 2H), 1.12 (d, J=6.2, 6H).

EXAMPLE 117

6-(1-Azepano)-4-trifluoromethyl-2(1H)-quinolinone (Compound 330, Structure 20 of Scheme III, Where $R^{3-8}$=H, X=Ethylene)

This compound was prepared in a similar fashion as that described in Example 101, General Procedures XIII and XIV but using azepane in place of piperidine. Compound 330 was isolated as a yellow solid: $R_f$ 0.52 (MeOH:CH$_2$Cl$_2$, 1:9); $^1$H NMR (500 MHz, CDCl$_3$) 9.80 (bs, 1H), 7.14 (s, 1H), 7.07 (dd, J=2.4, 9.3, 1H), 7.02 (bs, 1H), 6.93–6.95 (m, 1H), 3.51 (t, J=5.9, 4H), 1.57–1.82 (m, 4H), 1.55–1.60 (m; 4H).

EXAMPLE 118

(±)-6-(2-Hydroxyethyl-1-piperidino)-4-trifluoromethyl-2(1H)-quinolinone (Compound 331, Structure 20 of Scheme III, Where $R^{4-8}$=H, $R^3$= Hydroxymethyl, X=Methylene)

This compound was prepared in a similar fashion as that described in Example 101, General Procedures XIII and XIV but using 2-(tert-butyldimethylsilyloxymethyl) piperidine in place of piperidine. The silyl protection group was removed under the HCl hydrolysis condition. Compound 331 was isolated as a yellow solid: $R_f$ 0.28 (MeOH:CH$_2$Cl$_2$, 1:4); $^1$H NMR (500 MHz, CDCl$_3$) 11.7–11.9 (bs, 1H), 7.40 (J=2.4, 1H), 7.32–7.34 (m, 2H), 7.07 (bs, 1H), 3.78–3.82 (m, 2H), 3.62–3.66 (m, 1H), 3.32–3.35 (m, 1H), 3.15–3.20 (m, 1H), 1.57–1.84 (m, 6H).

EXAMPLE 119

6-(2,5-cis-Dimethyl-1-pyrrolino)-4-trifluoromethyl-2(1H)-quinolinone (Compound 332, Structure 20 of Scheme III, Where $R^{4-7}$=H, $R^3$=$R^8$=Methyl, X=a Double Bond)

This compound was prepared in a similar fashion as that described in Example 101, General Procedures XIII and XIV but using 2,5-dimethylpyrroline in place of piperidine. Diastereomerically pure Compound 332 was isolated as a yellow solid: $R_f$ 0.15 (MeOH:CH$_2$Cl$_2$, 1:19); $^1$H NMR (500 MHz, CDCl$_3$) 11.50–11.70 (bs, 1H), 7.32 (d, J=9.3, 1H), 7.07 (s, 1H), 7.02 (dd, J=2.4, 9.3, 1H), 6.91(bs, 1H), 5.83 (s, 2H) 4.50 (q, J=5.9, 2H), 1.39 (d, J=6.3, 6H).

EXAMPLE 120

(±)-6-(2-Propyl-1-piperidino)-4-trifluoromethyl-2(1H)-quinolinone (Compound 333, Structure 20 of Scheme III, Where $R^3$=Propyl, $R^{4-8}$=H, X=CH$_2$)

This compound was prepared in a similar fashion as that described in Example 101, General Procedures XIII and XIV from Compound 309 (Structure 17 of Scheme III) and 2-propylpiperidine. Compound 333 was isolated as a yellow solid: $^1$H NMR (CDCl$_3$, 500 MHz) 12.20–12.40 (bs, 1H), 7.35 (d, J=9.3, 1H), 7.31 (dd, J=2.4, 9.3, 1H), 7.16 (s, 1H), 7.07 (s, 1H), 4.74–4.78 (m, 1H), 3.28–3.31 (m, 1H), 3.02–3.07 (m, 1H), 1.51–1.80 (m, 6H), 1.18–1.42 (m, 4H), 0.86 (t, J=7.3, 3H).

EXAMPLE 121

(±)-6-(2-Methoxymethyl-1-piperidino)-4-trifluoromethyl-2(1H)-quinolinone (Compound 334, Structure 20 of Scheme III, Where $R^3$= Methoxymethyl, $R^{4-8}$=H, X=CH$_2$)

This compound was prepared in a similar fashion as that described in Example 101, General Procedures XIII and XIV from Compound 309 (Structure 17 of Scheme III) and 2-methoxymethylpiperidine. Compound 334 was isolated as a yellow solid: $^1$H NMR (CDCl$_3$, 500 MHz) 7.43 (dd, J=2.4, 9.3, 1H), 7.37 (s, 1H), 7.25–7.30 (m, 1H), 7.11 (s, 1H), 3.80–3.82 (m, 2H), 3.74 (s, 3H), 3.64–3.70 (m, 1H), 3.35–3.75 (m, 1H), 3.15–3.21 (m, 1H), 1.60–1.90 (m, 6H).

EXAMPLE 122

(±)-6-(2-Ethyl-1-piperidino)-4-trifluoromethyl-2(1H)-quinolinone (Compound 335, Structure 20 of Scheme III, Where $R^3$=Ethyl, $R^{4-8}$=H, X=CH$_2$)

This compound was prepared in a similar fashion as that described in Example 101, General Procedures XIII and XIV from Compound 309 (Structure 17 of Scheme III) and 2-ethylpiperidine. Compound 335 was isolated as a yellow solid: $^1$H NMR (CDCl$_3$, 500 MHz) 11.40–11.60 (bs, 1H), 7.29–7.30 (m, 2H), 7.16–7.18 (m, 1H), 7.05 (s, 1H), 3.61–3.65 (m, 1H), 3.27–3.30 (m, 1H), 3.02–30.7 (m, 1H), 1.42–1.83 (m, 8H), 0.84 (t, J=7.3, 3H).

EXAMPLE 123

6-(1-Cycloheptylamino)4-trifluoromethyl-2(1H)-quinolinone (Compound 336, Structure 20 of Scheme III, Where R3-8=H, X=—(CH$_2$)$_3$—)

This compound was prepared in a similar fashion as that described in Example 101, General Procedures XIII and XIV from Compound 309 (Structure 17 of Scheme III) and cycloheptylamine. Compound 336 was isolated as a yellow solid: $^1$H NMR (CDCl$_3$, 500 MHz) 11.20–11:40 (bs, 1H), 7.27–7.29 (m, 1H), 7.08 (dd, J=2.4, 9.3, 1H), 7.05 (s, 1H), 6.93 (s, 1H), 3.47–3.52 (m, 4H), 1.77–1.81(m, 4H, 1.53–1.62 (m, 4H), 1.32–1.36 (m, 2H).

EXAMPLE 124

(±)-6-(2-Ethoxycarbonyl-1-piperidino)-4-trifluoromethyl-2(1H)-quinolinone (Compound 337 Structure 20 of Scheme III, Where $R^3$= Ethoxycarbonyl, $R^{4-8}$=H, X=—CH$_2$—)

This compound was prepared in a similar fashion as that described in Example 101, General Procedures XIII and XIV from Compound 309 (Structure 17 of Scheme III) and ethyl pipecolinate. Compound 337 was isolated as a yellow solid: $^1$H NMR (CDCl$_3$, 500 MHz) 12.00–12.10 (bs, 1H), 7.35 (d, J=9.3, 1H), 7.31(dd, J=2.0, 8.8, 1H), 7.20 (s, 1H), 4.46 (dd, J=3.4, 5.4, 1H), 4.07–4.12 (m, 2H), 3.41–3.44 (m, 2H), 2.21–2.25 (m, 1H), 1.96–2.03 (m, 1H), 1.87–1.91 (m, 1H), 1.63–1.74 (m, 2H), 1.46–1.56 (m, 1H), 1.18 (t, J=7.3, 3H).

EXAMPLE 125

(±)-6-(2-Isopropyl-1-pyrrolidino)-4-trifluoromethyl-2(1H)-quinolinone (Compound 338, Structure 20 of Scheme III, Where $R^3$=Isopropyl, $R^{4-8}$=H, X=a Bond)

This compound was prepared in a similar fashion as that described in Example 101, General Procedures XIII and XIV from Compound 309 (Structure 17 of Scheme III) and 2-isopropylpyrrolidine. Compound 338 was isolated as a yellow solid: $^1$H NMR (CDCl$_3$, 500 MHz) 12.20–12.40 (bs, 1H), 7.35 (d, J=9.3, 1H), 7.07 (s, 1H), 7.02 (dd, J=2.4, 9.3, 1H), 6.87 (s, 1H), 3.69–3.72 (m, 1H), 3.55–3.59 (m, 1H), 3.23 (q, J=7.8, 1H), 2.16–2.19 (m, 1H), 1.92–2.06 (m, 4H), 0.97 (d, J=6.8, 3H), 0.83 (d, J=6.3, 3H).

EXAMPLE 126

(±)-6-(2-Hydroxycarbonyl-1-piperidino)-4-trifluoromethyl-2(1H)-quinolinone (Compound 339, Structure 20 of Scheme III, Where $R^3$=Carboxylic Acid, $R^{4-8}$=H, X=—$CH_2$—)

This compound was prepared by hydrolysis of Compound 337 (Structure 20 of Scheme III, where $R^3$=ethyl carboxylate, $R^{4-8}$=H, X=—$CH_2$—). Compound 339 was isolated as a yellow solid: $R_f$=0.23 (90:9:1 $CH_2Cl_2$:MeOH:$NH_4OH$).

EXAMPLE 127

6-(3,5-cis-Dimethyl-1-piperazino)-4-trifluoromethyl-2(1H)-quinolinone (Compound 340, Structure 20 of Scheme III, Where $R^3$=$R^4$=$R^7$=$R^8$=H, $R^5$=$R^6$=Methyl, X=NH)

This compound was prepared in a similar fashion as that described in Example 101, General Procedures XIII and XIV from Compound 309 (Structure 17 of Scheme III) and 1,6-cis-piperazine. Compound 340 was isolated as a yellow solid: $^1$H NMR ($d_6$-acetone, 500 MHz) 10.90–1100 (bs, 1H), 7.57 (dd, J=2.4, 8.8, 1H), 7.50 (d, J=8.8, 1H), 7.27 (s, 1H), 6.93 (s, 1H); 3.87 (d, J=13.2, 2H), 3.69–3.76 (bs, 2H), 3.03 (t, J=11.7, 2H), 1.47 (d, J=6.8, 6H).

EXAMPLE 128

(±)-6-(2-Benzyl-1-pyrrolidino)-4-trifluoromethyl-2(1H)-quinolinone (Compound 341, Structure 20 of Scheme III, Where $R^3$=Benzyl, $R^4$=$R^5$=$R^6$=$R^7$=$R^8$=H, X=a Bond)

This compound was prepared in a similar fashion as that described in Example 101, General Procedures XIII and XIV from Compound 309 (Structure 17 of Scheme III) and 2-benzylpyrrolidine. Compound 341 was isolated as a yellow solid: $^1$H NMR (CDCl$_3$, 500 MHz) 10.50–10.60 (bs, 1H), 7.31–7.36 (m, 2H), 7.23–7.25 (m, 4H), 7.08 (s, 1H), 7.05 (dd, J=2.4, 8.8, 1H), 7.01 (s, 1H), 3.98–4.02 (m, 1H), 3.48—3.52 (m, 2H), 3.25 (q, J=7.8, 1H), 3.07 (dd, J=2.9, 13.7, 1H), 2.57 (dd, J=9.8, 13.7, 1H), 1.93–2.01 (m, 3H).

EXAMPLE 129

(±)-6-(5-Methyl-2-oxo-1-pyrrolidino)-4-trifluoromethyl-2(1H)-quinolinone (Compound 342, Structure 20 of Scheme III, Where $R^3$, $R^4$=Carbonyl, $R^5$=$R^6$=$R^7$=H, $R^8$=Methyl, X=a Bond)

This compound was prepared in a similar fashion as that described in Example 101, General Procedures XIII and XIV from Compound 309 (Structure 17 of Scheme III) and 5-methyl-2-pyrrolidinone. Compound 342 was isolated as yellow oil: $^1$H NMR (CDCl$_3$, 500 MHz) 12.00–12.40 (bs, 1H), 7.77 (dd, J=2.0, 8.8, 1H), 7.73 (s, 1H), 7.48 (d, J=8.8, 1H), 7.12 (s, 1H), 4.36 (sextet, J=6.8, 1H), 2.66–2.73 (m, 1H), 2.57–2.64 (m, 1H), 2.42–2.48 (m, 1H), 1.80–1.86 (m, 1H), 1.25 (d, J=6.3, 3H).

EXAMPLE 130

(±)-6-(2-(2-Hydroxyethyl)-1-piperidino)-4-trifluoromethyl-2(1H)-quinolinone (Compound 343, Structure 20 of Scheme III, Where $R^3$=$R^4$=$R^5$=$R^6$=$R^7$=H, $R^8$=2-Hydroxyethyl, X=$CH_2$)

This compound was prepared in a similar fashion as that described in Example 101, General Procedures XIII and XIV from Compound 309 (Structure 17 of Scheme III) and 2-(2-tert-butyldimethylsilyloxyethyl)piperidine. Compound 343 was isolated as yellow oil: $^1$H NMR (CDCl$_3$, 500 MHz) 10.80–11.10 (bs, 1H), 7.25–7.32 (m, 2H), 7.20 (s, 1H), 7.06 (s, 1H), 4.00–4.07 (m, 2H), 3.94–3.99 (m, 1H), 3.32 (d, J=11.9, 1H), 3.04–3.08 (m, 1H), 1.82–1.97 (m, 3H), 1.65–1.76 (m, 5H).

EXAMPLE 131

(±)-6-(3-Hydroxy-1-pyrrolidino)-4-trifluoromethyl-2(1H)-quinolinone (Compound 344, Structure 20 of Scheme III, Where $R^3$=$R^4$=$R^6$=$R^7$=$R^8$=H, $R^5$=Hydroxy, X=a Bond)

This compound was prepared in a similar fashion as that described in Example 101, General Procedures XIII and XIV from Compound 309 (Structure 17 of Scheme III) and 3-tert-butyldimethylsilyloxypyrrolidine. Compound 344 was isolated as yellow solid: $^1$H NMR (CDCl$_3$, 500 MHz) 7.11(d, J=9.3, 1H), 6.07 (dd, J=2.4, 9.3, 1H), 6.78 (s, 1H), 6.60 (s, 1H), 4.39–4.41 (m, 1H), 3.33–3.38 (m, 2H), 3.17–3.23 (m, 1H), 3.09 (d, J=10.0, 1H), 1.91–2.03 (m, 1H), 1.89–1.86 (m, H).

EXAMPLE 132

(±)-6-(3-Acetyloxy-1-pyrrolidino)-4-trifluoromethyl-2(1H)-quinolinone (Compound 345, Structure 20 of Scheme III, Where $R^3$=$R^4$=$R^6$=$R^7$=$R^8$=H, $R^5$=Acetyloxy, X=a Bond)

This compound was prepared by acetylation of Compound 131 (Structure 20 of Scheme III, where $R^3$=$R^4$=$R^6$=$R^7$=$R^8$=H, $R^5$=hydroxy, X=a bond) and isolated as yellow solid. $^1$H NMR (CDCl$_3$, 500 MHz), 10.00–10.20 (bs, 1H), 7.20–7.21(m, 1H), 7.05 (s, 1H), 6.95 (dd, J=2.7, 9.2, 1H), 6.82 (s, 1H), 5.47 (m, 1H), 3.70 (dd, J=2.7, 11.0, 1H), 3.52 (q, J=11.0, 1H), 3.45 (dt, J=3.0, 8.5, 1H), 3.40 (d, J=11.0, 1H), 2.23–2.34 (m, 2H), 1.26 (s, 3H).

EXAMPLE 133

6-(3(R)-Hydroxy-1-pyrrolidino)-4-trifluoromethyl-2(1H)-quinolinone (Compound 346, Structure 20 of Scheme III, Where $R^{3-5}$=$R^{7-8}$=H, $R^6$=Hydroxy, X=a Bond)

This compound was prepared in a similar fashion as that described in Example 101, General Procedures XIII and XIV from Compound 309 (Structure 17 of Scheme III) and 3(R)-(tert-butyldimethylsilyloxy)pyrrolidine. Compound 346 was isolated as a yellow solid: $R_f$0.36 (MeOH:$CH_2Cl_2$, 1:9); $^1$H NMR (400 MHz, CDCl$_3$) 7.20 (d, J=9.3, 1H), 6.90–7.00 (m, 2H), 6.72 (s, 1H), 4.51–4.56 (m, 1H), 3.45–3.49 (m, 2H), 3.20–3.25 (m, 2H), 1.95–2.12 (m, 2H).

EXAMPLE 134

6-(1-Indolino)-4-trifluoromethyl-2(1H)-quinolinone (Compound 347, Structure 21 of Scheme III, Where n=0, m=1)

This compound was prepared in a similar fashion as that described in Example 101, General Procedures XIII and XIV from Compound 309 (Structure 17 of Scheme III) and indoline. Compound 347 was isolated as a yellow solid: $^1$H NMR (CDCl$_3$, 500 MHz) 11.70–11.80 (bs, 1H), 7.58–7.60 (m, 2H), 7.42 (d, J=9.3, 1H), 7.22 (d, J=7.3, 1H), 7.07–7.14 (m, 3H), 6.81 (dt, J=1.0, 7.3, 1H), 4.02 (t, J=8.3, 2H), 3.20 (t, J=8.3, 2H).

EXAMPLE 135

6-(1-Tetrahydroquinolino)-4-trifluoromethyl-2(1H)-quinolinone (Compound 348, Structure 21 of Scheme III, Where n=0, m=2)

This compound was prepared in a similar fashion as that described in Example 101, General Procedures XIII and XIV from Compound 309 (Structure 17 of Scheme III) and 1,2,3,4-tetrahydroquinoline. Compound 348 was isolated as a yellow solid: $^1$H NMR (CDCl$_3$, 500 MHz) 11.60–11.80 (bs, 1H), 7.61–7.62 (m, 1H), 7.56 (dd, J=2.4, 8.8, 1H), 7.40 (d, J=8.8, 1H), 7.08–7.10 (m, 2H), 6.94–6.97 (m, 1H), 6.75–6.78 (m, 1H), 6.70 (t, J=8.3, 1H), 3.68 (t, J=5.6, 2H), 2.88 (t, J=5.6, 2H), 2.05–2.12 (m, 2H).

EXAMPLE 136

6-(2-Tetrahydroisoquinolino)-4-trifluoromethyl-2(1H)-quinolinone (Compound 349, Structure 21 of Scheme III, Where n=m=1)

This compound was prepared in a similar fashion as that described in Example 101, General Procedures XIII and XIV from Compound 309 (Structure 17 of Scheme III) and 1,2,3,4-tetrahydroisoquinoline. Compound 349 was isolated as a yellow solid: $^1$H NMR (CDCl$_3$, 500 MHz) 10.80–11.0 (bs, 1H), 7.37 (d, J=2.0, 8.8, 1H), 7.20–7.31(m, 6H), 7.08 (s, 1H), 4.44 (s, 2H), 3.60 (t, J=5.9, 2H), 3.04 (t, J=5.9, 2H).

EXAMPLE 137

(±)-6-(1,3,3-Trimethyl-6-azabicyclo[3,2,1]octanyl-6-)-4-trifluoromethyl-2(1H)-quinolinone (Compound 350, Structure 22 of Scheme III)

This compound was prepared in a similar fashion as that described in Example 101, General Procedures XIII and XIV from Compound 309 (Structure 17 of Scheme III) and 1,3,3-trimethyl-6-azabicyclo[3.2.1]octane. Compound 350 was isolated as a yellow solid: $^1$H NMR (CDCl$_3$, 500 MHz) 12.40–12.50 (bs, 1H), 7.35 (d, J=9.3, 1H), 7.07 (s, 1H), 6.89 (dd, J=2.4, 9.3, 1H), 6.68 (s, 1H), 4.12 (q, J=6.8, 1H), 3.10 (q, J=8.8, 2H), 1.96–1.98 (m, 1H), 1.83–1.86 (m, 1H), 1.47–1.60 (m, 2H), 1.43 (d, J=10.7, 1H), 1.35 (d, J=13.6, 1H), 1.18 (s, 3H) 0.95 (3H), 0.77 (s, 3H).

EXAMPLE 138

(±)-6-(2-Trifluoromethyl-5-cis-methyl-1-oxazolidino)-4-trifluoromethyl-2(1H)-quinolinone (Compound 351, Structure 25 of Scheme IV, Where R$^2$=Methyl, R$^3$=Trifluoromethyl) and (±)-6-(2-Trifluoromethyl-5-trans-methyl-1-oxazolidino)-4-trifluoromethyl-2(1H)-quinolinone (Compound 352, Structure 25 of Scheme IV, Where R$^2$=Methyl, R$^3$= Trifluoromethyl)

These compounds were prepared from Compound 200 by the following General Procedure XV (Formation of oxazolidine from amine):

6-(N-1-Hydroxy-2-propyl)amino-4-trifluoromethyl-2(1H)-quinolinone (Compound 353, Structure 24 of Scheme IV, where R$^2$=methyl):

This compound was prepared in a similar fashion as that described in Example 3, General Procedure V but using 1-hydroxyacetone (Structure 23 of Scheme IV, where R$^2$=methyl) in place of acetone.

6-(2-Trifluoromethyl-5-methyl-1-oxazolidino)-4-trifluoromethyl-2(1H)-quinolinone (Compounds 351 and 352, Structure 25 of Scheme IV, Where R$^2$=Methyl, R$^3$=trifluoromethyl):

To a solution of Compound 353 in benzene (0.2–0.5 M) was added trifluoroacetaldehyde monohydrate or ethyl hemiacetal (3–5 equiv) in the presence of p-toluenesulfonic acid (2–10 mol %). The reaction mixture was refluxed for 5–15 h with azeotropic removal of water with a Dean-Stark condenser. The mixture was diluted with EtOAc and washed with 2 M NaHCO$_3$, and condensed. Chromatography afforded the desired products.

Compound 351 was isolated as a yellow solid: $^1$H NMR (400 MHz, CDCl$_3$) 12.1(bs, 1H), 7.42 (d, =9.3, 1H), 7.20 (s, 1H), 7.17 (d, J=9.3, 1H), 7.11 (s, 1H), 5.32 (q, J$_{H-F}$=4.9, 1H), 4.46 (dd, J=8.3, 6.8, 1H), 4.11–4.04 (m, 1H), 3.99 (dd, J=8.3, 8.3, 1H), 1.42 (d, J=5.9, 3H).

Compound 352 was isolated as a yellow solid: $^1$H NMR (400 MHz, CDCl$_3$) 12.1 (bs, 1H), 7.40 (d, J=9.3, 1H),7.17 (d, J=9.3, 1H),7.14 (s, 1H), 7.11 (s, 1H), 5.55 (q, J$_{H-F}$=4.4, 1H), 4.46 (dd, J=8.3, 2.4, 1H), 4.33–4.30 (m, 1H), 3.99 (d, J=8.3, 1H), 1.19 (d, J=6.3, 3H).

EXAMPLE 139

(±)-6-(2-Trifluoromethyl-5-cis-ethyl-1-oxazolidino)-4-trifluoromethyl-2(1H)-quinolinone (Compound 354, Structure 25 of Scheme IV, Where R$^2$=Ethyl, R$^3$=Trifluoromethyl) and (±)-6-(2-Trifluoromethyl-5-trans-ethyl-1-oxazolidino)-4-trifluoromethyl-2 (1H)-quinolinone (Compound 355, Structure 25 of Scheme IV, Where R$^2$=Ethyl, R$^3$=Trifluoromethyl)

These compounds were prepared in a similar fashion as that described in Example 138, General Procedure XV but using 1-hydroxy-2-butanone (Structure 23 of Scheme IV, where R$^2$=ethyl) in the place of 1-hydroxyacetone.

Compound 354 was isolated as a yellow solid: $^1$H NMR (500 MHz, CDCl$_3$) 12.7 (bs, 1H), 7.46 (d, J=8.8, 1H), 7.20 (s, 1H), 7.18 (d, J=8.8, 1H), 7.11 (s, 1H), 5.31 (q, J$_{H-F}$=4.9, 1H), 4.44 (dd, J=7.8, 7.2, 1H), 4.06 (dd, J=7.8, 7.4, 1H), 3.86–3.82 (m, 1H), 2.04–1.96 (m, 1H), 1.66–1.59 (m, 1H), 0.99 (t, J=7.3, 3H).

Compound 355 was isolated as a yellow solid: $^1$H NMR (500 MHz, CDCl$_3$) 12.0 (bs, 1H), 7.38 (d, J=8.8, 1H), 7.15 (d, J=8.8, 1H), 7.12 (s, 1H), 7.10 (s, 1H), 5.56 (q, J$_{H-F}$=4.4, 1H), 4.42 (dd, J=7.3, 6.8, 1H), 4.13–4.09 (m, 2H), 1.74–1.66 (m, 1H), 1.52–1.43 (m, 1H), 0.86 (t, J=7.3, 3H).

EXAMPLE 140

(±)-6-(5-Methyl-1-oxazolidino)-4-trifluoromethyl-2(1H)-quinolinone (Compound 356, Structure 25 of Scheme IV, Where R$^2$=Methyl, R$^3$=H)

These compounds were prepared in a similar fashion as that described in Example 138, General Procedure XV but using formaldehyde in the place of trifluoroacetaldehyde. Compound 356 was isolated as a yellow solid: $^1$H NMR (500 MHz, CDCl$_3$) 11.9 (bs, 1H), 7.36 (d, J=8.8, 1H), 7.09 (s, 1H), 6.91 (dd, J=8.8, 2.4, 1H), 6.81 (s, 1H), 5.05 (d, J=2.4, 1H), 4.84 (d, J=2.4, 1H), 4.19 (dd, J=8.3, 3.4, 1H), 3.96–3.93 (m, 1H), 3.85 (dd, J=8.3, 3.4, 1H), 1.31 (d, J=5.9, 3H).

EXAMPLE 141

6-(2,5-Dimethyl-1-pyrrolyl)-4-trifluoromethyl-2(1H)-quinolinone (Compound 357, Structure 20 of Scheme IV, Where R$^3$=R$^8$=Methyl, R$^4$, R$^5$=a Bond, R$^7$, R$^8$=a Bond, X=a Bond)

To PhH (2.5 mL) and AcOH (0.7 mL) was added Compound 200 (Structure 3 of Scheme IV) (23 mg, 0.10 mmol)

and acetonylacetone (Structure 28 of Scheme IV, where $R^2=R^3$=methyl, X=a bond) (14 mg, 0.12 mmol) and the reaction mixture refluxed for 4.5 h while removing water with a Dean-Stark trap. The cooled reaction mixture was diluted with EtOAc and washed successively with 2M HCl, satd. NaHCO$_3$, and brine. The organic layers were dried over MgSO$_4$, concentrated in vacuo, and chromatographed twice (MeOH:CH$_2$Cl$_2$, 1:9, then gradient of CH$_2$Cl$_2$ to MeOH:CH$_2$Cl$_2$, 1:9) to produce 18.0 mg (58%) of Compound 357 as a yellow solid: R$_f$0.20 (MeOH:CH$_2$Cl$_2$, 1:9); $^1$H NMR (500 MHz, CDCl$_3$) 11.00–11.20 (bs, 1H), 7.73 (s, 1H), 7.46–7.48 (m, 2H), 7.16 (s, 1H), 5.96 (s, 2H), 2.06 (s, 6H).

EXAMPLE 142

6-N-2,2,2-Trifluoroethyl-N-3,3,3-trifluoropropyl) amino-4-trifluoromethyl-2(1H)-quinolinone (Compound 358, Structure 7 of Scheme IV, Where $R^2$=2,2,2-Trifluoroethyl, $R^1$=3,3,3-Trifluoropropyl)

6-Amino-4-trifluoromethyl-2-isopropyloxyquinoline (Compound 359, Structure 26 of Scheme IV):

This compound was prepared from Compound 200 (Structure 3 of Scheme IV) in a similar fashion as that described in Example 101, General Procedure XII.

6-(N-3,3,3-Trifluoropropyl)amino-4-trifluoromethyl-2-isopropyloxyquinoline (Compound 360, Structure 26 of Scheme IV):

A mixture of Compound 359, 3,3,3-trifluoro-1-iodopropane and K$_2$CO$_3$ in DMF was heated at 100° C. for 2h and was quenched with water. Extraction with EtOAc, washing with brine and removal of solvent followed by chromatography afforded Compound 360 as yellow oil.

6-(N-2,2,2-Trifluoroethyl-N-3,3,3-trifluoropropyl) amino-4-trifluoromethyl-2(1H)-quinolinone (Compound 358, Structure 7 of Scheme IV, where $R^2$=2,2,2-trifluoroethyl, $R^3$=3,3,3-trifluoropropyl):

This compound was prepared from Compound 360 by reductive alkylation and acidic hydrolysis in similar fashion as that described in Example 2, General Procedure IV and Example 101, General Procedure XIV. Compound 358 was isolated as yellow solid. $^1$H NMR (400 MHz, acetone-d$_6$) 10.90 (s, 1H), 7.50 (d, J=9.2, 1H), 7.43 (dd, J=9.2, 2.5, 1H), 7.16 (s, 1H), 6.93 (s, 1H), 4.28 (q, J=9.2, 2H), 3.88–3.84 (m, 2H), 2.75–2.60 (m, 2H).

EXAMPLE 143

6-bis-N,N-Thiomethoxymethylamino-4-trifluoromethyl-2(1H)-quinolinone (Compound 361, Structure 7 of Scheme IV, Where $R^1=R^2$=Thiomethoxymethyl) and 6-bis-N,N-Thiomethoxymethylamino-4-trifluoromethyl-2-thiomethoxymethyloxyquinoline (Compound 362, Structure 27 of Scheme IV)

To a solution of Compound 200 (Structure 3 of Scheme IV) in THF was added NaH and chloromethyl methyl sulfide and the reaction mixture was stirred at rt for 1 h and quenched with water. Extraction with EtOAc, washing with brine, removal of solvent and chromatography afforded Compounds 361 and 362.

Compound 361 was isolated as yellow solid. $^1$H NMR (CDCl$_3$, 500 MHz) 7.36–7.38 (m, 3H), 7.08 (s, 1H), 5.40–5.50 (bs, 2H), 4.67 (s, 4H), 2.29 (s, 3H), 2.17 (s, 6H).

Compound 362 was isolated as yellow solid. $^1$H NMR (CDCl$_3$, 500 MHz) 11.80–12.00 (bs, 1H), 7.32–7.36 (m, 3H), 7.09 (s, 1H), 4.67 (s, 4H), 2.16 (t, J=20.5, 6H).

EXAMPLE 144

(±)-6-(2,5-trans-Diethyl-1-pyrrolidino)-4-trifluoromethyl-2(1H)-quinolinone (Compound 363, Structure 20 of Scheme IV, Where $R^2=R^8$=Ethyl, $R^4=R^5=R^6=R^7$=H, X=a Bond) and 6-(2,5-cis-Diethyl-1-pyrrolidino)-4-trifluoromethyl-2(1H)-quinolinone (Compound 364, Structure 20 of Scheme IV, Where $R^2=R^8$=Ethyl, $R^4=R^5=R^6=R^7$=H, X=a Bond)

These compounds were prepared by the following General Procedure XVI:

To a mixture of Compound 200 (Structure 3 of Scheme IV), acetic acid (10% equiv) and KOH (25% equiv) in methanol was added a diketone (2–5 equiv) and a reducing agent such as Na(CN)BH$_3$. The mixture was stirred at elevated temperature till the products were formed by TLC and quenched with water. Removal of solvent and chromatography of the crude residue afforded the pyrrolidinyl compounds in moderate yield.

Compound 363 was isolated as a major product: $^1$H NMR (500 MHz, CDCl$_3$) 7.23 (d, J=8.5, 1H), 6.99 (s, 1H), 6.91 (dd, J=8.5, 2.5, 1H), 6.74 (s, 1H), 3.69 (t, J=7.5, 2H), 1.73–1.70 (m, 2H), 1.81(d, J=5.0, 1H), 1.73–1.69 (m, 2H), 1.18–1.15 (m, 2H), 0.91(t, J=7.5, 6H).

Compound 364 was isolated as a minor product: $^1$H NMR (500MHz CDCl$_3$) 7.20 (d, J=9.0, 1H), 6.99 (s, 1H), 6.97 (dd, J=9.0, 2.4, 1H), 6.84 (m, 1H), 3.54 (m, 2H), 2.08–2.00 (m, 2H), 1.90–1.78 (m, 4H), 1.42–1.33 (m, 2H), 0.97 (t, J=7.5, 6H).

EXAMPLE 145

(±)-6-(2,5-trans-Dipropyl-1-pyrrolidino)-4-trifluoromethyl-2(1H)-quinolinone (Compound 365, Structure 20 of Scheme IV, Where $R^3=R^8$=Propyl, $R^4=R^5=R^6=R^7$=H, X=a Bond), 6-(2,5-cis-Dipropyl-1-pyrrolidino)-4-trifluoromethyl-2(1H)-quinolinone (Compound 366, Structure 20 of Scheme IV, Where $R^3=R^8$=Propyl, $R^4=R^5=R^6=R^7$=H, X=a Bond) and 6-(2,5-Dipropyl-1-pyrrolo)-4-trifluoromethyl-2(1H)-quinolinone (Compound 367, Structure 20 of Scheme IV, where $R^3=R^8$=Propyl, $R^4$, $R^5=R^6$, $R^7$=X=a Bond)

These compounds were prepared from Compound 200 (Structure 3 of Scheme IV) and 4,7-decanedione by General Procedure XVI described in Example 144.

Compound 365 was isolated as yellow solid. $^1$H NMR (CDCl$_3$, 500 MHz) 11.20–11.30 (bs, 1H), 7.23–7.31(m, 1H), 7.04 (s, 1H), 6.92 (dd, J=2.4, 8.8, 1H) 6.76 (s, 1H), 3.77 (t, J=7.8, 2H), 2.09–2.14 (m, 2H), 1.80–1.84 (m, 2H), 1.61–1.68 (m, 2H), 1.26–1.57 (m, 4H), 0.99–1.17 (m, 2H), 0.95 (t, J=7.3, 6H).

Compound 366 was isolated as yellow oil: $^1$H NMR (CDCl$_3$, 500 MHz) 10.60–10.70 (bs, 1H), 7.22 (d, J=9.3, 1H), 7.03 (s, 1H), 6.97 (dd, J=2.9, 9.3, 1H), 6.86 (s, 1H), 3.60–3.68 (m, 2H), 2.00–2.18 (m, 2H), 1.77–1.83 (m, 4H), 1.31–1.47 (m, 6H), 1.00 (t, J=7.3, 6H).

Compound 367 was isolated as yellow solid. $^1$H NMR (CDCl$_3$, 500 MHz) 12.60–12.80 (bs, 1H), 7.75 (s, 1H), 7.61 (d, J=8.3, 1H), 7.51 (dd, J=2.4, 8.8, 1H), 7.19 (s, 1H), 6.00 (s, 2H), 2.30 (t, J=7.3, 4H), 1.51 (sextet, J=7.8, 4H), 0.85 (t, J=7.3, 6H).

EXAMPLE 146

(±)-6-(2,5-trans-Dibutyl-1-pyrrolidino)-4-trifluoromethyl-2(1H)- quinolinone (Compound 369, Structure 20 of Scheme IV, Where $R^3$=$R^8$=Butyl, $R^4$=$R^5$=$R^6$=$R^7$=H, X=a Bond) and 6-(2,5-cis-Dibutyl-1-pyrrolidino)-4-trifluoromethyl-2(1H)-quinolinone (Compound 368, Structure 20 of Scheme IV, Where $R^3$=$R^8$=Butyl, $R^4$=$R^5$=$R^6$=$R^7$=H, X=a Bond)

These compounds were prepared from Compound 200 (Structure 3 of Scheme IV) and 5,8-dodecanedione by General Procedure XVI described in Example 144.

Compound 369 was isolated as yellow solid. $^1$H NMR (CDCl$_3$, 500 MHz) 9.80–10.00 (bs, 1H), 7.15 (d, J=8.8, 1H), 7.06 (s, 1H), 6.89 (dd, J=2.4, 9.3, 1H), 6.75 (s, 1H), 3.73–3.75 (m, 2H), 2.04–2.13 (m,2H), 1.80–1.88 (m, 2H), 1.60–1.69 (m, 2H), 1.26–1.48 (m, 8H), 0.89–0.94 (m, 6H).

Compound 368 was isolated as yellow oil: $^1$H NMR (CDCl$_3$, 500 MHz) 9.40–9.60 (bs, 1H), 7.12 (d, J=8.8, 1H), 7.01 (s, 1H), 6.94–6.95 (m, 1H), 6.85 (s, 1H), 3.56–3.64 (m, 2H), 2.00–2.05 (m, 2H), 1.81–1.90 (m, 4H), 1.26–1.48 (m, 1H), 0.95 (t, J=6.3, 6H).

EXAMPLE 147

(±)-6-(2,6-trans-Diethyl-1-piperidino)-4-trifluoromethyl-2(1H)-quinolinone (Compound 371, Structure 20 of Scheme IV, Where $R^3$=$R^8$=Ethyl, $R^4$=$R^5$=$R^6$=$R^7$=H, X=CH$_2$) and 6-(2,6-cis-Diethyl-1-piperidino)-4-trifluoromethyl-2(1H)-quinolinone (Compound 370, Structure 20 of Scheme IV, Where $R^3$=$R^8$=Ethyl, $R^4$=$R^5$=$R^6$=$R^7$=H, X=CH$_2$)

These compounds were prepared from Compound 200 (Structure 3 of Scheme IV) and 3,7-nonanedione by General Procedure XVI described in Example 144.

Compound 371 was isolated as yellow solid. $^1$H NMR (CDCl$_3$, 500 MHz) 11.40–11.60 (bs, 1H), 7.27–7.31 (m, 3H), 7.06 (s, 1H), 3.24–3.26 (m, 2H), 1.85–1.89 (m, 2H), 1.50–1.59 (m, 4H), 1.48–1.50 (m, 2H), 1.38–1.48 (m, 2H), 0.77 (t, J=7.3, 6H).

Compound 370 was isolated as yellow solid: $^1$H NMR (CDCl$_3$, 500 MHz) 11.20–11.40 (bs, 1H), 7.31–7.36 (m, 3H), 7.06 (s, 1H), 3.09–3.12 (m, 2H), 1.77–1.81 (m, 2H), 1.49–1.53 (m, 2H), 1.23–1.39 (m, 6H), 0.82 (t, J=7.3, 6H).

EXAMPLE 148

(±)-6-(2,6-trans-Dimethyl-1-piperidino)-4-trifluoromethyl-2(1H)-quinolinone (Compound 373, Structure 20 of Scheme IV, Where $R^3$=$R^8$=Methyl, $R^4$=$R^5$=$R^6$=$R^7$=H, X=CH$_2$) and 6-(2,6-cis-Dimethyl-1-piperidino)-4-trifluoromethyl-2(1H)-quinolinone (Compound 372, Structure 20 of Scheme IV, Where $R^3$=$R^8$=Methyl, $R^4$=$R^5$=$R^6$=$R^7$=H, X=CH$_2$)

These compounds were prepared from Compound 200 (Structure 3 of Scheme IV) and 2,6-heptanedione by General Procedure XVI described in Example 144.

Compound 373 was isolated as yellow solid. $^1$H NMR (500 MHz, CDCl$_3$) 11.88 (bs, 1H), 7.38–7.36 (m, 3H), 7.08 (s, 1H), 3.52 (q, J=6.3, 2H), 1.97–1.90 (m, 2H), 1.68–1.51 (m, 4H), 0.93 (d, J=5.9, 6H).

Compound 372 was isolated as yellow solid: $^1$H NMR (CDCl$_3$, 500 MHz) 12.00–12,20 (bs, 1H), 7.58 (bs, 1H), 7.47 (dd, J=2.0, 8.8, 1H), 7.42 (dd, J=1.0, 8.8, 1H), 7.10 (s, 1H), 2.91–2.96 (m, 2H), 1.76–1.84 (m, 3H), 1.52–1.57 (m, 1H), 1.41–1.48 (m, 2H), 0.77 (d, J=6.3, 6H).

EXAMPLE 149

6-(N-Propyl-N-2,2,2-trifluoroethyl)amino-4-methyl-2(1H)-quinolinone (Compound 374, Structure 31 of Scheme V, Where R=Methyl, $R^1$=$R^2$=$R^3$=$R^4$=H, $R^5$=Propyl, $R^6$=2,2,2-Trifluoroethyl)

6-Amino-4-methyl-2(1H)-quinolinone (Compound 375, Structure 30 of Scheme V, where R=methyl, $R^1$=$R^2$=$R^3$=$R^4$=H)

This compound was prepared in a similar fashion as that described in Example 1, General Procedures II and III but using 4-methyl-2(1H)-quinolinone (Compound 376, Structure 29 of Scheme V, where R=methyl, $R^1$=$R^2$=$R^3$=$R^4$=H) in place of Compound 202. Compound 375 was isolated as a solid: R$_f$0.26 (MeOH:CH$_2$Cl$_2$, 1:9); $^1$H NMR (500 MHz, CD$_3$OD) 7.19 (d, J=8.8, 1H), 7.08 (d, J=2.4, 1H), 7.04 (dd, J=2.4, 8.8, 1H), 6.47 (s, 1H), 2.47 (s, 3H).

6-(N-Propyl-N-2,2,2-trifluoroethyl)amino-4-methyl-2(1H)-quinolinone (Compound 374, Structure 31 of Scheme V, where R=methyl, $R^1$=$R^2$=$R^3$=$R^4$H, $R^5$=propyl, $R^6$=2,2,2-trifluoroethyl):

This compound was prepared in a similar fashion as that described in Example 9, General Procedure VI to install trifluoroethyl by using trifluoroacetic acid and Example 2, General Procedure IV to install the propyl. Compound 374 was isolated as a solid: R$_f$0.53 (MeOH:CH$_2$Cl$_2$, 1:19); $^1$H NMR (500 MHz, CDCl$_3$) 10.20–10.30 (bs, 1H); 7.18 (d, J=8.9, 1H), 7.00–7.07 (m, 1H), 6.97 (dd, J=2.4, 9.3, 1H), 6.55 (s, 1H), 3.89 (q, J=8.9, 2H), 3.39 (t, J=7.8, 2H), 2.46 (s, 3H), 1.64–1.67 (m, 2H), 0.96 (t, J=7.4, 3H).

EXAMPLE 150

6-(bis-2,2,2-Trifluoroethyl)amino-4-methyl-2(1H)-quinolinone (Compound 377, Structure 31 of Scheme V, Where R=Methyl, $R^1$=$R^2$=$R^3$=$R^4$=H, $R^5$=$R^6$=2,2,2-Trifluoroethyl)

This compound was prepared in a similar fashion as that described in Example 15, General Procedure VIII but using Compound 375 (Structure 30 of Scheme V, where R=methyl, $R^1$=$R^2$=$R^3$=$R^4$=H) in place of Compound 200. Compound 377 was isolated as a yellow solid: R$_f$0.40 (MeOH:CH$_2$Cl$_2$, 1:9); $^1$H NMR (500 MHz, CDCl$_3$) 10.80–11.00 (bs, 1H), 7.16–7.25 (m, 3H), 6.56 (bs, 1H), 4.06 (q, J=8.5, 4H), 2.45 (s, 3H).

EXAMPLE 151

6-(2,5-Dimethyl-1-pyrrolo)-4-methyl-2(1H)-quinolinone (Compound 378, Structure 20a of Scheme V, $R^4$, $R^5$=$R^6$, $R^7$=a Bond, $R^3$=$R^8$=Methyl, X=a Bond), (±)-6-(2,5-trans-Dimethyl-1-pyrrolidino)-4-methyl-2(1H)-quinolinone (Compound 379, Structure 20a of Scheme V, $R^3$=$R^8$=Methyl, $R^4$=$R^5$=$R^6$=$R^7$=H, X=a Bond) and 6-(2,5-cis-Dimethyl-1-pyrrolidino)-4-methyl-2(1H)-quinolinone (Compound 380, Structure 20a of Scheme V, $R^3$=$R^8$=Methyl, $R^4$=$R^5$=$R^6$=$R^7$=H, X=a Bond)

These compounds were prepared in a similar fashion as that described in Example 144, General Procedure XVI but using Compound 375 (Structure 30 of Scheme V, where R=methyl, $R^1$=$R^2$=$R^3$=$R^4$=H) in place of Compound 200.

Compound 378 was isolated as a yellow solid: $R_f$ 0.52 (MeOH:CH$_2$Cl$_2$, 1:9); $^1$H NMR (400 MHz, CDCl$_3$) 10.60–10.80 (bs, 1H), 7.54 (s, 1H), 7.37 (s, 2H), 6.63 (s, 1H), 5.94 (s, 2H), 2.48 (s, 3H), 2.04 (s, 6H).

Compound 379 was isolated as yellow solid. $^1$H NMR (400 MHz, CDCl$_3$) 11.15 (bs, 1H), 7.22 (d, J=8.9, 1H), 6.90 (dd, J=8.9, 2.5, 1H), 6.68 (d, J=2.5, 1H), 6.54 (s, 1H), 4.06(t, J=6.3, 2H), 2.45 (s, 3H), 2,27 (m, 2H), 1.67 (m, 2H), 1.13 (s, 3H), 1.11 (s, 3H).

Compound 380 was isolated as yellow solid. $^1$H NMR (400 MHz, CDCl$_3$) 10.48 (bs, 1H), 7.17 (d, J=8.9, 1H), 6.93 (dd, J=8.9, 2.5, 1H), 6.74 (d, J=2.5, 1H), 6.53 (s, 1H), 3.78 (m, 2H), 2.46 (s, 3H), 2.09 (m, 2H), 1.76 (m, 2H), 1.32 (s, 3H), 1.31(s, 3H).

EXAMPLE 152

6-(N-Isobutyl-N-2,2,2-trifluoroethyl)amino-4-methyl-2(1H)-quinolinone (Compound 381, Structure 31 of Scheme V, Where R=Methyl, $R^1$=$R^2$=$R^3$=$R^4$=H, $R^5$=Isobutyl, $R^6$=2,2,2-Trifluoroethyl)

This compound was prepared from Compound 375 (Structure 30 of Scheme V, where R=methyl, $R^1$=$R^2$=$R^3$=$R^4$=H) in a similar fashion as that described in Example 9, General Procedure VI to install trifluoroethyl from trifluoroacetic acid and Example 2, General Procedure IV to install the isobutyl. Compound 381was isolated as a solid: $R_f$ 0.18 (MeOH:CH$_2$Cl$_2$, 3:7); $^1$H NMR (500 MHz, CDCl$_3$) 11.80–12.00 (bs, 1H), 7.32 (d, J=9.3, 1H), 7.12 (dd, J=2.4, 9.3, 1H), 7.02 (d, J=2.9, 1H), 6.56 (s, 1H), 3.92 (q, J=8.8, 2H), 3.23 (d, J=7.3, 2H), 2.47 (s, 3H), 2.04 (quin, J=6.8, 1H), 0.95 (d J=6.8, 6H).

EXAMPLE 153

6-(N-2,2,2-Chlorodifluoroethyl)amino-4-methyl-2(1H)-quinolinone (Compound 382, Structure 31 of Scheme V, Where R=Methyl $R^1$=$R^2$=$R^3$=$R^4$=$R^5$=H, $R^6$=2,2,2-Chlorodifluoroethyl)

This compound was prepared from Compound 375 (Structure 30 of Scheme V, where R=methyl, $R^1$=$R^2$=$R^3$=$R^4$=H) and chlorodifluoroacetic acid in a similar fashion as that described in Example 9, General Procedure VI. Compound 382 was isolated as a solid: $^1$H NMR (CDCl$_3$) 10.28 (bs, 1H), 7.15 (d, J=8.6, 1H), 7.10 (d, J=8.6, 1H), 6.91 (s, 1H), 6.54 (s, 1H), 4.13 (t, J=7.2, 1H), 3.95 (m, 2H), 2.45 (s, 3H).

EXAMPLE 154

6-(bis-N,N-2,2,2-Chlorodifluoroethyl)amino-4-methyl-2(1H)-quinolinone (Compound 383, Structure 31 of Scheme V, Where R=Methyl, $R^1$=$R^2$=$R^3$=$R^4$=H, $R^5$=$R^6$=2,2,2-Chlorodifluoroethyl)

This compound was prepared from Compound 375 (Structure 30 of Scheme V, where R=methyl, $R^1$=$R^2$=$R^3$=$R^4$=H) and chlorodifluoroacetic acid in a similar fashion as that described in Example 9, General Procedure VI. Compound 383 was isolated as a solid: $^1$H NMR (CDCl$_3$) 11.50 (bs, 1H), 7.35 (d, J=9.7, 1H), 7.25–7.23 (m, 2H), 6.59 (s, 1H), 4.24 (t, J=12.0, 4H), 2.49 (s, 3H).

EXAMPLE 155

6-(N-2,2,2-Chlorodifluoroethyl-N-2,2,2-trifluoroethyl)amino-4-methyl-2(1H)-quinolinone (Compound 384, Structure 31 of Scheme V, Where R=Methyl, $R^1$=$R^2$=$R^3$=$R^4$=H, $R^5$=2,2,2-Trifluoroethyl, $R^6$=2,2,2-Chlorodifluoroethyl)

This compound was prepared from Compound 375 (Structure 30 of Scheme V, where R=methyl, $R^1$=$R^2$=$R^3$=$R^4$=H) in a similar fashion as that described in Example 9, General Procedure VI using chlorodifluoroacetic acid and trifluoroacetic acid sequentially. Compound 384 was isolated as a solid: $^1$H NMR (CDCl$_3$) 11.33 (bs, 1H), 7.37 (d, J=8.5, 1H), 7.23 (d, J=8.5, 1H), 7.20 (s, 1H), 4.20 (t, J=11.7, 2H), 4.09 (q, J=8.5, 2H), 2.48 (s, 3H).

EXAMPLE 156

6-N-Ethylamino-4-methyl-2(1H)-quinolinone (Compound 385, Structure 31 of Scheme V, Where R=Methyl, $R^1$=$R^2$=$R^3$=$R^4$=$R^5$=H, $R^6$=Ethyl)

This compound was prepared from Compound 375 (Structure 30 of Scheme V, where R=methyl, $R^1$=$R^2$=$R^3$=$R^4$=H) in a similar fashion as that described in Example 9, General Procedure VI using acetic acid. Compound 385 was isolated as a solid: $^1$H NMR (CDCl$_3$) 11.05 (bs, 1H), 7.23 (d, J=8.7, 1H), 6.87 (dd, J=8.7, 2.6, 1H), 6.75 (s, 1H), 6.54 (s, 1H), 3.65 (bs, 1H), 3.21 (q, J=7.1, 2H), 2.45 (s, 3H), 1.30 (t, J=7.1, 3H).

EXAMPLE 157

6-(N-Ethyl-N-2,2,2-trifluoroethyl)amino-4-methyl-2(1H)-quinolinone (Compound 386, Structure 31 of Scheme V, Where R=Methyl, $R^1$=$R^2$=$R^3$=$R^4$=H, $R^5$=2,2,2-Trifluoroethyl, $R^6$=Ethyl)

This compound was prepared from Compound 375 (Structure 30 of Scheme V, where R=methyl, $R^1$=$R^2$=$R^3$=$R^4$=H) in a similar fashion as that described in Example 9, General Procedure VI using acetic acid and trifluoroacetic acid sequentially. Compound 386 was isolated as a solid: $^1$H NMR (CDCl$_3$) 11.23 (bs, 1H), 7.36 (d, J=8.9, 1H), 7.08 (dd, J=9.0, 2.5, 1H), 6.98 (d, J=2.5, 1H), 6.58 (s, 1H), 3.87 (q, J=9.0, 2H), 3.52 (q, J=7.0, 2H), 2.48 (s, 3H), 1.22 (t, J=7.0, 3H).

EXAMPLE 158

6-N,N-Diethylamino-4-methyl-2(1H)-quinolinone (Compound 387, Structure 31 of Scheme V, Where R=Methyl, $R^1$=$R^2$=$R^3$=$R^4$=$R^5$=H, $R^6$=Ethyl)

This compound was prepared from Compound 375 (Structure 30 of Scheme V, where R=methyl, $R^1$=$R^2$=$R^3$=$R^4$=H) and acetic acid in a similar fashion as that described in Example 9, General Procedure VI. Compound 387 was isolated as a solid: $^1$H NMR (CDCl$_3$) 11.72 (bs, 1H), 7.29 (d, J=8.9, 1H), 7.02 (dd, J=11.6, 2.6, 1H), 6.83 (d, J=2.6, 1H), 6.55 (s, 1H), 3.38 (q, J=7.0, 4H), 2.47 (s, 3), 1.17 (t, J=7.0, 6H).

EXAMPLE 159

6-(bis-2,2,2-Trifluoroethyl)amino-4-ethyl-2(1H)-quinolinone (Compound 388, Structure 31 of Scheme V, Where R=Ethyl, $R^1$=$R^2$=$R^3$=$R^4$=H, $R^5$=$R^6$=2,2,2-Trifluoroethyl)

6-Amino-4-ethyl-2(1H)-quinolinone (Compound 389, Structure 30 of Scheme V, where R=ethyl, $R^1$=$R^2$=$R^3$=$R^4$=H):

This compound was prepared in a similar fashion as that described in Example 1, General Procedures II and III but using 4-ethyl-2(1H)-quinolinone (Compound 390, Structure 29 of Scheme V, where R=ethyl, $R^1$=$R^2$=$R^3$=$R^4$=H) in place of Compound 202. Compound 389 was isolated as a solid: $R_f$ 0.42 (MeOH:CH$_2$Cl$_2$, 1:9; $^1$H NMR (500 MHz, CD$_3$OD) 7.20 (d, J=8.8, 1H), 7.13 (d, J=2.4, 1H), 7.04 (dd, J=2.4, 8.8, 1H), 6.47 (s, 1H), 2.88 (q, J=7.3, 2H), 1.34 (t, J=7.3, 3H).

6-(bis-2,2,2-trifluoroethyl)amino-4-ethyl-2(1H)-quinolinone (Compound 388, Structure 31 of Scheme V, where R=ethyl, R$^1$=R$^2$=R$^3$=R$^4$=H, R$^5$=R$^6$=2,2,2-trifluoroethyl):

This compound was prepared from Compound 389 in a similar fashion as that described in Example 9, General Procedure VI to install trifluoroethyl from trifluoroacetic acid. Compound 388 was isolated as a solid: R$_f$0.53 (MeOH:CH$_2$Cl$_2$, 1:9); $^1$H NMR (500 MHz, CDCl$_3$) 12.20–12.40 (bs, 1H), 7.41 (d, J=9.3, 1H), 7.25 (d, J=2.4, 1H), 7.20 (dd, J=2.4, 9.3, 1H), 6.62 (s, 1H), 4.05 (q, J=8.8, 4H), 2.85 (q, J=7.3, 2H) 1.35 (t, J=7.3, 3H).

EXAMPLE 160

6-(bis-2,2,2-Trifluoroethyl)amino-4-isopropyl-2(1H)-quinolinone (Compound 391, Structure 31 of Scheme V, Where R=Isopropyl, R$^1$=R$^2$=R$^3$=R$^4$=H, R$^5$=R$^6$=2,2,2-Trifluoroethyl)

6-Amino-4-isopropyl-2(1H)-quinolinone (Compound 392, Structure 30 of Scheme V, where R=isopropyl, R$^1$=R$^2$=R$^3$=R$^4$=H):

This compound was prepared in a similar fashion as that described in Example 1, General Procedures II and III but using 4-isopropyl-2(1H)-quinolinone (Structure 29 of Scheme V, where R=isopropyl, R$^1$=R$^2$=R$^3$=R$^4$=H) in place of Compound 202.

6-(bis-2,2,2-trifluoroethyl)amino-4-isopropyl-2(1H)-quinolinone (Compound 391, Structure 31 of Scheme V, where R=isopropyl, R$^1$=R$^2$=R$^3$=R$^4$=H, R$^5$=R$^6$=2,2,2-trifluoroethyl):

This compound was prepared in a similar fashion as that described in Example 9, General Procedure VI from Compound 391 and trifluoroacetic acid as a yellow solid. $^1$H NMR (CDCl$_3$) 11.22 (bs, 1H), 7.42 (d, J=8.9, 1H), 7.27 (s, 1H), 7.18 (dd, J=8.9, 2.3, 1H), 6.65 (s, 1H), 4.04 (q, J=8.5, 4H), 3.30 (quin, J=6.7, 1H), 1.29 (d, J=6.7, 6H).

EXAMPLE 161

7-Fluoro-6-(bis-N,N-2,2,2-trifluoroethyl)amino-4-trifluoromethyl-2(1H)-quinolinone (Compound 393, Structure 31 of Scheme V, Where R=Trifluoromethyl, R$^1$=R$^2$=R$^4$=H, R$^3$=Fluoro, R$^5$=R$^6$=2,2,2-Trifluoroethyl)

7-Fluoro-4-trifluoromethyl-2(1H)-quinolinone (Compound 394, Structure 29 of Scheme V) V, where R=trifluoromethyl, R$^1$=R$^2$=R$^4$=H, R$^3$=fluoro)

This compound was prepared in a similar fashion as that described in Example 1, General Procedure I but using 3-fluoroaniline in place of aniline. Compound 394 was isolated as a yellow solid: $^1$H NMR (400 MHz, acetone-d$_6$) 11.30 (s, 1H), 7.87–7.85 (m, 1H), 7.27 (dd, J=2.5, 9.8, 1H), 7.16 (dt, J=2.5, 8.9, 1H), 6.92 (s, 1H).

5-Fluoro-4-trifluoromethyl-2(1H)-quinolinone (Compound 395, Structure 29 of Scheme V, where R=trifluoromethyl, R$^1$=R$^3$=R$^4$=H, R$^2$=fluoro)

This compound was isolated as a by-product: $^1$H NMR (400 MHz, acetone-d$_6$) 11.32 (s, 1H), 7.70–7.65 (m, 1H), 7.38 (d, J=8.5, 1H) 7.12–7.07 (m, 1H), 7.04 (s, 1H).

6-Amino-7-fluoro-4-trifluoromethyl-2(1H)-quinolinone (Compound 396, Structure 30 of Scheme V, where R=trifluoromethyl, R$^1$=R$^2$=R$^4$=H, R$^3$=fluoro):

This compound was prepared in a similar fashion as that described in Example 1, General Procedures II and III but using Compound 394 in place of Compound 202. Compound 396 was isolated as a yellow solid.

7-Fluoro-6-(bis-trifluoroethyl)amino-4-trifluoromethyl-2(1H)-quinolinone (Compound 393, Structure 31 of Scheme V, where R=trifluoromethyl, R$^1$=R$^2$=R$^4$=H, R$^3$=fluoro, R$^5$=R$^6$=2,2,2-trifluoroethyl):

This compound was prepared in a similar fashion as that described in Example 9, General Procedure VI to install trifluoroethyl from trifluoroacetic acid but using Compound 396 in place of Compound 200. Compound 393 was isolated as a yellow solid: $^1$H NMR (400 MHz, acetone-d$_6$) 11.28 (s, 1H), 7.79 (d, J=8.2, 1H), 7.34 (d, J=12.0, 1H), 6.94 (s, 1H), 4.45 (q, J=8.7, 4H).

EXAMPLE 162

8-Fluoro-6-(bis-N,N-2,2,2-trifluoroethyl)amino-4-trifluoromethyl-2(1H)-quinolinone (Compound 397, Structure 31 of Scheme V, Where R=Trifluoromethyl, R$^1$=R$^2$=R$^3$=H, R$^4$=Fluoro, R$^5$=R$^6$=2,2,2-Trifluoroethyl)

8-Fluoro-4-trifluoromethyl-2(1H)-quinolinone (Compound 398, Structure 29 of Scheme V, where R=trifluoromethyl, R$^1$=R$^2$=R$^3$=H, R$^4$=fluoro)

This compound was prepared in a similar fashion as that described in Example 1, General Procedure I but using 2-fluoroaniline in place of aniline. Compound 398 was isolated as a yellow solid: $^1$H NMR (400 MHz, acetone-d$_6$) 11.04 (s, 1H), 7.62 (d, J=8.7, 1H), 7.535–7.50 (m, 1H), 7.37–7.32 (m, 1H), 7.02 (s, 1H).

6-Amino-8-fluoro-4-trifluoromethyl-2(1H)-quinolinone (Compound 399, Structure 30 of Scheme V, where R=trifluoromethyl, R$^1$=R$^2$=R$^3$=H, R$^4$=fluoro):

This compound was prepared in a similar fashion as that described in Example 1, General Procedures II and III but using Compound 398 in place of Compound 202. Compound 399 was isolated as a yellow solid: $^1$H NMR (400 MHz, acetone-d$_6$) 11.25 (s, 1H), 6.97 (dd, J=2.2, 12.6, 1H), 6.96 (s, 1H), 6.87–6.86 (m, 1H), 5.16 (s, 2H).

8-Fluoro-6-(N-2,2,2-trifluoroethyl)amino-4-trifluoromethyl-2(1H)-quinolinone (Compound 400, Structure 31 of Scheme V, where R=trifluoromethyl, R$^1$=R$^2$=R$^3$=R$^6$=H, R$^4$=fluoro, R$^5$=2,2,2-trifluoroethyl):

This compound was prepared in a similar fashion as those described in Example 9, General Procedure VI but using Compound 399 in place of Compound 200. Compound 400 was isolated as a yellow solid: $^1$H NMR,(400 MHz, acetone-d$_6$) 10.88 (s, 1H), 7.15 (dd, J=12.9, 2,2, 1H), 6.97 (s, 1H), 6.95 (d, J=9.9, 1H), 6.07 (s, 1H), 4.09–4.02 (m, 2H).

8-Fluoro-6-(bis-2,2,2-trifluoroethyl)amino-4-trifluoromethyl-2(1H)-quinolinone (Compound 397, Structure 31 of Scheme V, where R=trifluoromethyl, R$^1$=R$^2$=R$^3$=H, R$^4$=fluoro, R$^5$=R$^6$=2,2,2-trifluoroethyl):

This compound was prepared in a similar fashion as those described in Example 9, General Procedure VI but using Compound 399 in place of Compound 200 and excess of NaBH$_4$. Compound 397 was isolated as a yellow solid: $^1$H NMR (400 MHz, acetone-d$_6$) 11.07 (s, 1H), 7.54 (dd, J=2.5, 13.5, 1H), 7.17 (s, 1H), 7.03 (s, 1H), 4.45 (q, J=8.7, 4H).

EXAMPLE 163

8-Fluoro-6-(N-2,2,2-trifluoroethyl-N-isopropyl)amino-4-trifluoromethyl-2(1H)-quinolinone (Compound 401, Structure 31 of Scheme V, Where R=Trifluoromethyl, R$^1$=R$^2$=R$^3$=H, R$^4$=Fluoro, R$^5$=2,2,2-Trifluoroethyl, R$^6$=Isopropyl)

This compound was prepared in a similar fashion as those described in Example 15, General Procedure VIII but using Compound 400 and acetone in place of Compound 200. Compound 401was isolated as a yellow solid: $^1$H NMR (400 MHz, acetone-d$_6$) 11.50 (s, 1H), 7.46 (d, J=2.5, 1H), 7.09 (s, 1H), 7.00 (s, 1H), 4.09 (q, J=8.5, 2H), 2.09–2.02 (m, 1H), 1.26 (d, J=7.0, 6H).

EXAMPLE 164

6-Amino-3-fluoro-4-trifluoromethyl-2(1H)-quinolinone (Compound 402, Structure 30 of Scheme V, Where R=Trifluoromethyl, $R^2$=$R^3$=$R^4$=H, $R^1$=Fluoro)

This compound was prepared in a similar fashion as that described in Example 1, General Procedures I, II and III but using ethyl 2,4,4,4-tetrafluoroacetoacetate in place of ethyl 4,4,4-trifluoroacetoacetate. Compound 402 was isolated as a yellow solid: $^1$H NMR (400 MHz, DMSO-d$_6$) 12.48 (s, 1H), 7.16 (d, J=8.7, 1H), 6.92 (dd, J=2,2, 8.8, 1H), 6.89 (d, J=2,2, 1H), 5.36 (bs, 1H).

EXAMPLE 165

3-Fluoro-6-(2,2,2-trifluoroethyl)amino-4-trifluoromethyl-2(1H)-quinolinone (Compound 403, Structure 31 of Scheme V, Where R= Trifluoromethyl, $R^2$=$R^3$=$R^4$=H, $R^1$=Fluoro) $R^5$=2,2,2-Trifluoroethyl)

This compound was prepared in a similar fashion as that described in Example 9, General Procedure VI but using Compound 402 (Structure 30 of Scheme V, where R=trifluoromethyl, $R^2$=$R^3$=$R^4$=H, $R^1$=fluoro) and TFA in place of Compound 200 and difluoroacetic acid. Compound 403 was isolated as a yellow solid: $^1$H NMR (400 MHz, DMSO-d$_6$) 12.55 (s, 1H), 7.26 (d, J=9.1, 1H), 7.15 (dd, J=2.1, 9.1, 1H), 6.98 (d, J=2.1, 1H), 6.54 (t, J=6.8, 1H), 3.95 (m, 2H).

EXAMPLE 166

3-Fluoro-6-(bis-2,2,2-trifluorofluoroethyl)amino-4-trifluoromethyl-2(1H)-quinolinone (Compound 404, Structure 22 of Scheme V, Where R= Trifluoromethyl, $R^2$=$R^3$=$R^4$=H, $R^1$=Fluoro, $R^5$=$R^6$=2,2,2-Trifluoroethyl)

This compound was prepared in a similar fashion as that described in Example 9, General Procedure VI but using Compound 402 (Structure 30 of Scheme V, where R=trifluoromethyl, $R^2$=$R^3$=$R^4$=H, $R^1$=fluoro) and TFA in place of Compound 200 and difluoroacetic acid. Compound 404 was isolated as a yellow solid: $^1$H NMR (400 MHz, DMSO-d$_6$) 12.67 (s, 1H), 7.53 (dd, J=2.1, 7.2, 1H), 7.36 (d, J=9.2, 1H), 7.18 (d, J=2.1, 1H), 4.39 (q, J=8.8, 4H).

EXAMPLE 167

6-(bis-Isobutylamino)-4-methyl-2(1H)-quinolinone (Compound 405, Structure 31 of Scheme V, Where R=Methyl, $R^1$=$R^2$=$R^3$=$R^4$=H, $R^5$=$R^6$=Isobutyl)

This compound was prepared in a similar fashion as that described in Example 9, General Procedure VI but using Compound 375 (Structure 30 of Scheme V, where R=methyl, $R^1$=$R^2$=$R^3$=$R^4$=H) and isobutyric acid. Compound 405 was isolated as a yellow solid: $^1$H NMR (CDCl$_3$, 500 MHz) 10.00–10.20 (bs, 1H), 7.12 (d, J=8.9, 1H), 6.98 (dd, J=2.4, 8.9, 1H), 6.78 (d, J=2.4, 1H), 6.52 (s, 1H), 3.17 (d, J=7.0, 4H), 2.44 (s, 3H), 2.07 (sextet, J=7.0, 2H), 0.93 (d, J=6.7, 12H).

EXAMPLE 168

3-Fluoro-6-(N-methyl-N-2,2,2-trifluorofluoroethyl) amino-4-trifluoromethyl-2(1H)-quinolinone (Compound 406, Structure 31 of Scheme V, Where R=Trifluoromethyl, $R^2$=$R^3$=$R^4$=H, $R^1$=Fluoro, $R^5$=2,2,2-Trifluoroethyl, $R^6$=Methyl)

This compound was prepared in a similar fashion as that described in Example 2, General Procedure IV but using Compound 403 (Structure 31 of Scheme V, where R=trifluoromethyl, $R^2$=$R^3$=$R^4$=$R^6$=H, $R^1$=fluoro, $R^5$=2,2,2-trifluoroethyl) and parafomaldehyde in place of Compound 200 and propionaldehyde. Compound 406 was isolated as a yellow solid: $^1$H NMR (400 MHz, CDCl$_3$) 12.25 (bs, 1H), 7.41 (d, J=8.7, 1H), 7.14 (dd, J=2,2, 8.8, 1H), 7.13 (d, J=2.1, 1H), 3.91 (q, J=8.8, 2H), 3.13 (s, 3H).

EXAMPLE 169

7-Bromo-6-isopropylamino-4-trifluoromethyl-2 (1H)-quinolinone (Compound 407, Structure 31of Scheme V, Where R=Trifluoromethyl, $R^1$=$R^2$=$R^4$=$R^6$=H, $R^3$=Bromo, $R^5$=Isopropyl)

6-Amino-7-bromo-4-trifluoromethyl-2(1H)-quinolinone (Compound 408, Structure 30 of Scheme V, where R=Trifluoromethyl, $R^1$=$R^2$=$R^4$=H, $R^3$=bromo):

To a solution of Compound 200 (Structure 3 of Scheme V) in methylene chloride (0.1–0.5 M) was added NBS (1.1 equiv) and the reaction mixture was stirred at room temperature for 30 min. The mixture was concentrated and chromatography afforded Compound 408 as a yellow solid.

7-Bromo-6-isopropylamino-4-trifluoromethyl-2(1H)-quinolinone (Compound 407, Structure 31 of Scheme V, where R=trifluoromethyl, $R^1$=$R^2$=$R^4$=$R^6$=H, $R^3$=bromo, $R^5$=isopropyl):

This compound was prepared in a similar fashion as that described in Example 3, General Procedure V but using Compound 408 in place of Compound 200. Compound 407 was isolated as a yellow solid: $^1$H NMR (400 MHz, CDCl$_3$) 11.3 (bs, 1H), 7.56 (s, 1H), 7.07 (s, 1H), 6.89 (s, 1H), 4.20 (d, J=5.8, 1H), 3.70–3.65 (m, 1H), 1.30 (d, J=6.3, 6H).

EXAMPLE 170

6-(bis-N,N-2,2,2-Trifluoroethyl)amino-4-hydroxy-2 (1H)-quinolinone (Compound 409, Structure 31 of Scheme V, Where R=Hydroxy, $R^1$=$R^2$=$R^3$=$R^4$= H, $R^5$=$R^6$=2,2,2-Trifluoroethyl)

This compound was prepared in a similar fashion as that described in Example 9, General Procedure VI from 6-amino-4-hydroxy-2(1H)-quinolinone (Compound 410, Structure 30 of Scheme V, where R=hydroxy, $R^1$=$R^2$=$R^3$=$R^4$=H) and trifluororacetic acid. Compound 409 was isolated as a yellow solid. $^1$H NMR (CDCl$_3$, 500 MHz) 7.55 (d, J=2.9, 1H), 7.40 (dd, J=2.9, 9.3, 1H), 7.31(d, J=9.3, 1H), 5.91(s, 1H), 4.23 (q, J=8.3, 4H).

EXAMPLE 171

6-(bis-N,N-2,2,2-Trifluoroethyl)amino-4-methoxy-2 (1H)-quinolinone (Compound 411, Structure 31 of Scheme V, Where R=Methoxy, $R^1$=$R^2$=$R^3$=$R^4$= H, $R^5$=$R^6$=2,2,2-Trifluoroethyl)

This compound was prepared in a similar fashion as that described in Example 9, General Procedure VI from 6-amino-4-methoxy-2(1H)-quinolinone (Compound 412, Structure 30 of Scheme V, where R=methoxy, $R^1$=$R^2$=$R^4$=H) H) and trifluororacetic acid. Compound 411was isolated as a yellow solid. $^1$H NMR (400 MHz, CDCl$_3$) 10.52 (bs, 1H), 7.44, (d, J=2.7, 1H), 7.29 (d, J=8.8, 1H), 7.18 (dd, J=8.8, 2.7, 1H), 6.01(s, 1H), 4.06 (q, J=8.53, 4H), 3.99 (s, 3H).

EXAMPLE 172

6-(bis-N,N-2,2,2-Trifluoroethyl)amino-4-difluoromethyl-2(1H)-quinolinone (Compound 413, Structure 31 of Scheme V, Where R=Difluoromethyl, $R^1$=$R^2$=$R^3$=$R^4$=H, $R^5$=$R^6$=2,2,2-Trifluoroethyl)

This compound was prepared in a similar fashion as that described in Example 9, General Procedure VI from 6-amino-4-difluoromethyl-2(1H)-quinolinone (Compound 414, Structure 30 of Scheme V, where R=difluoromethyl, $R^1$=$R^2$=$R^3$=$R^4$=H) and trifluororacetic acid. Compound 413 was isolated as a yellow solid. $^1$H NMR (CDCl$_3$, 500 MHz) 7.47 (dd, J=2.9, 9.3, 1H), 7.45 (m, 1H), 7.39 (d, J=9.3, 1H), 7.15 (t J=53.7, 1H), 6.86 (s, 1H), 4.26 (q, J=8.8, 4H).

EXAMPLE 173

6-(bis-N,N-2,2,2-Trifluoroethyl)amino-2(1H)-quinolinone (Compound 415, Structure 31 of Scheme V, Where R=$R^1$=$R^2$=$R^3$=$R^4$=H, $R^5$=$R^6$=2,2,2-Trifluoroethyl)

This compound was prepared in a similar fashion as that described in Example 9, General Procedure VI from 6-amino-2(1H)-quinolinone (Compound 416, Structure 30 of Scheme V, where R=$R^1$=$R^2$=$R^3$=$R^4$=H) and trifluororacetic acid. Compound 415 was isolated as a yellow solid. $^1$H NMR (CDCl$_3$, 500 MHz) 7.92 (d, J=9.8, 1H), 7.40 (dd, J=2.9, 8.8, 1H), 7.35 (d, J=2.9, 1H), 7.32 (d, J=8.8, 1H), 6.61 (d, J=9.8, 1H), 4.25 (q, J=8.8, 4H).

EXAMPLE 174

4-Chloro-6-(bis-N,N-2,2,2-trifluoroethyl)amino-2(1H)-quinolinone (Compound 417, Structure 31 of Scheme V, Where R=Chloro, $R^1$=$R^2$=$R^3$=$R^4$=H, $R^5$=$R^6$=2,2,2-Trifluoroethyl)

This compound was prepared in a similar fashion as that described in Example 9, General Procedure VI from 6-amino-4-chloro-2(1H)-quinolinone (Compound 418, Structure 30 of Scheme V, where R=chloro, $R^1$=$R^2$=$R^3$=$R^4$=H) and trifluororacetic acid. Compound 417 was isolated as a yellow solid. $^1$H NMR (500 MHz, CDCl$_3$) 10.30 (bs, 1H), 7.47 (d, J=2.4, 1H), 7.32 (d, J=9.3, 1H), 7.25 (dd, J=9.3, 2.4, 1H), 6.89 (s, 1H), 4.10 (q, J=8.3, 4H).

EXAMPLE 175

7-Methoxy-4-trifluoromethyl-2(1H)-quinolinone (Compound 419, Structure 29 of Scheme V, Where R=Trifluoromethyl, $R^1$=$R^2$=$R^4$=H, $R^3$=Methoxy)

In a 50-mL flask, a solution of meta-anisidine (5 mL, 44 mmol) and ethyl 4,4,4-trifluoroacetoacetate (7.8 mL, 53 mmol, 1.2 equiv) in toluene (5 mL) was heated to reflux for 16 h, cooled and the white precipitate filtered off and washed with hexane (10 mL). The crude precipitate was then heated in EtOH (15 mL) with a catalytic amount of p-toluenesulfonic acid. After complete conversion, 4–6 h, the solvent was removed and the crude reaction mixture was re-dissolved in EtOAc (200 mL) and washed with water (2×20 mL), Brine (20 mL), dried (MgSO$_4$), filtered and concentrated to give 4.0 g (37%) of Compound 419 as a white solid: $^1$H NMR (400 MHz, DMSO-d$_6$) 12.18 (s, 1H), 7.62 (dd, J=8.4, 1.5, 1H), 6.95 (dd, J=8.2, 2,2, 1H), 6.93 (s, 1H), 6.78 (s, 1H), 3.84 (s, 3H).

EXAMPLE 176

5,7-Dimethoxy-4-trifluoromethyl-2(1H)-quinolinone (Compound 420, Structure 29 of Scheme V, Where R=Trifluoromethyl, $R^1$=$R^4$=H, $R^2$=$R^3$=Methoxy)

This compound was prepared in a similar fashion as that described in Example 175 but using 3,5-dimethoxyaniline in place of 3-anisidine. Compound 420 was isolated as a white solid: $^1$H NMR (400 MHz, DMSO-d$_6$) 12.11 (bs, 1H), 6.71(s, 1H), 6.56 (d, J=2.2, 1H), 6.46 (d, J=2.2, 1H), 3.87 (s, 3H), 3.83 (s, 3H).

EXAMPLE 177

(R)-6-(2-Hydroxymethyl-1-pyrrolidino)-4-trifluoromethyl-2(1H)-quinolinone (Compound 421, Structure 33 of Scheme Va, Where n=1)

(R)-6-(2-Methoxycarbonyl-1-pyrrolidino)-4-trifluoromethyl-2-isopropyloxyquinoline (Compound 422, Structure 32 of Scheme VI, where R=methyl, n=1)

This compound was prepared in a similar fashion as that described in Example 101, General Procedures XIII and XIV from Compound 309 (Structure 17 of Scheme III) and D-proline methyl ester.

(R)-6-(2-Hydroxymethyl-1-pyrrolidino)-4-trifluoromethyl-2(1H)-quinolinone (Compound 421, Structure 33 of Scheme VI, where n=1)

This compound was prepared from Compound 422 by a metal hydride reduction and isolated as yellow solid. $^1$H NMR (CDCl$_3$, 500 MHz) 1.00–11.20 (bs, 1H), 7.26–7.27 (m, 1H), 7.12 (dd, J=2.7, 9.5, 1H), 7.06(s, 1H), 6.96 (s, 1H), 3.91–4.14 (m, 1H), 3.71(s, 2H), 3.58 (t, J=7.3, 1H), 3.19–3.24 (m, 1H), 2.05–2.16 (m, 5H).

EXAMPLE 178

(R)-6-(2-Methoxymethyl-1-pyrrolidino)-4-trifluoromethyl-2(1H)-quinolinone (Compound 423, Structure 34 of Scheme VI, Where R=Methoxymethyl, n=1)

This compound was prepared by methylation of Compound 421 and isolated as yellow solid. $^1$H NMR (CDCl$_3$, 500 MHz) 11.60–11.80 (bs, 1H), 7.32 (d, J=8.9, 1H), 7.08 (dd, J=2.4, 8.9, 1H), 7.07 (s, 1H), 6.96 (s, 1H), 3.92–3.97 (m, 1H), 3.44–3.54 (m, 2H), 3.40 (s, 3H), 3.30 (dd, J=7.9, 9.5, 1H), 3.16–3.21 (m, 1H), 2.01–2.13 (m, 4H).

EXAMPLE 179

(±)-6-(2-Chloromethyl-1-piperidino)-4-trifluoromethyl-2(1H)-quinolinone (Compound 424, Structure 34 of Scheme VI, Where R=Chloromethyl, n=2)

This compound was prepared from Compound 331 (Structure 33 of Scheme VI, where n=2) by tosylation and chloride displacement. Compound 424 was isolated as yellow solid. ¹H NMR (CDCl₃, 500 MHz) 11.60–11.70 (bs, 1H), 7.35 (bs, 2H), 7.25 (s, 1H), 7.08 (s, 1H), 3.96–4.00 (m, 1H), 3.62 (t, J=10.7, 1H), 3.44–3.47 (m, 1H), 3.29–3.33 (m, 1H), 3.01–3.06 (m, 1H), 2.08–2.18 (m, 1H), 1.82–1.91(m, 2H), 1.61–1.74 (m, 3H).

EXAMPLE 180

(±)-6-(2-Cyanothiomethyl-1-piperidino)-4-trifluoromethyl-2(1H)-quinolinone (Compound 425, Structure 34 of Scheme VI, Where R=CH₂SCN, n=2)

This compound was prepared from Compound 331 (Structure 33 of Scheme VI, where n=2) by tosylation and thiocyanate displacement. Compound 425 was isolated as yellow solid. ¹H NMR (CDCl₃, 500 MHz) 12.00–12,20 (bs, 1H), 7.39–7.42 (m, 2H), 7.29 (s, 1H), 7.10 (s, 1H), 4.02 (sextet, J=4.4, 1H), 3.25–3.27 (m, 1H), 3.16 (dd, J=4.9, 12.7, 1H), 3.05–3.10 (m, 2H), 1.96–2.05 (m, 2H), 1.68–1.80 (m, 4H).

EXAMPLE 181

(±)-6-(2-Thiomethoxymethyl-1-piperidino)-4-trifluoromethyl-2(1H)-quinolinone (Compound 426, Structure 34 of Scheme VI, Where R=—CH₂SMe, n=2)

This compound was prepared from Compound 331 (Structure 33 of Scheme VI, where n=2) by tosylation and methanethiol displacement. Compound 426 was isolated as yellow oil. ¹H NMR (CDCl₃, 500 MHz) 11.80–12.00 (bs, 1H), 7.32–7.36 (m, 2H), 7.23 (s, 1H), 7.08 (s, 1H), 3.92–3.95 (m, 1H), 3.28–3.31(m, 1H), 3.00–3.05 (m, 1H), 2.72 (dd, J=9.8, 13.2, 1H), 2.45 (dd, J=3.4, 13.2, 1H), 2.04–2.08 (m, 1H), 2.03 (s, 3H), 1.81–1.90 (m, 2H), 1.60–1.70 (m, 3H).

EXAMPLE 182

(±)-6-(2-Cyanomethyl-1-piperidino)-4-trifluoromethyl-2(1H)-quinolinone (Compound 427, Structure 34 of Scheme VI, Where R=Cyanomethyl, n=2)

This compound was prepared from Compound 331 (Structure 33 of Scheme VI, where n=2) by tosylation and cyanide displacement. Compound 427 was isolated as red solid. ¹H NMR (CDCl₃, 500 MHz) 12.20–12.40 (bs, 1H), 7.51–7.54 (m, 4H), 4.11–4.15 (m, 1H), 3.25–3.29 (m, 1H), 3.00–3.04 (m, 1H), 2.59 (dd, J=8.8, 17.1, 1H), 2.40 (dd, J=4.9, 17.1, 1H), 1.84–2.03 (m, 2H), 1.60–1.80 (m, 4H).

EXAMPLE 183

(±)-6-(2-Bromomethyl-1-piperidino)-4-trifluoromethyl-2(1H)-quinolinone (Compound 428, Structure 34 of Scheme VI, Where R=Bromomethyl, n=2)

This compound was prepared from Compound 331 (Structure 33 of Scheme VI, where n=2) by tosylation and bromide displacement. Compound 428 was isolated as red solid. ¹H NMR (CDCl₃, 500 MHz) 11.40–11.60 (bs, 1H), 7.34–7.35 (m, 2H), 7.25 (s, 1H), 7.08 (s, 1H), 4.00–4.03 (m, 1H), 3.50 (t, J=9.8, 1H), 3.27–3.34 (m, 2H), 3.02–3.06 (m, 1H), 2.15–2.18 (m, 1H), 1.83–1.92 (m, 2H), 1.61–1.73 (m, 3H).

EXAMPLE 184

(±)-6-(2-Iodomethyl-1-piperidino)-4-trifluoromethyl-2(1H)-quinolinone (Compound 429, Structure 34 of Scheme VI, Where R=Iodomethyl, n=2)

This compound was prepared from Compound 331 (Structure 33 of Scheme VI, where n=2) by tosylation and iodide displacement. Compound 429 was isolated as red solid. ¹H NMR (CDCl₃, 500 MHz) 11.80–12.00 (bs, 1H), 7.38 (m, 2H), 7.29–7.26 (m, 1H), 7.08 (s, 1H), 3.80–4.00 (m, 1H), 3.22–3.37 (m, 2H), 3.12–3.20 (m, 1H), 3.01–3.10 (m, 1H), 1.65–1.66 (m, 2H). 1.24–1.30 (m, 4H).

EXAMPLE 185

(+)R-6-(2-Iodomethyl-1-pyrrolidino)-4-trifluoromethyl-2(1H)-quinolinone (Compound 430, Structure 34 of Scheme VI, Where R=Iodomethyl, n=1)

This compound was prepared in a similar fashion as that described in Examples 101 and 184 from Compound 309 (Structure 17 of Scheme III) and D-proline and isolated as yellow solid. ¹H NMR (CDCl₃, 500 MHz) 12.5 (bs, 1H), 7.41 (d, J=8.9, 1H), 7.09 (s, 1H), 6.96 (dd, J=8.9, 2.4, 1H), 6.83 (s, 1H), 4.09–4.07 (m, 1H), 3.60–3.56 (m, 1H), 3.33–330 (m, 1H), 3.27–3.24 (m, 1H), 3.01(t, J=10.4, 1H), 2.19–2.05 (m, 4H).

EXAMPLE 186

(±)-6-(2-Fluoromethyl-1-piperidino)-4-trifluoromethyl-2(1H)-quinolinone (Compound 431, Structure 34 of Scheme VI, Where R=Fluoromethyl, n=2)

This compound was prepared from Compound 331 (Structure 33 of Scheme VI, where n=2) by tosylation and fluoride displacement. Compound 431 was isolated as red solid. ¹H NMR (CDCl₃, 500 MHz) 11.73 (bs, 1H), 7.32 (d, J=6.9, 1H), 7.21–7.19 (m, 1H), 7.06–7.04 (m, 2H), 4.95–4.82 (m, 1H), 3.83–3.75 (m, 2H), 3.61–3.40 (m, 2H), 2.01–1.70 (m, 6H).

EXAMPLE 187

(±)S-6-(2-Chloromethyl-1-piperidino)-4-trifluoromethyl-2(1H)-quinolinone (Compound 432, Structure 34 of Scheme VI, Where R=Chloromethyl, n=2) and (−)R-6-(2-Chloromethyl-1-piperidino)-4-trifluoromethyl-2(1H)-quinolinone (Compound 433, Structure 34 of Scheme VI, Where R=Chloromethyl, n=2)

These compounds were prepared from separation of Compound 424 by chiral HPLC and the absolute sterochemistry were established by independent synthesis from optically active commercial material. Compound 432: $[\alpha]_D$=+63; Compound 433: $[\alpha]_D$=−63.

EXAMPLE 188

(±)R-6-(2-Chloromethyl-1-pyrrolidino)-4-trifluoromethyl-2(1H)-quinolinone (Compound 434, Structure 34 of Scheme VI, Where R=Chloromethyl n=1) and (−)S-6-(2-Chloromethyl-1-pyrrolidino)-4-trifluoromethyl-2(1H)-quinolinone (Compound 435, Structure 34 of Scheme VI, Where R=Chloromethyl, n=1)

Compound 434 was prepared in a similar synthetic sequence as that described in Examples 101 and 179 from Compound 309 (Structure 17 of Scheme III) and D-proline. Compound 434was isolated as yellow solid. ¹H NMR (CDCl₃, 500 MHz) 11.90–12.10 (s, 1H), 7.37 (d, J=8.8, 1H), 7.08 (s, 1H), 7.07 (s, 1H), 6.88 (s, 1H), 4.01–4.04 (m, 1H), 3.63 (dd, J=2.4, 10.7, 1H), 3.54–3.57 (m, 1H), 3.31 (dd, J=9.8, 11.2, 1H), 3.22–3.27 (m, 1H), 2.10–2.23 (m, 4H).

Compound 435 was prepared in the same fashion from Compound 309 and L-proline.

EXAMPLE 189

R-6-(2-Difluoromethyl-1-pyrrolidino)-4-trifluoromethyl-2(1H)-quinolinone (Compound 436, Structure 34 of Scheme VI, Where R= Difluoromethyl, n=1)

Compound 436 was prepared in a similar synthetic sequence as that described in Examples 101 and 179 from Compound 309 (Structure 17 of Scheme III) and D-proline and isolated as yellow solid. $^1$H NMR (CDCl$_3$, 500 MHz) 11.80–12.00 (bs, 1H), 7.35(d, J=9.2, 1H), 7.13 (dd, J=2.4, 9.2, 1H), 7.08 (s, 1H), 7.02 (s, 1H), 5.81 (dt, J=3.6, 56.1, 1H), 4.03–4.09 (m, 1H), 3.66 (t, J=7.9, 1H), 3.26 (q, J=8.5, 1H), 2.04–2,28 (m, 4H).

EXAMPLE 190

(±)-6-(2l-(1l-Hydroxy-2,2,2-trifluoroethyl)-1-piperidino)-4-trifluoromethyl-2(1H)-quinolinone (Compound 437, Structure 36 of Scheme VI, Where R=Trifluoromethyl, n=2) and (±)-6-(2l-(1u-Hydroxy-2,2,2-trifluoroethyl)-1-piperidino)-4-trifluoromethyl-2(1H)-quinolinone (Compound 438, Structure 36 of Scheme VI, Where R= Trifluoromethyl, n=2)

(±)-6-(2-Formyl-1-piperidino)-4-trifluoromethyl-2(1H)-quinolinone (Compound 439, Structure 35 of Scheme VI, where R=formyl, n=2)

Compound 439 was prepared from Compound 331 (Structure 33 of Scheme VI, where n=2) by oxidation.

(±)-6-(2l-(1l-Hydroxy-2,2,2-trifluoroethyl)-1-piperidino)-4-trifluoromethyl-2(1H)-quinolinone (Compound 437, Structure 36 of Scheme VI, where R=trifluoromethyl, n=2) and (±)-6-(2l-(1u-Hydroxy-2,2,2-trifluoroethyl)-1-piperidino)-4-trifluoromethyl-2(1H)-quinolinone (Compound 438, Structure 36 of Scheme VI, where R=trifluoromethyl, n=2)

These compounds were prepared by the following General Procedure XVII from Compound 439:

To the aldehyde (2.2 mmol) in THF (22 mL) at –78° C. was added the nucleophile or the TMSCF$_3$ (2.9 mmol, equiv). The reaction mixture was warmed to rt and stirred for 5–24 h. Work up involved quenching with H$_2$O and extraction with EA. The organic layers were dried over MgSO$_4$, filtered, and concentrated in vacuo. by flash chromatography (EtOAc:hexane mixtures) afforded the desired products as diastereomers.

Compound 437 was isolated as yellow solid. $^1$H NMR (CDCl$_3$, 500 MHz) 10.65 (bs, 1H), 7.37–7.28 (m, 3H), 7.08 (s, 1H), 4.35–4.32 (m, 1H), 4.11–3.94 (m, 1H), 3.65 (d, J=15.6, 1H), 3.47 (s, 1H), 3.21–3.16 (m, 1H), 1.85–1.67 (m, 6H).

Compound 438 was isolated as yellow solid. $^1$H NMR (CDCl$_3$, 500 MHz) 11.50 (bs, 1H), 7.37–7.35 (m, 3H), 7.08 (s, 1H), 4.19–4.10 (m, 1H), 3.82–3.81(m, 1H), 3.25–3.22 (m, 2H), 2.48 (bs, 1H), 2.01–1.98 (m, 1H), 1.86–1.85 (m, 2H), 1.72–1.70 (m, 2H), 1.61–1.57 (m, 1H).

EXAMPLE 191

(±)-6-(2-Difluoromethyl-1-piperidino)-4-trifluoromethyl-2(1H)-quinolinone (Compound 440, Structure 34 of Scheme VI, Where R= Difluoromethyl, n=2)

Compound 440 was prepared in a similar fashion as that described in Example 179 from Compound 439 (Structure 35 of Scheme VI, where n=2) and isolated as yellow solid. $^1$H NMR (CDCl$_3$, 500 MHz) 11.60–11.80 (bs, 1H), 7.31–7.33 (m, 2H), 7.25 (s, 1H), 7.08(s, 1H), 5.90 (dt, J=4.3, 55.8, 1H), 3.97–4.02 (m, 1H), 3.42 (d, J=11.9, 1H), 3.24 (t, J=10.7, 1H), 2.04–2.06 (m, 1H). 1.85–1.89 (m, 2H), 1.69–1.72 (m, 3H).

EXAMPLE 192

(±)-6-(2-Aminomethyl-1-piperidino)-4-trifluoromethyl-2(1H)-quinolinone (Compound 441Structure 34 of Scheme VI, Where R= Aminomethyl, n=2)

Compound 441 was prepared in a similar fashion as that described in Example 179 from Compound 439 (Structure 35 of Scheme VI, where n=2) and isolated as yellow solid. $^1$H NMR (500 MHz, CDCl$_3$) 7.37 (dd, J=9.0, 2.5, 1H), 7.35 (d, J=9.0, 1H), 7.24 (m, 1H), 7.07 (s, 1H), 3.70 (m, 1H), 3.32 (m, 1H), 3.12 (m, 1H), 2.92 (dd, J=12.8, 5.9, 1H), 2.79 (dd, J=12.8, 6.5, 1H), 1.85–1.65 (m, 6H).

EXAMPLE 193

(R)-6-(2-Vinyl-1-pyrrolidino)-4-trifluoromethyl-2(1H)-quinolinone (Compound 442, Structure 34 of Scheme VI, Where R=Vinyl, n=1)

Compound 442 was prepared in a similar fashion as that described in Example 179 from (R)-6-(2-Formyl-1-pyrrolidino)-4-trifluoromethyl-2(1H)-quinolinone (Compound 443, Structure 35 of Scheme VI, where n=1) and isolated as yellow oil. $^1$H NMR (500 MHz, CDCl$_3$) 11.17 (s, 1H) 7.24 (d, J=8.9, 1H), 7.04 (s, 1H), 6.98 (dd, J=8.9, 2.4, 1H), 6.90 (m, 1H), 5.81(ddd, J=16.2, 10.4, 5.8, 1H), 5.15 (dd, J=10.4, 1.5, 1H), 5.14 (dd, J=16.2, 1.5, 1H), 4.20 (m, 1H), 3.55 (td, J=8.2, 2.9, 1H), 3.33 (q, J=7.5, 1H), 2,21(m, 1H), 2.06 (m, 2H), 1.91(m, 1H).

EXAMPLE 194

(±)-6-(2-Vinyl-1-piperidino)-4-trifluoromethyl-2(1H)-quinolinone (Compound 444, Structure 34 of Scheme VI, Where R=Vinyl, n=2)

Compound 444 was prepared in a similar fashion as that described in Example 179 from Compound 439 (Structure 35 of Scheme VI, where n=2) and isolated as yellow oil. $^1$H NMR (500 MHz, CDCl$_3$) 11.20 (s, 1H), 7.31(dd, J=9.1, 2.5, 1H), 7.26 (d, J=9.1, 1H), 7.25 (m, 1H), 7.04 (s, 1H), 5.78 (ddd, J=17.3, 10.7, 6.6, 1H), 5.08 (dd, J=10.7, 1.2, 1H), 5.05 (dd, J=17.3, 1.2, 1H), 4.15 (m, 1H), 3.24–3.17 (m, 2H), 2.05–1.63 (m, 6H).

EXAMPLE 195

(±)-6-(2-Benzyloxyethyl-1-piperidino)-4-trifluoromethyl-2(1H)-quinolinone (Compound 445, Structure 34 of Scheme VI, Where R= Benzyloxyethyl, n=2)

Compound 445 was prepared by benzylation of Compound 343 (Structure 34 of Scheme VI, where R=2-hydroxyethyl, n=2) and isolated as yellow oil. $^1$H NMR (500 MHz, CDCl$_3$) 11.40 (s, 1H), 7.36–7.22 (m, 7H), 7.18 (m, 1H), 7.06 (s, 1H), 4.40 (d, J=11.9, 1H), 4.38 (d, J=11.9, 1H), 4.05 (m, 1H), 3.43 (dd, J=9.2, 6.2, 1H), 3.40 (dd, J=9.2, 6.4, 1H), 3.33 (dd, J=11.9, 2.4, 1H), 3.05 (m, 1H), 1.92–1.63 (m, 8H).

EXAMPLE 196

(±)-6-(2-(2,2-Difluoroethyl)-1-piperidino)-4-trifluoromethyl-2(1H)-quinolinone (Compound 446, Structure 34 of Scheme VI, Where R=2,2-Difluoroethyl, n-=2)

Compound 446 was prepared from Compound ? (Structure ? of Scheme Va, where R=, n=2) and isolated as yellow solid. $^1$H NMR (500 MHz, CDCl$_3$) 10.95 (bs, 1H), 7.32 (dd, J=9.0, 2.5, 1H), 7.28 (d, J=9.0, 1H), 7.22 (m, 1H), 7.07 (s, 1H), 5.78 (tt, J=56.4, 4.6, 1H), 4.08 (m, 1H), 3.34 (m, 1H), 3.03 (m, 1H), 2.12–1.65 (m, 8H).

EXAMPLE 197

(±)-6-(2-Trifluoroacetamidomethyl-1-piperidino)-4-trifluoromethyl-2(1H)-quinolinone (Compound 447, Structure 34 of Scheme VI, Where R= Trifluoroacetamidomethyl, n=2)

Compound 447 was prepared by acetylation of Compound 441(Structure 34 of Scheme VI, where R=aminomethyl, n=2) and isolated as yellow solid. R$_f$=0.32 (1:1CH$_2$Cl$_2$:MeOH).

EXAMPLE 198

(±)-6-(2-(2-Ethoxyethyl)-1-piperidino)-4-trifluoromethyl-2(1H)-quinolinone (Compound 448, Structure 34 of Scheme VI, Where R=2-Ethoxyethyl, n=2)

Compound 448 was prepared by ethylation of Compound 343 (Structure 34 of Scheme VI, where R=2-hydroxyethyl, n=2) and isolated as yellow solid. $^1$H NMR (500 MHz, CDCl$_3$) 11.86 (bs, 1H), 7.36 (dd, J=9.3, 2.5 1H, 7.31 (d, J=9.3, 1H), 7.17 (bs, 1H), 7.07 (s, 1H), 4.02 (m, 1H), 3.40–3.31 (m, 5H), 3.06 (m, 1H), 1.90–1.62 (m, 8H), 1.15 (t, J=7.0, 3H).

EXAMPLE 199

(±)-6-(2-(4-Trifluoromethyl)benzyloxyethyl-1-piperidino)-4-trifluoromethyl-2(1H)-quinolinone (Compound 449, Structure 34 of Scheme VI, Where R=4-Trifluoromethylbenzyloxyethyl, n=2)

Compound 449 was prepared by benzylation of Compound 343 (Structure 34 of Scheme VI, where R=2-hydroxyethyl, n=2) and isolated as yellow solid. $^1$H NMR (CDCl$_3$, 500 MHz) 11.00–11.20 (bs, 1H), 7.58 (d, J=8.2, 2H), 7.38 (d, J=7.9, 2H), 7.31–7.33 (m, 1H), 7.22 (d, J=8.2, 1H), 7.18 (bs, 1H), 7.05 (s, 1H), 4.43 (s, 2H), 4.05–4.09 (m, 1H), 3.44 (q, J=6.7, 2H), 3.33 (d, J=11.9, 1H), 3.05–3.08 (m, 1H), 1.63–1.96 (m, 8H).

EXAMPLE 200

(+)-6-(2R-(1R-Hydroxy-2,2,2-trifluoroethyl)-1-pyrrolidino)4-trifluoromethyl-2(1H)-quinolinone (Compound 450, Structure 36 of Scheme VI, Where R=trifluoromethyl, n=1) and (−)6-(2R-(1S-Hydroxy-2,2,2-trifluoroethyl)-1-pyrrolidino)4-trifluoromethyl-2(1H)-quinolinone (Compound 451, Structure 36 of Scheme VI, Where R= Trifluoromethyl, n=1)

Compounds 450 and 451 were prepared in a similar synthetic sequence as that described in Example 190 from Compound 309 (Structure 17 of Scheme III) and D-proline. Compound 450 was isolated as yellow solid. $^1$H NMR (CDCl$_3$, 500 MHz) 10.10 (bs, 1H), 7.16–7.07 (m, 2H), 7.03 (s, 1H), 6.99 (s, 1H), 4.14 (d, J=6.8, 1H), 3.79 (d, J=6.8, 1H), 3.66–3.61 (m, 1H), 3.21–3.18 (m, 2H), 2.19–2.04 (m, 4H). Compound 451 was also isolated as yellow solid. $^1$H NMR (CDCl$_3$, 500 MHz) 11.05 (bs, 1H), 7.28 (d, J=8.9, 1H), 7.04–7.01 (m, 2H), 6.89 (s, 1H), 4.40–4.39 (m, 1H), 4.14 (d, J=7.3, 1H), 3.65 (dt, J=8.2, 3.7, 1H), 3.25 (q, J=7.9, 1H), 2.56 (s, 1H), 2.47–2.44 (m, 1H), 2,28–2,23 (m, 1H), 2.15–2.01 (m, 2H).

EXAMPLE 201

6-(2S-(1R-Hydroxy-2,2,2-trifluoroethyl)-1-pyrrolidino)-4-trifluoromethyl-2(1H)-quinolinone (Compound 452, Structure 36 of Scheme VI, Where R=Trifluoromethyl, n=1) and 6-(2S-(1S-Hydroxy-2,2,2-trifluoroethyl)-1-pyrrolidino)-4-trifluoromethyl-2(1H)-quinolinone (Compound 453, Structure 36 of Scheme VI, Where R= Trifluoromethyl, n=1)

Compounds 452 and 453 were prepared in a similar synthetic sequence as that described in Example 190 from Compound 309 (Structure 17 of Scheme III) and L-proline. Compounds 452 and 453 were isolated as yellow solid.

EXAMPLE 202

(±)-6-(2l-(11-Hydroxyethyl)-1-piperidino)-4-trifluoromethyl-2(1H)-quinolinone (Compound 454, Structure 36 of Scheme VI, Where R=Methyl, n=2) and (±)-6-(2l-(1u-Hydroxyethyl)-1-piperidino)-4-trifluoromethyl-2(1H)-quinolinone (Compound 455, Structure 36 of Scheme VI, Where R=Methyl, n=2)

These compounds were prepared in a similar fashion as that described in Example 190, General Procedure XVII from Compound 439 and methyl anion.

Compound 454 was isolated as yellow oil. $^1$H NMR (CDCl$_3$, 500 MHz) 10.00–10.20 (bs, 1H), 7.36 (dd, J=2.4, 8.8, 1H), 7.32 (s, 1H), 7.20 (d, J=9.3, 1H), 7.06 (s, 1H), 4.25–4.30 (m, 1H), 3.59 (d, J=14.0, 1H), 3.41–3.44 (m, 1H), 3.31–3.36 (m, 1H), 2.75 (bs, 1H), 1.60–1.75 (m, 6H), 1.29 (d, J=5.9, 3H).

Compound 455 was isolated as yellow oil. $^1$H NMR (CDCl$_3$, 500 MHz) 10.50–10.60 (bs, 1H), 7.38–7.40 (m, 1H), 7.30 (d, J=9.3, 1H), 7.07 (s, 1H), 3.95–3.98 (m, 1H), 3.23–3.25 (m, 1H), 3.11–3.25 (m, 2H), 1.84–1.94 (m, 3H), 1.67–1.78 (m, 4H), 1.10 (d, J=6.3, 3H).

EXAMPLE 203

(−)-6-(2S-(1S-Hydroxy-2,2,2-trifluoroethyl)-1-piperidino)-4-trifluoromethyl-2(1H)-quinolinone (Compound 456, Structure 36 of Scheme VI, Where R=trifluoromethyl, n=2) and (+)-6-(2R-(1R-Hydroxy-2,2,2-trifluoroethyl)-1-piperidino)-4-trifluoromethyl-2(1H)-quinolinone (Compound 457, Structure 36 of Scheme VI, Where R= trifluoromethyl, n=2)

Compounds 456 ($[\alpha]_D$=−28) and 457 ($[\alpha]_D$=+28) were prepared by chiral HPLC separation of Compound 438.

EXAMPLE 204

(−)-6-(2S-(1R-Hydroxy-2,2,2-trifluoroethyl)-1-piperidino)-4-trifluoromethyl-2(1H)-quinolinone (Compound 459, Structure 36 of Scheme VI, Where R=Trifluoromethyl, n=2) and (+)-6-(2R-(1S-Hydroxy-2,2,2-trifluoroethyl)-1-piperidino)-4-trifluoromethyl-2(1H)-quinolinone (Compound 458, Structure 36 of Scheme VI, Where R= Trifluoromethyl, n=2)

Compounds 458 ($[\alpha]_D$=+50) and 459 ($[\alpha]_D$=−51) were prepared by chiral HPLC separation of Compound 437.

EXAMPLE 205

(±)-6-2l-(1l-Acetyloxyethyl)-1-piperidino)-4-trifluoromethyl-2(1H)-quinolinone (Compound 460, Structure 37 of Scheme VI, Where $R^1$=Acetyl, R= Methyl, n=2)

This compound was prepared by acetylation of Compound 454 (Structure 36 of Scheme VI, where R=methyl, n=2) and isolated as yellow oil. $^1$H NMR (CDCl$_3$, 500 MHz) 10.80–11.00 (bs, 1H), 7.38–7.31 (m, 1H), 7.23 (d, J=9.3, 1H), 7.12 (s, 1H), 7.05 (s, 1H), 5.49–5.55 (m, 1H), 3.83–3.87 (m, 1H), 3.35 (d, J=13.2, 1H), 3.21–3.26 (m, 1H), 1.64–1.81 (m, 6H), 1.50 (s, 3H), 1.22 (d, J=6.3, 3H).

EXAMPLE 206

(±)-6-2l-(1u-Acetyloxyethyl)-1-piperidino)-4-trifluoromethyl-2(1H)-quinolinone (Compound 461, Structure 37 of Scheme VI, where $R^1$=Acetyl, R= Methyl, n=2)

This compound was prepared by acetylation of Compound 455 (Structure 36 of Scheme VI, where R=methyl, n=2) and isolated as yellow oil. $^1$H NMR (CDCl$_3$, 500 MHz) 11.80–12.00 (bs, 1H), 7.32 (d, J=9.3, 1H), 7.26–7.28 (m, 1H), 7.19 (s, 1H), 7.07 (s, 1H), 5.37–5.40 (m, 1H), 3.75–3.76 (m, 1H), 3.40–3.46 (m, 1H), 3.12–3.17 (m, 1H), 1.59–1.81 (m, 9H), 1.14 (d, J=6.3, 3H).

EXAMPLE 207

(±)-6-2l-(1u-Methoxy-2,2,2-trifluoroethyl)-1-piperidino)-4-trifluoromethyl-2(1H)-quinolinone (Compound 462, Structure 37 of Scheme VI, Where $R^1$=Methyl, R=Trifluoromethyl, n=2)

This compound was prepared by methylation of Compound 438 (Structure 36 of Scheme VI, where R=trifluoromethyl, n=2) and isolated as yellow solid. $^1$H NMR (CDCl$_3$, 500 MHz) 12.00–12.40 (bs, 1H), 7.37–7.39 (m, 2H), 7.27–7.29 (m, 1H), 7.13 (s, 1H), 3.99 (q, J=4.9, 1H), 3.76–3.80 (m, 1H), 3.53 (s, 3H), 3.44 (dt, J=4.0, 13.4, 1H), 3.24–3.29 (m, 1H), 2.01–2.08 (m, 1H), 1.61–1.86 (m, 5H).

EXAMPLE 208

(±)-6-2l-(1l-Methoxy-2,2,2-trifluoroethyl)-1-piperidino)-4-trifluoromethyl-2(1H)-quinolinone (Compound 463, Structure 37 of Scheme VI, Where $R^1$=Methyl, R=Trifluoromethyl, n=2)

This compound was prepared by methylation of Compound 437 (Structure 36 of Scheme VI, where R=trifluoromethyl, n=2) and isolated as yellow solid. $^1$H NMR (CDCl$_3$, 500 MHz) 12.00–12.40 (bs, 1H), 7.34–7.39 (m, 2H), 7.20 (s, 1H), 7.10–7.15 (bs, 1H), 4.14–4.17 (m, 1H), 3.89–3.94 (m, 1H), 3.57 (d, J=13.4, 1H), 3.35 (s, 3H), 3.19 (dt, J=3.0, 13.4, 1H), 1.61–1.89 (m, 6H).

EXAMPLE 209

7-Methoxy-6-(N-methyl-N-2,2,2-trifluoroethyl) amino-4-trifluoromethyl-2(1H)-quinolinone (Compound 464, Structure 41 of Scheme VII, Where R=Methyl)

2-Methoxy-N-2,2,2-trifluoroethyl-4-nitroaniline (Compound 465):

This compound was prepared in a similar fashion as that described in Example 2, General Procedure IV but using 2-amino-5-nitroanisole and trifluoroacetaldehyde hydrate in place of Compound 200 and propionaldehyde. Compound 465 was isolated as a light brown crystalline solid after recrystallization (1:1 EtOAc:hexanes, 30 mL): R$_f$ 0.52 (2:1 hexanes:EtOAc); $^1$H NMR (400 MHz, acetone-d$_6$) 7.87 (dd, J=8.9, 2.4, 1H), 7.69 (d, J=2.4, 1H), 6.96 (d, J=8.9, 1H), 6.38 (broad s, 1H), 4.20 (qd, J=9.3, 7.1, 2H), 4.00 (s, 3H).

4-Amino-2-methoxy-N-2,2,2-trifluoroethylaniline (Compound 466, Structure 39 of Scheme VII):

This compound was prepared by General Procedure III in Example 1 from Compound 465 (8.40 g, 33.6 mmol), zinc dust (9.66 g, 0.148 mmol), and calcium chloride dihydrate (10.9 g, 73.9 mmol) in 300 mL 95% EtOH/water. Compound 466 was isolated in 90% (6.7 g) yield as a deep purple oil: R$_f$ 0.25 (1:1 hexanes:EtOAc); $^1$H NMR (400 MHz, CDCl$_3$) 6.54 (d, J=8.1, 1H), 6.20–6.30 (m, 2H), 4.15 (broad s, 1H), 3.81 (s, 3H), 3.68 (qd, J=9.0, 7.4, 2H), 3.38 (broad s, 2H).

7-Methoxy-6-(N-2,2,2-trifluoroethyl)amino-4-trifluoromethyl-2(1H)-quinolinone (Compound 467, Structure 40 of Scheme VII):

This compound was prepared according to General Procedure I in Example 1 from Compound 466 (5.72 g, 26.0 mmol) and 4,4,4 trifluoroacetoacetate (4.56 mL, 5.74 g, 31.2 mmol) in 87 mL toluene, followed by treatment with 65 mL concentrated H$_2$SO$_4$. Compound 467 was isolated as a fluffy yellow solid: R$_f$ 0.19 (4:1 EtOAc:CH$_2$Cl$_2$); $^1$H NMR (400 MHz, acetone-d$_6$) 10.87 (broad s, 1H), 7.04 (s, 1H), 6.99 (broad s, 1H), 6.73 (s, 1H), 5.54 (broad m, 1H), 4.07 (app quint, J=8.4, 2H), 3.98 (s, 3H).

7-Methoxy-6-(N-methyl-N-2,2,2-trifluoroethyl)amino-4-trifluoromethyl-2(1H)-quinolinone (Compound 464, Structure 41 of Scheme VII, Where R=Methyl):

A solution of Compound 467 (24 mg, 0.070 mmol) and paraformaldehyde (21 mg, 0.70 mmol) in 1.4 mL acetic acid was stirred for 15 min, whereupon NaBH$_3$CN (22 mg, 0.35 mmol) was added. After 18 h, the mixture was partitioned between EtOAc (40 mL) and sat'd NaHCO$_3$ (40 mL). The organic layer was washed with brine (20 mL), dried over MgSO$_4$, filtered and concentrated. Flash chromatography (4:1 EtOAc:CH$_2$Cl$_2$) afforded 20 mg (81%) of Compound 464 as a yellow solid: R$_f$ 0.38 (4:1 EtOAc:CH$_2$Cl$_2$); $^1$H NMR (400 MHz, CDCl$_3$) 12.9 (broad s, 1H), 7.37 (broad s, 1H), 6.96 (s, 1H), 6.89 (s, 1H), 4.04 (s, 3H), 3.83 (q, J=9.3, 2H), 3.06 (s, 3H).

EXAMPLE 210

7-Methoxy-6-(N-ethyl-N-2,2,2-trifluoroethyl)amino-4-trifluoromethyl-2(1H)-quinolinone (Compound 468, Structure 41 of Scheme VII, Where R=Ethyl)

A solution of Compound 467 (Structure 40 of Scheme VII) (10 mg, 0.030 mmol) and acetaldehyde (13 mg, 0.30 mmol) in 1 mL acetic acid was stirred for 20 min, whereupon NaBH$_3$CN (9.4 mg, 0.15 mmol) was added. After 18 h, the mixture was partitioned between EtOAc (30 mL) and sat'd NaHCO$_3$ (30 mL). The organic layer was washed with brine (20 mL), dried over MgSO$_4$, filtered and concentrated. Flash chromatography (3:2 EtOAc:CH$_2$Cl$_2$) afforded 4.5 mg (41%) of Compound 468 as a yellow solid: R$_f$ 0.40 (3:2 EtOAc:CH$_2$Cl$_2$); $^1$H NMR (400 MHz, CDCl$_3$) 12.7 (broad s, 1H), 7.45 (broad s, 1H), 6.95 (s, 1H), 6.88 (s, 1H), 4.02 (s, 3H), 3.76 (q, J=9.4, 2H), 3.33 (q, J=7.1, 2H), 1.08 (t, J=7.0, 3H).

EXAMPLE 211

7-Hydroxy-6-(2,2,2-trifluoroethyl)amino-4-trifluoromethyl-2(1H)-quinolinone (Compound 469, Structure 42 of Scheme VI, Where R=H)

A suspension of Compound 467 (Structure 40 of Scheme VII) (34 mg, 0.10 mmol), NaH (60% mineral oil suspension, 16 mg, 0.40 mmol) and thiophenol (48 mg, 0.44 mmol) in 1.5 mL DMF was heated at 80° C. for 7 h. The mixture was poured into cold sat'd NH$_4$Cl (30 mL), and the aqueous layer was extracted with EtOAc (2×30 mL). The combined organic layers were washed with brine (20 mL), dried over MgSO$_4$, filtered, and concentrated. Flash chromatography (9:1 CH$_2$Cl$_2$:MeOH) afforded 13 mg (39%) of Compound 469 as a yellow solid: R$_f$ 0.17 (9:1 CH$_2$Cl$_2$:MeOH); $^1$H NMR (400 MHz, acetone-d$_6$) 10.9 (broad s, 1H), 9.8 (v broad s, 1H), 7.00 (s, 2H), 6.68 (s, 1H), 5.38–5.48 (m, 1H), 4.02–4.12 (m, 2H).

EXAMPLE 212

6-(N-Cyclopropylmethyl-N-2,2,2-trifluoroethyl) amino-7-methoxy-4-trifluoromethyl-2(1H)-quinolinone (Compound 470, Structure 41 of Scheme VII, Where R=Cyclopropylmethyl)

This compound was prepared according to General Procedure IV in Example 2 from Compound 467 (Structure 40 of Scheme VII) (33 mg, 0.097 mmol), cyclopropanecarboxaldehyde (34 mg, 0.48 mmol) and NaBH$_3$CN (37 mg, 0.59 mmol) in 1 mL trifluoroacetic acid to afford 38 mg (96%) of Compound 470 as a yellow solid: $^1$H NMR (400 MHz, CDCl$_3$) 11.0 (broad s, 1H), 7.46 (broad s, 1H), 6.86 (s, 1H), 6.74 (s, 1H), 3.88 (s, 3H), 3.84 (q, J=9.3, 2H), 3.08 (d, J=6.6, 2H), 0.80–0.90 (m, 1H), 0.40–0.50 (m, 2H), 0.07–0.13 (m, 2H).

EXAMPLE 213

6-(N-Cyclopropylmethyl-N-2,2,2-trifluoroethyl) amino-7-hydroxy-4-trifluoromethyl-2(1H)-quinolinone (Compound 471, Structure 42 of Scheme VII, Where R=Cyclopropylmethyl)

A suspension of Compound 470 (35 mg, 0.089 mmol), NaH (60% mineral oil suspension, 28 mg, 0.71 mmol) and thiophenol (83 mg, 0.76 mmol) in 1.3 mL DMF was heated at 105° C. for 4 h. The mixture was poured into cold water (20 mL) and neutralized with 2N NaHSO$_4$. The aqueous layer was extracted with EtOAc (2×20 mL), and the combined organic layers were washed with water (20 mL), brine (10 mL), dried over MgSO$_4$, filtered, and concentrated. Flash chromatography (7:3 EtOAc:CH$_2$Cl$_2$) afforded 14 mg (42%) of Compound 471 as a yellow solid: $^1$H NMR (400 MHz, CDCl$_3$) 12.3 (broad s, 1H), 7.60 (broad s, 2H), 7.03 (s, 1H), 6.93 (s, 1H), 3.64 (q, J=8.9, 2H), 2.94 (d, J=6.9, 2H), 0.75–0.85 (m, 1H), 0.42–0.52 (m, 2H), 0.05 (m, 2H).

EXAMPLE 214

6-(N-Isobutyl-N-2,2,2-trifluoroethyl)amino-7-methoxy-4-trifluoromethyl-2(1H)-quinolinone (Compound 472, Structure 41 of Scheme VII, Where R=Isobutyl)

This compound was prepared according to General Procedure IV in Example 2 from Compound 467 (Structure 40 of Scheme VII) (34 mg, 0.10 mmol), isobutyraldehyde (36 mg, 0.50 mmol) and NaBH$_3$CN (38 mg, 0.60 mmol) in 1 mL trifluoroacetic acid to afford 24 mg (61%) of Compound 472 as a yellow solid: $^1$H NMR (400 MHz, CDCl$_3$) 12.0 (broad s, 1H), 7.47 (broad s, 1H), 6.93 (s, 1H), 6.82 (s, 1H), 4.00 (s, 3H), 3.73 (q, J=9.3, 2H), 3.04 (d, J=7.2, 2H), 1.60–1.70 (m, 1H), 0.88 (t, J=6.6, 6H).

EXAMPLE 215

6-(N-Isobutyl-N-2,2,2-trifluoroethyl)amino-7-hydroxy-4-trifluoromethyl-2(1H)-quinolinone (Compound 473, Structure 42 of Scheme VII, Where R=Isobutyl)

A suspension of Compound 472 (Structure 41 of Scheme VII, where R=isobutyl) (19 mg, 0.048 mmol), NaH (60% mineral oil suspension, 15 mg, 0.38 mmol) and thiophenol (45 mg, 0.41 mmol) in 1.5 mL DMF was heated at 105° C. for 4 h. The mixture was poured into cold water (20 mL) and neutralized with 2N NaHSO$_4$. The aqueous layer was extracted with EtOAc (2×20 mL), and the combined organic layers were washed with water (20 mL), brine (10 mL), dried over MgSO$_4$, filtered, and concentrated. Flash chromatography (7:3 EtOAc:CH$_2$Cl$_2$) afforded 8.5 mg (46%) of Compound 473 as a yellow solid: $^1$H NMR (400 MHz, CDCl$_3$) 12.1 (broad s, 1H), 7.60 (s, 1H), 7.43 (broad s, 1H), 7.02 (s, 1H), 6.92 (s, 1H), 3.53 (q, J=8.9, 2H), 2.93 (d, J=7.0, 2H), 1.55–1.65 (m, 1H), 0.93 (d, J=6.6, 6H).

EXAMPLE 216

6-(bis-N,N-2,2,2-Trifluoroethyl)amino-4-trifluoromethylcoumarin (Compound 474, Structure 45 of Scheme VIII, Where R$^5$=R$^6$=2,2,2-Trifluoroethyl)

6-Amino-4-trifluoromethylcoumarin (Compound 475, Structure 44 of Scheme VIII):

This compound was prepared in a similar fashion as that described in Example 1, General Procedures I, II and III but using phenol in place of aniline. Compound 475 was isolated as a yellow solid: $^1$H NMR (500 MHz, CDCl$_3$) 7.21 (d, J=8.8, 1H), 7.10 (dd, J=8.8, 2.4, 1H), 7.00 (s, 1H), 6.81 (s, 1H), 5.09 (bs, 2H).

6-(bis-2,2,2-Trifluoroethyl)amino-4-trifluoromethylcoumarin (Compound 474, Structure of Scheme VIII, Where R$^5$=R$^6$=2,2,2-Trifluoroethyl):

This compound was prepared in a similar fashion as that described in Example 9, General Procedure VI but using Compound 475 and TFA in place of Compound 200 and difluoroacetic acid. Compound 474 was isolated as a yellow solid: $^1$H NMR (500 MHz, CDCl$_3$) 7.37 (d, J=9.3, 1H), 7.23 (dd, J=9.3, 2.9, 1H), 7.20 (s, 1H), 6.83 (s, 1H), 4.07 (q, J$_{H-F}$=8.3, 4H).

EXAMPLE 217

(±)-3,4-Dihydro-6-(bis-2,2,2-trifluoroethyl)amino-4-trifluoromethylcoumarin (Compound 476, Structure 46 of Scheme VIII, Where R$^5$=R$^6$=2,2,2-Trifluoroethyl)

This compound was prepared in a similar fashion as that described in Example 1, General Procedure III by hydrogenation of Compound 474 (Structure 45 of Scheme VIII, where R$^5$=R$^6$=2,2,2-trifluoroethyl). Compound 476 was isolated as a yellow solid: $^1$H NMR (500 MHz, CDCl$_3$) 7.07 (d, J=8.8, 1H), 6.98 (dd, J=8.8, 2.9, 1H), 6.82 (d, J=2.9, 1H), 4.07–3.97 (m, 4H), 3.67–3.64 (m, 1H), 3.15 (dd, J=17.1, 1.9, 1H), 2.95 (dd, J=17.1, 7.3, 1H).

EXAMPLE 218

6-(N-2,2,2-Trifluoroethyl)amino-4-trifluoromethylcoumarin (Compound 477, Structure 45 of Scheme VIII, Where R$^5$=H, R$^6$=2,2,2-Trifluoroethyl)

This compound was prepared in a similar fashion as that described in Example 2, General Procedure IV but using Compound 475 (Structure 44 of Scheme VIII) and trifluoroacetyraldehyde. Compound 477 was isolated as a yellow solid: $^1$H NMR (500 MHz, CDCl$_3$) 7.29 (d, J=8.8, 1H), 6.99 (dd, J=8.8, 2.9, 1H), 6.92 (s, 1H), 6.80 (s, 1H), 4.15 (t, J=6.3, 1H), 3.84–3.78 (m, 2H).

EXAMPLE 219

6-(N-Isopropyl-N-2,2,2-trifluoroethyl)amino-4-trifluoromethylcoumarin (Compound 478, Structure 45 of Scheme VIII, Where R$^5$=isopropyl, R$^6$=2,2,2-Trifluoroethyl)

This compound was prepared in a similar fashion as that described in Example 2, General Procedure IV from Compound 475 (Structure 44 of Scheme VIII) by using acetone and trifluoroacetyaldehyde sequentially. Compound 478 was isolated as a yellow solid: $^1$H NMR (500 MHz, CDCl$_3$) 7.33 (d, J=9.3, 1H), 7.24 (dd, J=9.3, 2.9, 1H), 7.18 (s, 1H), 6.79 (s, 1H); 4.01–3.96 (m, 1H), 3.80 (q, J$_{H-F}$=8.8, 2H), 1.24 (d, J=6.8, 6H).

EXAMPLE 220

6-N-Isobutylamino-4-trifluoromethylcoumarin (Compound 479, Structure 45 of Scheme VIII, Where R$^5$=Isobutyl, R$^6$=H)

This compound was prepared in a similar fashion as that described in Example 2, General Procedure IV from Compound 475 (Structure 44 of Scheme VIII) and isobutyraldehyde. Compound 479 was isolated as a yellow solid: $^1$H NMR (500 MHz, CDCl$_3$) 7.22 (d, J=8.8, 1H), 6.88 (dd, J=8.8, 2.4, 1H), 6.75 (s, 2H), 3.89 (bs, 1H), 2.95 (d, J=6.4, 2H), 1.94–1.88 (m, 1H), 1.02 (d, J=6.8, 6H).

EXAMPLE 221

6-N,N-Diethylamino-4-trifluoromethylcoumarin (Compound 480, Structure 45 of Scheme VIII, Where R$^5$=R$^6$=methyl)

This compound was prepared in a similar fashion as that described in Example 2, General Procedure IV from Compound 475 (Structure 44 of Scheme VIII) and acetaldehyde. Compound 480 was isolated as a yellow solid: $^1$H NMR (500 MHz, CDCl$_3$) 7.27 (d, J=9.3, 1H), 6.99 (dd, J=9.3, 2.9, 1H), 6.82 (s, 1H), 6.76 (s, 1H), 3.89 (q, J=7.3, 4H), 1.19 (t, J=7.3, 6H).

EXAMPLE 222

6-N,N-Dipropylamino-4-trifluoromethylcoumarin (Compound 481, Structure 45 of Scheme VIII, Where R$^5$=R$^6$=Propyl)

This compound was prepared in a similar fashion as that described in Example 2, General Procedure IV from Compound 475 (Structure 44 of Scheme VIII) and propionaldehyde. Compound 481 was isolated as a yellow solid: $^1$H NMR (500 MHz, CDCl$_3$) 7.25 (d, J=9.3, 1H), 6.94 (dd, J=9.3, 2.9, 1H), 6.77 (s, 1H), 6.75 (s, 1H), 3.27 (t, J=7.3, 4H), 1.65–1.57 (m, 4H), 0.95 (t, J=7.3, 6H).

EXAMPLE 223

6-N-Propylamino-4-trifluoromethylcoumarin (Compound 482, Structure 45 of Scheme VIII, Where R$^5$=H, R$^6$=Propyl)

This compound was prepared in a similar fashion as that described in Example 2, General Procedure IV from Compound 475 (Structure 44 of Scheme VIII) and propionaldehyde. Compound 482 was isolated as a yellow solid: $^1$H NMR (500 MHz, CDCl$_3$) 7.23 (d, J=8.8, 1H), 1.5 6.89 (dd, J=8.8, 2.4, 1H), 6.77 (s, 1H), 6.76 (s, 1H), 3.82 (bs, 1H), 3.10 (t, J=7.3, 2H), 1.71–1.64 (m, 2H), 1.03 (t, J=7.3, 3H).

EXAMPLE 224

6-(N-Isobutyl-N-propylamino)-4-trifluoromethylcoumarin (Compound 483, Structure 45 of Scheme VIII, Where R$^5$=Isobutyl, R$^6$=Propyl)

This compound was prepared in a similar fashion as that described in Example 2, General Procedure IV from Compound 475 (Structure 44 of Scheme VIII) by using propionaldehyde and isobutyraldehyde. Compound 483 was isolated as a yellow solid: $^1$H NMR (500 MHz, CDCl$_3$) 7.25 (d, J=9.3, 1H), 6.95 (dd, J=9.3, 2.9, 1H), 6.78 (s, 1H), 6.75 (s, 1H), 3.30 (t, J=7.8, 2 H), 3.11 (d, J=7.3, 2H), 2.05–1.99 (m, 1H), 1.63–1.57 (m, 2H), 0.95–0.93 (m, 9H).

EXAMPLE 225

6-(N-2,2,2-Trifluoroethyl-N-propylamino)-4-trifluoromethylcoumarin (Compound 484, Structure 45 of Scheme VIII, Where R$^5$=2,2,2-Trifluoroethyl, R$^6$=Propyl)

This compound was prepared in a similar fashion as that described in Example 2, General Procedure IV from Compound 475 (Structure 44 of Scheme VIII) by using propionaldehyde and trifluoroacetaldehyde. Compound 484 was isolated as a yellow solid: $^1$H NMR (500 MHz, CDCl$_3$) 7.31 (d, J=9.3, 1H), 7.08 (dd, J=9.3, 2.9, 1H), 6.98 (s, 1H), 6.79 (s, 1H), 3.89 (q, J$_{H-F}$=8.8, 2H), 3.47 (t, J=7.8, 2H), 1.68–1.63 (m, 2H), 0.96 (t, J=7.3, 3H).

EXAMPLE 226

1,4-Dihydro-4,4-dimethyl-6-methylamino-1,3-benzo[d]oxazin-2-one (Compound 485, Structure 52 of Scheme IX, Where R$^1$=R$^2$=R$^4$=Methyl, R$^5$=H, W=Oxygen)

1,4-Dihydro-4,4-dimethyl-1,3-benzo[d]oxazin-2-one (Compound 486, Structure 49 of Scheme IX, Where R$^1$=R$^2$=Methyl, W=Oxygen):

To a solution of 2-isopropenyl aniline (Structure 47 of Scheme IX, where R$^1$=methyl) (1 mL, 7.3 mmol) and dry methylene chloride (20 mL) was slowly added methylchloroformate (0.62 mL, 8.1 mmol). To this solution was added DMAP (0.9 g, 8.1 mmol) in methylene chloride (5 mL). Stirred at room temperature for 15 hrs. Partitioned reaction mixture between EtOAc (20 mL) and H$_2$O (5 mL). Washed organic layer with brine (3×10 mL), dried (Na$_2$SO$_4$) and concentrated in vacuo to afford crude as a colorless oil. Purified by silica flash chromatography (10% Hex/EtOAc) to afford 1.3 g of 2-isopropenyl-N-methylcarbamate aniline in 94% yield as a colorless oil. This product was dissolved in dichloroethane (20 mL) and treated with p-TsOH (1.4 g) then heated to reflux. After 2 hrs. the reaction mixture was quenched with saturated NaHCO$_3$ and extracted with EtOAc (20 mL). The organic layer was washed with brine (3×10 mL), dried (Na$_2$SO$_4$), and concentrated in vacuo. Purified by silica flash chromatography (50% Hex/EtOAc) to afford 1.1 g of Compound 486 in 92% yield as a white solid: $^1$H NMR (400 MHz, CDCl$_3$) 8.70 (br s, 1H), 7.22 (t, J=7.9, 1H), 7.13. (d, J=7.9, 1H), 7.05 (t, J=7.9, 1H), 6.86 (d, J=7.9, 1H), 1.71 (s, 6H).

6-Amino-1,4-dihydro-4,4-dimethyl-1,3-benzo[d]oxazin-2-one (Compound 487, Structure 51 of Scheme IX, Where R$^1$=R$^2$=Methyl, W=Oxygen):

To a solution of Compound 486 (50 mg, 0.28 mmol) and conc. H$_2$SO$_4$ (2 mL), chilled to 0° C., was added fuming HNO$_3$ (0.03 mL). After 15 min. poured reaction mixture onto ice and extracted with EtOAc (5 mL), washed with H$_2$O (5×1 mL) and brine (5×1 mL) then dried (Na$_2$SO$_4$) and concentrated in vacuo to afford the crude product as a yellow solid. Dissolved in 2:1 EtOAc/MeOH (5 mL) and hydrogenated over 10% Pd/C (10 mg) at rt and 1 atm. After 15 hrs. filtered through plug of silica gel to afford 50 mg of Compound 487 in 90% yield as a white solid: $^1$H NMR (400 MHz, acetone-d$_6$) 9.00 (br s, 1H), 6.93 (d, J=8.0, 1H), 6.60 (m, 2H), 1.64 (s, 6H).

1,4-Dihydro-4,4-dimethyl-6-methylamino-1,3-benzo[d]oxazin-2-one (Compound 485, Structure 52 of Scheme IX, Where $R^1=R^2=R^4$=Methyl, $R^5$=H, W=Oxygen):

This compound was prepared in a similar fashion as that described in Example 2, General Procedure IV but using Compound 487 and paraformaldehyde in place of Compound 200 and propionaldehyde. Compound 485 was isolated as a yellow solid: $^1$H NMR (400 MHz, CDCl$_3$) 7.82 (bs, 1H), 6.66 (d, J=8.5, 1H), 6.52 (d4, J=8.5, 2.1, 1H), 6.39 (d, J=2.1, 1H), 2.83 (s, 3H), 1.69 (s, 6H).

EXAMPLE 227

1,4-Dihydro-4,4-dimethyl-6-dimethylamino-1,3-benzo[d]oxazin-2-one (Compound 488, Structure 52 of Scheme IX, Where $R^1=R^2=R^4=R^5$=Methyl, W=Oxygen)

This compound was prepared in a similar fashion as that described in Example 15, General Procedure VIII from Compound 487 (Structure 51 of Scheme IX, where $R^1=R^2$=methyl, W=oxygen) (15 mg, 0.08 mmol) and paraformaldehyde (30 mg) to afford 5 mg (28%) of Compound 488 as a white solid: $^1$H NMR (400 MHz, CDCl$_3$) 7.66 (br s, 1H), 6.69 (d, J=8.6, 1H), 6.65 (dd, J=2.5, 8.6, 1H), 6.50 (d, J=2.5, 1H), 2.92 (s, 6H), 1.71 (s, 6H).

EXAMPLE 228

1,4-Dihydro-4,4-dimethyl-6-dipropylamino-1,3-benzo[d]oxazin-2-one (Compound 489, Structure 52 of Scheme IX, Where $R^1=R^2$=Methyl, $R^4=R^5$=Propyl, W=Oxygen)

This compound was prepared in a similar fashion as that described in Example 15, General Procedure VIII but using Compound 487 (Structure 51 of Scheme IX, where $R^1=R^2$=H, W=oxygen) and propionaldehyde in place of Compound 200 and paraformaldehyde. Compound 489 was isolated as a white solid: $^1$H NMR (400 MHz, CDCl$_3$) 7.52 (br s, 1H), 6.64 (d, J=8.5, 1H), 6.53 (dd, J=2.5, 8.5, 1H), 6.39 (d, J=2.5, 1H), 3.19 (t, J=7.5, 1H), 1.55 (m, 10H), 0.92 (t, J=7.5, 1H).

EXAMPLE 229

1,4-Dihydro-4,4-dimethyl-6-(bis-N,N-2,2,2-trifluoroethyl)amino-1,3-benzo[d]oxazin-2-one (Compound 490, Structure 52 of Scheme IX, Where $R^1=R^2$=Methyl, $R^4=R^5$=2,2,2-Trifluoroethyl, W=Oxygen)

This compound was prepared in a similar fashion as that described in Example 15, General Procedure VIII but using Compound 487 (Structure 51 of Scheme IX, where $R^1=R^2$=H, W=oxygen) and trifluoroacetaldehyde in place of Compound 200 and paraformaldehyde. Compound 490 was isolated as an orange oil: $^1$H NMR (400 MHz, CDCl$_3$) 8.05 (brs, 1H), 6.85 (dd, J=2.6, 8.7, 1H), 6.75 (d, J=8.7, 1H), 6.71 (d, J=2.6, 1H), 3.95 (q, J=8.6, 4H), 1.70 (s, 6H).

EXAMPLE 230

1,4-Dihydro-4,4-dimethyl-6-(N-2,2,2-trifluoroethyl)amino-1,3-benzo[d]oxazin-2-one (Compound 491, Structure 52 of Scheme IX, Where $R^1=R^2$=Methyl, $R^4$=2,2,2-Trifluoroethyl, $R^5$=H, W=Oxygen)

This compound was prepared in a similar fashion as that described in Example 2, General Procedure IV but using Compound 487 (Structure 51 of Scheme IX, where $R^1=R^2$=H, W=oxygen) and trifluoroacetaldehyde in place of Compound 200 and propionaldehyde. Compound 491 was isolated as a white solid; $^1$H NMR (400 MHz, CDCl$_3$) 8.16 (brs, 1H), 6.70 (d, J=8.5, 1H), 6.59 (dd, J=2.6, 8.5, 1H), 6.47 (d, J=2.6, 1H), 3.80 (brs, 1H), 3.73 (q, J=8.9, 2H), 1.69 (s, 6H).

EXAMPLE 231

(±)-1,4-Dihydro-4-methyl-6-diallylamino-1,3-benzo[d]oxazin-2-one (Compound 492, Structure 52 of Scheme IX, Where $R^1$=Methyl, $R^2$=H, $R^4=R^5$=Allyl, W=Oxygen)

(±)-1,4-Dihydro-4-methyl-1,3-benzo[d]oxazin-2-one (Compound 493, Structure 49 of Scheme IX, Where $R^1$=Methyl, R=H, W=Oxygen):

To a solution of 2-N-(tert-butoxycarbonyl)amino-(2-hydroxyethyl)benzene (0.58 g, 2.4 mmol) and dichloroethane (10 mL) was added TsOH (0.5 g, 2.6 mmol) and the reaction mixture was heated to reflux. After 20 minutes the reaction was quenched with saturated NaHCO$_3$ (10 mL) and extracted with EtOAc (20 mL). The organic layer was washed with brine (3×5 mL), dried (Na$_2$SO$_4$), and concentrated in vacuo. The crude product was purified by flash chromatography (50% EtOAc/hex) to afford 0.3 g (75%) of Compound 493 as a white solid: $^1$H NMR (400 MHz, CDCl$_3$) 8.64 (br s, 1H), 7.27 (t, J=7.8, 1H), 7.08 (d overlapping t, 2H), 6.86 (d, J=7.8, 1H), 5.50(q, J=6.7, 1H), 1.71 (d, J=6.7, 3H).

(±)-6-Amino-1,4-dihydro-4-methyl-1,3-benzo[d]oxazin-2-one (Compound 494, Structure 51 of Scheme IX, Where $R^1$=Methyl, $R^2$=H, W=Oxygen):

To a solution of Compound 493 (130 mg, 0.8 mmol) and conc. H$_2$SO$_4$ (3 mL), chilled to 0° C., was added fuming HNO$_3$ (0.06 mL). After 15 min. poured reaction mixture onto ice and extracted with EtOAc (5 mL), washed with H$_2$O (5×1 mL) and brine (5×1 mL) then dried (Na$_2$SO$_4$) and concentrated in vacuo to afford the crude product as a yellow solid. Dissolved in 2:1 EtOAc/MeOH (5 mL) and hydrogenated over 10% Pd/C (10 mg) at rt and 1 atm. After 15 hrs. filtered through plug of silica gel and purified by PTLC (20×20 cm, 1000 μm, 50% EtOAc/hex) to afford 100 mg of Compound 494 (70%) as a yellow solid: $^1$H NMR (400 MHz, CDCl$_3$) 8.47 (br s, 1H), 6.66 (d, J=8.3, 1H), 6.59 (dd, J=2.2, 8.3, 1H), 6.43 (d, J=2.2, 1H), 5.40 (q, J=6.6, 1H), 3.63 (br s, 2H), 1.67 (d, J=6.6, 1H).

1,4-Dihydro-4-methyl-6-diallylamino-1,3-benzo[d]oxazin-2-one (Compound 492, Structure 52 of Scheme IX, Where $R^1$=Methyl, $R^2$=H, $R^4=R^5$=Allyl, W=Oxygen)

This compound was prepared in a similar fashion as that described in Example 77, General Procedure IX but using Compound 494 in place of Compound 200. Compound 492 was isolated as a yellow oil: $^1$H NMR (400 MHz, CDCl$_3$) 6.66 (d, J=8.6, 1H), 6.60 (dd, J=2.5, 8.6, 1H), 6.42 (d, J=2.5, 1H), 5.82 (m, 2H), 5.43 (q, J=6.7, 1H), 5.16 (m, 4H), 3.88 (m, 4H), 1.65 (d, J=6.7, 3H).

EXAMPLE 232

6-Amino-3,4-dihydro-4,4-dimethyl-2(1H)-quinolinone (Compound 495, Structure 51 of Scheme IX, Where $R^1=R^2$=Methyl, W=Carbon)

To a solution of 3,4-dihydro-4,4-dimethyl-2(1H)-quinolinone (Compound 496, Structure 49 of Scheme IX, where $R^1=R^2$=methyl, W=carbon) (0.50 g, 2.8 mmol) and conc. H$_2$SO$_4$ (10 mL), chilled to 0° C., was added fuming HNO$_3$ (0.12 mL). After 15 min. poured reaction mixture onto ice and extracted with EtOAc (20 mL), washed with H$_2$O (5×5 mL) and brine (5×5 mL) then dried (Na$_2$SO$_4$) and concentrated in vacuo to afford the crude product as a yellow solid. Dissolved in 9:1 EtOAc/MeOH (20 mL) and hydrogenated over 10% Pd/C (50 mg) at room temperature and 1 atm. After 15 hrs. filtered through plug of silica gel to afford Compound 495 (0.48 g) in 89% yield as an orange solid: $^1$H NMR (400 MHz, CDCl$_3$) 7.67 (br s, 1H), 6.66 (d, J=2.3, 1H), 6.57 (d, J=8.3, 1H), 6.51 (dd, J=2.3, 8.3, 1H), 3.57 (br s, 2H), 2.43 (s, 2H), 1.28 (s, 6H).

EXAMPLE 233

6-Diallylamino-3,4-dihydro-4,4-dimethyl-2(1H)-quinolinone (Compound 497, Structure 52 of Scheme IX, Where R$^1$=R$^2$=Methyl, R$^4$=R$^5$=Allyl, W=Carbon)

This compound was prepared in a similar fashion as that described in Example 77, General Procedure IX but using Compound 495 (Structure 51 of Scheme IX, where R$^1$=R$^2$=methyl, W=carbon) in place of Compound 200. Compound 497 was isolated as a white solid: $^1$H NMR (400 MHz, CDCl$_3$) 7.40 (br s, 1H), 6.66 (d, J=2.7, 1H), 6.59 (d, J=8.0, 1H), 6.52 (dd, J=2.7, 8.0, 1H), 5.90 to 5.81 (m, 2H), 5.21 to 5.16 (m, 4H), 3.89 (d, J=5.0, 4H), 2.43 (s, 2H), 1.29 (s, 6H).

EXAMPLE 234

3,4-Dihydro-4,4-dimethyl-6-dipropylamino-2(1H)-quinolinone (Compound 498, Structure 52 of Scheme IX, Where R$^1$=R$^2$=Methyl, R$^4$=R$^5$=Propyl, W=Carbon)

This compound was prepared in a similar fashion as that described in Example 15, General Procedure VIII but using Compound 495 (Structure 51 of Scheme IX, where R$^1$=R$^2$=methyl, W=carbon) and propionaldehyde in place of Compound 200 and paraformaldehyde. Compound 498 was isolated as a white solid: $^1$H NMR (400 MHz, CDCl$_3$) 7.77 (br s, 1H), 6.62 (d, J=8.6, 1H), 6.60 (d, J=2.7, 1H), 6.46 (dd, J=2.7, 8.5, 1H), 3.20 (t, J=7.5, 4H), 2.44 (s, 2H), 1.60 (q, J=7.4, 4H), 1.31 (s, 6H), 0.93 (t, J=7.4, 6H).

EXAMPLE 235

3,4-Dihydro-4,4-dimethyl-6-propylamino-2(1H)-quinolinone (Compound 499, Structure 52 of Scheme IX, Where R$^1$=R$^2$=Methyl, R$^4$=Propyl, R$^5$=H, W=Carbon)

This compound was prepared in a similar fashion as that described in Example 2, General Procedure IV but using Compound 495 (Structure 51 of Scheme IX, where R$^1$=R$^2$=methyl, W=carbon) in place of Compound 200. Compound 499 was isolated as a colorless oil: $^1$H NMR (400 MHz, CDCl$_3$) 7.83 (br s, 1H), 6.59 (d, J=8.4, 1H), 6.54 (d, J=2.4, 1H), 6.41 (dd, J=2.4, 8.4, 1H), 3.56 (br s, 1H), 3.04 (t, J=7.1, 2H), 2.47 (s, 2H), 1.61 (q, J=7.4, 4H), 1.27 (s, 6H), 0.97 (t, J=7.4, 6H).

EXAMPLE 236

3,4-Dihydro-4,4-dimethyl-6-(N-2,2,2-trifluoroethyl)amino-2(1H)-quinolinone (Compound 500, Structure 52 of Scheme IX, Where R$^1$=R$^2$=Methyl, R$^4$=Trifluoroethyl, R$^5$=H, W=Carbon)

This compound was prepared in a similar fashion as that described in Example 2, General Procedure IV but using Compound 495 (Structure 51 of Scheme IX, where R$^1$=R$^2$=methyl, W=carbon) and trifluoroacetaldehyde in place of Compound 200 and propionaldehyde. Compound 500 was isolated as a white solid: $^1$H NMR (400 MHz, CDCl$_3$) 8.12 (brs, 1H), 6.64 (m, 2H), 6.51 (dd, J=2.5, 8.4, 1H), 3.85 (brs, 1H), 3.74 (m, 2H), 2.44 (s, 2H), 1.30 (s, 6H).

EXAMPLE 237

3,4-Dihydro-4,4-dimethyl-6-(bis-N,N-2,2,2-trifluoroethyl)amino-2(1H)-quinolinone (Compound 501, Structure 52 of Scheme IX, Where R$^1$=R$^2$=Methyl, R$^4$=R$^5$=Trifluoroethyl, W=Carbon)

This compound was prepared in a similar fashion as that described in Example 15, General Procedure VIII but using Compound 495 (Structure 51 of Scheme IX, where R$^1$=R$^2$=methyl, W=carbon) and trifluoroacetaldehyde in place of Compound 200 and paraformaldehyde. Compound 501 was isolated as a white solid: $^1$H NMR (400 MHz, CDCl$_3$) 8.17 (brs, 1H), 6.88 (d, J=2.6, 1H), 6.76 (dd, J=2.5, 8.6, 1H), 6.72 (d, J=8.6, 1H), 3.98 (q, J=8.6, 4H), 2.48 (s, 2H), 1.31 (s, 6H).

EXAMPLE 238

3,4-Dihydro-6-(N-2,2,2-trifluoroethyl)amino-2(1H)-quinolinone (Compound 502, Structure 52 of Scheme IX, Where R$^1$=R$^2$=R$^5$=H, R$^4$=Trifluoroethyl, W=Carbon)

6-Amino-3,4-dihydro-2(1H)-quinolinone (Compound 503, Structure 51 of Scheme IX, Where R$^1$=R$^2$=H, W=carbon):

To a solution of 3,4-dihdyro-2(1H)-quinolinone (Compound 504, Structure 49 of Scheme IX, where R$^1$=R$^2$=H, W=carbon) (1 g, 6.8 mmol) and conc. Sulfuric acid (15 mL) was added fuming nitric acid (0.3 mL in 3 mL of conc. Sulfuric acid). Stirred at 0 °C. for 30 min. then cast into ice to give a yellow precipitate. Filtered, washed with water and dried to afford 1.3 g (100%) of as a white crystalline solid. A solution of the above solid (200 mg, 1.04 mmol) and DCM (30 mL) was hydrogenated over 10% Pd/C (20 mg) at 1 atm and rt. After 15 hrs. filtered through Celite and concentrated in vacuo to afford 168 mg (100%) of Compound 503 as a white solid: $^1$H NMR (400 MHz, CDCl$_3$) 7.42 (brs, 1H), 6.53 (m, 3H), 3.52 (brs, 2H), 2.87 (t, J=7.1, 2H), 2.58 (t, J=7.1, 2H).

3,4-Dihydro-6-(N-2,2,2-trifluoroethyl)amino-2(1H)-quinolinone (Compound 502, Structure 52 of Scheme IX, Where R$^1$=R$^2$=R$^5$=H, R$^4$=Trifluoroethyl, W=Carbon):

This compound was prepared in a similar fashion as that described in Example 2, General Procedure IV but using Compound 503 and trifluoroacetaldehyde in place of Compound 200 and propionaldehyde. Compound 502 was isolated as a white solid: $^1$H NMR (400 MHz, CDCl$_3$) 7.79 (brs, 1H), 6.62 (d, J=8.5, 1H), 6.51 (m, 2H), 3.74 (q, J=8.9, 2H), 2.90 (t, J=7.2, 2H), 2.59 (t, J=7.2, 2H).

EXAMPLE 239

3,4-Dihydro-6-(bis-N,N-2,2,2-trifluoroethyl)amino-2(1H)-quinolinone (Compound 505, Structure 52 of Scheme IX, Where R$^1$=R$^2$=H, R$^4$=R$^5$=Trifluoroethyl, W=Carbon)

This compound was prepared in a similar fashion as that described in Example 15, General Procedure VIII but using Compound 503 and trifluoroacetaldehyde in place of Compound 200 and paraformaldehyde. Compound 505 was isolated as a white solid: $^1$H NMR (400 MHz, CDCl$_3$) 7.86 (brs, 1H), 6.76 (m, 2H), 6.68 (d, J=8.5, 1H), 3.98 (q, J=8.6, 4H), 2.94 (t, J=7.1, 2H), 2.62 (t, J=7.1, 2H).

EXAMPLE 240

5-(bis-N,N-2,2,2-Trifluoroethyl)amino-3,3-spirocyclohexyl-2-indolone (Compound 506, Structure 55 of Scheme X, Where $R^1=R^2=$ Trifluoroethyl)

5-Amino-3-spirocyclohexyloxindole (Compound 507, Structure 54 of Scheme X):

This compound was prepared in a similar fashion as that described in Example 1, General Procedures II and III but using 3-spirocyclohexyloxindole in place of Compound 202. Compound 507 was isolated as a white solid: $^1$H NMR (400 MHz, CDCl$_3$) 7.74 (bs, 1H), 6.86 (d, J=1.9, 1H), 6.69 (d, J=7.9, 1H), 6.55 (dd, J=2.2, 8.1, 1H), 3.54 (bs, 2H), 1.93–1.76 (mm, 4H), 1.73–1.57 (mm, 6H).

5-(bis-N,N-2,2,2-Trifluoroethyl)amino-3,3-spirocyclohexyl-2-indolone (Compound 506, Structure 55 of Scheme X, Where $R^1=R^2=$Trifluoroethyl):

This compound was prepared in a similar fashion as that described in Example 15, General Procedure VIII but using Compound 507 and trifluoroacetaldehyde in place of Compound 200 and paraformaldehyde. Compound 506 was isolated as a white solid: $^1$H NMR (400 MHz, CDCl$_3$) 8.52 (bs, 1H), 7.11 (s, 1H), 6.84 (s, 2H), 3.95 (q, J=8.7, 4H), 1.97–1.92 (m, 2H), 1.89–1.83 (m, 2H), 1.71–1.57 (m, 6H).

EXAMPLE 241

7-(bis-N,N-2,2,2-Trifluoroethyl)amino-1,4-benzoxazin-3(4H)-one (Compound 508, Structure 57 of Scheme X, Where $R^1=R^2=$Trifluoroethyl)

This compound was prepared in a similar fashion as that described in Example 9, General Procedure VI from 7-amino-1,4-benzoxazin-3(4H)-one (Compound 509, Structure 56 of Scheme X) and trifluoroacetic acid as white solid. $^1$H NMR (500 MHz, CDCl$_3$) 8.12 (bs, 1H), 6.72 (d, J=8.8, 1H), 6.59 (d, J=2.9, 1H), 6.53 (dd, J=8.8, 2.9, 1H), 4.61 (s, 2H), 3.97 (q, $J_{H-F}$=8.8, 4H).

EXAMPLE 242

6-(bis-N,N-2,2,2-Trifluoroethyl)amino-2,4-dichloroquinoline (Compound 510 Structure 59 of Scheme X, Where $R^1=R^2=$Trifluoroethyl)

This compound was prepared in a similar fashion as that described in Example 9, General Procedure VI from 6-amino-1,4-dichloro-2(1H)-quinolinone (Compound 511, Structure 58 of Scheme X) and trifluoroacetic acid as brown solid. $^1$H NMR (CDCl$_3$, 500 MHz) 7.99 (dd, J=1.0, 8.8, 1H), 7.47–7.50 (m, 3H), 4.22, J=8.8, 4H).

EXAMPLE 243

7-Amino-4-trifluoromethyl-2(1H-quinolinone (Compound 512, Structure 61 of Scheme XI, Where $R=R^1=H$)

A solution of 1,3-phenylenediamine (5.4 g, 50 mmol) and ethyl 4,4,4-trifluoroacetoacetate (11 g, 60 mmol) in ethanol (100 mL) was heated at reflux overnight to give rise to a yellow slurry. P-Toluenesulfonic acid monohydrate (0.19 g, 1.0 mmol) was added and the reaction mixture was allowed to stir at reflux for additional 24 h. The reaction was cooled to room temperature to generate a large amount of solid. Filtration of the solid followed by washing the solid with methanol (2×10 mL) afforded Compound 512 as a yellowish solid (8.5 g, 75%): $^1$H NMR (400 MHz, acetone-d$_6$) 10.91 (bs, 1H), 7.47 (dq, J=6.7, 2.4, 1H), 6.70 (dd, J=6.7, 2.2, 1H), 6.65 (d, J=2.2, 1H), 6.50 (s, 1H), 5.65 (bs, 2H).

EXAMPLE 244

7-Propylamino-4-trifluoromethyl-2(1H)-quinolinone (Compound 513, Structure 62 of Scheme XI, Where $R=R^1=R^2=H$, $R^3=$Propyl)

This compound was prepared in a similar fashion as that described in Example 2, General Procedure IV but using Compound 512 (Structure 61 of Scheme XI, where $R^1=R=$H) (100 mg, 0.45 mmol) in place of Compound 200. Compound 513 was isolated in 84% as a yellow solid: $^1$H NMR (400 MHz, acetone-d$_6$) 10.62 (bs, 1H), 7.46 (dq, J=9.0, 1.5, 1H), 6.68 (dd, J=9.0, 2.1, 1H), 6.57 (d, J=2.1, 1H), 6.48 (s, 1H), 5.99 (bs, 1H), 3.17 (m, 1H), 1.68 (hex, J=7.8, 2H), 1.01 (t, J=7.8, 3H).

EXAMPLE 245

7-Isopropylamino-4-trifluoromethyl-2(1H)-quinolinone (Compound 514, Structure 62 of Scheme XI, Where $R=R^1=R^2=H$, $R^3=$Isopropyl)

This compound was prepared in a similar fashion as that described in Example 2, General. Procedure IV but using Compound 512 (Structure 61 of Scheme XI, where $R^1=R=$H) (10 mg, 0.045 mmol) and acetone (58 mg, 1.0 mmol) in place of Compound 200 and propionaldehyde. Compound 514 was isolated in 66% as a yellow solid: $^1$H NMR (400 MHz, CDCl$_3$) 10.70 (bs, 1H), 7.58(dq, J=9.0, 1.8, 1H), 6.70 (s, 1H), 6.51 (dd, J=9.0, 2.3, 1H), 6.31 (d, J=2.3, 1H), 4.12 (d, J=6.0, 1H), 3.73 (m, 1H), 1.26 (d, J=6.2, 6H).

EXAMPLE 246

7-(2,2-Dimethylpropyl)amino-4-trifluoromethyl-2(1H)-quinolinone (Compound 515, Structure 62 of Scheme XI, Where $R=R^1=R^2=H$, $R^3=$2,2-Dimethylpropyl)

This compound was prepared in a similar fashion as that described in Example 2, General Procedure IV but using Compound 512 (Structure 61 of Scheme XI, where $R^1=R=$H) (10 mg, 0.045 mmol) and trimethylacetylaldehyde (86 mg, 1.0 mmol) in place of Compound 200 and propionaldehyde. Compound 515 was isolated in 60% as a yellow solid: $^1$H NMR (400 MHz, CDCl$_3$) 11.55 (bs, 1H), 7.56 (dq, J=9.0, 1.8, 1H), 6.71 (s, 1H), 6.58 (dd, J=9.1, 2.3, 1H), 6.42 (d, J=2.3, 1H), 4.30 (t, J=6.0, 1H), 3.00 (d, J=6.0, 1H), 1.02 (s, 3H).

EXAMPLE 247

7-(2-Methylpropyl)amino-4-trifluoromethyl-2(1H)-quinolinone (Compound 516, Structure 62 of Scheme XI, Where $R=R^1=R^2=H$, $R^3=$2-Methylpropyl)

This compound was prepared in a similar fashion as that described in Example 2, General Procedure IV but using Compound 512 (Structure 61 of Scheme XI, where $R^1=R=$H) (10 mg, 0.045 mmol) and isobutyraldehyde (72 mg, 1.0 mmol) in place of Compound 200 and propionaldehyde. Compound 516 was isolated in 67% as a yellow solid: $^1$H NMR (400 MHz, CDCl$_3$) 11.43 (bs, 1H), 7.57 (dq, J=9.0, 1.8, 1H), 6.70 (s, 1H), 6.55 (dd, J=9.1, 2.4, 1H), 6.38 (d, J=2.4, 1H), 4.34 (t, J=6.2, 1H), 3.04 (t, J=6.3, 1H), 1.01 (d, J=6.4, 6H).

EXAMPLE 248

7-Methylamino-4-trifluoromethyl-2(1H)-quinolinone (Compound 517, Structure 62 of Scheme XI, Where R=$R^1$=$R^2$=H, $R^3$=Methyl)

This compound was prepared in a similar fashion as that described in Example 2, General Procedure IV but using Compound 512 (Structure 61 of Scheme XI, where $R^1$=R=H) (10 mg, 0.045 mmol) and paraformaldehyde (10 mg, 0.33 mmol) in place of Compound 200 and propionaldehyde. Compound 517 was isolated in 73% as a yellow solid: $^1$H NMR (400 MHz, acetone-$d_6$) 10.68 (bs, 1H), 7.46 (dq, J=9.0, 1.5, 1H), 6.66 (dd, J=9.0, 2.1, 1H), 6.52 (d, J=2.1, 1H), 6.47 (s, 1H), 5.99 (bs, 1H), 2.88 (d, J=5.0, 3H).

EXAMPLE 249

7-Dimethylamino-4-trifluoromethyl-2(1H)-quinolinone (Compound 518, Structure 62 of Scheme XI, Where R=$R^1$=H, $R^3$=$R^2$=Methyl)

This compound was prepared in a similar fashion as that described in Example 15, General Procedure VIII but using Compound 512 (Structure 61 of Scheme XI, where $R^1$=R=H) (10 mg, 0.045 mmol) in place of Compound 200. Compound 518 was isolated in 50% as a yellow solid: $^1$H NMR (400 MHz, CDCl$_3$) 11.22 (bs, 1H), 7.63 (dq, J=9.0, 1.5, 1H), 6.72 (s, 1H), 6.71 (dd, J=9.0, 2.1, 1H), 6.43 (d, J=2.1, 1H), 3.10 (s, 6H).

EXAMPLE 250

7-Benzylamino-4-trifluoromethyl-2(H1H)-quinolinone (Compound 519, Structure 62 of Scheme XI, Where R=$R^1$=$R^2$=H, $R^3$=Benzyl)

This compound was prepared in a similar fashion as that described in Example 2, General Procedure IV but using Compound 512 (Structure 61 of Scheme XI, where $R^1$=R=H) and benzaldehyde in place of Compound 200 and propionaldehyde. Compound 519 was isolated as a yellow solid: $^1$H NMR (400 MHz, acetone-$d_6$) 10.96 (bs, 1H), 7.49 (dq, J=9.0, 1.5, 1H), 7.41 (d, J=7.6, 2H), 7.33 (t, J=7.6, 3H), 7.27 (t, J=7.6, 1H), 6.76 (dd, J=9.0, 2.1, 1 H), 6.60 (d, J=2.1, 1H), 4.45 (d, J=5.9, 2H).

EXAMPLE 251

7-(2,2,3,3,3-Pentafluoropropyl)amino-4-trifluoromethyl-2(1H)-quinolinone (Compound 520, Structure 62 of Scheme XI, Where R=$R^1$=$R^2$=H, $R^3$=2,2,3,3,3-Pentafluoropropyl)

This compound was prepared in a similar fashion as that described in Example 9, General Procedure VI but using Compound 512 (Structure 61 of Scheme XI, where $R^1$=R=H) (100 mg, 0.45 mmol) and pentafluoropropionic acid in place of Compound 200 and 2,2-difluoroacetic acid. Compound 520 was isolated in 50% as a yellow solid: $^1$H NMR (400 MHz, acetone-$d_6$) 10.88 (bs, 1H), 7.58 (dq, J=9.0, 1.5, 1H), 6.87 (dd, J=9.0, 2.1, 1H), 6.81 (d, J=2.1, 1H), 6.58 (s, 1H), 6.47 (bs, 1H), 4.14 (td, J=15.5, 6.5, 2H).

EXAMPLE 252

7-Butylamino-4-trifluoromethyl-2(1H)-quinolinone (Compound 521, Structure 62 of Scheme XI, Where R=$R^1$=$R^2$=H, $R^3$=Butyl)

This compound was prepared in a similar fashion as that described in Example 2, General Procedure IV but using Compound 512 (Structure 61 of Scheme XI, where $R^1$=R=H) (10 mg, 0.045 mmol) and butyraldehyde in place of Compound 200 and propionaldehyde. Compound 521 was isolated in 80% as a yellow solid: $^1$H NMR (400 MHz, CDCl$_3$) 11.40 (bs, 1H), 7.58 (dq, J=9.0, 1.5, 1H), 6.72 (s, 1H), 6.58 (dd, J=9.0, 2.1, 1H), 6.39 (d, J=2.1, 1H), 4.23 (t, J=6.0, 1H), 3.22 (q, J=6.5, 2H), 1.69–1.42 (m, 4H), 1.0 (t, J=7.3, 3H).

EXAMPLE 253

7-Ethylamino-4-trifluoromethyl-2(1H)-quinolinone (Compound 522, Structure 62 of Scheme XI, Where R=$R^1$=$R^2$=H, $R^3$=Ethyl)

This compound was prepared in a similar fashion as that described in Example 9, General Procedure VI but using Compound 512 (Structure 61 of Scheme XI, where $R^1$=R=H) (100 mg, 0.45 mmol) and acetic acid in place of Compound 200 and 2,2-difluoroacetic acid. Compound 522 was isolated in 89% as a yellow solid: $^1$H NMR (400 MHz, acetone-$d_6$) 10.78 (bs, 1H), 7.56 (dq, J=9.0, 1.5, 1H), 6.76 (dd, J=9.0, 2.1, 1H), 6.65 (d, J=2.1, 1H), 6.57 (s, 1H), 6.02 (bs, 1H), 3.32 (m, 2H), 1.36 (t, J=7.3, 3H).

EXAMPLE 254

7-(N-2,2,2-Trifluoroethyl)amino-4-trifluoromethyl-2(1H)-quinolinone (Compound 523, Structure 62 of Scheme XI, Where R=$R^1$=$R^2$=H, $R^3$=2,2,2-Trifluoroethyl)

This compound was prepared in a similar fashion as that described in Example 9, General Procedure VI but using Compound 512 (Structure 61 of Scheme XI, where $R^1$=R=H) (100 mg, 0.45 mmol) and trifluoroacetic acid in place of Compound 200 and 2,2-difluoroacetic acid. Compound 523 was isolated in 50% as a yellow solid: mp 238–239° C.; $^1$H NMR (400 MHz, acetone-$d_6$) 10.95 (bs, 1H), 7.56 (dq, J=9.0, 1.5, 1H), 6.86 (dd, J=9.0, 2.1, 1H), 6.80 (d, J=2.1, 1H), 6.60 (s, 1H), 6.50 (bs, 1H), 4.05 (m, 2H).

EXAMPLE 255

7-Cyclohexylamino-4-trifluoromethyl-2(1H)-quinolinone (Compound 524, Structure 62 of Scheme XI, Where R=$R^1$=$R^2$=H, $R^3$=Cyclohexyl)

This compound was prepared in a similar fashion as that described in Example 2, General Procedure IV but using Compound 512 (Structure 61 of Scheme XI, where $R^1$=R=H) and cyclohexanone in place of Compound 200 and propionaldehyde. Compound 524 was isolated as a yellow solid: $^1$H NMR (500 MHz, acetone-$d_6$) 10.6 (bs, 1H), 7.44 (dd, J=9.3, 2.4, 1H), 6.67 (dd, J=9.3, 2.4, 1H), 6.59 (d, J=2.4, 1H), 6.46 (s, 1H), 5.84 (d, J=7.3, 1H), 3.39–3.31 (m, 1H), 1.81–1.77 (m, 2H), 1.68–1.64 (m, 1H), 1.46–1.38 (m, 2H), 1.32–1.22 (m, 3H).

EXAMPLE 256

7-Cyclopentylamino-4-trifluoromethyl-2(1H)-quinolinone (Compound 525, Structure 62 of Scheme XI, Where R=$R^1$=$R^2$=H, $R^3$=Cycloentyl)

This compound was prepared in a similar fashion as that described in Example 2, General Procedure IV but using Compound 512 (Structure 61 of Scheme XI, where $R^1$=R=H) and cyclopentanone in place of Compound 200 and propionaldehyde. Compound 525 was isolated as a yellow solid: $^1$H NMR (500 MHz, acetone-d$_6$) 10.8 (bs, 1H), 7.45 (dd, J=8.8, 2.2, 1H), 6.67 (dd, J=8.8, 2.4, 1H), 6.59 (d, J=2.4, 1H), 6.48 (s, 1H), 5.98 (d, J=5.9, 1H), 3.90–3.84 (m, 1H), 2.09–2.04 (m, 2H), 1.79–1.71 (m, 2H), 1.68–1.55 (m, 4H).

EXAMPLE 257

7-Cyclobutylamino-4-trifluoromethyl-2(1H)-quinolinone (Compound 526, Structure 62 of Scheme XI, Where R=R$^1$=R$^2$=H, R$^3$=Cyclobutyl)

This compound was prepared in a similar fashion as that described in Example 2, General Procedure IV but using Compound 512 (Structure 61 of Scheme XI, where R$^1$=R=H) and cyclobutanone in place of Compound 200 and propionaldehyde. Compound 526 was isolated as a yellow solid: $^1$H NMR (500 MHz, DMSO-d$_6$) 11.8 (bs, 1H), 7.36 (d, J=9.3, 1H), 6.98 (d, J=5.9, 1H), 6.55 (dd, J=9.3, 1.5, 1H), 6.43 (s, 1H), 6.34 (d, J=1.5, 1H), 3.85–3.80 (m, 1H), 2.37–2.32 (m, 2H), 1.89–1.83 (m, 2H), 1.78–1.72 (m, 2H).

EXAMPLE 258

7-(2-Hydroxy-2-methylpropionyl)amino-4-trifluoromethyl-2(1H)-quinolinone (Compound 527, Structure 62 of Scheme XI, Where R=R$^1$=R$^2$=H, R$^3$=2-Hydroxy-2-methylpropionyl)

To a solution of Compound 512 (Structure 61 of Scheme XI, where R$^1$=R=H) (12 mg, 0.036 mmol) in THF (2 mL) was added 1-chlorocarbonyl-1-methylethyl acetate (10 mg, 0.06 mmol), the mixture was stirred at room temperature for a few minutes. Triethylamine (10 mg, 0.10 mmol) was added and the reaction was stirred for additional 2 h and then was quenched with 5% NaOH. The mixture was extracted with EtOAc (2×20 mL), washed with brine, and concentrated. Chromatography afforded Compound 527 as a white solid: mp 289–291° C.; $^1$H NMR (400 MHz, ODCD$_3$) 8.14 (d, J=2.0, 1H), 7.75 (dq, J=8.9, 2.0, 1H), 7.42 (dd, J=8.9, 2.1, 1H), 6.88 (s, 1H), 4.85 (s, 6H).

EXAMPLE 259

7-(Trifluoroacetamido)-4-trifluoromethyl-2(1H)-quinolinone (Compound 528, Structure 62 of Scheme XI, Where R=R$^1$=R$^2$=H, R$^3$=Trifluoroacetyl)

To a solution of Compound 512 (Structure 61 of Scheme XI, where R$^1$=R=H) (46 mg, 0.20 mmol) in 1 mL pyridine was added trifluoroacetic anhydride (0.14 mL, 1.0 mmol). After 16 h, the solution was partitioned between EtOAc (30 mL) and 1N NaHSO$_4$ (30 mL). The organic layer was washed sequentially with pH 6.88 phosphate buffer (20 mL) and brine (20 mL), dried over MgSO$_4$, filtered and concentrated. Flash chromatography (9:1 CH$_2$Cl$_2$:MeOH) afforded 54 mg (83%) of Compound 528: R$_f$ 0.24 (9:1 CH$_2$Cl$_2$:MeOH); $^1$H NMR (400 MHz, acetone-d$_6$) 11.3 (broad s, 1H), 10.7 (broad s, 1H), 8.41 (d, J=1.7, 1H), 7.81 (d, J=8.9, 1H), 7.58 (dd, J=9.0, 1.8, 1H), 6.92 (s, 1H).

EXAMPLE 260

1-Methyl-7-methylamino-4-trifluoromethyl-2(1H)-quinolinone (Compound 529, Structure 63 of Scheme XI, Where R=R$^1$=R$^2$=H, R$^3$=R$^4$=Methyl)

This compound was prepared in a similar fashion as that described in Example 92, General Procedure X from Compound 517 (Structure 62 of Scheme XI, where R=R$^1$=R$^2$=H, R$^2$=methyl). Compound 529 was isolated as a yellow solid: $^1$H NMR (400 MHz, CDCl$_3$) 7.63 (dq, J=9.0, 1.5, 1H), 6.78 (s, 1H), 6.57 (dd, J=9.0, 2.1, 1H), 6.37 (d, J=2.1, 1H), 4.42 (bs, 1H), 3.69 (s, 3H), 2.97 (d, J=5.2, 3H).

EXAMPLE 261

1-Methyl-7-dimethylamino-4-trifluoromethyl-2(1H)-quinolinone (Compound 530, Structure 63 of Scheme XI, Where R=R$^1$=H, R$^2$=R$^3$=R$^4$=Methyl)

This compound was prepared in a similar fashion as that described in Example 92, General Procedure X from Compound 518 (Structure 62 of Scheme XI, where R=R$^1$=H, R$^3$=R$^2$=methyl). Compound 530 was isolated as a yellow solid: $^1$H NMR (400 MHz, CDCl$_3$) 7.66 (dq, J=9.0, 1.5, 1H), 6.78 (s, 1H), 6.72(dd, J=9.0, 2.1, 1H), 6.39 (d, J=2.1, 1H), 3.70 (s, 3H), 3.13 (s, 6H).

EXAMPLE 262

1-Methyl-7-(N-methyl-N-isopropylamino)-4-trifluoromethyl-2(1H)-quinolinone (Compound 531, Structure 63 of Scheme XI, Where R=R$^1$=H, R$^2$=R$^4$=Methyl, R$^3$=Isopropyl)

This compound was prepared in a similar fashion as that described in Example 92, General Procedure X from Compound 514 (Structure 62 of Scheme XI, where R=R$^1$=R$^2$=H, R$^3$=isopropyl). Compound 531 was isolated as a yellow solid: $^1$H NMR (500 MHz, CDCl$_3$) 7.65 (dd, J=9.3, 2.4, 1H), 6.79 (dd, J=9.3, 2.4, 1H), 6.77 (s, 1H), 6.47 (d, J=2.4, 1H), 4.27–4.23 (m, 1H) 3.70 (s, 3H), 2.89 (s, 3H), 1.26 (d, J=6.3, 6H).

EXAMPLE 263

1-Methyl-7-(2,2,2-trifluoromethyl)amino-4-trifluoromethyl-2(1H)-quinolinone (Compound 532 Structure 63 of Scheme XI, Where R=R$^1$=R$^2$=H, R$^4$=Methyl, R$^3$=Trifluoromethyl)

This compound was prepared in a similar fashion as that described in Example 92, General Procedure X from Compound 523 (Structure 62 of Scheme XI, where R=R$^1$=R$^2$=H, R$^3$=2,2,2-trifluoroethyl). Compound 532 was isolated as a yellow solid: $^1$H NMR (500 MHz, CDCl$_3$+DMSO-d$_6$) 7.64 (dd, J=8.8, 2.0, 1H), 6.84 (s, 1H), 6.71 (dd, J=8.8, 2.0, 1H), 6.62 (d, J=2.0, 1H), 5.96 (bt, J=6.8, 1H), 3.93–3.86 (m, 2H), 3.68 (s, 3H).

EXAMPLE 264

3-Fluoro-7-(2,2,2-trifluoromethyl)amino-4-trifluoromethyl-2(1H)-quinolinone (Compound 533, Structure 62 of Scheme XI, Where R=Fluoro, R$^1$=R$^2$=H, R$^3$=Trifluoromethyl)
3-Fluoro-7-amino-4-trifluoromethyl-2(H1)-quinolinone (Compound 534, Structure 61 of Scheme XI, Where R=Fluoro, R$^1$=H):

This compound was prepared in a similar manner as that described in Example 1, General Procedures I, II and III but using ethyl 2,4,4,4-tetrafluoroacetoacetate in place of ethyl 4,4,4-trifluoroacetoacetate. Compound 534 was isolated as a white solid: $^1$H NMR (500 MHz, DMSO-d$_6$) 12.4 (bs, 1H), 7.39 (dd, J=8.8, 2.0, 1H), 6.64 (dd, J=9.3, 1.9, 1H), 6.50 (d, J=2.4, 1H), 6.05 (bs, 2H).

3-Fluoro-7-(2,2,2-trifluoromethyl)amino-4-trifluoromethyl-2(1H)-quinolinone (Compound 533, Structure 62 of Scheme XI, Where R=Fluoro, $R^1$=$R^2$=H, $R^3$=Trifluoromethyl):

Compound 534 was dissolved in trifluoroacetic acid (15 mL) and heated to 60° C. for 2 h, cooled to room temperature where sodium borohydride (350 mg, 9.25 mmol, 5.0 equiv) was carefully added in portions to the reaction mixture. After complete addition of sodium borohydride the reaction mixture was allowed to stir for 16 h, poured over ice and neutralized to pH 7 with NaOH pellets. A white precipitate was filtered from the aqueous solution, redissolved in EtOAc (200 mL), washed with water (25 mL), brine (25 mL), dried ($MgSO_4$), filtered and concentrated under reduced pressure to yield an off white solid. Purification by re-crystallization (MeOH) afforded 135 mg (22%) of Compound 533 as a white solid: $^1$H NMR (400 MHz, acetone-$d_6$) 11.18 (bs, 1H), 7.58 (dd, J=8.9, 2.1, 1H), 6.90 (dd, J=9.0, 2.2, 1H), 6.81 (d, J=2.3, 1H), 6.40 (bm, 1H), 4.04 (m, 2H).

EXAMPLE 265

3-Fluoro-7-isopropylamino-4-trifluoromethyl-2(1H1)-quinolinone (Compound 535, Structure 62 of Scheme XI, Where R=Fluoro, $R^1$=$R^2$=H, $R^3$=Isopropyl)

This compound was prepared in a similar fashion as that described in Example 2, General Procedure IV but using Compound 534 (Structure 61 of Scheme XI, where $R^1$=H, R=fluoro) and acetone in place of Compound 200 and propionaldehyde. Compound 535 was isolated as a yellow solid: $^1$H NMR (500 MHz, acetone-$d_6$) 11.0 (bs, 1H), 7.49 (d, J=9.1, 1H), 6.72 (d, J=9.1, 1H), 6.59 (t, J=2.4, 1H), 6.86 (s, 1H), 5.69 (bs, 1H), 3.71–3.67 (m, 1H), 1.24 (d, J=6.3, 6H).

EXAMPLE 266

3-Fluoro-7-cyclopentylamino-4-trifluoromethyl-2(1H)-quinolinone (Compound 536, Structure 62 of Scheme XI, Where R=Fluoro, $R^1$=$R^2$=H, $R^3$=Cyclopentyl)

This compound was prepared in a similar fashion as that described in Example 2, General Procedure IV but using Compound 534 (Structure 61 of Scheme XI, where $R^1$=H, R=fluoro) and cyclopentanone in place of Compound 200 and propionaldehyde. Compound 536 was isolated as a yellow solid: $^1$H NMR (500 MHz, acetone-$d_6$) 11.1 (bs, 1H), 7.49 (dd, J=9.3, 2.4, 1H), 6.73 (dd, J=9.3, 2.4, 1H), 6.61 (d, J=2.4, 1H), 5.88 (bs, 1H), 3.87–3.83 (m, 1H), 2.08–1.98 (m, 2H), 1.76–1.56 (m, 6H).

EXAMPLE 267

3-Fluoro-7-cyclohexylamino-4-trifluoromethyl-2(1H)-quinolinone (Compound 537, Structure 62 of Scheme XI, Where R=Fluoro, $R^1$=$R^2$=H, $R^3$=Cyclohexyl)

This compound was prepared in a similar fashion as that described in Example 2, General Procedure IV but using Compound 534 (Structure 61 of Scheme XI, where $R^1$=H, R=fluoro) and cyclocyclohexanone in place of Compound 200 and propionaldehyde. Compound 537 was isolated as a yellow solid: $^1$H NMR (500, acetone-$d_6$) 11.1 (bs, 1H), 7.48 (dd, J=9.3, 2.4, 1H), 6.73 (dd, J=9.3, 2.4, 1H), 6.61 (d, J=2.4, 1H), 5.74 (d, J=7.3, 1H), 3.36–3.31 (m, 1H), 1.81–1.77 (m, 2H), 1.67–1.64 (m, 1H), 1.43–1.37 (m, 2H), 1.31–1.21 (m, 3H).

EXAMPLE 268

3-Fluoro-7-cyclobutylamino-4-trifluoromethyl-2(1H)-quinolinone (Compound 538, Structure 62 of Scheme XI, Where R=Fluoro, $R^1$=$R^2$=H, $R^3$=Cyclobutyl)

This compound was prepared in a similar fashion as that described in Example 2, General Procedure IV but using Compound 534 (Structure 61 of Scheme XI, where $R^1$=H, R=fluoro) and cyclocyclobutanone in place of Compound 200 and propionaldehyde. Compound 538 was isolated as a yellow solid: $^1$H-NMR (500, acetone-$d_6$) 12.3 (bs, 1H), 7.41 (dd, J=8.8, 2.4, 1H), 6.88 (d, J=5.9, 1H), 6.63 (dd, J=8.8, 2.4, 1H), 6.37 (d, J=2.4, 1H), 3.84–3.80 (m, 1H), 2.38–2.32 (m, 2H), 1.91–1.83 (m, 2H), 1.80–1.72 (m, 2H).

EXAMPLE 269

3-Fluoro-7-propylamino-4-trifluoromethyl-2(1H)-quinolinone (Compound 539, Structure 62 of Scheme XI, Where R=Fluoro, $R^1$=$R^2$=H, $R^3$=Propyl)

This compound was prepared in a similar fashion as that described in Example 2, General Procedure IV but using Compound 534 (Structure 61 of Scheme XI, where $R^1$=H, R=fluoro) in place of Compound 200. Compound 539 was isolated as a yellow solid: $^1$H NMR (500, acetone-$d_6$) 11.0 (bs, 1H), 7.50 (dd, J=8.8, 2.2, 1H), 6.75 (dd, J=8.8, 2.2, 1H), 6.58 (d, J=2.4, 1H), 5.89 (bs, 1H), 3.18–3.14 (m, 2H), 1.70–1.65 (m, 2H), 0.99 (t, J=7.3, 3H).

EXAMPLE 270

3-Fluoro-1-methyl-7-(N-methyl-N-isopropyl)amino-4-trifluoromethyl-2(1H)-quinolinone (Compound 540, Structure 63 of Scheme XI, Where R=Fluoro, $R^1$=H, $R^2$=$R^4$=Methyl, $R^3$=Isopropyl)

This compound was prepared in a similar fashion as that described in Example 92, General Procedure X from Compound 535 (Structure 62 of Scheme XI, where R=fluoro, $R^1$=$R^2$=H, $R^3$=isopropyl). Compound 540 was isolated as a yellow solid: $^1$H NMR (500 MHz, acetone-$d_6$) 7.69 (dd, J=9.3, 2.4, 1H), 6.94 (dd, J=9.3, 2.4, 1H), 6.67 (d, J=2.4, 1H), 4.43–4.37 (m, 1H), 3.94 (s, 3H), 3.71 (s, 3H), 1.23 (d, J=6.3, 6H).

EXAMPLE 271

3-Fluoro-1-methyl-7-propylamino-4-trifluoromethyl-2(1H)-quinolinone (Compound 541, Structure 63 of Scheme XI, Where R=Fluoro, $R^1$=$R^2$=H, $R^4$=Methyl, $R^3$=Propyl)

This compound was prepared in a similar fashion as that described in Example 92, General Procedure X from Compound 539 (Structure 62 of Scheme XI, where R=fluoro, $R^1$=$R^2$=H, R=propyl). Compound 541 was isolated as a yellow solid: $^1$H NMR (400 MHz, $CDCl_3$) 7.63 (dd, J=9.1, 1.9, 1H), 6.62 (dd, J=9.1, 2.1, 1H), 6.38 (d, J=2.1, 1H), 4.23 (bs, 1H), 3.23 (s, 3H), 3.19 (t, J=7.1, 6H), 1.75–1.67 (m, 2H), 1.05 (t, J=7.4, 3H).

EXAMPLE 272

6-Fluoro-7-amino-4-trifluoromethyl-2(1H)-quinolinone (Compound 542, Structure 63 of Scheme XI, where $R^1$=Fluoro, R=H)

This compound was prepared in a similar manner as that described in Example 243 but using 4-fluoro-1,3- phenylenediamine (Structure 60 of Scheme XI, where $R^1$=fluorine) in place of 1,3-phenylenediamine. Compound 542 was isolated as a yellow solid: $^1$H NMR (400 MHz, CD$_3$OD) 7.35 (d, J=9.2, 1H), 6.71 (d, J=7.5, 1H), 6.65 (s, 1H).

EXAMPLE 273

6-Fluoro-7-propylamino-4-trifluoromethyl-2(1H)-quinolinone (Compound 543, Structure 62 of Scheme XI, Where $R^1$=Fluoro, R=$R^2$=H, $R^3$= Propyl)

This compound was prepared in a similar fashion as that described in Example 2, General Procedure IV but using Compound 542 (Structure 61 of Scheme XI, where $R^1$=fluoro, R=H) in place of Compound 200. Compound 543 was isolated as a yellow solid: $^1$H NMR (400 MHz, CDCl$_3$) 7.49 (d, J=7.5, 1H), 6.78 (s, 1H), 6.40 (d, J=7.5, 1H), 4.51 (br t, 1H), 3.22 (m, 2H), 1.74 (q, J=7.3, 2H), 1.07 (t, J=7.3, 3H).

EXAMPLE 274

6-Fluoro-7-isobutylamino-4-trifluoromethyl-2(1H)-quinolinone (Compound 544, Structure 62 of Scheme XI, Where $R^1$=Fluoro, R=$R^2$=H, $R^3$= Isobutyl)

This compound was prepared in a similar fashion as that described in Example 2, General Procedure IV but using Compound 542 (Structure 61 of Scheme XI, where $R^1$=fluoro, R=H) and isobutyraldehyde in place of Compound 200 and propionaldehyde. Compound 544 was isolated as a yellow solid: $^1$H NMR (400 MHz, CD$_3$OD) 7.30 (d, J=7.5, 1H), 6.61 (s, 1H), 6.59 (d, J=7.5, 1H), 3.05 (d, J=7.3, 2H), 2.00 (m, 1H), 1.00 (d, J=6.6, 6H).

EXAMPLE 275

6-Fluoro-1-methyl-7-propylamino-4-trifluoromethyl-2(H1)-quinolinone (Compound 545, Structure 63 of Scheme XI, Where $R^1$=Fluoro, R=$R^2$=H, $R^4$= Methyl, $R^3$=Propyl)

This compound was prepared in a similar fashion as that described in Example 92, General Procedure X from Compound 543 (Structure 62 of Scheme XI, where R=fluoro, R=$R^2$=H, $R^3$=propyl). Compound 545 was isolated as a yellow solid: $^1$H NMR (400 MHz, CD$_3$OD) 7.34 (d, J=9.2, 1H), 6.73 (s, 1H), 6.66 (d, J=7.6, 1H), 3.74 (s, 3H), 3.31 (m under solvent peak, 2H), 1.75 (m, 2H), 1.05 (t, J=7.4, 3H).

EXAMPLE 276

6-Fluoro-1-methyl-7-(N-methyl-N-propylamino)-4-trifluoromethyl-2(1H)-quinolinone (Compound 546, Structure 63 of Scheme XI, Where $R^2$=Fluoro, R=H, $R^2$=$R^4$=Methyl, $R^3$=Propyl)

This compound was prepared in a. similar fashion as that described in Example 92, General Procedure X from Compound 543 (Structure 62 of Scheme XI, where $R^1$=fluoro, R=$R^2$=H, $R^3$=propyl). Compound 546 was isolated as a yellow solid: $^1$H NMR (400 MHz, CD$_3$OD) 7.39 (d, J=15.3, 1H), 6.79 (s under d, 2H), 3.75 (s, 3H), 3.43 (m, 2H), 3.10 (s, 3H), 1.70 (m, 2H), 0.95 (t, J=7.4, 3H).

EXAMPLE 277

7-Amino-6-methyl-4-trifluoromethyl-2(1H)-quinolinone (Compound 547, Structure 61 of Scheme XI, Where $R^1$=Methyl, R=H)

This compound was prepared in a similar manner as that described in Example 243 but using 2,4-diaminotoluene (Structure 60 of Scheme XI, where $R^1$=methyl) in place of 1,3-phenylenediamine. Compound 547 was isolated as a white solid: $^1$H NMR (400 MHz, DMSO-d$_6$), 11.00 (br s, 1H), 7.21 (s, 1H), 6.54 (s, 1H), 6.45 (s, 1H), 2.10 (s, 3H).

EXAMPLE 278

7-Isobutylamino-6-methyl-4-trifluoromethyl-2(1H)-quinolinone (Compound 548, Structure 62 of Scheme XI, Where $R^1$=Methyl, $R^2$=Isobutyl, R=$R^3$=H)

This compound was prepared in a similar fashion as that described in Example 2, General Procedure IV but using Compound 547 (Structure 61 of Scheme XI, where $R^1$=methyl, R=H) and isobutyraldehyde in place of Compound 200 and propionaldehyde. Compound 548 was isolated as a yellow solid: $^1$H NMR (400 MHz, DMSO-d$_6$) 11.00 (br s, 1H), 7.22 (s, 1H), 6.45 (s, 1H), 6.40 (s, 1H), 6.05 (br t, 1H), 2.92 (m, 2H), 2.15 (s, 3H), 1.99 (m, 1H), 0.93 (d, J=6.6, 6H).

EXAMPLE 279

7-Propylamino-6-methyl-4-trifluoromethyl-2(1H)-quinolinone (Compound 549, Structure 62 of Scheme XI, Where $R^1$=Methyl, $R^2$=Propyl, R=$R^3$= H)

This compound was prepared in a similar fashion as that described in Example 2, General Procedure IV but using Compound 547 (Structure 61 of Scheme XI, where $R^1$=methyl, R=H) in place of Compound 200. Compound 549 was isolated as a yellow solid: $^1$H NMR (400 MHz, CDCl$_3$) 10.60 (br s, 1H), 7.42 (s, 1H), 6.70 (s, 1H), 6.33 (s, 1H), 4.05 (br t, 1H), 3.20 (m, 2H), 2.20 (s, 3H), 1.74 (q, J=7.4, 2H), 1.06 (t, J=7.4, 3H).

EXAMPLE 280

7-(1,1-Dimethyl-3-oxobutyl)amino-4-trifluoromethyl-2(1H)-quinolinone (Compound 550, Structure 64 of Scheme XII)

A solution of Compound 512 (Structure 61a of Scheme XII) (460 mg, 2.0 mmol) and a catalytic amount of acetic acid in acetone (5 mL) was stirred at room temperature overnight. Removal of solvent and chromatography of the reaction mixture afforded Compound 550 (100 mg, 15%) as a yellow solid: $^1$H NMR (400 MHz, CDCl$_3$) 11.03 (bs, 1H), 7.57 (dq, J=9.0, 1.8, 1H), 6.73 (d, J=2.1, 1H), 6.72 (s, 1H), 6.62 (dd, J=9.0, 2.1, 1H), 4.90 (bs, 1H), 2.89 (s, 2H), 2.14 (s, 3H), 1.52 (s, 6H).

EXAMPLE 281

7-(1,1,3-Trimethyl-3-hydroxybutyl)amino-4-trifluoromethyl-2(1H)-quinolinone (Compound 551, Structure 65 of Scheme XII)

To a solution of Compound 550 (Structure 61a of Scheme XII) (10 mg, 0.031 mmol) in THF at −78° C. was added MeLi (0.1 mL, 1.4 M in ether) and resulting mixture was stirred for 30 min. and quenched with water. Extraction with EtOAc followed by chromatography afforded Compound 551 (5.0 mg, 49%) as a yellow solid: $^1$H NMR (400 MHz, CDCl$_3$) 11.40 (bs, 1H), 7.53 (dq, J=9.0, 1.8, 1H), 6.71 (d, J=2.1, 1H), 6.70 (s, 1H), 6.60 (dd, J=9.0, 2.1, 1H), 5.50 (bs, 1H), 2.18 (s, 1H), 1.97 (s, 2H), 1.55 (s, 6H), 1.38 (s, 6H).

EXAMPLE 282

7-(1,1,3-Trimethyl-3-butenylamino)-4-trifluoromethyl-2(1H)-quinolinone (Compound 552, Structure 66 of Scheme XII)

A solution of Compound 551 (Structure 65 of Scheme XII) (7.0 mg, 0.020 mmol) in acetone was treated with catalytic amount of acetic acid at room temperature overnight and standard work-up provided Compound 552 (2.7 mg, 41%) as a yellow solid: $^1$H NMR (400 MHz, CDCl$_3$) 11.30 (bs, 1H), 7.61 (dq, J=8.8, 1.5, 1H), 6.85 (d, J=2.1, 1H), 6.85 (s, 1H), 6.75 (dd, J=8.8, 2.1, 1H), 5.21 (s, 1H), 4.39 (s, 1H), 2.73 (d, J=15.4, 1H), 2.17 (d, J=15.4, 1H), 1.78 (s, 3H), 1.68 (s, 3H), 1.50 (s, 3H).

EXAMPLE 283

7-(1-Phenylaminocarbonylisopropyl)amino-4-trifluoromethyl-2(1H)-quinolinone (Compound 553, Structure 69 of Scheme XIII)

7-Amino-2-ethoxy-4-trifluoromethylquinoline (Compound 554, Structure 67 of Scheme XIII):

This compound was prepared in a similar method as that described in Example 243. A solution of 1,3-phenylenediamine (5.4 g, 50 mmol) and ethyl 4,4,4-trifluoroacetoacetate (11 g, 60 mmol) in ethanol (100 mL) was heated at reflux overnight to give rise to a yellow slurry. P-Toluenesulfonic acid monohydrate (0.19 g, 1.0 mmol) was added and the reaction mixture was allowed to stir at reflux for additional 24 h. The reaction was cooled to room temperature to generate a large amount of solid. Filtration from the solid (Compound 512 as major product) and removal solvent provided the crude mixture. Chromatography of the mixture on a silica gel column afforded Compound 554 (1.4 g, 11%) as a yellow solid: $^1$H NMR (400 MHz, acetone-d$_6$) 7.70 (dq, J=9.5, 2.1, 1H), 7.05–7.01 (m, 2H), 6.86 (s, 1H), 5.44 (bs, 2H), 4.47 (q, J=7.0, 2H), 1.39 (t, J=7.0, 3H).

7-(1-Phenylaminocarbonylisopropyl)amino-2-ethoxy-4-trifluoromethylquinoline (Compound 555, Structure 68 of Scheme XIII):

To a flask charged with NaH (40 mg, 60% in mineral oil, 1.0 mmol) in THF (2 mL) was added a solution of Compound 554 (128 mg, 0.5 mmol) in THF (2 mL). A solution of N-phenyl-2-bromobutyratamide (121 mg, 0.5 mmol) in THF (2 mL) was introduced slowly in 15 min. and the reaction mixture was stirred at room temperature for 1 h, then quenched with water and extracted with EtOAc. Removal of solvent and chromatography of the crude residue afforded Compound 555 as a white solid: $^1$H NMR (400 MHz, CDCl$_3$) 8.74 (s, 1H), 7.81 (dq, J=9.5, 2.1, 1H), 7.50 (d, J=7.5, 2H); 7.31 (t, J=7.5, 2H), 7.11 (t, J=7.5, 1H), 7.00 (d, J=2.5, 1H), 6.96 (s, 1H), 6.85 (dd J=9.5, 2.5, 1H), 4.47 (q, J=7.2, 2H), 1.67 (s, 6H), 1.39 (t, J=7.2, 3H).

7-(1-Phenylaminocarbonylisopropyl)amino-4-trifluoromethyl-2(1H)-quinolinone (Compound 553, Structure 69 of Scheme XIII):

Treatment of Compound 555 with hydriodic acid (57% aqueous) at 60° C. for 2 h and standard work-up provided Compound 553 as a yellow solid: $^1$H NMR (400 MHz, CDCl$_3$) 11.10 (bs, 1H), 7.61 (dq, J=9.5, 2.1, 1H), 7.48 (d, J=7.5, 2H), 7.27 (t, J=7.5, 2H), 7.11 (t, J=7.5, 1H), 6.78 (s, 1H), 6.61 (dd, J=9.5, 2.5, 1H), 6.54 (d, J=2.5, 1H), 1.64 (s, 6H).

EXAMPLE 284

7-(2-Hydroxy-1,1-dimethylethyl)amino-4-trifluoromethyl-2(1H)-quinolinone (Compound 556, Structure 72 of Scheme XIII)

7-(N-Methyl-N-1-Phenylaminocarbonylisopropyl)amino-4-trifluoromethyl-2(1H)-quinolinone (Compound 557, Structure 70 of Scheme XIII):

To a flask charged with NaH (80 mg, 60% in mineral oil, 2.0 mmol) in THF (3 mL) was added a solution of Compound 554 (Structure 67 of Scheme XIII) (256 mg, 1.0 mmol) in THF (3 mL). A solution of N-phenyl-2-bromobutyratamide (242 mg, 1.0 mmol) in THF (4 mL) was introduced slowly in 15 min. and the reaction mixture was stirred at room temperature for 1 h. The reaction mixture was treated with iodomethane (0.3 mL, 4.5 mmol) and stirred for additional 1 h, then quenched with water and extracted with EtOAc. The crude mixture was treated with hydriodic acid at 40° C. for 3 h and quenched with 10% NaOH. Extraction with EtOAc and removal of solvent provided the crude product. Purification by chromatography afforded Compound 557 as a white solid (220 mg, 50%).

7-(N-2-Formyl-2-propyl)amino-4-trifluoromethyl-2(1H)-quinolinone (Compound 558, Structure 71 of Scheme XIII) and 7-(2-Hydroxy-1,1-dimethylethyl)amino-4-trifluoromethyl-2(1H)-quinolinone (Compound 556, Structure 72 of Scheme XIII):

Compound 557 (200 mg, 0.45 mmol) in THF (5 mL) was treated with DIBAL-H (1.5 mL, 1.0 M in toluene) at −60° C. for 1 h. Standard work-up followed by chromatography afforded Compound 558 (50 mg, 36%) and Compound 556 (70 mg, 51%). Compound 556 was isolated as a yellow solid: $^1$H NMR (400 MHz, acetone-d$_6$) 7.42 (dq, J=8.8, 1.9, 1H), 6.85 (d, J=2.1, 1H), 6.72 (dd, J=8.8, 2.1, 1H), 6.48 (s, 1H), 5.54 (s, 1H), 3.60 (s, 2H), 1.86 (s, 6H).

EXAMPLE 285

7-(1,1-Dimethylallyl)amino-4-trifluoromethyl-2 (1H)-quinolinone (Compound 559, Structure 73 of Scheme XIII)

To a mixture of Ph$_3$PCH$_2$Br—HCl (72 mg, 0.20 mmol) and NaN(SiMe$_3$)$_2$ (0.20 mL, 1.0 M in THF) in THF (3 mL) at room temperature was added a THF solution of Compound 558 (Structure 71 of Scheme XIII) (15 mg, 0.050 mmol) and the resulting mixture was stirred for 1 h. Standard work-up followed by chromatography afforded Compound 559 (10 mg, 83%) as a yellow oil: 1H NMR (400 MHz, CDCl$_3$) 11.71 (bs, 1H), 7.52 (dq, J=8.8, 1.5, 1H), 6.70 (s, 1H), 6.63 (dd, J=9.1, 2.2, 1H), 6.60 (d, J=2.2, 1H), 5.96 (dd, J=17.4, 10.6, 1H), 5.27 (d, J=17.4, 1H), 5.21 (d, J=10.6, 1H), 4.44 (s, 1H), 1.46 (s, 6H).

EXAMPLE 286

7-(1,1-Dimethylpropyl)amino-4-trifluoromethyl-2 (1H)-quinolinone (Compound 560, Structure 74 of Scheme XIII)

A solution of Compound 285 (Structure 73 of Scheme XIII) (5.0 mg, 0.017 mmol) in EtOAc was hydrogenated in the presence of a catalytic amount 10% Pd/C to afforded Compound 560 (3.0 mg, 60%) as a yellow oil: $^1$H NMR (400 MHz, CDCl$_3$) 11.71 (bs, 1H), 7.53 (dq, J=8.8, 1.5, 1H), 6.70 (s, 1H), 6.61 (dd, J=9.1, 2.2, 1H), 6.57 (d, J=2.2, 1H), 4.20 (bs, 1H), 1.78 (q, J=7.4, 2H), 1.39 (s, 6H), 0.90 (t, J=7.4, 3H).

EXAMPLE 287

7-(1-Methyl-1-acetylenylpropyl)amino]-4-(trifluoromethyl)-2(1H)-quinolinone (Compound 561, Structure 75 of Scheme XIV)

To a mixture of Compound 512 (Structure 61a of Scheme XIV) (1.8 g, 8.0 mmol), CuCl (40 mg, 0.40 mmol) in 50 mL THF was added triethylamine (0.89 g, 8.8 mmol) and 3-acetoxy-3-methyl-1-pentyne (1.1 g, 8.0 mmol). After 4 h, the mixture was partitioned between EtOAc (60 mL) and sat'd NH$_4$Cl (60 mL), and the aqueous layer was extracted with EtOAc (60 mL). The organic layers were washed with brine, dried over MgSO$_4$, filtered, and concentrated. Flash chromatography (1:1:1 EtOAc:hexanes:CH$_2$Cl$_2$) afforded 0.31 g (13%) of Compound 561 as a yellow solid: R$_f$ 0.30 (1:1:1 EtOAc:hexanes:CH$_2$Cl$_2$); $^1$H NMR (400 MHz, CDCl$_3$) 12.1 (bs, 1H), 7.55–7.65 (m, 1H), 6.93 (dd, J=9.0, 2.3, 1H), 6.88 (d, J=2.2, 1H), 6.75 (s, 1H), 4.36 (s, 1H), 2.49 (s, 1H), 1.80–2.00 (m, 2H), 1.60 (s, 3H), 1.08 (t, J=7.4, 3H).

EXAMPLE 288

7-(1-Ethyl-1-methylpropyl)amino-4-(trifluoromethyl)-2(1H)-quinolinone (Compound 562, Structure 76 of Scheme XIV)

A solution of Compound 561 (Structure 75 of Scheme XIV) (16 mg, 0.052 mmol) in EtOAc/EtOH (2:1) was hydrogenated in the presence of 10% Pd—C (2.4 mg, 15 wt %) to afford 10 mg (63%) of Compound 562 as a yellow foam: R$_f$ 0.30 (1:1:1 EtOAc:hexanes:CH$_2$Cl$_2$); $^1$H NMR (400 MHz, CDCl$_3$) 12.3 (bs, 1H), 7.48–7.56 (m, 1H), 6.70 (s, 1H), 6.58–6.65 (m, 2H), 4.14 (broad s, 1H), 1.76–1.90 (m, 2H), 1.62–1.74 (m, 2H), 1.29 (s, 3H), 0.87 (t, J=7.4, 3H).

EXAMPLE 289

8-Methyl-7-(3-methyl1–2-butenyl)amino-4-(trifluoromethyl)-2(1H)-quinolinone (Compound 563, Structure 79 of Scheme XV, Where R=3-Methyl-2-butenyl)

2-(tert-Butyloxycarbamoyl)-6-(3-methyl-2-butenyl) aminotoluene (Compound 564, Structure 77 of Scheme XV, R=3-Methyl-2-butenyl):

To an oven-dried 25-mL r.b. flask containing 2-amino-6-(tert-butyloxycarbamoyl)toluene (0.50 g, 2.3 mmol) in 10 mL glacial acetic acid at room temperature was added 3-methyl-2-butenal (senecialdehyde, 0.43 mL, 4.5 mmol, 2.0 equiv) and sodium cyanoborohydride (0.70 g, 11 mmol, 5.0 equiv), and the mixture was allowed to stir for 6 h. The mixture was then neutralized to pH 8 with the careful addition of saturated NaHCO$_3$. The mixture was then extracted with EtOAc (2×40 mL), and the combined organic layers were washed with brine, dried (Na$_2$SO$_4$), and concentrated under reduced pressure. Purification by flash chromatography (hexanes:EtOAc, 10:1 to 4:1 gradient) afforded 611 mg (94%) of Compound 564 as a white solid: $^1$H NMR (400 MHz, CDCl$_3$) 7.09 (t, 1H, J=8.0, 4-H), 6.96 (br d, 1H, J=8.0, 3-H), 6.46 (d, 1H, J=8.1, 5-H), 6.18 (br s, 1H, CONH), 5.36 (t, 1H, J=6.7, C═CH), 3.70 (d, 2H, J=6.7, NHCH$_2$CH═C), 3.40 (br s, 1H, ArNHCH$_2$), 2.00 (s, 3H, 1-CH$_3$), 1.76 and 1.71 [2s, 2×3H, CH═C(CH$_3$)$_2$], 1.50 [s, 9H, (CH$_3$)$_3$CO].

2-Amino-6-(3-methyl-2-butenyl)aminotoluene (Compound 565, Structure 78 of Scheme XV, R=3-Methyl-2-butenyl):

Treatment of Compound 564 with TFA removed the tert-butoxy protection group to give Compound 565 in high yield.

8-Methyl-7-(3-methyl-2-butenyl)amino-4-(trifluoromethyl)-2(1H)-quinolinone (Compound 563, Structure 79 of Scheme XV, Where R=3-Methyl-2-butenyl):

This compound was prepared in a similar fashion as that described in Example 243, but using Compound 565 (611 mg, 2.10 mmol) in place of 1,3-phenylenediamine. Compound 563 (261 mg, 40%) was isolated as a yellow solid: $^1$H NMR (400 MHz, CDCl$_3$) 9.12 (br s, 1H, CONH), 7.61 (br d, 1H, J=7.6, 5-H), 6.71 (s, 1H, 7-H), 6.68 (d, 1H, J=9.1, 6-H), 5.34 (t, 1H, J=5.9, C═CH), 4.03 (br s, 1H, ArNHCH$_2$), 3.84 (t, 2H, J=5.8, NHCH$_2$CH═C), 2.13 (s, 3H, 8-CH$_3$), 1.79 and 1.75 [2s, 2×3H, CH═C(CH$_3$)$_2$].

EXAMPLE 290

8-Methyl-7-(3-methylbutyl)amino-4-(trifluoromethyl)-2(1H)-quinolinone (Compound 566, Structure 79 of Scheme XV Where R=3-Methylbutyl)

To an oven-dried 25-mL r.b. flask containing Compound 289 (Structure 79 of Scheme XV, where R=3-methyl-2-butenyl) (74 mg, 0.24 mmol) in 2 mL 1,2-dichloroethane was added 0.3 mL TFA and 0.5 mL triethylsilane, and the mixture was heated to reflux for 8 h. Upon cooling to rt, the mixture was added to 5 mL saturated NaHCO$_3$ and extracted with 10 mL EtOAc. The organic layer was washed with brine, dried (Na$_2$SO$_4$), and concentrated under reduced pressure. The residue was purified by flash chromatography (silica gel, hexanes/EtOAc, 4:1 to 0:1 gradient), affording 28 mg (37%) of Compound 566 as a fluorescent yellow solid: $^1$H NMR (400 MHz, CDCl$_3$) 9.09 (br s, 1H, CONH), 7.61 (br d, 1H, J=7.6, 5-H), 6.70 (s, 1H, 7-H), 6.69 (d, 1H, J=9.1, 6-H), 3.99 (br s, 1H, (ArNHCH$_2$), 3.11 [t, 2H, J=6.8, NHCH$_2$CH$_2$CH(CH$_3$)$_2$], 2.11 (s, 3H, 8-CH$_3$), 1.7–1.4 [m, 3H, NHCH$_2$CH$_2$CH(CH$_3$)$_2$], 0.98 [d, 2×3H, J=6.7, CH(CH$_3$)$_2$].

EXAMPLE 291

8-Methyl-7-propylamino-4-(trifluoromethyl)-2(1H)-quinolinone (Compound 567, Structure 79 of Scheme XV, Where R=Propyl)

3-Amino-2-methyl-N-propylaminobenzene (Compound 568, Structure 78 of Scheme XV, Where R=Propyl):

To a solution of 2-methyl-3-nitroaniline (0.5 g, 3.3 mmol) and MeOH (20 mL) was added propionaldehyde (2.3 mL, 33 mmol), AcOH (1.9 mL, 33 mmol), and NaBH$_3$CN (2 g, 33 mmol). Reaction was stirred at rt for 2 hours then quenched with H$_2$O and concentrated in vacuo. Diluted with EtOAc (20 mL) and adjusted to pH=7 with saturated NaHCO$_3$. Washed organic layer with H$_2$O (3×10 mL) and brine (3×10 mL), dried (Na$_2$SO$_4$) and concentrated in vacuo. The crude product was purified by flash chromatography (5% EtOAc/hex) to afford 0.7 g of the 2-methyl-3-nitro-N-propylaminobenzene. A solution of the product and EtOAc (25 mL) was hydrogenated over 10% Pd/C (70 mg) at rt and 1 atm. After 15 hours filtered reaction mixture through a pad of Celite and concentrated the filtrate to afford the desired Compound 568 (0.10 g) as yellow oil.

Compound 568 was dissolved in EtOH (7 mL) and treated with ethyl-4,4,4-trifluoromethylacetoacetate (0.11 mL). This reaction mixture was heated to reflux for 15 hrs. Concentrated in vacuo and purified by flash chromatography (50% EtOAc/hex) to afford the tertiary alcohol (100 mg). The tertiary alcohol was dissolved in toluene and treated with p-TsOH (50 mg) and the reaction was heated to reflux for 15 hrs. The reaction mixture was concentrated in vacuo to afford a light red solid which was then washed with EtOH to afford 48 mg (5% overall yield) of Compound 567 as a white solid: $^1$H NMR (400 MHz, CD$_3$OD) 7.56 (m, 1H), 6.78 (d, J=9.2, 1H), 6.56 (s, 1H), 3.27 (m under solvent peak, 2H), 2.20 (3H), 1.68 (m, 2H), 1.01 (t, J=7.4, 3H).

EXAMPLE 292

8-Methyl-7-isobutylamino-4-(trifluoromethyl)-2 (1H)-quinolinone (Compound 569, Structure 79 of Scheme XV, Where R=Isobutyl)

3-Amino-2-methyl-N-isobutylaminobenzene (Compound 570, Structure 78 of Scheme XV, Where R=Isobutyl):

To a solution of 2-methyl-3-nitroaniline (Structure 28b of Scheme XV) (0.5 g, 3.3 mmol) and MeOH (20 mL) was added isobutyraldehyde (3 mL, 33 mmol), AcOH (1.9 mL, 33 mmol), and NaBH$_3$CN (2 g, 33 mmol). Reaction was stirred at rt for 2 hours then quenched with H$_2$O and concentrated in vacuo. Diluted with EtOAc (20 mL) and adjusted to pH=7 with saturated NaHCO$_3$. Washed organic layer with H$_2$O (3×10 mL) and brine (3×10 mL), dried (Na$_2$SO$_4$) and concentrated in vacuo. The crude product was purified by flash chromatography (5% EtOAc/hex) to afford 0.9 g of the N-isobutylamino-2-methyl-3-nitrobenzene. A solution of the product and EtOAc (25 mL) was hydrogenated over 10% Pd/C (90 mg) at room temperature and 1 atm. After 15 hours filtered reaction mixture through a pad of Celite and concentrated the filtrate to afford Compound 570 (0.45 g) as a white solid.

Compound 570 (100 mg) was dissolved in EtOH (7 mL) and treated with ethyl-4,4,4-trifluoromethylacetoacetate (0.1 mL). This reaction mixture was heated to reflux for 15 hrs. Concentrated in vacuo and purified by flash chromatography (50% EtOAc/hex) to afford the tertiary alcohol intermediate. The tertiary alcohol was dissolved in toluene (7 mL) and treated with p-TsOH (10 mg) and the reaction was heated to reflux for 15 hrs. The reaction mixture was concentrated in vacuo then purified by flash chromatography (10% EtOAc/ hexane to 100% EtOAc gradient) to afford 112 mg (67%) of Compound 569 as a white solid: $^1$H NMR (400 MHz, CD$_3$OD) 7.65 (d, J=9.2, 1H), 6.96 (d, J=9.2, 1H), 6.73 (s, 1H), 3.17 (d, J=7.1, 2H), 2.20 (s, 3H), 1.02 (d, J=6.7, 6H).

EXAMPLE 293

7-Amino-6-(2,2,2-trifluoroethoxy)-4-trifluoromethyl-2(1H)-quinolinone (Compound 571, Structure 83 of Scheme XVI)

2,4-Dinitrophenyl-(2,2,2-trifluoroethyl)ether (Compound 572, Structure 81 of Scheme XVI):

In a 100 mL flask, a solution of 2,4-dinitrofluorobenzene (1.0 mL) in acetone (20 mL) was treated with 2,2,2-trifluoroethanol (1.2 mL) and Et$_3$N (1.2 mL). The reaction mixture was warmed to 45–50° C. for 3 h, the volatiles were removed in vacuo, and the residue was dissolved in EtOAc (40 mL). The organic layer was washed with water (50 mL) and brine (50 mL). The aqueous layers were extracted with EtOAc (2×30 mL). The organic layers were combined, dried (K$_2$CO$_3$), filtered through a pad of Celite, and concentrated to afford orange oil. Purification by silica gel chromatography (hexane:EtOAc, 4:1) to afford 2.1 g (99%) of Compound 572 as an orange oil: $^1$H NMR (400 MHz, CDCl$_3$) 8.80 (d, J=2.8, 1H), 8.49 (dd, J=8.3, 2.8, 1H), 7.25 (d, J=8.3, 1H), 4.63 (q, J=7.6, 2H).

2,4-Diaminophenyl(2,2,2-trifluoroethyl)ether (Compound 573, Structure 82 of Scheme XVI):

In a 100 mL flask, a solution of Compound 572 (0.85 g) in 1:1 EtOH:EtOAc (40 mL) was treated with 10% Pd/C (0.2 g) and stirred under an atmosphere of hydrogen for 2 h. The reaction mixture was filtered and concentrated to afford 0.62 g (92%) of Compound 573 as a white solid: $^1$H NMR (400 MHz, acetone-d$_6$) 6.67 (d, J=8.5, 1H), 6.12 (d, J=2.6, 1H), 5.92 (dd, J=8.5, 2.6, 1H), 4.39 (q, J=8.9, 2H), 4.28 (br exch s, 2H), 4.17 (br exch s, 2H).

7-Amino-6-(2,2,2-trifluoroethoxy)-4-trifluoromethyl-2 (1H)-quinolinone (Compound 571, Structure 83 of Scheme XVI):

Compound 573 (0.62 g) was dissolved in toluene (20 mL), treated with 4,4,4-trifluoroacetoacetate (0.58 mL), and the reaction mixture was heated to reflux for 1 h. To this solution was added ZnCl$_2$ (0.26 g) and the reaction mixture was heated to reflux for 2 h. p-Toluenesulfonic acid hydrate (0.1 g) was added and the reaction mixture maintained a reflux for 1 h. The bulk of the volatiles were removed in vacuo and the residue was poured into 0.5 N NaHSO$_4$ (20 mL). The reaction mixture was extracted with EtOAc (3×30 mL). The extracts were washed with water (20 mL) and brine (20 mL), combined, dried (MgSO$_4$), filtered, and concentrated. The crude material was suspended in 15:1 CH$_2$Cl$_2$:MeOH and the yellow solid collected by filtration to afford 471 mg (43%) of Compound 571 as a yellow-white solid: R$_f$ 0.14 (15:1 CH$_2$Cl$_2$:MeOH); $^1$H NMR (400 MHz, DMSO-d$_6$) 11.94 (br s, 1H), 7.01 (s, 1H), 6.66 (s, 1H), 6.51 (s, 1H), 6.01 (br exch s, 2H), 4.76 (q, J=8.8, 2H).

EXAMPLE 294

7-Isobutylmino-6-(2,2,2-trifluoroethoxy)-4-trifluoromethyl-2(1H-quinolinone (Compound 574, Structure 84 of Scheme XVI, Where R=Isobutyl)

In a 20 mL r.b. flask, a solution of Compound 571 (Structure 83 of Scheme XVI) (39 mg) in AcOH (1 mL) was treated with isobutyraldehdye (16 μL) and Na(CN)BH$_3$ (11 mg). The reaction mixture was stirred overnight, poured into 20% KOH (6 mL), and extracted with EtOAc (3×6 mL). The extracts were washed with 20% KOH (6 mL) and brine (6 mL); combined, dried (MgSO$_4$), filtered, and concentrated. Purification by silica gel chromatography (CH$_2$Cl$_2$:MeOH, 30:1 to 15:1 gradient) afforded 19 mg (54%) of Compound 574 as a yellow solid: R$_f$ 0.32 (15:1 CH$_2$Cl$_2$:MeOH); $^1$H NMR (400 MHz, acetone-d$_6$) 10.72 (br exch s, 1H), 7.15 (s, 1H), 6.69 (s, 1H), 6.54 (s, 1H), 5.77 (br exch s, 1H), 4.77 (q, J=8.5, 2H), 3.11 (t, J=6.4, 2H), 0.99 (d, J=6.7, 6H). The methine proton is obscured by the acetone heptet.

EXAMPLE 295

7-(2-Picolylamino)-6-(2,2,2-trifluoroethoxy)-4-trifluoromethyl-2(1H)-quinolinone (Compound 575, Structure 84 of Scheme XVI, R=2-Picolyl)

In a 20 mL flask, a solution of Compound 293 (Structure 83 of Scheme XVI) (38 mg) in AcOH (1 mL) was treated with 2-pyridinecarboxaldehyde (16 μL) and Na(CN)BH$_3$ (11 mg). The reaction mixture was stirred overnight, poured into 20% KOH (6 mL), and extracted with EtOAc (3×6 mL). The extracts were washed with 20% KOH (6 mL) and brine (6 mL); combined, dried (MgSO$_4$), filtered, and concentrated. Purification by silica gel chromatography (CH$_2$Cl$_2$:EtOAc:MeOH, 85:10:5) afforded 31 mg (60%) of Compound 295 as a yellow solid: R$_f$ 0.18 (CH$_2$Cl$_2$:EtOAc:MeOH, 85:10:5); $^1$H NMR (400 MHz, acetone-d$_6$) 10.80 (br exch s, 1H), 8.56 (d, J=8.4, 1H), 7.77 (m, 1H), 7.41 (d, J=7.6, 1H), 7.25 (m, 1H), 7.20 (s, 1H), 6.72 (br exch s, 1H), 6.60 (s, 1H), 6.55 (s, 1H), 5.77 (br exch s, 1H), 4.85 (q, J=8.5, 2H), 4.61 (d, J=5.6, 2H).

EXAMPLE 296

7-Amino-6-methyl-4-trifluoromethyl-2(1H)-quinolinone (Compound 576, Structure 88 of Scheme XVII, R$^1$=Methyl, R$^2$=R$^3$=H)

This compound was prepared by the following General Procedure XVII (Condensation of 4-alkyl-1,3-phenylenediamine with acetoacetates or their corresponding hydrates followed by Knorr reaction mediated by p-toluenesulfonic acid):

To a solution of 4-alkyl-1,3-phenylenediamine (Structure 87 of Scheme XVII) in benzene or toluene (10 mL/mmol)

under $N_2$ was added an acetoacetate derivative (1.2 equiv) and the reaction mixture was heated at reflux for 4–8 h, then cooled and concentrated under reduced pressure. The crude mixture was then triturated with $Et_2O$:Hexane (3:1, 4 mL/mmol), then redissolved in toluene:EtOH (10:1, 10 mL/mmol) and treated with p-toluenesulfonic acid. The reaction mixture was then heated at reflux for 1–2 h. After cooling, the excess solvent was removed and the crude product redissolved in EtOAc (100 mL/mmol). The organic solution was washed with saturated $NaHCO_3$ (2×25 mL/mmol), Brine (25 mL/mmol), dried ($MgSO_4$), filtered, and concentrated under reduced pressure to afford the desired quinolinone as a white solid. If needed, the desired product was further purified by silica gel chromatography as indicated.

Compound 576 was prepared from 2,4-diaminotoluene (1.0 g, 8.2 mmol) in 40% yield (0.80 g) as yellow needles: $^1$H NMR (400 MHz, DMSO-$d_6$) 11.00 (br s, 1H), 7.21 (s, 1H), 6.54 (s, 1H), 6.45 (s, 1H), 2.10 (s, 3H).

EXAMPLE 297

7-Amino-6-ethyl-4-trifluoromethyl-2(1H)-quinolinone (Compound 577, Structure 88 of Scheme XVII, Where $R^1$=Ethyl, $R^2$=$R^3$=H)

2-Ethyl-5-nitroaniline (Compound 578, Structure 86 of Scheme XVII, Where $R^1$=Ethyl, $R^2$=$R^3$=H):

This compound is prepared according to the following General Procedure XVIII (nitration of amine):

A solution of an alkylaniline in conc $H_2SO_4$ (6 mL/mmol) was cooled to −10° C., then treated with a 25% solution of fuming $HNO_3$ (1.0 equiv) dissolved in $H_2SO_4$. The rate of addition is adjusted so as to keep the temperature below −5° C. After complete addition of the $HNO_3$ solution, the reaction was allowed to stir at −10° C. for 15 min, warmed to room temperature, poured over NaOH pellets (0.7 g/mL $H_2SO_4$) and ice. The aqueous solution was stirred over ice to dissolve all the NaOH, filtered then washed with water (2.0 mL/mmol) to afford the desired product as an yellow-orange solid.

Compound 578 was prepared from 2-ethylaniline (200 mg, 1.62 mmol) in 97% yield as a yellow oil: $^1$H NMR (400 MHz, CDCl$_3$) 7.59 (dd, J=8.3, 2.3, 1H), 7.50 (d, J=2.2, 1H), 7.17 (d, J=8.3, 1H), 3.90 (bs, 2H), 2.56 (q, J=7.6, 2H), 1.28 (t, J=7.4, 3H).

4-Ethyl-1,3-phenylenediamine (Compound 579, Structure 87 of Scheme XVII, Where $R^1$=Ethyl, $R^2$=$R^3$=H):

This compound is prepared according to General Procedure III from Compound 578 (110 mg, 0.66 mmol) in 76% yield. Compound 579 was isolated as a light brown oil: $^1$H NMR (400 MHz, CDCl$_3$) 6.84 (d, J=8.0, 1H), 6.12 (dd, J=8.0, 2.3, 1H), 6.06 (d, J=2.3, 1H), 3.50 (bs, 4H), 2.42 (q, J=7.5, 2H), 1.19 (t, J=7.5, 3H).

7-Amino-6-ethyl-4-trifluoromethyl-2(1H)-quinolinone (Compound 577, Structure 88 of Scheme XVII, Where $R^1$=Ethyl, $R^2$=$R^3$H):

This compound was prepared according to General Procedure XVII in Example 296 from Compound, 579 (69 mg, 0.50 mmol) and ethyl-4,4,4-trifluoroacetoacetate (0.09 mL, 0.62 mmol) and purified by flash chromatography (MeOH/$CH_2Cl_2$, 1% to 4% gradient), to afford 63 mg (52%) of Compound 577 as a yellow solid: $^1$H NMR (400 MHz, DMSO-$d_6$) 11.80 (s, 1H), 7.20 (s, 1H), 6.54 (s, 1H), 6.42 (s, 1H), 5.98 (s, 2H), 2.50 (m, 2H), 1.14 (t, J=7.4, 3H).

EXAMPLE 298

7-Amino-6-propyl-4-trifluoromethyl-2(1H)-quinolinone (Compound 580, Structure 88 of Scheme XVII, Where $R^1$=Propyl, $R^2$=$R^3$=H)

This compound is prepared in a similar fashion as that described in Examples 297 and 1, General Procedure XVIII, and III but using 2-propylaniline (Structure 85 of Scheme XVII, where $R^1$=propyl, $R^2$=$R^3$=H) (0.20 mL, 1.42 mmol) in place of 2-ethylaniline.

Data for 2-propyl-5-nitroaniline (Structure 86 of Scheme XVII, where $R^1$=propyl, $R^2$=$R^3$=H): $^1$H NMR (400 MHz, CDCl$_3$) 7.56 (dd, J=8.2, 2.3, 1H), 7.50 (d, J=2.3, 1H), 7.14 (d, J=8.3, 1H), 3.90 (bs, 2H), 2.52 (t, J=7.8, 2H), 1.66 (sex, J=7.5, 2H), 1.01 (t, J=7.3, 3H).

Data for 4-propyl-1,3-phenylenediamine (Structure 87 of Scheme XVII, where $R^1$=propyl, $R^2$=$R^3$H): $^1$H NMR (400 MHz, CDCl$_3$) 6.81 (d, J=8.1, 1H), 6.09 (dd, J=8.2, 2.3, 1H), 6.02 (d, J=2.3, 1H), 3.50 (bs, 4H), 2.40 (t, J=7.8, 2H), 1.58 (sex, J=7.5, 2H), 0.97 (t, J=7.3, 3H).

Data for Compound 580 (Structure 88 of Scheme XVII, where $R^1$=propyl, $R^2$=$R^3$=H): $^1$H NMR (400 MHz, DMSO-$d_6$) 11.78 (s, 1H), 7.17 (s, 1H), 6.52 (s, 1H), 6.41 (s, 1H), 5.96 (s, 2H), 2.45 (t, J=7.6, 2H), 1.52 (m, 2H), 0.92 (t, J=7.3, 3H).

EXAMPLE 299

7-Amino-6-sec-butyl-4-trifluoromethyl-2(1H)-quinolinone (Compound 581, Structure 88 of Scheme XVII, Where $R^1$=sec-Butyl, $R^2$=$R^3$=H)

This compound is prepared in a similar fashion as that described in Examples 297 and 1, General Procedure XVIII and III but using 2-s-butyl-aniline (Structure 85 of Scheme XVI, where $R^1$=sec-butyl, $R^2$=$R^3$=H) (0.20 mL, 1.28 mmol) in place of 2-ethylaniline.

Data for 2-sec-butyl-5-nitroaniline (Structure 86 of Scheme XVII, where $R^1$=sec-butyl, $R^2$=$R^3$=H): $^1$H NMR (400 MHz, CDCl$_3$) 7.60 (dd, J=8.5, 2.3, 1H), 7.50 (d, J=2.4, 1H), 7.19 (d, J=8.5, 1H), 3.92 (bs, 2H), 2.67 (sex, J=6.9, 1H), 1.66 (m, 2H), 1.25 (d, J=6.8, 3H), 0.91 (t, J=7.3, 3H).

Data for 4-sec-butyl-1,3-phenylenediamine (Structure 87 of Scheme XVII, where $R^1$=sec-butyl, $R^2$=$R^3$=H): $^1$H NMR (400 MHz, CDCl$_3$) 6.86 (d, J=8.3, 1H), 6.14 (dd, J=8.2, 2.4, 1H), 6.08 (d, J=2.3, 1H), 3.60 (bs, 4H), 2.53 (sex, J=6.9, 1H), 1.52 (m, 2H), 1.15 (d, J=6.7, 3H), 0.86 (t, J=7.2, 3H).

Data for Compound 581 (Structure 88 of Scheme XVII, where $R^1$=sec-butyl, $R^2$=$R^3$=H): $^1$H NMR (400 MHz, DMSO-$d_6$) 11.78 (s, 1H), 7.19 (s, 1H), 6.53 (s, 1H), 6.42 (s, 1H), 5.99 (s, 2H), 2.80 (m, 1H), 1.56–1.48 (m, 2H), 1.0 (t, J=3.8, 3H), 0.83 (t, J=7.3, 3H).

EXAMPLE 300

7-Amino-6-cyclohexyl-4-trifluoromethyl-2(1H)-quinolinone (Compound 582, Structure 88 of Scheme XVII, Where $R^1$=Cyclohexyl, $R^2$=$R^3$=H)

4-Cyclohexyl-3-nitroaniline (Compound 583, Structure 91 of Scheme XVII):

This compound is prepared according to General Procedure XVIII in Example 297 from 4-cyclohexyl-aniline (285 mg, 1.62 mmol) and $HNO_3$ (90 mg, 1.62 mmol) in 94% yield. Compound 583 was isolated as a white solid: $^1$H NMR (400 MHz, CDCl$_3$) 7.20 (d, J=8.4, 1H), 6.97 (d, J=2.5, 1H), 6.81 (dd, J=8.5, 2.5, 1H), 3.78 (bs, 2H), 2.85 (m, 1H), 1.83 (m, 4H), 1.75 (m, 1H), 1.36 (m, 4H), 1.23 (m, 1H).

4-Cyclohexyl-1,3-phenylenediamine (Compound 584, Structure 87 of Scheme XVII, Where $R^1$=Cyclohexyl, $R^2$=$R^3$=H):

This compound is prepared according to General Procedure III in Example 1 from Compound 583 (353 mg, 1.60 mmol) and purified by flash chromatography (MeOH/

$CH_2Cl_2$, 0% to 2% gradient). Compound 582 was isolated in 96% yield as a light brown oil: $^1H$ NMR (400 MHz, $CDCl_3$) 6.88 (d, J=8.1, 1H), 6.15 (dd, J=8.1, 2.3, 1H), 6.06 (d, J=2.4, 1H), 3.48 (bs, 4H), 2.35 (m, 1H), 1.84 (m, 4H), 1.75 (m, 1H), 1.37 (m, 4H), 1.25 (m, 1H).

7-Amino-6-cyclohexyl-1,2-dihydro-4-trifluoromethyl-2 (1H)-quinolinone (Compound 582, Structure 88 of Scheme XVII, Where $R^1$=Cyclohexyl, $R^2$=$R^3$=H):

This compound was prepared according to General Procedure XVII in Example 296 from Compound 584 (69 mg, 0.50 mmol) and ethyl 4,4,4-trifluoroacetoacetate (0.09 mL, 0.62 mmol) and purified by flash chromatography (MeOH/$CH_2Cl_2$, 1% to 4% gradient). Compound 582 was isolated in 52% yield as a white solid: $^1H$ NMR (400 MHz, DMSO-$d_6$) 11.78 (s, 1H), 7.21 (s, 1H), 6.53 (s, 1H), 6.41 (s, 1H), 5.99 (s, 2H), 2.60 (t, J=11.6, 1H), 1.82–1.69 (m, 5H), 1.50–1.41 (m, 2H), 1.29–1.21 (m, 3H).

EXAMPLE 301

6-Ethyl-7-(2,2,2-trifluoroethyl)amino-4-trifluoromethyl-2(1H)-quinolinone (Compound 585, Structure 89 of Scheme XVII, Where $R^1$=Ethyl, $R^2$=H, $R^3$=2,2,2-Trifluoroethyl)

This compound is prepared in a similar fashion as that described in Example 9, General Procedure VI but using Compound 577 (Structure 88 of Scheme XVII, where $R^1$=ethyl, $R^2$=$R^3$H) and TFA in place of Compound 200 and 2,2-difluoroacetic acid. Compound 585 was isolated as a white solid: $^1H$ NMR (400 MHz, $CD_3CN$) 9.72 (bs, 1H), 7.42 (s, 1H), 6.63 (s, 1H), 6.60 (s, 1H), 5.30 (bs, 1H), 3.96 (m, 2H), 2.58 (q, J=7.5, 2H), 1.20 (t, J=7.7, 3H).

EXAMPLE 302

6-Ethyl-7-methylamino-4-trifluoromethyl-2(1H)-quinolinone (Compound 586, Structure 89 of Scheme XVII, Where $R^1$=Ethyl, $R^2$=H, $R^2$=Methyl)

This compound is prepared in a similar fashion as that described in Example 2, General Procedure IV but using Compound 577 (Structure 88 of Scheme XVII, where $R^1$=ethyl, $R^2$=$R^3$=H) and paraformaldehyde in place of Compound 200 and propionaldehyde. Compound 586 was isolated as a white solid: $^1H$ NMR (400 MHz, $CD_3CN$) 10.85 (bs, 1H), 7.54 (s, 1H), 7.13 (s, 1H), 6.73 (s, 1H), 2.76 (q, J=7.5, 2H), 1.26 (t, J=7.4, 3H).

EXAMPLE 303

6-Ethyl-7-dimethylamino-4-trifluoromethyl-2(1H)-quinolinone (Compound 587, Structure 89 of Scheme XVII, Where $R^1$=Ethyl, $R^2$=$R^2$=Methyl)

This compound is prepared in a similar fashion as that described in Example 15, General Procedure VIII but using Compound 577 (Structure 88 of Scheme XVII, where $R^1$=ethyl, $R^2$=$R^3$=H) a in place of Compound 200. Compound 587 was isolated as a white solid: $^1H$ NMR (400 MHz, $CD_3CN$) 11.66 (bs, 1H), 7.60 (s, 1H), 6.90 (s, 1H), 6.88 (s, 1H), 2.83 (s, 6H), 2.76 (q, J=7.5, 2H), 1.29 (t, J=7.5, 3H).

EXAMPLE 304

6-Isobutyl-7-methylamino-4-trifluoromethyl-2(1H)-quinolinone (Compound 588Structure 89 of Scheme XVII, Where $R^1$=Isobutyl, $R^2$=H, $R^2$=Methyl)

This compound is prepared in a similar fashion as that described in Example 2, General Procedure IV but using Compound 581 (Structure 88 of Scheme XVII, where $R^1$=isobutyl, $R^2$=$R^3$=H) and paraformaldehyde in place of Compound 200 and propionaldehyde. Compound 588 was isolated as a white solid: $^1H$ NMR (400 MHz, $CDCl_3$) 11.36 (bs, 1H), 7.43 (d, J=1.8, 1H), 6.74 (s, 1H), 6.40 (s, 1H), 4.39 (bm, 1H), 3.00 (d, J=5.0, 3H), 2.58 (dt, J=6.8, 1H), 1.76–1.68 (m, 1H), 1.64–1.57 (m, 1H), 1.25 (d, J=2.8, 3H), 0.92 (t, J=7.6, 3H).

EXAMPLE 305

7-(1-Morpholino)-4-trifluoromethyl-2(1H)-quinolinone (Compound 589, Structure 88 of Scheme XVII, Where $R^1$=H, $NR^2R^3$=Morpholino)

1-(3-Nitrophenyl)morpholine (Compound 590, Structure 86 of Scheme XVII, where $R^1$=H, $NR^2R^3$=Morpholino):

In a 100 mL flask, a solution of 1-phenylmorpholine (Structure 85 of Scheme XVII, where $R^1$=H, $NR^2R^3$= morpholino) (0.63 g) in concentrated sulfuric acid (5 mL) was cooled to –5° C. To this solution, 90% fuming nitric acid (0.17 mL) was added dropwise via syringe over a 3-minute period. The reaction mixture was stirred for 5 min, poured onto ice (50 g), and neutralized by portionwise addition of $K_2CO_3$ (~5 g). The reaction mixture was poured into water (20 mL) and extracted with $CH_2Cl_2$ (3×50 mL). The extracts were washed with saturated $NaHCO_3$ (50 mL), combined, dried ($MgSO_4$), filtered through a pad of Celite, and concentrated to afford 0.78 g of an orange solid which was purified by silica gel chromatography (hexane:EtOAc, 8:1) to afford 0.33 g (41%) of Compound 590 as orange crystals: $^1H$ NMR (400 MHz, $CDCl_3$) 7.71 (m, 2H), 7.40 (t, J=8.1, 1H), 7.18 (dd, J=8.5, 2.4, 1H), 3.89 (t, J=4.8, 4H), 3.25 (t, J=4.8, 4H).

7-(1-Morpholino)-4-trifluoromethyl-2(1H)-quinolinone (Compound 589, Structure 88 of Scheme XVII, Where $R^1$=H, $NR^2R^3$=Morpholino):

In a 100 mL flask, a solution of Compound 590 (0.33 g) in EtOAc (12 mL) was treated with 10% Pd/C (50 mg) and stirred under an atmosphere of $H_2$ for 14 h. The reaction mixture was filtered and concentrated to afford 1-(3-aminophenyl)morpholine (Compound 591, Structure 87 of Scheme XVII, where $R^1$=H, $NR^2R^3$=morpholino) as a white solid, which was used without further purification. Compound 591 was dissolved in EtOH (10 mL), treated with ethyl 4,4,4-trifluoroacetoacetate (0.27 mL), and stirred at room temperature for 10 min. To this solution was added $ZnCl_2$ (0.26 g) and the reaction mixture was heated to reflux for 12 h. The bulk of the volatiles were removed in vacuo and the residue was poured into 0.5 N $NaHSO_4$ (20 mL). The reaction mixture was extracted with EtOAc (3×30 mL). The extracts were washed with water (20 mL) and brine (20 mL), combined, dried ($MgSO_4$), filtered, and concentrated. Purification by silica gel chromatography ($CH_2Cl_2$:MeOH, 60:1 to 15:1 gradient) afforded 22 mg (5%) of Compound 589 as a white solid: $R_f$ 0.19 (15:1 $CH_2Cl_2$:MeOH); $^1H$ NMR (400 MHz, acetone-$d_6$) 11.95 (br s, 1H), 7.50 (d, J=7.8, 1H), 7.02 (d, J=7.8, 1H), 6.77 (s, 1H), 6.63 (s, 1H), 3.75 (t, J=4.8, 4H), 3.25 (t, J=4.8, 4H).

EXAMPLE 306

5-Amino-7-chloro-4-trifluoromethyl-2(1H)-quinolinone (Compound 592, Structure 94 of Scheme XVIII, Where $R^1$=H, $R^2$=Chlrorine)

To a solution of 5-chloro-3-phenylenediamine (Structure 92 of Scheme XVIII, where $R^1$=H, $R^2$=chlorine) (2.5 g, 17.63 mmol) and EtOH (10 mL) was added ethyl 4,4,4- trifluoroacetoacetate (2.7 mL, 17.9 mmol). The dark reaction mixture was heated to reflux under nitrogen. After 15 hrs, the reaction mixture was filtered to afford 3.0 g (61%) of 5-Amino-7-chloro-4-hydroxy-4-trifluoromethyl-3,4-dihydro-2-(1H)-quinolinone (Compound 593, Structure 93 of Scheme XVIII, where $R^1$=H, $R^2$=chlorine) as a gray-brown solid: $^1$H NMR (400 MHz, DMSO-$d_6$) 10.12 (brs, 1H), 7.44 (s, 1H), 6.33 (d, J=2.1, 1H), 6.11 (d, J=2.1, 1H), 5.86 (s, 2H), 3.05 (d, J=16.4, 1H), 2.69 (d, J=16.4, 1H). The filtrate was purified by chromatography (5–50% EtOAc/hex) to afford 100 mg of Compound 592 as a yellow solid: $^1$H NMR (400 MHz, DMSO-$d_6$) 11.50 (brs, 1H), 6.82 (s, 1H), 6.70 (d, J=1.8, 1H), 6.67 (d, J=1.8, 1H), 5.68 (s, 2H).

Compound 593 was converted to Compound 592 by the treatment with an acid.

EXAMPLE 307

5-Propylamino-7-chloro-4-trifluoromethyl-2(1H)-quinolinone (Compound 594, Structure 96 of Scheme XVIII, Where R=Propyl, $R^1$=H, $R^2$=Chlrorine)

This compound was prepared in a similar fashion as that described in Example 2, General Procedure IV but using Compound 592 (Structure 94 of Scheme XVIII, where $R^1$=H, $R^2$=chlorine) (50 mg, 0.19 mmol) in place of Compound 200. Compound 594 was isolated in 90% yield as a yellow solid: $^1$H NMR (400 MHz, $CD_3OD$) 6.90 (s, 1H), 6.65 (s, 1H), 4.99 (brs, 1H), 3.10 (m, 2H), 1.62 (q, J=7.4, 2H), 1.05 (t, J=7.4, 3H).

EXAMPLE 308

7-Chloro-5-hydroxy-4-trifluoromethyl-2(1H)-quinolinone (Compound 595, Structure 95 of Scheme XVIII, Where $R^1$=H, $R^2$=Chlrorine)

A mixture of Compound 593 (Structure 93 of Scheme XVIII, where $R^1$=H, $R^2$=chlorine) (100 mg, 0.36 mmol), water (5 mL), concn. $H_2SO_4$ (4 mL) and ice (6 g) was cooled to 0° C. An aqueous solution (1 mL) of sodium nitrite (28 mg, 0.40 mmol) was added dropwise with stirring. The mixture was cautiously poured into 15 mL of boiling (140° C.) 10 M $H_2SO_4$. The boiling was continued for 10 min. and the mixture was diluted with water and cooled to room temperature to give a yellow/orange precipitate which was filtered and washed with water then dissolved in acetone and concentrated in vacuo to afford 80 mg (84%) of Compound 595 as a yellow solid: $^1$H NMR (400 MHz, acetone-$d_6$) 11.10 (brs, 1H), 10.25 (brs, 1H), 7.05 (d, J=1.8, 1H), 6.89 (s, 1H), 6.80 (d, J=1.8, 1H).

EXAMPLE 309

5-Amino-6-bromo-3,4-dihydro-4-hydroxy-4-trifluoromethyl-2(1H)-quinolinone (Compound 596, Structure 93 of Scheme XVIII, Where $R^1$=Bromine, $R^2$=H)
4-Bromophenylenediamine (Compound 597, Structure 92 of Scheme XVIII, Where $R^1$=Bromine, $R^2$=H):

A suspension of 2-bromo-5-nitroaniline (10 g, 46 mmol), zinc dust (15 g, 0.23 mol), and calcium chloride dihydrate (20 g, 0.14 mol) in 140 mL 95% EtOH/water was heated at reflux for 12 h. The mixture was filtered through Celite, washed with hot EtOAc and concentrated to a tan solid. Flash chromatography (50% EtOAc/hexanes) afforded 5.8 g (67%) of Compound 597: $^1$H NMR (400 MHz, $CDCl_3$) 7.13 (d, 1H, J=8.5), 6.12 (d, 1H, J=2.6), 6.01 (dd, 1H, J=8.5, 2.6), 3.95 (broad s, 2H), 3.56 (broad s, 2H).

5-Amino-6-bromo-3,4-dihydro-4-hydroxy-4-trifluoromethyl-2(1H)-quinolinone (Compound 596, Structure 93 of Scheme XVIII, Where $R^1$=Bromine, $R^2$=H):

To a solution of Compound 597 (5.7 g, 30 mmol) in 100 mL toluene was added ethyl trifluoroacetoacetate (4.9 mL, 34 mmol, 1.1 eq) dropwise. The solution was heated at reflux for 18 h. The solvent was allowed to cool to room temperature, then placed in a refrigerator (0° C.). The solid was filtered and rinsed with cold toluene. Flash chromatography (1:1 EtOAc:dichloromethane) afforded 3.6 g (37%) of Compound 596 as a tan solid: $^1$H NMR (400 MHz, acetone-$d_6$) 9.31 (broad s, 1H), 7.37 (d, 1H, J=8.5), 6.73 (s, 1H), 6.28 (d, 1H, J=8.5), 5.83 (broad s, 2H), 3.16 (d, AB, 1H, J=16.9), 2.97 (d, AB, 1H, J=16.9).

EXAMPLE 310

6-Bromo-5-chloro-4-trifluoromethyl-2(1H)-quinolinone (Compound 598, Structure 98 of Scheme XVIII, Where $R^1$=Bromine, $R^2$=H)
6-Bromo-5-chloro-3,4-dihydro-4-hydroxy-4-trifluoromethyl-2(1H)-quinolinone (Compound 599, Structure 97 of Scheme XVIII, Where $R^1$=Bromine, $R^2$=H):

In a dry flask, to a solution of $CuCl_2$ (2.5 g, 18 mmol, 2 eq) in 60 mL anhydrous acetonitrile was added t-butyl nitrite (2.1 mL, 18 mmol, 1.9 eq). The solution turned black. A solution of the aniline (3.0 g, 9.3 mmol) in 150 mL was added via cannula. The mixture was stirred at rt for 3 h, then partitioned with EtOAc (200 mL) and water (200 mL). The water layer was extracted with EtOAc (200 mL), washed with sat'd $NaHCO_3$ (100 mL), then brine (100 mL), dried ($MgSO_4$), filtered and concentrated. The crude material was purified by flash chromatography (95:5 hexanes:EtOAc, gradient to 50:50 hexanes:EtOAc) to afford 2.5 g (79%) of Compound 599 as an off-white solid: $^1$H NMR (400 MHz, $CDCl_3$) 9.74 (broad s, 1H), 7.66 (d, 1H, J=8.5), 6.82 (d, 1H, J=8.5), 5.08 (s, 1H), 3.19 (d, AB, 1H, J=17.2), 3.05 (d, AB, 1H, J=17.2).

6-Bromo-5-chloro-4-trifluoromethyl-2(1H)-quinolinone (Compound 598, Structure 98 of Scheme XVIII, Where $R^1$=Bromine, $R^2$=H):

A solution of Compound 599 (2.5 g, 7.3 mmol) in 22 mL conc. $H_2SO_4$ was heated at 90° C. for 1 h, whereupon TLC analysis (1:1 EtOAc:hexanes) showed complete consumption of starting material. The reaction was poured over ice, and a white precipitate formed. The solid was filtered and washed with hexanes. The solid was dissolved in hot EtOAc and filtered through Celite to afford 2.2 g (92%) of an off-white solid. $^1$H NMR (400 MHz, acetone-$d_6$) 11.4 (broad s, 1H), 7.99 (d, 1H, J=9.0), 7.49 (d, 1H, J=9.0), 7.22 (s, 1H).

EXAMPLE 311

6-(bis-N,N-2,2,2-Trifluoroethyl)amino-5-methoxy-4-trifluoromethyl-2(1H)-quinolinone (Compound 600, Structure 100 of Scheme XVIII, Where R=Methoxy, $R^1$=$R^2$=2,2,2-Trifluoroethyl)

This compound was prepared in a similar fashion as that described in Example 9, General Procedure VI from 6-amino-5-methoxy-4-trifluoromethyl-2(1H)-quinolinone (Compound 601, Structure 99 of Scheme XVIII, where R=methoxy) and trifluoroacetic acid. Compound 600 was isolated as yellow solid: $^1$H NMR ($CDCl_3$, 500 MHz) 12.00–12.20 (bs, 1H), 7.45 (d, J=8.8, 1H), 7.22 (d, J=2.9, 1H), 7.20 (s, 1H), 4.02 (q, J=8.8, 4H), 3.88 (s, 3H).

EXAMPLE 312

6-(N-2,2,2-Trifluoroethyl)amino-5-propyloxy-4-trifluoromethyl-2(1H)-quinolinone (Compound 602, Structure 100 of Scheme XVIII, Where R=Propyloxy, $R^1$=H, $R^2$=2,2,2-Trifluoroethyl)

This compound was prepared in a similar fashion as that described in Example 9, General Procedure VI from 6-amino-5-propyloxy-4-trifluoromethyl-2(1H)-quinolinone (Compound 603, Structure 99 of Scheme XVIII, where R=propyloxy) and trifluoroacetic acid. Compound 602 was isolated as yellow solid. $^1$H NMR (CDCl$_3$) 10.56 (bs, 1H), 7.18 (s, 1H), 4.14 (d, J=9.6, 1H), 7.11 (d, J=9.6, 1H), 4.45 (t, J=6.6, 1H), 3.83 (quin, J=7.4, 2H), 3.74 (t, J=6.6, 2H), 1.86 (q, J=7.3, 2H), 1.07 (t, J=7.4, 3H).

EXAMPLE 313

6-(bis-N,N-2,2,2-Trifluoroethyl)amino-5-propyloxy-4-trifluoromethyl-2(1H)-quinolinone (Compound 604, Structure 100 of Scheme XVIII, Where R=Propyloxy, $R^1$=$R^2$=2,2,2-Trifluoroethyl)

This compound was prepared in a similar fashion as that described in Example 9, General Procedure VI from Compound 603 (Structure 99 of Scheme XVIII, where R=propyloxy) and trifluoroacetic acid. Compound 604 was isolated as yellow solid. $^1$H NMR (CDCl$_3$) 10.75 (bs, 1H), 7.43 (d, J=9.0, 1H), 7.19 (s, 1H), 7.17 (d, J=9.0, 1H), 4.03 (q, J=8.9, 4H), 3.93 (t, J=7.1, 2H), 1.83 (q, J=7.3, 2H), 1.01 (t, J=7.4, 3H).

EXAMPLE 314

6-(N-2,2,2-Trifluoroethyl)amino-5-ethoxy-4-trifluoromethyl-2(1H)-quinolinone (Compound 605, Structure 100 of Scheme XVIII, Where R=Ethoxy, $R^1$=H, $R^2$=2,2,2-Trifluoroethyl)

This compound was prepared in a similar fashion as that described in Example 9, General Procedure VI from 6-amino-5-ethoxy-4-trifluoromethyl-2(1H)-quinolinone (Compound 606, Structure 99 of Scheme XVIII, where R=ethoxy) and trifluoroacetic acid. Compound 605 was isolated as yellow solid. $^1$H NMR (CDCl$_3$) 10.65 (bs, 1H), 7.17 (s, 1H), 7.11 (s, 1H), 4.44 (t, 7.2, 1H), 3.86–3.81 (m, 4H), 1.44 (t, J=6.9, 3H).

EXAMPLE 315

6-(bis-N,N-2,2,2-Trifluoroethyl)amino-5-ethoxy-4-trifluoromethyl-2(1H)-quinolinone (Compound 607, Structure 100 of Scheme XVIII, Where R=Ethoxy, $R^1$=$R^2$=2,2,2-Trifluoroethyl)

This compound was prepared in a similar fashion as that described in Example 9, General Procedure VI from Compound 606 (Structure 99 of Scheme XVIII, where R=ethoxy) and trifluoroacetic acid. Compound 607 was isolated as yellow solid. $^1$H NMR (CDCl$_3$) 11.05 (bs, 1H), 7.44 (s, 1H), 7.20 (s, 2H), 4.05 (m, 6H), 1.39 (t, J=6.9, 3H).

EXAMPLE 316

6-(N-2,2,2-Trifluoroethyl)amino-5-(3,3,3-trifluoropropyloxy)-4-trifluoromethyl-2(1H)-quinolinone (Compound 608, Structure 100 of Scheme XVIII, Where R=3,3,3-Trifluoropropyloxy, $R^1$=H, $R^2$=2,2,2-Trifluoroethyl)

This compound was prepared in a similar fashion as that described in Example 9, General Procedure VI from 6-amino-5-(3,3,3-trifluoropropyloxy)-4-trifluoromethyl-2(1H)-quinolinone (Compound 609, Structure 99 of Scheme XVIII, where R=3,3,3-trifluoropropyloxy) and trifluoroacetic acid. Compound 608 was isolated as yellow solid. $^1$H NMR (CDCl$_3$) 11.15 (bs, 1H), 7.92 (d, J=6.7, 1H), 7.72 (d, J=6.7, 1H), 7.59 (m, 2H), 4.23 (m, 2H), 1.67 (m, 2H), 1.41 (m, 2H).

EXAMPLE 317

6-(N-2,2,2-Trifluoroethyl)amino-5-chloro-4-trifluoromethyl-2(1H)-quinolinone (Compound 610, Structure 100 of Scheme XVIII, Where R=Chloro, $R^1$=H, $R^2$=2,2,2-Trifluoroethyl)

This compound was prepared in a similar fashion as that described in Example 9, General Procedure VI from 6-amino-5-chloro-4-trifluoromethyl-2(1H)-quinolinone (Compound 611, Structure 99 of Scheme XVIII, where R=chloro) and trifluoroacetic acid. Compound 610 was isolated as yellow solid. $^1$H NMR (CDCl$_3$) 11.15 (bs, 1H), 7.38 (d, J=9.1, 1H), 7.33 (s, 1H), 7.17 (d, J=9.1, 1H), 5.07 (t, J=8.3, 1H), 3.92 (quin, J=8.5, 2H).

EXAMPLE 318

6-(bis-N,N-2,2,2-Trifluoroethyl)amino-5-chloro-4-trifluoromethyl-2(1H)-quinolinone (Compound 612, Structure 100 of Scheme XVIII, Where R=Chloro, $R^1$=$R^2$=2,2,2-Trifluoroethyl)

This compound was prepared in a similar fashion as that described in Example 9, General Procedure VI from Compound 611 (Structure 99 of Scheme XVIII, where R=chloro) and trifluoroacetic acid. Compound 612 was isolated as yellow solid. $^1$H NMR (CDCl$_3$) 10.62 (bs, 1H), 7.6 (d, J=8.7, 1H), 7.39 (d, J=8.8, 1H), 7.34 (s, 1H), 3.83 (q, J=8.6, 4H).

EXAMPLE 319

6-Fluoro-4-trifluoromethyl-2(1H)-quinolinone (Compound 613, Structure 102 of Scheme XIX, Where $R^1$=$R^3$=$R^4$=H, $R^2$=Fluorine)

This compound was prepared in a similar fashion as that described in Example 1, General Procedure I but using 4-fluoroaniline (Structure 101 of Scheme XIX, where $R^3$=$R^4$=H, $R^2$=fluorine) in place of Compound 200. Compound 613 was isolated as a white solid: $^1$H NMR (400 MHz, acetone-d$_6$) 10.87 (s, 1H), 7.58–7.48 (m, 2H), 7.43 (d, J=9.7, 1H), 7.01 (s, 1H).

EXAMPLE 320

6-Chloro-4-trifluoromethyl-2(1H)-quinolinone (Compound 614, Structure 102 of Scheme XIX, Where $R^1$=$R^3$=$R^4$=H, $R^2$=Chlorine)

This compound was prepared in a similar fashion as that described in Example 1, General Procedure I but using 4-chloroaniline (Structure 101 of Scheme XIX, where $R^2$=fluorine, $R^3$=$R^4$=H) in place of Compound 200. Compound 614 was isolated as a white solid: $^1$H NMR (400 MHz, acetone-d$_6$+drop of DMSO-d$_6$) 10.90 (s, 1H), 7.68–7.60 (m, 2H), 7.53 (d, J=9.0, 1H), 7.01 (s, 1H).

EXAMPLE 321

6-Isopropyl-4-trifluoromethyl-2(1H)-quinolinone (Compound 615, Structure 102 of Scheme XIX, Where $R^1$=$R^3$=$R^4$=H, $R^2$=Isopropyl)

This compound was prepared in a similar fashion as that described in Example 1, General Procedure I but using 4-isopropylaniline (Structure 101 of Scheme XIX, where $R^2$=isopropyl, $R^3$=$R^4$=H) in place of Compound 200. Compound 615 was isolated as a white solid: $^1$H NMR (400 MHz, CDCl$_3$) 10.60 (s, 1H), 7.64 (s, 1H), 7.50 (d, J=8.1, 1H), 7.27 (d, J=8.1, 1H), 7.06 (s, 1H), 5.45 (q, J=5.6, 1H), 1.43 (d, J=5.6, 6H).

EXAMPLE 322

6-Cyclohexyl-4-trifluoromethyl-2(1H)-quinolinone (Compound 616, Structure 102 of Scheme XIX, Where $R^1=R^3=R^4=H$, $R^2=$Cyclohexyl)

This compound was prepared in a similar fashion as that described in Example 1, General Procedure I but using 4-cyclohexylaniline (Structure 101 of Scheme XIX, where $R^2=$cyclohexyl, $R^3=R^4=H$) in place of Compound 200. Compound 616 was isolated as a white solid: $^1$H NMR (400 MHz, CDCl$_3$) 11.75 (bs, 1H), 7.62 (s, 1H), 7.49 (dd, J=8.4, 1.5, 1H), 7.42 (d, J=8.7, 1H), 7.08 (s, 1H), 2.60 (bt, 1H), 1.90 (m, 4H), 1.78 (m, 1H), 1.43 (m, 4H), 1.26 (m, 1H).

EXAMPLE 323

6-(1-trans-Propenyl)-4-trifluoromethyl-2(1H)-quinolinone (Compound 617, Structure 102 of Scheme XIX, Where $R^1=R^3=R^4=H$, $R^2=$1-Propenyl)

This compound was prepared in a similar fashion as that described in Example 1, General Procedure I but using 4-(1-trans-propenyl)aniline (Structure 101 of Scheme XIX, where $R^2=$1-trans-propenyl, $R^3=R^4=H$) in place of Compound 200. Compound 617 was isolated as a white solid: $^1$H NMR (400 MHz, acetone-d$_6$) 11.60 (s, 1H), 7.76 (dd, J=8.6, 1.6, 1H) 7.65 (s, 1H), 7.48 (d, J=8.6, 1H), 6.93 (s, 1H), 6.54 (d, J=15.8, 1H), 6.38–6.32 (m, 1H), 1.88 (dd, J=6.4, 1.3, 3H).

EXAMPLE 324

6-Cyclohexyl-3-fluoro-4-trifluoromethyl-2(1H)-quinolinone (Compound 618, Structure 102 of Scheme XIX, Where $R^1=$Fluorine, $R^2=$Cyclohexyl $R^3=R^4=H$)

This compound was prepared in a similar fashion as that described in Example 1, General Procedure I but using 4-cyclohexylaniline (Structure 101 of Scheme XIX, where $R^2=$cyclohexyl, $R^3=R^4=H$) and ethyl 2,4,4,4-tetrafluoroacetoacetate in place of Compound 200 and 4,4,4-trifluoroacetoacetate. Compound 618 was isolated as a white solid: $^1$H NMR (400 MHz, DMSO-d$_6$) 12.48 (bs, 1H), 7.49 (m, 2H), 77.38 (d, J=7.6, 1H), 2.59 (m, 1H), 1.81 (m, 4H), 1.70 (m, 2H), 1.40 (m, 4H).

EXAMPLE 325

7-Fluoro-6-methyl-4-trifluoromethyl-2(1H)-quinolinone (Compound 619, Structure 102 of Scheme XIX, Where $R^1=R^3=H$, $R^2=$Methyl, $R^4=$Fluoro)

This compound was prepared in a similar fashion as that described in Example 1, General Procedure I but using 3-fluoro-4-methylaniline (Structure 101 of Scheme XIX, where $R^3=H$, $R^2=$methyl, $R^4=$fluoro) and 4,4,4-trifluoroacetoacetate in place of Compound 200. Compound 619 was isolated as a white solid: $^1$H NMR (400 MHz, acetone-d$_6$) 11.22 (s, 1H), 7.67 (d, J=7.3, 1H), 7.20 (d, J=10.6, 1H), 6.86 (s, 1H), 2.35 (d, J=1.4, 3H).

EXAMPLE 326

7-Difluoro-4-trifluoromethyl-2(1H)-quinolinone (Compound 620, Structure 102 of Scheme XIX, Where $R^1=R^2=H$, $R^3=R^4=$Fluoro)

This compound was prepared in a similar fashion as that described in Example 1, General Procedure I but using 3,5-difluoroaniline (Structure 101 of Scheme XIX, where $R^2=H$, $R^3=R^4=$fluoro) and 4,4,4-trifluoroacetoacetate in place of Compound 200. Compound 620 was isolated as a white solid: $^1$H NMR (400 MHz, acetone-d$_6$) 11.50 (s, 1H), 7.15 (dd, J=8.6, 2.5, 1H), 7.13–7.01 (m, 2H).

EXAMPLE 327

6-Methoxy-4-trifluoromethyl-2(1H)-quinolinone (Compound 621, Structure 102 of Scheme XIX, Where $R^1=R^3=R^4=H$, $R^2=$Methoxy)

This compound was prepared in a similar fashion as that described in Example 1, General Procedure I but using 4-methoxyaniline (Structure 101 of Scheme XIX, where $R^2=$methoxy, $R^3=R^4=H$) and 4,4,4-trifluoroacetoacetate in place of Compound 200. Compound 621 was isolated as a white solid: $^1$H NMR (400 MHz, acetone-d$_6$) 7.50 (d, J=9.0, 1H), 7.33 (dd, J=9.0 and 2.5, 1H), 7.19 (d, J=2.5, 1H), 6.95 (s, 1H), 3.88 (s, 3H).

EXAMPLE 328

6-Benzyloxy-4-trifluoromethyl-2(1H)-quinolinone (Compound 623, Structure 104 of Scheme XIX, Where $R^5=$Benzyl)
6-Hydroxy-4-trifluoromethyl-2(1H)-quinolinone (Compound 622, Structure 103 of Scheme XIX):

To a solution of Compound 621 (Structure 102 of Scheme XIX, where $R^1=R=R^4=H$, $R^2=$methoxy) (0.20 g, 0.82 mmol) in CH$_2$Cl$_2$ was added BBr$_3$ and the reaction mixture was allowed to stir at rt overnight. The reaction was quenched with H$_2$SO$_4$ (1 M aqueous), extracted with EtOAc and washed with NaHCO$_3$ (sat. aqueous). Recrystallization afforded Compound 622 (0.17 g, 88%) as a yellow solid: $^1$H NMR (400 MHz, acetone-d$_6$) 1.10 (bs, 1H), 8.75 (s, 1H), 7.43 (d, J=8.7, 1H), 7.30–7.18 (m, 2H), 6.93 (s, 1H).
6-Benzyloxy-4-trifluoromethyl-2(1H)-quinolinone (Compound 623, Structure 103 of Scheme XIX, where $R^5=$Benzyl):

A mixture of Compound 622, benzyl bromide (1 equiv) and Na$_2$CO$_3$ in acetone was stirred at rt overnight. Standard procedure afforded Compound 623 as a white solid: $^1$H NMR (400 MHz, acetone-d$_6$) 11.36 (s, 1H), 7.52–7.47 (m, 4H), 7.42–7.22 (m, 4H), 7.27 (s, 1H), 5.21 (s, 2H).

EXAMPLE 329

6-(3-Pentyloxy)-4-trifluoromethyl-2(1H)-quinolinone (Compound 624, Structure 104 of Scheme XIX, Where $R^5=$3-Pentyl)

A mixture of Compound 622 (Structure 103 of Scheme XVIII), 3-bromopentane and sodium hydride in DMF was heated at 130° C. for 2 h. The reaction was quenched with water and extracted with EtOAc. Removal of solvent followed by chromatography provided Compound 624 as a pale yellow solid: $^1$H NMR (400 MHz, acetone-d$_6$) 11.60 (s, 1H), 7.48 (d, J=9.0, 1H), 7.34 (dd, J=9.0, 2.5, 1H), 7.21 (s, 1H), 6.97 (s, 1H), 6.94 (s, 1H), 4.26–4.23 (m, 1H), 1.74–1.67 (m, 4H), 0.97 (t, J=7.4, 6H).

EXAMPLE 330

6-(1-Hydroxy-3,3,5,5-tetramethyl)cyclohexyl-4-trifluoromethyl-2(1H)-quinolinone (Compound 625, Structure 105 of Scheme XX, Where $R=R^1=R^2=R^5=R^6=H$, $R^3=R^4=$Methyl, n=1, Z=—CH$_2$CMe$_2$—)

This Compound was Prepared by the Following General Procedure XIX (Alkylation of an Arylbromide by a Ketone):

A solution of an arylbromide in dry THF (0.1–0.5 M) is cooled to −70° C. under a $N_2$ atmosphere. The aryl bromide is then treated, if needed for amide deprotonation, with n-BuLi (1.2 equiv) and stirred at −70° C. for 15 min before the addition of n-BuLi (1.2 equiv), the reaction mixture was allowed to stir an additional 20 min at −70° C., warmed to −30° C., where the dianion is then quenched with a ketone (2.0 equiv). The reaction mixture is then warmed to room temperature overnight, diluted with water and extracted with EtOAc (3×20 mL/mmol). The combined organic extracts were then washed with Brine (20 mL/mmol), dried (MgSO$_4$), filtered and concentrated. Purification by trituration (EtOAc/hexane, 20%) or recrystallization (MeOH) afforded the desired alcohol.

Compound 625 was prepared from Compound 308 (Structure 16a of Scheme XX, where R=R$^1$=H) as a white solid: $^1$H NMR (400 MHz, CDCl$_3$) 7.99 (s, 1H), 7.73 (d, J=8.8, 1H), 7.37 (d, J=8.8, 1H), 7.08 (s, 1H), 2.13 (s, 1H), 1.61 (m, 4H), 1.34 (s, 6H), 1.26 (m, 2H), 0.97 (s, 6H).

EXAMPLE 331

6-(3,3,5,5-Tetramethyl)cyclohexenyl-4-trifluoromethyl-2(1H)-quinolinone (Compound 626, Structure 106 of Scheme XX, Where R=R$^1$=R$^2$=R$^5$=R$^6$=H, R$^3$=R$^4$=Methyl, n=1, Z=—CH$_2$CMe$_2$—)

This compound was prepared by the following General Procedure XX (Dehydration of an alcohol):

A solution of the benzylic alcohol, such as Compound 625 (Structure 105 of Scheme XX, where R=R$^1$=R$^2$=R$^5$=R$^6$32 H, R$^3$=R$^4$=Methyl, n=1, Z=—CH$_2$CMe$_2$—), in CH$_2$Cl$_2$ (0.1M) is treated with trifluoroacetic acid (excess) or TsOH and stirred for 2 h at room temperature. The reaction mixture is then poured into cool saturated NaHCO$_3$ solution and the pH adjusted to pH 7. The reaction solution is then partitioned and the aqueous layer is extracted with CH$_2$Cl$_2$ (3×15 mL/mmol). The combined organic layers are then washed with water (10 mL/mmol), Brine (10 mL/mmol), dried (MgSO$_4$), filtered and concentrated to give crude olefin product. Purification by recrystallization (MeOH/EtOAc) gives pure olefin product in good yield.

Compound 626 was isolated as a white solid: $^1$H NMR (400 MHz, CDCl$_3$) 7.74 (s, 1H), 7.67 (d, J=8.0, 1H), 7.42 (d, J=8.0, 1H), 7.11 (s, 1H), 5.83 (s, 1H), 2.23 (s, 2H), 1.44 (s, 2H), 1.12 (s, 6H), 1.06 (s, 6H).

EXAMPLE 332

6-(5,5-Dimethycyclopentenyl)-4-trifluoromethyl-2 (1H)-quinolinone (Compound 627, Structure 106 of Scheme XX, Where R=R$^1$=R$^2$=R$^3$=R$^4$=H, R$^5$=R$^6$=Methyl, n=1, Z=Methylene)

This compound was prepared in a similar fashion as that described in Examples 330 and 331, General Procedures XIX and XX but using 2,2-dimethylcyclopentanone in place of 3,3,5,5-tetramethylcyclohexanone. Compound 627 was isolated as a white solid: $^1$H NMR (400 MHz, CDCl$_3$) 7.80 (s, 1H), 7.60 (d, J=8.0, 1H), 7.39 (d, J=8.0, 1H), 7.11 (s, 1H), 5.85 (t, J=4.0, 1H), 2.41 (td, J=4.0, J=8.0, 2H), 1.90 (t, J=8.0, 2H), 1.23 (s, 6H).

EXAMPLE 333

(±)-6-(2 2-Dimethycyclopentyl)-4-trifluoromethyl-2 (1H)-quinolinone (Compound 628, Structure 107 of Scheme XX, Where R=R$^1$=R$^2$=R$^3$=R$^4$=H, R$^5$=R$^6$=Methyl, n=1, Z=Methylene)

This compound was prepared in a similar fashion as that described in Example 1 General Procedure III from Compound 627 (Structure 106 of Scheme XX, where R=R$^1$=R$^2$=R$^3$=R$^4$=H, R$^5$=R$^6$=methyl, n=1, Z=methylene). Compound 628 was isolated as a white solid: $^1$H NMR (400 MHz, CDCl$_3$) 11.25 (br s, 1H), 7.62 (s, 1H), 7.45 (d, J=8.0, 1H), 7.30 (d, J=8.0, 1H), 7.07 (s, 1H), 2.79 (t, J=8.0, 2H), 2.06 (m, 2H), 1.86 (m, 2H), 1.62 (m, 2H), 1.00 (s, 3H), 0.62 (s, 3H).

EXAMPLE 334

6-(1-Hydroxycyclohexyl)-4-trifluoromethyl-2(1H)-quinolinone (Compound 629, Structure 105 of Scheme XX, Where R=R$^1$=R$^2$=R$^3$=R$^4$=R$^5$=R$^6$=H, n=2, Z=Methylene)

This compound was prepared according to General Procedure XIX in Example 330 from Compound 308 (Structure 16a of Scheme XX, where R=R$^1$=H) (1.0 g, 3.4 mmol) and cyclohexanone (0.71 mL, 6.8 mmol) to yield 485 mg (46%) of Compound 629 as a white solid: $^1$H NMR (400 MHz, DMSO-d$_6$) 12.26 (s, 1H), 7.88 (s, 1H), 7.75 (dd, J=8.7, 1.5, 1H), 7.38 (d, J=8.6, 1H), 6.96 (s, 1H), 4.91 (s, 1H), 1.77–1.62 (mm, 8H), 1.59–1.49 (m, 2H).

EXAMPLE 335

6-Cyclohexenyl-4-trifluoromethyl-2(1H)-quinolinone (Compound 630, Structure 106 of Scheme XX, Where R=R$^1$=R$^2$=R$^3$=R$^4$=R$^5$=R$^6$=H, n=2, Z=Methylene)

Compound 630 was prepared according to General Procedure XX in Example 331 by dehydration of Compound 629 (Structure 105 of Scheme XX, where R=R$^1$=R$^2$=R$^3$=R$^4$=R$^5$=R$^6$=H, n=2, Z=methylene) (1.0 g, 3.4 mmol) in 83% yield as a white solid: $^1$H NMR (400 MHz, CDCl$_3$) 11.07 (bs, 1H), 7.77 (s, 1H), 7.65 (dd, J=8.4, 1.5, 1H), 7.29 (d, J=8.6, 1H), 7.07 (s, 1H), 6.17 (bt, 1H), 2.43 (m, 2H), 2.25 (m, 2H), 1.81 (m, 2H), 1.68 (m, 2H).

EXAMPLE 336

6-Cyclohexyl-4-trifluoromethyl-2(1H)-thioquinolinone (Compound 631, Structure 108 of Scheme XX, Where R$^4$=R$^5$=H, n=2, Z=Methylene)

In 10-mL r.b. flask, a solution of Compound 616 (Structure 107 of Scheme XX, where R=R$^{1-6}$=H, n=2, Z=methylene) (39 mg, 0.13 mmol) in toluene (2 mL) was treated with Lawsson's reagent (66 mg, 0.16 mmol, 1.2 equiv). The reaction mixture was then stirred at room temperature overnight, diluted with EtOAc (80 mL), washed with sat. NaHCO$_3$ (15 mL), water (15 mL), Brine (15 mL), dried (MgSO$_4$), filtered and concentrated under reduced pressure to yield crude product. Purification by column chromatography (15% EtOAc/hexane) afforded 30 mg (73%) of Compound 631 as a yellow solid: $^1$H NMR (400 MHz, CDCl$_3$) 11.82 (bs, 1H), 7.71 (s, 1H), 7.65 (s, 1H), 7.53 (dd, J=8.6, 1.6, 1H), 7.39 (d, J=8.6, 1H), 2.62 (bs, 1H), 1.89–1.76 (mm, 6H), 1.45–1.40 (m, 4H).

EXAMPLE 337

6-Cyclopentenyl-4-trifluoromethyl-2(1H)-quinolinone (Compound 632, Structure 106 of Scheme XX, Where R=R$^1$=R$^2$=R$^3$=R$^4$=R$^5$=R$^6$=H, n=1, Z=Methylene)

This compound was made according to General Procedures XIX and XX in Examples 330 and 331 from Compound 308 (Structure 16a of Scheme XX, where R=R¹=H) (50 mg, 0.17 mmol) and cyclopentanone (0.02 mL, 0.26 mmol) to yield 15 mg (31%) of Compound 632 as white solid: $^1$H NMR (400 MHz, DMSO-d$_6$) 12.36 (bs, 1H), 7.88 (dd, J=8.7, 1.4, 1H), 7.55 (s, 1H), 7.41 (d, J=8.7, 1H), 6.99 (s, 1H), 6.33 (bm, 1H), 2.68 (m, 2H), 2.51 (m, 2H), 1.99 (m, J=6.6, 2H).

EXAMPLE 338

6-Cycloheptenyl-4-trifluoromethyl-2(1H)-quinolinone (Compound 633, Structure 106 of Scheme XX, Where R=R¹=R²=R³=R⁴=R⁵=R⁶=H, n=3, Z=Methylene)

Compound 633 was made according to General Procedures XIX and XX in Examples 330 and 331 from Compound 308 (Structure 16a of Scheme XX, where R=R¹=H) and cycloheptanone as a white solid: $^1$H NMR (400 MHz, DMSO-d$_6$) 12.31 (s, 1H), 7.63 (d, J=8.7, 1H), 7.51 (s, 1H), 7.39 (d, J=8.6, 1H), 6.98 (s, 1H), 6.11 (t, J=6.7, 1H), 2.57 (m, 2H), 2.29 (m, 2H), 1.80 (m, 2H), 1.60 (m, 2H), 1.51 (m, 2H).

EXAMPLE 339

6-Bromo-3-fluoro-4-trifluoromethyl-2(1H)-quinolinone (Compound 634, Structure 16a of Scheme XX, Where R=Fluorine, R¹=H)

In a 100-mL flask a solution of 4-bromoaniline (20 g, 116 mmol) and ethyl-4,4,4-trifluoroacetoacetate (25.5 mL, 175 mmol, 1.5 equiv) in toluene (5 mL) is heated to reflux for 5 h, cooled and excess solvent removed to provide N-(4-bromophenyl)-4,4,4-trifluoroacetoacetamide (Structure 15 of Scheme XX). The crude reaction mixture is then dissolved in CH$_2$Cl$_2$ (40 mL) and water (10 mL) and then treated with N-fluorobenzenesulfonimide (1.1 equiv) at room temperature overnight. The reaction mixture is then diluted with water (30 mL) and partitioned. The aqueous layer is extracted with CH$_2$Cl$_2$ (3×75 mL), the combined organic layers are then washed with sat NaHCO$_3$ (25 mL), saturated NH$_4$Cl (2×25 mL), water (25 mL), Brine (25 mL), dried (MgSO$_4$), filtered and concentrated to afford N-(4-bromophenyl)-2,4,4,4-tetrafluoroacetoacetamide (Structure 15a of Scheme XX). The crude product was then dissolved in concentrated H$_2$SO$_4$ (10 mL) and heated to 80° C. for 3–4 h, cooled to room temperature, and poured over NaOH pellets/ice. The cold aqueous solution was then filtered, the white precipitate was then redissolved in EtOAc (200 mL), washed with water (2×20 mL), Brine (25 mL), dried (MgSO$_4$), filtered and concentrated to yield Compound 634 as a white powder: $^1$H NMR (400 MHz, DMSO-d$_6$) 12.92 (bs, 1H), 7.83 (dd, J=8.0, 1.2, 1H), 7.77 (s, 1H), 7.41 (d, J=7.9, 1H).

EXAMPLE 340

6-Cyclohexenyl-3-fluoro-4-trifluoromethyl-2(1H)-quinolinone (Compound 635, Structure 106 of Scheme XX, Where R=Fluorine, R¹=R²=³=R⁴=R⁵=R⁶=H, n=2, Z=Methylene)

Compound 635 was made according to General Procedures XIX and XX in Examples 330 and 331 from Compound 634 (Structure 16a of Scheme XX, where R=fluorine, R¹=H) (50 mg, 0.16 mmol) and cyclohexanone (0.030 mL, 0.24 mmol) as a white solid in 20% yield: $^1$H NMR (400 MHz, DMSO-d$_6$) 12.80 (s, 1H), 7.72 (d, J=8.7, 1H), 7.59 (s, 1H), 7.38 (d, J=8.6, 1H), 6.18 (s, 1H), 2.37 (m, 2H), 2.19 (m, 2H), 1.74 (m, 2H), 1.62 (m, 2H).

EXAMPLE 341

6-Cyclohexyl-7-methoxy-4-trifluoromethyl-2(1H)-quinolinone (Compound 636, Structure 107 of Scheme XX, Where R=R²=R=R⁴=R⁵=R⁶=H, R¹=Methoxy, n=2, Z=Methylene)

6-Bromo-7-methoxy-4-trifluoromethyl-2(1H)-quinolinone (Compound 637, Structure 16a of Scheme XX, Where R=H, R¹=Methoxy):

To a 100-mL r.b. flask containing Compound 419 (Structure 29a of Scheme XX) (1.0 g, 4.11 mmol) in DMF (40 mL) was added, in portions, NBS (0.84 g, 4.73 mmol, 1.15 equiv). The reaction was allowed to stir overnight and poured into water (25 mL), the resulting precipitate was collected by vacuum filtration to yield 1.0 g (76%) of Compound 637: $^1$H NMR (400 MHz, DMSO-d$_6$) 12.31 (bs, 1H), 7.76 (s, 1H), 7.06 (s, 1H), 6.87 (s, 1H), 3.93 (s, 3H).

6-Cyclohexyl-7-methoxy-4-trifluoromethyl-2(1H)-quinolinone (Compound 636, Structure 107 of Scheme XX, Where R=R²=R=R⁴=R⁵=R⁶=H, R¹=Methoxy, n=2, Z=Methylene):

This compound is prepared according to General Procedures XIX, XX, and III in Examples 330, 331 and 1 from Compound 637 (350 mg) and cyclohexanone as a white solid in 38% yield: $^1$H NMR (400 MHz, DMSO-d$_6$) 12.17 (bs, 1H), 7.30 (s, 1H), 6.95 (s, 1H), 6.78 (s, 1H), 5.71 (bs, 1H), 3.84 (s, 3H), 2.28 (m, 2H), 2.14 (m, 2H), 1.67–1.63 (m, 4H).

EXAMPLE 342

6-Cyclopentyl-3-fluoro-4-trifluoromethyl-2(1H)-quinolinone (Compound 638, Structure 107 of Scheme XX, Where R=Fluorine, R¹=R²=³=R⁴=R⁵=R⁶=H, n=1, Z=Methylene)

Compound 638 was made according to General Procedures XIX, XX, and III in Examples 330, 331 and 1 from Compound 634 (Structure 16a of Scheme XX, where R=fluorine, R¹=H) and cyclopentanone as a white solid: $^1$H NMR (400 MHz, DMSO-d$_6$) 7.53 (m, 2H), 7.38 (d, J=8.4, 1H), 3.07 (quint., J=8.2, 1H), 2.03 (m, 2H), 1.78 (m, 2H), 1.66 (m, 2H), 1.53 (m, 2H).

EXAMPLE 343

(Z)-6-(1-Propyl-1-butenyl)-4-trifluoromethyl-2(1H)-quinolinone (Compound 639, Structure 106 of Scheme XX, Where R=R¹=R²=R³=R⁵=H, R⁴=Methyl, R⁶=Ethyl, n=1, Z=Two No-bond Hydrogens) and (E)-6-(1-Propyl-1-)butenyl-4-trifluoromethyl-2(1H)-quinolinone (Compound 640, Structure 106 of Scheme XX, Where R=R¹=R²=R³=R⁵=H, R⁴=Methyl, R⁶=Ethyl, n=1, Z=Two No-bond Hydrogens)

Compounds 639 and 640 were made according to General Procedures Procedures XIX and XX in Examples 330 and 331 from Compound 308 (Structure 16a of Scheme XX, where R=R¹=H) and 3-hexanone as a 1/2 mixture of E/Z isomers, Z-isomer: $^1$H NMR (400 MHz, CDCl$_3$) 11.10 (s, 1H), 7.74 (s, 1H), 7.60 (d, J=8.6, 1.5, 1H), 7.40 (d, J=8.6, 1H), 7.06 (s, 1H), 5.70 (t, J=7.2, 1H), 2.50 (t, J=7.4, 2H), 2028–2.20 (m, 2H), 1.46–1.13 (m, 2H), 1.00 (t, J=7.5, 3H), 0.88 (t, J=7.3, 3H); E-isomer: $^1$H NMR (400 MHz, CDCl$_3$) 11.10 (s, 1H), 7.58 (s, 1H), 7.40 (d, J=8.2, 1H), 7.32 (d, J=8.2, 1H), 7.06 (s, 1H), 5.53 (t, J=6.9, 1H), 2.33 (t, J=7.5, 2H), 1.96–1.78 (m, 2H), 1.46–1.31 (m, 2H), 0.96 (t, J=7.4, 3H), 0.87 (t, J=7.3, 3H).

EXAMPLE 344

6-(1-Propyl)butyl-4-trifluoromethyl-2(1H)-quinolinone (Compound 641, Structure 107 of Scheme XX, Where R=$R^1$=$R^2$=$R^3$=$R^5$=H, $R^4$=Methyl, $R^6$=Ethyl, n=1, Z=Two No-bond Hydrogens)

This compound was prepared in a similar fashion as that described in Example 1, General Procedure III by hydrogenation of Compounds 639 and 640 (Structure 106 of Scheme XX, where R=$R^1$=$R^2$=$R^3$=$R^5$=H, $R^4$=methyl, $R^6$=ethyl, n=1, Z=two no-bond hydrogens). Compound 641 was isolated as white solid: $^1$H NMR (400 MHz, CDCl$_3$) 11.24 (s, 1H), 7.55 (s, 1H), 7.41 (d, J=8.5, 1H), 7.28 (d, J=8.5, 1H), 7.07 (s, 1H), 2.65–2.60 (m, 1H), 1.69–1.51 (m, 4H), 1.22–1.10 (m, 4H), 0.85 (t, J=7.3, 6H).

EXAMPLE 345

(E)-6-(1-Methyl-1-)butenyl-4-trifluoromethyl-2(1H-quinolinone (Compound 642, Structure 106 of Scheme XX, Where R=$R^1$=$R^2$=$R^3$=$R^4$=$R^5$=H, $R^6$=Ethyl, n=1, Z=Two No-bond Hydrogens) and (Z)-6-(1-Methyl-1-)butenyl-4-trifluoromethyl-2(1H)-quinolinone (Compound 643, Structure 106 of Scheme XX, Where R=$R^1$=$R^2$=$R^3$=$R^4$=$R^5$=H, $R^6$=Ethyl, n=1, Z=Two No-bond Hydrogens)

Compounds 642 and 643 were made according to General Procedures XIX and XX in Examples 330 and 331 from Compound 308 (Structure 16a of Scheme XX, where R=$R^1$=H) and 2-pentanone as a 5/2 mixture of E/Z isomers: E-isomer: $^1$H NMR (400 MHz, CDCl$_3$) 10.97 (s, 1H), 7.78 (s, 1H), 7.67 (d, J=8.5, 1H), 7.28 (d, J=8.5, 1H), 7.07 (s, 1H), 5.81 (t, J=7.2, 1H), 2.25 (m, 2H), 2.10 (s, 3H), 1.09 (t, J=7.6, 3H); Z-isomer: $^1$H NMR (400 MHz, CDCl$_3$) 11.43 (s, 1H), 7.64 (d, J=1.3, 1H), 7.46 (dd, J=8.6, 1.3, 1H), 7.33 (d, J=8.6, 1H), 7.08 (s, 1H), 5.56 (t, J=7.4, 1H), 2.06 (s, 3H), 2.01–1.94 (m, 2H), 0.96 (t, J=7.4, 3H).

EXAMPLE 346

(±)-6-(1-Methyl)butyl-4-trifluoromethyl-2(1H)-quinolinone (Compound 644, Structure 107 of Scheme XX, Where R=$R^1$=$R^2$=$R^3$=$R^4$=$R^5$=H, $R^6$=Ethyl, n=1, Z=Two No-bond Hydrogens)

This compound was prepared in a similar fashion as that described in Example 1, General Procedure III by hydrogenation of Compounds 642 and 643 (Structure 106 of Scheme XX, where R=$R^1$=$R^2$=$R^3$=$R^4$=$R^5$=H, $R^6$=ethyl, n=1, Z=two no-bond hydrogens). Compound 644 was isolated as a white solid: $^1$H NMR (400 MHz, CDCl$_3$) 11.40 (s, 1H), 7.26 (s, 1H), 7.45 (d, J=8.5, 1H), 7.33 (d, J=8.5, 1H), 7.07 (s, 1H), 2.82–2.78 (m, 1H), 1.58 (q, J=7.7, 2H), 1.25 (d, J=4.1, 3H), 1.20–1.10 (m, 2H), 0.88 (t, J=7.2, 3H).

EXAMPLE 347

(E)-6-(1-Ethyl-1-)propenyl-4-trifluoromethyl-2(1H)-quinolinone (Compound 645, Structure 106 of Scheme XX, Where R=$R^1$=$R^2$=$R^3$=$R^4$=$R^5$=H, $R^6$=Methyl, n=1, Z=Two No-bond Hydrogens) and (Z)-6-(1-Ethyl-1-)propenyl-4-trifluoromethyl-2(1H)-quinolinone (Compound 646, Structure 106 of Scheme XX, Where R=$R^1$=$R^2$=$R^3$=$R^4$=$R^5$=H, $R^6$=Methyl, n=1, Z=Two No-bond Hydrogens)

Compounds 645 and 646 were made according to General Procedures XIX and XX in Examples 330 and 331 from Compound 308 (Structure 16a of Scheme XX, where R=$R^1$=H) and 3-pentanone as a 2/3 mixture of E/Z isomers: E-isomer: $^1$H NMR (400 MHz, CDCl$_3$) 11.10 (s, 1H), 7.62–7.59 (m, 1H), 7.42 (d, J=8.8, 1H), 7.33 (d, J=8.8, 1H), 7.08 (s, 1H), 5.77 (q, J=7.1, 1H), 2.55 (q, J=7.8, 2H), 1.83 (d, J=7.1, 3H), 1.02 (m, 3H); Z-isomer: $^1$H NMR (400 MHz, CDCl$_3$) 11.10 (s, 1H), 7.75 (s, 1H), 7.42 (d, J=8.8, 1H), 7.33 (d, J=8.8, 1H), 7.07 (s, 1H), 5.63 (q, J=6.9, 1H), 2.38 (q, J=7.8, 2H), 1.52 (d, J=7.1, 3H), 1.02 (m, 3H).

EXAMPLE 348

6-(1-Ethylpropyl)-4-trifluoromethyl-2(1H)-quinolinone (Compound 647, Structure 107 of Scheme XX, Where R=$R^1$=$R^2$=$R^3$=$R^4$=$R^5$=H, $R^6$=Methyl, n=1, Z=Two No-bond Hydrogens)

This compound was prepared in a similar fashion as that described in Example 1, General Procedure III by hydrogenation of Compounds 645 and 646 (Structure 106 of Scheme XX, where R=$R^1$=$R^2$=$R^3$=$R^4$=$R^5$=H, $R^6$=methyl, n=1, Z=two no-bond hydrogens). Compound 476 was isolated as white solid: $^1$H NMR (400 MHz, CDCl$_3$) 12.01 (s, 1H), 7.56 (s, 1H), 7.41 (dd, J=8.3, 1.5, 1H), 7.39 (d, J=8.3, 1H), 7.08 (s, 1H), 2.87–2.68 (m, 1H), 1.52–1.25 (m, 4H), 0.78 (t, J=7.3, 6H).

EXAMPLE 349

6-(1-Isopropyl-2-methyl-1-)propenyl-4-trifluoromethyl-2(1H)-quinolinone (Compound 648, Structure 106 of Scheme XX, Where R=$R^1$=$R^3$=$R^4$=H, $R^2$=$R^5$=$R^6$=Methyl, n=1, Z=Two No-bond Hydrogens)

Compound 648 was made according to General Procedures XIX and XX in Examples 330 and 331 from Compound 308 (Structure 16a of Scheme XX, where R=$R^1$=H) and 2,4-dimethyl-3-pentanone as a white solid: $^1$H NMR (400 MHz, CDCl$_3$) 11.10 (s, 1H), 7.47 (d, J=8.4, 1H), 7.45 (s, 1H), 7.27 (d, J=8.4, 1H), 7.11 (s, 1H), 3.12–3.07 (m, 1H), 1.85 (s, 3H), 1.38 (s, 3H), 0.88 (d, J=6.8, 6H).

EXAMPLE 350

6-(1-Isopropyl-2-methyl)propyl-4-trifluoromethyl-2(1H)-quinolinone (Compound 649, Structure 107 of Scheme XX, Where R=$R^1$=$R^3$=$R^4$=H, $R^2$=$R^5$=$R^6$=Methyl, n=1, Z=Two No-bond Hydrogens)

This compound was prepared in a similar fashion as that described in Example 1, General Procedure III by hydrogenation of Compound 648 (Structure 106 of Scheme XX, where R=$R^1$=$R^3$=$R^4$=H, $R^2$=$R^5$=$R^6$=methyl, n=1, Z=two no-bond hydrogens). Compound 649 was isolated as white solid: $^1$H NMR (400 MHz, CDCl$_3$) 11.10 (s, 1H), 7.52 (s, 1H), 7.36 (d, J=8.5, 1H), 7.31 (d, J=8.5, 1H), 7.07 (s, 1H), 2.21–2.15 (m, 3H), 0.87 (d, J=6.5, 6H), 0.74 (d, J=6.5, 6H).

EXAMPLE 351

(Z)-6-(1-Isobutyl-3-methyl-1-)butenyl-4-trifluoromethyl-2(1H)-quinolinone (Compound 650, Structure 106 of Scheme XX, Where R=$R^1$=$R^2$=$R^5$=H, $R^3$=$R^4$=Methyl, $R^6$=Isopropyl, n=1, Z=Two No-bond Hydrogens) and (E)-6-(1-Isobutyl-3-methyl-1-)butenyl-4-trifluoromethyl-2(1H)-quinolinone (Compound 651, Structure 106 of Scheme XX, Where R=$R^1$=$R^2$=$R^5$=H, $R^3$=$R^4$=Methyl, $R^6$=Isopropyl, n=1, Z=Two No-bond Hydrogens)

Compound 650 was made according to General Procedures XIX and XX in Examples 330 and 331 from Compound 308 (Structure 16a of Scheme XX, where R=$R^1$=H) and 2,6-dimethyl-4-heptanone as a white solid: $^1$H NMR (400 MHz, CDCl$_3$) 11.10 (s, 1H), 7.58 (s, 1H), 7.40 (s, 2H), 7.09 (s, 1H), 5.31 (d, J=10.1, 1H), 2.32–2.24 (m, 1H), 2.24 (d, J=7.2, 2-H), 1.49–1.44 (m, 1H), 0.94 (d, J=6.6, 6H), 0.84 (d, J=6.6, 6H).

Compound 651 was also isolated as a white solid: $^1$H NMR (400 MHz, CDCl$_3$) 11.10 (s, 2H), 7.73 (s, 1H), 7.62 (s, 1H), 7.11 (s, 1H), 5.53 (d, J=9.6, 1H), 2.78–2.69 (m, 1H), 2.44 (d, J=7.2, 2H), 1.60–1.51 (m, 1H), 1.06 (d, J=6.6, 6H), 0.84 (d, J=6.6, 6H).

EXAMPLE 352

6-Isobutyl-3-methyl)butyl-4-trifluoromethyl-2(1H)-quinolinone (Compound 652, Structure 107 of Scheme XX, Where R=$R^1$=$R^2$=$R^5$32 H, $R^3$=$R^4$=Methyl, $R^6$=Isopropyl, n=1, Z=Two No-bond Hydrogens)

This compound was prepared in a similar fashion as that described in Example 1, General Procedure III by hydrogenation of Compound 650 (Structure 106 of Scheme XX, where R=$R^1$=$R^2$=$R^5$=H, $R^3$=$R^4$=methyl, $R^6$=isopropyl, n=1, Z=two no-bond hydrogens). Compound 652 was isolated as a white solid: $^1$H NMR (400 MHz, CDCl$_3$) 11.31 (s, 1H), 7.56 (s, 1H), 7.41 (d, J=8.2, 1H), 7.35 (d, J=8.2, 1H), 7.04 (s, 1H), 2.82–2.78 (m, 1H), 1.55–1.38 (m, 4H), 1.32–1.25 (m, 2H), 0.86 (d, J=6.4, 6H), 0.81 (d, J=6.4, 6H).

EXAMPLE 353

6-(1-Propyl)butyl-4-trifluoromethyl-2(1H)-thioquinolinone (Compound 653, Structure 108 of Scheme XX, Where $R^4$=$R^5$=Methyl, n=1, Z=Two No-bond Hydrogens)

This compound was prepared in a similar method as that described in Example 95, General Procedure XI but using Compound 641 (Structure 107 of Scheme XX, where R=$R^1$=$R^2$=$R^3$=$R^5$=H, $R^4$=methyl, $R^6$=ethyl, n=1, Z=two no-bond protons) in place of Compound 209. Compound 653 was isolated as a yellow solid: $^1$H NMR (400 MHz, CDCl$_3$) 11.91 (s, 1H), 7.76 (s, 1H), 7.69 (s, 1H), 7.48 (d, J=8.5, 1H), 7.41 (d, J=8.5, 1H), 2.69–2.63 (m, 1H), 1.73–1.51 (m, 4H), 1.21–1.04 (m, 4H), 0.82 (t, J=7.2, 6H).

EXAMPLE 354

6-(3-Oxo-1-)Cyclopentenyl-4-trifluoromethyl-2(1H)-quinolinone (Compound 654, Structure 109 of Scheme XXI, Where R=H, $R^1$=Trifluoromethyl, n=0)

Compound 654 was made according to General Procedures XIX and XX in Examples 330 and 331 from Compound 308 (Structure 16b of Scheme XXI, where R=H) and 3-ethoxy-2-cyclopentenone as a white solid: $^1$H NMR (400 MHz, CDCl$_3$) 11.06 (s, 1H), 8.07 (s, 1H), 7.91 (d, J=8.6, 1H), 7.46 (d, J=8.8, 1H), 7.14 (s, 1H), 6.64 (s, 1H), 3.18–3.10 (m, 2H), 2.70–2.53 (m, 2H).

EXAMPLE 355

6-(3-oxo-1-)Cyclohexenyl-4-trifluoromethyl-2(1H)-quinolinone (Compound 655, Structure 109 of Scheme XXI, Where R=H, $R^1$=Trifluoromethyl, n=1)

Compound 655 was made according to General Procedures XIX and XX in Examples 330 and 331 from Compound 308 (Structure 16b of Scheme XXI, where R=H) and 3-ethoxy-2-cyclohexenone as a white solid: $^1$H NMR (400 MHz, CDCl$_3$) 11.06 (s, 1H), 7.97 (s, 1H), 7.79 (d, J=8.7, 1H), 7.47 (d, J=8.7, 1H), 7.13 (s, 1H), 6.47 (s, 1H), 2.85–2.81 (m, 2H), 2.54–2.51 (m, 2H), 2.27–2.21 (m, 2H), 2.27–2.21 (m, 2H).

EXAMPLE 356

6-(3-oxo-1-)Cyclopentenyl-3-methyl-4-difluoromethyl-2(1H)-quinolinone (Compound 656, Structure 109 of Scheme XXI, Where R=Methyl, $R^1$=Difluoromethyl, n=0)

To a suspension of Compound 308 (Structure 16b of Scheme XXI, where R=H) (250 mg, 0.90 mmol) in THF (4 mL) at −40° C., MeLi 1.4 M in ether (1.5 equiv) was added followed by n-BuLi 1.6 M in hexane (1.1 equiv). A solution of 3-ethoxy-2-cyclopentenone (1.1 equiv) in 1–5 THF (3 mL) was slowly added to this thick suspension via canula. The mixture was allowed to worm up slowly to room temperature and was allowed to stir over night. The reaction was quenched by HCl 10% until PH~1 then the organic layer was taken into EtOAC (3×20 mL), washed with brine (20 mL), and dried over Na$_2$SO$_4$. The solvent was removed under reduced pressure and the residue was crystallized out from EtOAc/EtOH. The resulting cake was further purified by HPLC reverse phase (MeOH/H$_2$O/Et$_3$N:60/40/0.5) to give Compound 656 as a white solid: $^1$H NMR (400 MHz, DMSO-d$_6$) 11.20 (s, 1H), 8.24 (d, J=1.6, 1H), 7.99 (dd, J=1.6, 8.6, 1H), 7.67 (t, J=5.1, 1H), 7.43 (d, J=8.6, 1H), 6.71 (d, J=1.3, 1H), 3.06–3.01 (m, 2H), 2.48–2.43 (m, 2H), 2.29 (s, 3H).

EXAMPLE 357

6-(3-Oxo-1-)Cyclohexenyl-3-methyl-4-difluoromethyl-2(1H)-quinolinone (Compound 657, Structure 109 of Scheme XXI, Where R=Methyl, $R^1$=Difluoromethyl, n=1)

This compound was prepared in a similar fashion as that described in Example 356 but using 3-ethoxy-2-cyclohexenone in place of 3-ethoxy-2-cyclopentenone. Compound 657 was isolated as a white solid: $^1$H NMR (400 MHz, CDCl$_3$) 10.15 (s, 1H), 8.24 (s, 1H), 7.70 (d, J=9.1, 1H), 7.27 (d, J=9.1, 1H), 7.17 (t, J=5.9, 1H), 6.48 (s, 1H), 2.85–2.78 (m, 2H), 2.55–2.49 (m, 2H), 2.42 (s, 3H), 2.24–2.18 (m, 2H).

EXAMPLE 358

(±)-6-(3-Hydroxy-1-)cyclohexenyl-4-trifluoromethyl-2(1H)-quinolinone (Compound 658, Structure 110 of Scheme XXI, Where R=H, $R^1$=Trifluoromethyl, n=1)

This compound was prepared by the following General Procedure XXI (Reduction of ketone):

To a solution of a ketone in dry THF (0.1–0.5 M) at ~78° C. was added a 2 equiv of 1.5 M DIBAL/toluene solution. After 30 min., the reaction mixture was quenched with saturated NH$_4$Cl and extracted with EtOAc. The organic layer was washed with H$_2$O (3×) and brine (3×), dried (Na$_2$SO$_4$) and concentrated in vacuo. Purification by flash chromatography afforded the alcohol as a white solid in good yield.

Compound 658 was isolated as a white solid: $^1$H NMR (400 MHz, DMSO-d$_6$) 11.20 (s, 1H), 7.77 (dd, J=8.8, 1.4, 1H), 7.62 (d, J=1.4, 1H), 7.41 (d, J=8.8, 1H), 6.99 (s, 1H), 6.10 (s, 1H), 4.82 (d, J=5.5, 2H), 2.37–2.27 (m, 2H), 1.90–1.87 (m, 2H), 1.71–1.65 (m, 1H), 1.53–1.44 (m, 1H).

EXAMPLE 359

6-(1-Hydroxy-1,1-diphenyl)methyl-4-trifluoromethyl-2(1H-quinolinone (Compound 659, Structure 111 of Scheme XXII)

Compound 659 was made according to General Procedures XIX in Examples 330 from Compound 308 (Structure 16 of Scheme XXII) and benzophenone as a white solid: $^1$H NMR (400 MHz, CDCl$_3$) 10.89 (s, 1H), 7.78 (d, J=1.8, 1H), 7.61 (dd, J=8.5, 1.8, 1H), 7.42 (d, J=8.5, 1H), 7.37–7.28 (m, 10H), 7.04 (s, 1H), 3.02 (s, 1H).

EXAMPLE 360

6-Diphenylmethyl-4-trifluoromethyl-2(1H)-quinolinone (Compound 660, Structure 112 of Scheme XXII)

To a solution of Compound 659 (Structure 111 of Scheme XXII) in dichloroethane was added an excess of TFA followed by an excess of triethylsilane. This mixture was allowed to stir over night at room temperature. Quenched by water the organic layer was taken into EtOAc washed with brine, dried over Na$_2$SO$_4$. The solvent was removed under reduced pressure. The resulting residue was purified by flash column chromatography to yield Compound 660 as a white solid: $^1$H NMR (400 MHz, CDCl$_3$) 1.10 (s, 1H), 7.55 (s, 1H), 7.41 (d, J=8.5, 1H), 7.35–7.24 (m, 10H), 7.33 (d, J=7.1, 4H), 7.04 (s, 1H), 5.63 (s, 1H).

EXAMPLE 361

6-(3-Hydroxy-3-methyl-1-)butynyl-4-trifluoromethyl-2(1H)-quinolinone (Compound 661, Structure 113 of Scheme XXII)

To a solution of Compound 308 (Structure 16 of Scheme XXII) (26 mg, 0.090 mmol), triphenylphosphine (152 mg, 0.06 mmol), CuI (4.2 mg, 0.02 mmol), 2-methyl-2-butynol (8.5 mg, 0.10 mmol) in triethylamine (1 mL) was added PdCl$_2$ (0.2 mg, 0.001 mmol) and the reaction mixture was heated at reflux for 20 min. Pyridine (0.3 mL) was added and the reaction was heated for additional hour. The reaction was quenched with 2 N HCl (20 mL), extracted with EtOAc (20 mL), and concentrated. Removal of solvent and chromatography of the crude residue afforded Compound 661 in 60% yield as a white solid: $^1$H NMR (500 MHz, DMSO-d$_6$) 12.5 (bs, 1H), 7.62 (d, J=8.8, 1H), 7.59 (s, 1H), 7.41 (d, J=8.8, 1H), 7.04 (s, 1H), 5.49 (s, 1H), 1.46 (s, 6H).

EXAMPLE 362

6-(1-Hydroxy)cyclopentyl-1,4-dihydro-4,4-dimethyl-1,3-benzo[d]oxazin-2-one (Compound 662 Structure 115 of Scheme XXIII, Where R$^4$=R$^5$=R$^6$=R$^7$=R$^8$=H, n=1, Z=Methylene) 6-Bromo-1,4-dihydro-4,4-dimethyl-1,3-benzo[d]oxazin-2-one (Compound 663, Structure 114 of Scheme XXIII):

To a solution of Compound 486 (Structure 49a of Scheme XXIII) (0.46 g, 2.6 mmol) and CCl$_4$ (20 mL) was added bromine (0.13 mL). Stirred at room temperature for 1.5 hrs. The reaction mixture was concentrated in vacuo to afford an orange solid. Washed solid with hot hexane and filtered to afford 0.61 g of Compound 663 in 91% yield as a light orange solid: $^1$H NMR (400 MHz, CDCl$_3$) 8.03 (br s, 1H), 7.37 (dd, J=1.9, 8.3, 1H), 7.26 (d under solvent peak, 1H), 6.69 (d, J=8.3, 1H), 1.71 (s, 6H).

6-(1-Hydroxy)cyclopentyl-1,4-dihydro-4,4-dimethyl-1,3-benzo[d]oxazin-2-one (Compound 662, Structure 115 of Scheme XXIII, Where R$^4$=R$^5$=R$^6$=R$^7$=R$^8$=H, n=1, Z=Methylene):

Compound 662 was prepared according to General Procedure XIX in Example 330 from Compound 663 (50 mg, 0.20 mmol) and cyclopentanone (0.02 mL, 0.24 mmol) in 44% yield (23 mg) as a white solid: $^1$H NMR (400 MHz, CD$_3$OD) 7.36 (d under dd, 2H), 6.83 (d, J=8.0, 1H), 5.48 (s, 1H), 1.95 (m, 6H), 1.83 (m, 2H), 1.67 (s, 6H).

EXAMPLE 363

6-(1-Cyclopentenyl)-1,4-dihydro-4,4-dimethyl-1,3-benzo[d]oxazin-2-one (Compound 664, Structure 116 of Scheme XXIII, Where R$^4$=R$^5$=R$^6$=R$^7$=R$^8$=H, n=1, Z=Methylene)

This compound was prepared in a similar fashion as that described in Example 331, General Procedure XX from Compound 662 (Structure 115 of Scheme XXIII, where R$^4$=R$^5$=R$^6$=R$^7$=R$^8$=H, n=1, Z=methylene). Compound 664 was isolated as a white solid: $^1$H NMR (400 MHz, CDCl$_3$) 8.14 (br s, 1H), 7.30 (dd, J=1.4, 8.3, 1H), 7.18 (d, J=1.4, 1H), 6.75 (d, J=8.3, 1H), 6.12 (m, 1H), 2.67 (m, 2H), 2.53 (m, 2H), 2.02 (quintet, J=7.3, 2H), 1.73 (s, 6H).

EXAMPLE 364

6-Cyclopentyl-1,4-dihydro-4,4-dimethyl-1,3-benzo[d]oxazin-2-one (Compound 665, Structure 118 of Scheme XXIII, Where R$^4$=R$^5$=R$^6$=R$^7$=R$^8$=H, n=1, Z=Methylene)

This compound was prepared in a similar fashion as that described in Example 1, General Procedure III by hydrogenation of Compound 664 (Structure 116 of Scheme XXIII, where R$^4$=R$^5$=R$^6$=R$^7$=R$^8$=H, n=1, Z=methylene). Compound 665 was isolated as a white solid: $^1$H NMR (400 MHz, CDCl$_3$) 8.79 (br s, 1H), 7.09 (d, J=8.1, 1H), 6.97 (s, 1H), 6.77 (d, J=8.1, 1H), 2.95 (m, 1H), 2.05 (m, 2H), 1.80 (m, 2H), 1.69 to 1.62 (m, 10H).

EXAMPLE 365

6-(1-Hydroxy)cyclohexyl-1,4-dihydro-4,4-dimethyl-1,3-benzo[d]oxazin-2-one (Compound 666, Structure 115 of Scheme XXIII, Where R$^4$=R$^5$=R$^6$=R$^7$=R$^8$=H, n=2, Z=Methylene)

This compound was prepared according to General Procedure XIX in Example 330 from Compound 663 (Structure 114 of Scheme XXIII) and cyclohexanone as a white solid; $^1$H NMR (400 MHz, CDCl$_3$) 7.33 (m, 2H), 6.72 (d, J=8.6, 1H), 1.76 to 1.60 (m, 1.6H).

EXAMPLE 366

6-(1-Cyclohexenyl)-1,4-dihydro-4,4-dimethyl-1,3-benzo[d]oxazin-2-one (Compound 667, Structure 116 of Scheme XXIII, Where R$^4$=R$^5$=R$^6$=R$^7$=R$^8$=H, n=2, Z=Methylene)

This compound was prepared in a similar fashion as that described in Example 331, General Procedure XX by dehydration of Compound 666 (Structure 115 of Scheme XXIII, where R$^4$=R$^5$=R$^6$=R$^7$=R$^8$=H, n=2, Z=methylene). Compound 667 was isolated as a white solid: $^1$H NMR (400

MHz, CDCl$_3$) 7.49 (br s, 1H), 7.24 (dd, J=1.4, 8.2, 1H), 7.14 (d, J=1.4, 1H), 6.70 (d, J=8.2, 1H), 6.05 (m, 1H), 2.36 (m, 2H), 2.20 (m,. 2H), 1.79 to 1.76 (m, 2H), 1.72 (s, 6H), 1.67 to 1.60 (m, 2H).

EXAMPLE 367

6-Cyclohexyl-1,4-dihydro-4,4-dimethyl-1,3-benzo[d]oxazin-2-one (Compound 668, Structure 118 of Scheme XXIII, Where R$^4$=R$^5$=R$^6$=R$^7$=R$^8$=H, n=2, Z=Methylene)

This compound was prepared in a similar fashion as that described in Example 1, General Procedure III by hydrogenation of Compound 667 (Structure 116 of Scheme XXIII, where R$^4$=R$^5$=R$^6$=R$^7$=R$^8$=H, n=2, Z=methylene). Compound 668 was isolated as a white solid: $^1$H NMR (400 MHz, CDCl$_3$) 8.61 (br s, 1H), 7.10 (dd, J=1.4, 8.2, 1H), 6.93 (d, J=1.4, 1H), 6.78 (d, J=8.2, 1H), 2.45 (m, 1H), 1.98 (m, 5H), 1.71 (s, 6H), 1.38 to 1.20 (m, 5H).

EXAMPLE 368

6-(1-Hydroxycycloheptyl)-1,4-dihydro-4,4-dimethyl-1,3-benzo[d]oxazin-2-one (Compound 669, Structure 115 of Scheme XXIII, Where R$^4$=R$^5$=R$^6$=R$^7$=R$^8$=H, n=3, Z=Methylene)

This compound was prepared according to General Procedure XIX in Example 330 from Compound 663 (Structure 114 of Scheme XXIII) and cycloheptanone as a white solid: $^1$H NMR (400 MHz, CDCl$_3$) 8.90 (br s, 1H), 7.31 (d under dd, 2H), 6.80 (d, J=8.7, 1H), 2.04 (m, 2H), 1.80 (m, 2H), 1.78 to 1.56 (m, 14H).

EXAMPLE 369

6-(1-Cycloheptenyl)-1,4-dihydro-4,4-dimethyl-1,3-benzo[d]oxazin-2-one (Compound 670, Structure 116 of Scheme XXIII, Where R$^4$=R$^5$=R$^6$=R$^7$=R$^8$=H, n=3, Z=Methylene)

This compound was prepared in a similar fashion as that described in Example 331, General Procedure XX by dehydration of Compound 669 (Structure 115 of Scheme XXIII, where R$^4$=R$^5$=R$^6$=R$^7$=R$^8$=H, n=3, Z=methylene). Compound 670 was isolated as a white solid: $^1$H NMR (400 MHz, CDCl$_3$) 8.86 (br s, 1H), 7.17 (dd, J=1.7, 8.2, 1H), 7.05 (d, J=1.7, 1H), 6.77 (d, J=8.2, 1H), 6.03 (t, J=6.7, 1H), 2.56 (m, 2H), 2.28 (m, 2H), 1.85 (m, 2H), 1.73 (s, 6H), 1.65 (m, 4H).

EXAMPLE 370

6-(1-Cycloheptyl)-1,4-dihydro-4,4-dimethyl-1,3-benzo[d]oxazin-2-one (Compound 671, Structure 118 of Scheme XXIII, Where R$^4$=R$^5$=R$^6$=R=R$^8$=H, n=3, Z=Methylene)

This compound was prepared in a similar fashion as that described in Example 1, General Procedure III by hydrogenation of Compound 670 (Structure 116 of Scheme XXIII, where R$^4$=R$^5$=R$^6$=$^7$=H, n=3, Z=methylene). Compound 671 was isolated as a white solid: $^1$H NMR (400 MHz, CDCl$_3$) 8.34 (br s, 1H), 7.05 (d, J=8.1, 1H), 6.92 (s, 1H), 6.73 (d, J=8.1, 1H), 2.62 (m, 1H), 1.85 to 1.51 (m, 24H).

EXAMPLE 371

6-(2,6,6-Trimethyl-1-)cyclohexenyl-1,4-dihydro-4,4-dimethyl-1,3-benzo[d]oxazin-2-one (Compound 672. Structure 116 of Scheme XXIII, Where R$^4$=R$^7$R$^8$=Methyl, R$^5$=R$^6$=H, n=2, Z=Methylene)

This compound was prepared in a similar fashion as that described in Examples 330 and 331, General Procedures XIX and XX by using Compound 663 (Structure 114 of Scheme XXIII) and 2,2,6-trimethylcyclohexanone. Compound 672 was isolated as a white solid: $^1$H NMR (400 MHz, CDCl$_3$) 9.85 (br s, 1H), 8.21 (d, J=8.4, 1H), 7.30 (d under dd, 2H), 5.92 (s, 1H), 2.38 (m, 2H), 2.18 (s, 3H), 1.85 (m, 2H), 1.75 (m, 8H), 1.33 (s, 3H).

EXAMPLE 372

(±)-6-(3,3,5-Trimethyl-1-)cyclohexenyl-1,4-dihydro-4,4-dimethyl-1,3-benzo[d]oxazin-2-one (Compound 673, Structure 116 of Scheme XXIII, Where R$^4$=R$^7$=R$^8$=H, R$^5$=R$^6$=Methyl, n=1, Z=2-Methylethylene) and (±)-6-(3,5,5-Trimethyl-1-)cyclohexenyl-1,4-dihydro-4,4-dimethyl-1,3-benzo[d]oxazin-2-one (Compound 674, Structure 116 of Scheme XXIII, Where R$^4$=R$^5$=R$^7$=R$^8$=H, R$^6$=Methyl, n=1, Z=2,2-Dimethylethylene)

These compounds were prepared in a similar fashion as that described in Examples 330 and 331, General Procedures XIX and XX by using Compound 663 (Structure 114 of Scheme XXIII) and 3,3,5-trimethylcyclohexanone. Compounds 673 and 674 were isolated as a 1/1 mixture as a white solid: $^1$H NMR (400 MHz, CDCl$_3$) 8.60 (br s, 2H), 7.24 (dd, J=2.0, 8.1, 2H), 7.13 (d, J=2.0, 2H), 6.78 (d, J=8.1, 2H), 5.85 (s, 1H), 5.74 (s, 1H), 2.35 (m, 2H), 2.20 (m, 2H), 2.04 (m, 2H), 1.92 (m, 2H), 1.74 (s, 6H), 1.73 (s, 6H), 1.51 (m, 4H), 1.08 (m, 18H).

EXAMPLE 373

(±)-6-(5-Methyl-1-)cyclohexenyl-1,4-dihydro-4,4-dimethyl-1,3-benzo[d]oxazin-2-one (Compound 675, Structure 116 of Scheme XXIII, Where R$^4$=R$^5$=R$^6$=R$^7$=R$^8$=H, n=2, Z=Methylmethine) and (±)-6-(3-Methyl-1-)cyclohexenyl-1,4-dihydro-4,4-dimethyl-1,3-benzo[d]oxazin-2-one (Compound 676, Structure 116 of Scheme XXIII, Where R$^4$=R$^6$=R$^7$=R$^8$=H, R$^5$=Methyl, n=1, Z=Ethylene)

These compounds were prepared in a similar fashion as that described in Examples 330 and 331, General Procedures XIX and XX by using Compound 663 (Structure 114 of Scheme XXIII) and $^3$-methylcyclohexanone. Compounds 675 and 676 were isolated as a 2/1 mixture as a white solid: $^1$H NMR (400 MHz, CDCl$_3$) 8.62 (br s, 2H), 7.25 (dd, J=2.0, 8.2, 2H), 7.14 (d, J=2.0, 2H), 6.77 (d, J=8.2, 2H), 6.04 (s, 1H), 5.89 (s, 1H), 2.43 to 2.25 (m, 13H), 1.73 (s, 6H), 1.72 (s, 6H), 1.07 (m, 6H).

EXAMPLE 374

(±)-6-(2,6-Dimethyl-1-)cyclohexenyl-1,4-dihydro-4,4-dimethyl-1,3-benzo[d]oxazin-2-one (Compound 677, Structure 116 of Scheme XXIII, Where R$^4$=R$^8$=Methyl, R$^5$=R$^6$=R$^7$=H, n=2, Z=Methylene)

This compound was prepared in a similar fashion as that described in Examples 330 and 331, General Procedures XIX and XX by using Compound 663 (Structure 114 of Scheme XXIII) and 2,6-dimethylcyclohexanone. Compound 677 was isolated as a white solid: $^1$H NMR (400 MHz, CDCl$_3$) 7.86 (br s, 1H), 6.94 (dd, J=1.6, 8.0, 1H), 6.85 (d, J=1.6, 1H), 6.73 (d, J=8.0, 1H), 2.42 (br m, 1H), 2.05 (m, 2H), 1.81 (m, 1H), 1.71 (s, 3H), 1.70 (s, 3H), 1.65 (m, 2H), 1.47 (s, 3H), 0.79 (d, J=6.9, 3H).

EXAMPLE 375

(±)-6-(2-Bicyclo[2.2.1]heptenyl)-1,4-dihydro-4,4-dimethyl-1,3-benzo[d]oxazin-2-one (Compound 678, Structure 116 of Scheme XXIII, Where R$^5$R$^8$=Bridged Ethylene, R$^4$=R$^5$=R$^8$=H, n=1, Z=Methylene)

This compound was prepared in a similar fashion as that described in Examples 330 and 3–331, General Procedures XIX and XX by using Compound 663 (Structure 114 of Scheme XXIII) and 2-norbornanone. Compound 678 was isolated as a white solid: $^1$H NMR (400 MHz, CDCl$_3$) 8;44 (br s, 1H), 7.28 (d, J=8.3, 1H), 7.16 (s, 1H), 6.77 (d, J=8.3, 1H), 6.22 (d, J=3.0, 1H), 3.27 (s, 1H), 3.00 (s, 1H), 1.83 (m, 2H), 1.77 (s, 3H), 1.76 (s, 3H), 1.52 (m, 1H), 1.25 (m, 1H), 1.10 (m, 2H).

EXAMPLE 376

(±)-6-(4,5-trans-Dimethyl-1-)cyclohexenyl-1,4-dihydro-4,4-dimethyl-1,3-benzo[d]oxazin-2-one (Compound 679, Structure 116 of Scheme XXIII, Where $R^4$=$R^5$=$R^6$=$R^7$=$R^8$=H, n=1, Z=1,2-trans-Dimethylethylene) and (±)-6-(3,4-trans-Dimethyl-1-)cyclohexenyl-1,4-dihydro-4,4-dimethyl-1,3-benzo[d]oxazin-2-one (Compound 680, Structure 116 of Scheme XXII, Where $R^4$=$R^6$=$R^7$=$R^8$=H, $R^5$= Methyl, n=1, Z=2-Methylethylene)

These compounds were prepared in a similar fashion as that described in Examples 330 and 331, General Procedures XIX and XX by using Compound 663 (Structure 114 of Scheme XXIII) and trans-3,4-dimethylcyclohexanone. Compounds 679 and 680 were isolated as a 2/1 mixture as a white solid: $^1$H NMR (400 MHz, CDCl$_3$) 8.68 (br s, 2H), 7.25 (dd, J=1.8, 8.4, 2H), 7.14 (d, J=1.8, 2H), 6.78 (d, J=8.4, 2H), 6.00 (brt, 1H), 5.83 (s, 1H), 2.35 to 2.25 (m, 4H), 2.05 (m, 4H), 1.85 (m, 4H), 1.73 (s, 6H), 1.72 (s, 6H), 1.26 (m, 2H), 1.03 (m, 12H).

EXAMPLE 377

6-(6,6-Dimethyl-1-)cyclohexenyl-1,4-dihydro-4,4-dimethyl-1,3-benzo[d]oxazin-2-one (Compound 681, Structure 116 of Scheme XXIII, Where $R^7$=$R^8$=Methyl, $R^4$=$R^1$=R=H, n=2, Z= Methylene)

This compound was prepared in a similar fashion as that described in Examples 330 and 331, General Procedures XIX and XX by using Compound 663 (Structure 114 of Scheme XXIII) and 2,2-dimethylcyclohexanone. Compound 681 was isolated as a white solid: $^1$H NMR (400 MHz, CDCl$_3$) 8.53 (br s, 1H), 6.99 (dd, J=1.7, 8.0, 1H), 6.88 (d, J=1.7, 1H), 6.73 (d, J=8.0, 1H), 5.42 (t, J=3.7, 1H), 2.11 (m, 2H), 1.71 (m, 8H), 0.99 (s, 6H).

EXAMPLE 378

6-(5,5-Dimethyl-1-)cyclopentenyl-1,4-dihydro-4,4-dimethyl-1,3-benzo[d]oxazin-2-one (Compound 682, Structure 116 of Scheme XXIII, Where $R^7$=$R^8$=Methyl, $R^4$=$R^5$=$R^6$=H, n=1, Z= Methylene)

This compound was prepared in a similar fashion as that described in Examples 330 and 331, General Procedures XIX and XX by using Compound 663 (Structure 114 of Scheme XXIII) and 2,2-dimethylcyclopentanone. Compound 511 was isolated as a white solid: $^1$H NMR (400 MHz, CDCl$_3$) 8.02 (br s, 1H), 7.19 (dd, J=1.8, 8.1, 1H), 7.09 (d, J=1.8, 1H), 6.73 (d, J=8.1, 1H), 5.70 (t, J=2.4, 1H), 2.36 (td, J=2.5, 7.1, 1H), 1.86 (t, J=7.1, 1H), 1.72 (s, 6H), 1.18 (s, 6H).

EXAMPLE 379

(±)-6-(3,3,5-cis-Trimethyl)cyclohexyl-1,4-dihydro-4,4-dimethyl-1,3-benzo[d]oxazin-2-one (Compound 683, Structure 118 of Scheme XXIII, Where $R^4$=$R^7$=$R^8$=H, $R^5$=$R^6$=Methyl, n=1, Z=2-Methylethylene) and (±)-6-(3,3,5-trans-Trimethyl) cyclohexyl-1,4-dihydro-4,4-dimethyl-1,3-benzo[d] oxazin-2-one (Compound 684, Structure 118 of Scheme XXIII, Where $R^4$=$R^7$=$R^8$=H, $R^5$=$R^6$= Methyl, n=1, Z=2-Methylethylene)

This compound was prepared in a similar fashion as that described in Example 1, General Procedure III by hydrogenation of Compounds 673/674 (Structure 116 of Scheme XXIII, where $R^4$=$R^7$=$R^8$=H, $R^5$=$R^6$=methyl, n=1, Z=2-methylethylene). Compounds 683 and 684 were isolated as a 2/1 mixture as a white solid: $^1$H NMR (400 MHz, CDCl$_3$) 8.39 (br s, 2H), 7.15 (dd, J=1.7, 8.2, 1H), 7.07 (dd, J=1.7, 8.2, 1H), 6.97 (d, J=1.7, 1H), 6.92 (d, J=1.7, 1H), 6.75 (d, J=8.2, 2H), 2.90 (m, 1H), 2.70 (m, 1H), 2.05 (m, 1H), 1.72 (s, 12H).

EXAMPLE 380

(±)-6-(3-cis-Methyl)cyclohexyl-1,4-dihydro-4,4-dimethyl-1,3-benzo[d]oxazin-2-one (Compound 685, Structure 118 of Scheme XXIII, Where $R^4$=$R^6$=$R^7$=$R^8$=H, $R^5$=Methyl, n=1, Z=2-Ethylene) and (±)-6-(3-trans-Methyl)cyclohexyl-1, 4-dihydro-4,4-dimethyl-1,3-benzo[d]oxazin-2-one (Compound 686, Structure 118 of Scheme XXIII, Where $R^4$=$R^6$=$R^7$=$R^8$=H, $R^5$=Methyl, n=1, Z= Ethylene)

These compounds were prepared in a similar fashion as that described in Example 1, General Procedure III by hydrogenation of compounds 675/676 (Structure 116 of Scheme XXIII, where $R^4$=$R^6$=$R^7$=$R^1$=H, $R^5$=methyl, n=1, Z=ethylene). Compounds 685 and 686 were isolated as a 2/1 mixture as a white solid: (major isomer) $^1$H NMR (400 MHz, CDCl$_3$) 7.86 (bs, 1H), 7.08 (dd, J=8.4, 2.1, 1H), 6.95 (d, J=2.1, 1H), 6.75 (d, J=8.4, 1H), 2.59 (m, 1H), 2.05 (m, 1H), 1.88–1.28 (m, 8H), 1.72 (s, 6H), 0.94 (d, J=7.5, 3H); (minor isomer) $^1$H NMR (400 MHz, CDCl$_3$) 7.86 (bs, 1H), 7.10 (dd, J=8.4, 2.1, 1H), 6.97 (d, J=2.1, 1H), 6.75 (d, J=8.4, 1H), 2.79 (m, 1H), 2.05 (m, 1H), 1.88–1.28 (m, 8H), 1.72 (s, 6H), 1.08 (d, J=7.5, 3H).

EXAMPLE 381

(±)-6-(2,6-cis,cis-Dimethyl)cyclohexyl-1,4-dihydro-4,4-dimethyl-1,3-benzo[d]oxazin-2-one (Compound 687, Structure 118 of Scheme XXIII, Where $R^5$=$R^6$=$R^7$=H, $R^4$=$R^8$=Methyl, n=1, Z=Ethylene)

This compound was prepared in a similar fashion as that described in Example 1, General Procedure III by hydrogenation of Compound 677 (Structure 116 of Scheme XXIII, where $R^4$=$R^8$=methyl, $R^5$=$R^6$=$R^7$=H, n=2, Z=methylene). Compound 687 was isolated as a white solid: $^1$H NMR (400 MHz, CDCl$_3$) 7.36 (br s, 1H), 7.17 (d, J=8.2, 1H), 7.02 (s, 1H), 6.65 (d, J=8.2, 1H), 2.74 (m, 1H), 1.86 (m, 2H), 1.71 (s, 6H), 1.50 to 1.40 (m, 4H), 0.63 (d, J=7.1, 6H).

EXAMPLE 382

(E)-6-(1,4-Dimethyl-1-)pentenyl-1,4-dihydro-4,4-dimethyl-1,3-benzo[d]oxazin-2-one (Compound 688, Structure 116 of Scheme XXIII, Where $R^4$= Methyl, $R^6$=Isopropyl, $R^5$=$R^7$=$R^8$=H, n=1, Z= Two No-bond Hydrogens)

This compound was prepared in a similar fashion as that described in Examples 330 and 331, General Procedures XIX and XX by using Compound 663 (Structure 114 of Scheme XXIII) and 5-methyl-2-hexanone. Compound 688 was isolated as a colorless oil: $^1$H NMR (400 MHz, CDCl$_3$) 8.92 (br s, 1H), 7.23 (dd, J=1.7, 8.0, 1H), 7.11 (d, J=1.7, 1H), 6.79 (d, J=8.0, 1H), 5.73 (t, J=8.0, 1H), 2.07 (t, J=8.0, 2H), 1.94 (s, 3H), 1.71–1.73 (m, 3H), 1.72 (s, 6H), 0.96 (s, 3H), 0.94 (s, 3H).

EXAMPLE 383

6-(1-Cyclohexenyl)-1,4-dihydro-4,4-dimethyl-1,3-benzo[d]oxazin-2-thione (Compound 689, Structure 117 of Scheme XXIII, Where $R^4$=$R^5$=$R^6$=$R^7$=$R^8$=H, n=2, Z=Methylene)

This compound was prepared in a similar method as that described in Example 95, General Procedure XI by treatment of Compound 667 (Structure 116 of Scheme XXIII, where R$^4$=R$^5$=R$^6$=R$^7$=R$^8$=H, n=2, Z=methylene) with Lawesson's reagent. Compound 689 was isolated as a white solid: $^1$H NMR (400 MHz, CDCl$_3$) 9.60 (br s, 1H), 7.29 (dd, J=1.8, 8.2, 1H), 7.13 (d, J=1.8, 1H), 6.81 (d, J=8.2, 1H), 6.08 (t, J=4.0, 1H), 2.35 (m, 2H), 2.20 (m, 2H), 1.80 to 1.76 (m, 8H), 1.68 to 1.60 (m, 2H).

EXAMPLE 384

6-(3-Oxo-1-)Cyclopentenyl-1,4-dihydro-4,4-dimethyl-1,3-benzo[d]oxazin-2-one (Compound 690, Structure 119 of Scheme XXIV, Where Y=O, n=0)

Compound 690 was made according to Examples 330 and 331, General Procedures XIX and XX by using Compound 663 (Structure 114 of Scheme XXIV) and 3-ethoxy-2-cyclopenten-1-one as a white solid: $^1$H NMR (400 MHz, CDCl$_3$) 8.53 (br s, 1H), 7.56 (dd, J=1.8, 8.3, 1H), 7.42 (d, J=1.8, 1H), 6.91 (d, J=8.3, 1H), 6.52 (s, 1H), 3.02 (m, 2H), 2.60 (m, 2H), 1.75 (s, 6H).

EXAMPLE 385

6-(3-Oxo-1-)Cyclohexenyl-1,4-dihydro-4,4-dimethyl-1,3-benzo[d]oxazin-2-one (Compound 691, Structure 119 of Scheme XXIV, Where Y=O, n=1)

Compound 691 was made according to General Procedures XIX and XX in Examples 330 and 331 from Compound 663 (Structure 114 of Scheme XXIV) and 3-ethoxy-2-cyclohexen-1-one as a white solid: $^1$H NMR (400 MHz, CDCl$_3$) 8.05 (br s, 1H), 7.44 (dd, J=1.9, 8.3, 1H), 7.34 (d, J=1.9, 1H), 6.85 (d, J=8.3, 1H), 6.34 (s, 1H), 2.75 (t, J=5.4, 2H), 2.49 (t, J=5.4, 2H), 2.16 (quintet, J=5.4, 2H), 1.75 (s, 6H).

EXAMPLE 386

(±)-6-(3-Hydroxy-1-)cyclohexenyl-1,4-dihydro-4,4-dimethyl-1,3-benzo[d]oxazin-2-one (Compound 692, Structure 120 of Scheme XXIV, Where Y=O, n=1)

This compound was prepared in a similar fashion as that described in Example 358, General Procedure XXI by reduction of Compound 691 (Structure 119 of Scheme XXIV, where Y=O, n=1). Compound 692 was isolated as a white solid: $^1$H NMR (400 MHz, CDCl$_3$) 8.70 (br s, 1H), 7.27 (d, J=8.2, 1H), 7.18 (s, 1H), 6.80 (d, J=8.2, 1H), 6.08 (s, 1H), 4.40 (br s, 1H), 2.41 to 2.36 (m, 2H), 1.94 to 1.92 (m, 2H), 1.71 (s, 6H), 1.70 to 1.63 (m, 3H).

EXAMPLE 387

(±)-6-(3-cis-Hydroxy)cyclohexyl-1,4-dihydro-4,4-dimethyl-1,3-benzo[d]oxazin-2-one (Compound 693, Structure 121 of Scheme XXIV, Where n=1)

This compound was prepared in a similar fashion as that described in Example 1, General Procedure III by hydrogenation of Compound 692 (Structure 120 of Scheme XXIV, where Y=O, n=1). Compound 693 was isolated as a white solid: $^1$H NMR (400 MHz, CDCl$_3$) 8.70 (br s, 1H), 7.27 (d, J=8.2, 1H), 7.18 (s, 1H), 6.80 (d, J=8.2, 1H), 6.08 (s, 1H), 4.40 (br s, 1H), 2.41 to 2.36 (m, 2H), 1.94 to 1.92 (m, 2H), 1.71 (s, 6H), 1.70 to 1.63 (m, 3H).

EXAMPLE 388

(±)-6-(3-Butyl-3-hydroxy-1-)cyclohexenyl-1,4-dihydro-4,4-dimethyl-1,3-benzo[d]oxazin-2-one (Compound 694, Structure 122 of Scheme XXIV, Where n=1)

To a solution of Compound 691 (Structure 119 of Scheme XXIV, where Y=O, n=1) 15 mg, 0.06 mmol) in dry THF (4 mL) at −78° C., was added a 1.6 M n-BuLi solution in hexane (0.04 mL). After 1 h the reaction was quenched with saturated NH$_4$Cl and extracted with EtOAc (10 mL). The organic layer was washed with brine (3×5 mL), dried (Na$_2$SO$_4$), and concentrated in vacuo. The crude product was purified by PTLC (20×20 cm, 250 μm, 30% EtOAc/hex) to afford 10 mg (56%) of Compound 694 as a colorless oil: $^1$H NMR (400 MHz, CDCl$_3$) 8.90 (br s, 1H), 7.26 (dd, J=1.7, 8.2, 1H), 7.15 (d, J=1.7, 1H), 6.81 (d, J=8.2, 1H), 5.91 (s, 1H), 2.38 (m, 2H), 1.86 (m, 2H), 1.80 to 1.61 (m, 10H), 1.39 (m, 4H), 0.93 (t, J=7.1, 3H).

EXAMPLE 389

6-(3-Oxo-1-)Cyclohexenyl-1,4-dihydro-4,4-dimethyl-1,3-benzo[d]oxazin-2-thione (Compound 695, Structure 119 of Scheme XXIV, where Y=S, n=1)

6-Bromo-1,4-dihydro-4,4-dimethyl-1,3-benzo[d]oxazin-2-thione (Compound 696, Structure 118a of Scheme XXIV):

This compound was prepared in a similar fashion as that described in Example 95, General Procedure XI from Compound 663 (Structure 114 of Scheme XXIV) as a white solid: $^1$H NMR (400 MHz, CDCl$_3$) 10.08 (br s, 1H), 7.41 (dd, J=2.0, 8.4, 1H), 7.27 (d, J=2.0, 1H), 6.81 (d, J=8.4, 1H), 1.73 (s, 6H).

6-(3-Oxo-1-)Cyclohexenyl-1,4-dihydro-4,4-dimethyl-1,3-benzo[d]oxazin-2-thione (Compound 695, Structure 119 of Scheme XXIV, where Y=S, n=1):

Compound 695 was made according to General Procedures XIX and XX in Examples 330 and 331 from Compound 696 and 3-ethoxy-2-cyclohexen-1-one as a yellow solid: $^1$H NMR (400 MHz, CDCl$_3$) 9.80 (br s, 1H), 7.50 (dd, J=1.7, 8.3, 1H), 7.34 (d, J=1.7, 1H), 6.95 (d, J=8.3, 1H), 6.42 (s, 1H), 2.75 (t, J=6.3, 2H), 2.51 (t, J=6.3, 2H), 2.17 (m, 2H), 1.78 (s, 6H).

EXAMPLE 390

(±)-6-(3-Hydroxy-1-)cyclohexenyl-1,4-dihydro-4,4-dimethyl-1,3-benzo[d]oxazin-2-thione (Compound 697, Structure 120 of Scheme XXIV, Where Y=S, n=1)

This compound was prepared in a similar fashion as that described in Example 358, General Procedure XXI by reduction of Compound 695 (Structure 119 of Scheme XXIV, where Y=S, n=1). Compound 697 was isolated as a white solid: $^1$H NMR (400 MHz, CDCl$_3$) 8.90 (br s, 1H), 7.31 (dd, J=1.6, 8.1, 1H), 7.19 (d, J=1.6, 1H), 6.75 (d, J=8.1, 1H), 6.09 (s, 1H), 4.42 (br m, 1H), 2.35 (m, 1H), 1.95 (m, 2H), 1.75 (s, 6H), 1.74 (m, 2H).

EXAMPLE 391

(±)-6-(1-Cyclohexenyl)-1,4-dihydro-4-methyl-1,3-benzo[d]oxazin-2-one (Compound 698, Structure 127 of Scheme XXV, Where R$^1$=R$^3$=H, R$^2$=Methyl, W=O)

(±)-1,4-Dihydro-4-methyl-1,3-benzo[d]oxazin-2-one (Compound 699, Structure 125 of Scheme XXV, Where R$^1$=R$^3$=H, R$^2$=Methyl, W=O):

To a solution of 2-tert-butoxycarbonylamino-α-methylbenzyl alcohol (0.58 g, 2.4 mmol) and 1,2-dichloroethane (10 mL) was added TsOH (0.5 g, 2.6 mmol) and the reaction mixture was heated to reflux. After 20 minutes the reaction was quenched with saturated NaHCO$_3$ (10 mL) and extracted with EtOAc (20 mL). The organic layer was washed with brine (3×5 mL), dried (Na$_2$SO$_4$), and concentrated in vacuo. The crude product was purified by flash chromatography (50% EtOAc/hex) to afford 0.30 g (75%) of Compound 699 as a white solid: $^1$H NMR (400 MHz, CDCl$_3$) 8.64 (br s, 1H), 7.27 (t, J=7.8, 1H), 7.08 (d overlapping t, 2H), 6.86 (d, J=7.8, 1H), 5.50 (q, J=6.7, 1H), 1.71 (d, J=6.7, 3H).

(±)-6-Bromo-1,4-dihydro-4-methyl-1,3-benzo[d]oxazin-2-one (Compound 700, Structure 126 of Scheme XXV, where R$^1$=R$^3$=H, R$^2$=Methyl, W=O):

To a solution of Compound 699 (0.15 g, 0.64 mmol) in CCl$_4$ (15 mL). was added bromine (0.1 mL, 0.64 mmol). Stirred at room temperature for 1 hr. The reaction mixture was concentrated in vacuo to afford an orange solid. Washed solid with hot hexane and filtered to afford 130 mg (84%) of Compound 700 as a tan solid: $^1$H NMR (400 MHz, CDCl$_3$) 7.74 (br s, 1H), 7.37 (dd, J=1.7, 8.5, 1H), 7.25 (d under solvent peak, 1H), 6.70 (d, J=8.5, 1H), 5.45 (q, J=6.6, 1H), 1.70 (d, J=6.6, 1H).

(±)-6-(1-Cyclohexenyl)-1,4-dihydro-4-methyl-1,3-benzo[d]oxazin-2-one (Compound 698, Structure 127 of Scheme XXV, Where R$^1$=R$^3$=H, R$^2$=Methyl, W=O):

Compound 527 was made according to General Procedures XIX and XX in Examples 330 and 331 from Compound 700 and cyclohexanone as a white solid: $^1$H NMR (400 MHz, CDCl$_3$) 8.60 (br s, 1H), 7.26 (dd under solvent peak, 1H), 7.09 (d, J=1.7, 1H), 6.78 (d, J=8.2, 1H), 6.07 (m, 1H), 5.50 (q, J=6.7, 1H), 2.38 (m, 2H), 2.19 (m, 1H), 1.78 (m, 2H), 1.71 (d, J=6.7, 3H), 1.67 (m, 2H).

EXAMPLE 392

6-(1-Cyclohexenyl)-1,4-dihydro-4,4,5-trimethyl-1,3-benzo[d]oxazin-2-one (Compound 701, Structure 127 of Scheme XXV, Where R$^1$=R$^2$=R$^3$=Methyl W=O)

2-(1-Hydroxyisopropyl)-3-methylaniline (Compound 702, Structure 124 of Scheme XXV, Where R$^1$=R$^2$=R$^2$=Methyl):

To a solution of 2-amino-6-methylbenzoic acid (Structure 123 of Scheme XXV, where R$^2$=methyl) (0.50 g, 3.3 mmol) and dry THF (20 mL) was added 3 M MeMgCl in THF (11 mL) at 0° C. The reaction was heated to 50° C. and stirred for 15 hrs. The reaction mixture was cooled to room temperature then poured into saturated NH$_4$Cl (20 mL) and extracted with EtOAc (20 mL). The organic layer was washed with brine (3×5 mL), dried (Na$_2$SO$_4$), and concentrated in vacuo. The crude product was purified by flash chromatography (100% hexane to 50% EtOAc/hex gradient) to afford 0.36 g (65%) of Compound 702 as a light orange oil: $^1$H NMR (400 MHz, CDCl$_3$) 6.89 (t, J=7.7, 1H), 6.52 (d under d, J=7.7, 2H), 2.40 (s, 3H), 1.75 (s, 6H).

1,4-Dihydro-4,4,5-trimethyl-1,3-benzo[d]oxazin-2-one (Compound 703, Structure 125 of Scheme XXV, Where R$^1$=R$^2$=R$^2$=Methyl, W=O):

To a solution of Compound 702 (0.36 g, 2.2 mmol) and dry THF (10 mL) was added DMAP (0.29 g, 2.4 mmol) and 1,1'-carbonyldiimidazole (0.39 g, 2.4 mmol). The reaction mixture was heated to 50° C. for 1.5 hrs. The reaction mixture was cooled to room temperature then poured into saturated NH$_4$Cl (20 mL) and extracted with EtOAc (20 mL). The organic layer was washed with brine (3×5 mL), dried (Na$_2$SO$_4$), and concentrated in vacuo. The crude product was purified by flash chromatography (50% EtOAc/hex) to afford 0.40 g (95%) of Compound 703 as a white solid: $^1$H NMR (400 MHz, CDCl$_3$) 7.97 (br s, 1H), 7.10 (t, J=7.8, 1H), 6.85 (d, J=7.8, 1H), 6.64 (d, J=7.8, 1H), 2.41 (s, 3H), 1.80 (s, 6H).

6-Bromo-1,4-dihydro-4,4,5-trimethyl-1,3-benzo[d]oxazin-2-one (Compound 704, Structure 126 of Scheme XXV, where R$^1$=R$^2$=R$^3$=methyl, W=O):

To a solution of Compound 703 (100 mg, 0.52 mmol) and CCl$_4$ (5 mL) was added bromine (0.05 mL, 1.0 mmol). Stirred at room temperature for 1.0 hr. The reaction mixture was concentrated in vacuo to afford an orange solid. Washed solid with hot hexane and filtered to afford 140 mg (100%) of Compound 704 as a tan solid: $^1$H NMR (400 MHz, CDCl$_3$) 8.18 (br s, 1H), 7.44 (d, J=8.5, 1H), 6.54 (d, J=8.5, 1H), 2.49 (s, 3H), 1.83 (s, 6H).

6-(1-Cyclohexenyl)-1,4-dihydro-4,4,5-trimethyl-1,3-benzo[d]oxazin-2-one (Compound 701, Structure 127 of Scheme XXV, where R$^1$=R$^2$=R$^3$=methyl, W=O):

Compound 701 was made according to General Procedures XIX and XX in Examples 330 and 331 from Compound 704 and cyclohexanone as a white solid: $^1$H NMR (400 MHz, CDCl$_3$) 7.52 (br s, 1H), 6.94 (d, J=8.0, 1H), 6.55 (d, J=8.0, 1H), 5.52 (m, 1H), 2.29 (s, 3H), 2.16 to 2.11 (m, 4H), 1.18 (s, 6H), 1.75 to 1.67 (m, 4H).

EXAMPLE 393

6-(1-Cyclohexenyl)-3,4-dihydro-4,4-dimethyl-2(1H)-quinolinone (Compound 705, Structure 127 of Scheme XXV, Where R$^1$=R$^2$=Methyl, R$^3$=H, W=Methylene)

6-Bromo-3,4-dihydro-4,4-dimethyl-2(1H)-quinolinone (Compound 706, Structure 126 of Scheme XXV, Where R$^1$=R$^2$=Methyl, R$^3$=H, W=Methylene):

To a solution of Compound 504 (Structure 125 of Scheme XXV, where R$^1$=R$^2$=methyl, R$^3$=H, W=methylene) (0.20 g, 1.1 mmol) and CCl$_4$ (20 mL) was added bromine (0.05 mL, 1.1 mmol). Stirred at room temperature for 1.5 hrs. The reaction mixture was concentrated in vacuo to afford an orange solid. Washed solid with hot hexane and filtered to afford 0.20 g of Compound 706 in 67% yield as a light orange solid: $^1$H NMR (400 MHz, CDCl$_3$) 8.40 (br s, 1H), 7.41 (d, J=2.1, 1H), 7.31 (dd, J=2.1, 8.4, 1H), 6.72 (d, J=8.4, 1H), 2.50 (s, 2H), 1.33 (s, 6H).

6-(1-Cyclohexenyl)-3,4-dihydro-4,4-dimethyl-2(1H)-quinolinone (Compound 705, Structure 127 of Scheme XXV, Where R$^1$=R$^2$=Methyl, R$^3$=H, W=Methylene):

Compound 705 was made according to General Procedures XIX and XX in Examples 330 and 331 from Compound 706 and cyclohexanone as a white solid: $^1$H NMR (400 MHz, CDCl$_3$) 8.05 (br s, 1H), 7.31 (d, J=1.8, 1H), 7.18 (dd, J=1.8, 8.3, 1H), 6.71 (d, J=8.3, 1H), 6.07 (td, J=2.3, J=4.1, 1H), 2.48 (s, 2H), 2.39 (m, 2H), 2.20 (m, 2H), 1.78 (m, 2H), 1.66 (m, 2H), 1.34 (s, 6H).

EXAMPLE 394

6-Cyclohexyl-3,4-dihydro-4,4-dimethyl-2(1H)-quinolinone (Compound 707, Structure 128 of Scheme XXV)

This compound was prepared in a similar fashion as that described in Example 1, General Procedure III by hydrogenation of Compound 705 (Structure 127 of Scheme XXV, where R$^1$=R$^2$=methyl, R$^3$=H, W=methylene). Compound 707 was isolated as a white solid: $^1$H NMR (400 MHz, CDCl$_3$) 8.03 (br s, 1H), 7.11 (d, J=1.5, 1H), 7.01 (dd, J=1.5, J=8.0, 1H), 6.69 (d, J=8.0, 1H), 2.47 (s, 2H), 1.87 to 1.74 (m, 4H), 1.42 to 1.26 (m, 13H).

EXAMPLE 395

(±)-8-Bromo-6-(1-cyclohexenyl)-1,4-dihydro-4-trifluoromethyl-1,3-benzo[d]oxazin-2-one (Compound 708, Structure 132 of Scheme XXVI)

(±)-N-tert-Butoxycarbonyl-2-(1-hydroxy-2,2,2-trifluoroethyl)aniline (Compound 709, Structure 129 of Scheme XXVI):

To a solution of N-tert-Boc-2-bromoaniline (1.0 mL, 3.8 mmol) in dry Et$_2$O/THF (1:1, 10 mL) was added 1.4 M MeLi/Et$_2$O (3.3 mL) at room temperature. After 15 min. the white turbid mixture was cannulated into a flask charged with 1.7 M t-BuLi/pentane (5 mL) and dry Et$_2$O/THF (1:1, 10 mL) at −78° C. Stirred at −78° C. for 1 hr then added ethyltrifluoroacetate (2.5 mL, 21 mmol, freshly distilled). Allowed reaction to slowly warm to rt overnight. Quenched with saturated NH$_4$Cl and extracted with EtOAc. Washed organic layer with brine, dried (Na$_2$SO$_4$) and concentrated in vacuo to afford a yellow oil. Purified by flash chromatography (hex to 25% EtOAc/hex) to give the desired 2-N-Boc-aminotriflouroacetophenone (0.28 g) as a white solid: $^1$H NMR (400 MHz, CDCl$_3$) 8.13 (d, J=7.4, 1H), 7.38 (dd, J=1.5, 7.4, 1H), 7.28 (t, J=7.4, 1H), 6.99 (br s, 1H), 6.91 (dt, J=1.5, 7.4, 1H), 1.52 (m, 9H). The trifluoroacetophenone was treated with NaBH$_4$ in methanol followed by standard work-up to afford Compound 709 as a white solid: $^1$H NMR (400 MHz, CDCl$_3$) 7.76 (d, J=7.9, 1H), 7.38 (m, 2H), 7.14 (t, J=7.9, 1H), 5.15 (m, 1H), 3.34 (d, J=4,4, 1H), 1.51 (m, 9H).

(±)-1,4-Dihydro-4-trifluoromethyl-1,3-benzo[d]oxazin-2-one (Compound 710, Structure 130 of Scheme XXVI):

To a solution of Compound 709 (0.24 g, 0.82 mmol) in dichloromethane (15 mL) was added TsOH (160 mg). Heated to reflux for 1.5 hr. Quenched with saturated NaHCO$_3$. Extracted with EtOAc, washed organic layer with brine, dried (Na$_2$SO$_4$) and concentrated in vacuo to afford 150 mg of Compound 710 as a white solid (84%): $^1$H NMR (400 MHz, CDCl$_3$) 7.23 (m, 2H), 6.87 (t, J=7.7, 1H), 6.78 (d, J=7.7, 1H), 5.07 (q, J=7.4, 1H).

(±)-6,8-Dibromo-1,4-dihydro-4-trifluoromethyl-1,3-benzo[d]oxazin-2-one (Compound 711, Structure 131 of Scheme XXVI):

To a solution of Compound 710 (50 mg, 0.23 mmol) and CCl$_4$ (5 mL) was added bromine (0.01 mL, 0.23 mmol) at room temperature. After 1 hr the reaction was concentrated in vacuo to afford a yellow foamy solid. Washed solid with hexane to afford 35 mg (41%) of Compound 711 as a solid: $^1$H NMR (400 MHz, CDCl$_3$) 7.35 (s, 1H), 7.29 (dd, J=2.4, 8.5, 1H), 6.64 (d, J=8.5, 1H), 5.04 (q, J=7.0, 1H), 4.00 (br s, 1H).

(±)-8-Bromo-6-(1-cyclohexenyl)-1,4-dihydro-4-trifluoromethyl-1,3-benzo[d]oxazin-2-one (Compound 708, Structure 132 of Scheme XXVI):

Compound 537 was made according to General Procedures XIX and XX in Examples 330 and 331 from Compound 711 and cyclohexanone as a white solid: $^1$H NMR (400 MHz, CDCl$_3$) 7.52 (d, J=2.0, 1H), 7.19 (d, J=2.0, 1H), 6.01 (m, 1H), 5.08 (m, 1H), 4.50 (br s, 1H), 2.31 (m, 2H), 2.17 (m, 2H), 1.76 (m, 2H), 1.64 (m, 2H).

EXAMPLE 396

5-(3-oxo-1-)Cyclohexenyl-3,3-dimethyl-2-indolone (Compound 712, Structure 134 of Scheme XXVII, Where R$^1$=R$^2$=Methyl, R$^3$R$^4$=Carbonyl, n=2)

5-Bromo-3,3-dimethyl-2-indolone (Compound 713, Structure 133 of Scheme XXVII, Where R$^1$R$^2$=Methyl):

This compound was prepared by the following General Procedure XXII (Alkylation and bromination of 2-indolone):

To a solution of 2-indolone (200 mg, 1.5 mmol) in dry THF (15 mL) and TMEDA (0.45 mL, 3.0 mmol) at −78° C. was added n-BuLi (1.9 mL, 1.6M in hex.). The reaction mixture was warmed to −20° C. and iodomethane was added (0.1 mL, 1.5 mmol). After 1 hr, added another equivalent of iodomethane (0.1 mL, 1.5 mmol). Warmed reaction mixture to room temperature and stirred for 15 hrs. Quenched reaction with saturated NH$_4$Cl (10 mL) and extracted with EtOAc (20 mL). The organic layer was washed with brine (3×10 mL), dried (Na$_2$SO$_4$), and concentrated in vacuo. Purified by flash chromatography (10% hexane/EtOAc to 50% hexane/EtOAc gradient) to afford 126 mg (52%) of 3,3-dimethyl-2-indolone as a white solid. Next, to a solution of the 3,3-dimethyl-2-indolone (126 mg, 0.78 mmol) and CCl4 (10 mL) was added bromine (0.04 mL, 0.78 mmol) at room temperature. After 1 hr, the reaction mixture was partitioned between EtOAc (10 mL) and brine (5 mL). The organic layer was washed with brine (3×5 mL), dried (Na$_2$SO$_4$), and concentrated in vacuo to afford 180 mg (96%) of Compound 713 as a white solid: $^1$H NMR (400 MHz, CDCl$_3$) 9.00 (br s, 1H), 7.38 (d, J=8.2, 1H), 7.35 (s, 1H), 6.97 (d, J=8.2, 1H), 1.44 (s, 6H).

5-(3-oxo-1-)Cyclohexenyl-3,3-dimethyl-2-indolone (Compound 712, Structure 134 of Scheme XXVII, Where R$^1$=R$^2$=Methyl, R$^3$R$^4$=Carbonyl, n=2):

Compound 712 was made according to General Procedures XIX and XX in Examples 330 and 331 from Compound 713 and 3-ethoxy-2-cyclohexen-1-one as a white solid: $^1$H NMR (400 MHz, CDCl$_3$) 9.45 (br s, 1H), 7.45 (d under dd, 2H), 7.02 (d, J=8.0, 1H), 6.44 (s, 1H), 2.79 (t, J=6.1, 2H), 2.50 (t, J=6.1, 2H), 2.17 (m, 2H), 1.44 (s, 6H).

EXAMPLE 397

(±)-5-(3-Hydroxy-1-)cyclohexenyl-3,3-dimethyl-2-indolone (Compound 714, Structure 135 of Scheme XXVII, n=2)

This compound was prepared in a similar fashion as that described in Example 358, General Procedure XXI by reduction of Compound 712 (Structure 134 of Scheme XXVII, where R$^1$=R$^2$=methyl, R$^3$R$^4$=carbonyl, n=2). Compound 714 was isolated as a white solid: $^1$H NMR (400 MHz, CDCl$_3$) 7.96 (br s, 1H), 7.24 (d under dd, 2H), 6.09 (br d, 1H), 4.41 (br s, 1H), 2.39 (m, 2H), 1.93 (m, 2H), 1.76 to 1.58 (m, 3H), 1.40 (s, 6H).

EXAMPLE 398

(±)-5-(3-Oxocyclohexyl)-3,3-dimethyl-2-indolone (Compound 715, Structure 136 of Scheme XXVII, Where R$^1$=R$^2$=Methyl, R$^3$R$^4$=Carbonyl, n=2)

This compound was prepared in a similar fashion as that described in Example 1, General Procedure III by hydrogenation of Compound 712 (Structure 134 of Scheme XXVII, where R$^1$=R$^2$=methyl, R$^3$R$^4$=carbonyl, n=2). Compound 715 was isolated as a white solid: $^1$H NMR (400 MHz, CDCl$_3$) 7.03 (d under dd, 2H), 6.78 (d, J=8.5, 1H), 2.49 (m, 1H), 1.86 (m, 3H), 1.81 (m, 1H), 1.39 to 1.25 (m, 10H).

EXAMPLE 399

5-Cyclohexyl-3,3-spirocyclohexyl-2-indolone (Compound 716, Structure 136 of Scheme XXVII, Where R$^1$R$^2$=Spirocyclohexyl, R$^3$=R$^4$=H, n=2)

5-Bromo-3,3-spirocyclohexyl-2-indolone (Compound 717, Structure 133 of Scheme XXVII, Where R$^1$R$^2$= Spirocyclohexyl):

This compound was prepared in a similar fashion as that described in Example 396, General Procedure XXII but using 1,5-diiodopentane in place of iodomethane. Compound 717 was isolated as a white solid: $^1$H NMR (400 MHz, CDCl$_3$) 7.98 (bs, 1H), 7.54 (s, 1H), 7.33 (dd, J=1.2, 8.2, 1H), 6.78 (d, 8.2, 1H), 1.94–1.58 (m, 10H).

5-Cyclohexyl-3,3-spirocyclohexyl-2-indolone (Compound 716, Structure 136 of Scheme XXVII, Where R$^1$R$^2$=Spirocyclohexyl, R$^3$=R$^4$=H, n=2):

Compound 716 was made according to General Procedures XIX, XX and III in Examples 330, 331 and 1 from Compound 717 and cyclohexanone as a white solid: $^1$H NMR (400 MHz, CDCl$_3$) 7.97 (bs, 1H), 7.27 (s, 1H), 7.04 (dd, J=1.1, 7.8, 1H), 6.81 (d, J=7.9, 1H), 2.48 (m, 1H), 1.94–1.65 (mm, 18H), 1.43–1.37 (m, 4H).

EXAMPLE 400

5-Cyclopentyl-3,3-spirocyclohexyl-2-indolone (Compound 718, Structure 136 of Scheme XXVII, Where R$^1$R$^2$=Spirocyclohexyl, R$^3$=R$^4$=H, n=1)

Compound 718 was made according to General Procedures XIX, XX and III in Examples 330, 331 and 1 from Compound 717 (Structure 133 of Scheme XXVII, where R$^1$R$^2$=spirocyclohexyl) and cyclopentanone as a white solid: $^1$H NMR (400 MHz, CDCl$_3$) 8.42 (bs, 1H), 7.31 (s, 1H), 7.08 (dd, J=1.0, 8.1, 1H), 6.83 (d, J=8.0, 1H), 2.97 (quint., J=7.5, 1H), 2.06 (m, 2H), 1.94 (m, 2H), 1.89–1.63 (m, 14H).

EXAMPLE 401

6-(1-Hydroxycyclohexyl)-2(3H)-benzothiozolone (Compound 719, Structure 138 of Scheme XXVIII)

Compound 719 was made according to General Procedures XIX in Examples 330 from 6-bromo-2(3H)-benzothiozolone (Structure 137 of Scheme XXVIII) (120 mg, 0.52 mmol) and cyclohexanone (0.11 mL, 1.04 mmol) in 87% yield (113 mg) as a white solid: $^1$H NMR (400 MHz, DMSO-d$_6$) 11.77 (bs, 1H), 7.63 (d, J=1.5, 1H), 7.38 (dd, J=8.4, 1.5, 1H), 7.03 (d, J=8.4, 1H), 4.70 (s, 1H), 1.64 (m, 8H), 1.48 (m, 2H).

EXAMPLE 402

6-Cyclohexenyl-2(3H)-benzothiozolone (Compound 720, Structure 139 of Scheme XXVIII)

Compound 720 was made according to General Procedures XX in Examples 331 by dehydration of Compound 719 (Structure 138 of Scheme XXVIII) as a white solid: $^1$H NMR (400 MHz, CDCl$_3$) 9.38 (s, 1H), 7.40 (d, J=1.5, 1H, 7.29 (dd, J=8.4, 1.8, 1H), 7.05 (d, J=8.4, 1H), 6.07 (bt, J=4.0, 1H), 2.39–2.36 (m, 2H), 2.21–2.18 (m, 2H), 1.81–1.75 (m, 2H), 1.68–1.63 (m, 2H).

EXAMPLE 403

3,4-Dihydro-6-isopropyl-3-methyl-2(1H)-quinazolinone (Compound 721, Structure 143 of Scheme XXIX, Where R=H, R$^1$=R$^2$=Methyl) 6-Bromo-3,4-dihydro-3-methyl-2(1H)-quinazolinone (Compound 722, Structure 141 of Scheme XXIX):

In a 100-mL r.b. flask, a solution of commercially available 3,4-dihydro-3-methyl-2(1H)-quinazolinone (Structure 140 of Scheme XXIX) (1.0 g, 6.2 mmol) in CH$_2$Cl$_2$ (30 mL) was treated with NBS (1.2 g, 6.8 mmol, 1.1 equiv) in portions. The reaction mixture was then allowed to stir at room temperature for 2 h, diluted with CH$_2$Cl$_2$ (125 mL), washed with water (2×30 mL), Brine (30 mL), dried (MgSO$_4$), filtered and concentrated under reduced pressure to yield 1.5 g (99%) of Compound 722 as a white solid: $^1$H NMR (400 MHz, CDCl$_3$) 7.26 (m, 1H), 7.16 (s, 1H), 6.57 (d, J=8.4, 1H), 4.41 (s, 2H), 3.02 (s, 3H).

3,4-Dihydro-6-isopropyl-3-methyl-2(1H)-quinazolinone (Compound 721, Structure 143 of Scheme XXIX, Where R=H, R$^1$=R$^2$=Methyl):

In a 25-mL r.b. flask, dichloro[1,1'-bis (diphenylphosphino)ferrocene]palladium (II) dichloromethane adduct (4 mg, 0.01–0.02 equiv) was flame-dried under a stream of N$_2$. The flask was them cooled to −70° C. where a solution of isopropyl magnesium chloride (2 M in THF) (0.62 mL, 3.0 equiv) was added followed by the addition of Compound 551 (100 mg, 0.41 mmol) in THF (2 mL). The reaction mixture was then allowed to warm to room temperature, stirred overnight, quenched with HCl (1 M, 5 mL), diluted with water (5 mL), and extracted with EtOAc (3×30 mL). The combined organic layers were then washed with water (15 mL), Brine (20 mL), dried (MgSO$_4$), filtered, and concentrated to give crude product. Compound 721 (5 mg, 6%) was isolated by reverse phase HPLC (ODS, 70% MeOH/water, 2.5 mL/min). Data for Compound 721: $^1$H NMR (400 MHz, CDCl$_3$) 7.01 (d, J=8.3, 1H), 6.89 (s, 1H), 6.74 (bs, 1H), 6.58 (d, J=8.1, 1H), 4,43 (s, 2H), 3.02 (s, 3H), 2.83 (m, 1H), 1.21 (d, J=6.9, 6H).

EXAMPLE 404

1-Benzyl-6-bromo-3,4-dihydro-3-methyl-2(1H)-quinazolinone (Compound 723, Structure 142 of Scheme XXIX)

This compound was prepared in a similar fashion as that described in Example 92, General Procedure X from Compound 722 (Structure 141 of Scheme XXIX) and benzyl bromide. Compound 723 was isolated as a white solid: $^1$H NMR (400 MHz, CDCl$_3$) 7.29 (m, 2H), 7.21 (m, 3H), 7.17 (m, 2H), 6.55 (d, J=9.2, 1H), 5.09 (s, 2H), 4,42 (s, 2H), 3.08 (s, 3H).

EXAMPLE 405

1-Benzyl-6-cyclohexyl-3,4-dihydro-3-methyl-2(1H)-quinazolinone (Compound 724, Structure 143 of Scheme XXIX, R$^1$R$^2$=Cyclohexyl, R=Benzyl)

Compound 724 was made according to General Procedures XIX, XX and III in Examples 330, 331 and 1 from Compound 723 (Structure 142 of Scheme XXIX) and cyclohexanone as a white solid: $^1$H NMR (400 MHz, CDCl$_3$) 7.26 (mm, 5H), 6.92 (d, J=8.5, 1H), 6.88 (s, 1H), 6.62 (d, J=8.4, 1H), 5.10 (s, 2H), 4,44 (s, 2H), 3.09 (s, 3H), 2.37 (m, 1H), 1.80 (m, 4H), 1.74–1.66 (m, 2H), 1.37–1.27 (m, 4H).

EXAMPLE 406

6-(2,3-Difluoro)phenyl-4-trifluoromethyl-2(1H)-quinolinone (Compound 725, Structure 145 of Scheme XXX, Where R=H, R$^1$=Trifluoromethyl, R$^2$=2,3-Difluorine)

2,3-Difluoro-benzeneboronic Acid (Compound 726, Structure 144 of Scheme XXX, Where R$^2$=2,3-Difluoro):

General Procedure XXIII (Boronic acid formation):

To a solution of an aryl bromide (0.5–1.0 M THF) cooled to −70° C. under an N$_2$ atmosphere was added n-BuLi (1.1 equiv) via syringe pump. The rate of addition is adjusted so that the internal temperature did not rise above −65° C. After complete addition of n-BuLi the reaction mixture was allowed to stir at −70° C. for 3 h before quenching with dry trimethyl borate (3.0 equiv), again adjusting the rate so that the internal temperature did not rise above −65° C. After complete addition of trimethyl borate the reaction mixture was then slowly warmed to room temperature overnight. The thick reaction mixture was then acidified to pH 2 with an HCl solution, extracted with EtOAc (20 mL/mmol), washed with brine (2 mL/mmol), dried (MgSO$_4$), filtered and concentrated. The crude product was then triturated with hexanes to give the desired boronic acid in quantitative yield.

Compound 726 was prepared according to General Procedure XXIII from 1,2-difluorobenzene (20 g, 0.18 mmol), n-BuLi (8.2 M in hexane, 21.4 mL, 0.18 mmol), and trimethyl borate (60 mL, 0.53 mmol) in quantitative yield. Compound 726 was isolated as a white solid: $^1$H NMR (400 MHz, CDCl$_3$) 7.56 (m, 1H), 7.28 (m, 1H), 7.15 (mm, 1H), 5.05 (d, J=5.6, 2H).

6-(2,3-Difluoro)phenyl-4-trifluoromethyl-2(1H)-quinolinone (Compound 725, Structure 145 of Scheme XXX, Where R=H, R$^1$=Trifluoromethyl, R$^2$=2,3-Difluorine):

General Procedure XXIV (Suzuki coupling of 6-bromoquinolinones to aryl boronic acids):

To a 10-mL flask charged with a solution of a 6-bromo-2(1H)-quinolinone (25 mg, 0.09 mmol, 1 equiv) in DME (0.1 M) was sequentially added tetrakis(triphenylphosphine)-palladium (0.02–0.05 equiv), aryl boronic acid (R$^2$B(OH)$_2$) (1.5 equiv, 0.1 M in ethanol), and K$_2$CO$_3$ (2.0 equiv, 2.0 M). The yellow reaction mixture was heated to reflux overnight. The now clear reaction solution was cooled, diluted with EtOAc, washed with water (2×15 mL), Brine (20 mL), dried (MgSO$_4$), filtered and concentrated under reduced pressure. The crude product was then purified by trituration with EtOAc/hexane (15%) followed by recrystallization from MeOH/EtOAc to yield the desired product as a white solid in 40–80% overall yield.

Compound 725 was made according to General Procedure XXIV from Compound 308 (Structure 16c of Scheme XXX, where R=H, R$^1$=trilfuoromethyl) and Compound 726 as a white solid: $^1$H NMR (400 MHz, CDCl$_3$) 12.46 (bs, 1H), 8.00 (s, 1H), 7.81 (d, J=8.6, 1H), 7.57 (d, J=8.6, 1H), 7.21 (m, 3H), 7.16 (s, 1H).

EXAMPLE 407

4-Trifluoromethyl-6-(3-nitro)phenyl-2(1H)-quinolinone (Compound 727, Structure 145 of Scheme XXX, Where R=H, R$^1$=Trifluoromethyl, R$^2$=3-Nitro)

This compound was made according to General Procedure XXIV in Example 406 from Compound 308 (Structure 16c of Scheme XXX, where R=H, R$^1$=trilfuoromethyl) and commercially available 3-nitrozeneboronic acid. Compound 727 was isolated as a white solid: $^1$H NMR (400 MHz, CDCl$_3$) 12.02 (bs, 1H), 8.45 (d, J=2.0, 1H), 8.26 (dd, J=8.0, 2.3, 1H), 8.04 (s, 1H), 7.93 (d, J=7.7, 1H), 7.88 (d, J=8.3, 1H), 7.68 (t, J=7.9, 1H), 7.19 (s, 1H).

EXAMPLE 408

4-Trifluoromethyl-6-(3,5-dichloro)phenyl-2(1H)-quinolinone (Compound 728, Structure 145 of Scheme XXX, Where R=H, R$^1$=Trifluoromethyl, R$^2$=3,5-Dichloro)

This compound was made according to General Procedure XXIV in Example 406 from Compound 308 (Structure 16c of Scheme XXX, where R=H, R$^1$=trilfuoromethyl) and commercially available 2,3-dichlorobenzeneboronic acid. Compound 728 was isolated as a white solid: $^1$H NMR (400 MHz, DMSO-d$_6$) 12.46 (s, 1H), 8.02 (dd, J=8.7, 1.5, 1H), 7.82 (s, 1H), 7.69 (d, J=1.7, 2H), 7.65 (d, J=1.8, 1H), 7.54 (d, J=8.6, 1H), 7.07 (s, 1H).

EXAMPLE 409

4-Trifluoromethyl-6-(3-fluoro-5-N-hydroxyliminomethyl)phenyl-2(1H)-quinolinone (Compound 729, Structure 146 of Scheme XXX, Where R=H, R$^1$=Trifluoromethyl, R$^3$=3-Fluoro-5-(N-hydroxyliminomethyl)

4-Trifluoromethyl-6-(3-fluoro-5-formylmethylphenyl)-2(1H)-quinolinone (Compound 730, Structure 145 of Scheme XXX, Where R=H, R$^1$=Trifluoromethyl, R$^2$=3-Fluoro-5-formyl):

This compound was made according to General Procedure XXIV in Example 406 from Compound 308 (Structure 16c of Scheme XXX, where R=H, R$^1$=trilfuoromethyl) (500 mg, 1.70 mmol) and 3-fluoro-5-formylbenzeneboronic acid (350 mg, 2.55 mmol, 1.5 equiv). The crude product could not be purified and was used directly in the following step. 4-Trifluoromethyl-6-(3-fluoro-5-(N-hydroxyimino)methylphenyl)-2(1H)-quinolinone (Compound 729, Structure 146 of Scheme XXX, Where R=H, R$^1$=Trifluoromethyl, R$^3$=3-Fluoro-5-(N-hydroxyliminomethyl):

The crude Compound 730 was dissolved in EtOH and treated with hydroxylamine-hydrochloride salt (180 mg, 2.55 mmol, 1.5 equiv) and pyridine (0.2 mL, 2.55 mmol, 1.5 equiv) at room temperature overnight. The crude product was then concentrated, dissolved in EtOAc (200 mL), washed with sat. NH$_4$Cl (10 mL), water (10 mL), Brine (10 mL), dried (MgSO$_4$), filtered and concentrated. The crude product was then recrystallized from MeOH/EtOAc to afford desired Compound 729 as a white solid: $^1$H NMR (400 MHz, DMSO-d$_6$) 12.45 (bs, 1H), 11.54 (s, 1H), 8.27 (s, 1H), 8.01 (dd, J=7.0, 1.7, 1H), 7.85 (s, 1H), 7.72 (s, 1H), 7.55 (d, J=8.4, 1H), 7.53 (dd, J=11.2, 1.5, 1H), 7.43 (dd, J=9.8, 1.5, 1H), 7.06 (s, 1H).

EXAMPLE 410

4-Trifluoromethyl-6-(3-fluoro-5-cyano)phenyl-2(1H-quinolinone (Compound 731, Structure 146 of Scheme XXX, Where R=H, R$^1$=Trifluoromethyl, R$^3$=3-Fluoro-5-cyano)

In a 25 mL flask, a solution of Compound 729 (Structure 145 of Scheme XXX, where R=H, R$^1$=trifluoromethyl, R$^2$=3-fluoro-5-(N-hydroxyliminomethyl) in methylene chloride was treated with thionyl chloride (1.1 equiv) at room temperature for 30 min. till the reaction went completion by TLC. The reaction was quenched with K$_2$CO$_3$ and extracted with EtOAc. Removal of solvent and chromatography afforded Compound 731 as a white solid: $^1$H NMR (400 MHz, DMSO-d$_6$) 12.49 (s, 1H), 8.06 (m, 2H), 7.93 (dd, J=10.1, 1.5, 1H), 7.89 (m, 2H), 7.55 (d, J=8.7, 1H), 7.08 (s, 1H).

EXAMPLE 411

4-Trifluoromethyl-6-(3-fluoro-5-chloro)phenyl-2(1H)-quinolinone (Compound 732, Structure 145 of Scheme XXX, Where R=H, R$^1$=Trifluoromethyl, R$^2$=3-Fluoro-5-chloro)

3-Chloro-5-fluorobenzeneboronic Acid (Compound 733, Structure 144 of Scheme XXX, Where R$^2$=3-Fluoro-5-chloro):

This compound was prepared according to General Procedure XXIII in Example 406 from 1-bromo-3-chloro-5-fluorobenzene (20 g, 0.18 mmol), n-BuLi (8.2 M in hexane, 21 mL, 0.18 mmol), and trimethyl borate (60 mL, 0.53 mmol) to give 2,3-difluoro-benzeneboronic acid as a white solid.

4-Trifluoromethyl-6-(3-fluoro-5-chloro)phenyl-2(1H)-quinolinone (Compound 732, Structure 145 of Scheme XXX, Where R=H, R$^1$=Trifluoromethyl, R$^2$=3-Fluoro-5-chloro):

This compound was made according to General Procedure XXIV in Example 406 from Compound 308 (Structure 16c of Scheme XXX, where R=H, R$^1$=trilfuoromethyl) and Compound 733. Compound 732 was isolated as a white solid: $^1$H NMR (400 MHz, DMSO-d$_6$) 12.45 (s, 1H), 8.03 (d, J=8.7, 1H), 7.58–7.52 (m, 3H), 7.48 (d, J=8.7, 1H), 7.07 (s, 1H).

EXAMPLE 412

4-Trifluoromethyl-6-(4-hydroxymethyl)phenyl-2(1H)-quinolinone (Compound 734, Structure 145 of Scheme XXX, Where R=H, R$^1$=Trifluoromethyl, R$^2$=4-Hydroxymethyl)

This compound was made according to General Procedure XXIV in Example 406 from Compound 308 (Structure 16c of Scheme XXX, where R=H, R$^1$=trilfuoromethyl) and commercially available 4-hydroxymethylbenzeneboronic acid. Compound 734 was isolated as a white solid: $^1$H NMR (400 MHz, CDCl$_3$) 12.43 (s, 1H), 7.97 (d, J=8.5, 1H), 7.82 (s, 1H), 7.61 (d, J=8.1, 2H), 7.54 (d, J=8.6, 1H), 7.44 (d, J=8.1, 2H), 7.04 (s, 1H), 5.26 (bs, 1H), 4.56 (d, J=5.0, 2H).

EXAMPLE 413

4-Trifluoromethyl-6-(3-acetylphenyl)-2(1H)-quinolinone (Compound 735, Structure 145 of Scheme XXX, Where R=H, R$^1$=Trifluoromethyl, R$^2$=3-Acetyl)

This compound was made according to General Procedure XXIV in Example 406 from Compound 308 (Structure 16c of Scheme XXX, where R=H, R$^1$=trilfuoromethyl) and commercially available 3-acetylbenzeneboronic acid. Compound 735 was isolated as a white solid: $^1$H NMR (400 MHz, DMSO-d$_6$) 12.45 (s, 1H), 8.15 (s, 1H), 8.04 (d, J=8.8, 1H), 8.00 (d, J=7.8, 1H), 7.91 (d, J=8.0, 1H), 7.86 (s, 1H), 7.67 (t, J=7.7, 1H), 7.58 (d, J=8.6, 1H), 7.06 (s, 1H), 2.66 (s, 3H).

EXAMPLE 414

4-Trifluoromethyl-6-(4-ethylphenyl)-2(1H)-quinolinone (Compound 736, Structure 145 of Scheme XXX, Where R=H, R$^1$=Trifluoromethyl, R$^2$=4-ethyl)

This compound was made according to General Procedure XXIV in Example 406 from Compound 308 (Structure 16c of Scheme XXX, where R=H, R$^1$=trilfuoromethyl) and commercially available 4-ethylbenzeneboronic acid. Compound 736 was isolated as a white solid: $^1$H NMR (400 MHz, CDCl$_3$) 11.78 (bs, 1H), 8.00 (s, 1H), 7.84 (d, J=8.6, 1H), 7.53 (d, J=8.0, 2H), 7.48 (d, J=8.6, 1H), 7.32 (d, J=8.0, 2H), 7.13 (s, 1H), 2.72 (q, J=7.5, 2H), 1.29 (t, J=7.6, 3H).

EXAMPLE 415

4-Trifluoromethyl-6-(3-ethoxylphenyl)-2(1H)-quinolinone (Compound 737, Structure 145 of Scheme XXX, Where R=H, R$^1$=Trifluoromethyl, R$^2$=3-Ethoxyl)

This compound was made according to General Procedure XXIV in Example 406 from Compound 308 (Structure 16c of Scheme XXX, where R=H, R$^1$=trilfuoromethyl) and commercially available 3-methoxybenzeneboronic acid. Compound 737 was isolated as a white solid: $^1$H NMR (400 MHz, CDCl$_3$) 12.25 (bs, 1H), 8.02 (s, 1H), 7.84 (d, J=8.5, 1H), 7.53 (d, J=8.6, 1H), 7.41 (t, J=8.0, 1H), 7.19 (d, J=6.5, 1H), 7.14 (m, 2H), 6.95 (d, J=8.3, 1H), 3.89 (s, 3H).

EXAMPLE 416

4-Trifluoromethyl-6-(3-methylphenyl)-2(1H)-quinolinone (Compound 738, Structure 145 of Scheme XXX, Where R=H, R$^1$=Trifluoromethyl, R$^2$=3-Methyl)

This compound was made according to General Procedure XXIV in Example 406 from Compound 308 (Structure 16c of Scheme XXX, where R=H, R$^1$=trilfuoromethyl) and commercially available 3-methylbenzeneboronic acid. Compound 738 was isolated as a white solid: $^1$H NMR (400 MHz, CDCl$_3$) 12.38 (bs, 1H), 8.01 (s, 1H), 7.84 (d, J=8.6, 1H), 7.54 (d, J=8.5, 1H), 7.38 (m, 3H), 7.22 (d, J=6.8, 1H), 7.15 (s, 1H), 2.46 (s, 3H).

EXAMPLE 417

4-Trifluoromethyl-6-(3-trifluoromethylphenyl)-2(1H)-quinolinone (Compound 739, Structure 145 of Scheme XXX, Where R=H, R$^1$=Trifluoromethyl, R$^2$=3-Trifluoromethyl)

This compound was made according to General Procedure XXIV in Example 406 from Compound 308 (Structure 16c of Scheme XXX, where R=H, R$^1$=trilfuoromethyl) and commercially available 3-trifluoromethylbenzeneboronic acid. Compound 739 was isolated as a white solid: $^1$H NMR (400 MHz, DMSO-d$_6$) 12.46 (bs, 1H), 8.06 (d, J=8.6, 1H), 7.97 (d, J=6.8, 1H), 7.93 (s, 1H), 7.86 (s, 1H), 7.75 (m, 2H), 7.57 (8.7, 1H), 7.07 (s, 1H).

EXAMPLE 418

4-Trifluoromethyl-6-(3-chlorophenyl)-2(1H)-quinolinone (Compound 740, Structure 145 of Scheme XXX, Where R=H, R$^1$=Trifluoromethyl, R$^2$=3-Chloro)

This compound was made according to General Procedure XXIV in Example 406 from Compound 308 (Structure 16c of Scheme XXX, where R=H, R$^1$=trilfuoromethyl) and commercially available 3-chlorobenzeneboronic acid. Compound 740 was isolated as a white solid: $^1$H NMR (400 MHz, DMSO-d$_6$) 12.46 (s, 1H), 8.01 (d, J=7.0, 1H), 7.82 (s, 1H), 7.71 (s, 1H), 7.62 (d, J=7.7, 1H), 7.56–7.47 (m, 3H), 7.07 (s, 1H).

EXAMPLE 419

4-Trifluoromethyl-6-(3-fluorophenyl)-2(1H)-quinolinone (Compound 741, Structure 145 of Scheme XXX, Where R=H, R$^1$=Trifluoromethyl, R$^2$=3-Fluoro)

This compound was made according to General Procedure XXIV in Example 406 from Compound 308 (Structure 16c of Scheme XXX, where R=H, R$^1$=trilfuoromethyl) and commercially available 3-fluorobenzeneboronic acid. Compound 741 was isolated as a white solid: $^1$H NMR (400 MHz, DMSO-d$_6$) 12.46 (s, 1H), 8.00 (dd, J=8.5, 1.8, 1H), 7.84 (s, 1H), 7.68–7.49 (m, 4H), 7.24 (t, J=9.3, 1H), 7.06 (s, 1H).

EXAMPLE 420

4-Trifluoromethyl-6-(2-methylphenyl)-2(1H)-quinolinone (Compound 742, Structure 145 of Scheme XXX, Where R=H, $R^1$=Trifluoromethyl, $R^2$=2-Methyl)

This compound was made according to General Procedure XXIV in Example 406 from Compound 308 (Structure 16c of Scheme XXX, where R=H, $R^1$=trilfuoromethyl) and commercially available 2-methylbenzeneboronic acid. Compound 742 was isolated as a white solid: $^1$H NMR (400 MHz, DMSO-$d_6$) 12.42 (s, 1H), 7.68 (dd, J=9.6, 1.4, 1H), 7.53 (m, 2H), 7.33–7.23 (m, 4H), 7.04 (s, 1H), 2.51 (s, 3H).

EXAMPLE 421

4-Trifluoromethyl-6-(4-formyl)phenyl-2(1H)-quinolinone (Compound 743, Structure 145 of Scheme XXX, Where R=H, $R^1$=Trifluoromethyl, $R^2$=4-Formyl)

This compound was made according to General Procedure XXIV in Example 406 from Compound 308 (Structure 16c of Scheme XXX, where R=H, $R^1$=trilfuoromethyl) and commercially available 4-formylbenzeneboronic acid. Compound 743 was isolated as a white solid: $^1$H NMR (400 MHz, DMSO-$d_6$) 12.49 (s, 1H), 10.08 (s, 1H), 8.08 (d, J=10.3, 1H), 8.04 (d, J=8.2, 2H), 7.92 (s, 1H), 7.91 (d, J=8.2, 2H), 7.58 (d, J=8.6, 1H), 7.07 (s, 1H).

EXAMPLE 422

4-Trifluoromethyl-6-(4-tert-butylphenyl)-2(1H)-quinolinone (Compound 744, Structure 145 of Scheme XXX, Where R=H, $R^1$=Trifluoromethyl, $R^2$=4-tert-Butyl)

This compound was made according to General Procedure XXIV in Example 406 from Compound 308 (Structure 16c of Scheme XXX, where R=H, $R^1$=trilfuoromethyl) and commercially available 4-tert-butylbenzeneboronic acid. Compound 744 was isolated as a white solid: $^1$H NMR (400 MHz, DMSO-$d_6$) 12.40 (s, 1H), 7.95 (d, J=7.8, 1H), 7.81 (s, 1H), 7.58–7.51 (m, 4H), 7.04 (s, 1H), 1.32 (s, 9H).

EXAMPLE 423

4-Trifluoromethyl-6-(2-methylphenyl)-2(1H)-quinolinone (Compound 745, Structure 145 of Scheme XXX, Where R=H, $R^1$=Trifluoromethyl, $R^2$=2-Methoxy)

This compound was made according to General Procedure XXIV in Example 406 from Compound 308 (Structure 16c of Scheme XXX, where R=H, $R^1$ trifluoromethyl) and commercially available 2-methoxybenzeneboronic acid. Compound 745 was isolated as a white solid: $^1$H NMR (400 MHz, DMSO-$d_6$) 12.38 (s, 1H), 7.81 (s, 1H), 7.77 (dd, J=8.6, 1.4, 1H), 7.49 (d, J=8.4, 1H), 7.38 (dt, J=8.3,1.7, 1H), 7.34 (dd, J=7.9, 1.5, 1H), 7.15 (d, J=8.1, 1H), 7.07 (t, J=7.5, 1H), 7.02 (s, 1H), 3.78 (s, 3H).

EXAMPLE 424

4-Trifluoromethyl-6-(2-fluorophenyl)-2(1H)-quinolinone (Compound 746, Structure 145 of Scheme XXX, Where R=H, $R^1$=Trifluoromethyl, $R^2$=2-Fluoro)

This compound was made according to General Procedure XXIV in Example 406 from Compound 308 (Structure 16c of Scheme XXX, where R=H, $R^1$=trilfuoromethyl) and commercially available 2-fluorobenzeneboronic acid. Compound 746 was isolated as a white solid: $^1$H NMR (400 MHz, DMSO-$d_6$) 12.42 (bs, 1H), 7.85 (d, J=8.8, 1H), 7.81 (s, 1H), 7.55 (m, 2H), 7.45 (m, 1H), 7.35 (m, 2H), 7.04 (s, 1H).

EXAMPLE 425

4-Trifluoromethyl-6-(4-acetylphenyl)-2(1H)-quinolinone (Compound 747, Structure 145 of Scheme XXX, Where R=H, $R^1$=Trifluoromethyl, $R^2$=4-Acetyl)

This compound was made according to General, Procedure XXIV in Example 406 from Compound 308 (Structure 16c of Scheme XXX, where R=H, $R^1$=trilfuoromethyl) and commercially available 4-acetylbenzeneboronic acid. Compound 747 was isolated as a white solid: $^1$H NMR (400 MHz, DMSO-$d_6$) 12.06 (bs, 1H), 8.06 (m, 3H), 7.87 (dd, J=8.7, 1.5, 1H), 7.69 (d, J=8.4, 2H), 7.55 (d, J=8.6, 1H), 7.15 (s, 1H), 2.65 (s, 3H).

EXAMPLE 426

4-Trifluoromethyl-6-(4-methylphenyl)-2(1H)-quinolinone (Compound 748, Structure 145 of Scheme XXX, Where R=H, $R^1$=Trifluoromethyl, $R^2$=4-Methyl)

This compound was made according to General Procedure XXIV in Example 406 from Compound 308 (Structure 16c of Scheme XXX, where R=H, $R^1$=trilfuoromethyl) and commercially available 4-methylbenzeneboronic acid. Compound 748 was isolated as a white solid: $^1$H NMR (400 MHz, DMSO-$d_6$) 11.65 (bs, 1H), 8.00 (s, 1H), 7.83 (d, J=8.4, 1H), 7.49 (m, 3H), 7.29 (d, J=8.0, 2H), 7.13 (s, 1H), 2.42 (s, 3H).

EXAMPLE 427

4-Trifluoromethyl-6-(4-fluorophenyl)-2(1H)-quinolinone (Compound 749, Structure 145 of Scheme XXX, Where R=H, $R^1$=Trifluoromethyl, $R^2$=4-Fluoro)

This compound was made according to General Procedure XXIV in Example 406 from Compound 308 (Structure 16c of Scheme XXX, where R=H, $R^1$=trilfuoromethyl) and commercially available 4-fluorobenzeneboronic acid. Compound 749 was isolated as a white solid: $^1$H NMR (400 MHz, DMSO-$d_6$) 12.3 (bs, 1H), 7.94 (d, J=8.2, 1H), 7.79 (s, 1H), 7.69 (dd, J=8.4, 5.8, 2H), 7.54 (d, J=8.6, 1H), 7.33 (t, J=8.7, 2H), 7.04 (s, 1H).

EXAMPLE 428

4-Trifluoromethyl-6-(4-methoxyphenyl)-2(1H)-quinolinone (Compound 750, Structure 145 of Scheme XXX, Where R=H, $R^1$=Trifluoromethyl, $R^2$=4-Methoxy)

This compound was made according to General Procedure XXIV in Example 406 from Compound 308 (Structure 16c of Scheme XXX, where R=H, $R^1$=trilfuoromethyl) and commercially available 4-methoxybenzeneboronic acid. Compound 750 was isolated as a white solid: $^1$H NMR (400 MHz, DMSO-$d_6$) 12.39 (s, 1H), 7.93 (d, J=8.5, 1H), 7.77 (s, 1H), 7.58 (d, J=8.7, 2H), 7.52 (d, J=8.7, 1H), 7.07 (d, J=8.7, 2H), 7.03 (s, 1H), 3.81 (s, 3H).

EXAMPLE 429

4-Trifluoromethyl-6-(3,5-bis-trifluoromethyl)phenyl-2(1H)-quinolinone (Compound 751, Structure 145 of Scheme XXX, Where R=H, R$^1$=Trifluoromethyl, R$^2$=3,5-di-Trifluoromethyl)

This compound was made according to General Procedure XXIV in Example 406 from Compound 308 (Structure 16c of Scheme XXX, where R=H, R$^1$=trilfuoromethyl) and commercially available 3,5-di-trifluorobenzeneboronic acid. Compound 751 was isolated as a white solid: $^1$H NMR (400 MHz, DMSO-d$_6$) 12.02 (bs, 1H), 8.00 (s, 3H), 7.92 (s, 1H), 7.84 (dd, J=7.8, 1.9, 1H), 7.58 (d, J=8.5, 1H), 7.19 (s, 1H).

EXAMPLE 430

4-Trifluoromethyl-6-(4-trifluoromethoxyphenyl)-2(1H)-quinolinone (Compound 752, Structure 145 of Scheme XXX, Where R=H, R$^1$=Trifluoromethyl, R$^2$=4-Trifluoromethoxy)

This compound was made according to General Procedure XXIV in Example 406 from Compound 308 (Structure 16c of Scheme XXX, where R=H, R$^1$=trilfuoromethyl) and commercially available 4-trifluoromethoxybenzeneboronic acid. Compound 752 was isolated as a white solid: $^1$H NMR (400 MHz, DMSO-d$_6$) 8.00 (d, J=8.5, 1H), 7.83 (s, 1H), 7.78 (d, J=8.6, 2H), 7.56 (d, J=8.7, 1H), 7.50 (d, J=8.5, 2H), 7.06 (s, 1H).

EXAMPLE 431

4-Trifluoromethyl-6-(2,4-dichlorophenyl)-2(1H)-quinolinone (Compound 753, Structure 145 of Scheme XXX, Where R=H, R$^1$=Trifluoromethyl, R$^2$=2,4-Dichloro)

This compound was made according to General Procedure XXIV in Example 406 from Compound 308 (Structure 16c of Scheme XXX, where R=H, R$^1$=trilfuoromethyl) and commercially available 2,4-dichlorobenzeneboronic acid. Compound 753 was isolated as a 40 white solid: $^1$H NMR (400 MHz, DMSO-d$_6$) 12.47 (s, 1H), 7.77 (d, J=1.8, 1H), 7.75 (dd, J=8.4, 1.3, 1H), 7.69 (s, 1H), 7.53 (m, 3H), 7.06 (s, 1H).

EXAMPLE 432

3-Fluoro-4-trifluoromethyl-6-(2-fluorophenyl)-2(1H)-quinolinone (Compound 754, Structure 145 of Scheme XXX, Where R=Fluoro, R$^1$=Trifluoromethyl, R$^2$=2-Fluoro)

This compound was made according to General Procedure XXIV in Example 406 from 6-Bromo-3-fluoro-4-trifluoromethyl-2(1H)-quinolinone (Compound 634, Structure 16c of Scheme XXX, where R=fluoro, R$^1$=trilfuoromethyl) and commercially available 2-fluorobenzeneboronic acid. Compound 754 was isolated as a white solid: $^1$H NMR (400 MHz, DMSO-d$_6$) 12.59 (bs, 1H), 7.86 (s, 1H), 7.72 (d, J=8.5, 1H), 7.52 (m, 2H), 7.44 (m, 1H), 7.33 (m, 2H).

EXAMPLE 433

3-Fluoro-4-trifluoromethyl-6-(2,4-dichlorophenyl)-2(1H)-quinolinone (Compound 755, Structure 145 of Scheme XXX, where R=fluoro, R$^1$=Trifluoromethyl, R$^2$=2,4-Dichloro)

This compound was made according to General Procedure XXIV in Example 406 from Compound 634 (Structure 16c of Scheme XXX, where R=fluoro, R$^1$=trifuoromethyl) and commercially available 2,4-dichlorobenzeneboronic acid. Compound 755 was isolated as a white solid: $^1$H NMR (400 MHz, DMSO-d$_6$) 12.88 (bs, 1H), 7.80 (s, 1H), 7.72 (m, 2H), 7.58 (m, 2H), 7.49 (d, J=8.2, 1H).

EXAMPLE 434

4-Trifluoromethyl-6-(4-hydroxyphenyl)-2(1H)-quinolinone (Compound 756, Structure 146 of Scheme XXX, Where R=H, R$^1$=Trifluoromethyl, R$^3$=4-Hydroxy)

This compound was prepared in a similar fashion as that described in Example 211 from Compound 750 (Structure 145 of Scheme XXX, where R=H, R$^1$=trifluoromethyl, R$^2$=4-methoxy). Compound 585 was isolated as a white solid: $^1$H NMR (400 MHz, DMSO-d$_6$) 12.38 (bs, 1H), 9.67 (bs, 1H), 7.89 (d, J=8.5, 1H), 7.74 (s, 1H), 7.48 (m, 3H), 7.02 (s, 1H), 6.89 (d, J=8.4, 1H).

EXAMPLE 435

6-Bromo-4-methyl-2(1H)-quinolinone (Compound 757, Structure 16c of Scheme XXX, Where R=H, R$^1$=Methyl)

This compound was prepared in a similar fashion as that described in Example 1, General Procedure I by Knorr reaction of 4-bromoaniline and ethyl acetoacetate. Compound 757 was isolated as a white solid: $^1$H NMR (400 MHz, DMSO-d$_6$) 11.7 (s, 1H), 7.86 (d, J=2.1, 1H), 7.66 (dd, J=7.5, 2.1, 1H), 7.27 (d, J=7.5, 1H), 6.45 (s, 1H), 2.41 (s, 3H).

EXAMPLE 436

4-Methyl-6-(3-methoxyphenyl)-2(1H)-quinolinone (Compound 758, Structure 145 of Scheme XXX, Where R=H, R$^1$=Methyl, R$^2$=3-Methoxy)

This compound was made according to General Procedure XXIV in Example 406 from Compound 757 (Structure 16c of Scheme XXX, where R=H, R$^1$=methyl) and commercially available 3-methoxybenzeneboronic acid. Compound 758 was isolated as a white solid: $^1$H NMR (400 MHz, CDCl$_3$) 11.0 (s, 1H), 7.88 (d, J=2.0, 1H), 7.74 (dd, J=8.5, 2.1, 1H), 7.51 (d, J=8.5, 1H), 7.39 (t, J=7.9, 1H), 7.20 (dt, J=7.9, 1.8, 1H), 7.14 (t, J=1.8, 1H), 6.92 (dt, J=7.9, 1.8, 1H), 6.64 (s, 1H), 2.56 (s, 3H).

EXAMPLE 437

4-Methyl-6-(3-chlorophenyl)-2(1H)-quinolinone (Compound 759, Structure 145 of Scheme XXX, Where R=H, R$^1$=Methyl, R$^2$=3-Chloro)

This compound was made according to General Procedure XXIV in Example 406 from Compound 757 (Structure 16c of Scheme XXX, where R=H, R$^1$=methyl) and commercially available 3-chlorobenzeneboronic acid. Compound 759 was isolated as a white solid: $^1$H NMR (400 MHz, CDCl$_3$) 11.1 (s, 1H), 7.83 (d, J=2.0, 1H), 7.72 (dd, J=8.5, 2.1, 1H), 7.60 (t, J=7.9, 1H), 7.55–7.35 (m, 4H), 6.65 (s, 1H), 2.58 (s, 3H).

EXAMPLE 438

4-Methyl-6-(3-chloro-2-methylphenyl)-2(1H)-quinolinone (Compound 760, Structure 145 of Scheme XXX, Where R=H, R$^1$=Methyl, R$^2$=3-Chloro-2-methyl).

This compound was made according to General Procedure XXIV in Example 406 from Compound 757 (Structure 16c of Scheme XXX, where R=H, R$^1$=methyl) and commercially available 3-chloro-2-methylbenzeneboronic acid. Compound 760 was isolated as a white solid: $^1$H NMR (400 MHz, DMSO-d$_6$) 11.70 (s, 1H), 7.65–7.25 (m, 6H), 6.45 (s, 1H), 2.43 (s, 3H), 2.27 (s, 3H).

EXAMPLE 439

4-Methyl-6-(2,3-dichlorophenyl)-2(1H)-quinolinone (Compound 761, Structure 145 of Scheme XXX, Where R=H, R$^1$=Methyl, R$^2$=2,3-Dichloro)

This compound was made according to General Procedure XXIV in Example 406 from Compound 757 (Structure 16c of Scheme XXX, where R=H, R$^1$=methyl) and commercially available 2,3-dichlorobenzeneboronic acid. Compound 761 was isolated as a white solid: $^1$H NMR (400 MHz, DMSO-d$_6$) 11.70 (s, 1H), 7.75–7.35 (m, 6H), 6.43 (s, 1H), 2.45 (s, 3H).

EXAMPLE 440

4-Methyl-6-(2,4-dichlorophenyl)-2(1H)-quinolinone (Compound 762, Structure 145 of Scheme XXX, Where R=H, R$^1$=Methyl, R$^2$=2,4-Dichloro)

This compound was made according to General Procedure XXIV in Example 406 from Compound 757 (Structure 16c of Scheme XXX, where R=H, R$^1$=methyl) and commercially available 2,4-dichlorobenzeneboronic acid. Compound 762 was isolated as a white solid: $^1$H NMR (400 MHz, CDCl$_6$) 11.00 (s, 1H), 7.72 (s, 1H), 7.57 (d, J=8.5, 1H), 7.53 (s, 1H), 7.40–7.30 (m, 3H), 6.61 (s, 1H), 2.52 (s, 3H).

EXAMPLE 441

4-Methyl-6-(2-methylphenyl)-2(1H)-quinolinone (Compound 763, Structure 145 of Scheme XXX, Where R=H, R$^1$=Methyl, R$^2$=2-Methyl)

This compound was made according to General Procedure XXIV in Example 406 from Compound 757 (Structure 16c of Scheme XXX, where R=H, R$^1$=methyl) and commercially available 2-methylbenzeneboronic acid. Compound 763 was isolated as a white solid: $^1$H NMR (400 MHz, CDCl$_6$) 11.00 (s, 1H), 7.62 (s, 1H), 7.50 (s, 2H), 7.35–7.27 (m, 4H), 6.65 (s, 1H), 2.52 (s, 3H), 2.30 (s, 3H).

EXAMPLE 442

4-Trifluoromethyl-6-phenyl-2(1H)-quinolinone (Compound 764, Structure 145 of Scheme XXX, Where R=H, R$^1$=Trifluoromethyl, R$^2$=H)

This compound was made according to General Procedure I in Example 1 by Knorr reaction of 4-phenylaniline (Structure 147 of Scheme XXX, where R$^2$=H) and ethyl 4,4,4-trifluoroacetoaceate. Compound 764 was isolated as a white solid: $^1$H NMR (400 MHz, CDCl$_3$) 11.61 (s, 1H), 8.05 (s, 1H), 7.87 (d, J=8.6, 1H), 7.61 (d, J=7.4, 2H), 7.50 (m, 3H), 7.43 (t, J=7.4, 1H), 7.16 (s, 1H).

EXAMPLE 443

4-Trifluoromethyl-6-propio-2(1H)-quinolinone (Compound 765, Structure 149 of Scheme XXXI, Where R=Ethyl)
4-Trifluoromethyl-6-propio-2-isopropyloxyquinoline (Compound 766, Structure 148 of, Scheme XXXI, Where R=ethyl):

This compound was prepared according to the, following General Procedure XXV:

To a solution of Compound 309 (Structure 17 of Scheme XXXI) in THF at −70° C. was added n-BuLi and the mixture was stirred for 10 min. A Weinreb's amide such as N-methyl-N-methoxypropionamide in THF was added to the reaction mixture and the reaction was slowly warmed up to rt and quenched with water. Extraction with EtOAc and washing the organic layer with brine afforded a crude mixture, which was concentrated and chromatographied to give Compound 766.

4-Trifluoromethyl-6-propio-2(1H)-quinolinone (Compound 765, Structure 149 of Scheme XXXI, Where R=Ethyl):

Compound 765 was prepared from Compound 766 upon hydrolysis that is described in Example 101 as General procedure XIV. $^1$H NMR (400 MHz, acetone-d$_6$) 11.40 (s, 1H), 8.41 (s, 1H), 8.26 (d, J=8.7, 1H), 7.61 (d, J=8.7, 1H), 7.03 (s, 1H), 3.11 (q, J=6.9, 2H), 1.19 (t, J=6.9, 3H).

EXAMPLE 444

4-Trifluoromethyl-6-(1-ethylaminopropyl)-2(1H)-quinolinone (Compound 767, Structure 150 of Scheme XXXI, Where R$^1$=Ethyl, R$^2$=H)

To a mixture of Compound 765 (Structure 149 of Scheme XXXI) and ethylamine in methanol were added TFA and NaCNBH$_3$. The reaction mixture was stirred at rt for 1 h, quenched with water, extracted with EtOAc and concentrated. Chromatography afforded Compound 767 as white solid. $^1$H NMR (400 MHz, acetone-d$_6$) 11.60 (s, 1H), 7.75 (s, 1H), 7.67 (dd, J=8.5, 1.6, 1H) 7.50 (d, J=8.5, 1H), 6.90 (s, 1H), 3.69 (t, J=6.5, 1H), 3.31 (s, 1H), 2.64–2.48 (m, 1H), 2.46–2.38 (m, 1H), 1.81–1.70 (m, 1H), 1.68–1.60 (m, 1H), 1.04 (t, J=7.1, 3H), 0.82 (t, J=7.4, 3H).

EXAMPLE 445

4-Trifluoromethyl-6-(1-N-ethyl-N-methylaminopropyl)-2(1H)-quinolinone (Compound 768, Structure 150 of Scheme XXXI, Where R$^1$=Ethyl, R$^2$=Methyl)

This compound was prepared from Compound N 16 and formaldehyde in a similar fashion as that described in Example 2, General procedure IV as a white solid. $^1$H NMR (400 MHz, acetone-d$_6$) 11.42 (s, 1H), 7.64 (s, 1H), 7.61 (d, J=8.5, 1H) 7.51 (d, J=8.5, 1H), 2.54–2.48 (m, 1H), 2.36–2.32 (m, 1H), 2.20 (s, 3H), 2.01–1.95 (m, 1H), 1.79–1.72 (m, 1H), 1.01 (t, J=7.0, 3H), 0.77 (t, J=7.3, 3H).

EXAMPLE 446

4-Trifluoromethyl-6-(1-hydroxy-1-methyl-2-oxopropyl)-2(1H)-quinolinone (Compound 769, Structure 152 of Scheme XXXI, Where R$^1$=Methyl, R$^1$=Acetyl)
4-Trifluoromethyl-6-(1-hydroxy-1-methyl-2,2-dimethoxypropyl)-2-isopropyloxyquinoline (Compound 770, Structure 151 of Scheme XXXI, R=Methyl, R$^1$=1,1-Dimethoxyethyl):

This compound was prepared from Compound 309 (Structure 17 of Scheme XXXI) and 3,3-dimethoxy-2-butanone in a similar fashion as that described in Example 330, General procedure XIX.

4-Trifluoromethyl-6-(1-hydroxy-1-methyl-2-oxopropyl)-2 (1H)-quinolinone (Compound 769, Structure 152 of Scheme XXXI, Where R$^1$=Methyl, R$^1$=Acetyl):

This compound was prepared from hydrolysis of Compound 770 in a similar fashion as that described in Example 101, General Procedure XIV as yellow oil. $^1$H NMR (400 MHz, CDCl$_3$) 10.72 (s, 1H), 7.96 (s, 1H), 7.68 (d, J=8.9, 1H), 7.50 (d, J=8.9, 1H), 7.13 (s, 1H), 4.62 (s, 1H), 2.12 (d, J=1.9, 3H), 1.8 (s, 1H).

EXAMPLE 447

4-Trifluoromethyl-6-(4,4,4-trifluoro-1(E)-butenyl)-2 (1H)-quinolinone (Compound 771, Structure 153 of Scheme XXXI, Where R$^2$=H, R$^3$=2,2,2-Trilfuoroethyl)

4-Trifluoromethyl-6-(4,4,4-trifluorobutyro)-2-isopropyloxyquinoline (Compound 772, Structure 148 of Scheme XXXI, Where R=3,3,3-Trifluoropropyl):

This compound was prepared in a similar fashion as that described in Example 443, General Procedure XXV from Compound 309 (Structure 17 of Scheme XXXI) and N-methyl-N-methoxybutyramide.

4-Trifluoromethyl-6-(1-hydroxy-4,4,4-trifluorobutyl)-2-isopropyloxyquinoline (Compound 773, Structure 152 of Scheme XXXI, Where R=H, R$^1$=3,3,3-Trifluoropropyl):

This compound was prepared in a similar fashion as that described in Example 358, General Procedure XXI from Compound 772.

4-Trifluoromethyl-6-(4,4,4-trifluoro-1(E)-butenyl)-2(1H)-quinolinone (Compound 771, Structure 153 of Scheme XXXI, Where R$^2$=H, R$^3$=2,2,2-Trilfuoroethyl):

This compound was prepared in a similar fashion as that described in Example 101, General Procedure XIV from Compound 773 as the only product. $^1$H NMR (400 MHz, acetone-d$_6$) 11.17 (s, 1H), 7.89 (d, J=8.1, 1H), 7.75 (s, 1H), 7.53 (d, J=8.6, 1H), 6.96 (s, 1H), 6.89 (d, J=15.9, 1H), 6.33–6.25 (m, 1H), 3.26–3.17 (m, 1H).

EXAMPLE 448

4-Trifluoromethyl-6-(1-(3,3,3-trifluoropropyl)-1(E)-propenyl)-2(1H)-quinolinone (Compound 774, Structure 153 of Scheme XXXI, Where R$^2$=3,3,3-Trifluoropropyl, R$^3$=Methyl)

4-Trifluoromethyl-6-(1-ethyl-1-hydroxy-4,4,4-trifluorobutyl)-2-isopropyloxyquinoline (Compound 775, Structure 151 of Scheme XXXI, Where R=Methyl, R$^1$=3,3,3-Trifluoropropyl):

To a solution of Compound 772 (Structure 148 of Scheme XXXI, where R=3,3,3-trifluoropropyl) in THF was added EtMgBr in THF and the reaction mixture was stirred at rt overnight till the starting material was consumed by TLC. The reaction was quenched by water, extracted with EtOAc, washed with brine and concentrated. Chromatography afforded Compound 775 as oil.

4-Trifluoromethyl-6-(1-(3,3,3-trifluoropropyl)-1(E)-propenyl)-2(1H)-quinolinone (Compound 774, Structure 153 of Scheme XXXI, Where R$^2$=3,3,3-Trifluoropropyl, R$^3$=methyl):

This compound was prepared in a similar fashion as that described in Example 101, General Procedure XIV from Compound 775 as yellow oil. $^1$H NMR (500 MHz, CDCl$_3$) 11.99 (s, 1H), 7.60 (s, 1H), 7.47 (d, J=8.5, 1H), 7.43 (dd, J=8.5, 2.0, 1H), 7.13 (s, 1H), 5.76 (q, J=7.0, 1H), 2.66 (t, J=8.5, 2H), 2.12–2.05 (m, 2H), 1.66 (d, J=7.0, 3H).

EXAMPLE 449

4-Trifluoromethyl-6-(1-ethyl-4,4,4-trifluoro-1(E)-butenyl)-2(1H)-quinolinone (Compound 776, Structure 153 of Scheme XXXI R$^2$=Ethyl, R$^3$=2,2, 2-Trifluoroethyl) and 4-Trifluoromethyl-6-(1-ethyl-4,4,4-trifluoro-1(Z)-butenyl)-2(1H)-quinolinone (Compound 777, Structure 153 of Scheme XXXI, R$^2$=Ethyl, R$^3$=2,2,2-Trifluoroethyl)

Compound 776 was isolated from the hydrolysis of Compound 775, Structure 151 of Scheme XXXI, where R=ethyl, R$^1$=3,3,3-trifluoropropyl) as that described in Example 448 as the E-isomer. $^1$H NMR (500 MHz, CDCl$_3$) 11.02 (s, 1H), 7.77 (s, 1H), 7.61 (dd, J=8.5, 2.0, 1H), 7.39 (s, 1H), 7.34 (d, J=8.5, 1H), 7.10 (s, 1H), 5.63 (t, J=7.5, 1H), 3.08–3.02 (m, 2H), 2.57 (q, J=7.5, 2H), 1.01 (t, J=7.5, 3H).

Compound 777 was isolated from the hydrolysis of Compound 775, Structure 151 of Scheme XXXI, where R=ethyl, R$^1$=3,3,3-trifluoropropyl) as that described in Example 448 as the Z-isomer. $^1$H NMR (500 MHz, CDCl$_3$) 11.60 (s, 1H), 7.56 (s, 1H), 7.37 (s, 2H), 7.09 (s, 1H), 5.52–5.57 (m, 1H), 2.71–2.66 (m, 2H), 2.45–2.40 (m, 2H), 1.02 (t, J=7.4, 3H).

EXAMPLE 450

2-Chloro-4-trifluoromethyl-6-(bis-N,N-2,2,2-trifluoroethyl)aminoquinoline (Compound 778, Structure 154 of Scheme XXXII, Where R$^1$=R$^2$=2, 2,2-Trifluoroethyl)

This compound was prepared from Compound 223 (Structure 7 of Scheme XXXII, where R=R$^2$=2,2,2-trifluoroethyl) from the following procedure.

To the quinolinone (20.0 mg, 0.05 mmol) in toluene (0.25 mL) was added POCl$_3$ (30.0 microlitres, 0.30 mmole, 6 equiv). The resulting reaction mixture was heated to 110° C. for 4–8 h, cooled to rt, diluted with EA (25 mL) and washed with 20% KOH (2×25 mL). The organic layers were dried over MgSO$_4$, filtered, and concentrated in vacuo. Purification of the resulting oil by flash chromatography (EtOAc:hexane mixtures) afforded the 2-chloro-6-amino-quinolines.

Compound 778 was isolated as yellow solid; $^1$H NMR (CDCl$_3$, 500 MHz) 8.06 (d, J=9.8, 1H), 7.66 (s, 1H), 7.53 (dd, J=2.4, 9.3, 1H), 7.41 (bs, 1H), 4.21 (q, J=8.3, 4H).

EXAMPLE 451

2-Methoxy-4-trifluoromethyl-6-(bis-2,2,2-trifluoroethyl)aminoquinoline (Compound 779, Structure 155 of Scheme XXXII, Where R= Methoxy, R$^1$=R$^2$=2,2,2-Trifluoroethyl)

This compound was prepared from Compound 778 from the following General Procedure XXVI:

A mixture of Compound 778 (Structure 154 of Scheme XXXII, where R$^1$=R$^2$=2,2,2-trifluoroethyl) NaOMe (1.5 equiv) in methanol was heated at reflux for 2 h till the starting material was consumed by TLC. The reaction was quenched by water and a solid was precipitated. Filtration followed washing with methanol afforded the 2-methoxyquinoline in 70–90% yield.

Compound 779 was isolated as a white solid. $^1$H NMR (400 MHz, acetone-d$_6$) 7.89 (d, J=9.3, 1H) 7.77 (dd, J=9.1, 2.3, 1H), 7.49 (s, 1H), 7.30 (s, 1H), 4.51 (q, J=8.6, 4H), 4.05 (s, 3H).

EXAMPLE 452

2-Isopropyloxy-4-trifluoromethyl-6-(bis-2,2,2-trifluoroethyl)aminoquinoline (Compound 780, Structure 155 of Scheme XXXII, Where R= Isopropyloxy, R$^1$=R$^2$=2,2,2-Trifluoroethyl)

This compound was prepared from Compound 223 in a similar fashion as that described in Example 101, General Procedure XII as yellow oil. $^1$H NMR (400 MHz, acetone-d$_6$) 7.71 (d, J=9.3, 1H) 7.61 (dd, J=9.3, 2.8, 1H), 7.35 (s, 1H), 7.08 (s, 1H), 5.40–5.34 (m, 1H), 4.36 (q, J=8.7, 4H), 1.25 (d, J=6.2, 6H).

EXAMPLE 453

2-Ethoxy-4-trifluoromethyl-6-(bis-2,2,2-trifluoroethyl)aminoquinoline (Compound 781, Structure 155 of Scheme XXXII, Where R=Ethoxy, $R^1=R^2=$2,2,2-Trifluoroethyl)

This compound was prepared from Compound 778 (Structure 154 of Scheme XXXII, where $R^1=R^2=$2,2,2-trifluoroethyl) in a similar fashion as that described in Example 451, General Procedure XXVI as yellow oil. $^1$H NMR (500 MHz, CDCl$_3$) 7.83 (d, J=10.2, 1H), 7.39–7.37 (m, 2H), 7.21 (s, 1H), 4.51 (q, J=6.8, 2H), 4.14 (q, $J_{H\text{-}F}$=8.8, 4H), 1.44 (t, J=6.8, 3H).

EXAMPLE 454

2-Acetyloxy-4-trifluoromethyl-6-(bis-2,2,2-trifluoroethyl)aminoquinoline, (Compound 782, Structure 155 of Scheme XXXII, Where R= Acetyloxy, $R^1=R^2=$2,2,2-Trifluoroethyl)

This compound was prepared from Compound 223 and acetic anhydride by the following General Procedure XXVII.

To a solution of 220 mg (0.46 mmol) of Compound 223 (Structure 7 of Scheme XXXII, where $R^1=R^2=$2,2,2-trifluoroethyl) in 10 mL THF in a 100 mL rb flask was added Et$_3$N (0.3 mL, 2.5 mmol) followed by Ac$_2$O (0.3 mL, 4 mmol) and DMAP (5 mg, 0.01 eq). The mixture was stirred at rt for 3 h and then 50 mL water was added. Extracted with 50 mL EtOAc, and the organic layer was quickly washed with 2.5 N HCl (2×50 mL), sat NaHCO$_3$, and brine, and dried over MgSO$_4$. Concentration and purification by chromatography (silica gel, hex: EtOAc 5:1) afforded 192 mg of Compound 782 as yellow solid. $^1$H NMR (500 MHz, CDCl$_3$) 8.02 (d, J=9.8, 1H), 7.51 (dd, J=9.3, 2.9, 1H), 7.49 (s, 1H), 7.45 (s, 1H), 4.20 (q, $J_{H\text{-}F}$=8.8, 4H), 2.41 (s, 3H).

EXAMPLE 455

2-(2-Dimethylamino)ethoxy-4-trifluoromethyl-6-(bis-2,2,2-trifluoroethyl)aminoquinoline (Compound 783, Structure 155 of Scheme XXXII, Where R=2-Dimethylaminoethoxy, $R^1=R^2=$2,2,2-Trifluoroethyl)

This compound was prepared from Compound 778 (Structure 154 of Scheme XXXII, where $R^1=R^2=$2,2,2-trifluoroethyl) and 2-dimethylaminoethanol in a similar fashion as that described in Example 451, General Procedure XXVI as yellow oil. $^1$H NMR (400 MHz, CDCl$_3$) 7.83 (d, J=10.4, 1H), 7.30–7.39 (m, 2H), 7.28 (s, 1H), 4.57 (t, J=5.5, 2H), 4.14 (q, J=8.4, 2H), 2.76 (t, J=5.5, 2H), 2.36 (s, 6H).

EXAMPLE 456

2-Isobutyryloxy-4-trifluoromethyl-6-(bis-2,2,2-trifluoroethyl)aminoquinoline Compound 784, Structure 155 of Scheme XXXII, Where R= Isobutyryloxy. $R^1=R^2$ =2,2,2-Trifluoroethyl)

This compound was prepared from Compound 223 (Structure 7 of Scheme XXXII, where $R^1=R^2=$2,2,2-trifluoroethyl) and isobutyric anhydride in a similar fashion as that described in Example 454, General Procedure XXVII as a yellow solid. $^1$H NMR (500 MHz, CDCl$_3$) 8.04 (d, J=9.3, 1H), 7.50 (dd, J=9.3, 2.9, 1H), 7.45 (s, 1H), 7.44 (s, 1H), 4.20 (q, $J_{H\text{-}F}$=8.8, 4H), 2.95–2.89 (m, 1H), 1.39 (d, J=6.8, 6H).

EXAMPLE 457

2-(2,2-Dimethyl)propyryloxy-4-trifluoromethyl-6-(bis-2,2,2-trifluoroethyl)-aminoquinoline (Compound 785, Structure 155 of Scheme XXXII, Where R=tert-Butyryloxy, $R^1=R^2=$2,2,2-Trifluoroethyl)

This compound was prepared from Compound 223 (Structure 7 of Scheme XXXII, where $R^1=R^2=$2,2,2-trifluoroethyl) and valeric anhydride in a similar fashion as that described in Example 454, General Procedure XXVII as a yellow solid. $^1$H NMR (500 MHz, CDCl$_3$) 8.05 (d, J=9.3, 1H), 7.50 (dd, J=9.3, 2.9, 1H), 7.45 (s, 1H), 7.42 (s, 1H), 4.20 (q, $J_{H\text{-}F}$=8.3, 4H), 1.45 (s, 9H).

EXAMPLE 458

2-N,N-Dimethylcarbamyloxy-4-trifluoromethyl-6-(bis-2,2,2-trifluoroethyl)-aminoquinoline (Compound 786, Structure 155 of Scheme XXXII, Where R=Dimethylaminocarbonyloxy, $R^1=R^2=$2,2,2-Trifluoroethyl)

This compound was prepared from Compound 223 (Structure 7 of Scheme XXXII, where $R^1=R^2=$2,2,2-trifluoroethyl) and dimethylcarbamyl chloride in a similar fashion as that described in Example 454, General Procedure XXVII as a yellow solid. $^1$H NMR (500 MHz, CDCl$_3$) 8.02 (d, J=9.3, 1H), 7.55 (s, 1H), 7.49 (dd, J=9.3, 2.9, 1H), 7.44 (s, 1H), 4.19 (q, $J_{H\text{-}F}$=8.3, 4H), 3.18 (s, 1H), 3.06 (s, 3H).

EXAMPLE 459

2-Cyano-4-trifluoromethyl-6-(bis-2,2,2-trifluoroethyl)aminoquinoline (Compound 787, Structure 155 of Scheme XXXII, Where R=Cyano, $R^1=R^2=$2,2,2-Trifluoroethyl)

This compound was prepared from Compound 778 (Structure 154 of Scheme XXXII, where $R^1=R^2=$2,2,2-trifluoroethyl) in a similar fashion as that described in Example 451, General Procedure XXVI as yellow solid. $^1$H NMR (CDCl$_3$, 500 MHz) 8.21 (d, J=9.8, 1H), 7.92 (s, 1H), 7.63 (dd, J=2.9, 9.8, 1H), 7.42 (s, 1H), 4.27 (q, J=8.4, 4H).

EXAMPLE 460

4-Trifluoromethyl-6-(bis-2,2,2-trifluoroethyl)amino-2(1H)-quinolinone oxime (Compound 788, Structure 156 of Scheme XXXII, Where R=H, $R,^1=R^2=$2,2,2-Trifluoroethyl)

This compound was prepared from Compound 223 (Structure 7 of Scheme XXXII, where $R^1=R^2=$2,2,2-trifluoroethyl) as yellow solid. $^1$H NMR (CDCl$_3$, 500 MHz) 11.20–11.40 (bs, 1H), 7.72 (s, 1H), 7.36 (d, J=10.2, 1H), 7.28–7.31 (m, 2H), 4.11 (q, J=8.3, 4H).

EXAMPLE 461

6-(N-2,2,2-Trifluoroethyl-N-nitroso)amino-4-trifluoromethyl-2(1H)-quinolinone (Compound 789, Structure 157 of Scheme XXXIII, Where R=2,2,2-Trifluoroethyl)

A 100 mL rb flask was charged with a solution of Compound 209 (Structure 7a of Scheme XXXIII, where R=2,2,2-trifluoroethyl) (410 mg, 1.32 mmol) in 15 mL conc.

HCl and cooled in an ice bath. A solution of NaNO$_2$ (170 mg, 2.5 mmol, 2 eq) in 5 mL water was added dropwise in 20 min and the mixture was stirred in an ice bath for 2 h, then 10 mL water was added and the solids were filtered and washed with water to give Compound 789 as white solid. $^1$H NMR (500 MHz, acetone-d$_6$) 11.4 (bs, 1H), 8.01–7.98 (m, 2H), 7.75 (d, J=9.3, 1H), 7.08 (s, 1H), 5.06 (q, J$_{H-F}$=9.3, 2H).

EXAMPLE 462

6-(N-Isobutyl-N-nitroso)amino-4-trifluoromethyl-2 (1H)-quinolinone (Compound 790 Structure 157 of Scheme XXXIII, Where R=Isobutyl)

This compound was prepared in a similar fashion as that described in Example 461 from Compound 206 (Structure 7a of Scheme XXXIII, where R=isobutyl) and isolated as white solid. $^1$H NMR (500 MHz, CDCl$_3$) 12.0 (bs, 1H), 7.94 (dd, J=9.3, 2.0, 1H), 7.88 (s, 1H), 7.56 (d, J=9.3, 1H), 7.18 (s, 1H), 3.95 (d, J=7.3, 2H), 2.05–2.00 (m, 1H), 0.88 (d, J=6.8, 6H).

EXAMPLE 463

6-(N-Isobutyl-N-nitroso)amino-4-trifluoromethyl-2 (1H)-quinolinone (Compound 791, Structure 158 of Scheme XXXIII, Where R=2,2,2-Trifluoroethyl, R$^1$=H, R$^2$=Isopropyl)

Compound 789 (Structure 157 of Scheme XXXIII, where R=2,2,2-trifluoroethyl) was dissolved in a mixture of EtOH (15 mL) and HOAc (10 mL) in a 100 mL rb flask, cooled in an ice bath, and zinc dust (0.5 g, 7.7 mmol, 6 eq) was added in small portions in 20 min. The bright yellow suspension was stirred at rt for 16 h, filtered and rinsed with EtOAc (50 mL) and water (50 mL). 20 mL brine was added and the layers were separated. The water layer was extracted with 50 mL EtOAc, and the combined organic layers were washed with brine (50 mL), and dried over MgSO$_4$. Concentration and purification by chromatography (Silica gel, hex: EtOAc 3:1 to 1:1 gradient) afforded an inseparable mixture of starting material and hydrazine, that was used in the next step.

To a solution of the above mixture (12 mg, 0.04 mmol) in 5 mL TFA in a 100 mL rb flask was added acetone (0.2 mL, excess) and the mixture was stirred at rt for 6 h. NaCNBH$_3$ (200 mg, 3.3 mmol) was added in portions over a 2 hour period, and the mixture was stirred at rt for 16 h. 20 mL water was slowly added and the water layer was extracted with EtOAc (3×25 mL). The combined org. layers were washed with brine and dried over MgSO$_4$. Concentration in vacuo and purification by column chromatography (Silica gel, hex:EtOAc 4:1 to 2:1 gradient) afforded Compound 791 as yellow solid. $^1$H NMR (500 MHz, DMSO-d$_6$) 11.5 (bs, 1H), 7.39–7.37 (m, 2H), 7.31 (d, J=9.8, 1H), 7.08 (s, 1H), 4.09 (q, J=8.8, 2H), 3.77 (s, 1H), 3.25–3.20 (m, 1H), 1.06 (d, J=6.3, 6H).

EXAMPLE 464

6-(4,5-Dihydro-3-methyl-1-pyrazoly)-4-trifluoromethylquinolin-2(1H)-one (Compound 792, Structure 160 of Scheme XXXIII, Where R$^1$=Methyl, R$^2$=H)

6-Hydrazino-4-trifluoromethylquinolin-2(1H)-one (Compound 793, Structure 159 of Scheme XXXIII)

In a 250 mL rb flask a suspension of Compound 200 (structure 3 of Scheme XXXIII) (2.28 g, 10 mmol) in 10 mL conc. HCl was cooled to –1° C. and a solution of NaNO$_2$ (0.40 g, 12 mmol) in water (5 mL) was added dropwise in 20 min. The dark yellow suspension was stirred at –1° C. for 1 h and then a solution of SnCl$_2$.2H$_2$O (5.2 g, 15 mmol) in conc HCl (10 mL) was added dropwise in 10 min. The light yellow suspension of Compound 793 was stirred at –1° C. for 2 h and then used directly or kept in a refrigerator at –1° C. until it was used (the crude compound can be stored for at least one month without decomposition).

6-(4,5-Dihydro-3-methyl-1-pyrazoly)-4-trifluoromethylquinolin-2(1H)-one (Compound 792, Structure 160 of Scheme XXXIII, Where R$^1$=Methyl, R$^2$=H)

This compound was prepared by condensation of Compound 793 and 1-buten-3-one as yellow solid. $^1$H NMR (500 MHz, CDCl$_3$) 10.2 (bs, 1H), 7.55 (dd, J=8.8, 2.4, 1H), 7.21 (d, J=8.8, 1H), 7.11 (bs, 1H), 7.05 (s, 1H), 3.72 (t, J=10.0, 2H), 2.90 (t, J=10.2, 2H), 2.11 (s, 3H).

EXAMPLE 465

(±)-6-(4,5-Dihydro-3-ethyl-5-methyl-1-pyrazoly)-4-trifluoromethylquinolin-2(1H)-one (Compound 794, Structure 160 of Scheme XXXIII, Where R$^1$=ethyl, R$^2$=Methyl)

This compound was prepared from the condensation of Compound 793 (Structure 159 of Scheme XXXIII) and 2-hexen-4-one as yellow solid. $^1$H NMR (500 MHz, DMSO-d$_6$) 12.1 (bs, 1H), 7.41 (dd, J=8.8, 2.4, 1H), 7.34 (d, J=8.8, 1H), 7.21 (bs, 1H), 6.92 (s, 1H), 4.37–4.28 (m, 1H), 3.12 (dd, J=17.1, 10.2, 1H), 2.53 (dd, J=17.1, 4.9, 1H), 2.37 (q, J=7.3, 2H), 1.12 (t, J=7.3, 3H), 1.12 (d, J=5.9, 3H).

EXAMPLE 466

6-(N-Acetyl-N-dimethylimino)amino-4-trifluoromethylquinolin-2(1H)-one (Compound 795, Structure 161 of Scheme XXXIII)

A mixture of Compound 793 (Structure 159 of Scheme XXXIII) and acetic acid in acetone was heated in a sealed tube at 100° C. for 2 h. The reaction mixture was concentrated and chromatographied to afford Compound 795 as major product as yellow solid. $^1$H NMR (500 MHz, DMSO-d$_6$) 12.5 (bs, 1H), 7.79 (dd, J=9.3, 2.4, 1H), 7.65 (s, 1H), 7.54 (d, J=9.3, 1H), 7.08 (s, 1H), 2.22 (s, 3H), 2.14 (s, 3H), 1.94 (s, 3H).

Steroid Receptor Activity

Utilizing the "cis-trans" or "co-transfection" assay described by Evans et al., *Science*, 240:889–95 (May 13, 1988), the disclosure of which is herein incorporated by reference, the compounds of the present invention were tested and found to have strong, specific activity as both agonists, partial agonists and antagonists of AR. This assay is described in further detail in U.S. Pat. Nos. 4,981,784 and 5,071,773, the disclosures of which are incorporated herein by reference.

The co-transfection assay provides a method for identifying functional agonists and partial agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay, and in standard IR binding assays, according to the following illustrative Examples.

EXAMPLE 467

Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following plasmids: pShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor", 266 *J. Biol. Chem.*, 510 (1991).

The reporter plasmid, MTV-LUC, contains the cDNA for firefly luciferase (LUC) under control of the mouse mammary tumor virus (MTV) long terminal repeat, a conditional promoter containing an androgen response element. See e.g, Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11 beta, 17beta)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]pronanamide; Schering-Plough) as an AR antagonist; estradiol (Sigma) as an ER agonist and ICI 164,384 (N-butyl-3,17-dihydroxy-N-methyl-(7-alpha, 17-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-alpha-[acetylthio]-17-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

$$\text{LUC response}/\beta\text{-Gal rate}$$

where $\beta\text{-Gal rate}=\beta\text{-Gal}\cdot 1\times 10^{-5}/\beta\text{-Gal incubation time}$.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist were quantified ($IC_{50}$). In addition, the efficacy of antagonists was determined as a function (%) of maximal inhibition.

IR Binding Assay

AR Binding: For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J. J. Clapp, eds., *Ligand Assay*, Masson Publishing U.S.A., Inc., New York, pp. 45–99, (1981), the disclosure of which is herein incorporated by reference. For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equation to the $IC_{50}$ values, where:

$$K_i = (1 + [^3\text{H-DHT}])/K_d \text{ for } ^3\text{H-DHT}$$

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equivuation to the $IC_{50}$ values, the labeled ligand concentration and the $K_d$ of the labeled ligand.

The agonist, antagonist and binding activity assay results of selected androgen receptor modulator compounds of present invention and the standard reference compounds on AR, as well as the cross-reactivity of selected compounds on the PR, ER, MR and GR receptors, are shown in Tables 1–2 below. Efficacy is reported as the percent maximal response observed for each compound relative to the reference agonist and antagonist compounds indicated above. Also reported in Tables 1–2 for each compound is its antagonist potency or $IC_{50}$ (which is the concentration (nM), required to reduce the maximal response by 50%), its agonist potency or $EC_{50}$ (nM).

TABLE 1

Cotransfection and competitive binding data of selected androgen receptor modulator compounds of present invention and the reference agonist compound, dihydrotestosterone (DHT), and reference antagonists compound, 2-hydroxyflutamide (Flut) and Casodex (Cas), on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | $K_i$ (nM) |
| 204 | 34 | 2022 | 72 | 27 | 54 |
| 218 | 78 | 2.0 | na | na | 4.4 |
| 219 | 73 | 1.3 | na | na | 50 |
| 220 | 68 | 1280 | 54 | 29 | 222 |
| 221 | 114 | 23 | na | na | 147 |
| 222 | 81 | 2.2 | na | na | 6.3 |
| 223 | 95 | 0.15 | na | na | 1.0 |
| 224 | 108 | 41 | na | na | 206 |
| 225 | 90 | 0.4 | na | na | 0.9 |
| 227 | na | na | 73 | 14 | 38 |
| 232 | 55 | 3.4 | na | na | 7.6 |
| 238 | 77 | 5.3 | na | na | 17 |
| 239 | 83 | 2.0 | na | na | 7.4 |
| 241 | 73 | 2.9 | na | na | 30 |
| 242 | 66 | 2.8 | na | na | 32 |
| 246 | 115 | 0.35 | na | na | 7.1 |
| 254 | 78 | 0.90 | na | na | 12 |
| 255 | 135 | 25 | na | na | 67 |
| 259 | 97 | 1.9 | na | na | 6.3 |
| 262 | 58 | 5.9 | na | na | 29 |
| 269 | 85 | 11 | na | na | 14 |
| 272 | na | na | 67 | 7.0 | >1000 |
| 274 | 67 | 1.6 | na | na | 1.4 |
| 280 | 78 | 2.2 | na | na | 2.4 |
| 285 | 111 | 1.0 | na | na | 6.2 |
| 287 | 34 | 8.3 | 53 | 4.1 | >1000 |
| 290 | 37 | 32 | 50 | 50 | >1000 |
| 295 | 30 | 50 | 49 | 3.6 | 86 |
| 297 | 43 | 22 | 43 | 3.2 | 58 |
| 307 | na | na | 43 | 3.2 | 61 |
| 311 | 42 | 143 | 38 | 13 | 12 |
| 314 | 83 | 5.3 | na | na | 4.6 |
| 328 | 93 | 1.7 | na | na | 48 |
| 330 | 81 | 3.9 | na | na | 55 |
| 331 | 44 | 21 | 42 | 5.7 | >1000 |
| 332 | 121 | 14 | na | na | 19 |
| 341 | na | na | 85 | 15 | 277 |
| 347 | na | na | 89 | 59 | 970 |
| 348 | na | na | 81 | 24 | 62 |
| 350 | 73 | 29 | na | na | 165 |
| 351 | 79 | 23 | na | na | 31 |
| 352 | 113 | 12 | ma | na | 25 |
| 365 | 36 | 55 | 43 | 14 | 124 |
| 366 | na | na | 85 | 31 | >1000 |
| 374 | 77 | 2.2 | na | na | 6.2 |
| 377 | 89 | 0.45 | na | na | 1.4 |
| 381 | 72 | 1.8 | na | na | 7.8 |
| 423 | 57 | 86 | na | na | 22 |
| 426 | 93 | 45 | na | na | 28 |
| 432 | 96 | 8.0 | na | na | 32 |
| 433 | 120 | 6.4 | na | na | 1.5 |
| 444 | 83 | 73 | na | na | 26 |
| 445 | 104 | 26 | na | na | 5.8 |
| 449 | 83 | 16 | na | na | 8.4 |
| 457 | 85 | 3.0 | na | na | 3.2 |
| 474 | 73 | 0.60 | na | na | 1.8 |
| 490 | 113 | 12 | na | na | 12 |
| 501 | 110 | 5.8 | na | na | 16 |
| 513 | na | na | 84 | 26 | 37 |
| 514 | na | na | 87 | 55 | 79 |
| 520 | na | na | 76 | 58 | 36 |
| 523 | 29 | 1000 | 62 | 24 | 16 |
| 526 | na | na | 89 | 43 | 161 |
| 528 | 36 | 1300 | 59 | 26 | nd |
| 532 | na | na | 85 | 73 | 159 |
| 535 | na | na | 76 | 60 | >1000 |
| 536 | na | na | 76 | 28 | 188 |
| 559 | na | na | 92 | 122 | 118 |

TABLE 1-continued

Cotransfection and competitive binding data of selected androgen receptor modulator compounds of present invention and the reference agonist compound, dihydrotestosterone (DHT), and reference antagonists compound, 2-hydroxyflutamide (Flut) and Casodex (Cas), on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | $K_i$ (nM) |
| 571 | na | na | 69 | 14 | 71 |
| 581 | 39 | 65 | 23 | 5000 | 24 |
| 582 | na | na | 92 | 26 | 43 |
| 602 | na | na | 85 | 27 | 45 |
| 615 | 23 | 2800 | 82 | 48 | 56 |
| 616 | na | na | 92 | 17 | 15 |
| 630 | 30 | 221 | 67 | 13 | 109 |
| 632 | na | na | 75 | 36 | 112 |
| 633 | 33 | 38 | 51 | 7.5 | 97 |
| 645/646 | 48 | 848 | 68 | 4.1 | 36 |
| 647 | 42 | 233 | 64 | 31 | 81 |
| 655 | na | na | 70 | 70 | >1000 |
| 659 | na | na | 70 | 44 | 40 |
| 667 | na | na | 89 | 27 | 7.4 |
| 675/676 | na | na | 93 | 57 | 192 |
| 689 | na | na | 89 | 40 | 132 |
| 694 | 25 | 935 | 90 | 64 | >1000 |
| 698 | na | na | 84 | 17 | 32 |
| 721 | na | na | 85 | 32 | >1000 |
| 725 | na | na | 87 | 79 | >1000 |
| 737 | na | na | 92 | 89 | >1000 |
| 738 | na | na | 91 | 27 | >1000 |
| 741 | na | na | 92 | 27 | 322 |
| 753 | na | na | 76 | 51 | 74 |
| 758 | na | na | 94 | 87 | 3.6 |
| 762 | na | na | 81 | 63 | nd |
| 764 | na | na | 87 | 30 | 16 |
| HO-Flut | na | na | 83 | 25 | 34 |
| Casodex | na | na | 81 | 201 | 117 |
| DHT | 100 | 4.3 | na | na | 1.7 | na = not active (i.e. efficacy of <20 and potency of >10,000); nd = not determined.

TABLE 2

Co-transfection and competitive binding data for selective progesterone receptor modulator compounds of present invention and the reference agonist compound, progesterone (Prog), and reference antagonists compound, RU486 on PR.

| Cmpd No. | PR Agonist CV-1 Cells | | PR Antagonist CV-1 Cells | | PR Binding |
|---|---|---|---|---|---|
| | Efficacy (%) | Potency (nM) | Efficacy (%) | Potency (nM) | $K_i$ (nM) |
| 242 | na | na | 95 | 200 | 70 |
| 251 | na | na | 91 | 747 | 930 |
| 473 | na | na | 55 | 880 | 508 |
| 631 | na | na | 75 | 796 | 136 |
| 667 | na | na | 89 | 70 | 144 |
| 671 | na | na | 62 | 200 | >1000 |
| 689 | 105 | 2700 | 47 | 35 | 23 |
| 695 | na | na | 90 | 20 | 203 |
| 697 | na | na | 58 | 316 | >1000 |
| 725 | na | na | 92 | 149 | 400 |
| 727 | na | na | 90 | 108 | 161 |
| 731 | na | na | 89 | 64 | 154 |
| 735 | na | na | 84 | 326 | 915 |
| Prog | 100 | 2.9 | na | na | 3.5 |
| ZK299 | na | na | 95 | 2.2 | 18 | na = not active (i.e. efficacy of <20 and potency of >10,000)

Pharmacological and Other Applications

As will be discernible to those skilled in the art, the androgen or progesterone receptor modulator compounds of the present invention can be readily utilized in pharmacological applications where AR or PR antagonist or agonist activity is desired, and where it is desired to minimize cross reactivities with other steroid receptor related IRs. In vivo applications of the invention include administration of the disclosed compounds to mammalian subjects, and in particular to humans.

The following Example provides illustrative pharmaceutical composition formulations:

EXAMPLE 468

Hard gelatin capsules are prepared using the following ingredients:

| | Quantity (mg/capsule) |
|---|---|
| COMPOUND 219 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

| | Quantity (mg/capsule) |
|---|---|
| COMPOUND 219 | 140 |
| Cellulose, microcrystalline | 200 |
| Silicon dioxide, fumed | 10 |
| Stearic acid | 10 |
| Total | 350 mg |

The components are blended and compressed to form tablets each weighing 360 mg.

Tablets, each containing 60 mg of active ingredient, are made as follows:

| | Quantity (mg/capsule) |
|---|---|
| COMPOUND 219 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:

| COMPOUND 219 | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| COMPOUND 219 | 100 mg |
|---|---|
| Saturated fatty acid glycerides | 1,000 mL |
| Total | 100 mL |

The compound is dissolved in the glycerol and then the solution is slowly diluted with isotonic saline. The solution of the above ingredients is then administered intravenously at a rate of 1 mL per minute to a patient.

While description of the preferred embodiments and processing conditions have been provided, the scope of the invention is not to be limited thereto or thereby. Various modifications and alterations of the present invention will be apparent to those skilled in the art without departing from the scope and spirit of the present invention.

The invention is further described below in the form of non-limiting enumerated embodiments.

What is claimed is:

1. A compound having the formula:

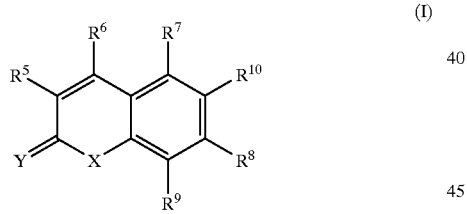

(I)

wherein:
$R^1$ and $R^2$ are each independently selected from the group of $COR^3$, $CSR^3$, $SO_2R^3$, NO, $NR^3R^4$, $C_1$–$C_8$ alkyl, $C_2$–$C_8$ alkenyl, $C_2$–$C_8$ alkynyl, $C_1$–$C_8$ haloalkyl, $C_2$–$C_8$ haloalkenyl, $C_2$–$C_8$ haloalkynyl, $C_1$–$C_8$ heteroalkyl, $C_2$–$C_8$ heteroalkenyl, $C_2$–$C_8$ heteroalkynyl, $(CH_2)_nR^{3A}$, aryl, and heteroaryl, wherein the aryl, and heteroaryl are optionally substituted with F, Cl, Br, I, OH, $OR^3$, $NR^3R^4$, CN, $NO_2$, $SR^3$, $SO_2R^3$, $SO_2R^3$, $C_1$–$C_4$ alkyl, $C_1$–$C_4$ haloalkyl or $C_1$–$C_4$ heteroalkyl; or $R^1$ and $R^2$ taken together form a three- to nine-membered alkyl, alkenyl, heteroalkyl, or heteroalkenyl nonaromatic ring, wherein the alkyl, alkenyl, heteroalkyl, or heteroalkenyl ring are optionally substituted with F, Cl, Br, I, OH, $OR^3$, $NR^3R^4$, $C_1$–$C_4$ alkyl, $C_1$–$C_4$ haloalkyl or $C_1$–$C_4$ heteroalkyl;

$R^3$ is selected from the group of $C_1$–$C_8$ alkyl, $C_2$–$C_8$ alkenyl, $C_2$–$C_9$ alkynyl, $C_1$–$C_8$ haloalkyl, and $C_1$–$C_8$ heteroalkyl;

$R^{3A}$ is aryl or heteroaryl, wherein the aryl and heteroaryl is optionally substituted with halogen, CN, $NO_2$, $C_1$–$C_4$ alkyl, $C_1$–$C_4$ haloalkyl or $C_1$–$C_4$ heteroalkyl;

$R^4$ is selected from the group of hydrogen, $C_1$–$C_4$ alkyl, $C_1$–$C_4$ haloalkyl and $C_1$–$C_4$ heteroalkyl;

$R^5$ is selected from the group of hydrogen, F, Cl, Br, I, $OR^3$, and $C_1$–$C_4$ alkyl;

$R^6$ is selected from the group of F, Cl, Br, I, $CH_3$, $CF_3$, $CHF_2$, $CFH_2$, CN, $CF_2Cl$, $CF_2OR^3$, $OR^3$, $SR^3$, $SO_2R^3$, $SO_2R^3$, $CO_2R^3$, $NR^3R^4$, $C_1$–$C_4$ alkyl, $C_2$–$C_4$ alkenyl, $C_2$–$C_4$ alkynyl, $C_1$–$C_4$ haloalkyl, $C_2$–$C_4$ haloalkenyl, $C_2$–$C_4$ haloalkynyl, $C_1$–$C_4$ heteroalkyl, $C_2$–$C_4$ heteroalkenyl, and $C_2$–$C_4$ heteroalkynyl;

$R^7$ is selected from the group of hydrogen, F, Cl, Br, I, CN, OH, $OR^3$, $C_1$–$C_8$ alkyl, $C_1$–$C_8$ haloalkyl, and $C_1$–$C_8$ heteroalkyl;

$R^8$ is hydrogen or halogen;

$R^9$ is selected from the group of hydrogen, F, Br, Cl, I, OH, $OR^3$, $NR^3R^4$, $SR^3$, $SO_2R^3$, $SO_2R^3$, $C_1$–$C_4$ alkyl, $C_1$–$C_4$ haloalkyl and $C_1$–$C_4$ heteroalkyl;

$R^{10}$ is selected from the group of:

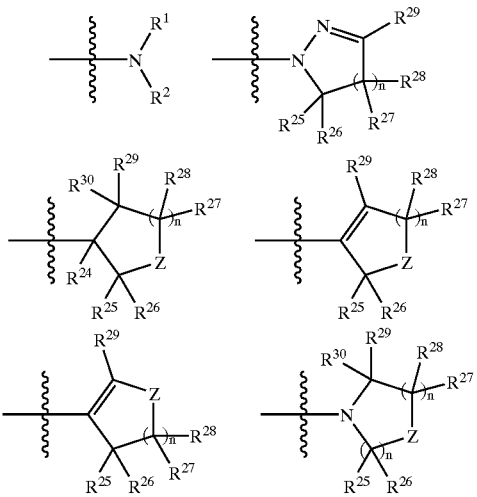

$R^{16}$ is selected from the group of hydrogen, $C_1$–$C_8$ alkyl, $C_1$–$C_8$ haloalkyl, $C_1$–$C_8$ heteroalkyl, $CH_2R^{3A}$, aryl, heteroaryl, $COR^{17}$, $CO_2R^{17}$, and $CONR^{17}R^{17}$;

$R^{17}$ is selected from the group of hydrogen, $C_1$–$C_4$ alkyl, $C_1$–$C_4$ haloalkyl and $C_1$–$C_4$ heteroalkyl;

$R^{24}$ is hydrogen, OH or $OR^3$;

$R^{25}$ and $R^{30}$ are each independently selected from the group of hydrogen, F, Cl, Br, I, OH, $OR^3$, $NR^3R^4$, $SR^3$, $SO_2R^3$, $SO_2R^3$, $C_1$–$C_6$ alkyl, $C_1$–$C_6$ haloalkyl, $C_1$–$C_6$ heteroalkyl, $C_2$–$C_6$ alkynyl and $C_2$–$C_6$ alkenyl, wherein the alkyl, haloalkyl, and heteroalkyl are optionally substituted with F, Cl, Br, I, $OR^3$, $NR^3R^4$, $C_1$–$C_4$ alkyl, $C_1$–$C_4$ haloalkyl, $C_1$–$C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1$–$C_4$ alkyl; or $R^{26}$ through $R^{29}$ are each independently selected from the group of hydrogen, F, Cl, Br, I, OH, $OR^3$, $NR^3R^4$, $SR^3$, $SOR^3$, $SO_2R^3$, $C_1$–$C_6$ alkyl, $C_1$–$C_6$ haloalkyl, $C_1$–$C_6$ heteroalkyl, $C_2$–$C_6$ alkynyl and $C_2$–$C_6$ alkenyl; or any two of $R^{25}$ $R^{26}$, $R^{27}$, $R^{28}$, $R^{29}$ and $R^{30}$ taken together form a three to seven-membered alkyl or alkenyl or nonaromatic heteroalkyl ring; or any four of $R^{25}$, $R^{26}$, $R^{27}$, $R^{28}$, $R^{29}$ and $R^{30}$ taken together form a fused aromatic ring;

X is $NR^{16}$;

Y is selected from the group of O, S, $NR^3$, $NOR^3$ and $CR^3R^4$;

Z is selected from the group of O, S, $NR^3$, C=O, and $CR^{25}R^{26}$; or

Z is two hydrogens;

and n is 1, 2 or 3;

and pharmaceutically acceptable salts thereof.

2. A compound of claim 1, wherein:

$R^3$ is $C_1-C_6$ alkyl;

$R^{3A}$ is optionally substituted aryl or heteroaryl;

$R^4$ is hydrogen or $C_1-C_4$ alkyl;

$R^5$ is selected from the group of hydrogen, halogen and optionally substituted $C_1-C_6$ alkyl;

$R^7$ is hydrogen or halogen;

$R^8$ is hydrogen; and $R^9$ is hydrogen or halogen.

3. A compound of claim 2, wherein:

$R^{25}$ and $R^{30}$ are each independently selected from the group of hydrogen, OH, $C_1-C_6$ alkyl, $C_1-C_6$ haloalkyl, $C_1-C_6$ heteroalkyl, wherein the alkyl, haloalkyl, and heteroalkyl are optionally substituted with F, Cl, $OR^3$, $NR^3R^4$, $C_1-C_4$ alkyl, $C_1-C_4$ haloalkyl, $C_1-C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1-C_4$ alkyl;

$R^{26}$ through $R^{29}$ are each independently hydrogen, OH, $C_1-C_6$ alkyl or $C_1-C_6$ haloalkyl; and Y is selected from the group of O, S, and $NOR^3$.

4. A compound of claim 1, wherein:

$R^1$ and $R^2$ are each independently selected from the group of $COR^3$, $CSR^3$, $SO_2R^3$, NO, $NR^3R^4$, $C_1-C_8$ alkyl, $C_2-C_8$ alkenyl, $C_2-C_8$ alkynyl, $C_1-C_8$ haloalkyl, $C_2-C_8$ haloalkenyl, $C_2-C_8$ haloalkynyl, $C_1-C_8$ heteroalkyl, $C_2-C_8$ heteroalkenyl, $C_2-C_8$ heteroalkynyl, $(CH_2)_nR^{3A}$, aryl, and heteroaryl, wherein the aryl, and heteroaryl are optionally substituted with F, Cl, Br, I, $OR^3$, $NR^3R^4$, CN, $NO_2$, $SR^3$, $SOR^3$, $SO_2R^3$, $C_1-C_4$ alkyl, $C_1-C_4$ haloalkyl or $C_1-C_4$ heteroalkyl ;

$R^3$ is $C_1-C_6$ alkyl;

$R^{3A}$ is optionally substituted aryl or heteroaryl;

$R^4$ is hydrogen or $C_1-C_6$ alkyl;

$R^5$ is selected from the group of hydrogen, halogen and optionally substituted $C_1-C_6$ alkyl;

$R^7$ is hydrogen or halogen;

$R^8$ is hydrogen;

$R^9$ is hydrogen or halogen;

$R^{16}$ is hydrogen;

$R^{25}$ and $R^{30}$ are each independently selected from the group of hydrogen, OH, $C_1-C_6$ alkyl, $C_1-C_6$ haloalkyl, $C_1-C_6$ heteroalkyl, wherein the alkyl, haloalkyl, and heteroalkyl are optionally substituted with F, Cl, $OR^3$, $NR^3R^4$, $C_1-C_4$ alkyl, $C_1-C_4$ haloalkyl, $C_1-C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1-C_4$ alkyl;

$R^{26}$ through $R^{29}$ are each independently hydrogen, OH, $C_1-C_6$ alkyl, or $C_1-C_6$ haloalkyl; and Y is selected from the group of O, S, and $NOR^3$.

5. A compound of claim 1, wherein:

$R^1$ and $R^2$ taken together form a three- to nine-membered alkyl, alkenyl, heteroalkyl, or heteroalkenyl nonaromatic ring, wherein the alkyl, alkenyl, heteroalkyl, or heteroalkenyl ring are optionally substituted with F, Cl, Br, I, $OR^3$, $NR^3R^4$, $C_1-C_4$ alkyl, $C_1-C_1-C_4$ haloalkyl or $C_1-C_4$ heteroalkyl;

$R^3$ is $C_1-C_6$ alkyl;

$R^{3A}$ is optionally substituted aryl or heteroaryl;

$R^4$ is hydrogen or $C_1-C_6$ alkyl;

$R^5$ is selected from the group of hydrogen, halogen and optionally substituted $C_1-C_6$ alkyl;

$R^7$ is hydrogen or halogen;

$R^8$ is hydrogen;

$R^9$ is hydrogen or halogen;

$R^{16}$ is hydrogen;

$R^{25}$ and $R^{30}$ are each independently selected from the group of hydrogen, OH, $C_1-C_6$ alkyl, $C_1-C_6$ haloalkyl, $C_1-C_6$ heteroalkyl, wherein the alkyl, haloalkyl, and heteroalkyl are optionally substituted with F, Cl, $OR^3$, $NR^3R^4$, $C_1-C_4$ alkyl, $C_1-C_4$ haloalkyl, $C_1-C_4$ heteroalkyl aryl or heteroaryl, and wherein the aryl and heteroaryl are optionally substituted with F, Cl, Br, I, CN, $NO_2$, OH, $OCH_3$, $CF_3$ or $C_1-C_4$ alkyl;

$R^{26}$ through $R^{29}$ are each independently hydrogen, halogen, OH, $C_1-C_6$alkyl, or $C_1-C_6$ haloalkyl; and Y is selected from the group of O, S, and $NOR^3$.

6. A compound of claim 1, wherein:

$R^1$ and $R^2$ are each independently selected from the group of $COR^3$, $CSR^3$, $SO_2R^3$, $C_1-C_8$ alkyl, $C_2-C_8$ alkenyl, $C_1-C_8$ haloalkyl, $C_2-C_8$ haloalkenyl, $C_1-C_8$ heteroalkyl, $C_2-C_8$ heteroalkenyl, $CH_2R^{3A}$, aryl and heteroaryl, wherein the aryl or heteroaryl are optionally substituted with F, Cl, Br, CN, $NO_2$, $OR^3$, $NR^3R^4$, $SR^3$, COMe, $COCF_3$, $C_1-C_4$ alkyl, or $C_1-C_4$ haloalkyl; or $R^3$ is $C_1-C_8$ alkyl, $C_2-C_8$ alkenyl, $C_1-C_8$ haloalkyl, and $C_1-C_8$ heteroalkyl;

$R^{3A}$ is heteroaryl or aryl, wherein the heteroaryl and aryl are optionally substituted with F, Cl, Br, CN, OMe, SMe, $C_1-C_4$ alkyl, or $C_1-C_4$ haloalkyl;

$R^4$ is selected from the group of hydrogen, $C_1-C_4$ alkyl, $C_2-C_4$ alkenyl, $C_1-C_4$ haloalkyl, and $C_1-C_4$ heteroalkyl;

$R^5$ is selected from the group of hydrogen, F, Cl, Br, OH, OMe, and $C_1-C_4$ alkyl;

$R^6$ is selected from the group of F, Cl, Br, $CH_3$, $CF_3$, $CHF_2$, $CFH_2$, CN, $CF_2Cl$, $CF_2OR^3$, $OR^3$, $SR^3$, $NR^3R^4$, $C_1-C_4$ alkyl, $C_2-C_4$ alkenyl, $C_1-C_4$ haloalkyl, $C_2-C_4$ haloalkenyl, $C_1-C_4$ heteroalkyl, and $C_2-C_4$ heteroalkenyl;

$R^7$ is selected from the group of hydrogen, F, Cl, Br, $OR^3$, $NR^3R^4$, $SR^3$, $C_1-C_8$ alkyl, $C_1-C_8$ haloalkyl, and $C_1-C_8$ heteroalkyl;

$R^8$ is hydrogen;

$R^9$ is selected from the group of hydrogen, F, Br, Cl, $OR^3$, $NR^3R^4$, $SR^3$, $C_1-C_4$ alkyl, and $C_1-C_4$ haloalkyl;

$R^{10}$ is selected from the group of:

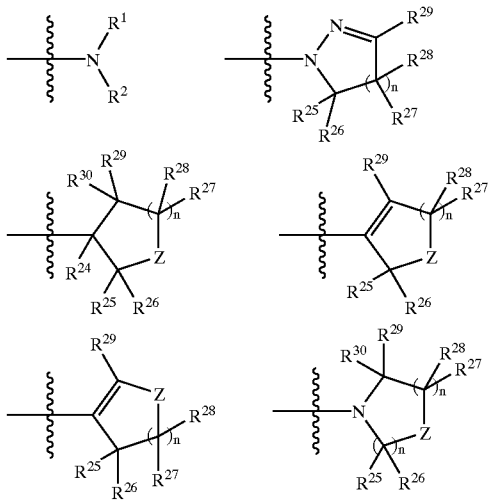

$R^{16}$ is selected from the group of hydrogen, $C_1$–$C_8$ alkyl, $C_1$–$C_8$ haloalkyl, $C_1$–$C_8$ heteroalkyl, $COR^{17}$, $CO_2R^{17}$, and $CONR^{17}R^{17}$;

$R^{17}$ is selected from the group of $C_1$–$C_4$ alkyl, $C_1$–$C_4$ haloalkyl and $C_1$–$C_4$ heteroalkyl;

$R^{24}$ is hydrogen, OH, or $OR^3$;

$R^{25}$ and $R^{30}$ are each independently selected from the group of hydrogen, OH, $C_1$–$C_6$ alkyl, $C_1$–$C_6$ haloalkyl, $C_1$–$C_6$ heteroalkyl, wherein the alkyl, haloalkyl, and heteroalkyl are optionally substituted with F, Cl, $OR^3$, $NR^3R^4$, $C_1$–$C_4$ alkyl, $C_1$–$C_4$ haloalkyl, $C_1$–$C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1$–$C_4$ alkyl;

$R^{26}$ through $R^{29}$ are each independently selected from the group of hydrogen, F, Cl, Br, $OR^3$, $NR^3R^4$, $C_1$–$C_6$ alkyl, $C_1$–$C_6$ haloalkyl, $C_1$–$C_6$ heteroalkyl and $C_2$–$C_6$ alkenyl;

any two of $R^{25}$, $R^{26}$, $R^{27}$, $R^{28}$, $R^{29}$ and $R^{30}$ taken together form a three to seven-membered alkyl or alkenyl or heteroalkyl-nonaromatic ring; or any four of $R^{25}$, $R^{26}$, $R^{27}$, $R^{28}$, $R^{29}$ and $R^{30}$ taken together form a fused aromatic ring;

X is $NR^{16}$;

is selected from the group of O, S, $NR^3$, NOH, and $NOR^3$;

Z is selected from the group of O, S, $NR^3$, and $CR^{25}R^{26}$, or

Z is two hydrogens; and n is 1 or 2.

7. A compound of claim 1, wherein:

$R^1$ and $R^2$ are each independently selected from the group of $COR^3$, $C_1$–$C_8$ alkyl, $C_2$–$C_8$ alkenyl, $C_1$–$C_8$ haloalkyl, $C_2$–$C_8$ haloalkenyl, $C_1$–$C_8$ heteroalkyl, $CH_2R^{3A}$, aryl, and heteroaryl, wherein the aryl and heteroaryl are optionally substituted with F, Cl, Br, OH, OMe, SH, OMe, SMe, CN, $NO_2$, $CF_3$, Me, COMe, or $COCF_3$; or $R^3$ is $C_1$–$C_6$ alkyl or $C_1$–$C_6$ haloalkyl;

$R^{3A}$ is heteroaryl or aryl, wherein the heteroaryl and aryl are optionally substituted with F, Cl, Br, CN, OMe, $C_1$–$C_4$ alkyl, or $C_1$–$C_4$ haloalkyl;

$R^4$ is hydrogen or $C_1$–$C_4$ alkyl;

$R^5$ is selected from the group of hydrogen, F, Cl, OMe, and $C_1$–$C_4$ alkyl;

$R^6$ is selected from the group of F, Cl, Br, $C_1$–$C_4$ alkyl, $C_1$–$C_4$ haloalkyl $CF_3$, $CHF_2$, $CFH_2$, CN, $CF_2Cl$, $CF_2OMe$, and OMe;

$R^7$ is selected from the group of hydrogen, F, Cl, Me, OMe, and $CF_3$;

$R^8$ is selected from the group of hydrogen, F, and Cl;

$R^9$ is selected from the group of hydrogen, F, Cl, OH, Me, OMe, and $CF_3$;

$R^{10}$ is selected from the group of:

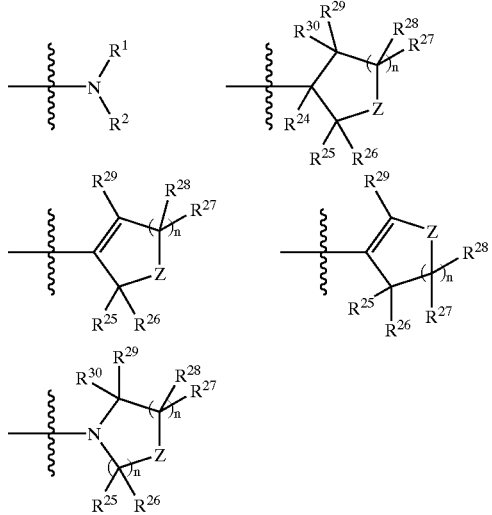

$R^{16}$ is selected from the group of hydrogen, $C_1$–$C_6$ alkyl, $C_1$–$C_6$ haloalkyl, $COR^{17}$, $CO_2R^{17}$, and $CONR^{17}R^{17}$;

$R^{17}$ is selected from the group of $C_1$–$C_4$ alkyl, $C_1$–$C_4$ halo alkyl and $C_1$–$C_4$ heteroalkyl;

$R^{24}$ is hydrogen or OH;

$R^{25}$ and $R^{30}$ are each independently selected from the group of hydrogen, OH, $C_1$–$C_6$ alkyl, $C_1$–$C_6$ haloalkyl, $C_1$–$C_6$ heteroalkyl, wherein the alkyl, haloalkyl, and heteroalkyl are optionally substituted with F, Cl, $OR^3$, $NR^3R^4$, $C_1$–$C_4$ alkyl, $C_1$–$C_4$ haloalkyl, $C_1$–$C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1$–$C_4$ alkyl;

$R^{26}$ through $R^{29}$ are each independently selected from the group of hydrogen, F, Cl, OH, OMe, $C_1$–$C_6$ alkyl, $C_1$–$C_6$ haloalkyl, and $C_1$–$C_6$ heteroalkyl; or any two of $R^{25}$ $R^{26}$, $R^{27}$, $R^{28}$, $R^{29}$ and $R^{30}$ taken together form a four to six-membered alkyl or alkenyl nonaromatic ring; or any four of $R^{25}$ $R^{26}$, $R^{27}$, $R^{28}$, $R^{29}$ and $R^{30}$ taken together form a fused aromatic ring;

X is $NR^{16}$;

Y is selected from the group of O, S, and $NOR^3$;

Z is O or $CR^{25}R^{26}$; or

Z is two hydrogens; and n is 1 or 2.

8. A compound of claim 1, wherein:

$R^1$ and $R^2$ are each independently selected from the group of $C_1$–$C_8$ alkyl, $C_2$–$C_8$ alkenyl, $C_1$–$C_8$ haloalkyl, $C_1$–$C_8$ heteroalkyl, and $CH_2R^{3A}$; or $R^3$ is $C_1$–$C_6$ alkyl, or $C_1$–$C_6$ haloalkyl;

$R^{34}$ is heteroaryl or aryl, wherein the heteroaryl and aryl are optionally substituted with F, Cl, Br, CN, $CF_3$, OMe, or $C_1$–$C_4$ alkyl;

$R^4$ is hydrogen;

$R^5$ is selected from the group of hydrogen, F, Cl, OMe, and Me;

$R^6$ is selected from the group of F, Cl, $C_1$–$C_4$ alkyl, $CF_3$, $CHF_2$, $CFH_2$, $CF_2Cl$, $CF_2OMe$, and OMe;

$R^7$ is selected from the group of hydrogen, F, Cl, Me, OMe;

$R^8$ is hydrogen;

$R^9$ is selected from the group of hydrogen, F, Cl, Me, OMe, $CF_3$;

$R^{10}$ is selected from the group of:

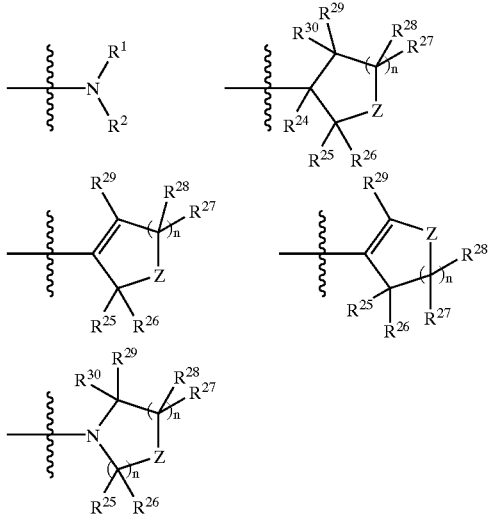

$R^{24}$ is hydrogen or OH;

$R^{25}$ and $R^{30}$ are each independently selected from the group of hydrogen, OH, $C_1$–$C_6$ alkyl, $C_1$–$C_6$ haloalkyl, $C_1$–$C_6$ heteroalkyl, wherein the alkyl, haloalkyl, and heteroalkyl are optionally substituted with F, Cl, $OR^3$, $NR^3R^4$, $C_1$–$C_4$ alkyl, $C_1$–$C_4$ haloalkyl, $C_1$–$C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1$–$C_4$ alkyl;

$R^{26}$ through $R^{29}$ are each independently selected from the group of hydrogen, F, Cl, OH, OMe, $C_1$–$C_4$ alkyl, and $C_1$–$C_4$ haloalkyl;

X is NH;

Y is O or S;

Z is $CR^{25}R^{26}$; and n is 1 or 2.

9. A compound of claim 1, wherein $R^{10}$ is represented by the formula:

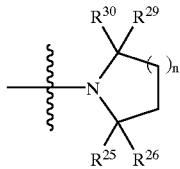

wherein:

$R^{25}$ and $R^{30}$ are each independently selected from the group of hydrogen, OH, $C_1$–$C_6$ alkyl, $C_1$–$C_6$ haloalkyl, $C_1$–$C_6$ heteroalkyl, wherein the alkyl, haloalkyl, and heteroalkyl are optionally substituted with F, Cl, $OR^3$, $NR^3R^4$, $C_1$–$C_4$ alkyl, $C_1$–$C_4$ haloalkyl, $C_1$–$C_4$ heteroalkyl, aryl or heteroaryl, and wherein the aryl and heteroaryl are optionally substituted with F, Cl, Br, I, CN, $NO_2$, OH, $OCH_3$, $CF_3$ or $C_1$–$C_4$ alkyl;

$R^{26}$ and $R^{29}$ are each independently selected from the group of hydrogen, F, Cl, Br, I, OH, $OR^3$, $NR^3R^4$, $SR^3$, $SOR^3$, $SO_2R^3$, $C_1$–$C_6$ alkyl, $C_1$–$C_6$ haloalkyl, $C_1$–$C_6$ heteroalkyl, $C_2$–$C_6$ alkynyl and $C_2$–$C_6$ alkenyl;

$R^3$ is selected from the group of hydrogen, $C_1$–$C_8$ alkyl, $C_2$–$C_8$ alkenyl, $C_2$–$C_8$ alkynyl, $C_1$–$C_8$ haloalkyl, and $C_1$–$C_8$ heteroalkyl;

$R^4$ is selected from the group of hydrogen, $C_1$–$C_4$ alkyl, $C_1$–$C_4$ haloalkyl, and $C_1$–$C_4$ heteroalkyl; and n is 1, 2, or 3.

10. A compound of claim 1, wherein $R^{10}$ is represented by the formula:

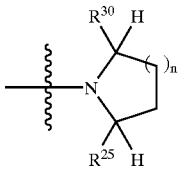

wherein:

$R^{25}$, $R^{30}$ are each independently selected from the group of hydrogen, F, Cl, Br, I, $OR^3$, $NR^3R^4$, $SR^3$, $SOR^3$, $SO_2R^3$, $COR^3$, $CO_2R^3$, $C_1$–$C_6$ alkyl, $C_1$–$C_6$ haloalkyl, $C_1$–$C_6$ heteroalkyl, $C_2$–$C_6$ alkynyl and $C_2$–$C_6$ alkenyl, wherein the alkyl, haloalkyl, and heteroalkyl are optionally substituted with aryl or heteroaryl, and wherein the aryl and heteroaryl are optionally substituted with F, Cl, Br, I, CN, $NO_2$, OH, $OCH_3$, $CF_3$ or $C_1$–$C_6$ alkyl;

$R^3$ is selected from the group of hydrogen, $C_1$–$C_8$ alkyl, $C_2$–$C_8$ alkenyl, $C_2$–$C_8$ alkynyl, $C_1$–$C_8$ haloalkyl, and $C_1$–$C_8$, heteroalkyl; and $R^4$ is selected from the group of hydrogen, $C_1$–$C_4$ alkyl, $C_1$–$C_4$ haloalkyl, and $C_1$–$C_4$ heteroalkyl;

n is 1, 2, or 3.

11. A compound of claim 1, wherein $R^{10}$ is represented by the formula:

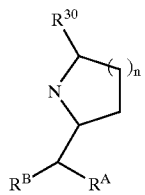

wherein:

$R^{30}$ is hydrogen, $C_1$–$C_4$ alkyl or $C_1$–$C_4$ haloalkyl;

$R^A$ is selected from the group of hydrogen, $OR^C$, $O_2CR^C$, $(CH_2)_nOR^C$, $NHR^C$, $NHCOR^C$, F, Cl, Br, I, CN, SCN, and $SCH_3$;

$R^B$ is selected from the group of hydrogen, F, Cl, Br, I, $CHF_2$, $CF_3$, $C_1$–$C_6$ alkyl, aryl, and heteroaryl, wherein the alkyl, aryl and heteroaryl are optionally substituted with F, Cl, Br, I, CN, $NO_2$, OH, $OCH_3$, $CF_3$, or $C_1$–$C_4$ alkyl;

$R^C$ is selected from the group of hydrogen, $C_1$–$C_8$ alkyl, $C_2$–$C_8$ alkenyl, $C_2$–$C_8$ alkynyl, $C_1$–$C_8$ haloalkyl, $C_1$–$C_8$ heteroalkyl, and $(CH_2)_nR^D$;

$R^D$ is aryl or heteroaryl, optionally substituted with F, Cl, Br, I, CN, NO$_2$, OH, OCH$_3$, CF$_3$, or C$_1$–C$_6$ alkyl; and n is 1, 2, or 3.

12. A compound according to claim 1, wherein the compound is an androgen receptor modulator.

13. A compound according to claim 12, wherein the compound is an androgen receptor antagonist.

14. A compound according to claim 12, wherein the compound is an androgen receptor agonist.

15. A compound according to claim 12, wherein the compound is an androgen receptor partial agonist.

16. A compound according to claim 1, wherein the compound is a progesterone receptor modulator.

17. A compound according to claim 16, wherein the compound is a progesterone receptor antagonist.

18. A compound according to claim 16, wherein the compound is a progesterone receptor agonist.

19. A compound according to claim 16, wherein the compound is a progesterone receptor partial agonist.

20. A compound according to claim 1, wherein the compound is selected from the group of:

6-Dimethylamino-4-trifluoromethyl-2(1H)-quinolinone (Compound 217);

6-Diethylamino-4-trifluoromethyl-2(1H)-quinolinone (Compound 218);

6-Dipropylamino-4-trifluoromethyl-2(1H)-quinolinone (Compound 219);

6-Dibutylamino-4-trifluoromethyl-2(1H)-quinolinone (Compound 220);

6-Diisobutylamino-4-trifluoromethyl-2(1H)-quinolinone (Compound 221);

6-(bis-Cyclopropylmethyl)amino-4-trifluoromethyl-2(1H)-quinolinone (Compound 222);

6-(bis-2,2,2-Trifluoroethyl)amino-4-trifluoromethyl-2(1)-quinolinone (Compound 223);

6-(bis-2,2,3,3,3-Pentafluoropropyl)amino-4-trifluoromethyl-2(1H)-quinolinone (Compound 224);

6-(bis-2-Chloro-2,2-difluoroethyl)amino-4-trifluoromethyl-2(1H)-quinolinone (Compound 225);

6-(bis-2-Bromoethyl)amino-4-trifluoromethyl-2(1H)-quinolinone (Compound 226);

6-(bis-N-2,2,2-Trichloroethyl)amino-4-trifluoromethyl-2(1H)-quinolinone (Compound 228);

6-(N-2,2,2-Chlorodifluoroethyl-N-2,2,2-Trichloroethyl)amino-4-trifluoromethyl-2(1H)-quinolinone (Compound 229);

6-(bis-N-2,2-Difluoroethyl)amino-4-trifluoromethyl-2(1H)-quinolinone (Compound 230);

6-(N-2,2-Dichloroethyl-N-2,2,2-trichloroethyl)amino-4-trifluoromethyl-2(1H)-quinolinone (Compound 231);

6-(bis-N-2,2-Dichloroethyl)amino-4-trifluoromethyl-2(1H)-quinolinone (Compound 232);

6-(N-2,2-Dichloroethyl-N-2,2-difluoroethyl)amino-4-trifluoromethyl-2(1H)-quinolinone (Compound 233);

6-(N-2,2-Dichloroethyl-N-2,2,2-chlorodifluoroethyl)amino-4-trifluoromethyl-2(1H)-quinolinone (Compound 234);

6-(N-Isopropyl-N-methyl)amino-4-trifluoromethyl-2(1H)-quinolinone (Compound 235);

6-(N-Methyl-N-cyclopentyl)amino-4-trifluoromethyl-2(1H)-quinolinone (Compound 236);

6-(N-Methyl-N-isobutyl)amino-4-trifluoromethyl-2(1H)-quinolinone (Compound 237);

6-(N-Ethyl-N-propyl)amino-4-trifluoromethyl-2(1H)-quinolinone (Compound 238);

6-(N-Ethyl-N-isopropyl)amino-4-trifluoromethyl-2(1H)-quinolinone (Compound 239);

6-(N-Ethyl-N-1-methylpropyl)amino-4-trifluoromethyl-2(1H)-quinolinone (Compound 240);

6-(N-Ethyl-N-isobutyl)amino-4-trifluoromethyl-2(1H)-quinolinone (Compound 241);

6-(N-Ethyl-N-2,2-dimethylpropyl)amino-4-trifluoromethyl-2(1H)-quinolinone (Compound 242);

6-(N-Ethyl-N-cyclopentyl)amino-4-trifluoromethyl-2(1H)-quinolinone (Compound 243);

6-(N-Ethyl-N-1-acetylethyl)amino-4-trifluoromethyl-2(1H)-quinolinone (Compound 244);

(±)-6-(N-Ethyl-N-1-methyl-2-hydroxypropyl)amino-4-trifluoromethyl-2(1H)-quinolinone (Compound 245);

6-(N-Ethyl-N-2,2,2-trifluoroethyl)amino-4-trifluoromethyl-2(1H)-quinolinone (Compound 246);

6-(N-Ethyl-N-3-furylmethyl)amino-4-trifluoromethyl-2(1H)-quinolinone (Compound 247);

(±)-6-(N-Ethyl-N-2,2-dimethoxyisopropyl)amino-4-trifluoromethyl-2(1H)-quinolinone (Compound 248);

6-(N-Isopropyl-N-propyl)amino-4-trifluoromethyl-2(1H)-quinolinone (Compound 249);

6-(N-2-Hydroxyethyl-N-propyl)amino-4-trifluoromethyl-2(1H)-quinolinone (Compound 250);

(±)-6-(N-Propyl-N-1-methylbutyl)amino-4-trifluoromethyl-2(1H)-quinolinone (Compound 251);

(±)-6-(N-Propyl-N-1,2-dimethylpropyl)amino-4-trifluoromethyl-2(1H)-quinolinone (Compound 252);

6-(N-Propyl-N-isobutyl)amino-4-trifluoromethyl-2(1H)-quinolinone (Compound 253);

6-(N-Propyl-N-cyclopropylmethyl)amino-4-trifluoromethyl-2(1H)-quinolinone (Compound 254);

(±)-6-(N-Propyl-N-1-methylpropyl)amino-4-trifluoromethyl-2(1H)-quinolinone (Compound 255);

6-(N-2-Hydroxyethyl-N-isopropyl)amino-4-trifluoromethyl-2(1H)-quinolinone (Compound 256);

6-(N-Isopropyl-N-cyclopropylmethyl)amino-4-trifluoromethyl-2(1H)-quinolinone (Compound 257);

6-(N-Methyl-N-2,2,2-trifluoroethyl)amino-4-trifluoromethyl-2(1H)-quinolinone (Compound 258);

6-(N-2,2,2-trifluoroethyl-N-isobutyl)amino-4-triflouromethyl-2(1H)-quinolinone (Compound 259);

6-(N-2,2,2-trifluoroethyl-N-isopropyl)amino-4-trifluoromethyl-2(1H)-quinolinone (Compound 260);

6-(N-2,2,2-Trifluoroethyl-N-cyclopropylmethyl)amino-4-trifluoromethyl-2(1H)-quinolinone (Compound 261);

(±)-6-(N-2,2,2-Trifluoroethyl-N-1-methylpropyl)amino-4-trifluoromethyl-2(1H)-quinolinone (Compound 262);

(±)-6-(N-2,2,2-Trfluoroethyl-N-2-chloroisopropyl)amino-4-trifluoromethyl-2(1H)-quinolinone (Compound 263);

(+)-6-(N-2,2,2-Trifluoroethyl-N-2-chloroisopropyl)amino-4-trifluoromethyl-2(1H)-quinolinone (Compound 264);

(−)-6-(N-2,2,2-Trifluoroethyl-N-2-chloroisopropyl)amino-4-trifluoromethyl-2(1H)-quinolinone (Compound 265);

6-(N-2,2,2-Trifluoroethyl-N-3-furfuryl)amino-4-trifluoromethyl-2(1H)-quinolinone (Compound 266);

6-(N-2,2,2-Trifluoroethyl-N-3-thiophenemethyl)amino-4-trifluoromethyl-2(1H)-quinolinone (Compound 267);

6-(N-2,2,2-Trifluoroethyl-N-3,3-dimethylbutyl)amino-4-trifluoromethyl-2(1H)-quinolinone (Compound 268);

6-(N-2,2,2-Trifluoroethyl-N-2-thiophenemethyl)amino-4-trifluoromethyl-2(1H)-quinolinone (Compound 269);

6-(N-2,2,2-Tifluoroethyl-N-2-furfuryl)amino-4-trifluoromethyl-2(1H)-quinolinone (Compound 270);

6-(N-Butyl-N-2,2,2-trifluoroethyl)amino-4-trifluoromethyl-2(1H)-quinolinone (Compound 271);

6-(bis-N,N-Benzyl)amino-4-trifluoromethyl-2(1H)-quinolinone (Compound 272);

6-(N-2,2,2-Trifluoroethyl-N-cyclobutyl)amino-4-trifluoromethyl-2(1H)-quinolinone (Compound 273);

6-(N-2,2,2-Trifluoroethyl-N-2,2-dichloroethyl)amino-4-trifluoromethyl-2(1H)-quinolinone (Compound 274);

6-(N-2,2,2-Trifluoroethyl-N-2-chloroethyl)amino-4-trifluoromethyl-2(1H)-quinolinone (Compound 275);

6-(N-Benzyl-N-2,2,2-trifluoroethyl)amino-4-trifluoromethyl-2(1H)-quinolinone (Compound 276);

6-(N-4-Fluorobenzyl-N-2,2,2-trifluoroethyl)amino-4-trifluoromethyl-2(1H)-quinolinone (Compound 277);

6-(N-Propyl-N-2,2,2-trifluoroethyl)amino-4-trifluoromethyl-2(1H)-quinolinone (Compound 278);

6-(N-2,2,3,3,3-Pentafluoropropyl-N-2,2,2-trifluoroethyl)amino-4-trifluoromethyl-2(1H)-quinolinone (Compound 279);

6-Diallylamino-4-trifluoromethyl-2(1H)-quinolinone (Compound 280);

6-(N-Isobutyl-N-allyl)amino-4-trifluoromethyl-2(1H)-quinolinone (Compound 281);

6-(N-Isopropyl-N-allyl)amino-4-trifluoromethyl-2(1H)-quinolinone (Compound 282);

6-(N-Allyl-N-2,2,2-trifluoroethyl)amino-4-trifluoromethyl-2(1H)-quinolinone (Compound 283);

6-(N-Allyl-N-cyclopropylmethyl)amino-4-trifluoromethyl-2(1H)-quinolinone (Compound 285);

6-(N-Allyl-N-2,2,2-trifluoroacetyl)amino-4-trifluoromethyl-2(1)-quinolinone (Compound 286);

6-(N-2,2,2-Trifluoroethyl-N-2,2,2-trifluoroacetyl)amino-4-trifluoromethyl-2(1H)-quinolinone (Compound 287);

6-(N-Allyl-N-propyl)amino-4-trifluoromethyl-2(1H)-quinolinone (Compound 288);

(±)-6-(N-2-Hydroxyisopropyl-N-2,2,2-trifluoroethyl)amino-4-trifluoromethyl-2(1H)-quinolinone (Compound 289);

(±)-6-(N-Isobutyl-N-2,2,2-trifluoroisopropyl)amino-4-trifluoromethyl-2(1H)-quinolinone (Compound 290);

6-(N-2,2-Difluoroethyl-N-2,2,2-trifluoroethyl)amino-4-trifluoromethyl-2(1H)-quinolinone (Compound 291);

6-(N-2,2-Dimethylpropyl-N-2,2,2-trifluoroethyl)amino-4-trifluoromethyl-2(1H)-quinolinone (Compound 292);

6-(N-2,2-Difluoro-2-chloroethyl-N-2,2,2-trifluoroethyl)amino-4-trifluoromethyl-2(1H)-quinolinone (Compound 293);

6-(N-2,2-Difluoro-2-chloroethyl-N-2,2-difluoroethyl)amino-4-trifluoromethyl-2(1H)-quinolinone (Compound 294);

6-(N-2,2,2-Trifluoroethyl-N-methylsufonyl)amino-4-trifluoromethyl-2(1H)-quinolinone (Compound 295);

1-Methyl-6-(N-propyl-N-isobutyl)amino-4-trifluoromethyl-2(1H)-quinolinone (Compound 296);

1-Methyl-6-(bis-2,2,2-trifluoroethyl)amino-4-trifluoromethyl-2(1H)-quinolinone (Compound 297);

1-Ethyl-6-(bis-2,2,2-trifluoroethyl)amino-4-trifluoromethyl-2(1H)-quinolinone (Compound 298);

6-(bis-N,N-2,2,2-Trifluoroethyl)amino-4-trifluoromethyl-2(1H)-thioquinolinone (Compound 300);

(±)-6-(N-2,2,2-Trifluoroethyl-N-2,2,2-trifluoroisopropyl)amino-4-trifluoromethyl-2(1H)-quinolinone (Compound 301);

(+)-6-(N-2,2,2-Trifluoroethyl-N-2,2,2-trifluoroisopropyl)amino-4-trifluoromethyl-2(1H)-quinolinone (Compound 302);

(−)-6-(N-2,2,2-Trifluoroethyl-N-2,2,2-trifluoroisopropyl)amino-4-trifluoromethyl-2(1H)-quinolinone (Compound 303);

6-(1-Piperdinyl)-4-trifluoromethyl-2(1H)-quinolinone (Compound 311);

6-(1-Pyrrolidinyl)-4-trifluoromethyl-2(1H)-quinolinone (Compound 312);

6-(1-Morpholino)-4-trifluoromethyl-2(1H)-quinolinone (Compound 313);

(±)-6-(2-Methyl-1-piperidino)-4-trifluoromethyl-2(1H)-quinolinone (Compound 314);

(+)-6-(2-Methyl-1-piperidino)-4-trifluoromethyl-2(1H)-quinolinone (Compound 315);

(−)-6-(2-Methyl-1-piperidino)-4-trifluoromethyl-2(1H)-quinolinone (Compound 316);

6-(N-phenyl-N-ethylamino)-4-trifluoromethyl-2(1H)-quinolinone (Compound 319);

6-(N-phenyl-N-ethylamino)-4-trifluoromethyl-2-isopropyloxyquinoline (Compound 320);

6-(N-phenyl-N-2,2,2-trifluoroethylamino)-4-trifluoromethyl-2(1H)-quinolinone (Compound 321);

(±)-6-(3-Methyl-1-piperidino)-4-trifluoromethyl-2(1H)-quinolinone (Compound 322);

6-(4-Methyl-1-piperidino)-4-triflouromethyl-2(1H)-quinolinone (Compound 323);

6-(cis-3,5-Dimethyl-1-piperidino)-4-trifluoromethyl-2(1H)-quinolinone (Compound 324);

6-(2,6-cis-Dimethyl-1-piperidino)-4-triflouromethyl-2(1H)-quinolinone (Compound 325);

6-(2,6-trans-Dimethyl-1-piperidino)-4-trifluoromethyl-2(1H)-quinolinone (Compound 326);

(±)-6-(2-Methyl-1-pyrrolidino)-4-trifluoromethyl-2(1H)-quinolinone (Compound 327);

6-(2,5-cis-Dimethyl-1-pyrrolidino)-4-trifluoromethyl-2(1H)-quinolinone (Compound 328);

(±)-6-(2,5-trans-Dimethyl-1-pyrrolidino)-4-trifluoromethyl-2(1H)-quinolinone (Compound 329);

6-(1-Azepano)-4-trifluoromethyl-2(1H)-quinolinone (Compound 330);

(±)-6-(2-Hydroxymethyl-1-piperidino)-4-trifluoromethyl-2(1H)-quinolinone (Compound 331);

6-(2,5-cis-Dimethyl-1-pyrrolino)-4-trifluoromethyl-2(1H)-quinolinone (Compound 332);

(±)-6-(2-Propyl-1-piperidino)-4-trifluoromethyl-2(1H)-quinolinone (Compound 333);

(±)-6-(2-Methoxymethyl-1-piperidino)-4-trifluoromethyl-2(1H)-quinolinone (Compound 334);

(±)-6-(2-Ethyl-1-piperidino)-4-trifluoromethyl-2(1H)-quinolinone (Compound 335);

6-(1-Heptamethyleneimino)-4-trifluoromethyl-2(1H)-quinolinone (Compound 336);

(±)-6-(2-Ethoxycarbonyl-1-piperidino)-4-trifluoromethyl-2(1H)-quinolinone (Compound 337);

(±)-6-(2-Isopropyl-1-pyrrolidino)-4-trifluoromethyl-2(1H)-quinolinone (Compound 338);

(±)-6-(2-Hydroxycarbonyl-1-piperidino)-4-trifluoromethyl-2(1H)-quinolinone (Compound 339);

6-(3,5-cis-Dimethyl-1-piperazino)-4-trifluoromethyl-2(1H)-quinolinone (Compound 340);

(±)-6-(2-Benzyl-1-pyrrolidino)-4-trifluoromethyl-2(1H)-quinolinone (Compound 341);

(±)-6-(5-Methyl-2-oxo-1-pyrrolidino)-4-trifluoromethyl-2(1H)-quinolinone (Compound 342);

(±)-6-(2-(2-Hydroxyethyl)-1-piperidino)-4-trifluoromethyl-2(1H)-quinolinone (Compound 343);

(±)-6-(3-Hydroxy-1-pyrrolidino)-4-trifluoromethyl-2(1H)-quinolinone (Compound 344);

(±)-6-(3-Acetyloxy-1-pyrrolidino)-4-trifluoromethyl-2(1H)-quinolinone (Compound 345);

(±)-6-(3-Hydroxy-1-pyrrolidino)-4-trifluoromethyl-2(1H)-quinolinone (Compound 346);

6-(1-Indolino)-4-trifluoromethyl-2(1H)-quinolinone (Compound 347);

6-(1-Tetrahydroquinolino)-4-trifluoromethyl-2(1H)-quinolinone (Compound 348);

6-(2-Tetrahydroisoquinolino)-4-trifluoromethyl-2(1H)-quinolinone (Compound 349);

(±)-6-(1,3,3-Trimethyl-6-azabicyclo[3,2,1]octanyl-6-)-4-trifluoromethyl-2(1H)-quinolinone (Compound 350);

(±)-6-(2-Trifluoromethyl-5-cis-methyl-1-oxazolidino)-4-trifluoromethyl-2(1H)-quinolinone (Compound 351);

(±)-6-(2-Trifluoromethyl-5-trans-methyl-1-oxazolidino)-4-trifluoromethyl-2(1H)-quinolinone (Compound 352);

(±)-6-(2-Trifluoromethyl-5-cis-ethyl-1-oxazolidino)-4-trifluoromethyl-2(1H)-quinolinone (Compound 354);

(±)-6-(2-Trifluoromethyl-5-trans-ethyl-1-oxazolidino)-4-trifluoromethyl-2(1H)-quinolinone (Compound 355);

(±)-6-(5-Methyl-1-oxazolidino)-4-trifluoromethyl-2(1H)-quinolinone (Compound 356);

6-(N-2,2,2-Trifluoroethyl-N-3,3,3-trifluoropropyl)amino-4-trifluoromethyl-2(1H)-quinolinone (Compound 358);

6-bis-N,N-Thiomethoxymethylamino-4-trifluoromethyl-2(1H)-quinolinone (Compound 361);

(±)-6-(2,5-trans-Diethyl-1-pyrrolidino)-4-trifluoromethyl-2(1H)-quinolinone (Compound 363);

6-(2,5-cis-Diethyl-1-pyrrolidino)-4-trifluoromethyl-2(1H)-quinolinone (Compound 364);

(±)-6-(2,5-trans-Dipropyl-1-pyrrolidino)-4-trifluoromethyl-2(1H)-quinolinone (Compound 365);

6-(2,5-cis-Dipropyl-1-pyrrolidino)-4-trifluoromethyl-2(1H)-quinolinone (Compound 366);

6-(2,5-cis-Dibutyl-1-pyrrolidino)-4-trifluoromethyl-2(1H)-quinolinone (Compound 368);

(±)-6-(2,5-trans-Dibutyl-1-pyrrolidino)-4-trifluoromethyl-2(1H)-quinolinone (Compound 369);

6-(2,6-cis-Diethyl-1-piperidino)-4-trifluoromethyl-2(1H)-quinolinone (Compound 370);

(±)-6-(2,6-trans-Diethyl-1-piperidino)-4-trifluoromethyl-2(1H)-quinolinone (Compound 371);

6-(2,6-cis-Dimethyl-1-piperidino)-4-trifluoromethyl-2(1H)-quinolinone (Compound 372);

(±)-6-(2,6-trans-Dimethyl-1-piperidino)-4-trifluoromethyl-2(1H)-quinolinone (Compound 373);

6-(N-Propyl-N-2,2,2-trifluoroethyl)amino-4-methyl-2(1H)-quinolinone (Compound 374);

6-(bis-2,2,2-Trifluoroethyl)amino-4-methyl-2(1H)-quinolinone (Compound 377);

(±)-6-(2,5-trans-dimethyl-1-pyrrolidino)-4-methyl-2(1H)-quinolinone (Compound 379);

6-(2,5-cis-dimethyl-1-pyrrolidino)-4-methyl-2(1H)-quinolinone (Compound 380);

6-(N-Isobutyl-N-2,2,2-trifluoroethyl)amino-4-methyl-2(1H)-quinolinone (Compound 381);

6-(bis-N,N-2,2,2-Chlorodifluoroethyl)amino-4-methyl-2(1H)-quinolinone (Compound 383);

6-(N-2,2,2-Chlorodifluoroethyl-N-2,2,2-trifluoroethyl)amino-4-methyl-2(1H)-quinolinone (Compound 384);

6-(N-Ethyl-N-2,2,2-trifluoroethyl)amino-4-methyl-2(1H)-quinolinone (Compound 386);

6-N,N-Diethylamino-4-methyl-2(1H)-quinolinone (Compound 387);

6-(bis-2,2,2-trifluoroethyl)amino-4-ethyl-2(1H)-quinolinone (Compound 388);

6-(bis-2,2,2-trifluoroethyl)amino-4-isopropyl-2(1H)-quinolinone (Compound 391);

7-Fluoro-6-(bis-trifluoroethyl)amino-4-trifluoro(methyl-2(1H)-quinolinone (Compound 393);

8-Fluoro-6-(N-2,2,2-trifluoroethyl-N-isopropyl)amino-4-trifluoromethyl-2(1H)-quinolinone (Compound 401);

3-Fluoro-6-(bis-2,2,2-trifluorofluoroethyl)amino-4-trifluoromethyl-2(1H)-quinolinone (Compound 404);

6-(bis-Isobutylamino)-4-methyl-2(1H)-quinolinone (Compound 405);

3-Fluoro-6-(N-methyl-N-2,2,2-trifluorofluoroethyl)amino-4-trifluoromethyl-2(1H)-quinolinone (Compound 406);

6-(bis-N,N-2,2,2-Trifluoroethyl)amino-4-methoxy-2(1H)-quinolinone (Compound 411);

6-(bis-N,N-2,2,2-Trifluoroethyl)amino-4-difluoromethyl-2(1H)-quinolinone (Compound 413);

4-Chloro-6-(bis-N,N-2,2,2-trifluoroethyl)amino-2(1H)-quinolinone (Compound 417);

(R)-6-(2-Hydroxymethyl-1-pyrrolidino)-4-trifluoromethyl-2(1H)-quinolinone (Compound 421);

(R)-6-(2-Methoxymethyl-1-pyrrolidino)-4-trifluoromethyl-2(1H)-quinolinone (Compound 423);

(±)-6-(2-Chloromethyl-1-piperidino)-4-trifluoromethyl-2(1H)-quinolinone (Compound 424);

(±)-6-(2-Cyanothiomethyl-1-piperidino)-4-trifluoromethyl-2(1H)-quinolinone (Compound 425);

(±)-6-(2-Thiomethoxymethyl-1-piperidino)-4-trifluoromethyl-2(1H)-quinolinone (Compound 426);

(±)-6-(2-Cyanomethyl-1-piperidino)-4-trifluoromethyl-2(1H)-quinolinone (Compound 427);

(±)-6-(2-Bromomethyl-1-piperidino)-4-trifluoromethyl-2(1H)-quinolinone (Compound 428);

(±)-6-(2-Iodomethyl-1-piperidino)-4-trifluoromethyl-2(1H)-quinolinone (Compound 429);

(+)R-6-(2-Iodomethyl-1-pyrrolidino)-4-trifluoromethyl-2 (1H)-quinolinone (Compound 430);
(±)-6-(2-Fluoromethyl-1-piperidino)-4-trifluoromethyl-2 (1H)-quinolinone (Compound 431);
(+)S-6-(2-Chloromethyl-1-piperidino)-4-trifluoromethyl-2(1H)-quinolinone (Compound 432);
(−)R-6-(2-Chloromethyl-1-piperidino)-4-trifluoromethyl-2(1H)-quinolinone (Compound 433);
(+)R-6-(2-Chloromethyl-1-pyrrolidino)-4-trifluoromethyl-2(1H)-quinolinone (Compound 434);
(−)S-6-(2-Chloromethyl-1-pyrrolidino)-4-trifluoromethyl-2(1H)-quinolinone (Compound 435);
R-6-(2-Difluoromethyl-1-pyrrolidino)-4-trifluoromethyl-2(1H)-quinolinone (Compound 436);
(±)-6-(2-(1l-Hydroxy-2,2,2-trifluoroethyl)-1-piperidino)-4-trifluoromethyl-2(1H)-quinolinone (Compound 437);
(±)-6-(2l-(1u-Hydroxy-2,2,2-trifluoroethyl)-1-piperidino)-4-triflouromethyl-2(1H)-quinolinone (Compound 438);
(±)-6-(2-Formyl-1-piperidino)-4-trifluoromethyl-2(1H)-quinolinone (Compound 439);
(±)-6-(2-Difluoromethyl-1-piperidino)-4-trifluoromethyl-2(1H)-quinolinone (Compound 440);
(±)-6-(2-Aminomethyl-1-piperidino)-4-trifluoromethyl-2 (1H)-quinolinone (Compound 441);
(R)-6-(2-Vinyl-1-pyrrolidino)-4-trifluoromethyl-2(1H)-quinolinone (Compound 442);
(R)-6-(2-Formyl-1-pyrrolidino)-4-triflouromethyl-2(1H)-quinolinone (Compound 443);
(±)-6-(2-Vinyl-1-piperidino)-4-trifluoromethyl-2(1H)-quinolinone (Compound 444);
(±)-6-(2-Benzyloxyethyl-1-piperidino)-4-trifluoromethyl-2(1H)-quinolinone (Compound 445);
(±)-6-(2-(2,2-Difluoroethyl)-1-piperidino)-4-trifluoromethyl-2(1H)-quinolinone (Compound 446);
(±)-6-(2-Trifluoroacetamidomethyl-1-piperidino)-4-trifluoromethyl-2(1H)-quinolinone (Compound 447);
(±)-6-(2-(2-Ethoxyethyl)-1-piperidino)-4-trifluoromethyl-2(1H)-quinolinone (Compound 448);
(±)-6-(2-(4-Trifluoromethyl)benzyloxyethyl-1-piperidino)-4-trifluoromethyl-2(1H)-quinolinone (Compound 449);
(+)-6-(2R-(1R-Hydroxy-2,2,2-trifluoroethyl)-1-pyrrolidino)-4-trifluoromethyl-2(1H)-quinolinone (Compound 450);
(−)6-(2R-(1S-Hydroxy-2,2,2-trifluoroethyl)-1-pyrrolidino)-4-trifluoromethyl-2(1H)-quinolinone (Compound 451);
6-(2S-(1R-Hydroxy-2,2,2-trifluoroethyl)-1-pyrrolidino)-4-trifluoromethyl-2(1H)-quinolinone (Compound 452);
6-(2S-(1S-Hydroxy-2,2,2-trifluoroethyl)-1-pyrrolidino)-4-trifluoromethyl-2(1H)-quinolinone (Compound 453);
(±)-6-(2l-(1-Hydroxyethyl)-1-piperidino)-4-trifluoromethyl-2(1H)-quinolinone (Compound 454);
(±)-6-(2l-(1u-Hydroxyethyl)-1-piperidino)-4-trifluoromethyl-2(1H)-quinolinone (Compound 455);
(−)-6-(2S-(1S-Hydroxy-2,2,2-trifluoroethyl)-1-piperidino)-4-trifluoromethyl-2(1H)-quinolinone (Compound 456);
(+)-6-(2R-(1R-Hydroxy-2,2,2-trifluoroethyl)-1-piperidino)-4-trifluoromethyl-2(1H)-quinolinone (Compound 457);
(+)-6-(2R-(1S-Hydroxy-2,2,2-trifluoroethyl)-1-piperidino)-4-trifluoromethyl-2(1H)-quinolinone (Compound 458);
(−)-6-(2S-(1R-Hydroxy-2,2,2-trifluoroethyl)-1-piperidino)-4-trifluoromethyl-2(1H)-quinolinone (Compound 459);
(±)-6-(2l-(1-Acetyloxyethyl)-1-piperidino)-4-triflouromethyl-2(1H)-quinolinone (Compound 460);
(±)-6-(2l-(1u-Acetyloxyethyl)-1-piperidino)-4-trifluoromethyl-2(1H)-quinolinone (Compound 461);
(±)-6-(2l-(1u-Methoxy-2,2,2-trifluoroethyl)-1-piperidino)-4-trifluoromethyl-2(1H)-quinolinone (Compound 462);
(±)-6-(2l-(1l-Methoxy-2,2,2-trifluoroethyl)-1-piperidino)-4-trifluoromethyl-2(1H)-quinolinone (Compound 463);
7-Methoxy-6-(N-methyl-N-2,2,2-trifluoroethyl)amino-4-trifluoromethyl-2(1H)-quinolinone (Compound 464);
7-Methoxy-6-(N-ethyl-N-2,2,2-trifluoroethyl)amino-4-trifluoromethyl-2(1H)-quinolinone (Compound 468);
6-(N-Cyclopropylmethyl-N-2,2,2-trifluoroethyl)amino-7-methoxy-4-trifluoromethyl-2(1H)-quinolinone (Compound 470);
6-(N-Cyclopropylmethyl-N-2,2,2-trifluoroethyl)amino-7-hydroxy-4-trifluoromethyl-2(1H)-quinolinone (Compound 471);
6-(N-Isobutyl-N-2,2,2-trifluoroethyl)amino-7-methoxy-4-trifluoromethyl-2(1H)-quinolinone (Compound 472);
6-(N-Isobutyl-N-2,2,2-trifluoroethyl)amino-7-hydroxy-4-trifluoromethyl-2(1H)-quinolinone (Compound 473);
6-(bis-N,N-2,2,2-trifluoroethyl)amino-5-methoxy-4-trifluoromethyl-2(1H)-quinolinone (Compound 600);
6-(bis-N,N-2,2,2-Trifluoroethyl)amino-5-propyloxy-4-trifluoromethyl-2(1H)-quinolinone: (Compound 604);
6-(bis-N,N-2,2,2-Trifluoroethyl)amino-5-ethoxy-4-trifluoromethyl-2(1H)-quinolinone (Compound 607);
6-(bis-N,N-2,2,2-Trifluoroethyl)amino-5-chloro-4-trifluoromethyl-2(1H)-quinolinone (Compound 612);
6-Cyclohexyl-4-trifluoromethyl-2(1H)-quinolinone (Compound 616);
6-Cyclohexyl-3-fluoro-4-trifluoromethyl-2(1H)-quinolinone (Compound 618);
6-(1-Hydroxy-3,3,5,5-tetramethyl)cyclohexyl-4-trifluoromethyl-2(1H)-quinolinone (Compound 625);
6-(3,3,5,5-Tetramethyl)cyclohexenyl-4-trifluoromethyl-2(1H)-quinolinone (Compound 626);
6-(5,5-Dimethycyclopentenyl)-4-trifluoromethyl-2(1H)-quinolinone (Compound 627);
6-(2,2-Dimethycyclopentyl)-4-trifluoromethyl-2(1H)-quinolinone (Compound 628);
6-(1-Hydroxycyclohexyl)-4-trifluoromethyl-2(1H)-quinolinone (Compound 629);
6-Cyclohexenyl-4-trifluoromethyl-2(1H)-quinolinone (Compound 630);
6-Cyclohexyl-4-triflouromethyl-2(1H)-thioquinolinone (Compound 631);
6-Cyclopentenyl-4-trifluoromethyl-2(1H)-quinolinone (Compound 632);

6-Cycloheptenyl-4-trifluoromethyl-2(1H)-quinolinone (Compound 633);
6-Cyclohexenyl-3-fluoro-4-trifluoromethyl-2(1H)-quinolinone (Compound 635);
6-Cyclohexyl-7-methoxy-4-trifluoromethyl-2(1H) quinolinone (Compound 636);
6-Cyclopentyl-3-fluoro-4-trifluoromethyl-2(1H)-quinolinone (Compound 638);
(Z)-6-(1-Propyl-1-)butenyl-4-trifluoromethyl-2(1H)-quinolinone (Compound 639);
(E)-6-(1-Propyl-1-)butenyl-4-trifluoromethyl-2(1H)-quinolinone (Compound 640);
6-(1-Propyl)butyl-4-trifluoromethyl-2(1H)-quinolinone (Compound 641);
(E)-6-(1-Methyl-1-)butenyl-4-trifluoromethyl-2(1H)-quinolinone (Compound 642);
(Z)-6-(1-Methyl-1-)butenyl-4-trifluoromethyl-2(1H)-quinolinone (Compound 643);
(±)-6-(1-Methyl)butyl-4-trifluoromethyl-2(1H)-quinolinone (Compound 644);
(E)-6-(1-Ethyl-1-)propenyl-4-trifluoromethyl-2(1H)-quinolinone (Compound 645);
(Z)-6-(1-Ethyl-1-)propenyl-4-trifluoroethyl-2(1H)-quinolinone (Compound 646);
6-(1-Ethyl)propyl-4-triflouromethyl-2(1H)-quinolinone (Compound 647);
6-(1-Isopropyl-2-methyl-1-)propenyl-4-trifluoromethyl-2(1H)-quinolinone (Compound 648);
6-(1-Isopropyl-2-methyl)propyl-4-trifluoromethyl-2(1H)-quinolinone (Compound 649);
(Z)-6-(1-Isobutyl-3-methyl-1-)butenyl-4-trifluoromethyl-2(1H)-quinolinone (Compound 650);
(E)-6-(1-Isobutyl-3-methyl-1-)butenyl-4-trifluoromethyl-2(1H)-quinolinone (Compound 651);
6-(1-Isobutyl-3-methyl)butyl-4-trifluoromethyl-2(1H)-quinolinone (Compound 652);
6-(1-Propyl)butyl-4-trifluoromethyl-2(1H)-thioquinolinone (Compound 653);
6-(3-Oxo-1-)cyclopentenyl-4-trifluoromethyl-2(1H)-quinolinone (Compound 654);
6-(3-Oxo-1-)cyclohexenyl-4-trifluoromethyl-2(1H)-quinolinone (Compound 655);
6-(3-Oxo-1-)cyclopentenyl-3-methyl-4-difluoromethyl-2(1H)-quinolinone (Compound 656);
6-(3-Oxo-1-)cyclohexenyl-3-methyl-4-difluoromethyl-2(1H)-quinolinone (Compound 657);
4-Trifluoromethyl-6-(1-(3,3,3-trifluoropropyl)-1(E)-propenyl)-2(1H)-quinolinone (Compound 774);
4-Trifluoromethyl-6-(1-ethyl-4,4,4-trifluoro-1(E)-butenyl)-2(1H)-quinolinone (Compound 776);
4-Trifluoromethyl-6-(1-ethyl-4,4,4-trifluoro-1(Z)-butenyl)-2(1H)-quinolinone (Compound 777);.

21. A method for affecting androgen receptor activity in a mammal, comprising administering to said mammal a compound according to claim 1.

22. A method for affecting progesterone receptor activity in a mammal, comprising administering to said mammal a compound according to claim 1.

23. A method for modulating a process in a mammal mediated by androgen receptors, comprising administering to a mammal a pharmaceutically effective amount of a compound according to claim 1.

24. A method for modulating a process in a mammal mediated by progesterone receptors, comprising administering to a mammal a pharmaceutically effective amount of a compound according to claim 1.

* * * * *